(12) United States Patent
Hassanein et al.

(10) Patent No.: US 11,944,088 B2
(45) Date of Patent: *Apr. 2, 2024

(54) EX VIVO ORGAN CARE SYSTEM

(71) Applicant: TransMedics, Inc., Andover, MA (US)

(72) Inventors: Waleed H. Hassanein, North Andover, MA (US); Tamer I. Khayal, North Andover, MA (US); Ahmed Elbetanony, North Andover, MA (US); Jeff Barnes, Medford, MA (US); Greg Ritchie, Rowley, MA (US); Richard Bringham, North Andover, MA (US); Mark Anderson, Danvers, MA (US); John Sullivan, Groton, MA (US)

(73) Assignee: TRANSMEDICS, INC., Andover, MA (US)

(*) Notice: Subject to any disclaimer, the term of this patent is extended or adjusted under 35 U.S.C. 154(b) by 53 days.

This patent is subject to a terminal disclaimer.

(21) Appl. No.: 17/509,520

(22) Filed: Oct. 25, 2021

(65) Prior Publication Data

US 2022/0039373 A1 Feb. 10, 2022

Related U.S. Application Data

(63) Continuation of application No. 16/130,255, filed on Sep. 13, 2018, now Pat. No. 11,154,050, which is a continuation of application No. 14/728,771, filed on Jun. 2, 2015, now Pat. No. 10,076,112.

(60) Provisional application No. 62/006,871, filed on Jun. 2, 2014, provisional application No. 62/006,878, filed on Jun. 2, 2014.

(51) Int. Cl.
A01N 1/00 (2006.01)
A01N 1/02 (2006.01)
C12M 3/00 (2006.01)

(52) U.S. Cl.
CPC ............................... A01N 1/0247 (2013.01)

(58) Field of Classification Search
CPC ............................ A01N 1/0247; C12M 21/08
See application file for complete search history.

(56) References Cited

U.S. PATENT DOCUMENTS

| | | | |
|---|---|---|---|
| 3,253,595 A | 5/1966 | Keller, Jr. et al. | |
| 3,388,803 A | 6/1968 | Scott | |
| 3,406,531 A | 10/1968 | Koski et al. | |
| 3,468,136 A | 9/1969 | Koski et al. | |
| 3,537,956 A | 11/1970 | Falcone | |

(Continued)

FOREIGN PATENT DOCUMENTS

| | | |
|---|---|---|
| AU | 2019236595 B2 | 12/2021 |
| CA | 2144952 A1 | 3/1994 |

(Continued)

OTHER PUBLICATIONS

US 11,758,904 B2, 09/2023, Freed (withdrawn)
(Continued)

*Primary Examiner* — Nathan A Bowers
(74) *Attorney, Agent, or Firm* — Wilmer Cutler Pickering Hale and Dorr LLP

(57) ABSTRACT

The invention generally relates to systems, methods, and devices for ex vivo organ care. More particularly, in various embodiments, the invention relates to caring for a liver ex vivo at physiologic or near-physiologic conditions.

30 Claims, 156 Drawing Sheets

(56) References Cited

U.S. PATENT DOCUMENTS

| | | |
|---|---|---|
| 3,545,221 A | 12/1970 | Koski et al. |
| 3,545,605 A | 12/1970 | Robins |
| 3,587,567 A | 6/1971 | Schiff |
| 3,607,646 A | 9/1971 | de Roissart |
| 3,632,473 A | 1/1972 | Belzer et al. |
| 3,639,084 A | 2/1972 | Goldhaber |
| 3,654,085 A | 4/1972 | Fritz et al. |
| 3,660,241 A | 5/1972 | Michielsen |
| 3,738,914 A | 6/1973 | Thorne et al. |
| 3,772,153 A | 11/1973 | De Roissart |
| 3,777,507 A | 12/1973 | Burton et al. |
| 3,843,455 A | 10/1974 | Bier et al. |
| 3,851,646 A | 12/1974 | Sarns |
| 3,881,990 A | 5/1975 | Burton et al. |
| 3,995,444 A | 12/1976 | Clark et al. |
| 4,004,298 A | 1/1977 | Freed |
| 4,069,826 A | 1/1978 | Sessions |
| 4,186,253 A | 1/1980 | Yokoyama et al. |
| 4,186,565 A | 2/1980 | Toledo-Pereyra |
| 4,231,354 A | 11/1980 | Kurtz et al. |
| 4,415,556 A | 11/1983 | Bretschneider |
| 4,598,697 A | 7/1986 | Numazawa et al. |
| 4,605,644 A | 8/1986 | Foker |
| 4,666,425 A | 5/1987 | Fleming |
| 4,719,201 A | 1/1988 | Foker |
| 4,723,939 A | 2/1988 | Anaise |
| 4,745,759 A | 5/1988 | Bauer et al. |
| 4,759,371 A | 7/1988 | Franetzki |
| 4,801,299 A | 1/1989 | Brendel et al. |
| 4,847,470 A | 7/1989 | Bakke |
| 4,920,044 A | 4/1990 | Bretan, Jr. |
| 5,051,352 A | 9/1991 | Martindale et al. |
| 5,066,578 A | 11/1991 | Wikman-Coffelt |
| 5,141,847 A | 8/1992 | Sugimachi et al. |
| 5,145,771 A | 9/1992 | Lemasters et al. |
| 5,157,930 A | 10/1992 | McGhee et al. |
| 5,200,398 A | 4/1993 | Strasberg et al. |
| 5,217,860 A | 6/1993 | Fahy et al. |
| 5,285,657 A | 2/1994 | Bacchi et al. |
| 5,306,711 A | 4/1994 | Andrews |
| 5,326,706 A | 7/1994 | Yland et al. |
| 5,338,662 A | 8/1994 | Sadri |
| 5,354,268 A | 10/1994 | Peterson et al. |
| 5,356,593 A | 10/1994 | Heiberger et al. |
| 5,356,771 A | 10/1994 | O'Dell |
| 5,358,931 A | 10/1994 | Rubinsky et al. |
| 5,362,622 A | 11/1994 | O'Dell et al. |
| 5,370,989 A | 12/1994 | Stern et al. |
| 5,381,510 A | 1/1995 | Ford et al. |
| 5,385,821 A | 1/1995 | O'Dell et al. |
| 5,395,314 A | 3/1995 | Klatz et al. |
| 5,405,742 A | 4/1995 | Taylor |
| 5,407,669 A | 4/1995 | Lindstrom et al. |
| 5,407,793 A | 4/1995 | Del Nido et al. |
| 5,472,876 A | 12/1995 | Fahy |
| 5,473,791 A | 12/1995 | Holcomb et al. |
| 5,494,822 A | 2/1996 | Sadri |
| 5,498,427 A | 3/1996 | Menasche |
| 5,505,709 A | 4/1996 | Funderburk et al. |
| 5,514,536 A | 5/1996 | Taylor |
| 5,552,267 A | 9/1996 | Stern et al. |
| 5,554,123 A | 9/1996 | Herskowitz |
| 5,554,497 A | 9/1996 | Raymond |
| 5,571,801 A | 11/1996 | Segall et al. |
| 5,584,804 A | 12/1996 | Klatz et al. |
| 5,586,438 A | 12/1996 | Fahy |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,654,266 A | 8/1997 | Chen et al. |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A | 2/1998 | Minten |
| 5,723,281 A | 3/1998 | Segall et al. |
| 5,733,894 A | 3/1998 | Segall et al. |
| 5,747,071 A | 5/1998 | Segall et al. |
| 5,752,929 A | 5/1998 | Klatz et al. |
| 5,759,148 A | 6/1998 | Sipin |
| 5,770,149 A | 6/1998 | Raible |
| 5,776,063 A | 7/1998 | Dittrich et al. |
| 5,786,136 A | 7/1998 | Mayer |
| 5,787,544 A | 8/1998 | Meade |
| 5,807,737 A | 9/1998 | Schill et al. |
| 5,823,799 A | 10/1998 | Tor et al. |
| 5,843,024 A | 12/1998 | Brasile |
| 5,856,081 A | 1/1999 | Fahy |
| 5,882,328 A | 3/1999 | Levy et al. |
| 5,965,433 A | 10/1999 | Gardetto et al. |
| 5,998,240 A | 12/1999 | Hamilton et al. |
| 6,024,698 A | 2/2000 | Brasile |
| 6,034,109 A | 3/2000 | Ramasamy et al. |
| 6,042,550 A | 3/2000 | Haryadi et al. |
| 6,046,046 A | 4/2000 | Hassanein |
| 6,050,987 A | 4/2000 | Rosenbaum |
| 6,090,776 A | 7/2000 | Kuberasampath et al. |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,217,546 B1 | 4/2001 | Hinchliffe et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,402,461 B1 | 6/2002 | Tebby |
| 6,475,716 B1 | 11/2002 | Seki |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,526,974 B1 | 3/2003 | Brydon et al. |
| 6,569,615 B1 | 5/2003 | Thatte et al. |
| 6,582,375 B2 | 6/2003 | Melvin et al. |
| 6,582,953 B2 | 6/2003 | Brasile |
| 6,600,941 B1 | 7/2003 | Khuri |
| 6,609,987 B1 | 8/2003 | Beardmore |
| 6,631,830 B2 | 10/2003 | Ma et al. |
| 6,642,045 B1 | 11/2003 | Brasile |
| 6,673,594 B1 | 1/2004 | Owen et al. |
| 6,696,238 B2 | 2/2004 | Murphy et al. |
| 6,740,484 B1 | 5/2004 | Khirabadi et al. |
| 6,764,462 B2 | 7/2004 | Risk, Jr. et al. |
| 6,783,328 B2 | 8/2004 | Lucke et al. |
| 6,792,309 B1 | 9/2004 | Noren |
| 6,794,124 B2 | 9/2004 | Steen |
| 6,811,965 B2 | 11/2004 | Vodovotz et al. |
| 6,837,851 B1 | 1/2005 | Coroneo |
| 6,878,339 B2 | 4/2005 | Akiyama et al. |
| 6,894,690 B2 | 5/2005 | Capers |
| 6,906,325 B2 | 6/2005 | Quek |
| 6,925,324 B2 | 8/2005 | Shusterman |
| 6,953,655 B1 | 10/2005 | Hassanein et al. |
| 6,974,436 B1 | 12/2005 | Aboul-Hosn et al. |
| 7,001,354 B2 | 2/2006 | Suzuki et al. |
| 7,008,380 B1 | 3/2006 | Rees et al. |
| 7,045,279 B1 | 5/2006 | Laske et al. |
| 7,122,371 B1 | 10/2006 | Ma |
| 7,238,165 B2 | 7/2007 | Vincent et al. |
| 7,316,666 B1 | 1/2008 | Entenman et al. |
| 7,410,474 B1 | 8/2008 | Friend et al. |
| 7,431,727 B2 | 10/2008 | Cole et al. |
| 7,452,711 B2 | 11/2008 | Daykin |
| 7,572,622 B2 | 8/2009 | Hassanein et al. |
| 7,651,835 B2 | 1/2010 | Hassanein et al. |
| 7,811,808 B2 | 10/2010 | Van Der Plaats et al. |
| 8,167,869 B2 | 5/2012 | Wudyka |
| 8,304,181 B2 | 11/2012 | Hassanein et al. |

(56) References Cited

U.S. PATENT DOCUMENTS

| | | |
|---|---|---|
| 8,323,954 B2 | 12/2012 | Kravitz et al. |
| 8,409,846 B2 | 4/2013 | Hassanein et al. |
| 8,420,380 B2 | 4/2013 | Fishman et al. |
| 8,465,970 B2 | 6/2013 | Hassanein et al. |
| 8,535,934 B2 | 9/2013 | Hassanein et al. |
| 8,585,380 B2 | 11/2013 | Hassanein et al. |
| 8,715,305 B2 | 5/2014 | Pate et al. |
| 8,822,203 B2 | 9/2014 | Hassanein et al. |
| 9,055,740 B2 | 6/2015 | Hassanein et al. |
| 9,215,867 B2 | 12/2015 | Hassanein et al. |
| 9,457,179 B2 | 10/2016 | Hassanein et al. |
| 9,462,802 B2 | 10/2016 | Fishman et al. |
| 9,706,768 B2 | 7/2017 | Freed et al. |
| 9,894,894 B2 | 2/2018 | Hassanein et al. |
| 10,076,112 B2 | 9/2018 | Hassanein et al. |
| 10,124,093 B1 | 11/2018 | Francis et al. |
| 10,321,676 B2 | 6/2019 | Hassanein et al. |
| 10,327,441 B2 | 6/2019 | Freed et al. |
| 10,362,780 B2 | 7/2019 | Kay et al. |
| 10,433,539 B2 | 10/2019 | White et al. |
| 10,736,314 B2 | 8/2020 | Hassanian et al. |
| 10,750,738 B2 | 8/2020 | Hassanian et al. |
| 11,122,795 B2 | 9/2021 | Hassanian et al. |
| 11,154,050 B2 | 10/2021 | Hassanein et al. |
| 11,191,263 B2 | 12/2021 | Hassanein et al. |
| 11,570,985 B2 | 2/2023 | Hassanein et al. |
| 11,723,357 B2 | 8/2023 | Hassanein et al. |
| 11,785,939 B2 | 10/2023 | Freed |
| 2001/0003652 A1 | 6/2001 | Freeman |
| 2001/0018569 A1 | 8/2001 | Erbel et al. |
| 2001/0025191 A1 | 9/2001 | Montgomery |
| 2002/0012988 A1 | 1/2002 | Brasile |
| 2002/0102720 A1 | 8/2002 | Steen |
| 2002/0132220 A1 | 9/2002 | Berens et al. |
| 2002/0151950 A1 | 10/2002 | Okuzumi |
| 2002/0164795 A1 | 11/2002 | Gen |
| 2002/0177117 A1 | 11/2002 | Wolf |
| 2002/0187132 A1 | 12/2002 | Mcgregor et al. |
| 2002/0198504 A1 | 12/2002 | Risk et al. |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0073912 A1 | 4/2003 | Melvin et al. |
| 2003/0074760 A1 | 4/2003 | Keller |
| 2003/0086830 A1 | 5/2003 | Haywood et al. |
| 2003/0111604 A1 | 6/2003 | Quek |
| 2003/0124503 A1 | 7/2003 | Olivencia-Yurvati et al. |
| 2003/0135152 A1 | 7/2003 | Kollar et al. |
| 2003/0147466 A1 | 8/2003 | Liang |
| 2003/0168064 A1 | 9/2003 | Daly et al. |
| 2004/0015042 A1 | 1/2004 | Vincent et al. |
| 2004/0017658 A1 | 1/2004 | Lo et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1 | 6/2004 | Mathis et al. |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0193096 A1 | 9/2004 | Cooper |
| 2004/0202993 A1 | 10/2004 | Poo et al. |
| 2004/0221719 A1 | 11/2004 | Wright et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2004/0258745 A1 | 12/2004 | Kai et al. |
| 2005/0010118 A1 | 1/2005 | Toyoda et al. |
| 2005/0019917 A1 | 1/2005 | Toledo-Pereyra et al. |
| 2005/0027237 A1 | 2/2005 | Weiner |
| 2005/0037330 A1 | 2/2005 | Fischer et al. |
| 2005/0063860 A1 | 3/2005 | Carpenter et al. |
| 2005/0085762 A1 | 4/2005 | Vijay et al. |
| 2005/0142532 A1 | 6/2005 | Poo et al. |
| 2005/0147958 A1 | 7/2005 | Hassanein et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2005/0202394 A1 | 9/2005 | Dobson |
| 2005/0253390 A1 | 11/2005 | Blazek |
| 2005/0255442 A1 | 11/2005 | Brassil et al. |
| 2006/0034941 A1 | 2/2006 | Dobson |
| 2006/0039870 A1 | 2/2006 | Turner |
| 2006/0074470 A1 | 4/2006 | Bartels et al. |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0148062 A1 | 7/2006 | Hassanein et al. |
| 2006/0154357 A1 | 7/2006 | Hassanein et al. |
| 2006/0154358 A1 | 7/2006 | Hassanein et al. |
| 2006/0154359 A1 | 7/2006 | Hassanein et al. |
| 2006/0160204 A1 | 7/2006 | Hassanein et al. |
| 2006/0166360 A1 | 7/2006 | Berthiaume et al. |
| 2006/0182722 A1 | 8/2006 | Hering et al. |
| 2006/0292544 A1 | 12/2006 | Hassanein et al. |
| 2007/0009881 A1 | 1/2007 | Arzt et al. |
| 2007/0098694 A1 | 5/2007 | Khuri et al. |
| 2007/0135752 A1 | 6/2007 | Domash et al. |
| 2007/0135760 A1 | 6/2007 | Williams |
| 2007/0196461 A1 | 8/2007 | Weers |
| 2007/0275364 A1 | 11/2007 | Hassanein et al. |
| 2008/0009815 A1 | 1/2008 | Grabenkort et al. |
| 2008/0017191 A1 | 1/2008 | Davies et al. |
| 2008/0017194 A1 | 1/2008 | Hassanein et al. |
| 2008/0057488 A1 | 3/2008 | Steen |
| 2008/0234768 A1 | 9/2008 | Hassanein et al. |
| 2008/0286746 A1 | 11/2008 | Poo et al. |
| 2008/0295839 A1 | 12/2008 | Habashi |
| 2009/0142830 A1 | 6/2009 | Yamashiro et al. |
| 2009/0143417 A1 | 6/2009 | Smith et al. |
| 2009/0182302 A1 | 7/2009 | Garabet |
| 2009/0191614 A1* | 7/2009 | Miyahara ................ G01K 1/20 |
| | | 435/286.1 |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2010/0028850 A1 | 2/2010 | Brassil |
| 2010/0056966 A1 | 3/2010 | Toth |
| 2010/0092939 A1 | 4/2010 | Belous et al. |
| 2010/0119554 A1 | 5/2010 | Dobson |
| 2010/0204663 A1 | 8/2010 | Wudyka |
| 2010/0322826 A1 | 12/2010 | Locascio et al. |
| 2010/0322862 A1 | 12/2010 | Ruoslahti et al. |
| 2011/0002926 A1 | 1/2011 | Matthews et al. |
| 2011/0076666 A1 | 3/2011 | Brassil |
| 2011/0129810 A1 | 6/2011 | Owen et al. |
| 2011/0136096 A1 | 6/2011 | Hassanein et al. |
| 2011/0177487 A1 | 7/2011 | Simsir et al. |
| 2011/0190572 A1 | 8/2011 | Brophy et al. |
| 2011/0212431 A1 | 9/2011 | Bunegin et al. |
| 2011/0294108 A1 | 12/2011 | Argoudelis et al. |
| 2012/0064050 A1 | 3/2012 | Calle et al. |
| 2012/0077771 A1 | 3/2012 | Fallouh et al. |
| 2012/0183945 A1 | 7/2012 | Steen et al. |
| 2012/0277681 A1 | 11/2012 | Kravitz et al. |
| 2012/0282591 A1 | 11/2012 | Thatte et al. |
| 2012/0330438 A1 | 12/2012 | Keshavjee et al. |
| 2013/0011823 A1 | 1/2013 | Hassanein et al. |
| 2013/0078710 A1 | 3/2013 | Hassanein et al. |
| 2013/0102917 A1 | 4/2013 | Colbaugh et al. |

(56) References Cited

U.S. PATENT DOCUMENTS

| | | |
|---|---|---|
| 2013/0144227 A1 | 6/2013 | Locke et al. |
| 2013/0157248 A1 | 6/2013 | Fishman et al. |
| 2013/0220325 A1 | 8/2013 | Davis et al. |
| 2013/0295552 A1 | 11/2013 | Hassanein et al. |
| 2014/0001745 A1 | 1/2014 | Lehmann et al. |
| 2014/0007961 A1 | 1/2014 | Steen et al. |
| 2014/0017658 A1 | 1/2014 | Steinman et al. |
| 2014/0017660 A1 | 1/2014 | Steinman et al. |
| 2014/0135738 A1 | 5/2014 | Panian |
| 2014/0220550 A1 | 8/2014 | Van Der Plaats et al. |
| 2014/0283828 A1 | 9/2014 | Acker et al. |
| 2014/0308654 A1 | 10/2014 | Kay et al. |
| 2014/0315175 A1 | 10/2014 | Nguyen et al. |
| 2014/0377849 A1 | 12/2014 | Kay et al. |
| 2015/0017710 A1 | 1/2015 | Freed et al. |
| 2015/0079580 A1 | 3/2015 | Hassanein et al. |
| 2015/0093738 A1 | 4/2015 | Potenziano et al. |
| 2015/0230453 A1 | 8/2015 | Fontes et al. |
| 2015/0246164 A1 | 9/2015 | Heaton et al. |
| 2015/0275176 A1 | 10/2015 | Kobayashi et al. |
| 2015/0342177 A1 | 12/2015 | Hassanein et al. |
| 2016/0113269 A1 | 4/2016 | Woodard et al. |
| 2016/0262634 A1 | 9/2016 | Steen et al. |
| 2016/0361476 A1* | 12/2016 | Huang .............. A61M 1/895 |
| 2017/0000110 A1 | 1/2017 | Korkut et al. |
| 2017/0015963 A1 | 1/2017 | Ott |
| 2017/0042141 A1 | 2/2017 | Kay et al. |
| 2017/0049096 A1 | 2/2017 | Kay et al. |
| 2019/0021308 A1 | 1/2019 | Hassanein et al. |
| 2020/0128813 A1 | 4/2020 | Kay et al. |
| 2020/0337298 A1 | 10/2020 | Hassanein et al. |
| 2020/0352155 A1 | 11/2020 | Fishman et al. |
| 2021/0244017 A1 | 8/2021 | Ritchie et al. |
| 2022/0039373 A1 | 2/2022 | Hassanein et al. |
| 2022/0071197 A1 | 3/2022 | Hassanein et al. |
| 2022/0232823 A1 | 7/2022 | Hassanein et al. |
| 2022/0361482 A1 | 11/2022 | Hassanein |
| 2023/0210104 A1 | 7/2023 | Hassanein |
| 2023/0263156 A1 | 8/2023 | Hassanein |

FOREIGN PATENT DOCUMENTS

| | | |
|---|---|---|
| CA | 2881613 A1 | 11/2007 |
| CA | 2861545 A1 | 7/2013 |
| CA | 2521324 C | 12/2014 |
| CA | 2985229 | 2/2023 |
| CN | 1232723 A | 10/1999 |
| CN | 1269471 A | 10/2000 |
| CN | 2418882 Y | 2/2001 |
| CN | 1452863 A | 11/2003 |
| CN | 2616058 Y | 5/2004 |
| CN | 1849102 A | 10/2006 |
| CN | 103596426 A | 2/2014 |
| CN | 103893205 A | 7/2014 |
| CN | 203724222 U | 7/2014 |
| CN | 104770361 A | 7/2015 |
| DE | 4201259 A1 | 7/1993 |
| DE | 10121159 A1 | 11/2002 |
| DE | 102005048625 A1 | 4/2007 |
| EP | 0347923 | 12/1989 |
| EP | 0376763 | 7/1990 |
| EP | 1062870 B1 | 1/2003 |
| EP | 1488743 A2 | 12/2004 |
| EP | 1017271 B1 | 1/2006 |
| EP | 1942726 A2 | 7/2008 |
| EP | 3347084 | 11/2020 |
| EP | 4032401 A1 | 7/2022 |
| FR | 2830183 A1 | 4/2003 |
| JP | S57-010695 | 1/1982 |
| JP | 63270601 | 11/1988 |
| JP | H02-282301 A | 11/1990 |
| JP | 02-306901 A | 12/1990 |
| JP | H03-74302 A | 3/1991 |
| JP | 04-099701 A | 3/1992 |
| JP | H04-128201 A | 4/1992 |
| JP | 06-056601 | 3/1994 |
| JP | 06-305901 | 11/1994 |
| JP | H07-196401 A | 8/1995 |
| JP | H08-89518 A | 4/1996 |
| JP | 08-511012 | 11/1996 |
| JP | H09-500481 A | 1/1997 |
| JP | 2001061956 A | 3/2001 |
| JP | 2001516768 A | 10/2001 |
| JP | 2002-119586 A | 4/2002 |
| JP | 2003-206201 A | 7/2003 |
| JP | 2003-315220 A | 11/2003 |
| JP | 2004513889 A | 5/2004 |
| JP | 2004525290 A | 8/2004 |
| JP | 2004529938 A | 9/2004 |
| JP | 2008-515914 A | 5/2008 |
| JP | 2009-521931 A | 6/2009 |
| JP | 2010-525076 A | 7/2010 |
| JP | 2011-511000 A | 4/2011 |
| JP | 2016-053030 A | 4/2016 |
| JP | 6144238 B2 | 6/2017 |
| JP | 6625384 B2 | 12/2019 |
| JP | 2020-138976 A | 9/2020 |
| JP | 6756775 B2 | 9/2020 |
| WO | WO-8805261 A1 | 7/1988 |
| WO | WO-9502326 A1 | 1/1995 |
| WO | WO-95/03680 A1 | 2/1995 |
| WO | WO-9531897 A1 | 11/1995 |
| WO | WO-9618293 A1 | 6/1996 |
| WO | WO-9629865 A1 | 10/1996 |
| WO | WO-9722244 A1 | 6/1997 |
| WO | WO-9746091 A1 | 12/1997 |
| WO | WO-9915011 A1 | 4/1999 |
| WO | WO-00/18226 A2 | 4/2000 |
| WO | WO-0022927 A1 | 4/2000 |
| WO | WO-200027189 A1 | 5/2000 |
| WO | WO-00/35340 A1 | 6/2000 |
| WO | WO-0060936 A1 | 10/2000 |
| WO | WO-200101774 A1 | 1/2001 |
| WO | WO-0226034 A2 | 4/2002 |
| WO | WO-02/35929 A1 | 5/2002 |
| WO | WO-02089571 A1 | 11/2002 |
| WO | WO-2003026419 A1 | 4/2003 |
| WO | WO-2004017838 | 3/2004 |
| WO | WO-2004026031 A2 | 4/2004 |
| WO | WO-2006042138 A2 | 4/2006 |
| WO | WO-2006060309 | 6/2006 |
| WO | WO-2006076590 A2 | 7/2006 |
| WO | WO-2006124820 A2 | 11/2006 |
| WO | WO-2007079185 A2 | 7/2007 |
| WO | WO-2007124044 A2 | 11/2007 |
| WO | WO-2008106724 A1 | 9/2008 |
| WO | WO-2008108996 A1 | 9/2008 |
| WO | WO-08150587 A2 | 12/2008 |
| WO | WO-2009/099939 A2 | 8/2009 |
| WO | WO-2011002926 A2 | 1/2011 |
| WO | WO-2011072012 A2 | 6/2011 |
| WO | WO-2012142487 A1 | 10/2012 |
| WO | WO-2012148685 | 11/2012 |
| WO | WO-2013068751 | 5/2013 |
| WO | WO-2013068752 A2 | 5/2013 |
| WO | WO-2013068753 | 5/2013 |
| WO | WO-2013106908 A1 | 7/2013 |
| WO | WO-2014011547 A2 | 1/2014 |
| WO | WO-2014059316 A1 | 4/2014 |
| WO | WO-2014194349 A2 | 12/2014 |
| WO | WO-2015126853 A1 | 8/2015 |
| WO | WO-2015143552 A1 | 10/2015 |
| WO | WO-2015154170 A1 | 10/2015 |
| WO | WO-2015154172 A1 | 10/2015 |
| WO | WO-2015154193 A1 | 10/2015 |
| WO | WO-2015187737 | 12/2015 |
| WO | WO-2016090498 A1 | 6/2016 |

(56) References Cited

FOREIGN PATENT DOCUMENTS

| WO | WO-2017044465 | 3/2017 |
|---|---|---|
| WO | WO-2017205967 A1 | 12/2017 |

OTHER PUBLICATIONS

"2002 Design & Engineering Awards, Portable Organ Preservation System", Science (2002) (1 page).
"Celsior™ Cold Storage Solution", Sangstat Medical Corporation (internet reference) (1999) (5 pages).
"History of Transplantation and Organ Preservation," Barr Laboratories, Inc. (2004) (4 pages).
"Human heart beats on its own outside body", USA Today (2001) (1 page).
"Human Heart Kept Alive Outside Body for First Time in Study of Portable Organ Preservation System™ at University of Pittsburgh Medical Center", UPMC, McGowan Institute for Regenerative Medicine (2001) (2 pages).
"Machine Keeps Human Kidney Alive for 24-Hours", American Academy of Anti-Aging Medicine, www.worldhealth.net, Aug. 25, 2001, Accessed Jul. 5, 2006, 1 page.
"Machine may be organ transplant breakthrough", USA Today, by Stephen J. Carrera (<http://www.usatoday.com/news/health/2001-08-25-organ.htm>) (Aug. 5, 2001) (1 page).
"New discovery in organ transplantation", MSNBC Chicago, No Author Listed (2001) (www.nbc5/com <http://www.nbc5/com>) (1 page).
"The Nation: Warm-Storage Device May Aid Organ Transplants", Dow Jones Publications Library (2001) (1 page).
"ViaSpan (Belzer UW) Cold Storage Solution", Barr Laboratories, Inc. (2002), 2 pages.
"Warm storage for donor organs", University of Chicago Magazine (2001) (1 page).
Ahmad, N. et al., "A pathophysiologic study of the kidney tubule to optimize organ preservation solutions", Kidney International 66(1):77-90 (2004), 14 pages.
Aitchison, J.D. et al., "Functional assessment of non-heart-beating donor lungs: prediction of post-transplant function", European Journal of Cardio-thoracic Surgery, 20:187-194 (2001) (8 pages).
Aitchison, J.D. et al., "Nitric Oxide During Perfusion Improves Posttransplantation Function of Non-Heart-Beating Donor Lungs", Transplantation, 75(12):1960-1964, Jun. 27, 2003, 5 pages.
Anathaswamy, A., "Machine keeps organs alive for longer", NewScientist.com, Aug. 16, 2001, (<http://www.newscientist.com/article.ns?id=dn1168&print=true> (1 page).
Aoki, M. et al., "Anti-CD18 Attenuates Deleterious Effects of Cardiopulmonary Bypass and Hypothermic Circulatory Arrest in Piglets", J. Card. Surg. 10(Suppl):407-17 (1995) (11 pages).
Baker, L.E. et al., "Artificial Maintenance Media for Cell and Organ Cultivation", Journal of Experimental Medicine, 70:29-38, Jul. 1, 1939 (15 pages).
Bando, K. et al., "Oxygenated perfluorocarbon, recombinant human superoxide dismutase, and catalase ameliorate free radical induced myocardial injury during heart preservation and transplantation", J. Thorac Cardiovasc Surg. 96:930-8 (Dec. 1988), 9 pages.
Barinov, E.F., "Hormonal-metabolic disturbances during biological preservation of the heart", Fiziologicheskii Zhurnal (Kiev), 29(3):293-299 (1983) (8 pages)—Russian Language with English Abstract.
Belzer, F.O., "Formula for Belzer MPS Solution", University of Wisconsin-Madison Organ Preservation, (<http://www.surgery.wisc.edu/transplat/research/southard/BelzerMPS.shtml>) (Oct. 3, 2003) (2 pages).
Benichou, J. et al., "Canine and Human Liver Preservation for 6 to 18 HR by Cold Infusion", Transplantation, 24(6):407-411 (Dec. 1977) (5 pages).
Birkett, D. et al., "The Fatty Acid Content and Drug Binding Characteristics of Commercial Albumin Preparations", Clinica Chimica Acta 85:253-258 (1978), 6 pages.

Blanchard, J.M. et al., "Techniques for Perfusion and Storage of Heterotopic Heart Transplants in Mice", Microsurgery, 6:169-174 (1985), 6 pages.
Boggi, U. et al., "Pancreas Preservation with University of Wisconsin and Celsior Solutions", Transplantation Proceedings 36(3):563-565 (2004), 3 pages.
Boggi, U. et al., "Pancreas Preservation With University of Wisconsin and Celsior Solutions: A Single-Center, Prospective, Randomized Pilot Study", Transplantation 27:77(8):1186-1190 (2004), 5 pages.
Botha, P., "Extended Donor Criteria in Lung Transplantation", Current Opinion in Organ Transplantation, 14:206-210, 2009 (5 pages).
Boyle, E.M. Jr. et al., "Ischemia-Reperfusion Injury", Ann. Thorac. Surg. 64:S24-S30 (1997), 7 pages.
Brandes, H. et al. "Influence of High Molecular Dextrans on Lung Function in an ex Vivo Porcine Lung Model," Journal of Surgical Research, 101:2, 225-231 (2001) (7 pages).
Brasile, L. et al., "Organ Preservation Without Extreme Hypothermia Using an Oxygent™ Supplemented Perfusate", Art. Cells, Blood Subs., and Immob. Biotech., 22(4):1463-68 (1994), 6 pages.
Burt, J.M. et al., "Myocardial function after preservation for 24 hours", J. Thorac. Cardiovasc Surg., 92(2):238-46 (1986), 9 pages.
Calhoon, J.H. et al., "Twelve-Hour Canine Heart Preservation With A Simple, Portable Hypothermic Organ Perfusion Device", Ann. Thorac. Surg., 62:91-3 (1996), 3 pages.
Canelo R. et al., "Experience with Hystidine Tryptophan Ketoglutarate Versus University Wisconsin Preservation Solutions in Transplantation", Int. Surg. 88(3):145-151 (2003), 8 pages.
Carrier, B., "Chapter 4: Hypoxia and Oxygenation", Alaska Air Medical Escort Training Manual, Fourth Edition, pp. 71-82, 2006, 12 pages.
Chambers, D.J. et al., "Long-Term Preservation of the Heart: The Effect of Infusion Pressure During Continuous Hypothermic Cardioplegia", The Journal of Heart and Lung Transplantation, 11(4):665-75 (1992), 11 pages.
Chen, E. P. et al., "Milrinone Improves Pulmonary Hemodynamics and Right Ventricular Function in Chronic Pulmonary Hypertension", Ann Thorac Surg, 63:814-821, 1997 (8 pages).
Chen, F. et al., "Development of New Organ Preservation Solutions in Kyoto University", Yonsei Medical Journal, 45(6):1107-14 (2004), 8 pages.
Chien, S. et al., "A simple technique for multiorgan preservation", The Journal of Thoracic and Cardiovascular Surgery, 95(1):55-61 (1988), 7 pages.
Chien, S. et al., "Canine Lung Transplantation After More than Twenty-four Hours of Normothermic Preservation", The Journal of Heart and Lung Transplantation, 16(3)40-51 (1997), 12 pages.
Chien, S. et al., "Functional Studies of the Heart During a 24-Hour Preservation Using a New Autoperfusion Preparation", The Journal of Heart and Lung Transplantation, 10(3):401-8 (1991), 8 pages.
Chinchoy, Edward Cheng-wey; "The Development, Refinement, and Uses of a Physiologically Working Isolated Ex Vivo Swine Heart Model", A thesis submitted to the Faculty of the Graduate School of the University of Minnesota, Dec. 1999 (136 pages).
Christophi, C. et al., "A Comparison of Standard and Rapid Infusion Methods of Liver Preservation During Multi-Organ Procurement", Aust. N.Z.J. Surg., 61(9):692-694 (1991), 3 pages.
Cimino, Adria, "Doctor develops device to preserve donated organs", Mass High Tech (2001), 2 pages.
CNN.com, "Heart kept beating outside body", Associated Press CNN News Health Section (Oct. 7, 2001, 02:59) (CNN.com/Health with WebMD.com), 2 pages.
Collins, B.H., "Organ Transplantation: What Is the State of the Art?", Annals of Surgery, 238(6 Suppl):S72-S89 (2003), 18 pages.
Cronin, D.C. et al., "Chapter 21: Liver Transplantation at The University of Chicago", Clinical Transplants 231-238 (1999), 9 pages.
Daemen, J.H.C. et al., "Short-term outcome of kidney transplants from non-heart-beating donors after preservation by machine perfusion", Transpl. Int. 9(Supp 1):S76-S80 (1996), 5 pages.

(56) References Cited

OTHER PUBLICATIONS

Definition of Examine, Merriam-Webster Dictionary on-line. www.merriam-webster.com/dictionary/examine, Printed Feb. 9, 2011, (1 page).

Demertzis, S. et al., "University of Wisconsin Versus St. Thomas' Hospital Solution for Human Donor Heart Preservation", Ann Thorac Surg 55:1131-7 (1993), 7 pages.

den Butter, G. et al., "Comparison of solutions for preservation of the rabbit liver as tested by isolated perfusion", Transpl. Int. 8(6):466-471 (1995), 6 pages.

Denham, B.S. et al., "Twenty-Four Hour Canine Renal Preservation By Pulsatile Perfusion, Hypothermic Storage, and Combinations of the Two Methods", Transplantation Proceedings, 9(3):1553-1556 (1977), 4 pages.

Dobrian, A. et al., "In vitro formation of oxidatively-modified and reassembled human low-density lipoproteins: antioxidant effect of albumin", Biochimica et Biophysica Acta (BBA) 1169:12-24 (1993), 13 pages.

Drexler, H. et al., "Effect of L-arginine on coronary endothelial function in cardiac transplant recipients. Relation to vessel wall morphology," Circulation 89(4):1615-1623 (1994) (10 pages).

Duarte, J.D. et al., "Pharmacologic treatments for pulmonary hypertension; exploring pharmacogenomics", Future Cardiol., 9(3):335-349, 2013 (15 pages).

Egan, T. M. et al., "Ex Vivo Evaluation of Human Lungs for Transplant Suitability", Ann Thorac Surg, vol. 81, No. 4, pp. 1205-1213 (Apr. 2006) (9 pages).

Eiseman, B. et al., "A disposable liver perfusion chamber", Surgery 60(6):1183-1186 (1966), 4 pages.

Engelman, R.M. et al., "Influence of Steroids on Complement and Cytokine Generation After Cardiopulmonary Bypass", Ann Thorac Surg 60(3):801-04 (1995) (4 pages).

European Extended Search Report issued in EP 16844964.3, dated Apr. 26, 2019 (7 pages).

European Search Report for European Patent Application No. 08795820.3 dated Apr. 17, 2014 (6 pages).

European Search Report for European Patent Application No. 09707471.0 dated May 27, 2014 (7 pages).

European Search Report issued for European Application No. EP19204566.4, dated May 25, 2020 (7 pages).

European Search Report issued in EP12770852.7, dated Sep. 23, 2014, 8 pages.

Extended European Search Report issued in EP15803127.8, dated May 22, 2018 (14 pages).

Extended European Search Report issued in European Application No. 17172411.5, dated Nov. 8, 2017 (7 pages).

Fabregas, L., "UPMC tests machine to aid heart transplants", Pittsburg Tribune-Review (2002), 2 pages.

Faggian, G. et al., "Donor Organ Preservation in High-Risk Cardiac Transplantation", Transplantation Proceedings 36:617-619 (2004), 3 pages.

Featherstone, R.L. et al. "Comparison of Phosphodiesterase Inhibitors of Differing Isoenzyme Selectivity Added to St. Thomas' Hospital Cardioplegic Solution Used for Hypothermic Preservation of Rat Lungs", Am J Respir Crit Care Med, Mar. 2000,162(3):850-856 (7 pages).

Fehrenberg, C. et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney", Nephron Physiol 96:52-58 (2004) (7 pages).

Ferrera, R. et al., "Comparison of Different Techniques of Hypothermic Pig Heart Preservation", Ann Thorac Surg 57(5):1233-1239 (1994), 7 pages.

File History for U.S. Appl. No. 60/616,835, filed Oct. 7, 2004 (82 pages).

File History for U.S. Appl. No. 60/694,971, filed Jun. 28, 2005 (280 pages).

File History for U.S. Appl. No. 60/725,168, filed Oct. 6, 2005 (699 pages).

Finn, A. et al., "Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass", J Thorac Cardiovasc Surg 111(2):451-459 (1996), 9 pages.

Fourcade, C., et al., "Nouvelle Méthode De Conservation Du Rein Avec Une Solution De Collins", <<A New Method of Kidney Preservation with Collins' Solution,>> Biomed. 21(7):308-11 (1974), English Abstract, 5 pages.

Fraser, C.D. Jr. et al., "Evaluation of Current Organ Preservation Methods for Heart-Lung Transplantation", Transplantation Proceedings, 20(1 Suppl. 1):987-990 (1988), 4 pages.

Gever, J., "Technique to Repair Damaged Donor Lungs for Graft Passes Clinical Test", MedPage Today, https://www.medpagetoday.org/surgery/transplantation/12245, Accessed Jul. 11, 2020, dated Dec. 19, 2008 (4 pages).

Givertz, M.M. et al., "Effect of Bolus Milrinone on Hemodynamic Variables and Pulmonary Vascular Resistance in Patients With Severe Left Ventricular Dysfunction: A Rapid Test for Reversibility of Pulmonary Hypertension", JACC, 28(7):1775-1780, Dec. 1996 (6 pages).

Glucose, The Merck Index, 11th ed. Entry 4353 (pp. 699-700) (1989), 3 pages.

Gohrbandt, B., et al., "Glycine intravenous donor preconditioning is superior to glycine supplementation to low-potassium dextran flush preservation and improves graft function in a large animal lung transplantation model after 24 hours of cold ischemia", The Journal of Thoracic and Cardiovascular Surgery, 131(3):724-729, Mar. 2006 (6 pages).

Grynberg, A. et al., "Fatty Acid Oxidation in the Heart", Journal of Cardiovascular Pharmacology, 28(Suppl. 1):S11-S17 (1996) (8 pages).

Guarrera, J.V. et al., "Pulsatile Machine Perfusion With Vasosol Solution Improves Early Graft Function After Cadaveric Renal Transplantation", Transplantation 77(8):1264-1268 (2004), 5 pages.

Gundry, S.R. et al., "Successful Transplantation of Hearts Harvested 30 Minutes After Death From Exsanguination", Ann Thorac Surg 53(5):772-775 (1992), 4 pages.

Habazetti, H. et al., "Improvement in Functional Recovery of the Isolated Guinea Pig Heart After Hyperkalemic Reperfusion With Adenosine", J Thorac Cardiovasc Surg 111(1):74-84 (1996) (11 pages).

Hachida, M. et al., Abstract "Efficacy of myocardial preservation using HTK solution in continuous 120 min cross-clamping method—a comparative study with GIK method", Nippon Kyobu Geka Gakkai Zasshi. 41(9):1495-1501 (1993), 1 page, retrieved on Jul. 21, 2006.

Hai, Human Body Atlas, First Edition, Liaoning Science and Technology Publishing House, p. 120, Oct. 31, 2011 (3 pages)—with English Translation.

Han, B. et al., "Study on the clinical efficacy of specific phosphodiesterase inhibitor in patients with pulmonary hypertension due to left heart disease", Experimental and Therapeutic Medicine, 16:1175-1186, 2018 (12 pages).

Hardesty, R.L. et al., Original Communications, "Autoperfusion of the heart and lungs for preservation during distant procurement", J Thorac Cardiovasc Surg, 93(1):11-18 (1987) (8 pages).

Hartman, J.C., "The Role of Bradykinin and Nitric Oxide in the Cardioprotective Action of ACE Inhibitors", Ann Thorac Surg 60:789-792 (1995), 4 pages.

Hassanein, W.H. et al., "A Novel Approach for 12 Hour Donor Heart Preservation, Presented at the 70th Scientific Sessions of The American Heart Association", Abstract was published in Circulation (1997), 1 page.

Hassanein, W.H. et al., "Continuous Perfusion of Donor Hearts in the Beating State Extends Preservation Time and Improves Recovery of Function", The Journal of Thoracic and Cardiovascular Surgery, pp. 821-830 (1998), 10 pages.

Heil, J.E. et al., "A Controlled Comparison of Kidney Preservation by Two Methods: Machine Perfusion and Cold Storage", Transplantation Proceedings 19(1):2046 (1987), 1 page.

Hoeper, M.M. et al., "Intensive Care Unit Management of Patients with Severe Pulmonary Hypertension and Right Heart Failure", Am J Respir Crit Care Med, 184:1114-1124, 2011 (11 pages).

(56) References Cited

OTHER PUBLICATIONS

Howarth, F.C. et al., "Effects of extracellular magnesium and beta adrenergic stimulation on contractile force and magnesium mobilization in the isolated rat heart", Magnesium Research, 7:187-197, 1994 (13 pages).
Hui-Li, G. "The Management of Acute Pulmonary Arterial Hypertension", Cardiovascular Therapeutics, 29:153-175, 2011 (23 pages).
Hülsmann, W.C. et al., "Loss of cardiac contractility and severe morphologic changes by acutely lowering the pH of the perfusion medium: protection by fatty acids", Bragen 20256, Biochimica et Biophysica Acta., 1033:214-218 (1990) (5 pages).
Ida, K. "Titanium for Medical and Dental Use", Japanese journal of medical electronics and biological engineering, 24(1):47-54, 1986 (12 pages)—with English Summary.
Imber, C. et al., "Advantages of Normothermic Perfusion Over Cold Storage in Liver Preservation", Transplantation, 73(5):701-709 (2002), 9 pages.
International Search Report and Written Opinion for International Application No. PCT/US2012/033626 dated Sep. 20, 2012 (12 pages).
International Search Report and Written Opinion issued by the U.S. Patent and Trademark Office as Searching Authority, in International Application No. PCT/US16/50512, dated Dec. 12, 2016 (9 pages).
International Search Report, issued by the European Patent Office as Searching Authority, in PCT/US07/009652 International Search Report, dated Apr. 18, 2008, 5 pages.
International Search Report, issued by the European Patent Office as Searching Authority, issued in PCT/US98/19912, dated May 3, 1999 (4 pages).
International Search Report, issued by the U.S. Patent Office as Searching Authority, issued in PCT/US08/61454 International search report dated Dec. 5, 2008 (2 pages).
International Search Report, issued by the U.S. Patent Office as Searching Authority, issued in PCT/US09/032619, dated Jun. 4, 2009 (4 pages).
Janßen, H. et al., "UW is Superior to Celsior and HTK in the Protection of Human Liver Endothelial Cells Against Preservation Injury", Liver Transplantation, 10(12):1514-1523 (2004), 10 pages.
Jaski, B.E. et al., "Positive inotropic and vasodilator actions of milrinone in patients with severe congestive heart failure. Doseresponse relationships and comparison to nitroprusside", J. Clin Invest., 75(2):643-649, 1985 (8 pages).
Jirsch, D.W. et al., "Ex Vivo Evaluation of Stored Lungs", The Annals of Thoracic Surgery, 10(2):163-168, Aug. 1970 (6 pages).
Johnson, Kerry et al, "POPS: Portable Organ Preservation System", UPMC Health System and TransMedics, Inc. (No date) (1 page).
Johnston, R., "What's Normal About DLCO?", PFT Blog, Jan. 1, 2014 (17 pages).
Kawakami, et al., "Successful Preservation of the Isolated Canine Heart for 24 Hours by Low Pressure-Low Temperature Continuous Perfusion", Japanese Annals of Thoracic Surgery, Japan, 7(6):543-547, Dec. 25, 1987 (13 pages)—English Translation.
Kawamura, T. et al., "Long-Term Preservation of Canine Pancreas by a New Simple Cold Storage Method Using Perfluorochemical—The Two-Layer Cold Storage Method (Euro-Collins' Solution/Perfluorochemical)-", Kobe J. Med. Sci., 38(2):135-145 (1992), 11 pages.
Kelly, R.F., "Current strategies in lung preservation", J. Lab Clin Med, 136:427-440 (2000), 14 pages.
Keshavjee, S.H. et al., "A method for safe twelve-hour pulmonary preservation", J Thorac Cardiovasc Surg, 98:529-534 (1989), 6 pages.
Keshavjee, S.H. et al., "The role of dextran 40 and potassium in extended hypothermic lung preservation for transplantation", Journal of Thoracic and Cardiovascular Surgery, 103(2):314-325, Feb. 1992 (12 pages).
Kioka, Y. et al., "Twenty-Four-Hour Isolated Heart Preservation by Perfusion Method With Oxygenated Solution Containing Perfluorochemicals and Albumin", The Journal of Heart Transplantation, 5(6):437-443 (Nov./Dec. 1986), 7 pages.
Koike, et al., "An Experimental Study on the Hypothermic Preservation of the Rabbit Heart Using Glucose-Insulin-Potassium Solution—Intermittent Perfusion Method Versus Simple Immersion Method", Japanese Annals of Thoracic Surgery, 7(6):527-532, Dec. 25, 1987 (16 pages)—English Translation.
Kozaki, K. et al., "Usefulness of a Combination of Machine Perfusion and Pentoxifylline for Porcine Liver Transplantation From Non-Heart-Beating Donors With Prolonged Hypotension", Transplantation Proceedings, 29:3476-3477 (1997), 2 pages.
Kubono, K. et al., "Examination of Plasma and Corpuscle Adenosine Concentration in Normal Subject by Radioimmunoassay", Rinshou Kagaku (Clinical Chemistry, 20(2):72-77, Jun. 1991 (6 pages)—Japanese Language.
Kuroda, Y. et al., "A New, Simple Method for Cold Storage of the Pancreas Using Perfluorochemical", Transplantation, 46(3):457-460 (1988), 4 pages.
Lasley, R.D. et al., "Protective Effects of Adenosine in the Reversibly Injured Heart", Ann Thorac Surg, 60(3):843-846 (1995), 4 pages.
Lawrence, C., "Machine preserves organs outside body," Chicago Sun Times (2001), 1 page.
Lefer, A.M., "Attenuation of Myocardial Ischemia-Reperfusion Injury With Nitric Oxide Replacement Therapy", Ann Thorac Surg 60(3):847-851 (1995), 5 pages.
Li, G. et al., "Functional Recovery in Rabbit Heart after Preservation with a Blood Cardioplegic Solution and Perfusion," J Heart Lung Transplant, 12(2)263-270 (1993) (8 pages).
Li, X. et al., "Insulin in University of Wisconsin Solution Exacerbates the Ischemic Injury and Decreases the Graft Survival Rate in Rat Liver Transplantation", Transplantation, 15:76(1):44-49 (2003), 6 pages.
Li, X. et al., "Insulin in UW Solution Exacerbates Hepatic Ischemia / Reperfusion Injury by Energy Depletion Through the IRS-2 / SREBP-1c Pathway", Liver Transplantation, 10(9):1173-1182 (2004), 10 pages.
Liu,J. et al., "Annexin V Assay-proven Anti-apoptotic Effect of Ascorbic Acid 2-glucoside after Cold Ischemia/Reperfusion Injury in Rat Liver Transplantation", Acta Med. Okayama, 57(5):209-216 (2003), 8 pages.
Lobato, E.B. et al., "Treatment with phosphodiesterase inhibitors type III and V: milrinone and sildenafil is an effective combination during thromboxane-induced acute pulmonary hypertension", British Journal of Anaesthesia, 96(3):317-322, 2006 (6 pages).
Macchiarini, P. et al. "Ex Vivo Lung Model of Pig-To-Human Hyperacute Xenograft Rejection", The Journal of Thoracic and Cardiovascular Surgery, 114:3, 315-325 (1997) (11 pages).
Mankad, P. et al., "Endothelial dysfunction caused by University of Wisconsin preservation solution in the rat heart", J Thorac Cardiovasc Surg 104(6): 1618-1624 (1992), 7 pages.
Matsuno, N. et al., "Effectiveness of Machine Perfusion Preservation as a Viability Determination Method for Kidneys Procured from Non-Heart-Beating Donors," Transplantation Proceedings, 26(4):2421-2422 (1994) (2 pages).
Matsuno, N. et al., "The Effect of Machine Perfusion Preservation Versus Cold Storage on the Function of Kidneys From Non-Heart-Beating Donors", Transplantation, 57(2):293-294 (1994) (2 pages).
Menasché, P. et al., "Experimental evaluation of Celsior®, a new heart preservation solution," Eur J Cardio-thorac Surg 8:207-213 (1994), 7 pages.
Menasché, P. et al., "Improved recovery of heart transplants with a specific kit of preservation solutions," The Journal of Thoracic and Cardiovascular Surgery, 105(2):353-363 (1993), 11 pages.
Menasché, P., "The inflammatory response to cardiopulmonary bypass and its impact on postoperative myocardial function", Current Opinion in Cardiology, 10:597-604 (1995) (8 pages).
Moisiuk, Y. et al., "Histidine-Tryptophan-Ketoglutarate Versus Euro-Collins for Preservation of Kidneys From Non-Heart-Beating Donors", Transplantation Proceedings, 28(1):202 (1996) (1 page).
Moller-Pedersen, T. et al., "Evaluation of potential organ culture media for eye banking using human donor corneas", Br J Ophthamol, 85(9):1075-1079 (2001), 5 pages.

(56) References Cited

OTHER PUBLICATIONS

Morimoto, T. et al., "A Simple Method for Extended Heart-Lung Preservation by Autoperfusion", Trans Am Soc Artif Intern Organs, 30:320-324 (1984), 5 pages.
Nicholson, M.L. et al., "A Comparison of Renal Preservation by Cold Storage and Machine Perfusion Using a Porcine Autotransplant Model", Transplantation 78(3):333-337 (2004), 5 pages.
No Author Listed, "Custodiol® HTK Solution for Multi-Organ Protection", Saudi Center for Organ Transplantation, Date Unknown, originally cited to U.S. Patent Office Jun. 30, 2014, in U.S. Appl. No. 12/892,451 (2 pages).
No Author Listed, "Soltran Kidney perfusion fluid", Baxter, No Month Listed—2001-2004 (1 page).
No Author Listed, "The comprehensive resource for physicians, drug and illness information", Viaspan™ DuPont Pharma Cold Storage Solution, Date Unknown (3 pages).
No Author Listed, "UW Solution Composition", Date Unknown (1 page).
No Author Listed, "UW Solution Composition", DuPont Pharmaceutical, Date Unknown (1 page).
No Author Listed. "Custodiol HTK" Physicians' Desk Reference, 57th Edition, Thomson PDR. ISBN:1-56363-445-457. No Month Listed—2003 (3 pages).
Odagiri, S. et al., "Pusatile Assist Device: New Pulsatile Pump Using Pulsatile Assist Device-Hemodynamic Comparison of Pulsatile V-A Bypass (VABP), Pulsatile Left Heart Bypass (LHBP) and Constant Flow Left Heart Bypass (LHB)", Journal of Japan Surgical Society, 83(6):515-523, Jun. 1982, 12 pages—English Abstract.
Opelz, G. et al., "Advantage of Cold Storage Over Machine Perfusion for Preservation of Cadaver Kidneys", Transplantation, 33(1):64-68 (1982), 5 pages.
Opelz, G. et al., "Comparative Analysis of Kidney Preservation Methods", Transplantation Proceedings 28(1):87-90 (1996), 4 pages.
Open Anesthesia—Milrinone: pharmacology, https://www.openanesthesia.org/milrinone_pharmacology/, accessed 2019 (3 pages).
Ota, K. et al., "Artificial Organ", Current State and Future of Substitution of Functions, pp. 150-151, 1983 (7 pages)—English Translation.
PCT/US 98/19912 International search report dated May 3, 1999 (4 pages).
PCT/US08/61454 International search report dated Dec. 5, 2008 (3 pages).
PCT/US09/032619 International Search report, dated Jun. 4, 2009 (4 pages).
Pearl, J.M. et al., Loss of endothelium-dependent vasodilatation and nitric oxide release after myocardial protection with University of Wisconsin solution, Cardiovascular Surgery 107(1):257-264 (1994) (8 pages).
Petrovsky, B.V. et al., "Justification and Application of a New Method for Transorganic Oxygen Preservation of the Kidneys", Vestn. Akad. Med. Nauk, USSR., (2):69-82 (1989)—English Abstract, 15 pages.
Pinsky, D. et al., "Restoration of the CAMP Second Messenger Pathway Enhances Cardiac Preservation for Transplantation in a Heterotopic Rat Model", J. Clin. Invest. 92(6):2994-3002 (1993) (9 pages).
Ploeg, R.J. et al., "Successful 72-Hour Cold Storage of Dog Kidneys With UW Solution", Transplantation, 46(2):191-196 (1988), 6 pages.
Pokorny, H. et al., "Histidine-tryptophan-ketoglutarate solution for organ preservation in human liver transplantation—a prospective multi-centre observation study", Transpl Int 17(5):256-260 (2004), (5 pages).
Poston, R.S. et al., "Optimizing Donor Heart Outcome After Prolonged Storage With Endothelial Function Analysis and Continuous Perfusion", Ann Thorac Surg, 78:1362-1370, 2004 (9 pages).
Potdar, S. et al., "Initial experience using histidine-tryptophan-ketoglutarate solution in clinical pancreas transplantation", Clin Transplant, 18(6):661-665 (2004), 5 pages.

Pozniak, A., "Keeping Hearts Alive Doctors Develop a High-Tech System to Salvage Donated Organs", ABC News.com, (Dec. 7, 2001) (<http://abcnews.go.com/print?id=117085>), (2 pages).
Probst, R. et al. "Carbohydrate and fatty acid metabolism of cultured adult cardiac myocytes", Am. J. Physiol. 250 (Heart, Circ. Physiol. 19):H853-H860 (1986) (8 pages).
Pruitt, "Pharmacological Treatment of Respiratory Disorders", RT Magazine, http://www.rtmagazine.com/2007/05/pharmacological-treatment-of-respiratory-disorders, May 3, 2007, accessed Jan. 1, 2019 (6 pages).
Rao, M.V. et al., "Magnesium Sulfate: Chemical and Technical Assessment", MgSO4 (CTA), 2007 (5 pages).
Rao, V. et al., "Donor Blood Perfusion Improves Myocardial Recovery After Heart Transplantation", J. Heart Lung Transplant. 16(6):667-673 (1997) (7 pages).
Reddy, S.P. et al., "Preservation of Porcine Non-Heart-Beating Donor Livers by Sequential Cold Storage and Warm Perfusion", Transplantation, 77(9):1328-1332 (2004), 5 pages.
Richens, D. et al., "Clinical Study of Crystalloid Cardiplegia vs Aspartate-Enriched Cardioplegia Plus Warm Reperfusion for Donor Heart Preservation", Transplantation Proceedings 25(1):1608-1610 (1993) (3 pages).
Rinder, C.S. et al., "Blockade of C5a and C5b-9 Generation Inhibits Leukocyte and Platelet Activation during Extracorporeal Circulation", J. Clin. Invest. 96:3(1564-1572) 1995 (9 pages).
Rosenkranz, E.R., "Substrate Enhancement of Cardioplegic Solution: Experimental Studies and Clinical Evaluation", Ann Thorac Surg 60:797-800 (1995) (4 pages).
Rossi, L. et al., "Innovations-report: New organ preservation solution easier to use", (<http://www.innovations-report.com/html/reports/medicine_report-18854.html>), Feb. 6, 2003 (2 pages).
Rossi, L., "Portable Organ Preservation System™ Keeps Human Heart Alive Outside Body", PITT Campaign Chronicle (Oct. 7, 2001), 2 pages.
Russell, H.E., Jr. et al., "An Evaluation of Infusion Therapy (Including Dextran) for Venous Thrombosis", Circulation, 33:839-846, Jun. 1966 (8 pages).
Saez, D.G. et al., "Evaluation of the Organ Care System in Heart Transplantation With an Adverse Donor/Recipient Profile", Ann. Thorac. Surg., 98:2099-2106, 2014 (8 pages).
Sato, H. et al., "Supplemental L-Arginine During Cardioplegic Arrest and Reperfusion Avoids Regional Postischemic Injury", J Thorac Cardiovasc Surg 110(2):302-314 (1995), 13 pages.
Schmid, T. et al., "The Use of Myocytes as a Model for Developing Successful Heart Preservation Solutions", Transplantation 52(1):20-26 (Jul. 1991) (7 pages).
Schon, M.R. et al., "Liver Transplantation After Organ Preservation With Normothermic Extracorporeal Perfusion", Annals of Surgery 233(1):114-123 (2001), 10 pages.
Schwalb, H. et al., "New Solution for Prolonged Myocardial Preservation for Transplantation", The Journal of Heart and Lung Transplantation 17(2):222-229 (1998), 8 pages.
Seccombe, J.F. et al., "Coronary Artery Endothelial Function After Myocardial Ischemia and Reperfusion", Ann Thorac Surg 60(3):778-788 (1995), 11 pages.
Segel, L.D. et al., "Posttransplantation Function of Hearts Preserved with Fluorochemical Emulsion", J Heart Lung Transplant, 13(4):669-680 (1994), 12 pages.
Segel,L.D. et al., "Recovery of Sheep Hearts After Perfusin Preservation or Static Storage with Crystalloid Media", The Journal of Heart and Lung Transplantation, 17(2):11-221 (1998) (11 pages).
Sekine, M. et al., "Effect of Obese and Aging on Blood Fatty Acid Consumption in Japanese", Bulletin of the Graduate School of Human Life Science, Showa Women's University, 4:63-70, 1995 (8 pages)—English Abstract.
Semat, H., et al., "Physics, Chapter 9: Hydrodynamics (Fluids in Motion)", Hydrodynamics. University of Nebraska—Lincoln. Pap143. Jan. 1, 1958 (18 pages).
Shimokawa, S. et al., "A New Lung Preservation Method of Topical Cooling by Ambient Cold Air Combined with High-Frequency Oscillation: An Experimental Study", Transplantation Proceedings, 26(4):2364-2366 (1994) (3 pages).

(56) References Cited

OTHER PUBLICATIONS

Shimokawa, S. et al., "A New Lung Preservation Method of Topical Cooling by Ambient Cold Air: An Experimental Study", Transplantation Proceedings, 23 (1):653-654 (1991) (2 pages).
Shirakura, R. et al., "Multiorgan Procurement from Non-Heart-Beating Donors by use of Osaka University Cocktail, Osaka Rinse Solution, and the Portable Cardiopulmonary Bypass Machine", Transplantation Proceedings, 25(6):3093-3094 (1993) (2 pages).
Siobal, M.S. "Pulmonary Vasodilators", Respir Care, 52(7):885-899, Jul. 2007 (15 pages).
Southard, J., "The Right Solution for Organ Preservation", Business Briefings: Global Surgery 79-84 (2004) (6 pages).
Steen, S. et al., "Transplantation of lungs from non-heart-beating donors after functional assessment ex vivo", Ann Thorac Surg, 76:244-252, 2003, 11 pages.
Stubenitsky, B.M. et al., "Kidney preservation in the next millenium", Transpl Int, 12:83-91 (1999), 9 pages.
Sunamori, M. et al., "Relative Advantages of Nondepolarizing Solution to Depolarizing University of Wisconsin Solution in Donor Heart Preservation", Transplantation Proceedings, 25(1): 1613-1617 (1993), 5 pages.
Synchrony Definition, http://dictionary.reference.com/browse/synchrony, Random House Unabridged Dictionary, 2006 (1 page).
Tang, D.G. et al., "Warm Ischemia Lung Protection With Pinacidil: An ATP Regulated Potassium Channel Opener", Ann Thorac Surg, 76:385-90 (2003), 6 pages.
Tesi, R.J. et al., "Pulsatile Kidney Perfusion for Preservation and Evaluation: Use of High-Risk Kidney Donors to Expand the Donor Pool", Transplantation Proceedings, 25(6):3099-3100 (1993) (2 pages).
Turpin, B.P. et al., "Perfusion of Isolated Rat Adipose Cells", The Journal of Clinical Investigation, 60:442-448 (1977), 7 pages.
U.S. Food and Drug Administration, Center for Drug Evaluation and Research, "Drugs@FDA—Solu-Medrol: Label and Approval History", (Available online at http://www.accessdata.fda.gov/scripts/cder/drugsatfda/index.cfm?fuseaction=Search.Label_ApprovalHistory#apphist . . . ), accessed Feb. 9, 2010 (3 pages).
U.S. Food and Drug Administration, Center for Drug Evaluation and Research, "Drugs@FDA—Solu-Medrol: Drug Details", (Accessible online at http://www.accessdata.fda.gov/scripts/cder/drugsatfda/index.cfm?fuseaction=Search.DrugDetails . . . ), accessed Feb. 9, 2010 (1 page).
Venuta, F. et al., "History of lung transplantation", Journal of Thoracic Disease, 9(12):5458-5471, Dec. 2017 (14 pages).
Vinten-Johansen, J. et al., "Reduction in Surgical Ischemic-Reperfusion Injury With Adenosine and Nitric Oxide Therapy", Ann Thorac Surg 60(3):852-857 (1995), 6 pages.
Voiglio, E. et al. "Rat Multiple Organ Blocks: Microsurgical Technique of Removal for Ex Vivo Aerobic Organ Preservation Using a Fluorocarbon Emulsion", Microsurgery 20:3, 109-115 (2000) (7 pages).
Watanabe, S. et al., "Effects of free fatty acids on the binding of bovine and human serum albumin with steroid hormones", Biochimica et Biophysica Acta (BBA), 1289:385-396 (1996), 12 pages.
Wei, Y. et al., "Protective Effect of Specific Phosphodiesterase Inhibitor Milrione for Donor Lungs", Chinese Journal of New Drugs, 16(21):1762-1765, 2007—English Translation issued by U.S. Patent and Trademark Office, Aug. 2020 (17 pages).
Wei, Zhengqiang, et al., "A Study on the Preservation of Rat Kidney with HX-III Solution", J WCUMS, 31(3):347-349 (2000)—English Abstract, 5 pages.
Wicomb, W. et al., "Orthotopic transplantation of the baboon heart after 20 to 24 hours' preservation by continuous hypothermic perfusion with an oxygenated hyperosmolar solution", J Thorac Cardiovasc Surg, 83(1):133-140 (1982), 8 pages.
Wicomb, W.N. et al., "24-Hour Rabbit Heart Storage With UW Solution", Transplantation, 48(1):6-9 (1989), 4 pages.
Wicomb, W.N. et al., "Cardiac Transplantation Following Storage of the Donor Heart by a Portable Hypothermic Perfusion System", The Annals of Thoracic Surgery, 37(3):243-248 (1984), 6 pages.
Wright, N. et al. "A porcine ex vivo paracorporeal model of lung transplantation", Laboratory Animals Ltd. Laboratory Animals, 34:1, 56-62 (2000) (7 pages).
Yang, W. et al., "Effect of Hypoxia and Reoxygenation on the Formation and Release of Reactive Oxygen Species by Porcine Pulmonary Artery Endothelial Cells", Journal of Cellular Physiology, 164:414-423 (1995) (10 pages).
Yeung, J., et al., "Physiologic assessment of the ex vivo donor lung for transplantation", The Journal of Heart and Lung Transplantation, 31(10):1120-1126, Oct. 2012 (7 pages).
Yland, M.J. et al., "New Pulsatile Perfusion Method for Non-Heart-Beating Cadaveric Donor Organs: A Preliminary Report", Transplantation Proceedings, 25(6):3087-3090 (1993), 4 pages.
Zhang, Z. et al., "Research Progress on Preservation of Severed Limbs", Chinese Journal of Reparative and Reconstructive Surgery, 14(3):189-192 (2000)—English Abstract, 8 pages.
European Extended Search Report issued in EP20206681.7, dated Apr. 26, 2021 (8 pages).
Wittwer, et al., "Experimental Lung Transplantation: Impact of Preservation Solution and Route of Delivery", The Journal of Heart and Lung Transplantation, 24(8):1081-1090, Aug. 2005 (10 pages).
European Extended Search Report issued in European Patent Application No. 22158928.6. dated Jun. 29, 2022 (13 pages).
Asparagine, Encyclopedia.com, https://www.encyclopedia.com/science-and-technology/biochemistry/biochemistry/asparagine, accessed May 7, 2022 (3 pages).
Cysteine, Encyclopedia.com, https://www.encyclopedia.com/science-and-technology/biochemistry/biochemistry/cysteine, accessed May 7, 2022 (4 pages).
European Commission, Scientific Committee on Food, "Opinion on Substances for Nutritional Purposes Which Have Been Proposed for Use in the Manufacture of Foods for Particular Nutritional Purposes ('Parnuts')", SCF/CS/ADD/NUT/20/Final, http://www.europa.eu.int/comm/dg24/health/sc/scf/index_en.html, Dec. 5, 1999 (19 pages).
Glutamine, Encyclopedia.com, https://www.encyclopedia.com/science-and-technology/biochemistry/biochemistry/glutamine, accessed May 7, 2022 (7 pages).
Andreasson, et al., "Ex vivo lung perfusion in clinical lung transplantation—State of the art", European Journal of Cardio-Thoracic Surgery, 46:779-788, 2014 (10 pages).
Becker, et al., "Evaluating acellular versus cellular perfusate composition during prolonged ex vivo lung perfusion after initial cold ischaemia for 24 hours", Transplant International, 29:88-97, 2016, published online Aug. 27, 2015 (10 pages).
FDA Premarket Approval 510k (extracts), "Perfadex® Solution for Lung Perfusion", dated Mar. 8, 2001 (61 pages).
FDA Premarket Approval 510k, "Perfadex® with THAM", dated Oct. 9, 2008 (5 pages).
FDA Summary of Safety and Probable Benefit, "XVIVO Perfusion System (XPS™) with STEEN Solution™ Perfusate", HUD Designation No. 08-0194, Notice of Approval dated Aug. 12, 2014 (52 pages).
Fisher, et al., "An observational study of Donor Ex Vivo Lung Perfusion in UK lung transplantation: DEVELOP-UK", Health Technology Assessment, vol. 20, No. 85, Nov. 2016 (310 pages).
Ingemansson, et al., "Importance of Calcium in Long-Term Preservation of the Vasculature", Ann Thorac Surg, 61:1158-1162, 1996 (5 pages).
Loor, et al., "Prolonged EVLP Using OCS Lung: Cellular and Acellular Perfusates", Author Manuscript published in final edited form as Transplantation, 101(10):2303-2311, Oct. 2017 (20 pages).
Munshi, et al., "Donor management and lung preservation for lung transplantation", Lancet Respir Med, 1:318-328, published online Feb. 20, 2013 (11 pages).
Zalewska, et al., National Standards for Organ Retrieval from Deceased Donors (extracts), NHS Blood and Transplant, UK National Health Service, MPD1043/8, effective date Oct. 15, 2018 (50 pages).
Pego-Fernandes, et al., "Ex vivo lung perfusion: initial Brazilian experience", J. Bras. Pneumol., 35(11):1107-1112, 2009 (6 pages).
Perfadex Guidelines, NHS Cardiothoracic Advisory Group (CTAG), Mar. 2016 (2 pages).

(56) References Cited

OTHER PUBLICATIONS

Rega, et al., "Long-term Preservation With Interim Evaluation of Lungs From a Non-Heart-Beating Donor After a Warm Ischemic Interval of 90 Minutes", Annals of Surgery, 238(6):782-793, Dec. 2003 (12 pages).
Steen Solution, Consultation Procedure Public Assessment Report (CPAR), European Medicines Agency, EMEA/CHMP/329441/2005, Aug. 8, 2012 (20 pages).
Wallinder, et al., "Transplantation of initially rejected donor lungs after ex vivo lung perfusion", Cardiothoracic Transplantation, 144(5):1222-1228, Nov. 2012 (7 pages).
Xvivo Perfusion, RedEye Equity Research, May 29, 2020 (3 pages).
Albes, et al., "Influence of the Perfusate Temperature on Lung Preservation: Is There an Optimum?", European Surgical Research, 29:5-11, 1997 (7 pages).
Besterman, et al., "Regulation of protein synthesis in lung by amino acids and insulin", American Journal of Physiology: Endocrinology and Metabolism, 245(5):E508-E514, Nov. 1, 1983 (7 pages).
Erasmus, et al., "Normothermic ex vivo lung perfusion of non-heart-beating donor lungs in pigs: from pretransplant function analysis towards a 6-h machine preservation", Transplant International, 19(7):589-593, Jul. 1, 2006 (5 pages).
"The secret of the turtle", <https://mag.ebmpapst.com/en/industries/medical/the-secret—of-the- turtle_2433/>, mag: The Magazine of ebm-papst, Sep. 2009 (5 pages).
Baker, et al., "Calcium Content of St. Thomas' II Cardioplegic Solution Damages Ischemic Immature Myocardium", Annals of Thoracic Surgery, 52(4):993-999, Oct. 1991 (7 pages).
Charest, et al., "Design and validation of a clinical-scale bioreactor for long-term isolated lung culture", Author Manuscript published in Final Edited form as Biomaterials, 52:79-87, Jun. 2015 (22 pages).
De Hart, et al., "An ex vivo platform to simulate cardiac physiology: a new dimension for therapy development and assessment", The International Journal of Artificial Organs, 34(6): 495-505, Jun. 2011 (11 pages).
Dobson, et al., "Adenosine and lidocaine: A new concept in nondepolarizing surgical myocardial arrest, protection, and preservation", Journal Thoracic and Cardiovascular Surgery, 127(3):794-805, Mar. 2004 (12 pages).
Ebel, et al., "Lidocaine reduces ischaemic but not reperfusion injury in isolated rat heart", British Journal Anaesthesia, 86(6): 846-852, 2001 (7 pages).
Ely, et al., "Protective Effects of Adenosine In Myocardial Ischemia", Circulation, 85(3): 893-904, Mar. 1992 (12 pages).
European Extended Search Report issued in European Patent Application No. 15867786.4, dated Feb. 8, 2019 (14 pages).
European Extended Search Report issued in European Patent Application No. 17805438.3, dated Jan. 28, 2020 (14 pages).
European Extended Search Report issued in European Patent Application No. 15853016.2, dated Mar. 9, 2018 (12 pages).
European Extended Search Report issued in European Patent Application No. 13738530.8, dated Jan. 25, 2016 (9 pages).
European Extended Search Report issued in European Patent Application No. 15775970.5, dated Oct. 24, 2017 (10 pages).
European Extended Search Report issued in European Patent Application No. 15767752.7, dated Nov. 30, 2017 (7 pages).
European Extended Search Report issued in European Patent Application No. 18879106.5, dated Dec. 17, 2020 (8 pages).
European Search Report issued in European Patent Application No. 15867786.4, dated Sep. 3, 2018 (11 pages).
Gao, et al., "Role of Troponin I Proteolysis in the Pathogenesis of Stunned Myocardium", Circulation Research, 80(3): 393-399, Mar. 1, 1997 (17 pages).
Hearse, et al., "Protection of the myocardium during ischemic arrest", Journal Thoracic Cardiovascular Surgery, 81(6):873-879, Jun. 1981 (7 pages).
International Preliminary Report on Patentability issued in International Application No. PCT/CA2015/051316 dated Apr. 10, 2017 (5 pages).
International Preliminary Report on Patentability issued in International Application No. PCT/CA15/50297, dated Oct. 12, 2016 (6 pages).
International Preliminary Report on Patentability issued in International Application No. PCT/CA15/51084, dated Feb. 15, 2017 (3 pages).
International Preliminary Report on Patentability, issued in International Application No. PCT/CA2015/050201 dated Sep. 27, 2016 (5 pages).
International Preliminary Report on Patentability, issued in International Application No. PCT/CA2013/000031 dated Apr. 23, 2014 (8 pages).
International Search Report and Written Opinion issued by the Canadian Patent Office as International Searching Authority in International Application No. PCT/CA2015/051316, dated Mar. 16, 2016 (8 pages).
International Search Report and Written Opinion issued by Canadian Patent Office as International Searching Authority in International Application No. PCT/CA13/00031, dated Apr. 15, 2013 (9 pages).
International Search Report and Written Opinion issued by Canadian Patent Office as International Searching Authority in International Application No. PCT/CA18/51474, dated Mar. 4, 2019 (6 pages).
International Search Report and Written Opinion issued by the Canadian Patent Office as International Searching Authority in International Application No. PCT/CA15/50201, dated Jun. 10, 2015 (8 pages).
International Search Report and Written Opinion issued by the Canadian Patent Office as International Searching Authority in International Application No. PCT/CA15/50297, dated Jul. 13, 2015 (8 pages).
International Search Report and Written Opinion issued by the Canadian Patent Office as International Searching Authority in International Application No. PCT/CA15/51084, dated Feb. 5, 2016 (8 pages).
Jakobsen, et al., "Adenosine instead of supranormal potassium in cardioplegia: It is safe, efficient, and reduces the incidence of postoperative atrial fibrillation. A randomized clinical trial", Journal of Thoracic and Cardiovascular Surgery, 145(3):812-818, Mar. 2013 (7 pages).
Lim, et al., "Computational analysis of the effect of the type of LVAD flow on coronary perfusion and ventricular afterload", J. Physiol Sci., 59:307-316, 2009 (10 pages).
Mehaffey, et al., "Airway pressure release ventilation during ex vivo lung perfusion attenuates injury", Journal Thoracic Cardiovascular Surgery, 153(1): 197-204, Jan. 2017 (8 pages).
Muhlbacher, et al., "Preservation Solutions for Transplantation", Transplantation Proceedings, 31(5):2069-2070, Aug. 1999 (2 pages).
Nelson, et al., "Abstract 736: Determination of Optimum Ventilation Strategy for Ex-Vivo Lung Perfusion: Comparing Negative and Positive Pressure Ventilation", Journal of Heart and Lung Transplantation, 34(4 Supplement): S270, Apr. 2015 (1 page).
O'Blenes, et al., "Protecting the aged heart during cardiac surgery: The potential benefits of del Nido cardioplegia", Journal Thoracic and Cardiovascular Surgery, 141(3):762-770, Mar. 2011 (9 pages).
Popov, et al., "Ex Vivo Lung Perfusion—State of the Art in Lung Donor Pool Expansion", Medical Science Monitor Basic Research, 21:9-14, Feb. 3, 2015 (6 pages).
Raymondos, et al., "Combined Negative- and Positive-Pressure Ventilation for the Treatment of ARDS", Case Reports in Critical Care, Article ID714902, 2015 (5 pages).
Robinson, et al., "Lowering the calcium concentration in St. Thomas' Hospital cardioplegic solution improves protection during hypothermic ischemia", Journal Thoracic and Cardiovascular Surgery, 101(2):314-325, Feb. 1991 (12 pages).
Rudd, et al., "Eight hours of cold static storage with adenosine and lidocaine (Adenocaine) heart preservation solutions: Toward therapeutic suspended animation", Journal Thoracic Cardiovascular Surgery, 142(6): 1552-1561, Dec. 2011 (10 pages).

(56) References Cited

OTHER PUBLICATIONS

Rudd, et al., "Toward a new cold and warm nondepolarizing, normokalemic arrest paradigm for orthotopic heart transplantation", The Journal of Thoracic and Cardiovascular Surgery, 137(1): 198-207, Jan. 2009 (10 pages).

Sutherland, et al., "The Isolated Blood And Perfusion Fluid Perfused Heart", https://www.southalabama.edu/ishr/help/hearse/, Cardiovascular Research—The Centre for Cardiovascular Biology and Medicine, The Rayne Institute, King's College, St Thomas' Hospital, London, UK; originally retrieved on Oct. 16, 2017, accessed Aug. 28, 2023 (12 pages).

Takemoto, et al., "The reciprocal protective effects of magnesium and calcium in hyperkalemic cardioplegic solutions on ischemic myocardium", Basic Research in Cardiology, 87(6):559-569, 1992 (11 pages).

Tane, et al., "Ex Vivo Lung Perfusion: A Key Tool for Translational Science in the Lungs", Chest, 151(6): 1220-1228, Jun. 2017 (9 pages).

Taylor, et al., "Registry of the International Society for Heart and Lung Transplantation: Twenty-sixth Official Adult Heart Transplant Report—2009", Journal Heart and Lung Transplantation, 28(10): 1007-1022, Oct. 2009 (16 pages).

Tipton, et al., "The use of Langendorff preparation to study the bradycardia of training", Medicine and Science in Sports, 9(4):220-230, 1977 (11 pages).

Unitslab.com, Online Converter, Lidocaine, https://unitslab.com/node/178, retrieved Aug. 29, 2023 (3 pages).

White et al., "Abstract 735: Impact of Initial Acidic Reperfusion on the Functional Recovery of DCD Hearts During Ex Vivo Heart Perfusion", Journal of Heart and Lung Transplantation, 34(4Supplemental): S269-S270, Apr. 2015 (2 pages).

White, et al., "Abstract 385: Impact of Initial Acidic Reperfusion on the Functional Recovery of DCD Hearts During Ex Vivo Heart Perfusion", Canadian Journal Cardiology, 30:S251-252, 2014 (2 pages).

White, et al., "Impact of Reperfusion Calcium and pH on the Resuscitation of Hearts Donated After Circulatory Death", Annals of Thoracic Surgery, 103:122-130, Jan. 2017 (9 pages).

Wild et al., "PEEP and CPAP", British Journal of Anaesthesia, 1(3): 89-92, 2001 (4 pages).

Zhong, et al., "The management experience of long duration roller pump ventricular assist device," Chinese Journal of ECC, 9(3): 134-137, Sep. 15, 2011 (4 pages)—English Abstract Only.

Definition of Medium, Collins English Dictionary, https://www.collinsdictionary.com/us/dictionary/english/medium#:~:text=You%20use%20medium%20to%20describe,middling%20More%20Synonyms%20of%20medium, accessed Sep. 14, 2023 (2 pages).

Definition of Aqueous from Cambridge Dictionary, https://dictionary.cambridge.org/us/dictionary/english/aqueous, accessed Sep. 14, 2023 (2 pages).

Yokoyama, H. et al., "Isolated Dog Hearts Prepared in Cold Tyrode Solution and Reperfused with Arterial Blood Are Functionally and Ultrastructurally Normal", The Tohoku Journal of Experimental Medicine, 156:121-134, 1988 (14 pages).

\* cited by examiner

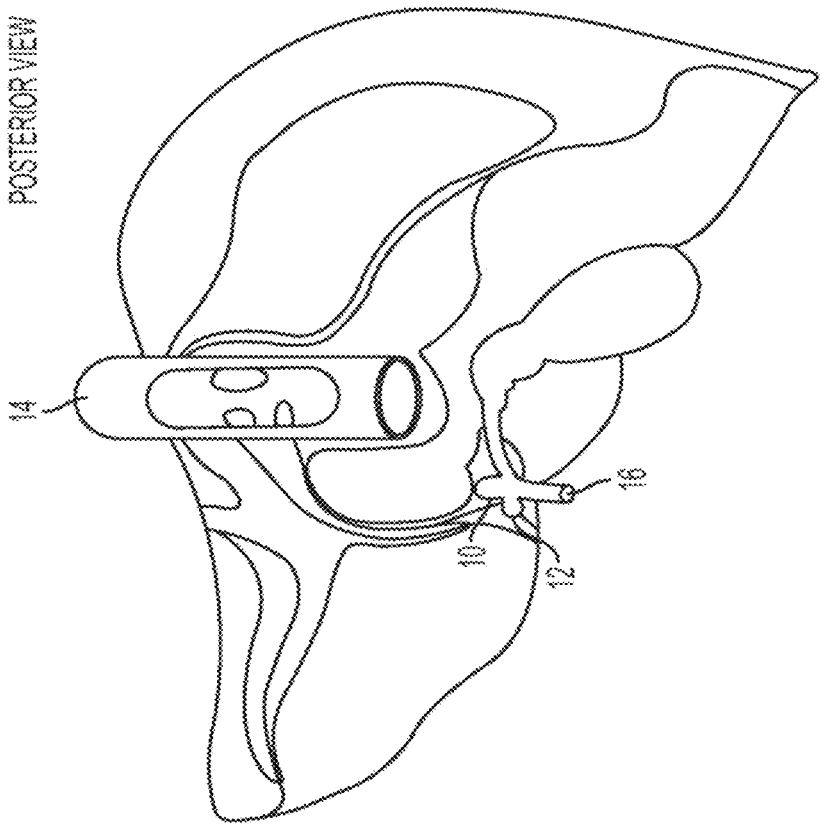
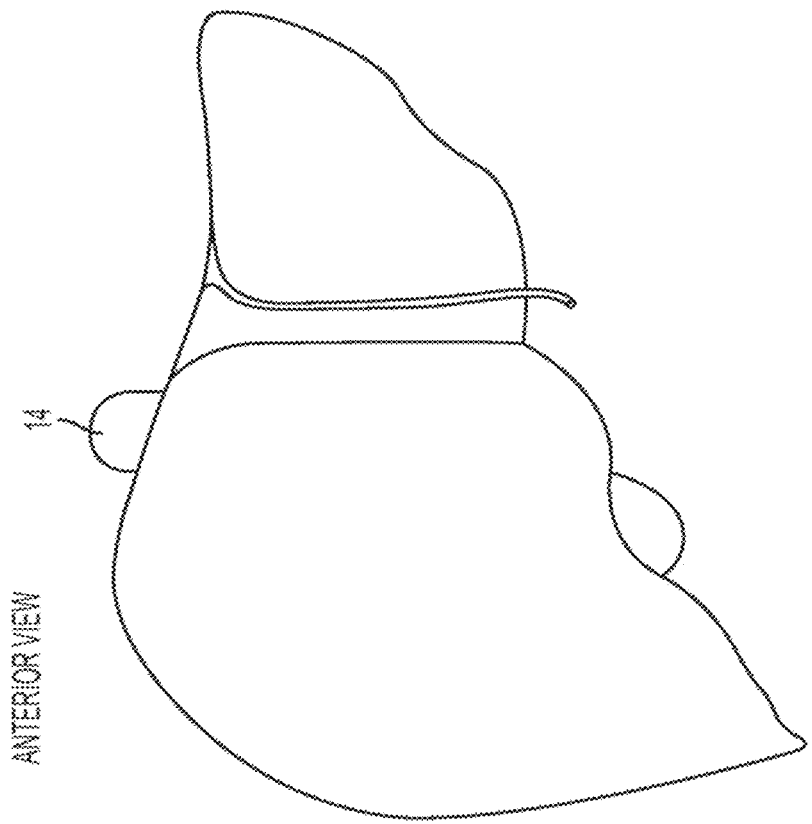
FIG. 1

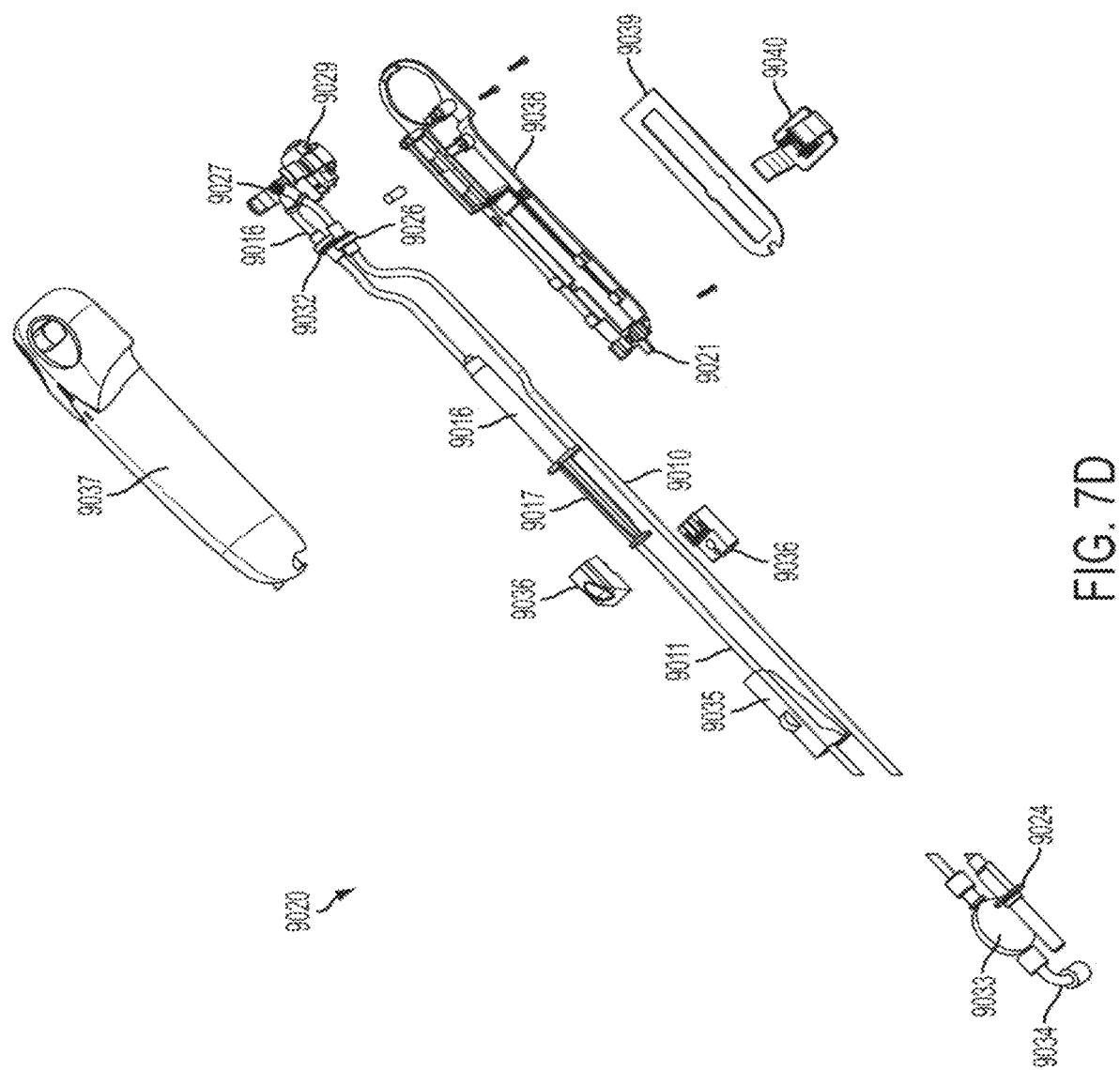

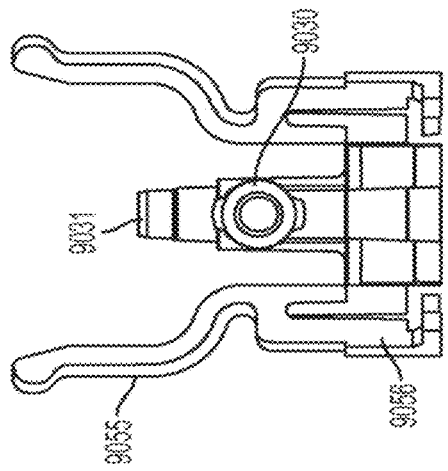
FIG. 7M
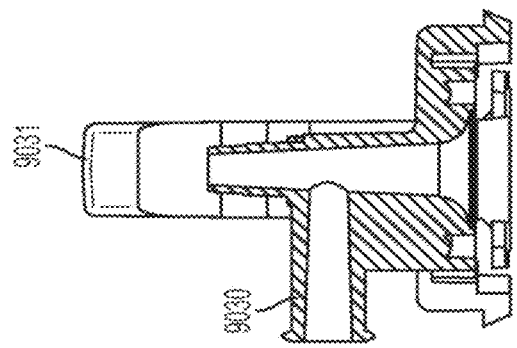
FIG. 7N
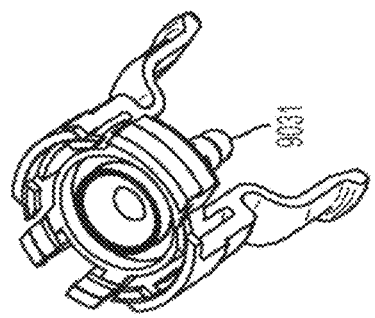
FIG. 7L
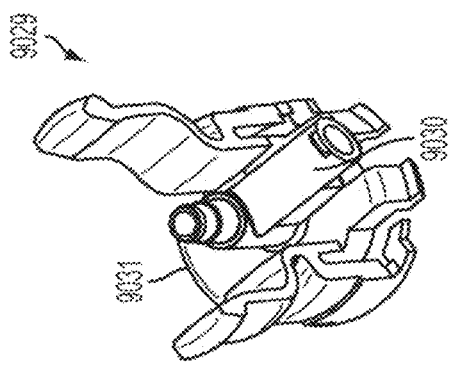
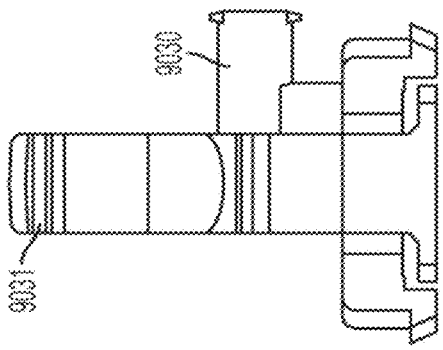
FIG. 7O
FIG. 7P

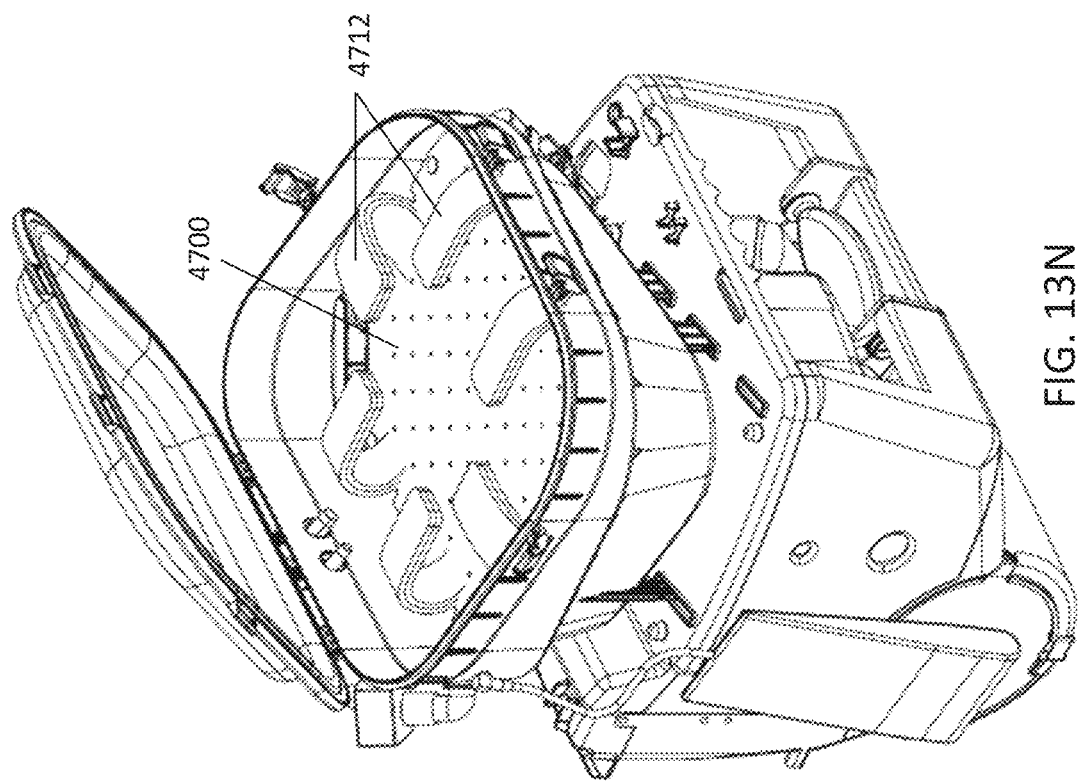

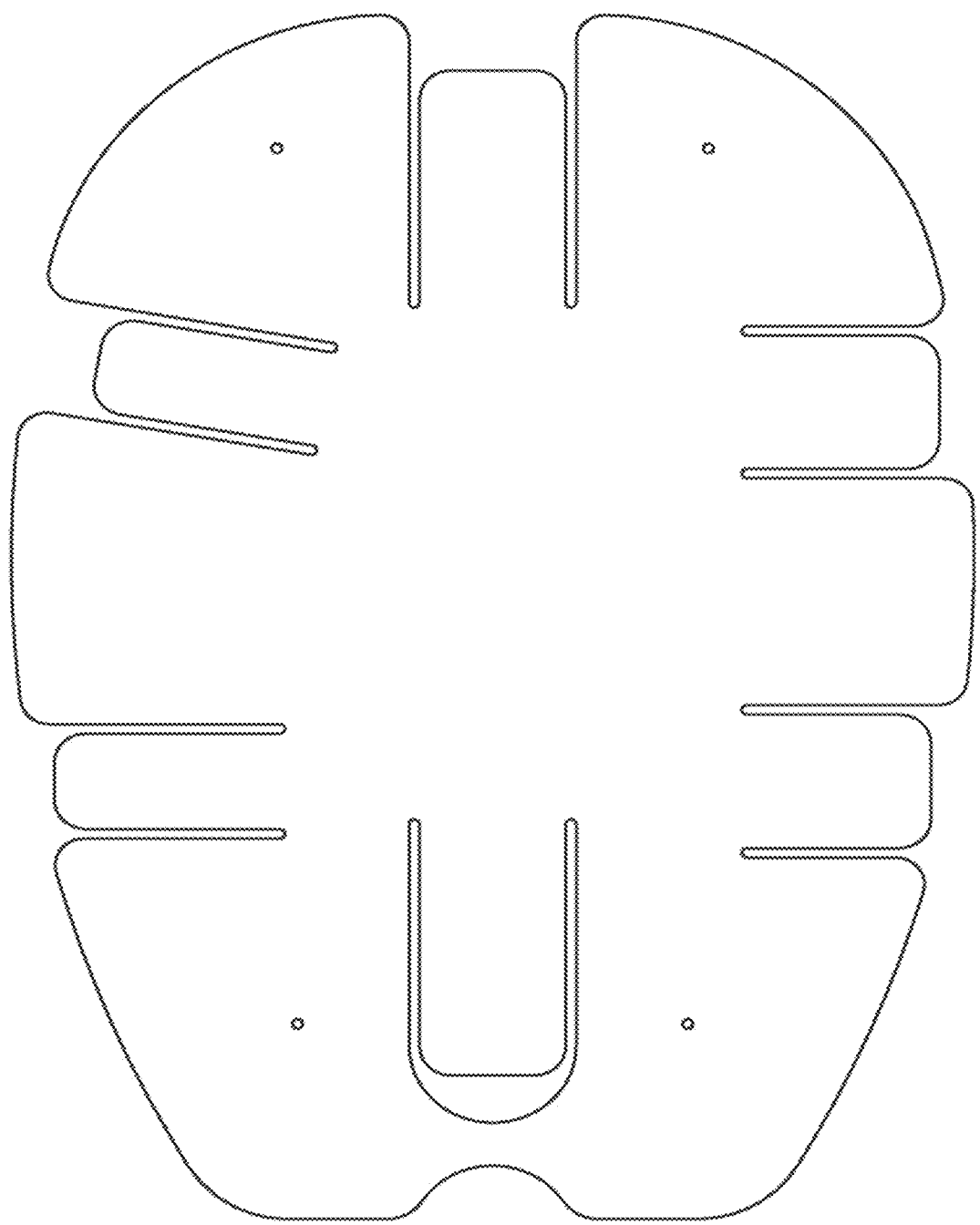

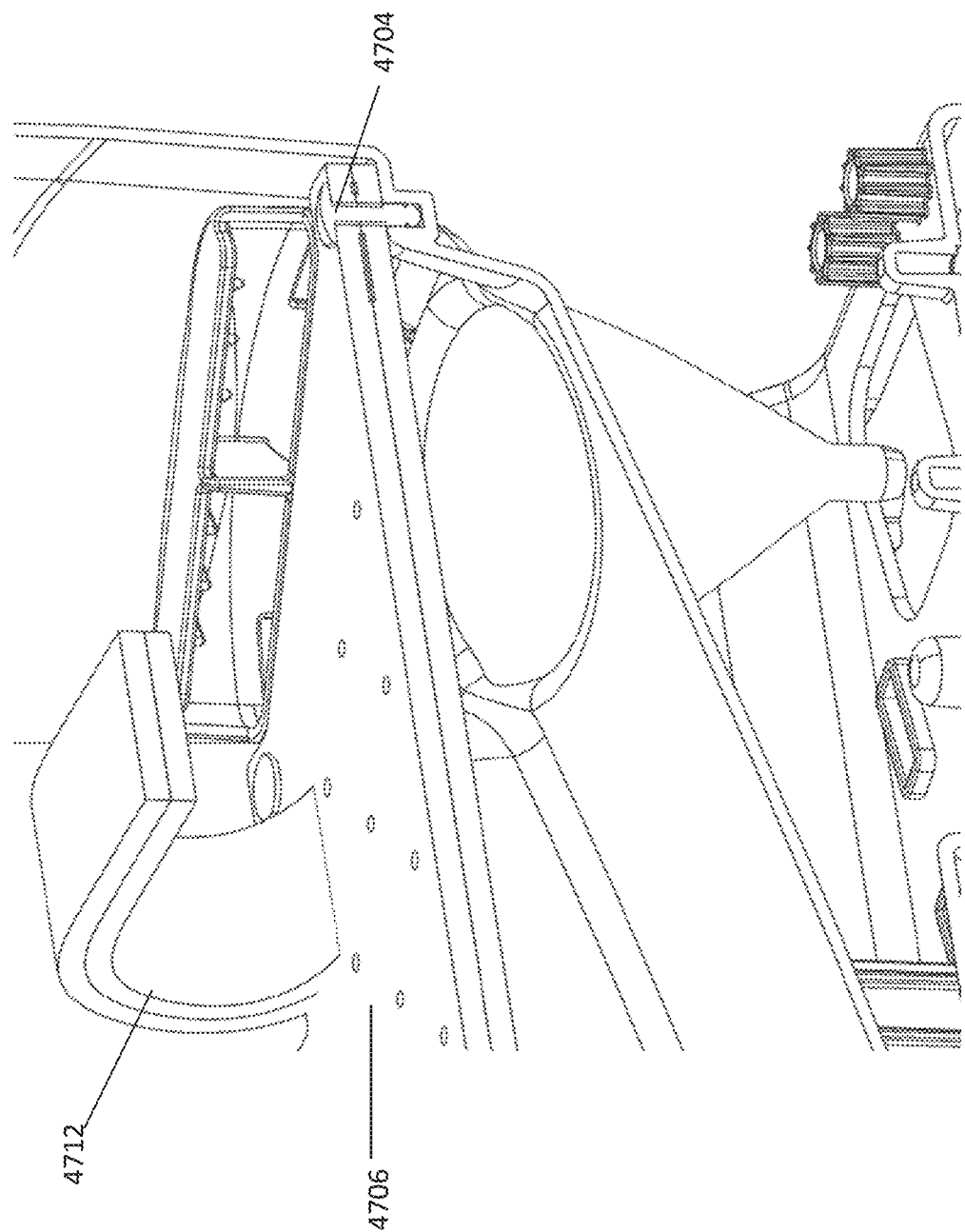

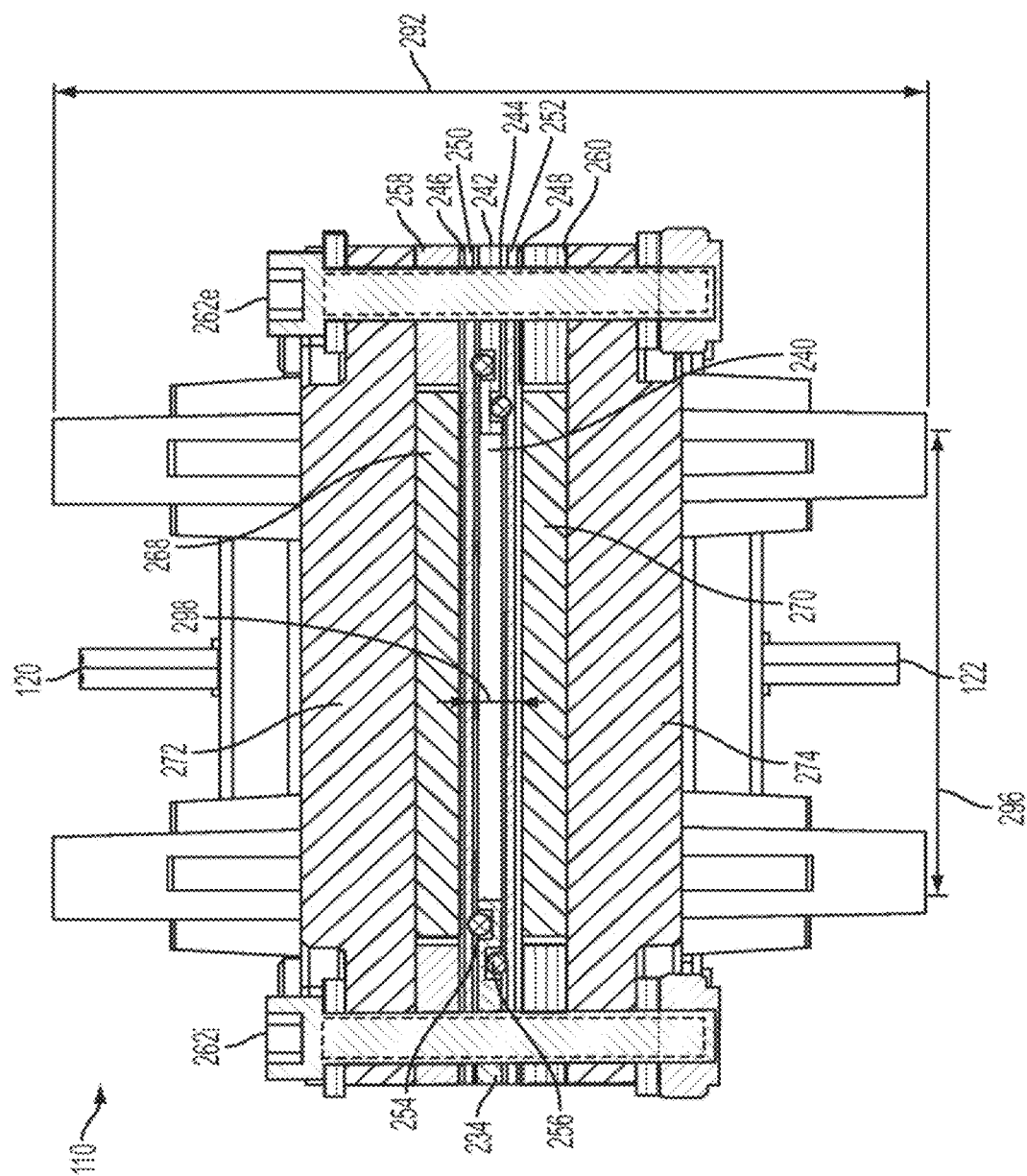

EX VIVO ORGAN CARE SYSTEM

CROSS-REFERENCE TO RELATED APPLICATIONS

This application is a continuation of U.S. patent application Ser. No. 16/130,255 filed Sep. 13, 2018; which is a continuation of U.S. patent application Ser. No. 14/728,771 filed Jun. 2, 2015, issued as U.S. Pat. No. 10,076,112; which claims the benefit under 35 U.S.C. § 119(e), of provisional application U.S. Ser. No. 62/006,871, filed Jun. 2, 2014, entitled, "EX VIVO ORGAN CARE SYSTEM", and U.S. Ser. No. 62/006,878, filed Jun. 2, 2014, entitled, "EX VIVO ORGAN CARE SYSTEM", the entire subjects of which are incorporated herein by reference.

FIELD OF THE INVENTION

The invention generally relates to systems, methods, and devices for ex vivo organ care. More particularly, in various embodiments, the invention relates to caring for an organ ex vivo at physiologic or near-physiologic conditions.

BACKGROUND

Current organ preservation techniques typically involve hypothermic storage of the organ packed in ice along with a chemical perfusate solution. In the case of a liver transplant, tissue damage resulting from ischemia can occur when hypothermic techniques are used to preserve the liver ex vivo. The severity of these injuries can increase as a function of the length of time the organ is maintained ex-vivo. For example, continuing the liver example, typically it may be maintained ex-vivo for about seven hours before it becomes unusable for transplantation. This relatively brief time period limits the number of recipients who can be reached from a given donor site, thereby restricting the recipient pool for a harvested liver. Even within this time limit, the liver may nevertheless be significantly damaged. A significant issue is that there may not be any visible indication of the damage. Because of this, less-than-optimal organs may be transplanted, resulting in post-transplant organ dysfunction or other injuries. Thus, it is desirable to develop techniques that can extend the time during which an organ such a liver can be preserved in a healthy state ex-vivo and enable assessment capabilities. Such techniques would reduce the risk of transplantation failure and enlarge potential donor and recipient pools.

SUMMARY

The below summary is exemplary only, and not limiting. Other embodiments of the disclosed subject matter are possible.

Embodiments of the disclosed subject matter can provide techniques relating to portable ex vivo organ care, such as ex vivo liver organ care. In some embodiments, the liver care system can maintain the liver at, or near, normal physiological conditions. To this end, the system can circulate an oxygenated, nutrient enriched perfusion fluid to the liver at or near physiological temperature, pressure, and flow rate. In some embodiments, the system employs a blood product-based perfusion fluid to more accurately mimic normal physiologic conditions. In other embodiments, the system uses a synthetic blood substitute solution, while in still other embodiments, the solution can contain a blood product in combination with a blood substitute product.

Some embodiments of the disclosed subject matter relate to a method for using lactate and liver enzyme measurements to evaluate the: i) overall perfusion status of an isolated liver, ii) metabolic status of an isolated liver, and/or iii) the overall vascular patency of an isolated donor liver. This aspect of the disclosed subject matter is based on the ability of liver cells to produce/generate lactate when they are starved for oxygen and metabolize/utilize lactate for energy production when they are well perfused with oxygen.

Some embodiments of the organ care system can include a module that has a chassis, and an organ chamber assembly that is mounted to the chassis and is adapted to contain a liver during perfusion. The organ care system can include a fluid conduit with a first interface for connecting to an hepatic artery of the liver, a second interface for connecting to the portal vein, a third interface for connecting to the inferior vena cava and a fourth interface to connect to the bile duct. The organ care system can include a lactate sensor for sensing lactate in the fluid being provided to and/or flowing from the liver. The organ care system can also include sensors for measuring the pressures and flows of the hepatic artery, portal vein, and/or inferior vena cava.

Some embodiments can relate to a method of determining liver perfusion status. For example, a method for evaluating liver perfusion status can include the steps of placing a liver in a protective chamber of an organ care system, pumping a perfusion fluid into the liver, providing a flow of the perfusion fluid away from the liver, measuring the lactate value of the fluid leading away from the liver, measuring the amount of bile produced by the liver, and evaluating the status of the liver using the measured lactate values, oxygen saturation level, and/or the quantity and quality of bile produced.

Some embodiments can relate to a method for providing a physiologic rate of flow and a physiologic pressure for both the hepatic artery and for the portal vein. In some embodiments the flow is sourced by a single pump. In particular, the system can include a mechanism for the user to manually divide a single source of perfusate to the hepatic artery and portal vein, and to adjust the division for physiologic flow rates and pressures. In other embodiments the system automatically divides the single source of perfusate flow to the hepatic artery and portal vein to result in physiologic pressures and rates of flow using, for example, an automatic control algorithm.

Some embodiments of the organ care system can include a nutritional subsystem that infuses the perfusion fluid with a supply of maintenance solutions as the perfusion fluid flows through the system, and in some embodiments, while it is in the reservoir. According to one feature, the maintenance solutions include nutrients. According to another feature, the maintenance solutions include a supply of therapeutics and/or additives to support extended preservation (e.g., vasodilators, heparin, bile salts, etc.) for reducing ischemia and/or other reperfusion related injuries to the liver.

In some embodiments, the perfusion fluid includes blood removed from the donor through a process of exsanguination during harvesting of the liver. Initially, the blood from the donor is loaded into the reservoir and the cannulation locations in the organ chamber assembly are bypassed with a bypass conduit to enable normal mode flow of perfusion fluid through the system without a liver being present, aka "priming tube". Prior to cannulating the harvested liver, the system can be primed by circulating the exsanguinated donor blood through the system to warm, oxygenate and/or filter it. Nutrients, preservatives, and/or other therapeutics may also be provided during priming via the infusion pump of the nutritional subsystem. During priming, various parameters may also be initialized and calibrated via the operator interface. Once primed and running appropriately, the pump flow can be reduced or cycled off, the bypass conduit can be removed from the organ chamber assembly, and the liver can be cannulated into the organ chamber assembly. The pump flow can be restored or increased, as the case may be.

In some embodiments, the system can include a plurality of compliance chambers. The compliance chambers are effectively small inline fluid accumulators with flexible, resilient walls for simulating the human body's vascular compliance. As such, they can aid the system in more accurately mimicking blood flow in the human body, for example, by filtering/reducing fluid pressure spikes due, for example, to flow rate changes. In one configuration, compliance chambers are located in the perfusate path to the portal vein and on the output of the perfusion fluid pump. According to one embodiment, a compliance chamber is located next to a clamp used for regulating pressure to effect physiologic hepatic artery and portal vein flows.

In some embodiments, the organ chamber assembly includes a pad or a sac assembly sized and shaped for interfitting within a bottom of the housing. Preferably, the pad assembly includes a pad formed from a material resilient enough to cushion the organ from mechanical vibrations and shocks during transport. In the case of the organ chamber assembly being configured to receive a liver, according to one feature, the pad of the invention includes a mechanism to conform the pad to differently sized and shaped livers so as to constrain them from the effects of shock and vibration encountered during transport.

Some embodiments of the organ care system are divided into a multiple use module and a single use module. The single use module can be sized and shaped for interlocking with the portable chassis of the multiple use module for electrical, mechanical, gas and fluid interoperation with the multiple use module. According to one embodiment, the multiple and single use modules can communicate with each other via an optical interface, which comes into optical alignment automatically upon the single use disposable module being installed into the portable multiple use module. According to another feature, the portable multiple use module can provide power to the single use disposable module via spring loaded connections, which also automatically connect upon the single use disposable module being installed into the portable multiple use module. According to one feature, the optical interface and spring loaded connections can ensure that connection between the single and multiple modules is not lost due to jostling, for example, during transport over rough terrain.

In some embodiments, the disposable single-use module includes a plurality of ports for sampling fluids from the perfusate paths. The ports can be interlocked such that sampling fluid from a first of the plurality of ports prohibits simultaneously sampling fluids from a second port of the plurality. This safety feature reduces the likelihood of mixing fluid samples and inadvertently opening the ports. In one embodiment, the single use module includes ports for sampling from one or more of the hepatic artery, portal vein, and/or IVC interfaces.

Some embodiments of the disclosed subject matter are directed at a method of providing therapy to a liver. Exemplary methods can include placing a liver in a protective chamber of a portable organ care system, pumping a perfusion fluid into the liver via a hepatic artery and portal vein, providing a flow of the perfusion fluid away from the liver via the vena cava, operating a flow control to alter a flow of the perfusion fluid such that the perfusion fluid is pumped into the liver via a hepatic artery and portal vein and flows away from the liver via a vena cava, and administering a therapeutic treatment to the liver. The treatments can include, for example, administering one or more of immunosuppressive treatment, chemotherapy, gene therapy and irradiation therapy to the liver. Other treatments may include surgical applications including split transplant and cancer resection.

In some embodiments, the disclosed subject matter can include a perfusion circuit for perfusing a liver ex-vivo, the perfusion circuit including a single pump for providing pulsatile fluid flow of a perfusion fluid through the circuit; a gas exchanger; a divider configured to divide the perfusion fluid flow into a first branch and a second branch; wherein the first branch is configured to provide a first portion of the perfusion fluid to a hepatic artery of the liver at a high pressure and low flow rate, wherein the first branch is in fluid pressure communication with the pump; wherein the second branch is configured to provide the remainder of the perfusion fluid to a portal vein of the liver at a relatively low pressure and high flow rate, wherein the second branch is in fluid pressure communication with the pump; the second branch further comprising a clamp located between the divider and the liver for selectively controlling the flow of perfusion fluid to the portal vein; the second branch further comprising a compliance chamber between the divider and the liver configured to reduce the pulsatile flow characteristics of the perfusion fluid from the pump to the portal vein; wherein the pump is configured to communicate fluid pressure through the first and second branches to the liver; a drain configured to receive perfusion fluid from an uncannulated inferior vena cava of the liver; and a reservoir positioned entirely below the liver and located between drain and the pump, configured to receive the perfusion fluid from the drain and store a volume of fluid. Other embodiments are possible.

In some embodiments, the disclosed subject matter can include a solution pump including a stepper motor in communication with a threaded rod; a carriage that is connected to the rod and configured to move along a linear axis as the rod rotates, the carriage being configured to compress a plunger of a syringe when moved in a first direction and being configured to retract the plunger of the syringe when moved in a second direction; a clamp configured to connect to the plunger; a connection assembly including a port configured to couple to a tip of the syringe; a first one way valve configured to allow fluid to flow into the syringe through the port as the syringe is retracted; a second one way valve configured to allow fluid to flow away from the syringe through the port as the syringe is compressed; a pressure sensor coupled to the connection assembly for determining a pressure of the fluid within the connection assembly; a controller configured to control operation of the stepper motor; and a sensor configured to determine when the syringe is fully retracted. Other embodiments are possible.

In some embodiments, the disclosed subject matter can include a method including rotating a rod to cause a carriage connected to the rod to move along a linear axis of the rod, compressing a plunger of a syringe as the carriage moves in a first direction along the linear axis, delivering fluid from the syringe into a port of a connection assembly and through a first one-way valve as the plunger is compressed, retracting a plunger of a syringe as the carriage moves in a second direction along the linear axis, delivering fluid to the syringe through a second one-way valve, and through the port of the connection assembly as the plunger is retracted, sensing a pressure of fluid in the connection assembly, and sensing a location of the plunger when the syringe is retracted. Other embodiments are possible.

In some embodiments, the disclosed subject matter can include an ex-vivo perfusion liquid for machine perfusion of donor livers comprising an energy-rich component, a bile salt, an electrolyte, and a buffering component. The liquid can include a blood product. The energy-rich component can be one or more compounds selected from the group consisting of a carbohydrate, pyruvate, flavin adenine dinucleotide (FAD), β-nicotinamide adenine dinucleotide (NAD), β-nicotinamide adenine dinucleotide phosphate (NADPH), a phosphate derivative of nucleoside, a coenzyme, and metabolite and precursor thereof. The liquid further includes one or more components selected from the group consisting of an anti-clotting agent, a lipid, cholesterol, a fatty acid, oxygen, an amino acid, a hormone, a vitamin, and a steroid. The perfusion solution is essentially free of carbon dioxide. Other embodiments are possible.

These and other embodiments of the disclosed subject matter will be more fully understood after a review of the following figures, and detailed description.

BRIEF DESCRIPTION OF THE FIGURES

The following drawings are intended show non-limiting examples of the disclosed subject matter. Other embodiments are possible.

FIG. 1 is an exemplary diagram of a liver.

FIGS. 16A-16J show an exemplary pad and components thereof and a flexible material support surface that can be used in embodiments of the organ care system.

FIG. 18A-18G show an exemplary heater assembly and components thereof that can be used within an embodiment of the organ care system.

FIG. 72 demonstrates that both arms maintained bile production rate of >10 ml/hr.

DETAILED DESCRIPTION

Figure 2:
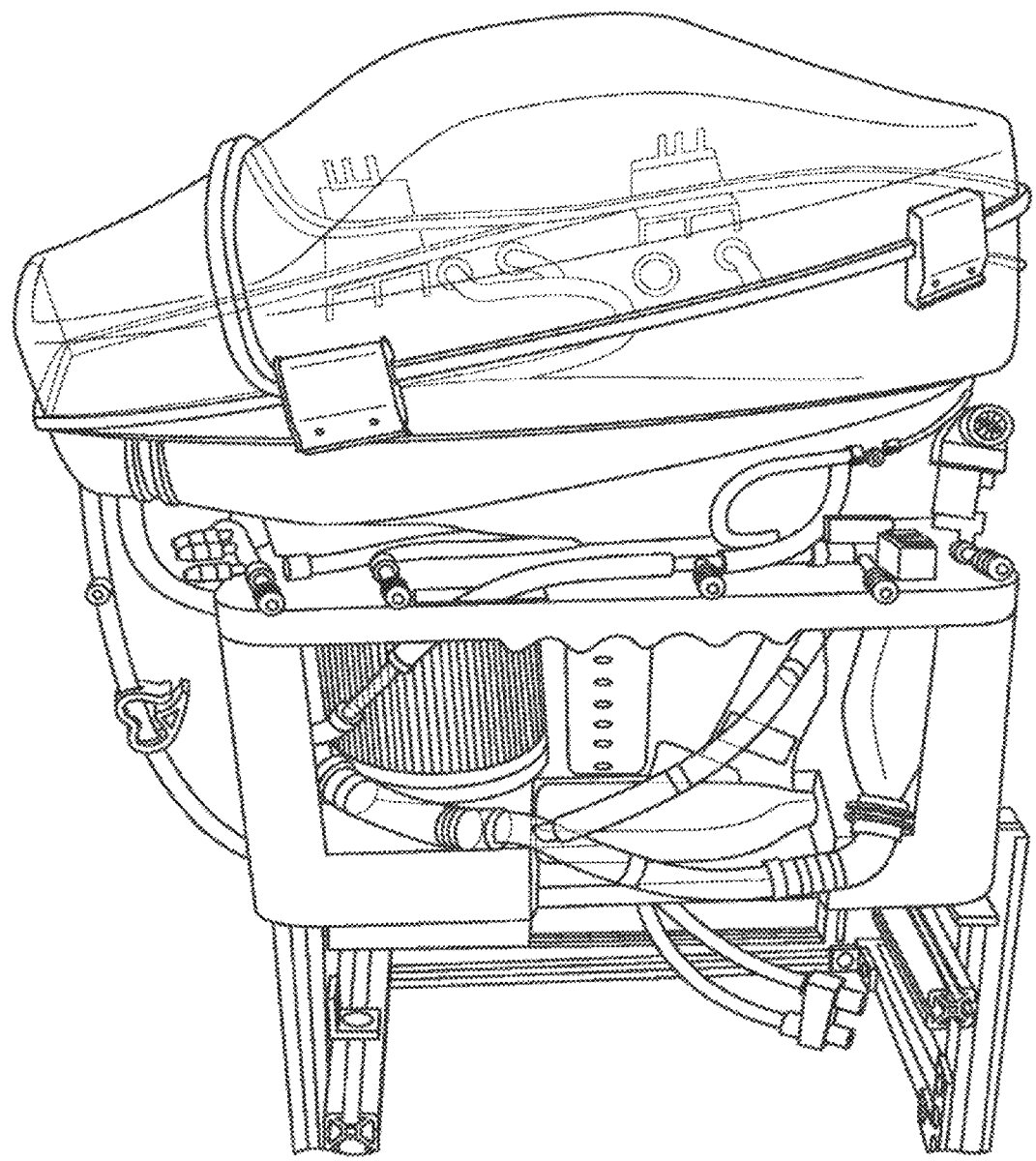
FIG. 2 is a line drawing of an exemplary single use module.

While the following description uses section headings, these are included only as a convenience to the reader. The section headings are not intended to be limiting or impose any restriction on the subject matter herein. For example, components described in one section of the description can be included in other sections additionally or alternatively. The embodiments disclosed herein are exemplary only and it is within the scope of the present disclosure that the disclosed embodiments and various features may be interchanged with one another.

I. INTRODUCTION

A. General Summary

Embodiments of the disclosed subject matter can provide techniques for maintaining a liver ex vivo, such as during a transplant procedure. The system can maintain a liver in conditions mimicking the human body. For example, the system can supply a blood substitute to an ex vivo liver in a manner that simulates the blood flow provided by the body. More specifically, the system can provide a flow of blood substitute to a hepatic artery and portal vein of a liver having flow and pressure characteristics similar to the human body. In some embodiments, the desired flows can be achieved using a pumping system that employs a single pump. The system can also warm the blood substitute to a normothermic temperature that simulates the human body and can provide nutrients to the blood substitute to maintain the liver and to promote the normal generation of bile by the liver. By performing these techniques, the length of time that a liver can be maintained outside the body can be extended, thereby making the geographical distance between donors and recipients less important than it previously was. Also, some of the embodiments disclosed herein that are used to maintain the liver ex vivo can also be used to assess the condition of the liver pre-transplant. In some embodiments, the techniques described herein can also be used to treat an injured and/or diseased liver ex vivo using treatments that would otherwise be harmful to the body if performed in vivo. Other embodiments are within the scope of the disclosed subject matter.

While the disclosure herein focuses on embodiments that are intended to maintain or treat a liver, the disclosure is not limited as such. For example, techniques described herein can also be used, or can be adapted for use with other organs such as lungs, a heart, intestines, a pancreas, a kidney, a spleen, a bladder, a gallbladder, a stomach, skin, and a brain.

II. LIVER COMPARED WITH OTHER ORGANS

While the liver is one of many organs in the human body, the liver can present challenges during ex vivo maintenance and transport that do not exist with other organs such as the heart and lungs. Some exemplary differences and considerations are described next.

A. Liver Uses Two Perfusate Inflow Supplies

Importantly, the liver uses two unique input paths for perfusate as compared with only one for other organs. Hepatic circulation is unique as featured by its dual vascular blood supply, each having different flow characteristics. Referring to FIG. 1, which is an exemplary conceptual drawing of a liver 100, the liver uses two blood supplies, the portal vein 10 and the hepatic artery 12. In particular, the hepatic artery delivers blood to the liver having high pressure, pulsatile flow, but of relatively low flow rate. Hepatic blood flow typically accounts for about one-third of the total liver blood flow. The portal vein delivers blood to the liver having a low pressure and minimal pulsatility at a higher flow rate. Portal vein flow typically accounts for about two-thirds of the total blood flow to the liver.

The dual blood supply expected by the liver can present challenges when one tries to artificially supply physiologic blood flow thereto when the organ is in an ex vivo system. While the challenges can be difficult when using a dual-pump design, they can be intensified when using a single-pump design. Some embodiments of the subject matter disclosed herein can address these challenges.

B. Assisted Drainage of Blood

In vivo, the liver is positioned beneath the diaphragm. Due to this positioning, liver blood flow and venous drainage via the inferior vena cava 14 is typically enhanced by diaphragmatic contraction as a result of pressure exerted on the liver. When the diaphragm moves in tandem with the lungs as air is drawn in and expelled by the lungs, the movement of the diaphragm can act on the liver by applying pressure to the organ, thereby pushing blood out of the tissue. It is desirable to mimic this phenomenon in an ex-vivo liver to help encourage blood flow out of the liver and prevent blood buildup in the organ.

C. Oncotic Pressure

To minimize edema formation in an ex vivo liver, the perfusate should have high oncotic pressure, for example, dextran, 25% albumin, and/or fresh frozen plasma. In some embodiments, oncotic pressure of the circulating perfusate is maintained between 5-35 mmHg, and more specifically between 15-25 mmHg. Non-limiting examples of possible oncotic pressures are 15, 16, 17, 18, 19, 20, 21, 22, 23, 24, and 25 mmHg, or any ranges bounded by the values noted here.

D. Metabolism and $CO_2$ Levels

The liver is a metabolic hub in the body and is in a constant state of metabolism. Most compounds absorbed by the intestine first pass through the liver, which is thus able to regulate the level of many metabolites in the blood. For example, the conversion of sugars into fat and other energy stores (e.g., gluconeogenesis and glycolysis) results in production of $CO_2$. The liver consumes about 20% of the total body oxygen. As a result, the liver produces higher levels of $CO_2$ than most other organs. In vivo, the organ is able to self-regulate to remove excess carbon dioxide from the organ. However, for an ex-vivo organ, it can be desirable to remove excess carbon dioxide from the organ to maintain physiologic levels of oxygen and carbon dioxide and thus pH. The system described in this application can facilitate establishment of blood chemistry equilibrium suitable for organ preservation ex vivo.

E. Bile Production

The liver is an excrement producing organ. The excrement, bile, is usually produced and excreted by the organ in vivo. Bile is produced in the liver by hepatocytes. In vivo, the liver utilizes bile salts to create bile, and bile salts are recycled through the enterohepatic circulation system back to the liver to be reused. The bile salts in turn stimulate the hepatocytes to produce more bile. Ex vivo, bile salts are not recycled back to the liver. As a result, it can be desirable to supplement perfusate with bile salts to aid the organ in producing bile. Additionally, in some instances, the bile produced by the liver can provide an indication (e.g., quantity, color and consistency) of the suitability of the organ for transplant.

F. Supporting a Liver

The liver is the largest solid organ in the body, but it is delicate and fragile. In the body, it is protected by the rib cage and other organs. Unlike many other organs, the liver does not include protective elements and is not defined by a rigid structure. Therefore, when the liver is removed from the body and maintained ex-vivo, it should be treated more delicately than other organs. For example, it can be desirable to provide proper support for the liver, place the liver on a low friction surface, and/or cover the organ with a wrap to protect the organ from damage during transport and while being maintained ex vivo.

G. Perfusate

Given the liver's wide range of vital functions when compared with other organs (e.g., detoxification, protein synthesis, glycogen storage, and production of biochemicals necessary for digestion), the perfusion fluid used in the organ care system described herein can be specially designed to maintain the liver in close to its physiological state to maintain its regular functions. For instance, because the liver is in a constant state of metabolism consuming energy, the oxygen content in the perfusion fluid can be maintained at close to or more than the physiological level to meet its high demand as a metabolic warehouse. Similarly, the perfusion fluid can also be designed to include sufficient concentration of energy-rich components, such as carbohydrates and electrolytes, to provide the liver with an energy source to carry out its functions.

The flow rate of the perfusion fluid can be also properly adjusted to ensure that oxygen and nutrients are delivered to an ex vivo liver at a suitable rate. Furthermore, the carbon dioxide content in the perfusion liquid can be lower than the level in physiological state, thus further driving the equilibrium of the liver's biological reactions to metabolism and oxidation. In some embodiments, the perfusion fluid used herein does not contain significant amount of carbon dioxide or is free from all carbon dioxide. In some embodiments, the perfusion fluid used herein also contains sufficient amount of bile salt to sustain the need of the liver to produce bile. Thus, the perfusion fluid for the organ care system described herein can be designed to maintain the liver's regular cellular functions to maintain the liver in a viable state.

III. DESCRIPTION OF EXEMPLARY SYSTEM COMPONENTS

A. General Architecture

FIG. 3 shows an exemplary organ care system 600 that can be used to preserve an organ such as a liver when the organ is ex vivo during, for example, a transplant operation or medical procedure. At a general level, the organ care system 600 is configured to provide conditions to an ex vivo organ that mimic the conditions the organ experiences when in vivo. For example, in the case of a liver, the organ care system 600 can provide a perfusate flow to the organ in a manner that mimics blood flow in a human body (e.g., flow, pressure, and temperature) and provide similar environmental characteristics (e.g., temperature).

In some embodiments, the organ care system 600 can be divided into two parts: a disposable single-use portion (e.g., 634) and a non-disposable multiple-use portion (e.g., 650) (also referred to herein as a single-use module and a multiple-use module). As the names imply, the single-use portion can be replaced after a liver is transported and the multiple-use portion can be reused. At a general level, though not required, the single-use portion includes those portions of the system that come into direct contact with biological material whereas the multiple-use portion includes those components that do not come into contact with biological material. In some embodiments, all of the components in the single-use portion are sterilized before use, whereas the components in the multiple-use portion are not. Each of the portions are described in detail below. This configuration allows a method of operation where, after use, the entire single-use module 634 can be discarded and replaced with a new single-use module. This can allow the system 600 to be available for use again after a short turnaround time.

Typically the single and multiple use portions can be configured to be removably connected to one another via a mechanical interface. Additionally, the single and multiple use portions can include mechanical, gas, optical, and/or electrical connections to allow the two portions to interact with one another. In some embodiments, the connections between the portions are designed to be connected/unconnected from one another in a modular fashion.

The disposable module 634 and the multiple use module 650 can be constructed at least in part of material that is durable yet light-weight such as polycarbonate plastic, carbon fiber epoxy composites, polycarbonate ABS-plastic blend, glass reinforced nylon, acetal, straight ABS, aluminum, and/or magnesium. In some embodiments, the weight of the entire system 600, is less than 100 pounds, including the multiple use module, organ, batteries, gas tank, and priming, nutritional, preservative and perfusion fluids, and less than about 50 pounds, excluding such items. In some embodiments, the weight of the single use module 634 is less than 12 pounds, excluding any solutions. In some embodiments, the multiple use module, excluding all fluids, batteries, and gas supply, weighs less than 50 pounds.

With the cover removed and the front panel open, an operator can have easy access to many of the components of the disposable 634 and multiple use 650 modules. For example, the operator can access the various components of the single and multiple use modules and can install and/or remove the single use module from to/from the multiple use module.

While certain components are described herein as being in the single-use portion or the multiple-use portion of the system 600, this is exemplary only. That is, components identified herein as being located in the single-use portion can also be located in the multiple-use portion and vice-versa.

B. Exemplary Multiple Use Module

Referring to FIGS. 3A-3I, the multiple use module can include several components including a housing, a cart, a battery, a gas supply, at least part of a perfusion fluid pump, an infusion pump, and a control system.

1. Cart/Housing

Referring to FIGS. 3A-3I, an exemplary embodiment of the organ care system is shown as organ care system 600 can include a housing 602 and a cart 604. The cart 604 can include a platform and wheels for transporting the system 600 from place to place. A latch 603 can secure the housing 602 to the cart 604. To further aid in portability, the system 600 can also include a handle hinge mounted to the left side of the housing 602, along with two rigidly mounted handles 612a and 612b mounted on the left and right sides of the housing 602. The housing 602 can further include a removable top lid (not shown) and a front panel 615 hinged to a lower panel by hinges 616a and 616b. The cover can include handles for aiding with removal.

The system 600 can include an AC power cable 618, along with a frame for securing the power cable, both which can be located on the lower section of the left side of the housing 602. A power switch 622, which can also located on the lower section of the left side, can enable an operator to restart the system software and electronics.

Figure 3A:
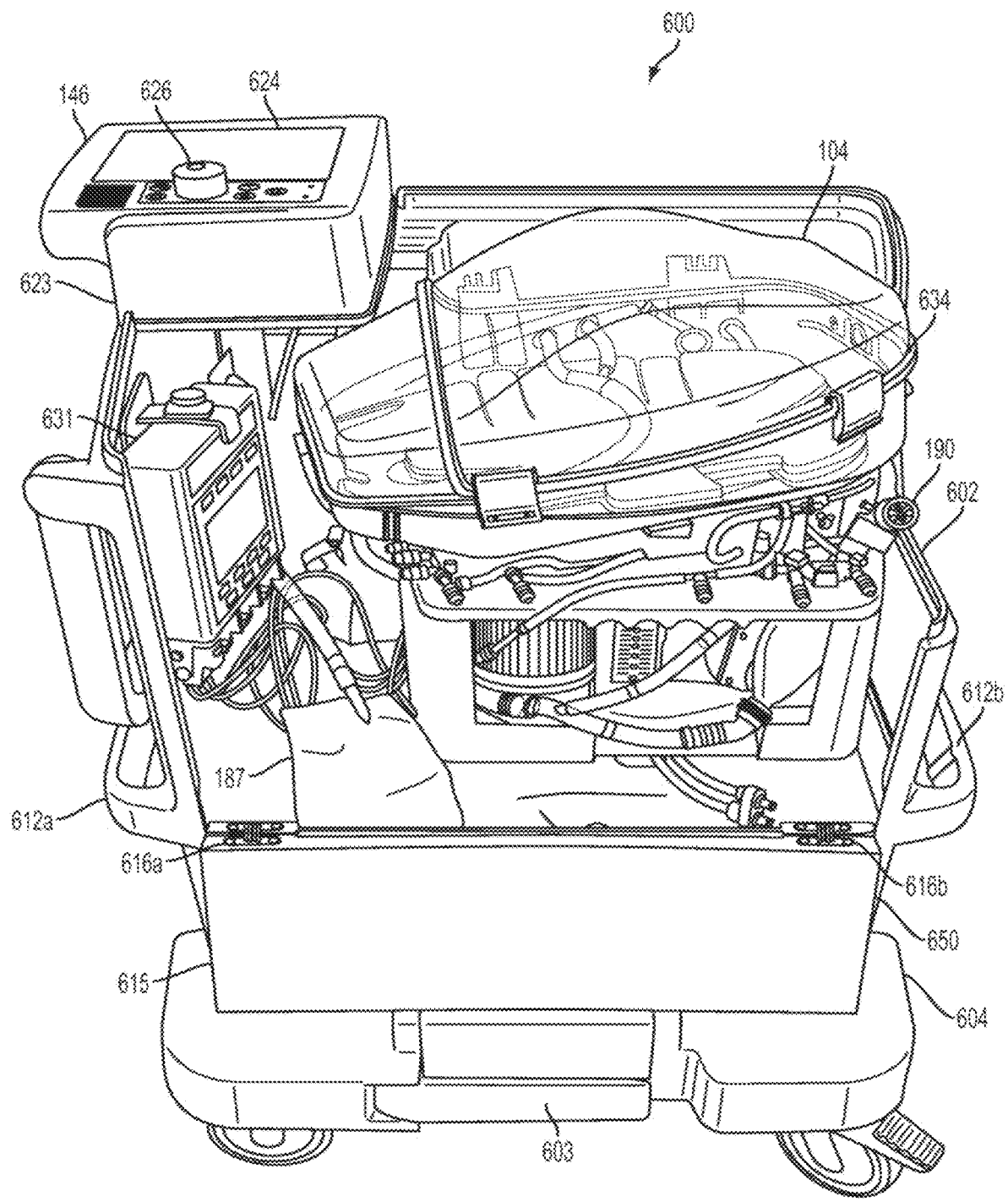
FIGS. 3A-3I show various views of an exemplary organ care system and components thereof.
Figure 3B:
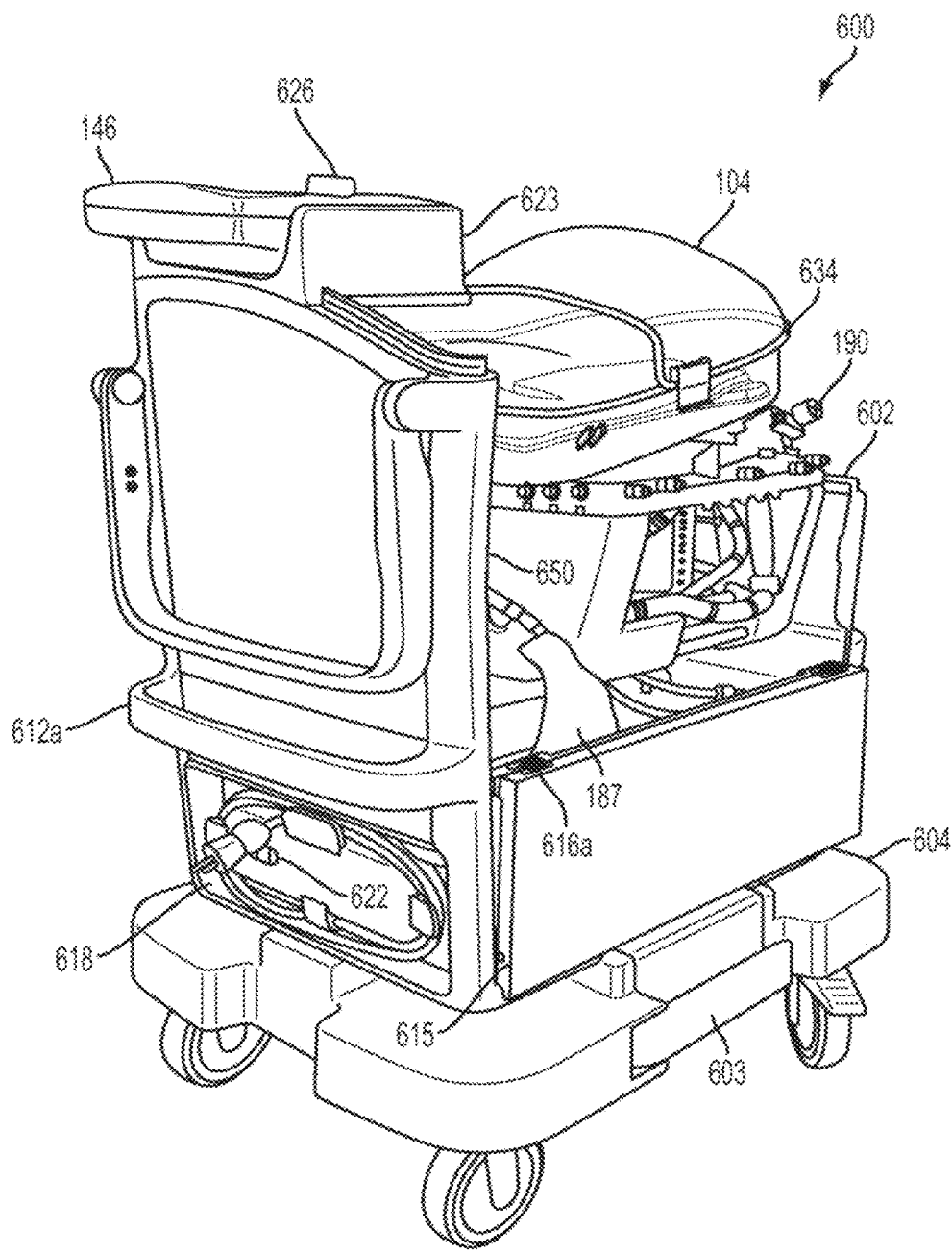
Figure 3C:
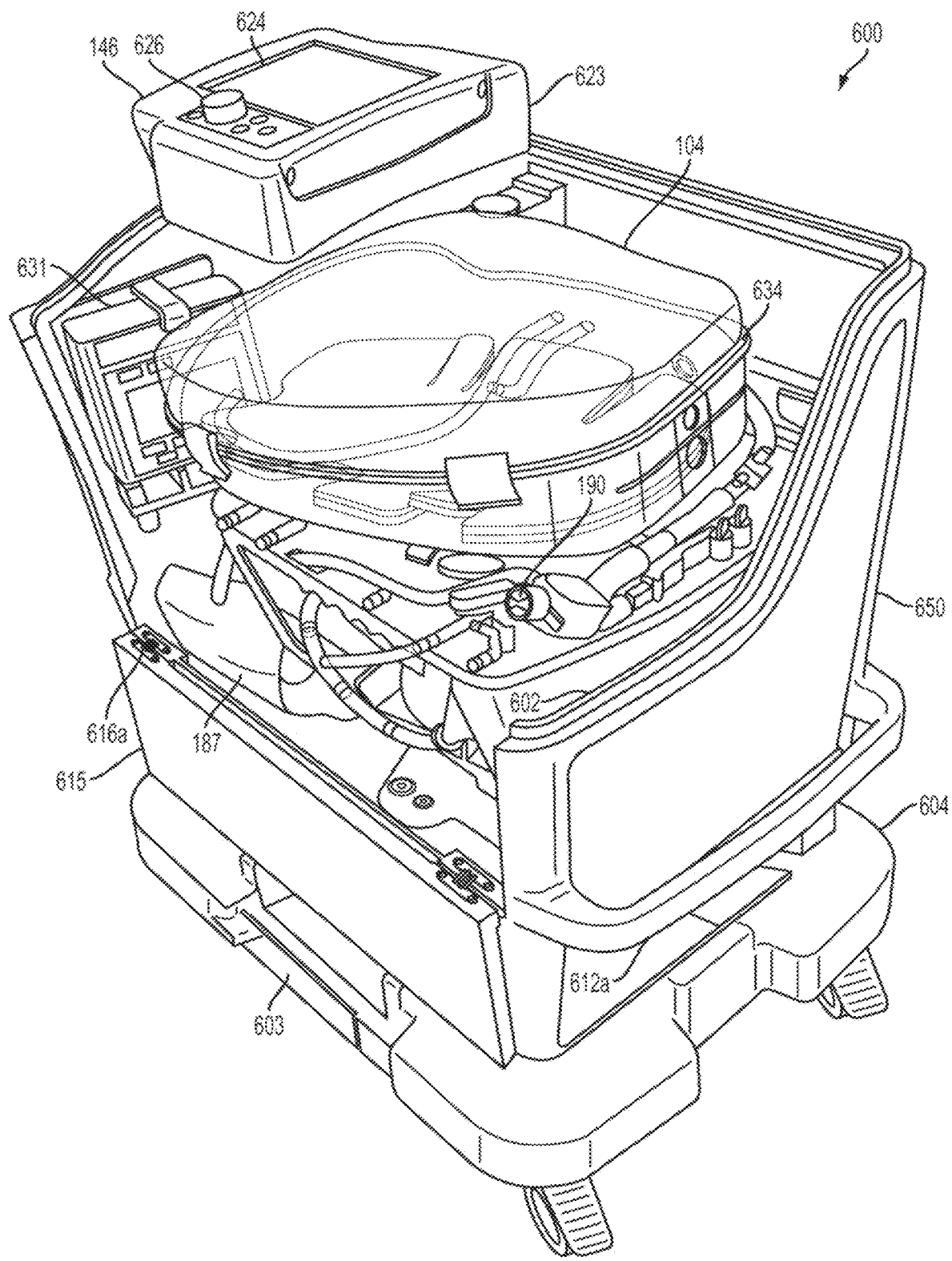
Figure 3D:
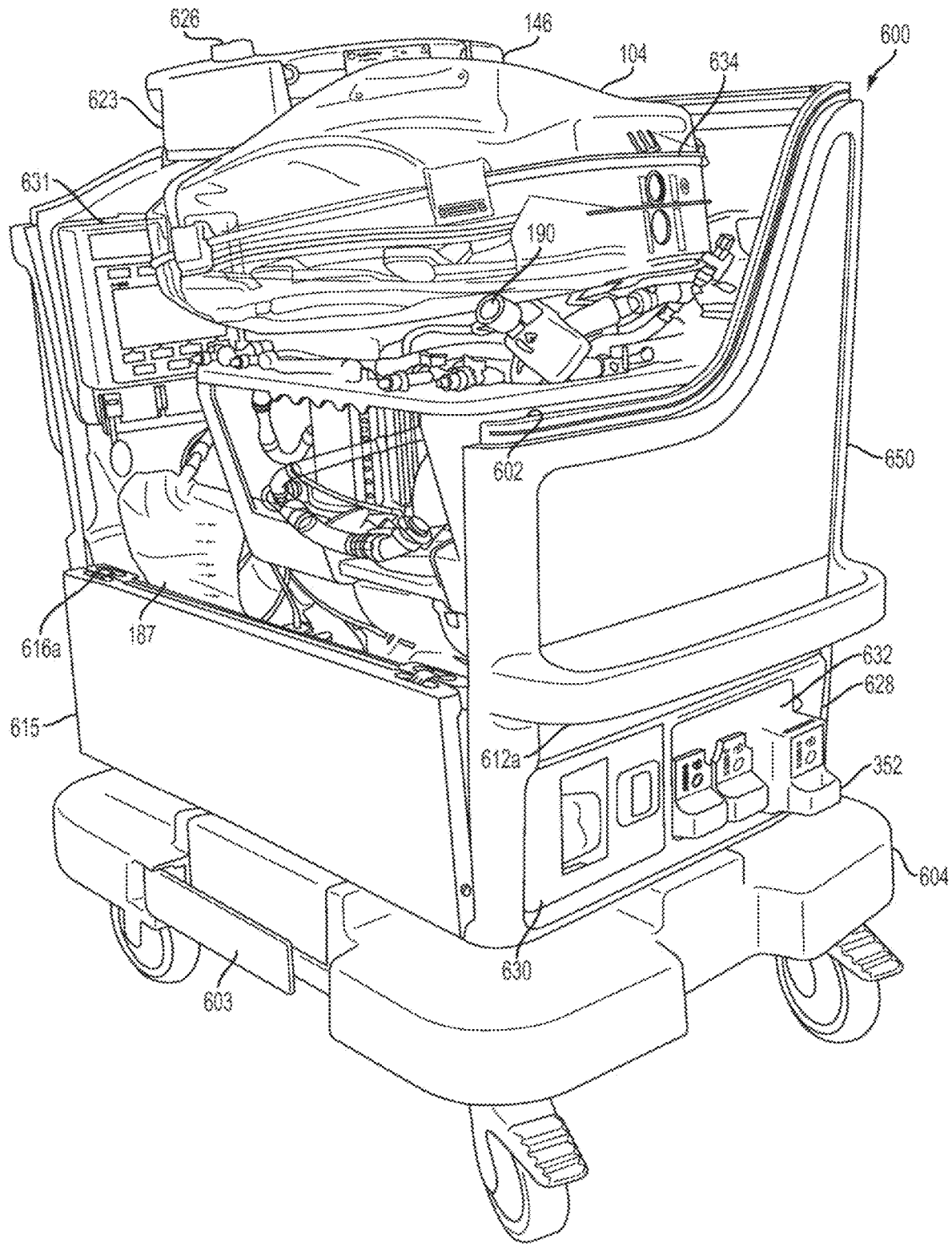
Figure 3E:
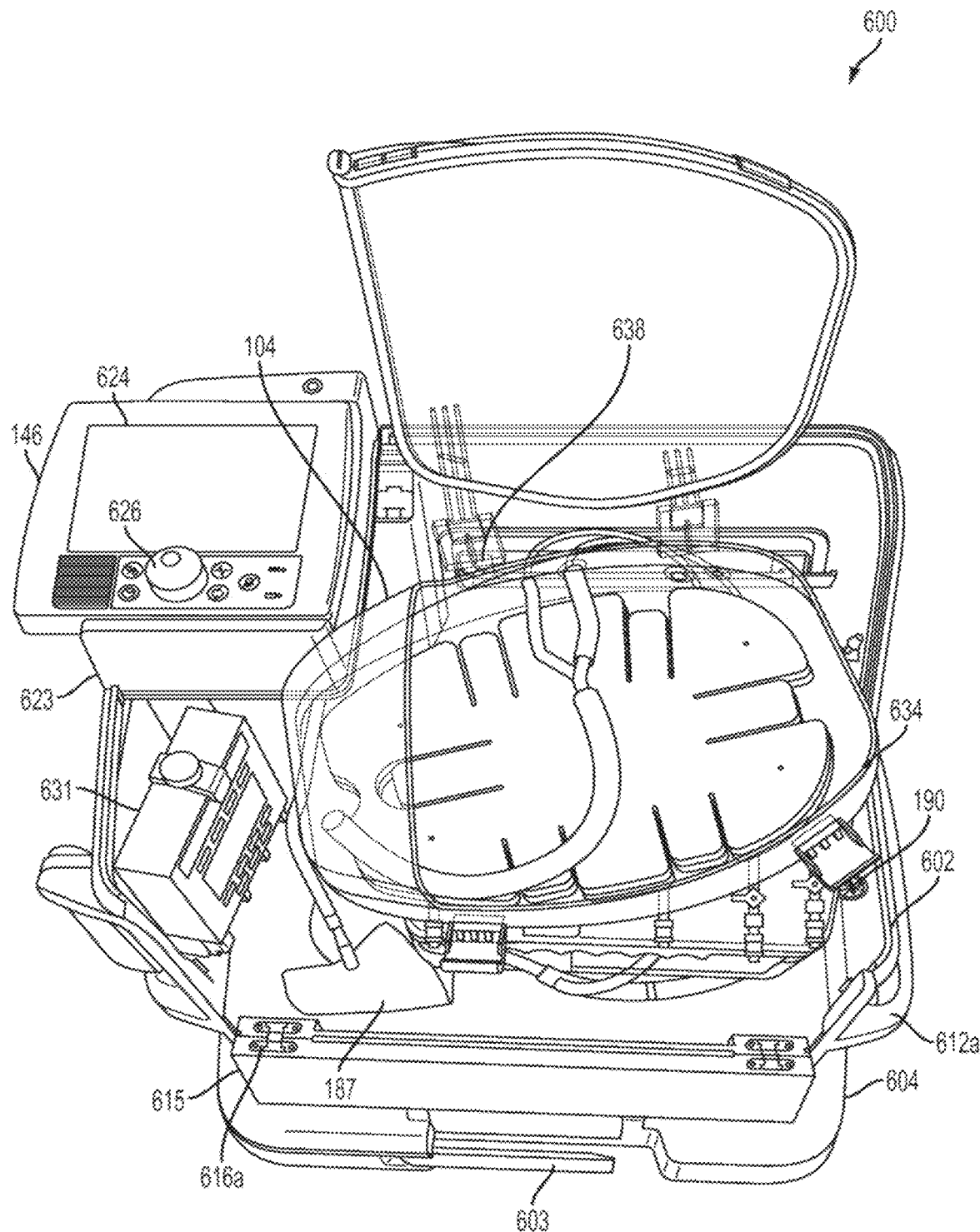
Figure 3F:
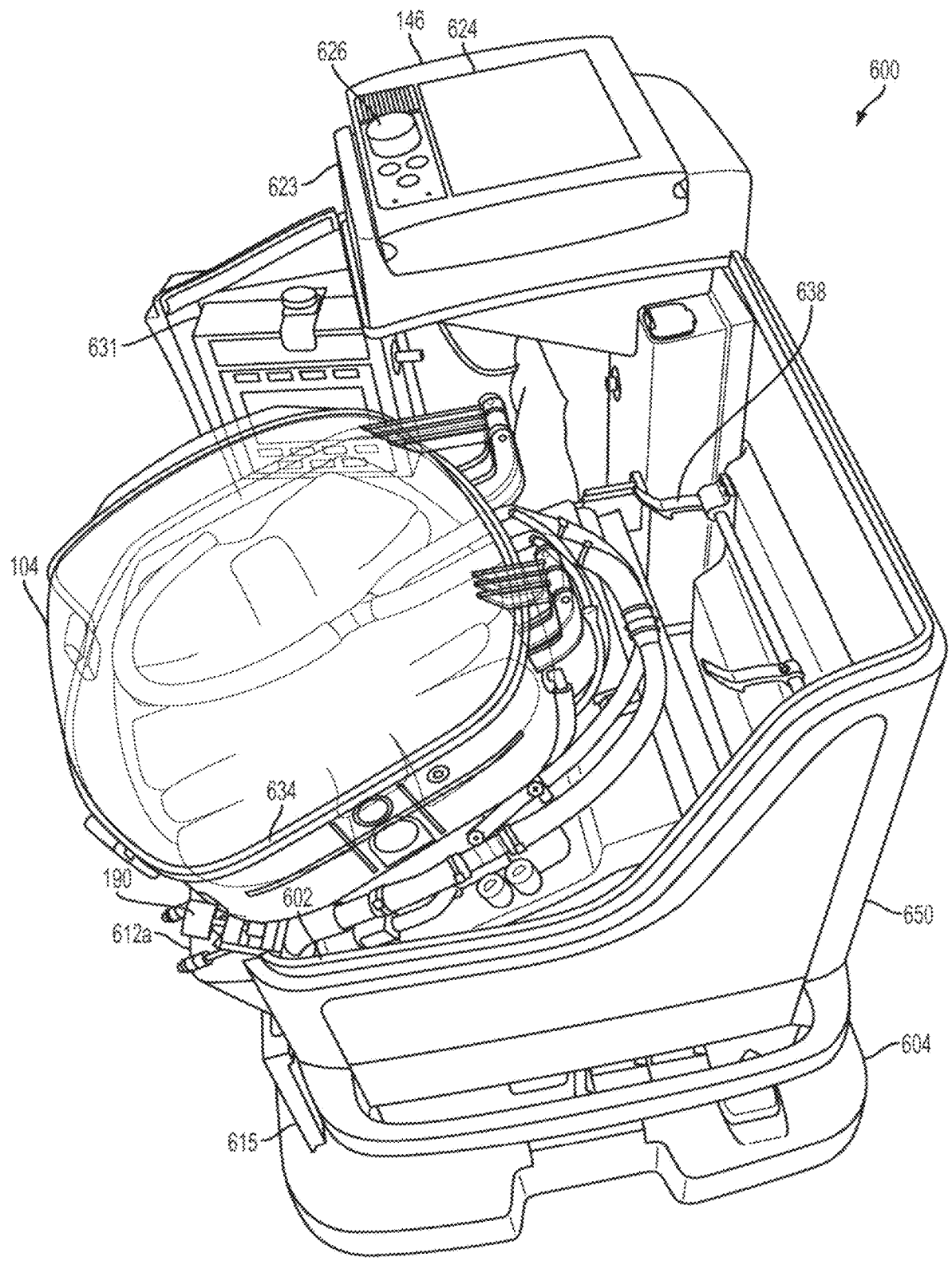
Figure 3G:
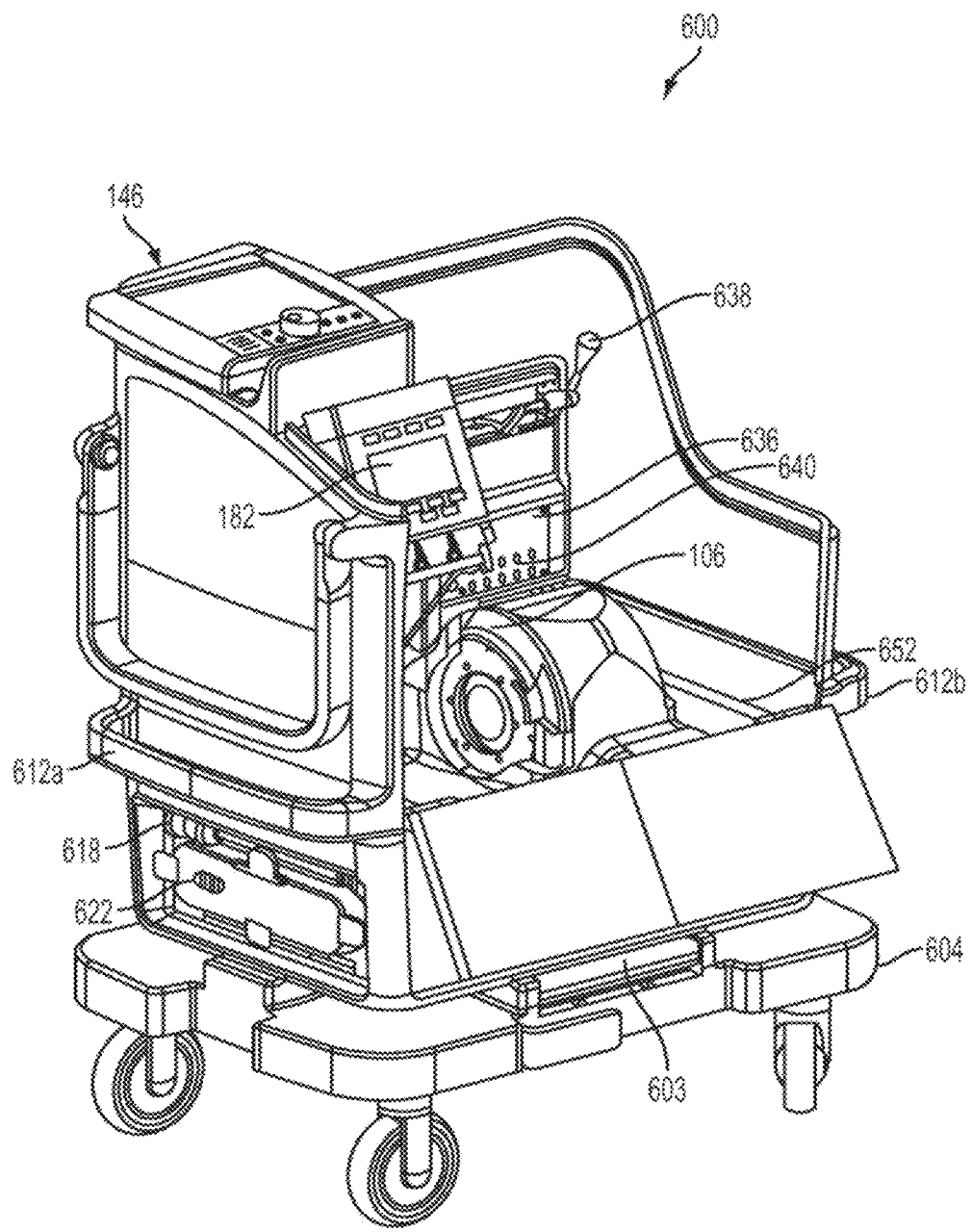
Figure 3H:
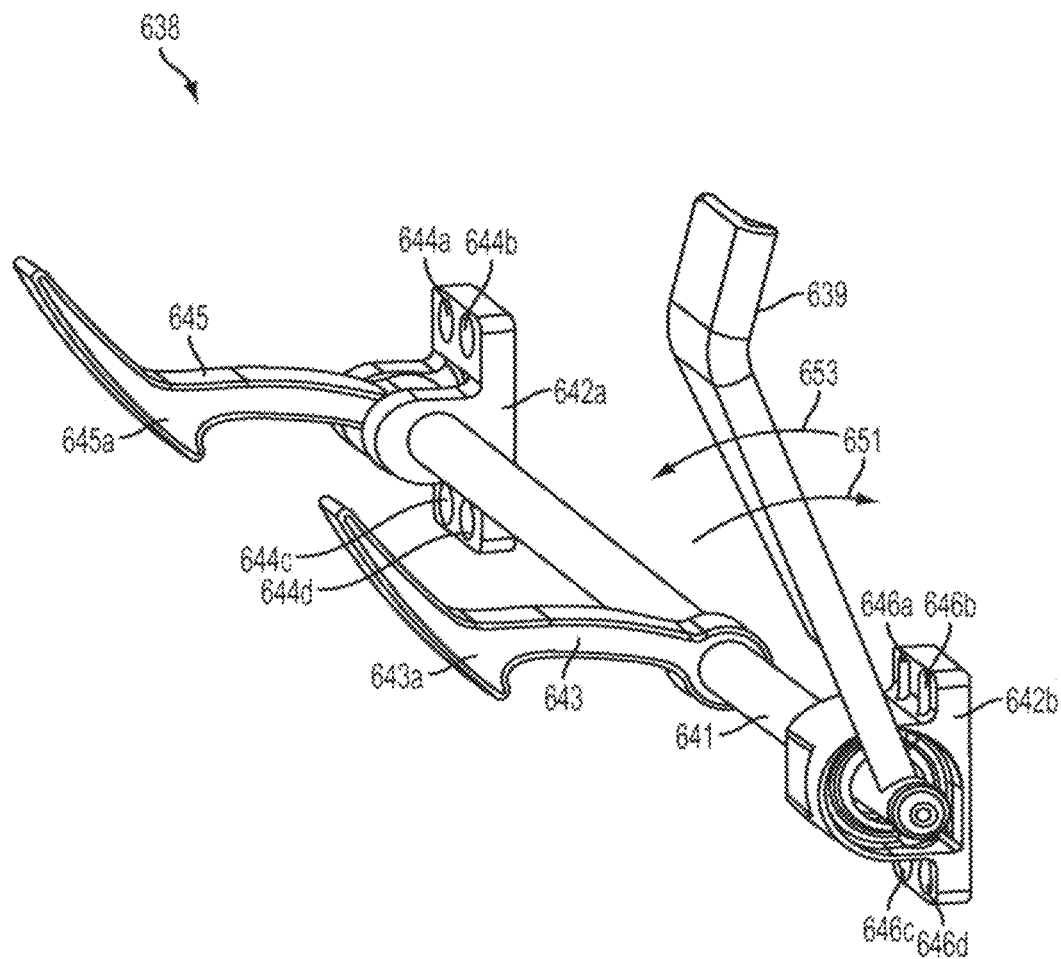
Figure 3I:
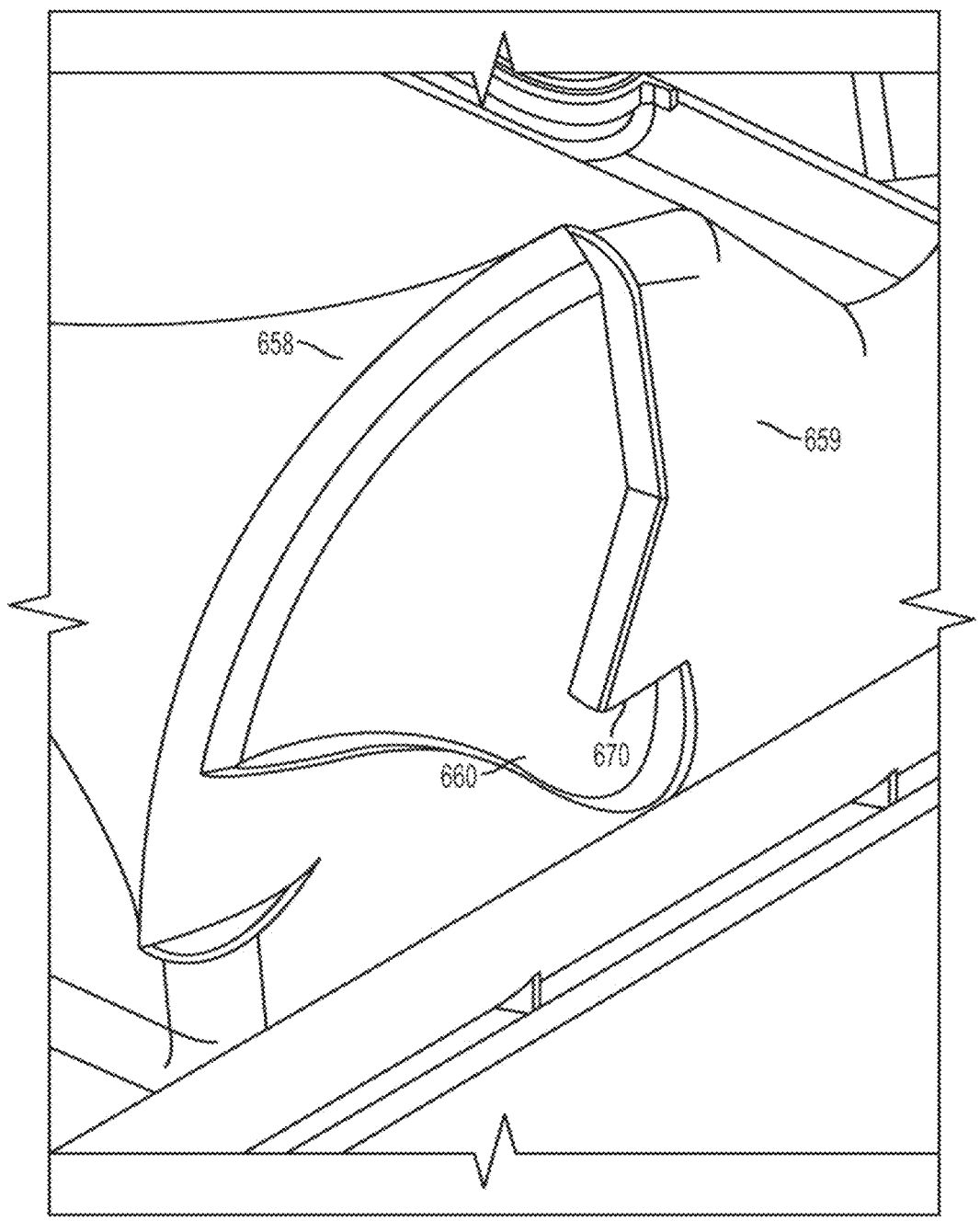

FIG. 3G shows a front perspective view of the multiple use module 650 with the single use module 634 removed. As shown, the multiple use module 650 can include the cart 604 and the housing 602, along with all of the components mounted to/in it. The multiple use module 650 also includes a bracket assembly 638 for receiving and locking into place the single use module 634. An exemplary bracket assembly 638 is shown in FIG. 3H.

In some embodiments, the housing 602 can include a fluid tight basin, which is configured to capture any perfusion fluid and/or any other fluid that may inadvertently leak from the upper portion of the housing 602 and prevent it from reaching the lower section of the housing 602. Thus, in some embodiments, the basin can shield the electronic components of the system 600 from leaked fluid. In some embodiments, the basin 652 can be sized to accommodate the entire volume of fluids used in the system 600 at any particular time.

The system 600 can also include the operator interface module 146, along with a cradle 623 for holding the operator interface module 146. The operator interface module 146 can include a display 624 for displaying information to an operator. The operator interface module 146 can also include a rotatable and depressible knob 626 for selecting between multiple parameters and display screens. The knob 626 can also be used to set parameters for automatic control of the system 600, as well as to provide manual control over the operation of the system 600. In some embodiments, the operator interface module 146 can include its own battery and may be removed from the cradle 623 and used in a wireless mode. While in the cradle 623, power connections can enable the operator interface module 146 to be charged. The operator interface module can also include control buttons for controlling the pump, silencing or disabling alarms, entering or exiting standby mode, and starting the perfusion clock, which initiates the display of data obtained during organ care.

Figure 5:
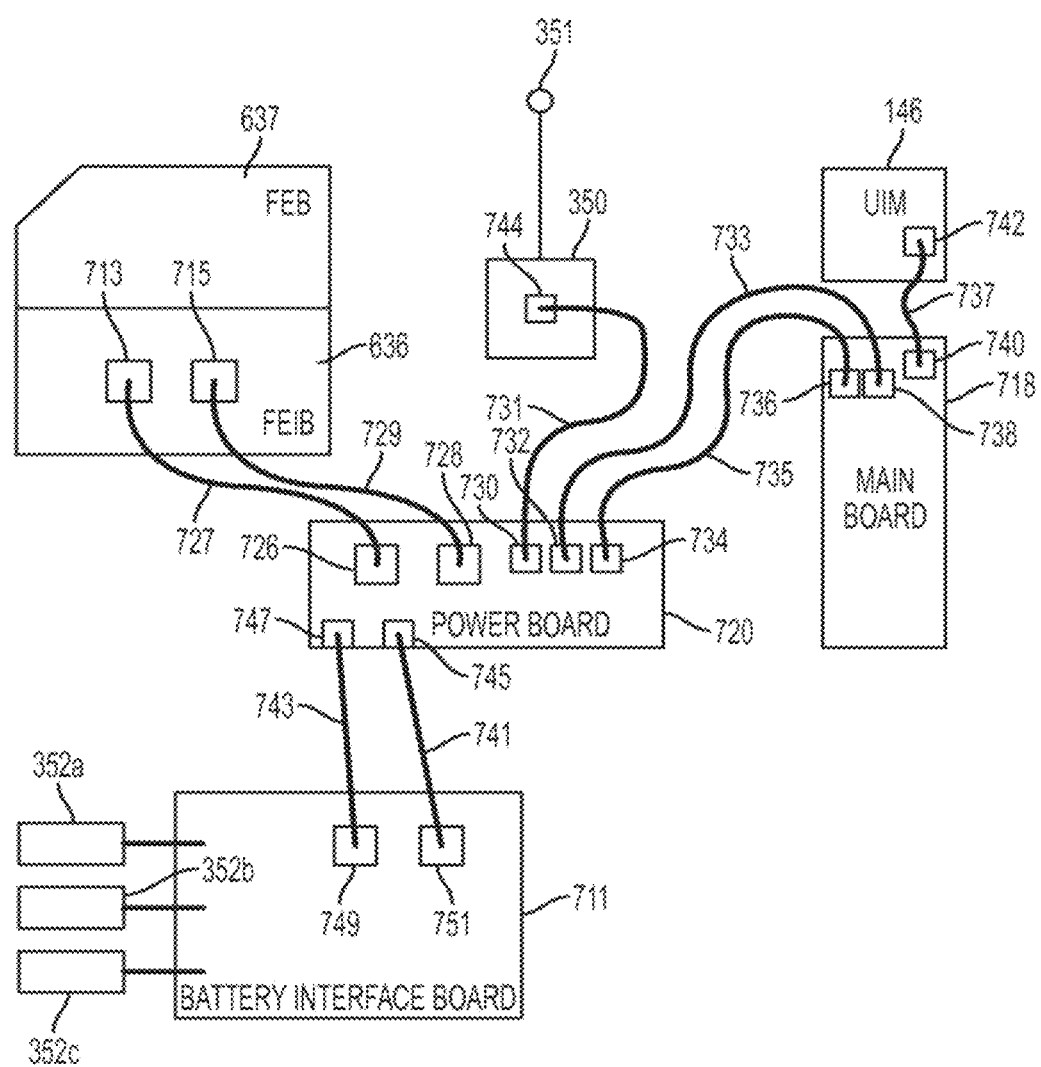
FIG. 5 shows an exemplary system that can be used within an embodiment of the organ care system.

Referring also to FIG. 5, the system 600 can also include a plurality of interconnected circuit boards for facilitating power distribution and data transmission to, from and within the system 600. For example, the multiple use module 650 can include a front end interface circuit board 636, which optically and electromechanically couples to the front end circuit board 637 of the single use module 650. The system 600 can further include a main board 718, a power circuit board 720, and a battery interface board 711 located on the multiple use module 650. The main board 718 can be configured to allow the system 600 to be fault tolerant, in that if a fault arises in the operation of a given circuit board, the main board 718 can save one or more operational parameters (e.g., pumping parameters) in non-volatile memory. When the system 600 reboots, it can then recapture and continue to perform according to such parameters. Additionally, the system 600 can divide critical functions among multiple processors so that if one processor fails the remaining critical functions can continue to be served by the other processors.

2. Power system

Figure 4:
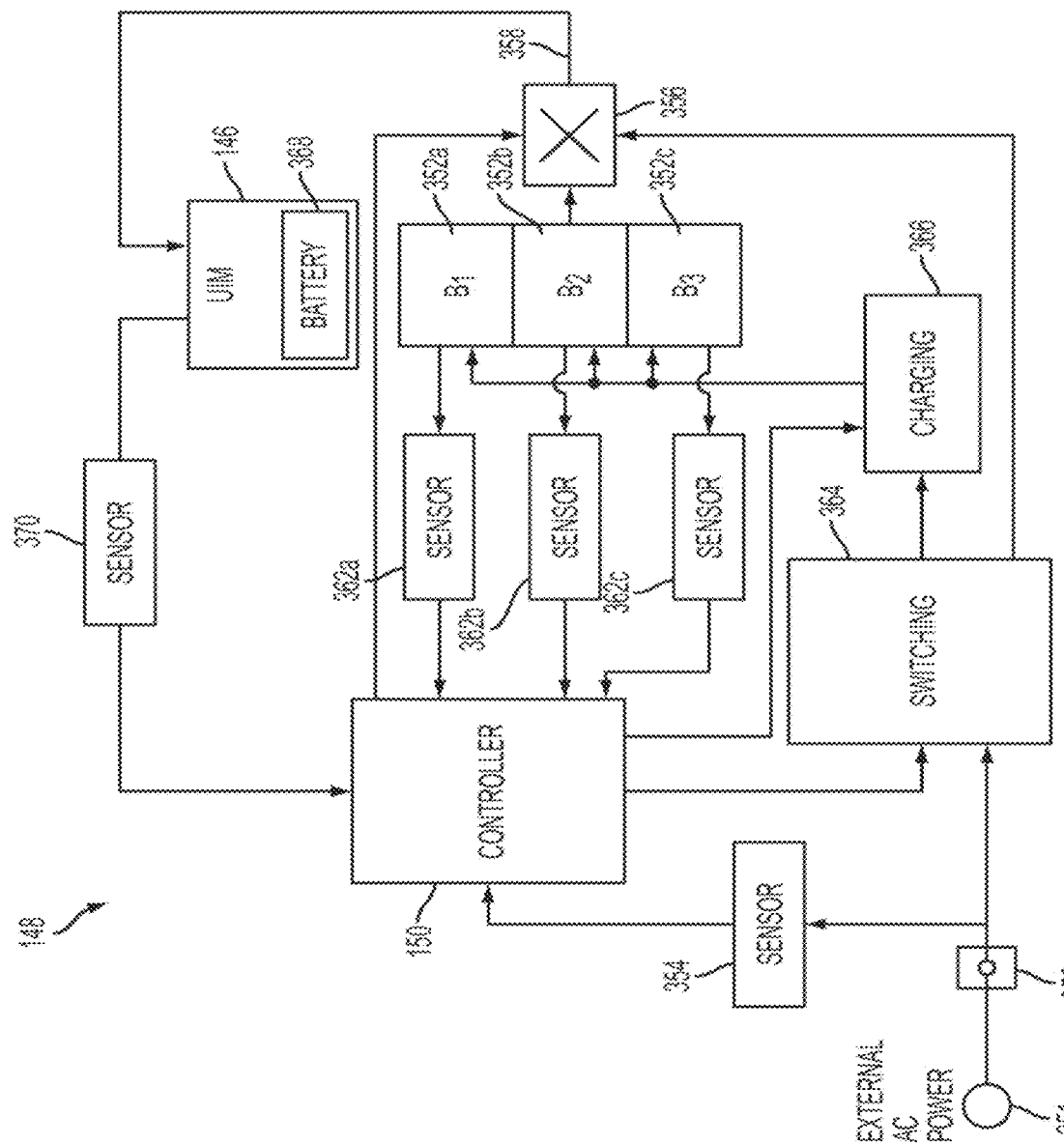
FIG. 4 shows an exemplary system that can be used within an embodiment of the organ care system.

Referring also to FIG. 4, the multiple-use portion of the system 600 can include a power subsystem 148 that is configured to provide power to the system 600. The power subsystem 148 can provide power to the system 600 using swappable batteries and/or an external power source. In some embodiments, the power subsystem 148 can be configured to switch between external power and an onboard battery, without interruption of system operation. The power subsystem 148 can also be configured to automatically allocate externally supplied power between powering the system 600, charging the batteries, and charging internal batteries of the operator interface module 146. The batteries in the power system can be used as the primary power source and/or as a backup power source in the event the external power source fails or becomes insufficient. Additionally, the power system 148 can be configured to be compatible with multiple types of external power sources. For example, the power system can be configured to receive multiple input voltages (e.g., 100V-230V), multiple frequencies (e.g., 50-60 Hz), single phase power, three-phase power, AC, and/or DC power. Additionally, in some embodiments the operator interface module 146 can have its own battery 368.

The housing 602 can include a battery bay 628 that is configured to hold one or more batteries 352. In embodiments with more than one battery, the battery bay 628 can also include a lockout mechanism 632 that is configured to prevent more than one battery from being removed from the battery bay 628 at any given time while the system 600 is operating. This feature can provide an additional level of fault tolerance to help ensure that a source of power is always available. The system 600 can also include a tank bay 630 that can be configured to receive one or more tanks of gas.

Referring to the conceptual drawing of FIG. 5 cabling 731 can bring power (such as AC power 351) from a power source 350 to the power circuit board 720 by way of connectors 744 and 730. The power supply 350 can convert the AC power to DC power and distribute the DC power as described above. The power circuit board 720 can couple DC power and a data signal 358 via respective cables 727 and 729 from the connectors 726 and 728 to corresponding connectors 713 and 715 on the front end interface circuit board 636. Cable 729 can carry both power and a data signal to the front end interface board 636. Cable 727 can carry power to the heater 110 via the front-end interface board 636. The connectors 713 and 715 can interfit with corresponding connectors 712 and 714 on the front end circuit board 637 on the single use module 634 to provide power to the single use module 634.

The power circuit board 720 can also provide DC power 358 and a data signal from the connectors 732 and 734, respectively, on the power circuit board 720 to corresponding connectors 736 and 738 on the main circuit board 718 by way of the cables 733 and 735. The cable 737 can couple DC power 358 and a data signal from a connector 740 on the main circuit board 718 to the operator interface module 146 by way of a connector 742 on the operator interface module cradle 623. The power circuit board 720 can also provide DC power 358 and a data signal from connectors 745 and 747 via cables 741 and 743 to connectors 749 and 751 on a battery interface board 711. Cable 741 can carry the DC power signal and cable 743 can carry the data signal. Battery interface board 711 can distribute DC power and data to the one or more batteries 352 (in FIG. 5, batteries 352*a*, 352*b*, and 352*c*), which can contain electronic circuits that allow them to communicate the respective charges so that the controller 150 can monitor and control the charging and discharging of the one a more batteries 352.

3. Perfusion Fluid Pump

The system 600 can include a pump 106 that is configured to pump perfusate through the organ care system. The perfusate is typically a blood product-based perfusion fluid that can mimic normal physiologic conditions. In some embodiments, the perfusate can be a synthetic blood substitute solution and/or the perfusate can be a blood product in combination with a blood substitute product. In the embodiments where the perfusion fluid is blood-product based, it typically contains red blood cells (e.g., oxygen carrying cells). The perfusate is described more fully below.

In some embodiments, the pump 106 can have a systolic phase and a diastolic phase. The amount of perfusate pumped by the pump 106 can be varied by changing one or more characteristics of the pump itself. For example, the number of strokes per minute and/or the stroke displacement can be changed to achieve the desired flow rate and pressure characteristics. In some embodiments, the pump 106 can be configured to use a stroke rate of 1-150 st/min and a displacement of 0.1-1.5". More specifically, however, a nominal stroke rate of 60 st/min±5 st/min can be used with a displacement of 0.5". These values are exemplary only and values outside of these ranges can also be used. By varying the characteristics of the pump 106 flow rates of between 0.0 and 10 L/min can be achieved.

In some embodiments, a perfusion fluid pump 106 is split into two separable portions: a pump driver portion located in the multiple-use portion 650 and a pump interface assembly in the single-use portion 634. This interface assembly of the single-use portion can isolate the pump driver of the multiple-use portion from direct blood biologic contact.

Figure 6A:
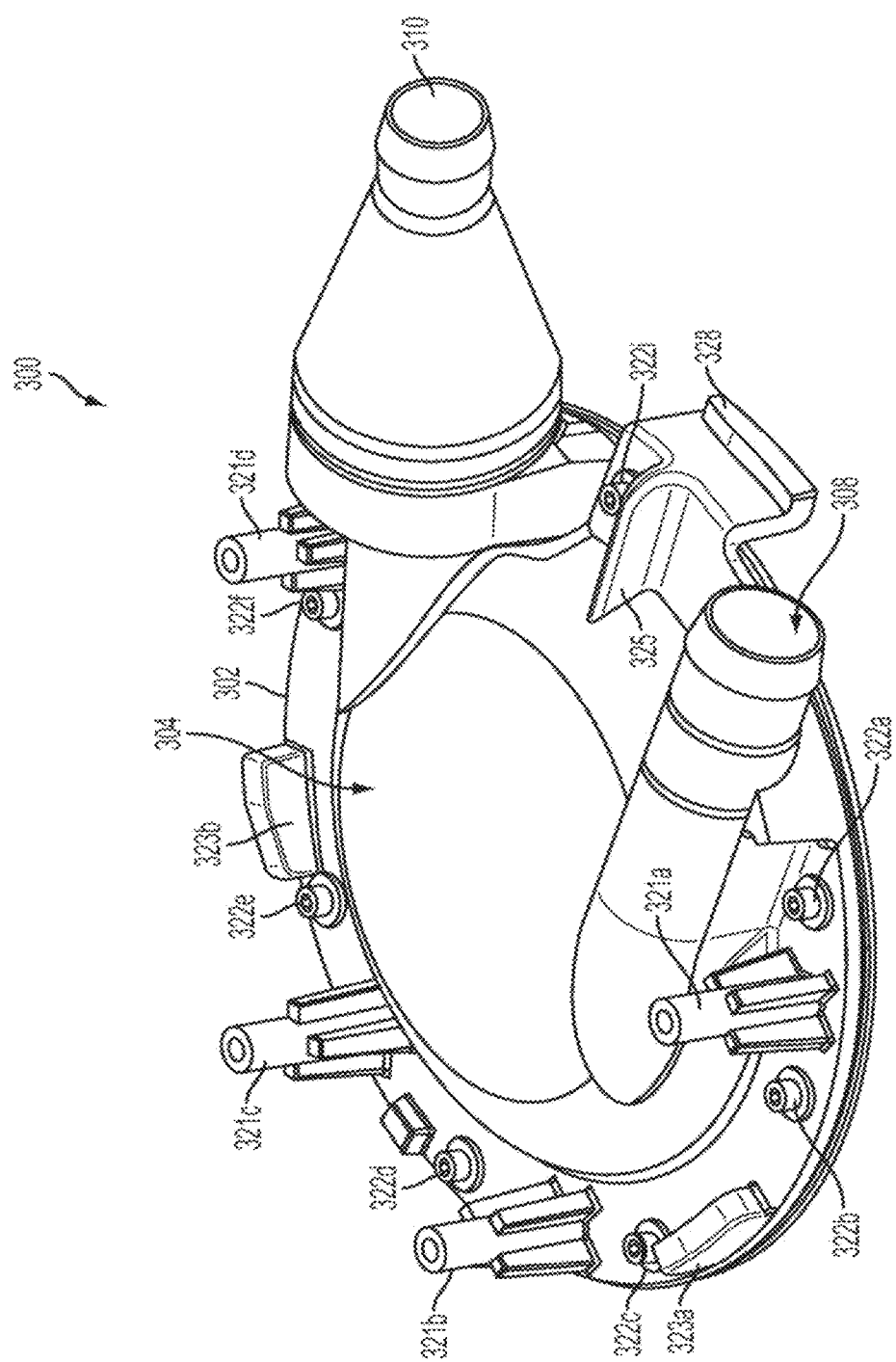
FIGS. 6A-6E show an exemplary pump configuration that can be used within an embodiment of the organ care system.
Figure 6B:
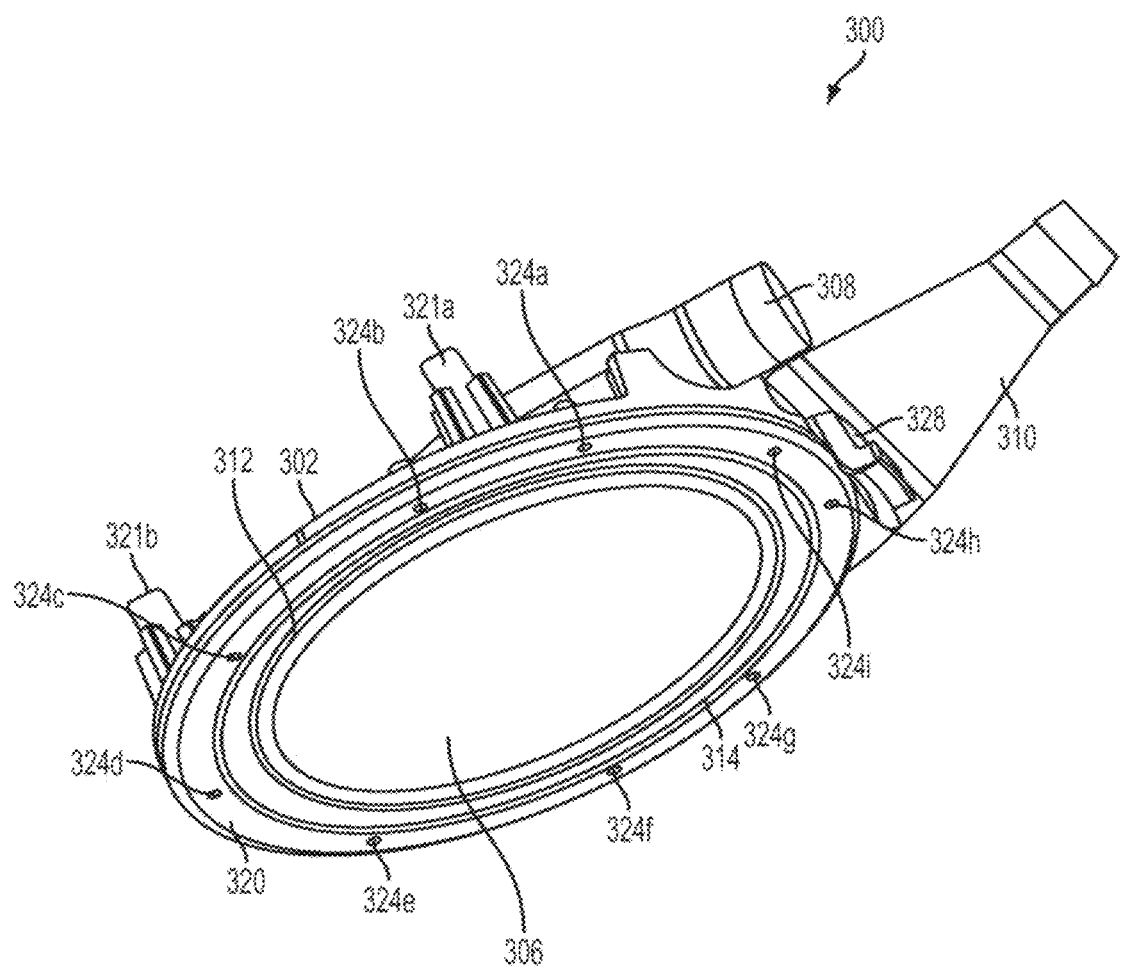
Figure 6C:
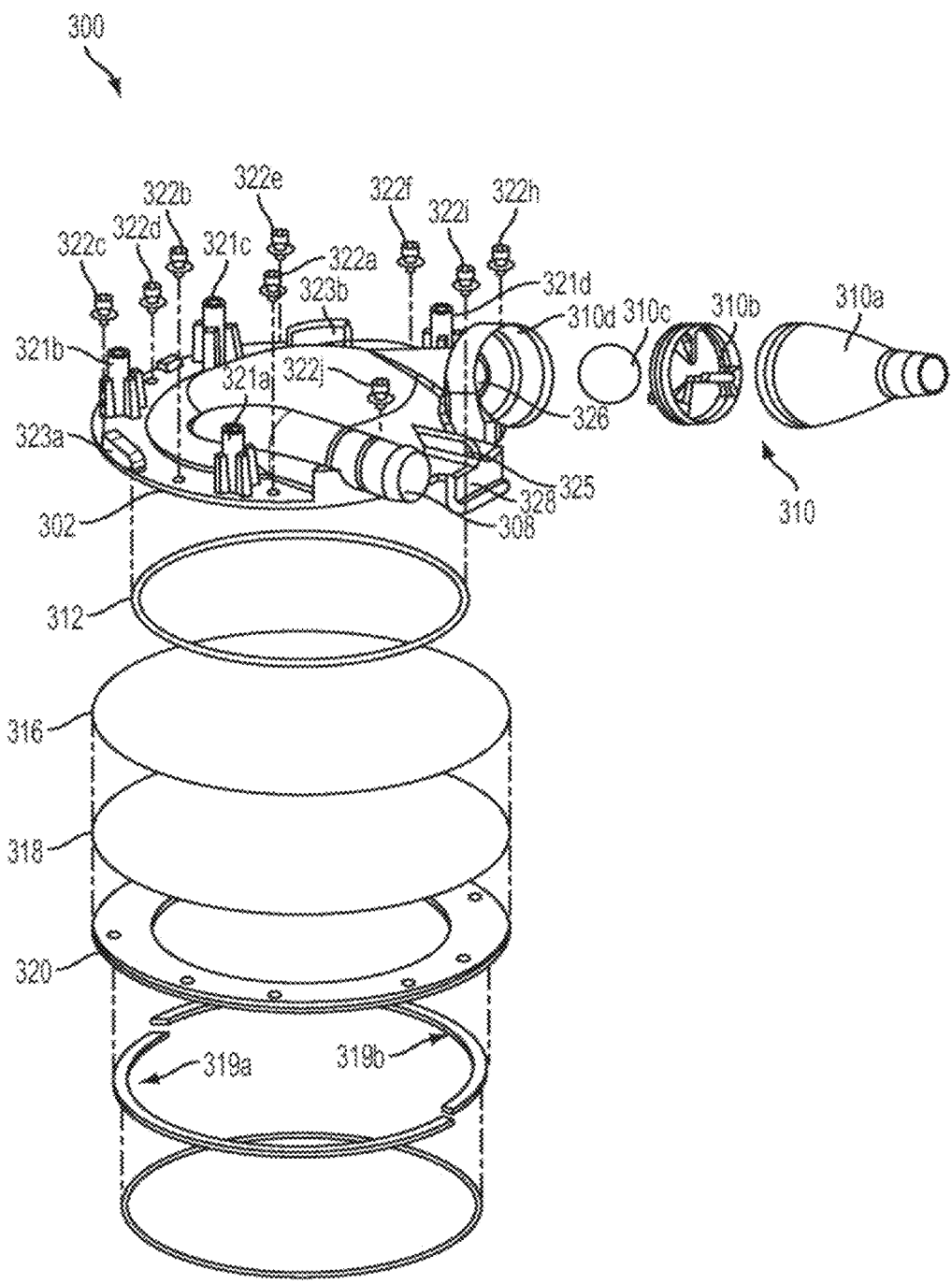
Figure 6D:
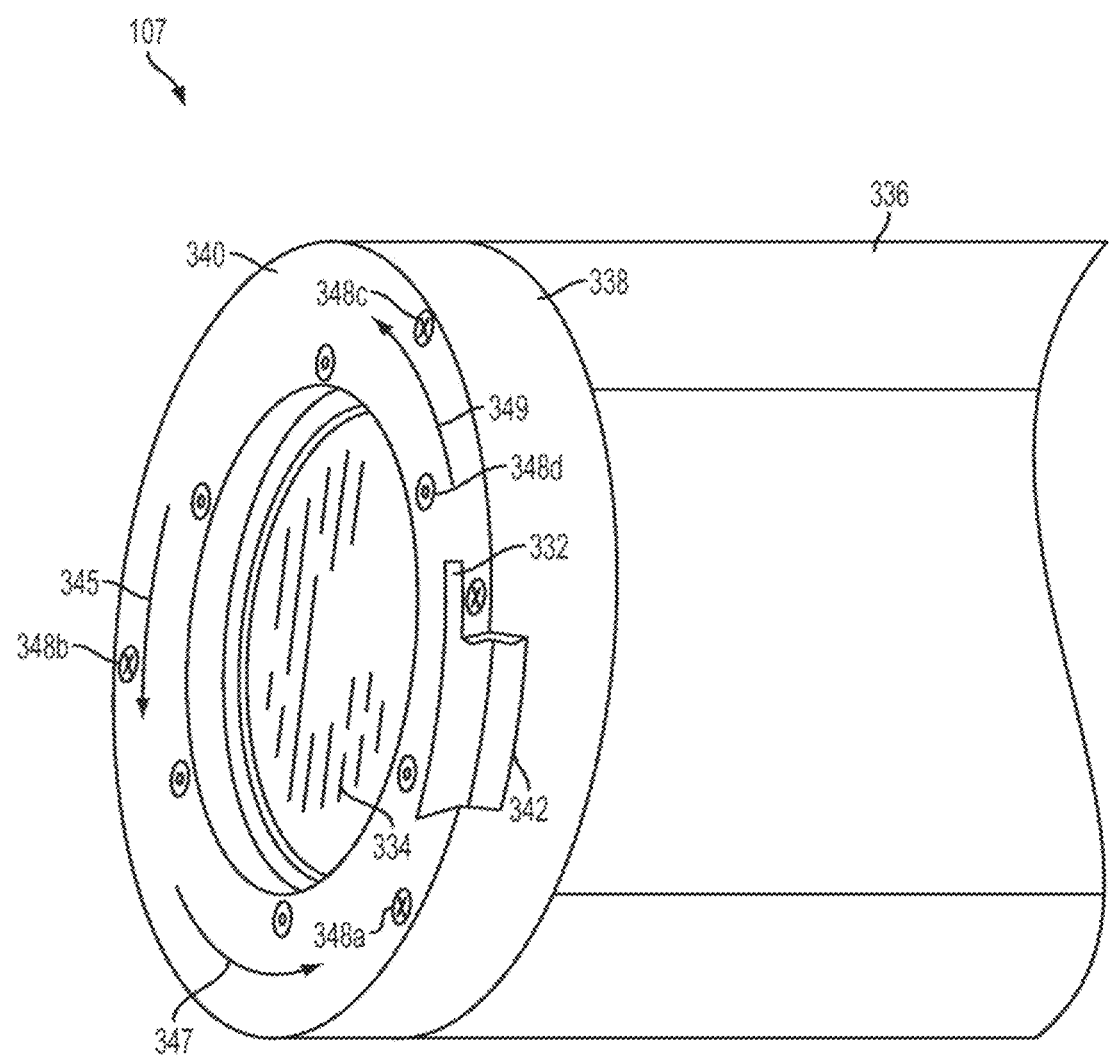
Figure 6E:
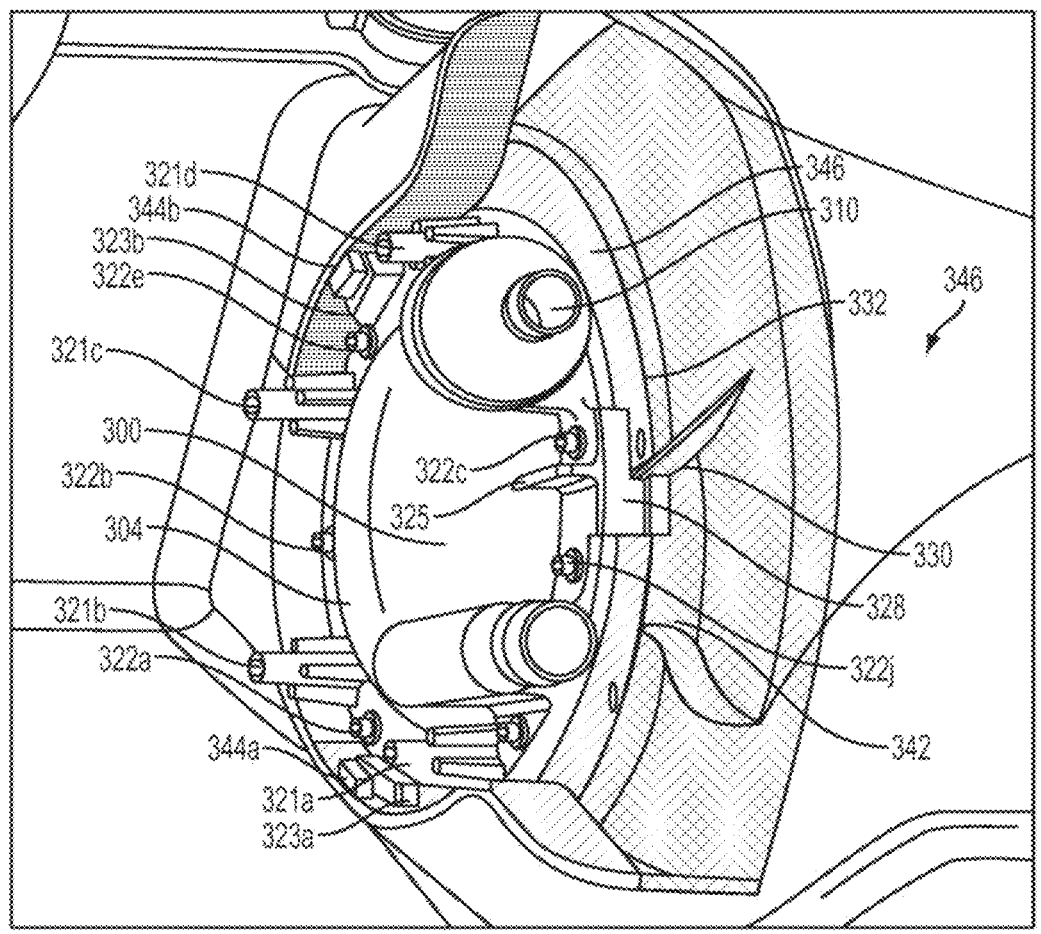

FIGS. 6A-6D show an exemplary embodiment of the pump 106. FIGS. 6A-6C show various views of a pump interface assembly 300 according to an exemplary embodiment. FIG. 6D shows a perspective view of an exemplary pump-driver portion 107 of the perfusion fluid pump 106. FIG. 6E shows the pump interface assembly 300 mated with the pump-driver portion 107 of the perfusion fluid pump assembly 300, according to one exemplary embodiment.

The pump interface assembly 300 includes a housing 302 having an outer side 304 and an inner side 306. The interface assembly 300 includes an inlet 308 and an outlet 310. The pump interface assembly 300 can also include inner 312 and outer 314 O-ring seals, two deformable membranes 316 and 318, a doughnut-shaped bracket 320, and half-rings 319*a* and 319*b* that fit between the o-ring 314 and the bracket 320. The half-rings 319*a* and 319*b* can be made of foam, plastic, or other suitable material.

The inner O-ring 312 can fit into an annular track along a periphery of the inner side 306. The first deformable membrane 316 can mount over the inner O-ring 312 in fluid tight interconnection with the inner side 306 of the housing 302 to form a chamber between an interior side of the first deformable membrane 316 and the inner side 306 of the housing 302. A second deformable membrane 318 can fit on top of the first deformable membrane 316 to provide fault tolerance in the event that the first deformable membrane 316 rips or tears. Illustratively, the deformable membranes 316 and 318 can be formed from a thin polyurethane film (about 0.002 inches thick). However, any suitable material of any suitable thickness may be employed. Referring to FIGS. 6A and 6B, the bracket 320 can mount over the second deformable membrane 318 and the rings 319*a* and 319*b* and can affix to the housing 302 along a periphery of the inner side 306. Threaded fasteners 322*a*-322*i* can attach the bracket 320 to the housing 302 by way of respective threaded apertures 324*a*-324*i* in the bracket 320. The outer O-ring 314 can interfit into an annular groove in the bracket 320 for providing fluid tight seal with the pump assembly 106. Prior to inserting O-ring 314 into the annular groove in bracket 320, the half-rings 319*a* and 319*b* are typically placed in the groove. The O-ring 314 can then be compressed and positioned within the annular groove in bracket 320. After being positioned within the annular groove, the O-ring 314 can expand within the groove to secure itself and the half-rings 319*a* and 319*b* in place.

The pump interface assembly 300 can also include heat stake points 321*a*-321*c*, which project from its outer side 304. The points 321a-321c can receive hot glue to heat-stake the pump interface assembly 300 to a C-shaped bracket 656 of the single use portion of the system 300.

As shown in FIG. 6C, the fluid outlet 310 includes an outlet housing 310a, an outlet fitting 310b, a flow regulator ball 310c and an outlet port 310d. The ball 310c is sized to fit within the outlet port 310d but not to pass through an inner aperture 326 of the outlet 310. The fitting 310b is bonded to the outlet port 310d (e.g., via epoxy or another adhesive) to capture the ball 310c between the inner aperture 326 and the fitting 310b. The outlet housing 310a is similarly bonded onto the fitting 310b.

In operation, the pump interface assembly 300 is configured and aligned to receive a pumping force from a pump driver 334 of the perfusion fluid pump assembly 106 and translate the pumping force to the perfusion fluid 108, thereby circulating the perfusion fluid 108 to the organ chamber assembly 104. According to the exemplary embodiment, the perfusion fluid pump assembly 106 can include a pulsatile pump having a driver 334, which can contact the membrane 318. The fluid inlet 308 can draw perfusion fluid 108, for example, from the reservoir 160, and provide the fluid into the chamber formed between the inner membrane 316 and the inner side 306 of the housing 302 in response to the pump driver moving in a direction away from the deformable membranes 316 and 318, thus deforming the membranes 316 and 318 in the same direction.

As the pump driver moves away from the deformable membranes 316 and 318, the pressure head of the fluid 108 inside the reservoir 160 causes the perfusion fluid 108 to flow from the reservoir 160 into the pump assembly 106. In this respect, the pump assembly 106, the inlet valve 191 and the reservoir 160 are oriented to provide a gravity feed of perfusion fluid 108 into the pump assembly 106. At the same time, the flow regulator ball 310c is drawn into the aperture 326 to prevent perfusion fluid 108 from also being drawn into the chamber through the outlet 310. It should be noted that the outlet valve 310 and the inlet valve 191 are one way valves in the illustrated embodiment, but in alternative embodiments the valves 310 and/or 191 are two-way valves. In response to the pump driver 334 moving in a direction toward the deformable membranes 316 and 318, the flow regulator ball 310c moves toward the fitting 310b to open the inner aperture 326, which enables the outlet 310 to expel perfusion fluid 108 out of the chamber formed between the inner side 306 of the housing 302 and the inner side of the deformable membrane 316. A separate one-way inlet valve 191, shown between the reservoir 160 and the inlet 308 in FIG. 1, stops any perfusion fluid from being expelled out of the inlet 308 and flowing back into the reservoir 160.

In embodiments of the system 600 that are split into the single use module 634 and the multiple use module 650, the pump assembly 107 can rigidly mount to the multiple use module 650, and the pump interface assembly 300 can rigidly mount to the disposable single use module 634. The pump assembly 106 and the pump interface assembly 300 can have corresponding interlocking connections, which mate together to form a fluid tight seal between the two assemblies 107 and 300.

More particularly, as shown in the perspective view of FIG. 6D, the perfusion fluid pump assembly 107 can include a pump driver housing 338 having a top surface 340, and a pump driver 334 housed within a cylinder 336 of the housing 338. The pump driver housing 338 can also include a docking port 342, which includes a slot 332 sized and shaped for mating with a flange 328 projecting from the pump interface assembly 300. The top surface 340 of the pump driver housing 338 can mount to a bracket 346 on the non-disposable multiple use module 650. The bracket 346 can include features 344a and 344b for abutting the tapered projections 323a and 323b, respectively, of the pump interface assembly 300. The bracket 346 can also include a cutout 330 sized and shaped for aligning with the docking port 342 and the slot 332 on the pump driver housing 338.

Operationally, the seal between the pump interface assembly 300 and the fluid pump assembly 107 can be formed in two steps, illustrated with reference to FIGS. 6D and 6E. In a first step, the flange 328 is positioned within the docking port 342, while the tapered projections 323a and 323b are positioned on the clockwise side next to corresponding features 344a and 344b on the bracket 346. In a second step, as shown by the arrows 345, 347 and 349, the pump interface assembly 300 and the fluid pump assembly 106 are rotated in opposite directions (e.g., rotating the pump interface assembly 300 in a counter clockwise direction while holding the pump assembly 106 fixed) to slide the flange 328 into the slot 332 of the docking port 342. At the same time, the tapered projections 323a and 323b slide under the bracket features 344a and 344b, respectively, engaging inner surfaces of the bracket features 344a and 344b with tapered outer surfaces of the tapered projections 323a and 323b to draw the inner side 306 of the pump interface assembly 300 toward the pump driver 334 and to interlock the flange 328 with the docking ports 342, and the tapered projections 323a and 323b with the bracket features 344a and 344b to form the fluid tight seal between the two assemblies 300 and 106.

In some embodiments, the system 100 can be configured such that the flow characteristics including pressure and flow volume of the perfusion fluid provided to the hepatic artery and the portal vein are directly controlled and under pressure generated by the pump 106 (e.g., the hepatic artery and portal veins can be in fluid pressure communication with the pump 106). This embodiment is different from an embodiment where a pump provides perfusion fluid to a reservoir (e.g., a reservoir located above the liver) and then uses gravity to provide fluid pressure to the liver.

4. Solution Infusion Pump

The system 600 can include a solution pump 631 that can be configured to inject one or more solutions into the perfusion module circuit. In some embodiments of the organ care system 600, the solution pump 631 can be an off-the-shelf pump such as a MedSystem III from CareFusion Corporation of San Diego, CA, and/or can be a solution pump as described below with respect to FIGS. 7A-7P. The infusion solutions provided by the solution pump 631 can be used to, for example provide ongoing management of the organ such as inotropic support, glucose control, pH control. Additionally, while the solution pump 631 is generally considered part of the multiple use module 650, parts of the solution pump 631 can be single use and replaced each time the system is used.

The solution pump 631 can be configured to provide one or more solutions simultaneously (also referred to has having one or more channels). In some embodiments, the solution pump 631 can provide three solutions: a maintenance solution, bile salts, and a vasodilator such as epoprostenol sodium. Each of these solutions are described more fully below. The solution pump 631 can support multiple infusion rates (e.g., from 1 to 200 ml/hr, although higher/lower rates are also possible). The infusion rate can be adjustable in time increments (e.g., 1 ml/hour increment, although higher/lower rates are possible) and changes to the infusion rate typically take effect within five seconds, although this is not required. At infusion rates of 10 ml/hr and below, the infused volume can be accurate to within +/−10% of the infusion rate set point, although this is not required. At infusion rates above 10 ml/hr, the infused volume can be accurate to within +/−5% of the infusion rate set point, although this is not required.

The solution pump can be configured to maintain any required accuracy with input pressures (static pressures relative to the solution pump line connection) of 0 to −50 mmHg on the solution side and 0 to +220 mmHg on the organ side. Preferably, infusions should not have any flow discontinuities greater than three seconds. After the solution pump has been de-aired, air bubbles larger than 50 uL are typically not injected into the perfusion module. In some embodiments, the portion of the line between the solution pump 631 and the organ can include a valve (e.g., a pinch valve) to further control the flow of solution to the organ. The solution pump 631 can provide status information for each channel such as infusion state and error.

The solution pump 631 can be used with one or more disposable cartridges that provide the solution. For example, the portion of the line between the solution supply and the solution pump 631 can include a spike to connect to an IV bag. In embodiments that include a disposable cartridge to supply the solution, the cartridge should be capable of operating for at least 24 hours.

The solution pump 631 can be configured to be controlled via one or more communication ports. For example, the solution pump 631 can be controlled via commands received over via a serial port, a network (e.g., Ethernet, WiFi), and/or cellular communications. Various aspects of the solution pump 631 can be controlled such as initial available volume of solution for each channel, infusion state (e.g., infusing or paused). A general and/or alarm status for each channel can also be accessible via the communication port. The status for each channel can include an indication of: whether a disposable cartridge is present, an initial volume is available, an infusing state, an infusing rate, time remaining until empty, and total volume infused. Additionally, the solution pump 631 can be configured so that each channel has fault-mode infusion rate capable of being written/read via the communication port. In some embodiments sensors disposed throughout the organ care system 600 can be connected (directly or indirectly through the controller 150) to facilitate automatic control the solution pump 631 by the controller 150 using an open or closed feedback loop.

The solution pump 631 can be configured to indicate when failures occur. For example, when a failure or occlusion is detected the solution pump 631 can illuminate a fault indicator associated with the faulted channel and/or send a notification via the communication port. The solution pump 631 can be configured to pause the infusion in a channel that has faulted and can restart the infusion after the fault or occlusion has been cleared. In embodiments where the infusion rates are set via the communication port, in the event that signals to/from the communication port are lost, the solution pump 631 can be configured to set the infusion rate to a preprogrammed fault-mode infusion rate.

The solution pump 631 can include one or more fault detection algorithms/mechanisms. For example, if a hardware failure is detected the solution pump 631 can alert a device connected to the communication port that a hardware fault has occurred. If a solution and/or organ side occlusion is detected, the solution pump 631 can alert the device connected via communication port that the occlusion has occurred. The solution pump 631 can be configured to carry out self-tests including power on and background self-tests. The results of the self-tests can be indicated on the solution pump 631 itself and/or communicated via the communication port.

Figure 7A:
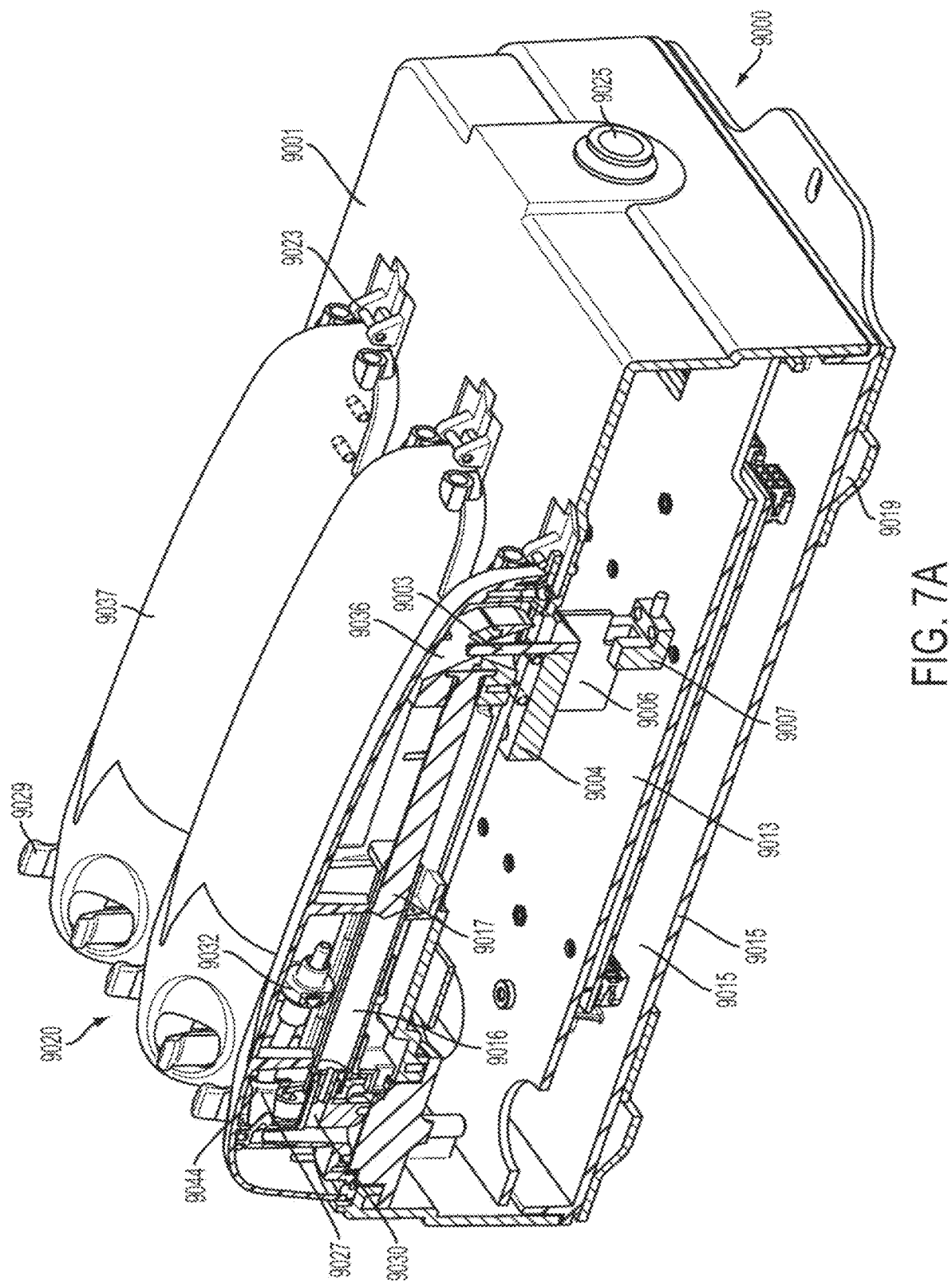
FIGS. 7A-7Q show an exemplary solution infusion pump that can be used within an embodiment of the organ care system.

As noted above, the solution pump can be an off-the-shelf solution pump and/or a custom design pump. Referring to FIGS. 7A-7P, an exemplary embodiment of a custom-designed solution pump 631 is shown and described.

Some embodiments of the solution pump disclosed herein can use a syringe connected to a motor to control the delivery of an infusion solution. By increasing the diameter of the syringe, the capacity of the syringe to hold fluid can be increased. This increased fluid capacity can reduce the number of times the syringe is exchanged for a new, pre-loaded syringe. However, syringes with an increased diameter can result in the loss of precision during the delivery of solution because as the diameter increases, the amount of solution delivered when the plunger is depressed one unit also increases. Another exemplary embodiment of the solution pump uses a relatively small diameter syringe that can allow for greater precision in the delivery of solution. However, the solution can quickly run out due to the syringe's low fluid capacity. Exchanging the syringe with a new, pre-loaded syringe can create problems such as introducing air bubbles, interrupting the solution delivery, causing an inconvenience for users, and creating accessibility challenges. Thus, in some embodiments, a relatively small diameter syringe can be connected to an external source of fluid solution and the perfusion circuit via fluid lines and a series of one-way valves. In these embodiments, as the syringe is depressed, solution can flow through a one-way valve and into the perfusion circuit. When the syringe is retracted, the solution can flow through another one-way valve from the external fluid source into the syringe to refill it with solution. Thus, some embodiments of this design can allow fine precision control of solution delivery (e.g., by using a smaller diameter syringe) while eliminating the need to replace a preloaded syringe with another.

Figure 7B:
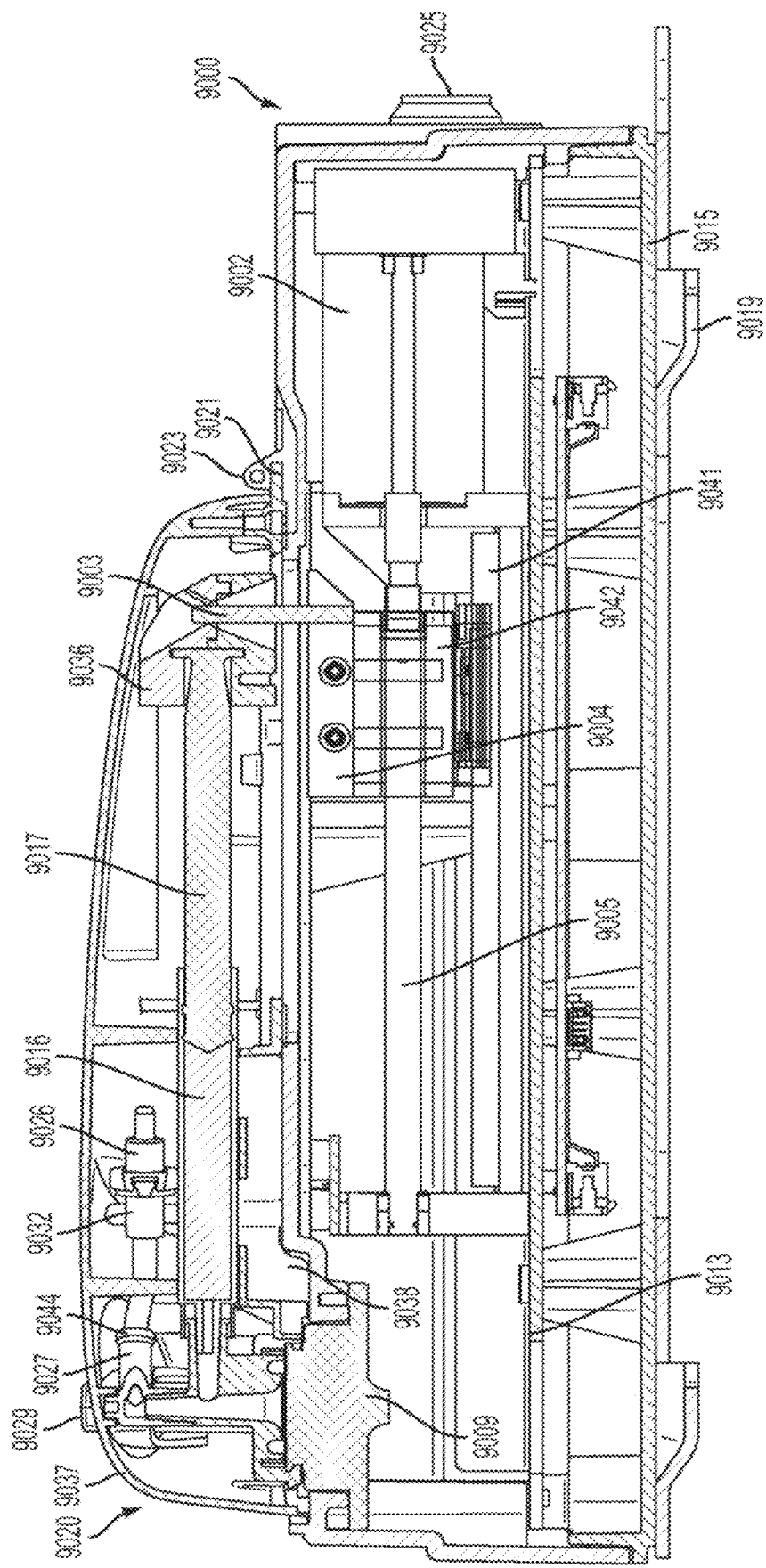
Figure 7C:
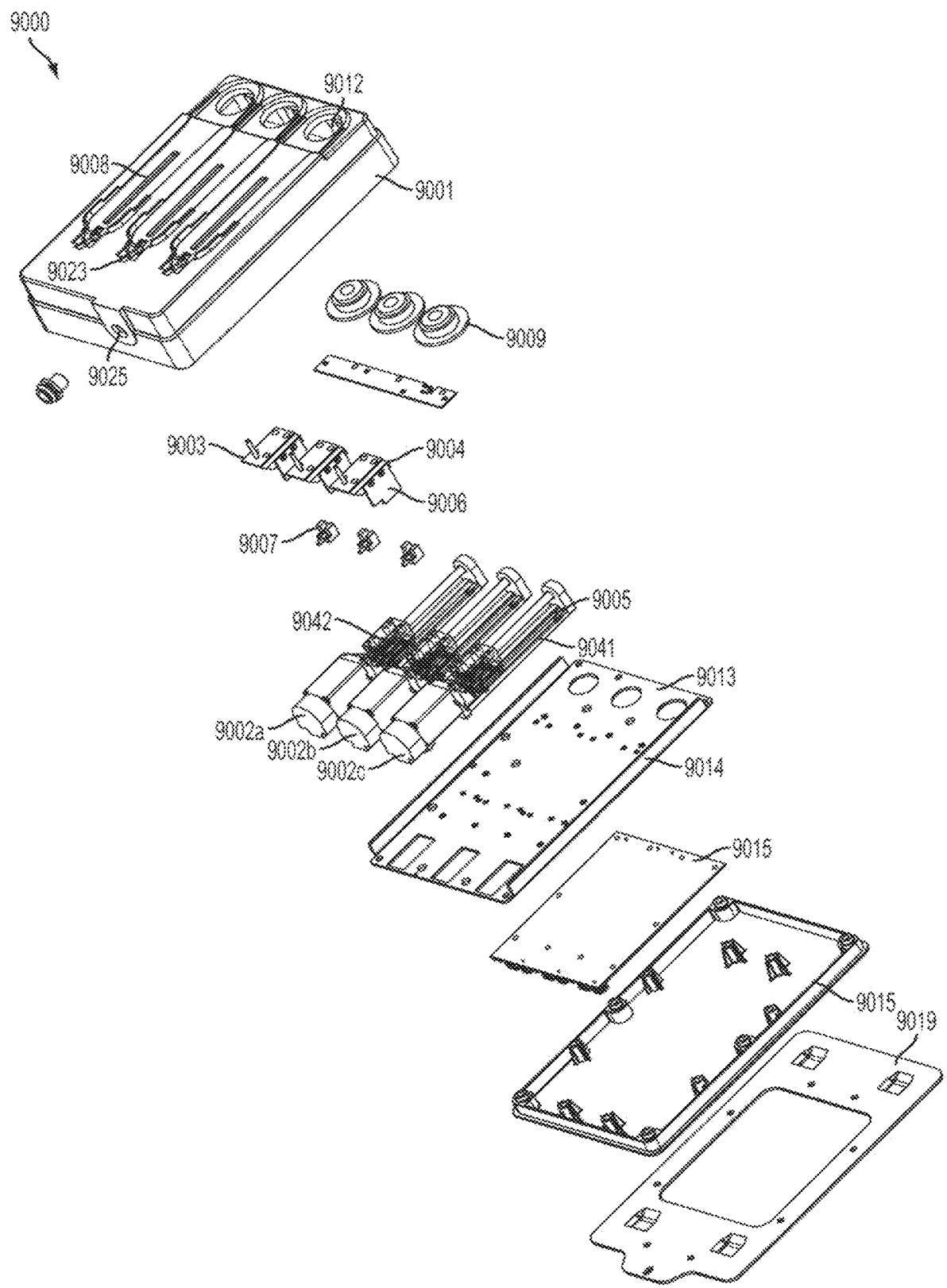
Figure 7E:
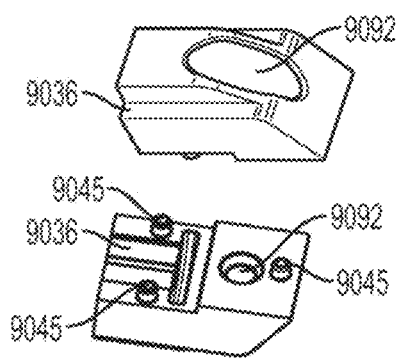
Figure 7G:
Figure 7F:
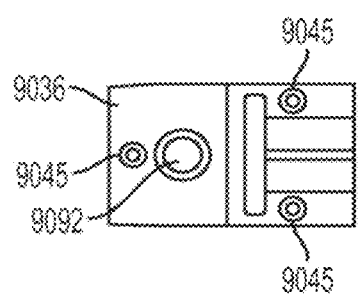
Figure 7H:
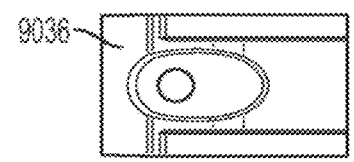

Referring to FIGS. 7A-7P, an exemplary embodiment of a solution pump 9000 is shown. In this embodiment, the solution pump 9000 can use a removable/replaceable cassette 9020 to provide infusion solutions. FIGS. 7C and 7D show an exploded view of the solution pump 9000 and an infusion cassette 9020, respectively. In this embodiment, the solution pump 9000 includes three channels, and thus, is configured to provide up to three different solutions. Other embodiments can include more or fewer channels.

The solution pump 9000 can be a syringe pump driven by a stepper motors 9002a, 9002b, 9002c. The stepper motors 9002 can rotate respective lead screws 9005. Carriages 9042 with carriage covers 9004 communicate with the lead screw 9005 and can move back and forth along the screw 9005. The inside of carriages 9042 can also be threaded with matching threads to facilitate movement along the lead screw 9005 as the lead screw 9005 rotates. Additionally, the carriages 9042 can also move along linear rails 9041 that facilitate movement back and forth along the lead screws 9005. Pins 9003 can be attached to the carriage covers 9004 and to a carrier 9036 that is configured to hold a syringe plunger 9017 so that as the carriages 9042 move back and forth along the lead screws 9005, the plunger can be depressed and retracted. The pins 9003 can be threaded to facilitate attachment to the carrier 9036, although this is not required. In the embodiment shown in FIGS. 7E, 7F, 7G, 7H, the carrier 9036 can be shaped to fit around and hold the plunger 9017. The carrier 9036 can be manufactured in two pieces that can press fit together using protrusions 9045, fit together via screws, and/or any other fastener to clamp the syringe plunger.

In some embodiments, the stepper motor 9002 can be configured to operate at different speeds depending on whether the syringe is being extended or compressed. For example, when the syringe is being compressed (e.g. during infusion) the motor can move at a low speed such as four steps per second, whereas when the syringe is being extended (e.g., during refill) the motor can be moved at high speed such as 16,000 steps per second. Other speeds are possible. Additionally, each stepper motor 9002 can include an optical encoder on a motor shaft enclosed therein (or elsewhere) that can be used to track the position and/or speed of the motor 9002. Accordingly, the position of the plunger of the syringe can be calculated.

In the embodiment shown in FIG. 7C, the stepper motors 9002a, 9002b, 9002c are positioned in parallel to one another, although other configurations are possible. The pins 9003 pass through slots 9008 in a top cover 9001 and can attach to the carrier 9036 that connects to a plunger 9017 of syringe 9016. The connection between the carriage 9042 and the plunger 9017 via the pins 9003 and the carrier 9036 can be used to depress and retract the syringe, which can cause the syringe to provide fluid, or refill itself with fluid when properly connected. For example, as the stepper motor 9002 rotates the lead screw 9005 in a clockwise manner, the carriage 9042 and the carriage cover 9004 with pin 9003 connected to carrier 9036 and plunger 9017 can move in a direction to cause the plunger 9017 to depress and release fluid solution from the syringe 9016. When stepper motor rotates in a counterclockwise manner, the carriage 9042 can move in an opposite direction and the plunger 9017 can be caused to retract, thereby refilling the syringe 9016 with fluid from a fluid source, such as an external IV bag.

The solution pump 9000 can include optical switch 9007 that can be used to detect when the syringe is in a "home" or other position. In some embodiments, the home position can be a position when the syringe is extended and filled with solution, although other home positions are possible. The optical switch 9007 can be U-shaped and can be configured to transmit an optical beam between the two upper portions of the U (e.g., by having a transmitter on one side and a receiver on the other). In some embodiments, when the carriage 9042 is in its home position, a flag 9006 on the carriage cover 9004 can interrupt the optical beam from the optical switch 9007, thus providing information on the position of the syringe. The flag 9006 can be made of any material that interrupts the optical beam such as opaque plastic and/or metal. In some instances it can be possible that the solution pump 9000 loses track of the position of the carriage 9042 because of, for example, a malfunction. If this occurs, the carriage 9042 can return to the home position, leaving the syringe 9016 filled and the plunger 9017 extended. This can allow the pump 9000 reattain the position of the syringe without accidentally providing any additional solution. In some embodiments of the solution pump 9000, an additional optical switch 9007 can be included to determine when the syringe is nearly or completely empty.

The solution pump 9000 can also include pressure sensors 9009 to detect blockages in the delivery line 9010 or output line 9011. An alarm can indicate when the pressure sensors 9009 detect a blockage by sensing a pressure over or under predetermined thresholds. The pressure sensor can be any commercially available sensor suitable for this purpose. In one embodiment, the sensor can be a MEMSCAP SP854 transducer with hydraulic fluid and a diaphragm. The pressure sensors 9009 can extend through the openings 9012 in the top cover 9001.

The stepper motor 9002, linear rails 9041, and pressure sensors 9009 can be mounted to the structural plate 9013. A printed circuit board ("PCB") 9015 can be mounted to the opposite side of the structural plate 9013 and include electronics used to operate the solution pump 9000. The plate 9013 can be made out of aluminum or any other suitable material and can contain a flange 9014 to provide increased stiffness. The plate can also contain a series of mounting holes to provide a connection point to the top cover and bottom cover.

The top cover 9001 can engage a bottom cover 9018 to enclose the solution pump 9000. The two parts can engage along the edges and can be secured with screws or another fastener. A mounting plate 9019 can attach to the bottom cover 9018 (labeled as 9015 in some drawings) and to, for example, the inner wall of the system 600. The top cover 9001 can also include an opening 9025 for connector cables that can connect elsewhere in the system 600, such as to the controller 150.

The solution pump 9000 can engage an infusion cassette 9020 that contains the syringe 9016. In one embodiment the top cover 9001 can include a boss 9023 with a pin. As shown in FIGS. 7A, 7B, a tab 9021 on the infusion cassette 9020 can engage the pin on the boss 9023 to provide a connection between the solution pump 9000 and the infusion cassette 9020. Additionally, the solution pump 9000 can engage the infusion cassette 9020 via a circumferential groove on the pressure sensors 9009 that can be received by a pinch release portion 9022 of the infusion cassette 9020.

The infusion cassette 9020 can include the delivery line 9010 with an IV bag spike 9024 at one end that can be connected to an IV bag or other external source of solution. The other end of the delivery line 9010 can be connected to a one-way check valve 9026 that is designed to allow fluid to only flow away from the IV bag and toward the syringe 9016. The one-way check valve 9026 can be connected to a connector 9027. An output line 9011 can be connected to a second one-way check valve 9032 that is designed to allow fluid to only flow away from the syringe 9016 and towards a port 9034. The one-way check valve 9032 can also be connected to the connector 9027. The output line 9011 can include a filter 9033 that filters particulate and air from the solution. The filter 9033 can be any filter with hydrophobic properties that are suitable for this purpose. The output line 9011 can also be coupled to the port 9034 that connects to the perfusion module. Port 9034 can include a luer fitting. The output line 9011 can also include a roller clamp 9035 that can close the output line 9011. During use, the roller clamp 9035 can be kept open to allow fluid to pass through the output line 9011.

Figure 7I:
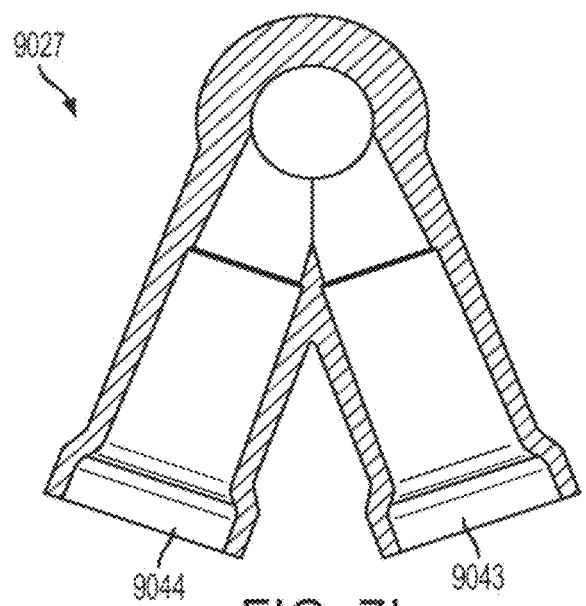
Figure 7J:
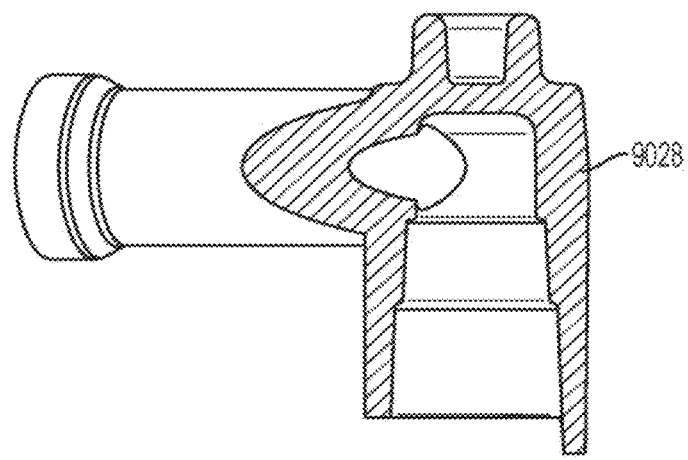
Figure 7K:
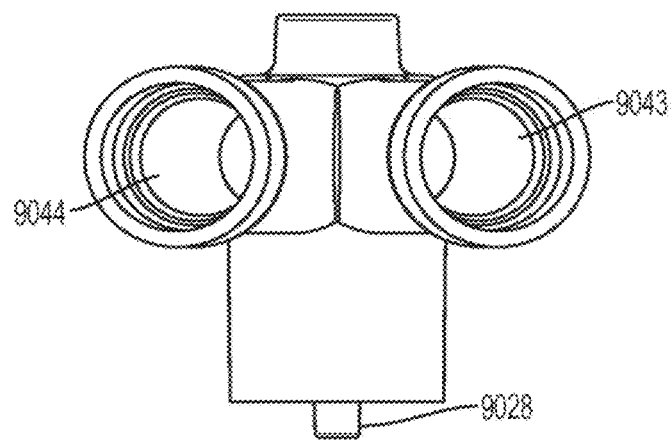

Referring to FIGS. 7I-7K, the connector 9027 can be, for example, a Y-connector. The connector 9027 can include connectors 9043, 9044. Connector 9043 can be connected to the delivery line 9010 and connector 9044 can be connected to the output line 9011. Connector 9027 can also include vertical infusion line. The vertical infusion line can connect to a connector mount. The connector 9027 can also include an alignment tab 9028.

Referring to FIGS. 7L-7P, an exemplary connector mount 9029 is shown. Connector mount 9029 can include a connection port 9031 that can be coupled to the connector 9027 and a syringe mount 9030 that can be coupled to the syringe 9016. A pressure membrane (not shown) can be placed in the connector mount 9029 to monitor the pressure in the fluid circuit between the syringe 9016, the delivery line 9010, and the output line 9011 (e.g., using the pressure sensor 9009). The pressure membrane can be attached to the connector mount 9029 at a location opposite the connection port 9031. The connector mount 9029 can also be used to removably attach the cassette 9020 to the top cover 9001 using a snap connector. For example, wings 9055 can extend through openings in the top cover 9037. By squeezing the wings 9055 together a bottom portion 9056 can be flexed outwards releasing it from a corresponding connector portion on, for example, the pressure sensor 9009.

In one embodiment, the syringe 9016 can deliver fluid as the plunger 9017 is compressed by the movement of the carriage 9042 along the lead screw 9005 by the stepper motor 9002. The fluid from the syringe can pass into the vertical infusion line, past the one-way check valve 9032, into the output line 9011, through the filter 9033, and into the perfusion fluid being circulated in the system 600. Once the plunger 9017 is nearly or fully compressed so that there is little or no fluid to deliver from the syringe, the syringe can be retracted, allowing fluid to pass from the IV bag (not shown), through delivery line 9010, past the one-way check valve 9026, into the vertical infusion line, and into the syringe 9016, thus refilling the syringe.

The infusion cassette can include a top cover 9037 that can engage a bottom cover 9038, thus enclosing the syringe 9016. A gasket 9039 can provide a seal around slots 9008 in top cover 9001 to keep fluid from entering the solution pump 9000 through the slots 9008. The gasket can be made of any suitable sealing material, including foam. A shipping lock 9040 can retain the plunger 9017 and carrier in the fully retracted position so that carriage 9042 can be engaged in the home position. One purpose of the shipping lock 9040 can be to ensure that the hole 9092 in carrier 9036 is at the correct location so that the drive pin 9003 protrudes into the hole 9092 when the user installs the cassette 9020. The shipping lock 9040 can be removed before use.

As will be appreciated, the type and configuration of syringe used in the cassette 9020 can affect how the system is controlled. For example, as the bore of the syringe increases, less travel of the plunger is needed to provide a given amount of solution. Additionally, syringes can have different capacities which can affect how often the syringe needs to be refilled. Thus, it can be beneficial for the solution pump 9000 to know what kind of syringe is installed in cassette 9020. Accordingly, in some embodiments the system 9000 includes a mechanism by which it can determine what type of syringe is included in the cassette 9020. For example, in an embodiment of the solution pump 9000 is configured to work with two different types of syringes, the pump can include a magnet and Hall effect sensor that can be configured to determine which of the two types of syringes is being used. For example, the cassette 9020 can include a magnet having N and S poles. The magnet can be oriented so that only one of the two poles interacts with the Hall effect sensor. When the first type of syringe is used, the N pole can be configured to interact with the Hall effect sensor and, likewise, when the second type of syringe is used, the S pole can be configured to interact with the Hall effect sensor. By determining which of the two poles is interacting with the Hall effect sensor, the solution pump 9000 can determine which type of syringe is being used in the cassette 9020. The sensor configuration is exemplary only, and other sensors can be used to determine which type of syringes being used in the cassette 9020.

The solution pump 9000 can be controlled by one or more control systems. For example, the solution pump 9000 can be controlled by the controller 150 and/or can include an internal control system. Regardless of the location of the controller, the controller can be configured to know how many partial or full rotations of the stepper motor 9002 are required to provide the necessary amount of solution and/or to refill the syringe. Thus, for example, the controller can know that it takes 40 steps of the stepper motor to provide 1 mL of solution. In some embodiments, the amount of solution provided by the solution pump 9000 can be manually controlled and/or can be controlled automatically by the controller 150.

The solution pump 631 can be configured to provide solution flow rates that vary between 0.5 and 200 mL/hr, although other rates are possible.

Some embodiments of the solution pump 631 can include a priming cycle that can be used to prime and eliminate air within the lines of the pump 631. For example, a user can assemble a complete line set dry and perform priming cycle until air is eliminated. For example, each priming cycle can advance 3 mL of air (or solution) using a special fast-forward and fast refill movement. In some embodiments, the prime cycle is under user control and/or can be performed automatically.

In some embodiments, when the motor 9002 is operated at a high speed (e.g., during refill and/or priming), the high-speed cycle can include a ramp-up and ramp down periods going into and coming out of high-speed operation. These ramp-up and ramp down periods can be used to overcome the rotational inertia of the motor 9002. This function can be implemented by the firmware and/or controller is controlling the pump 631 using, for example lookup tables that have been calculated to adjust the pulse rates of the motors 9002 for constant acceleration and/or deceleration. The ramp-up and ramp down periods can also be used during low-speed operation.

In some embodiments, the solution pump 631 can be configured to compensate for inherent backlash that can be caused when the direction of travel of the syringe is reversed. For example, fluid flow can be particularly affected by the backlash inherent in the motor 9002 and lead screw 9005. Errors caused by backlash can affect the resumption of infusion flow after a refill cycle. To offset these possible errors, firmware within the pump and/or the controller can capture the pressure in the syringe chamber at the end of all infusion strokes. The fast refill cycle can then be executed and the firmware and/or controller can advance the plunger at a moderately fast rate until the pressure in the syringe chamber is equal to the pressure captured during the last infusion strokes. When that pressure is reached, all system backlash has typically been resolved and the pump can continue infusing at the desired rate.

While stepper motors typically provide the highest torque for a given motor size, and can be easy to drive, they can also consume high amounts of power and can generate large amounts of mechanical noise. Thus, in some embodiments of the pump 631, firmware and/or the controller can include a dynamic torque function that can operate the motors 9002 at the minimal torque required at any given time. This can be accomplished using digital to analog converters that control the current limit of each stepper motor driver, which can in turn control the torque provided by the motor. Accordingly, stepper motor torque can be adjusted to efficiently provide the required motion. At rest, a small current can be provided to the motor to maintain its static position without slipping. At the start of each forward infusion stroke, the stepper motor can be run at the selected infusion rate with a predefined minimal torque. If the encoder indicates that the stepper is not moving as desired, the torque can be increased until the proper movement is achieved. In this way, the forward infusion stroke can be performed at the minimal torque required to do the job.

The solution pump 631 can also be configured to make up for slippage between the actual position and the desired position of the syringe plunger. For example, when firmware and/or the controller determines that the syringe position (e.g. provided by an encoder) has slipped behind the desired profile, it can double the rate until the syringe position catches up. This process of slipping, torque increase, and/or rate doubling can happen quickly enough to provide uninterrupted infusion at the selected rate.

Figure 7Q:
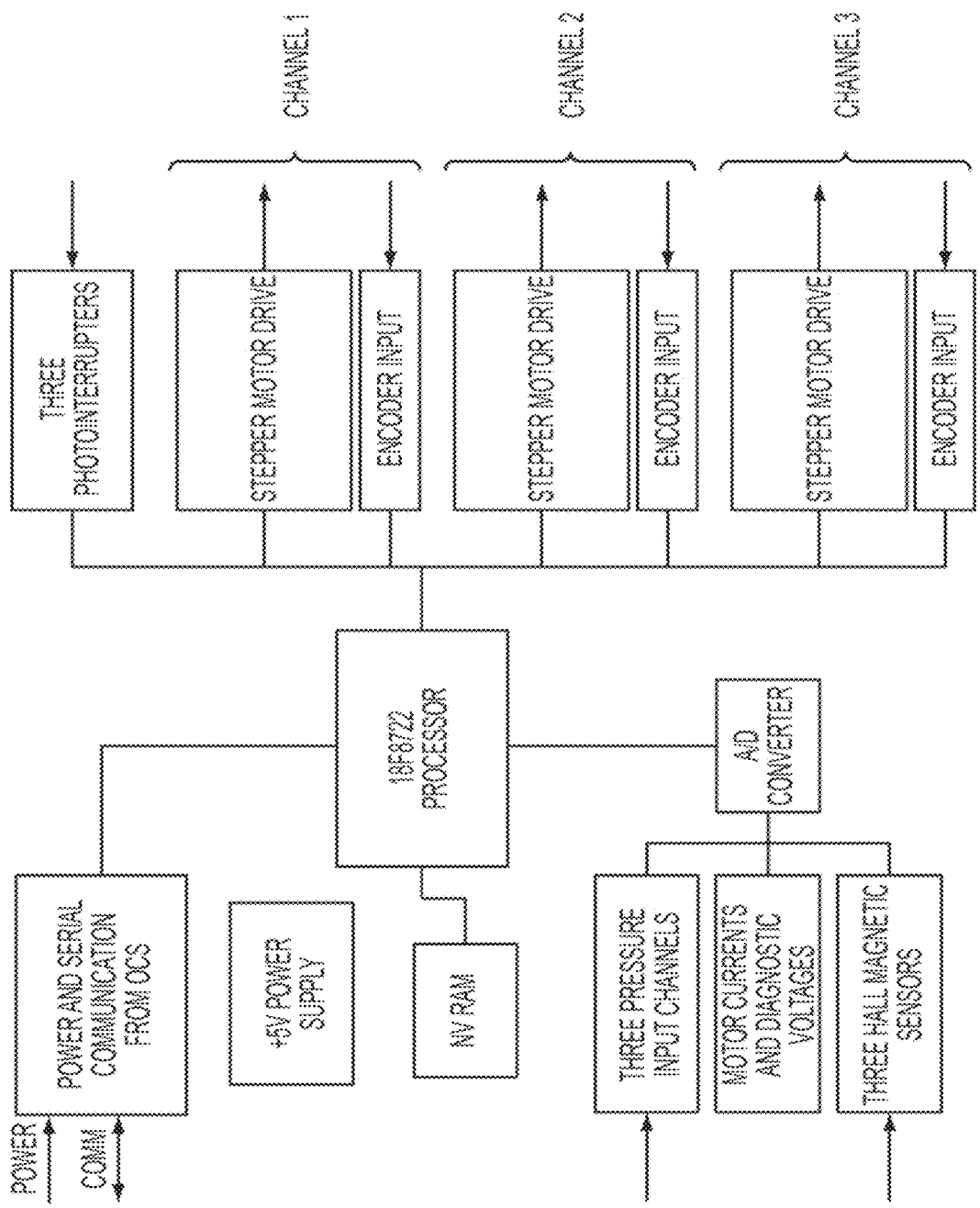

FIG. 7Q shows an exemplary embodiment of a microcontroller architecture that can be included in the solution pump 631, although this is not required and other configurations are possible. In this embodiment, the microcontroller architecture includes a processor (e.g. PIC 18F8722 processor) that receives inputs from, for example, the controller 150, pressure input sensors, motor current and diagnostic voltage sensors, Hall magnetic sensors, photo interrupters, and/or encoder inputs. Using the information it receives, the processor can provide feedback to the controller 150 and/or can control the stepper motor drive to actuate the syringes in the respective channels.

5. Gas System, Including Variable Delivery Rate Control

The multiple use module 650 can include an on-board gas supply such as one or more common gas cylinders that can fit into the gas tank bay 630 and/or an oxygen concentrator. The gas supply system can include: i) one or more regulators to reduce the pressure of the gas provided by one or more gas cylinders, ii) pressure sensors that are configured to measure the pressure in the gas supply, and ii) gas pressure gauge that can provide a visual indication of the fullness of the gas supply. Each of these components can be manually controlled and/or can be connected and automatically controlled by the controller 150. For example, the controller 150 can automatically regulate the gas flow into the gas exchanger 114. While the gas provided by the gas provided by the gas source can vary, in some embodiments, the gas supply can provide a gas comprised of 85% $O_2$, 1% $CO_2$, and the balance $N_2$ with a blend process accuracy of 0.030%, while in some embodiments the gas supply can be between 50% $O_2$ and 95% O2 and the balance $N_2$ and/or Ar. In some embodiments the multiple gasses can be supplied premixed from a single cylinder or can be provided from multiple gas cylinders and mixed within the system 600. In some embodiments gas can be supplied from a portable oxygen concentrator, such as the Oxus Portable Oxygen Concentrator from Oxus, Inc. of Rochester Hills, MI, or a Freestyle series portable oxygen concentrator available from AirSep, or Buffalo, NY.

In some embodiments the system 600 can support a gas flow rate of 0-1000 mL/min and can have a set point resolution of 50 ml/min with a gas flow delivery accuracy of ±20% in the range from 200-1000 mL/min. The system 600 and the gas supply 172 can be configured to provide a gas flow in the event of a circulatory pump fault. The ranges listed above are exemplary, and values outside of those specifically identified can also be used. Lastly, in some embodiments the system 600 and the gas supply 172 can be configured to provide an indicator of the pressure in the gas supply 172 via multiple interfaces (e.g., via a gauge on the gas supply 172 and/or the operator interface module 146).

6. Controller and User Interface

The system 600 can include a control system (e.g., controller 150) that controls the overall operation of the system 600 and the components used therein. At a general level, the control system can include an onboard computer system that is connected to one or more of the components in the system 600 and to one or more sensors, network connections, and/or user inputs. Using the information obtained from the sensors, network connections, and/or user inputs, the control system can control the various components in the system 600. For example, the control system can be used to implement one or more open or closed feedback systems to control operation of the system 600. The control system can be a common off-the-shelf computer and/or a specially designed computer system. It should be noted that although the system 600 is described conceptually with reference to a single controller, the control of the system 600 can be distributed in a plurality of controllers or processors. For example, any or all of the described subsystems may include a dedicated processor/controller. Optionally, the dedicated processors/controllers of the various subsystems may communicate with and via a central controller/processor. For example, in some embodiments, a single controller located in the multiple-use module 650 can control the entire system 600, in other embodiments a single controller located in the single-use module 634 can control the entire system 600, and in still other embodiments, the controller can be split between the single-use module 634 and the multiple-use module 650.

As a further example, in some embodiments, the controller 150 can be located on the main circuit board 718 and can perform all control and processing required by the system 600. However, in other embodiments, the controller 150 can distributed, locating some processing functionality on the front end interface circuit board 636, some on the power circuit board 720, and/or some in the operator interface module 146. Suitable cabling can be provided between the various circuit boards, depending on whether and the degree to which the controller 150 is distributed within the system 600.

Figure 8:
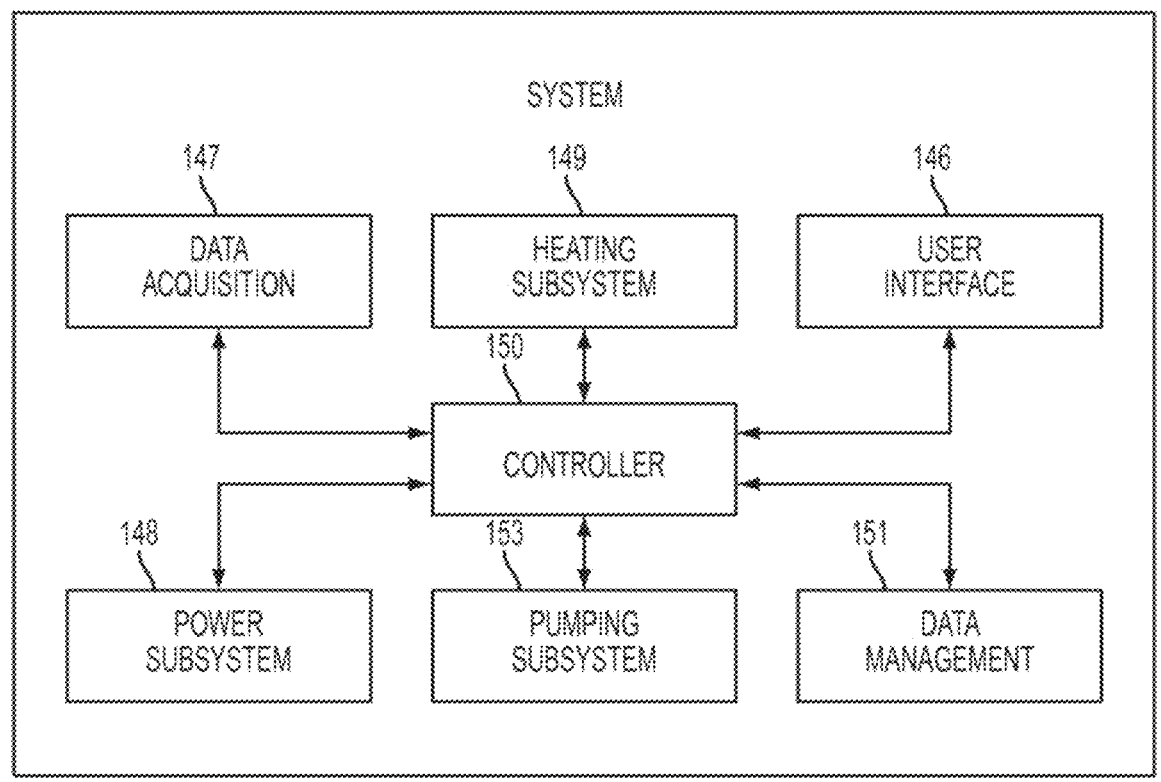
FIG. 8 shows an exemplary system that can be used within an embodiment of the organ care system.

FIG. 8 depicts an exemplary block diagram of an illustrative control scheme for the system 600. For example, the system 600 can include a controller 150 for controlling operation of the system 600. As shown, the controller 150 can connect interoperationally several subsystems: an operator interface 146 that can assist an operator in monitoring and controlling the system 600 and in monitoring the condition of the organ; a data acquisition subsystem 147 that can include various sensors for obtaining data relating to the organ and to the system 600, and for conveying the data to the controller 150; a power management subsystem 148 for providing fault tolerant power to the system 600; a heating subsystem 149 for providing controlled energy to the heater 110 for warming the perfusion fluid 108; a data management subsystem 151 for storing and maintaining data relating to operation of the system 600 and with respect to the liver; and a pumping subsystem 153 for controlling the pumping of the perfusion fluid 108 through the system 600.

Figure 9:
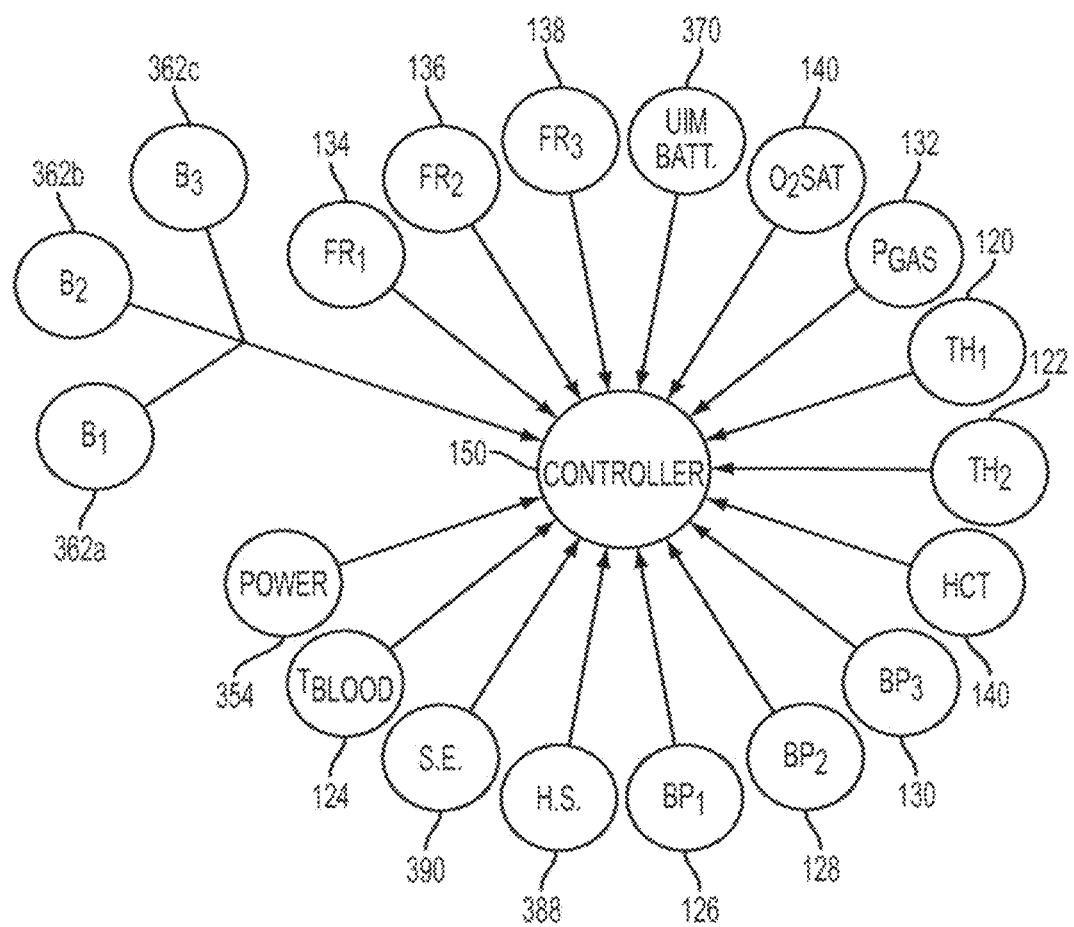
FIG. 9 shows an exemplary system that can be used within an embodiment of the organ care system.

An exemplary embodiment of the data acquisition subsystem 147 will now be described with reference to FIG. 9. In this embodiment, the data acquisition subsystem 147 include sensors for obtaining information pertaining to how the system 600 and the liver is functioning. The data acquisition subsystem 147 can provide this information to the controller 150 for processing. For example, the data acquisition subsystem 147 can be coupled to the following sensors: temperature sensors 120, 122, 124; pressure sensors 126, 128, 130 (which can be the pressure sensors 130a, 130b referred to elsewhere herein); flow rate sensors 134, 136, 138; the oxygenation/hematocrit/temperature sensor 140;

Hall sensors 388; shaft encoder 390; battery sensors 362*a*, 362*b*, 362*c*; external power available sensor 354; and operator interface module battery sensor 370; a gas pressure sensor 132. How the system 600 uses the information from the data acquisition subsystem 147 will now be described with regard to the heating 149, power management 148, pumping 153, data management 151, and operator interface 146 subsystems.

Figure 10:
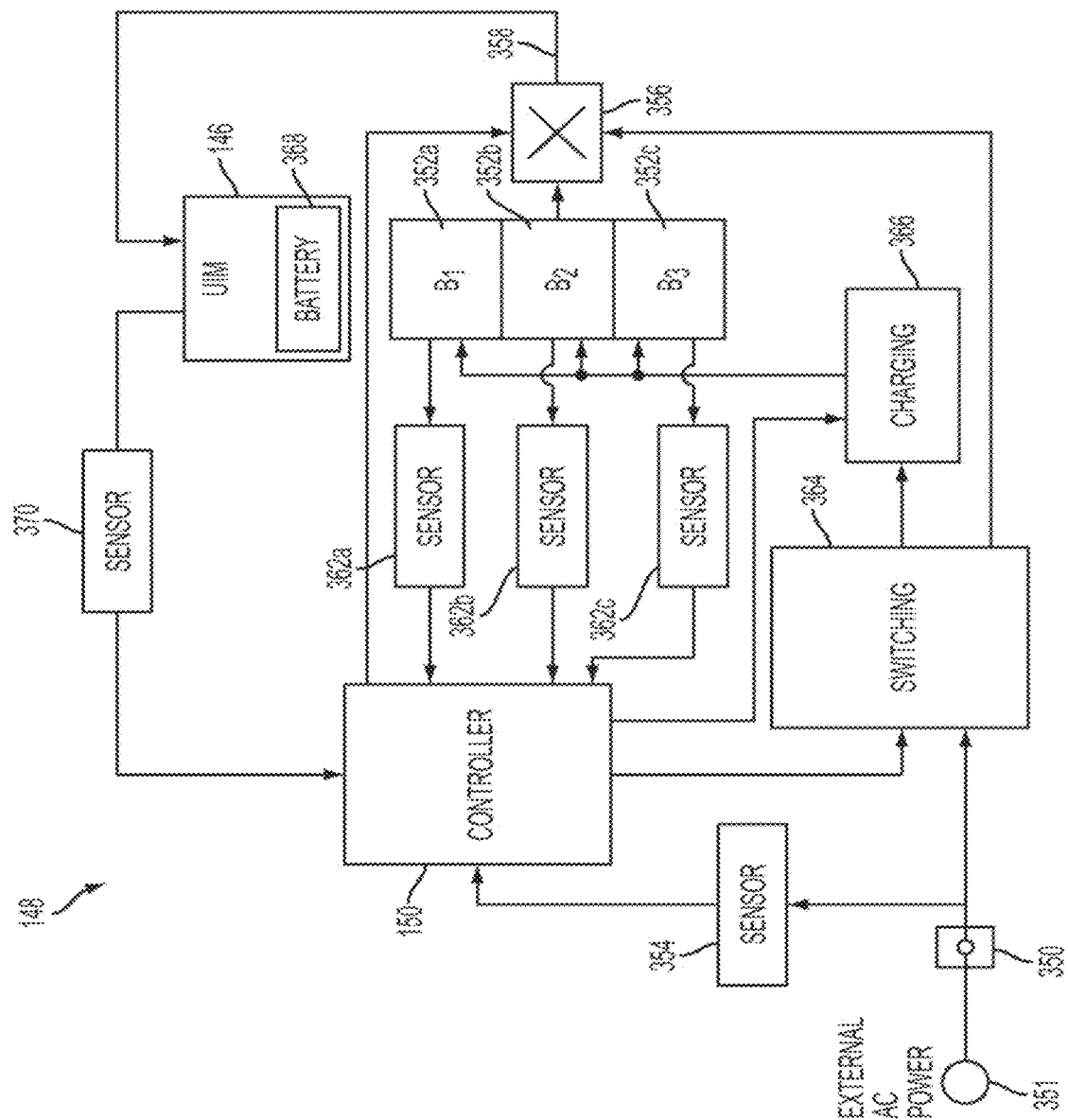
FIG. 10 shows an exemplary system that can be used within an embodiment of the organ care system.

Referring to FIG. 10, this figure depicts an exemplary block diagram of the power management system 148 for providing fault tolerant power to the system 600. The system 600 can be powered by one of multiple sources such as an external power source (e.g., 60 Hz, 120 VAC in North America or 50 Hz, 230 VAC in Europe) or by any of the one or more batteries 352. While the remainder of this description refers to an AC power source as the external power source, it is to be understood that a DC power source can also be used. The controller 150 can receive data from an AC line voltage availability sensor 354, which can indicate whether the AC voltage 351 is available and/or sufficient for use by the system 600.

In response to the controller 150 detecting that external power is not available, the controller 150 can signal the power switching circuitry 356 to provide system power from the one or more batteries 352. The controller 150 can determine from the battery charge sensors 362 which of the one or more batteries 352 is most fully charged, and can then switch that battery into operation by way of the switching network 356. The system can be designed to prevent interruptions in the operation of the system 600 as the power is switched from one source to another.

Alternatively, in response to the controller 150 detecting that suitable external power is available, the controller 150 can determine whether to use the external power for providing system power and for providing power to the user interface module 146, for charging the one or more batteries 352, and/or for charging the internal battery of user interface module 146, which can also have its own internal charger and charging controller. To use available external power (e.g., AC power 141) the controller 150 can draw the external power into the power management system 148 by signaling through the switching system 164. In the event that the external power source is AC, the power management system 148 can also receive the external AC and convert it to a DC for providing power to the system 600. The power management system 148 can be universal and can handle any line frequencies or line voltages commonly used throughout the world. According to the illustrative embodiment, in response to a low battery indication from one or more of the battery sensors 362, the controller 150 can also direct power via the switching network 364 and the charging circuit 366 to the appropriate battery. In response to the controller 150 receiving a low battery signal from the sensor 370 (which can monitor a battery in the user interface module 146), it can also or alternatively direct a charging voltage 367 to the user interface battery 368. In some embodiments, the power management subsystem 148 can select batteries to power the system 600 using an algorithm to best provide for battery longevity, including selecting in order of least-charged first as well as other factors, such as least number of charge cycles. If the battery that is currently being used to power the system 600 is removed by the user, the power management subsystem 148 can automatically switch to the next battery per the algorithm to continue powering the system 600.

Figure 11:
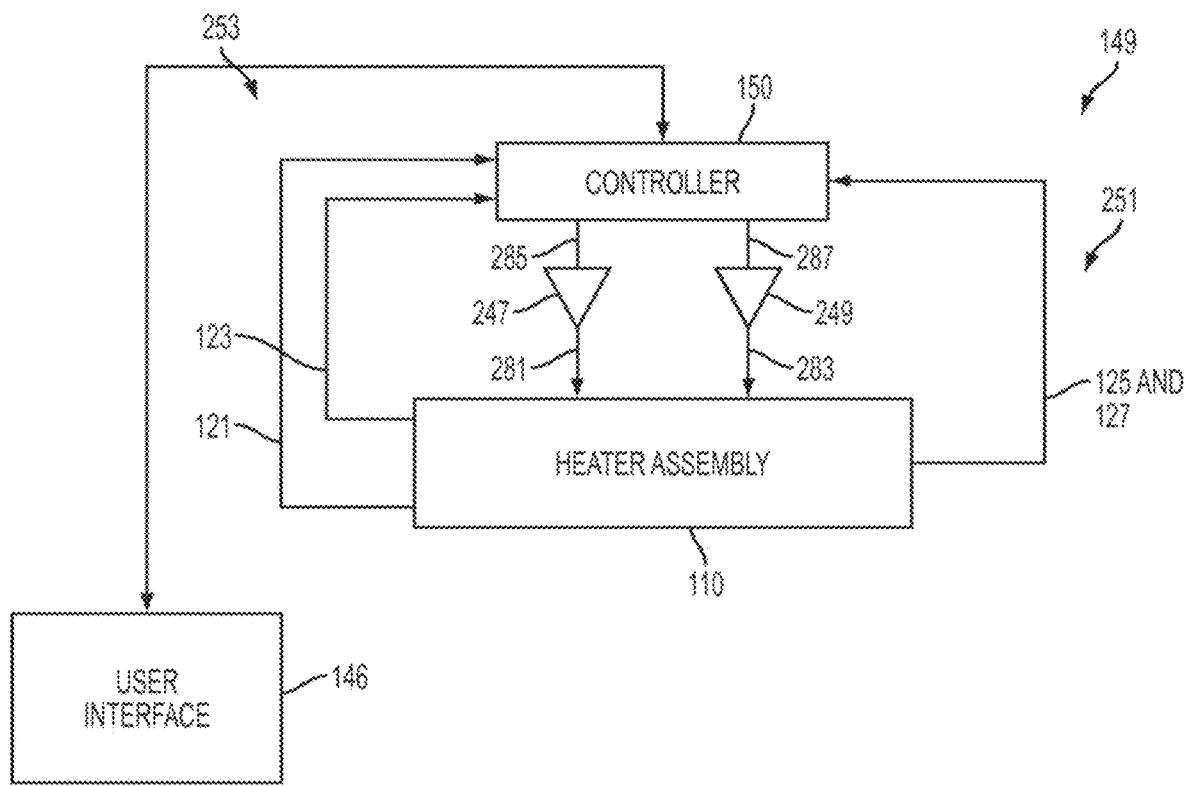
FIG. 11 shows an exemplary system that can be used within an embodiment of the organ care system.

Referring to FIG. 11, an exemplary embodiment of the heating subsystem 149 is shown. The heating subsystem 149 can control the temperature of the perfusion fluid 108 within the system 600 through, for example, a dual feedback loop approach. In the first loop 251 (the perfusion fluid temperature loop), the perfusion fluid temperature thermistor sensor 124 provides two (fault tolerant) signals 125 and 127 to the controller 150. The signals 125 and 127 are typically indicative of the temperature of the perfusion fluid 108 as it exits the heater assembly 110. The controller 150 can regulate the drive signals 285 and 287 to the drivers 247 and 249, respectively. The drivers 247 and 249 can convert corresponding digital level signals 285 and 287 from the controller 150 to heater drive signals 281 and 283, respectively, having sufficient current levels to drive the first 246 and second 248 heaters to heat the perfusion fluid 108 to within a desired temperature range. In response to the controller 150 detecting that the perfusion fluid temperatures 125 and 127 are below the desired temperature range, it can set the drive signals 281 and 283 to the first 246 and second 248 heaters, respectively, to a sufficient level to continue to heat the perfusion fluid 108. Conversely, in response to the controller 150 detecting that the perfusion fluid temperatures 125 and 127 are above the desired temperature range, it can decrease the drive signals 281 and 283 to the first 246 and second 248 heaters, respectively. In response to detecting that the temperature of the perfusion fluid 108 is within the desired temperature range, the controller 150 can maintain the drive signals 281 and 283 at constant or substantially constant levels. The temperature control system can be controlled to warm the perfusate to a temperature range between 0-50° C., and more specifically between 32-42° C., and even more specifically between 32-37° C. These ranges are exemplary only and the temperature control system can be controlled to warm the perfusate to any temperature range falling within 0-50° C. The desired temperature can be user-selectable and/or automatically controlled by the controller 150. As used herein and in the claims, "normothermic" is defined a temperature between 34-37° C.

In some embodiments, the controller 150 can vary the drive signals 281 and 283, which can control the first and second heaters, in substantially the same manner. However, this is not required. For example, each heater 246 and 248 may respond differently to a particular current or voltage level drive signal. In such a case, the controller 150 can drive each heater 246 and 248 at a slightly different level to obtain the same temperature from each. In some embodiments, the heaters 246 and 248 can each have an associated calibration factor, which the controller 150 stores and employs when determining the level of a particular drive signal to provide to a particular heater to achieve a particular temperature result. In certain configurations, the controller 150 can set one of the thermistors in dual sensor 124 as the default thermistor, and will use the temperature reading from the default thermistor in instances where the thermistors give two different temperature readings. In some embodiments, where the temperature readings are within a pre-defined range, the controller 150 can use the higher of the two readings. The drivers 247 and 249 can apply the heater drive signals 281 and 283 to corresponding drive leads 282*a* and 282*b* on the heater assembly 110.

In the second loop 253 (the heater temperature loop), the heater temperature sensors 120 and 122 can provide signals 121 and 123, indicative of the temperatures of the heaters 246 and 248, respectively, to the controller 150. According to the illustrated embodiment, a temperature ceiling can be established for the heaters 246 and 248 (e.g., by default, operator selection, or automatically determined by the controller 150), above which the temperatures of the heaters 246 and 248 are not allowed to rise. As the temperatures of the heaters 246 and 248 rise and approach the temperature ceiling, the sensors 121 and 123 can indicate the same to the controller 150, which can then lower the drive signals 281 and 283 to the heaters 246 and 248 to reduce or stop the supply of power to the heaters 246 and 248. Thus, while a low temperature signal 125 or 127 from the perfusion fluid temperature sensor 124 can cause the controller 150 to increase power to the heaters 246 and 248, the heater temperature sensors 120 and 122 ensure that the heaters 246 and 248 are not driven to a degree that would cause their respective heater plates 250 and 252 to become hot enough to damage the perfusion fluid 108.

In some embodiments, the controller 150 can be configured to maintain the perfusion fluid temperature between 0-50° C. In some embodiments the perfusate is maintained within a temperature range of 32-42° C., or in some more specific embodiments in the rage of 35-37° C. In some embodiments, the controller can be configured to limit the temperature of the heater plates 250 and 252 to 38° C., 39° C., 40° C., 41° C., or 42° C. All of the ranges and numbers identified herein are exemplary and values outside of these ranges can also be used. Lastly, to the extent that the claims recite "substantially" in connection with a specific temperature value or range, this means that the temperature is to be within the operational temperature swing range of the heater/control system used. For example, if the claimed temperature is "substantially 32° C.," and a heater/control system is used in an accused product that maintains the temperature within ±5% of a desired value, then any temperature that is ±5% of 32° C. is "substantially 32° C."

As can be seen, the second loop 253 can be configured to override the first loop 251, if necessary, such that temperature readings from temperature sensors 120 and 122 indicating that the heaters 246 and 248 are approaching the maximum allowable temperature override the effect of any low temperature signal from the perfusion fluid temperature sensor 124. In this respect, the subsystem 149 can ensure that the temperature of the heater plates 250 and 252 do not rise above the maximum allowable temperature, even if the temperature of the-perfusion fluid 108 has not reached the desired temperature value. This override feature can be particularly important during failure situations. For example, if the perfusion fluid temperature sensors 124 both fail, the second loop 253 can stop the heater assembly 110 from overheating and damaging the perfusion fluid 108 by switching control exclusively to the heater temperature sensors 120 and 122 and dropping the temperature set point to a fixed value. In some embodiments, the controller 150 can take into account two time constants assigned to the delays associated with the temperature measurements from the heaters 246 and 248 and perfusion fluid 108 to optimize the dynamic response of the temperature controls.

In some embodiments, the user can be provided with the option to disable the blood warming feature of the system 600. In this manner, the system can more efficiently support cooling of the liver during the post-preservation chilling procedure. In some embodiments, the heater assembly 110 (or a separate device, such as a gas exchanger with integrated cooling interface) can function as a chiller to cool the temperature of the perfusion fluid.

Figure 12A:
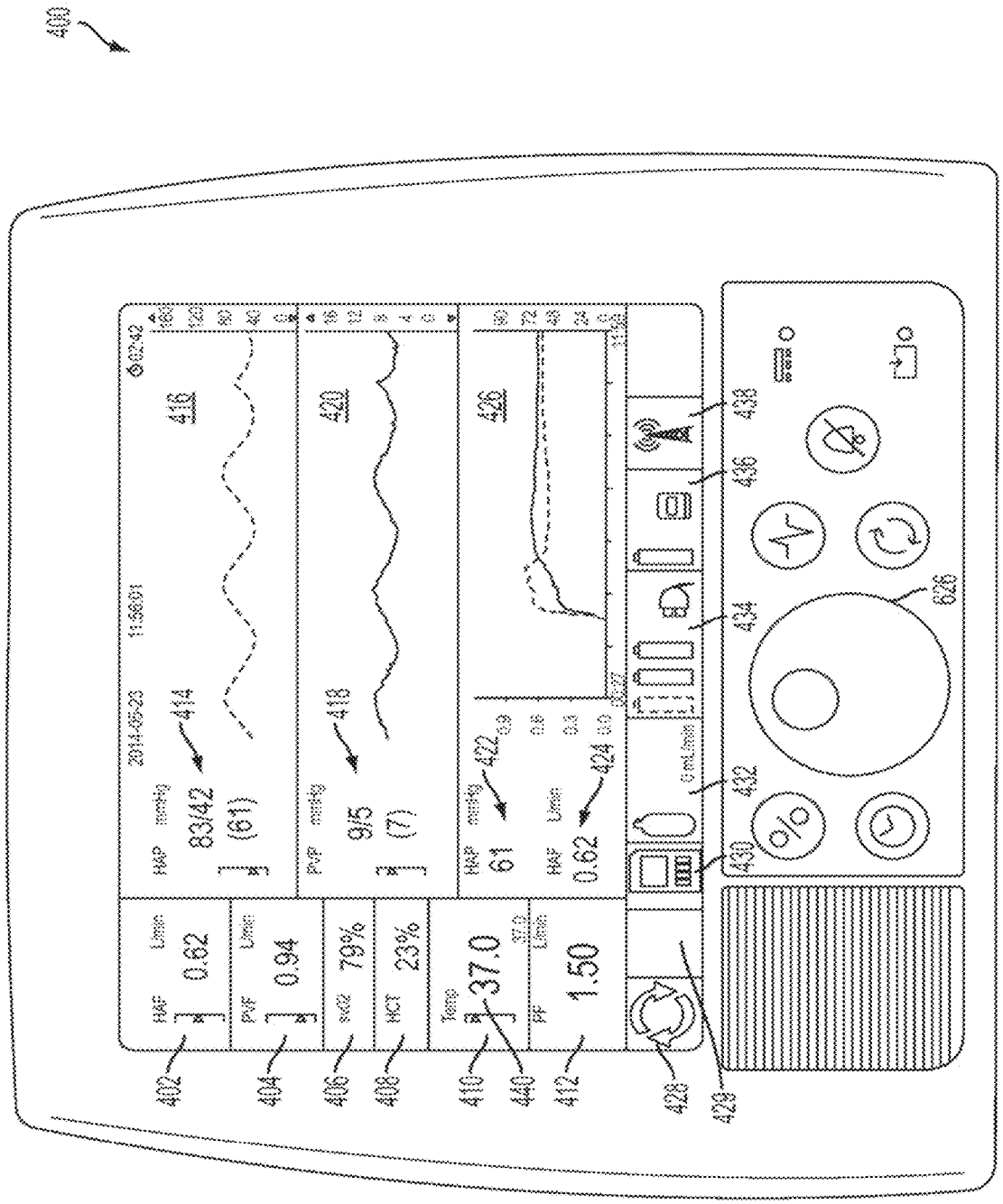
FIGS. 12A-12G show exemplary graphical user interfaces that can be used within an embodiment of the organ care system.

Turning now to the operator interface subsystem 146, FIGS. 12A-12G show various exemplary display screens of the operator interface subsystem 146. The display screens can enable the operator to receive information from and provide commands to the system 600. FIG. 12A depicts an exemplary top level "home page" screen 400. From the screen 400 an operator can typically access most if not all of the data available from the data acquisition subsystem 147, and can typically provide any desired commands to the controller 150. For example, a user can monitor and adjust the pumping subsystem 153 via the screen 400. As described in more detail in reference to FIGS. 12B-12G, the screen 400 can also allow the operator to access more detailed display screens for obtaining information, providing commands and setting operator selectable parameters.

In this exemplary embodiment, the screen 400 includes various portions each displaying different pieces of information and/or accepting different inputs. However, screen 400 is exemplary only and the information displayed by the screen 400 can be customized by the user (e.g., using dialog 590 described below in FIG. 12F). The values displayed on the screen 400 can be updated at regular intervals such as once every second. In this particular example, the screen 400 includes the following portions:

Portion 402 that displays the hepatic artery flow rate. This value can be an indication of the flow at the flow sensor 138*b*.

Portion 404 that displays the portal vein flow rate. This value can be an indication of the flow at the flow sensor 138*a*.

Portion 406 that displays the oxygen saturation ($SvO_2$) of the perfusion fluid leaving the liver as measured by, for example, the sensor 140.

Portion 408 that displays the hematocrit (HCT) level of the perfusion fluid leaving the liver as measured by, for example, the sensor 140.

Portion 410 that displays the desired and measured temperature of the perfusate. In this embodiment, the larger, top number represents the measured temperature whereas the smaller number listed below represents the temperature at which the desired perfusate temperature is set. The temperature can be measured from one of more locations such as at the output of the heater assembly 110 using the temperature sensors 120 and 122, and in some embodiments sensor 140.

Portion 412 that displays the flow rate as measured by flow sensor 136.

Portion 414 that displays systolic/diastolic pressure in the hepatic artery. The number in parentheses below the systolic/diastolic pressures is an arithmetic mean of the pressure waveform. This systolic/diastolic/mean pressure in the hepatic artery can be determined by the pressure sensor 130*a*.

Portion 416 that displays a waveform of the hepatic artery pressure over time.

Portion 418 that displays systolic/diastolic pressure in the portal vein. Number in parentheses below the systolic/diastolic pressures is an arithmetic mean of the two. The systolic/diastolic pressure in the portal vein can be determined by the pressure sensor 130*b*.

Portion 420 that displays a waveform of the portal vein pressure over time.

Portion 422 that displays the hepatic artery pressure averaged over time (e.g., two minutes).

Portion 424 that displays the hepatic artery flow rate averaged over time (e.g., two minutes).

Portion 426 that a graphical representation of the values from portion 422 and 424 over time. In this embodiment, the graph represents a 3½ hour time window. In some embodiments, the portion 426 can be controlled by the user to show different periods of time.

Portion 428 that displays an icon showing that the perfusion pump is running.

Portion 429 (which is not illuminated in this example) can show an organ type indicator that indicates which organ is being perfused and which mode of operation is being used. For example, an "M" can be used to indicate that the system 600 is in a maintenance mode.

Portion 430 that displays the status of a storage medium included in the system 600 (e.g., an SD card).

Portion 432 that displays the flow rate from the onboard gas supply. This portion can also display the amount of time remaining before the onboard gas supply runs out.

Portion 434 that displays the status of the power supply system. In this embodiment, the system 600 includes three batteries, where each battery has a corresponding status indicator showing the degree to which the battery is charged. This portion also indicates whether the system 600 is connected to an external power source (by showing a plug icon). In some embodiments, this portion can also include a numerical indication of the amount of time that the batteries can run the system 600 in the current mode of operation.

Portion 436 that displays the status and charge remaining of the battery included in the operator interface module 146. This portion can also include an indication of the amount of time remaining for which the battery in the operator interface module 146 can support it in a wireless mode of operation.

Portion 438 that displays the status of a network and/or cellular connection. This portion can also identify whether the operator interface module 146 is operating in a wireless 464 fashion, along with a graphical representation 463 of the strength of the wireless connection between the operator interface module 146 and the remainder of the system 600.

Additional portions can be displayed to show when one or more alarms and/or portions of the system 600 have been disabled by the user.

As can be seen in FIG. 12A-12G some portions can also include alarm range indicators (e.g., indicator 440) that indicates where the current value falls within an allowable range. Each portion can also include an alarm indicator (not shown) indicating that the respective values are outside of the range indicated by the corresponding range indicator. The range indicator for each respective value can be tied to the alarm values set in dialog 512 or independently set by the user. The screen 400 can be implemented on a touch screen interface. In portions that accept user input, the user can touch a specific portion to change the value therein using the knob 626.

Figure 12B:
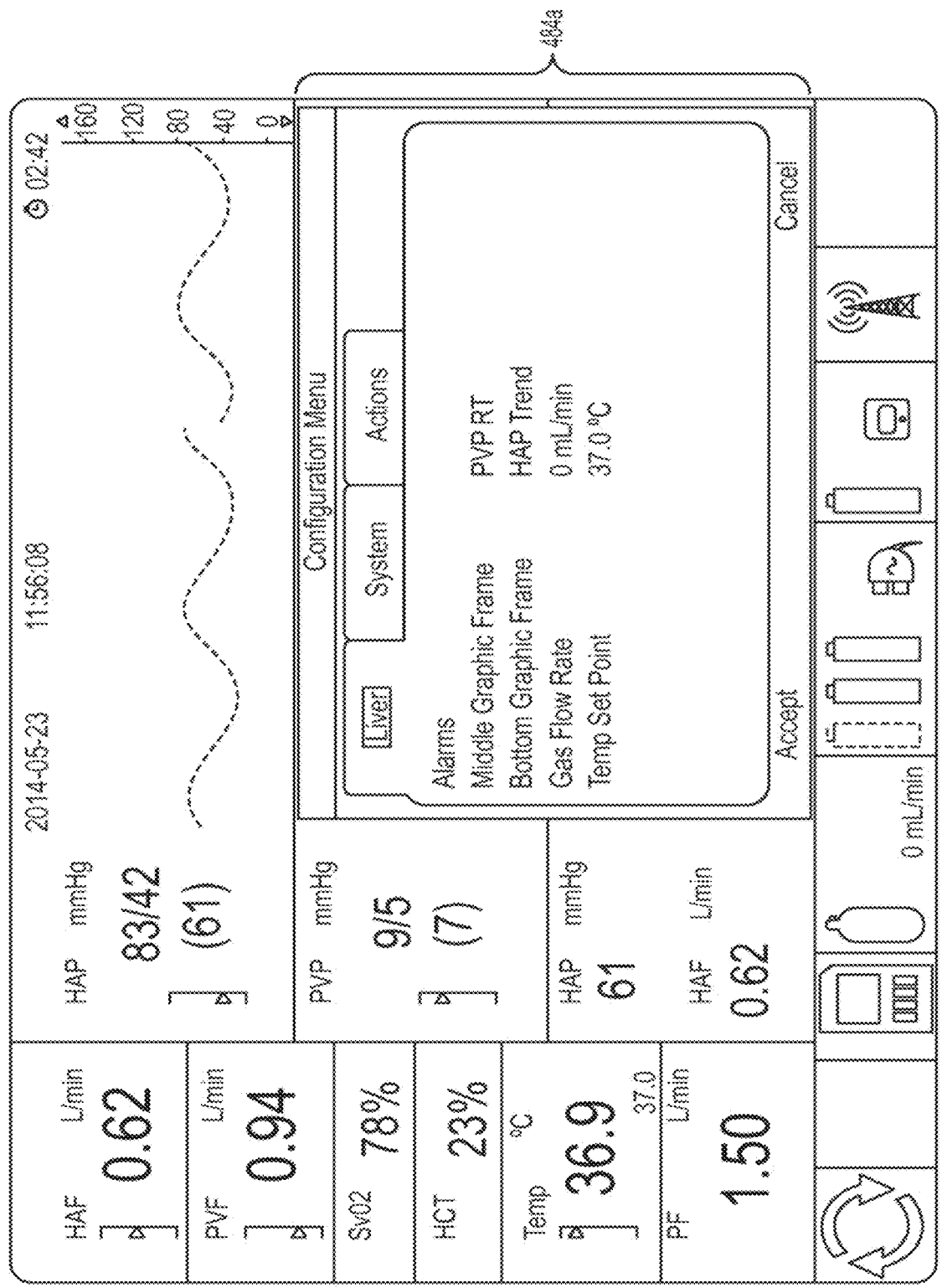
Figure 12C:
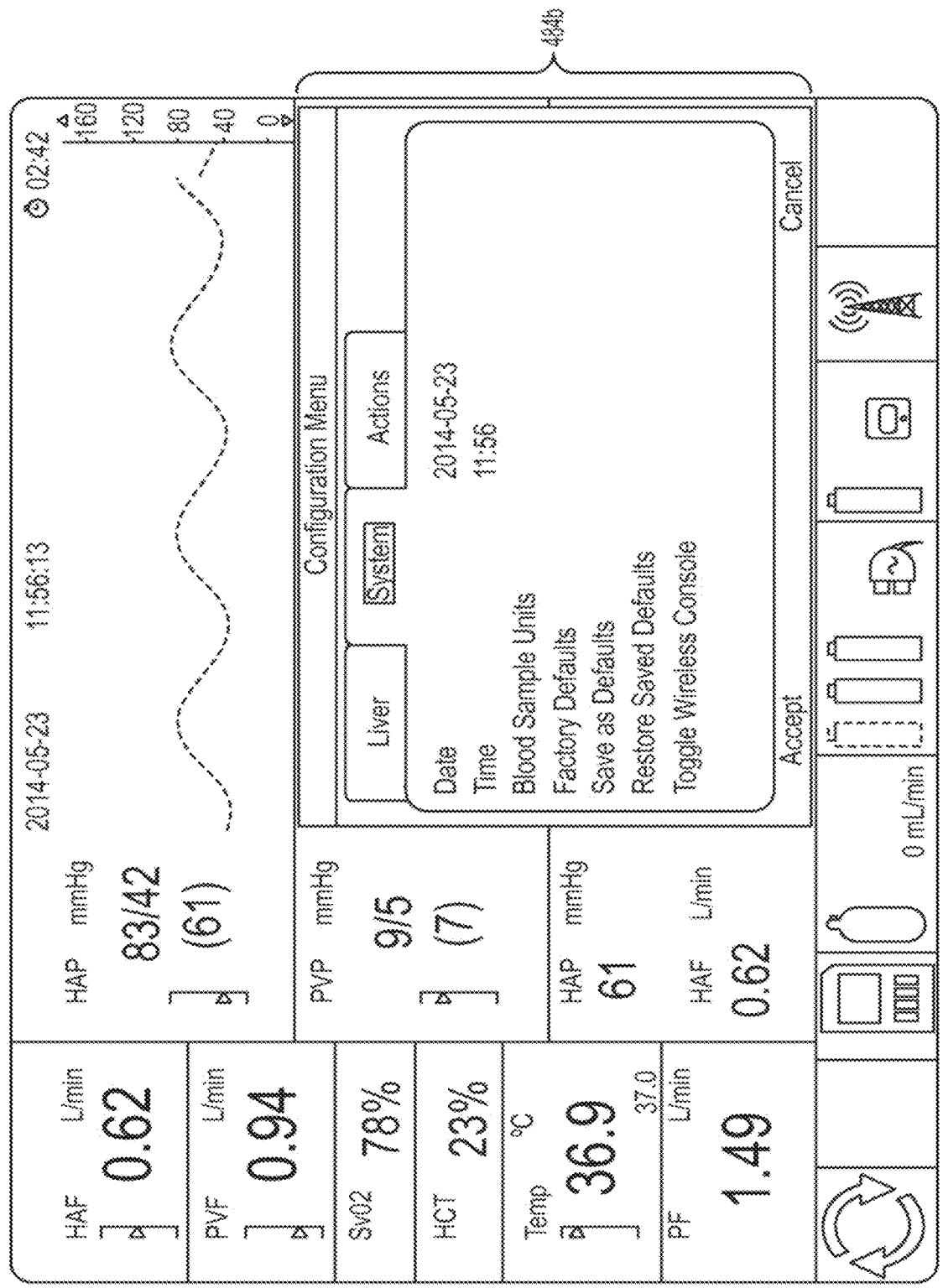
Figure 12D:
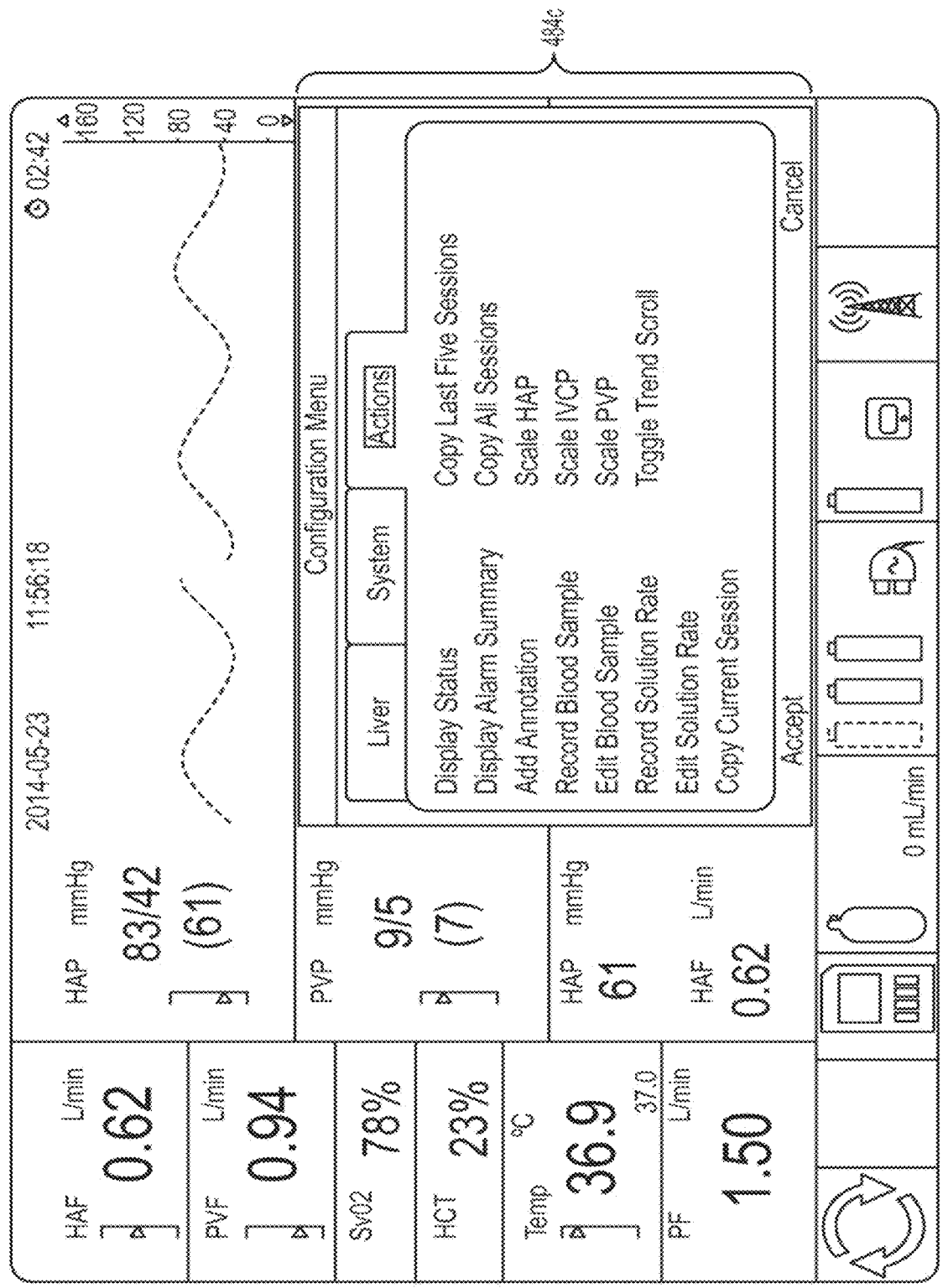

Referring to FIGS. 12B, 12C, and 12D, a user can select to enter a configuration menu 484. In some embodiments of the system, the configuration menu 484 can be limited to a portion of the screen so that the user can continue to monitor the information displayed on the screen. Using the configuration menu, the user can program desired operational parameters for the system 600. In this embodiment of the configuration menu 484, the menu has three tabbed pages 484a, 484b, 484c ("Liver," "System," and "Actions").

In tabbed page 484a, the Liver tab is shown. In this tab the user is able to enter alarm dialog 512 (described below with respect to FIG. 12E), select the data shown in the middle graphic frame, select the data shown in the bottom graphic frame, set the desired gas flow rate, and set the desired temperature. Changes made in the tabbed page 484a can be reflected in the screen 400.

In tabbed page 484b, the System tab is shown. In this tab, the user can adjust one or more display features of the system 600. For example, the user can select which units are used to display the various measurements (e.g., pascal versus mmHg), can restore factory defaults, can store new default settings, and can restore saved default settings. From this tab a service technician can also enable a wireless connection from a service laptop to the system 600. Changes made in the tabbed page 484b can be reflected in the screen 400.

In tabbed page 484c, the Actions tab is shown. In this menu, the user can display the status of the machine, display a summary of all of the alarms, can adjust the scale of displayed measurements, and/or can interact with the data stored by the system 600. For example, in some embodiments the user can withdraw a sample of the perfusion fluid and perform an external test on it. The user can then manually enter the value obtained by the external test into the data stream being maintained by the system 600. In this manner, system 600 can include all data relevant to the organ being transplanted, regardless of whether that data was generated externally from the system 600.

Figure 12E:
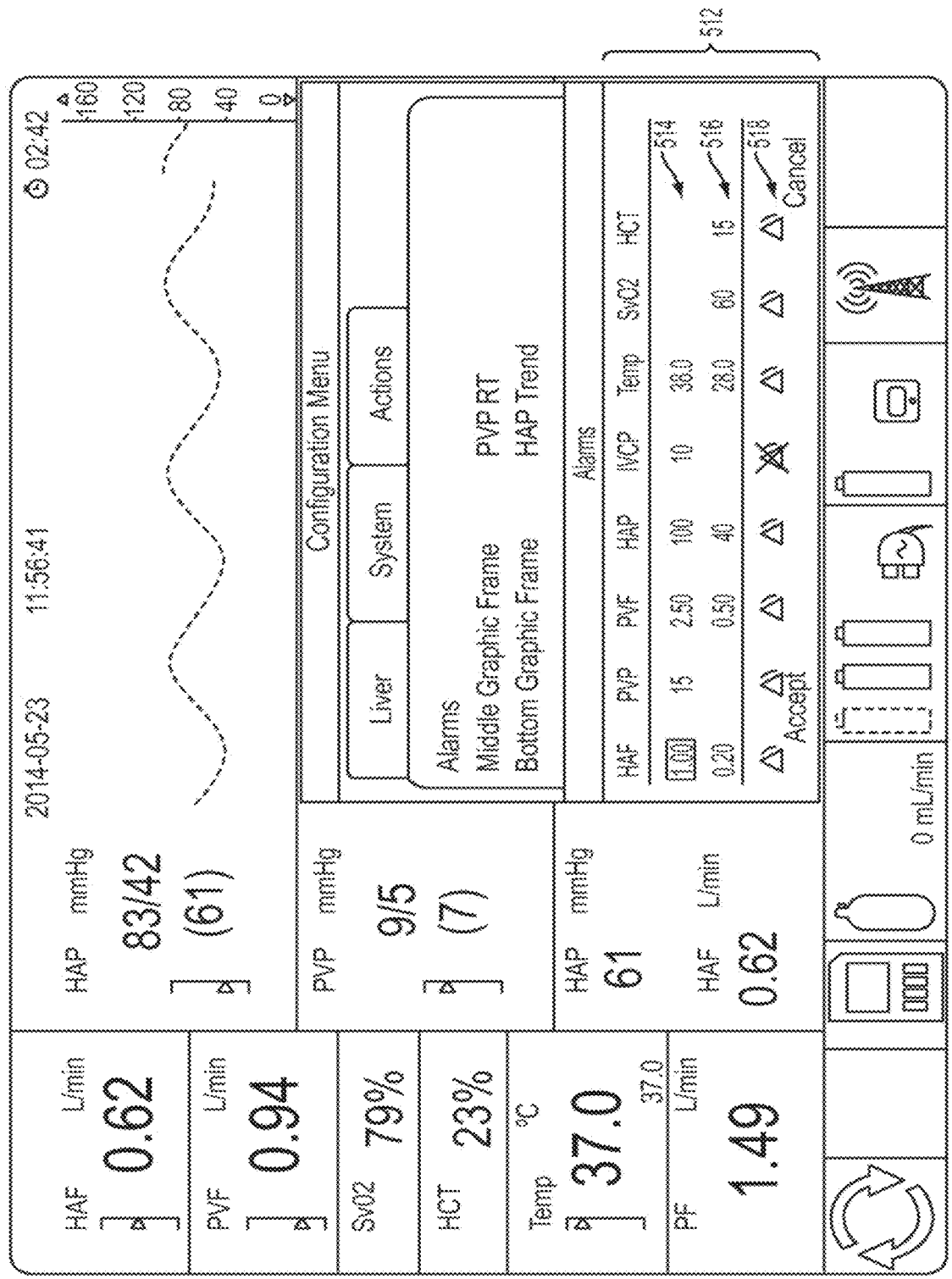

Referring to FIG. 12E, alarm dialog 512 displays the parameters associated with the operation of the system 600. In this embodiment, there are alarms for hepatic artery flow (HAF), portal vein pressure (PVP), hepatic artery pressure (HAP), inferior vena cava pressure (IVCP), perfusion fluid temperature (Temp), oxygen saturation ($SvO_2$), hematocrit (HCT). More of fewer parameters can be included in the dialog 512. Row 514 indicates an upper alarm limit (e.g., a value above this number will cause an alarm) and row 516 indicates a lower alarm limit (e.g., a value below this number will cause an alarm). The user can also enable/disable individual alarms by selecting the associated alarm icon in row 518. The icons in row 518 can indicate whether an individual alarm is enabled or disabled (e.g., in FIG. 12E the alarm for IVCP is disabled). The alarm limits can be predetermined, user settable, and/or determined in real-time by the controller 150. In some embodiments, the system 600 can be configured to automatically switch between sets of alarm limits for a given flow mode upon changing the flow mode. Changes made in the dialog 512 can be reflected in the screen 400.

Figure 12F:
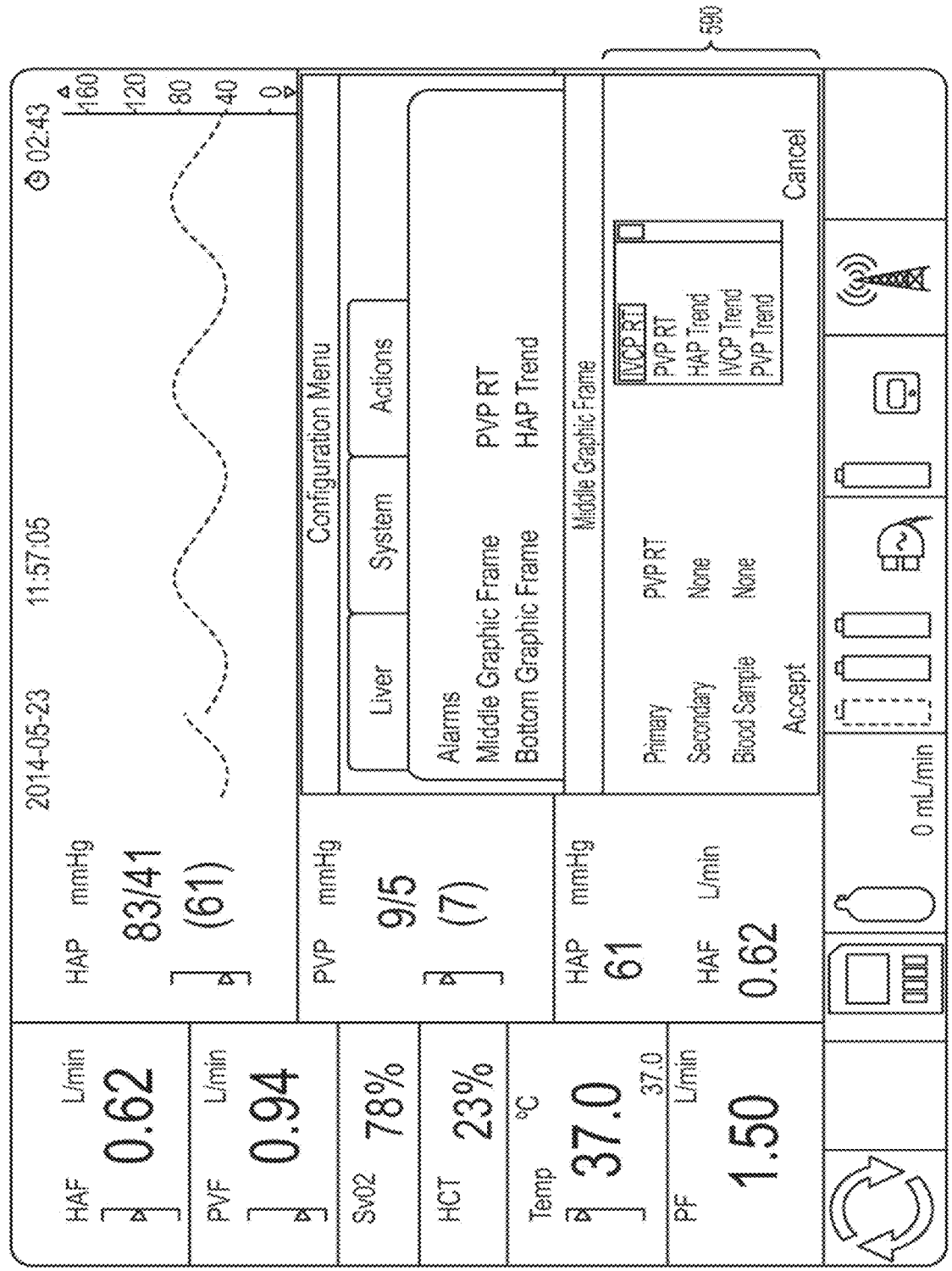

FIG. 12F shows an exemplary user interface (dialog 590) in which a user can select what the various portions of screen 400 display. For example, in FIG. 12F, the user can choose to display the realtime waveform of the hepatic artery pressure, portal vein pressure or IVC pressure, or choose to display trend graphs for those or other measured parameters in a portion of the screen 400. Other waveforms can also be calculated and displayed by the controller 150.

Figure 12G:
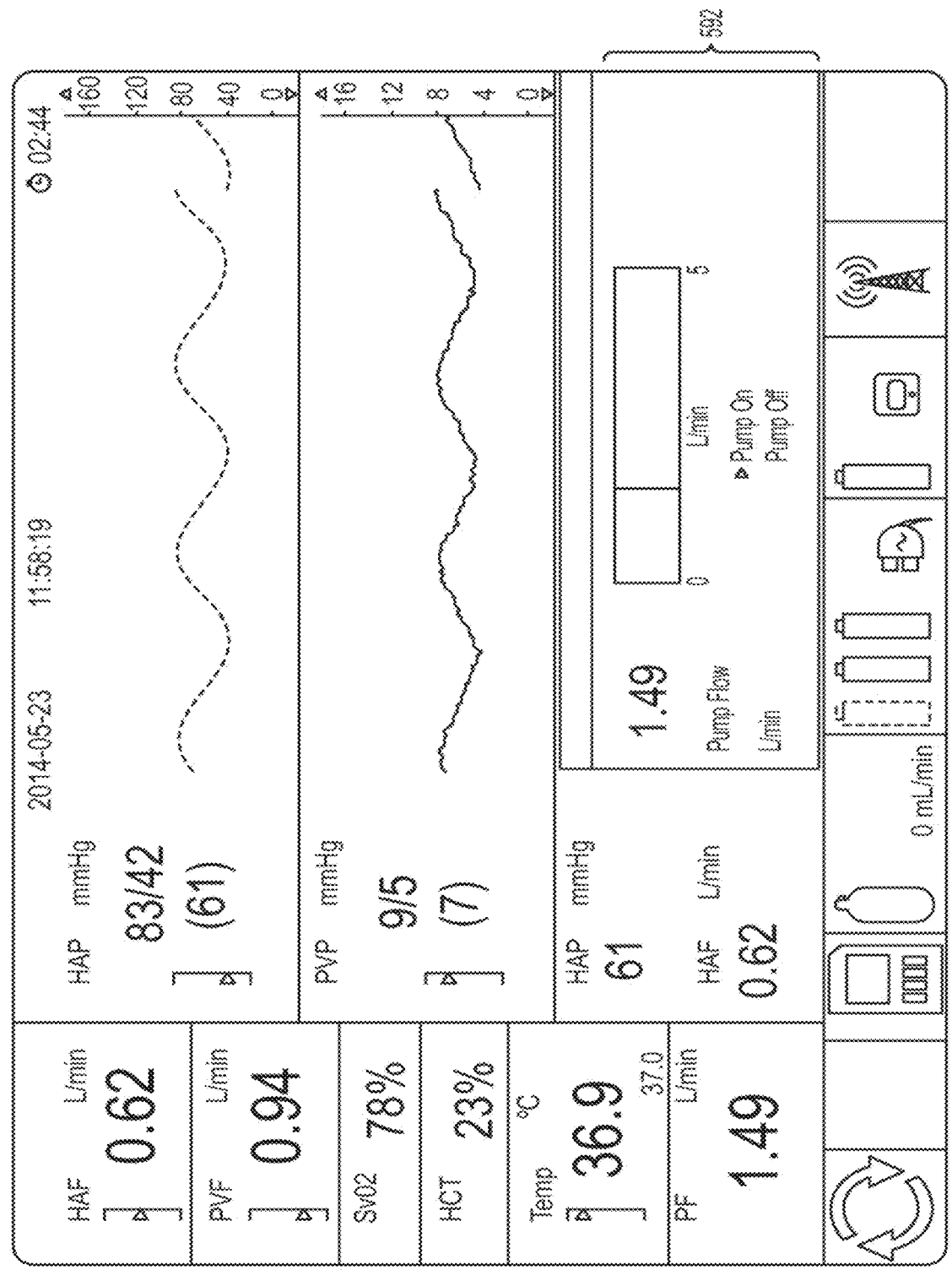

FIG. 12G shows an exemplary user interface (dialog 592) in which a user can adjust parameters of the pumping subsystem 153. In this example, the user can adjust the pump flow and turn the pump on/off.

The data management subsystem 151 can receive and store data and system information from the various other subsystems. The data and other information can be downloaded to a portable memory device and organized within a database, as desired by an operator. The stored data and information can be accessed by an operator and displayed through the operator interface subsystem 146. The data management system 151 can be configured to store in the information in one or more places. For example, the data management subsystem 151 can be configured to store data in storage that is internal to the system 600 (e.g., a hard drive, a flash drive, an SD card, a compact flash card, RAM, ROM, CD, DVD) and/or external to the system (e.g., a remote storage memory or Cloud storage).

In embodiments using external storage, the data management subsystem 151 (or another part of the controller 150) can communicate with the external storage over various communication connections such as point-to-point network connections, intranets, and the Internet. For example, the data management subsystem 151 can communicate with a remote storage medium or "the Cloud" (e.g., data servers and storage devices on a shared and/or private network) via a WiFi network (e.g., 802.11), a cellular connection (e.g., LTE), a Bluetooth (e.g., 802.15), infrared connection, a satellite-based connection, and/or a hard-wired network connection (e.g., Ethernet). In some embodiments, the data management subsystem can be configured to automatically detect the best network connection to communicate with the remote storage device and/or Cloud. For example, the data management subsystem can be configured to default to known WiFi networks and automatically switch to a cellular network when no known WiFi networks are available. Remote and Cloud based embodiments are discussed more fully below.

Figure 12H:
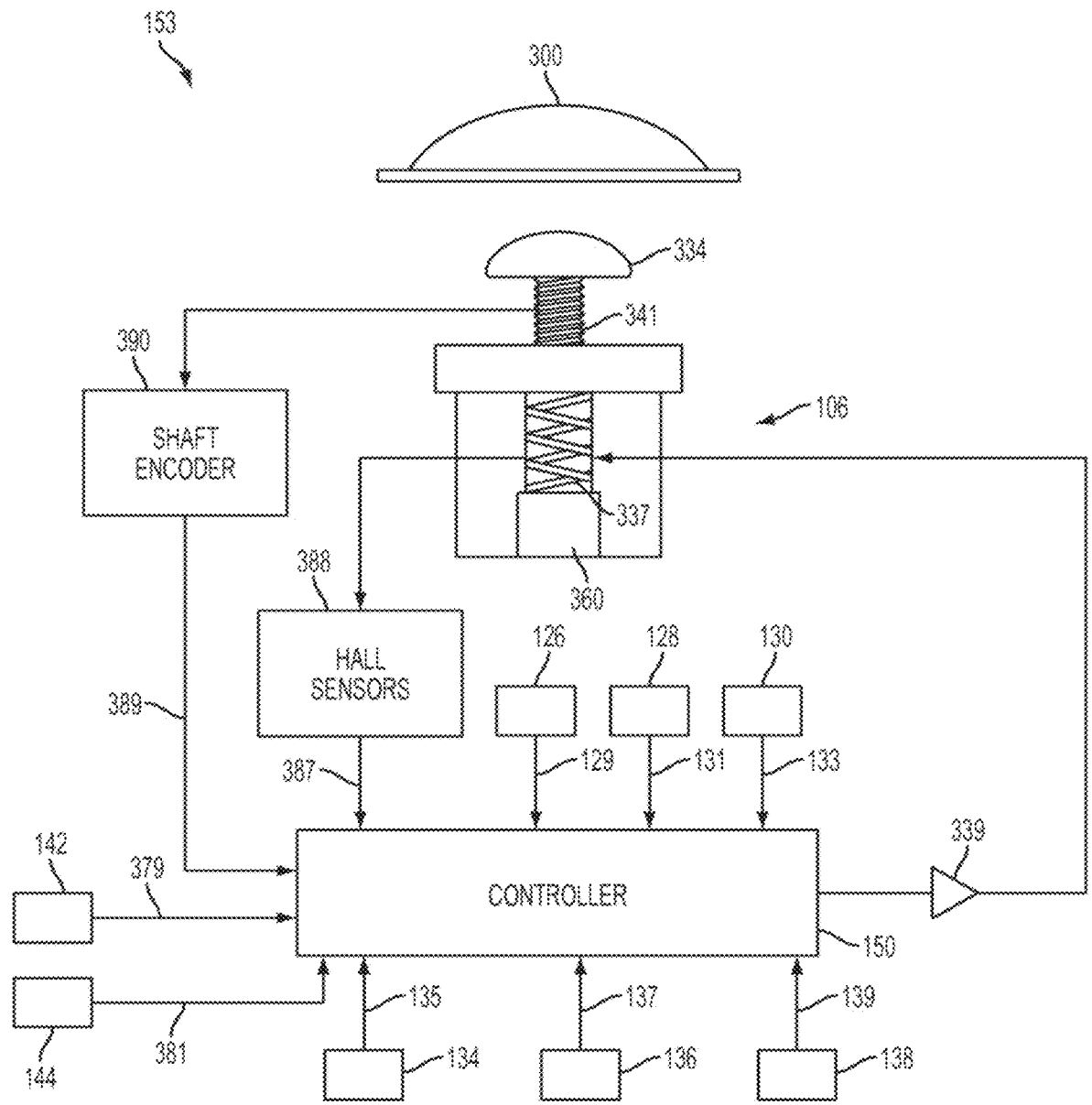
FIG. 12H shows an exemplary system that can be used within an embodiment of the organ care system.

Referring to FIG. 12H, the pumping subsystem 153 will now be described in further detail. The controller 150 can operate the pumping subsystem 153 by sending a drive signal 339 to a brushless three-phase pump motor 360 using Hall Sensor feedback. The drive signal 339 can cause the pump motor shaft 337 to rotate, thereby causing the pump screw 341 to extent and retract the pump driver 334. According to the illustrative embodiment, the drive signal 339 is controlled to change a rotational direction and rotational velocity of the motor shaft 337 to cause the pump driver 334 to extract and retract cyclically. This cyclical motion can pump the perfusion fluid through the system 600.

The controller 150 can receive a first signal 387 from the Hall sensors 388 positioned integrally within the pump motor shaft 337 to indicate the position of the pump motor shaft 337 for purposes of commutating the motor winding currents. The controller 150 can receive a second higher resolution signal 389 from a shaft encoder sensor 390 indicating a precise rotational position of the pump screw 341. From the current motor commutation phase position 387 and the current rotational position 389, the controller 150 can calculate the appropriate drive signal 339 (both magnitude and polarity) to cause the necessary rotational change in the motor shaft 337 to cause the appropriate position change in the pump screw 341 to achieve the desired pumping action. By varying the magnitude of the drive signal 339, the controller 150 can vary the pumping rate (i.e., how often the pumping cycle repeats) and by varying the rotational direction changes, the controller 150 can vary the pumping stroke volume (e.g., by varying how far the pump driver 334 moves during a cycle). Generally speaking, the cyclical pumping rate regulates the pulsatile rate at which the perfusion fluid 108 is provided to the liver, while (for a given rate) the pumping stroke regulates the volume of perfusion fluid provided to the liver.

Both the rate and stroke volume affect the flow rate, and indirectly the pressure, of the perfusion fluid 108 to the liver. As described herein, the system 600 can include three flow rate sensors 134, 136 and 138, and three pressure sensors 126, 128, and 130. The sensors 134, 136, and 138 can provide corresponding flow rate signals 135, 137 and 139 to the controller 150. Similarly, the sensors 126, 128 and 130 can provide corresponding pressure signals 129, 131 and 133 to the controller 150. The controller 150 can use all of these signals in feedback to ensure that the commands that it is providing to the perfusion pump 106 have the desired effect on the system 600. In some instances, the controller 150 can generate various alarms in response to a signal indicating that a particular flow rate or fluid pressure is outside an acceptable range. Additionally, employing multiple sensors enables the controller 150 to distinguish between a mechanical issue (e.g., a conduit blockage) with the system 600 and a biological issue with the liver.

While the above discloses the use of three pressure sensors, this is not required. In many of the embodiments described herein only two pressure sensors are used (e.g., pressure sensors 130a, 130b). In this instance, the input for the third pressure sensor can be ignored. However, in some embodiments of the system disclosed herein a third pressure sensor can be used to measure the pressure in the perfusion fluid flowing from the inferior vena cava (or elsewhere in the system 100). In this instance, the controller 150 can process the pressure signal from the sensor as described above.

The pumping system 153 can be configured to control the position of the pump driver 334 during each moment of the pumping cycle to allow for finely tuned pumping rate and volumetric profiles. This can enable the pumping system 153 to supply perfusion fluid 108 to the liver with any desired pulsatile pattern. According to one illustrative embodiment, the rotational position of the shaft 337 can be sensed by the shaft encoder 390 and adjusted by the controller 150 at least about 100 increments per revolution. In another illustrative embodiment, the rotational position of the shaft 337 is sensed by the shaft encoder 390 and adjusted by the controller 150 at least about 1000 increments per revolution. According to a further illustrative embodiment, the rotational position of the shaft 337 is sensed by the shaft encoder 390 and adjusted by the controller 150 at least about 2000 increments per revolution. The position of the pump screw 341 and thus the pump driver 334 can be calibrated initially to a reference position of the pump screw 341.

As described above, the system 600 can be manually controlled using the controller 150. However, some or all of the control of the system can be automated and performed by the controller 150. For example, the controller 150 can be configured to automatically control the pump 106 flow of the perfusion fluid (e.g., pressure flow rate), the solution pump 631, the pump 106, the gas exchanger 114, the heater 110, and/or the flow clamp 190. Control of the system 600 can be accomplished using minimal, or even no intervention by the user. For example, the controller 150 can be programmed with one or more predetermined routines and/or can use information from the various sensors in the system 600 to implement open and/or closed feedback loops. For example, if the controller determines that the oxygenation level of the perfusion fluid flowing out of the IVC is too low or the $CO_2$ level is too high, the controller 150 can adjust the supply of gas to the gas exchanger 114 accordingly. As another example, the controller 150 can control the infusion of one or more solutions based on the sensor 140 and/or any other sensor in the system 600. As a still further example, if the controller senses that the liver is producing too much $CO_2$, the controller can reduce the temperature of the liver to 35° C. (assuming it was previously being maintained as a higher temperature) to reduce the metabolic rate, and accordingly the rate of $CO_2$ production or $O_2$ consumption. As yet another example, the controller 150 can modulate gas flow to the gas exchanger 114 based on measurements from one or more sensors in the system 600.

In some embodiments, the controller 150 can be configured to control aspects of the system 600 as a function of lactate value in the perfusion fluid. In one embodiment, multiple perfusion fluid lactate values can be obtained over time. For example, a user can withdraw a perfusion fluid sample and use an external blood gas analyzer to determine a lactate value and/or the system 600 can use an onboard lactate sensor (e.g., a lactate sensor located in the measurement drain 2804). The lactate value can be measured in the IVC or elsewhere and can be repeated at predetermined time intervals (e.g., every 30 minutes). The controller 150 can analyze the trend of the lactate values over time. If the lactate is trending down or staying relatively even, this can be an indication that the liver is being properly perfused. If the lactate is trending upwards, this can be in indication of improper perfusion, which can result in the controller 150 increasing pump flow, adjusting the rate of infused vasodilator, and/or modifying the gas flow to the gas exchanger 114.

Automating the control process can provide many benefits including providing finer control over the parameters of the system, which can result in a healthier liver and/or reducing the burden on the user.

In some embodiments, the system 600 can include a global positioning device to track the geographic location of the system.

C. Exemplary Single Use Module

Turning now to the single use module, an exemplary embodiment is described herein as the single-use module 634, although other embodiments are possible. As noted above, this portion of the system 600 typically contains at least all of the components of the system 600 that come into contact with biological material such as the perfusate along with various peripheral components, flow conduits, sensors, and support electronics used in connection with the same. After the system 600 is used to transport an organ, the single-use module can be removed from the system 600 and discarded. A new (and sterile) single-use module can be installed into the system 600 to transport a new organ. In some embodiments, the module 634 does not include a processor, instead relying on the controller 150, which can be distributed between the front end interface circuit board 636, the power circuit board 720, the operator interface module 146, and the main circuit board 718, for control. However, in some embodiments, the single-use module can include its own controller/processor (e.g., on the front end circuit board 637).

Referring to FIGS. 13A-13H, an exemplary single use module 634 is shown. FIGS. 13M-R show another exemplary single use module 634 with an alternatively shaped organ chamber 104. Note, however, in some of the views certain components have been omitted to clarify the drawings (e.g., some of the tubing connectors, ports, and/or clamps have been omitted).

The single-use module 634 can include a chassis 635 having upper 750a and lower 750b sections. The upper section 750a can include a platform 752 for supporting various components. The lower section 750b can support the platform 752 and can include structures for pivotably connecting with the multiple use module 650.

The lower chassis section 750b can include a C-shaped mount 656 for rigidly mounting the perfusion fluid pump interface assembly 300, and the projection 662 for sliding into and snap fitting with the slot 660. In some embodiments, the lower chassis section 750b can also provide structures for mounting parts of the perfusion circuit including the following components: gas exchanger 114, heater assembly 110, reservoir 160, perfusate flow compliance chambers 184, 186. In some embodiments, the lower chassis section 750b can also contain, via appropriate mounting hardware, various sensors such as the sensor 140, the flow rate sensors 136, 138a, 138b, and the pressure sensors 130a, 130b. The lower chassis section 750b can also mount the front end circuit board 637. This embodiment is exemplary only, and components listed above as being part of the lower chassis section 750b can be located elsewhere such as in the upper section 750a (e.g., the pressure sensors 130a, 130b).

Figure 13A:
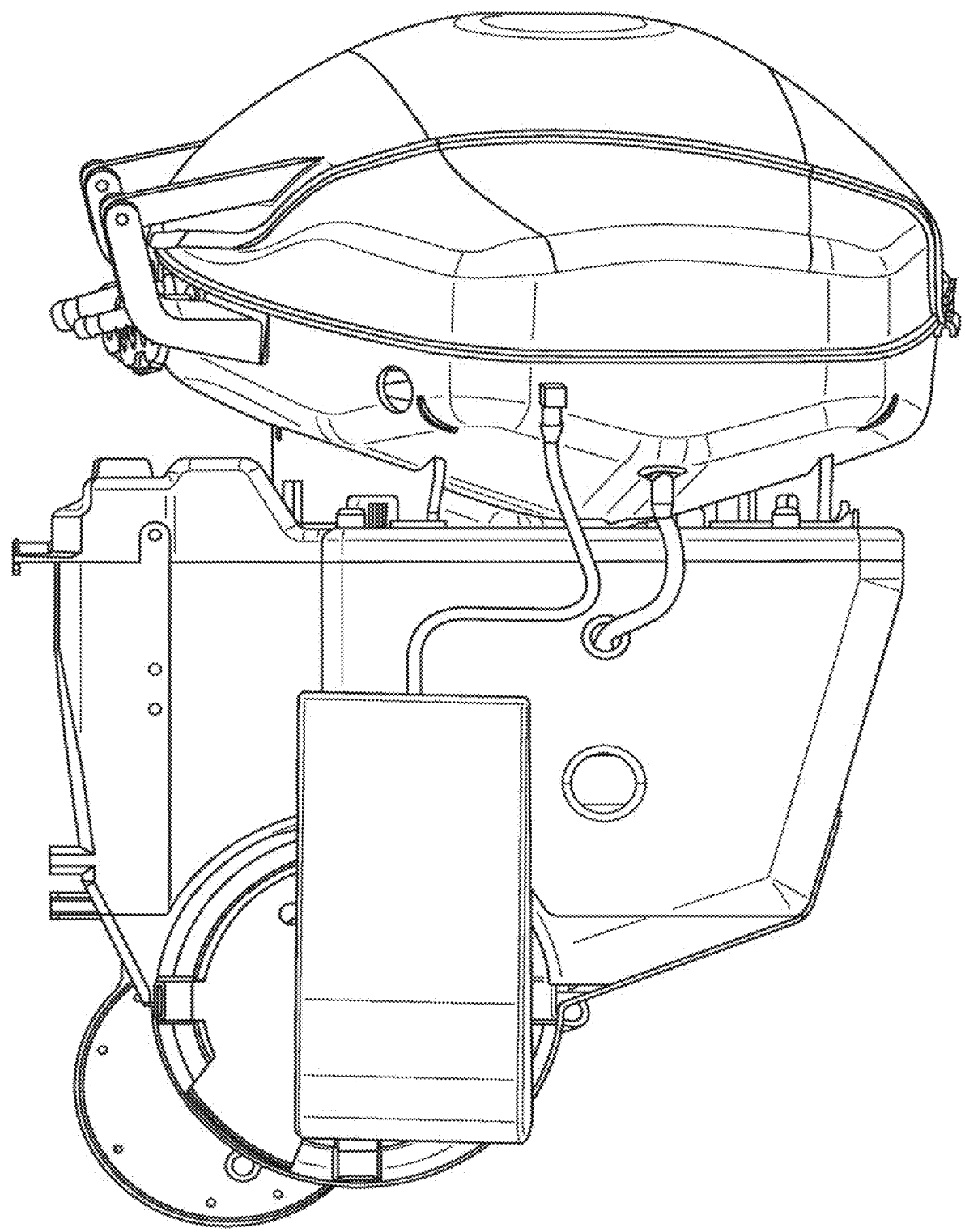
FIGS. 13A-13R show exemplary embodiments of a single use module and components thereof that can be used in an embodiment of the organ care system.
Figure 13B:
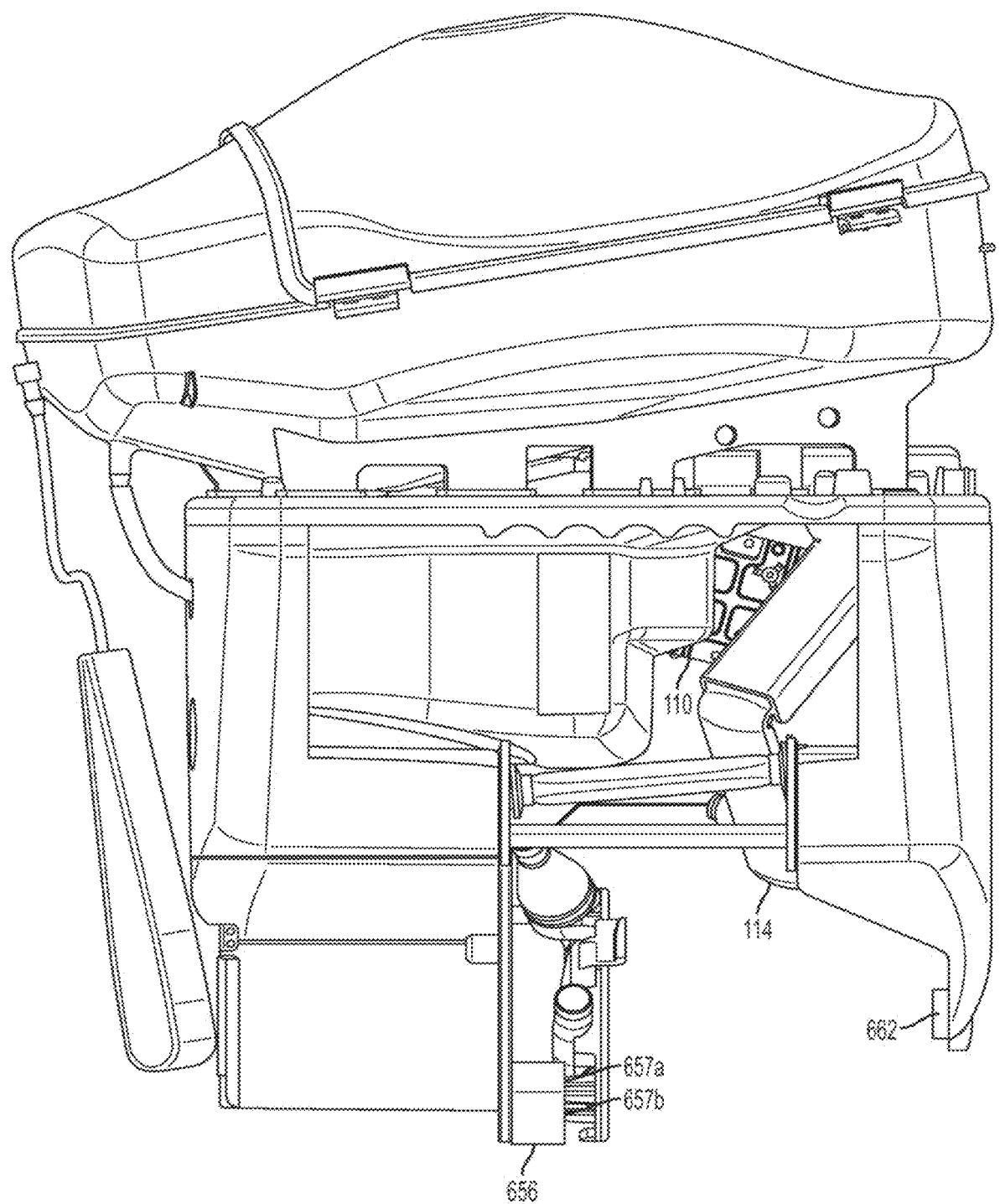
Figure 13C:
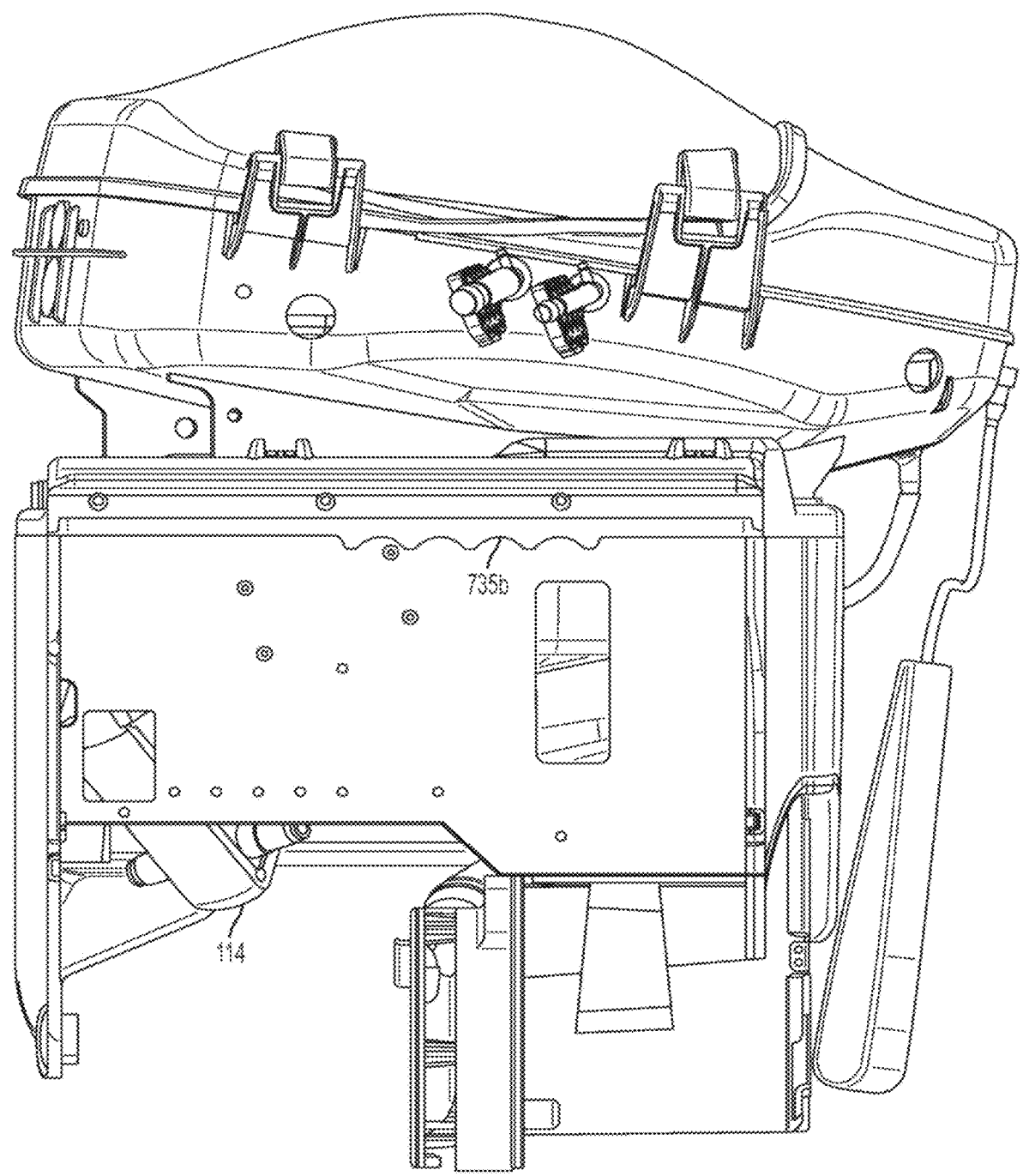
Figure 13D:
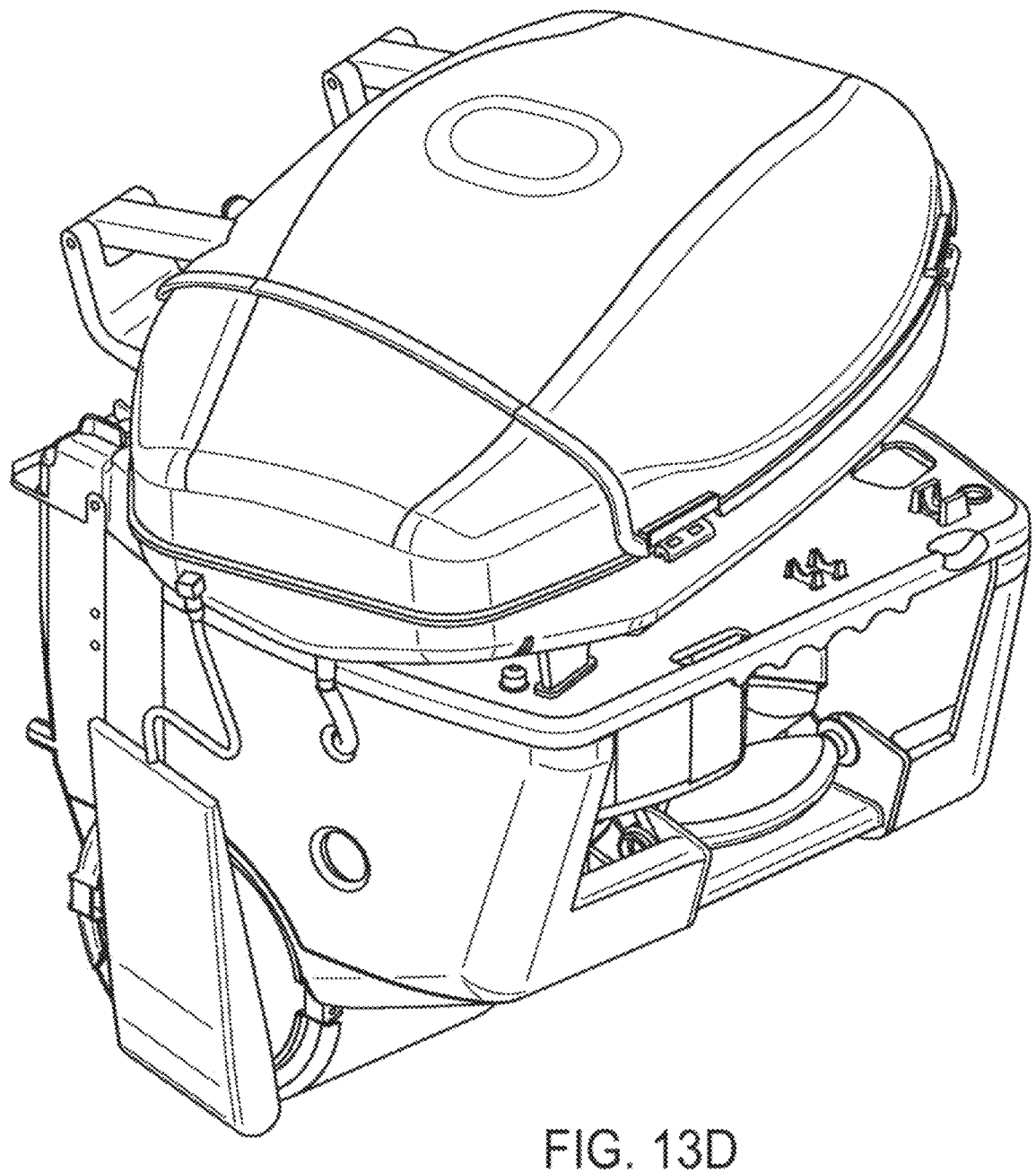
Figure 13E:
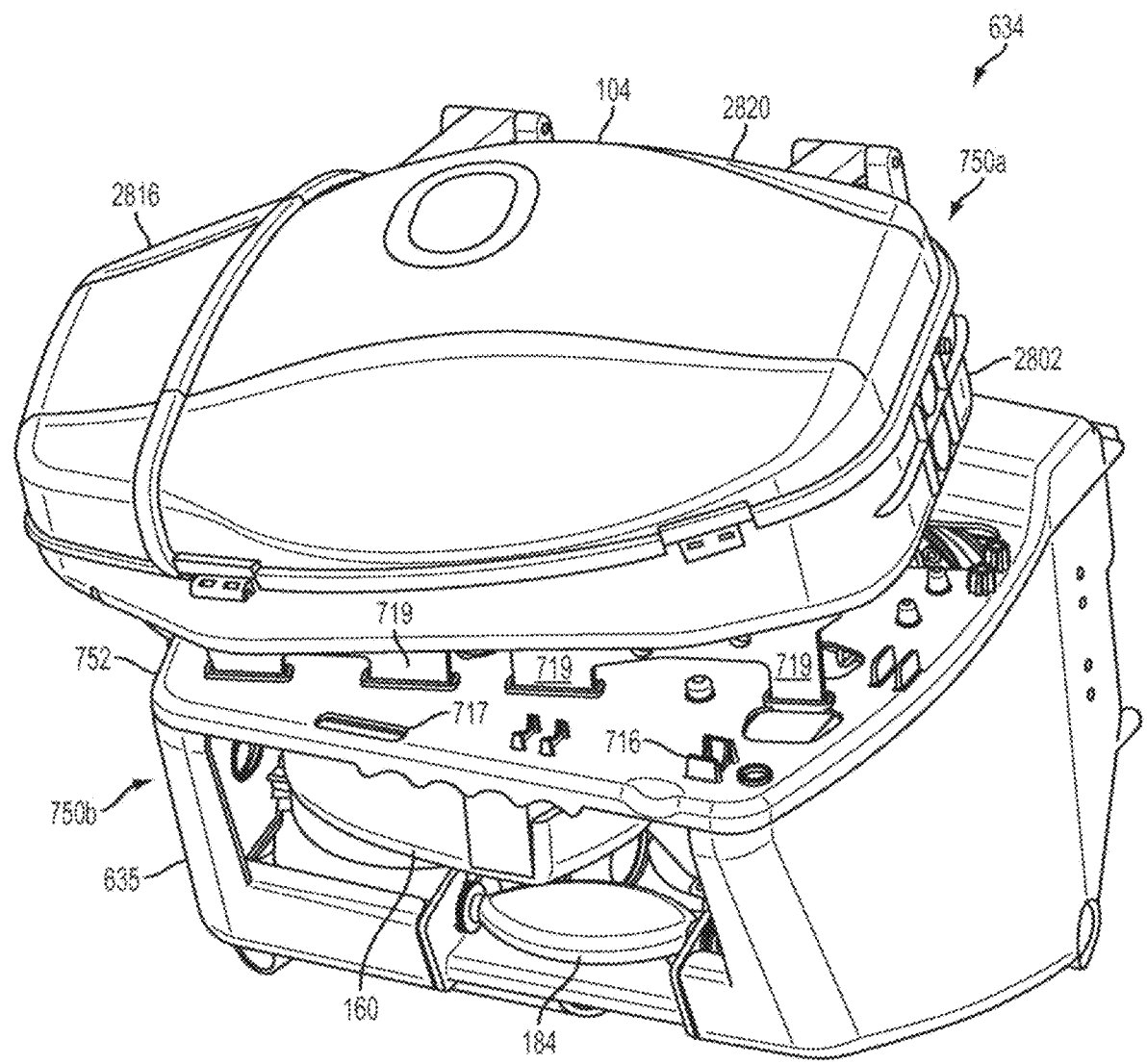
Figure 13F:
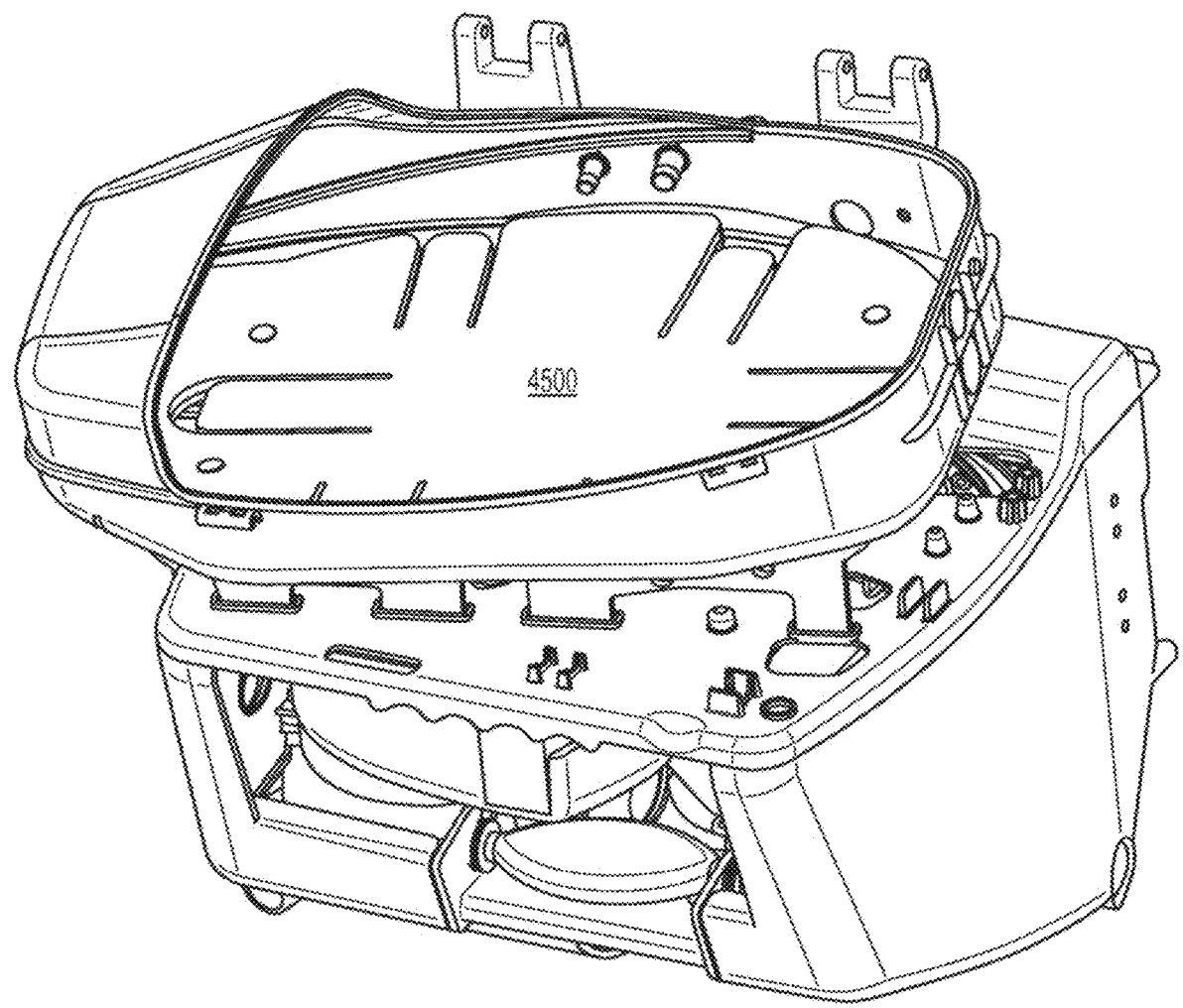
Figure 13H:
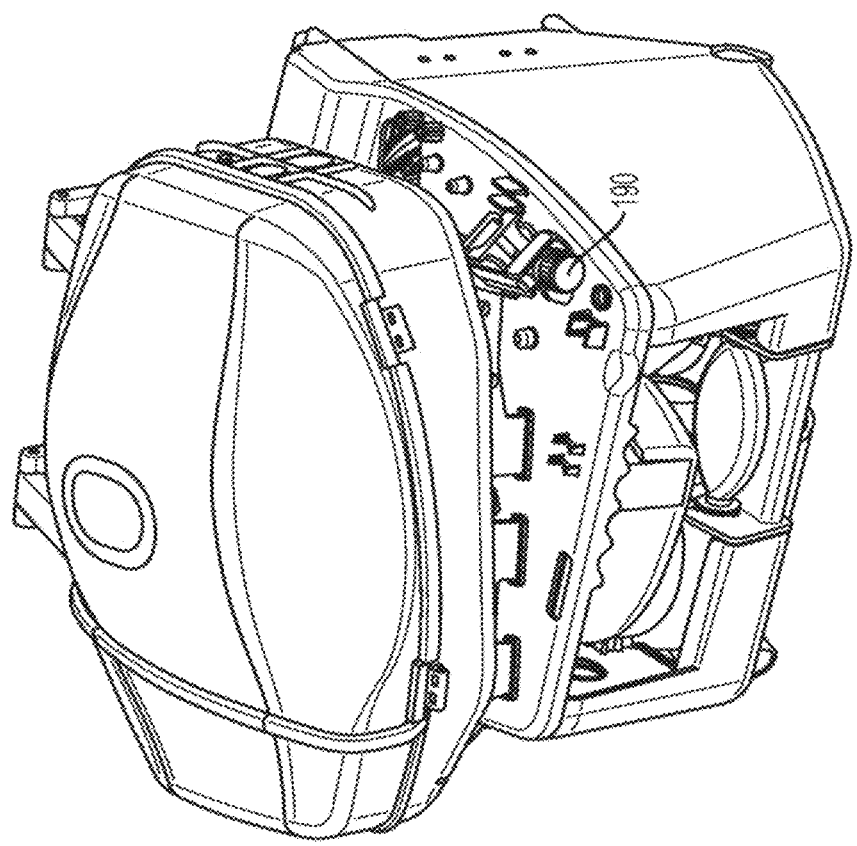
Figure 13G:
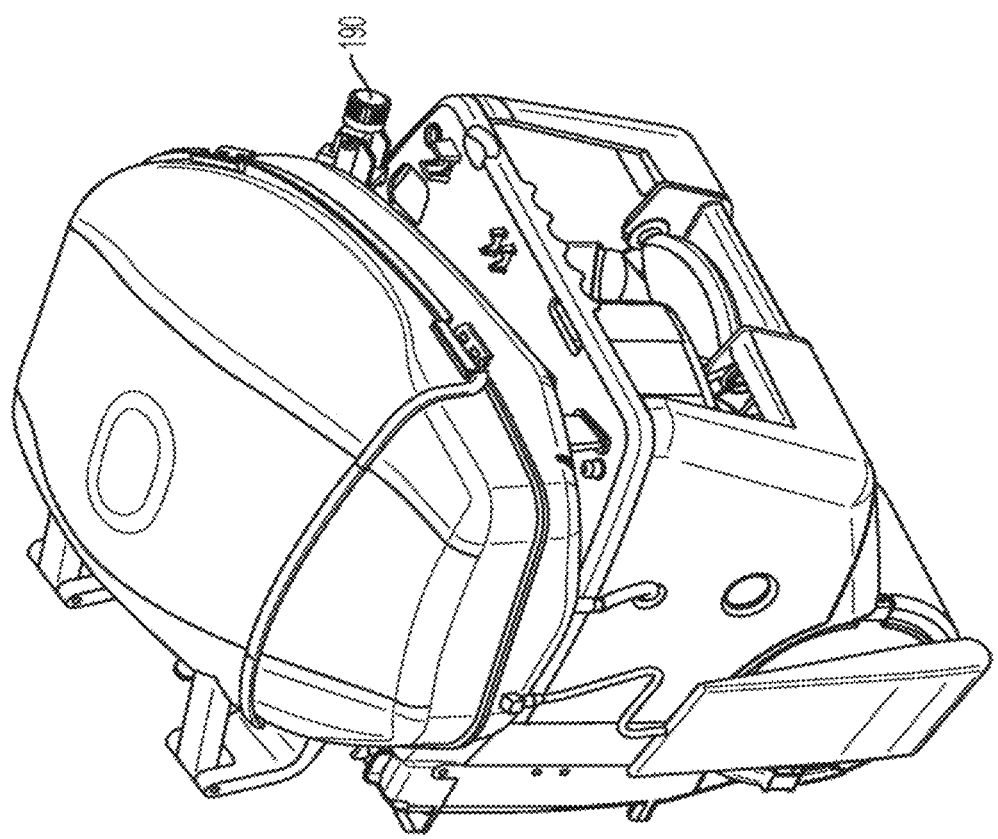
Figure 13I:
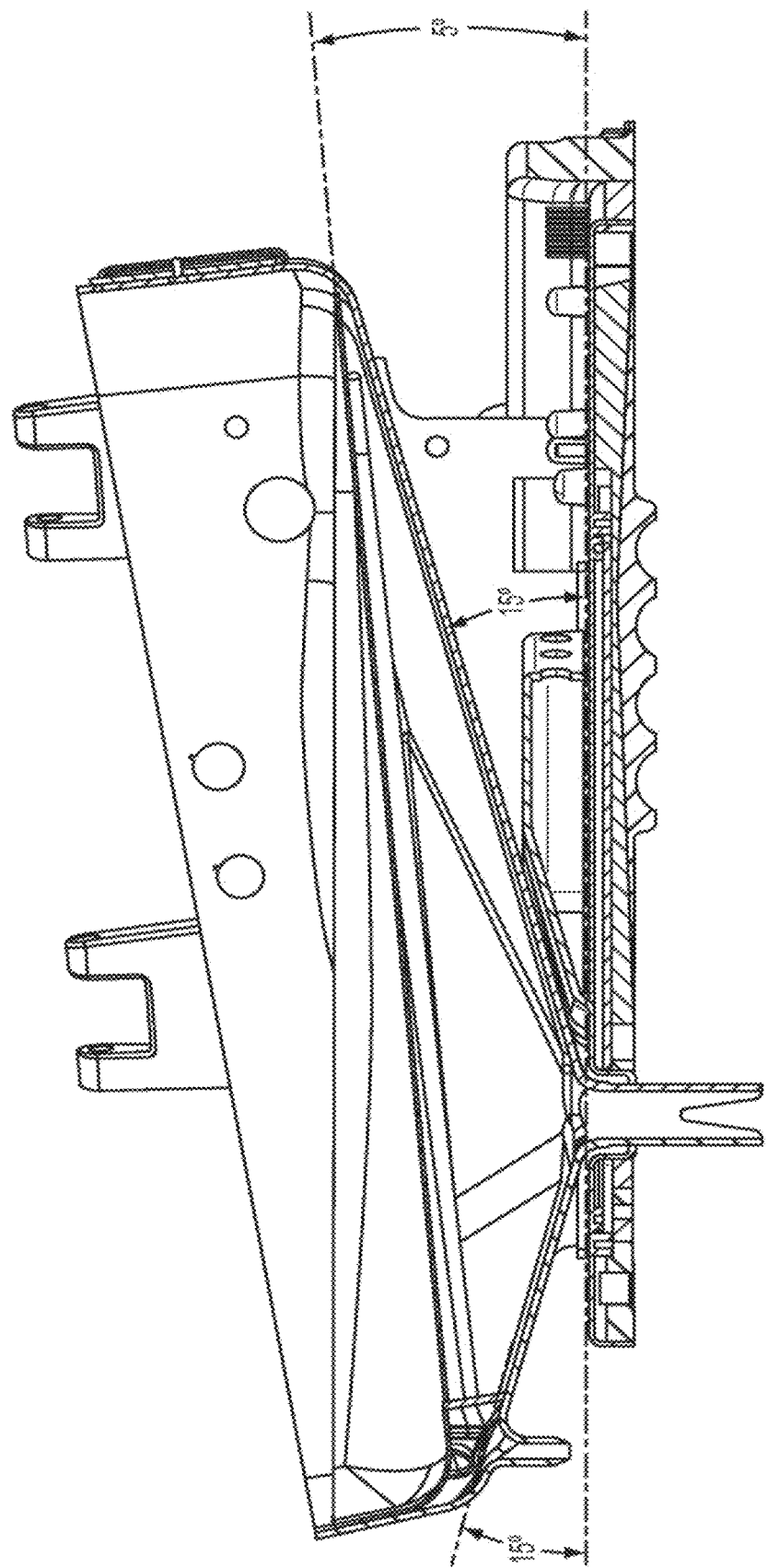

The upper chassis section 750a can include the platform 752. The platform 752 can include handles 753a and 753b formed therein to assist in installing and removing the single use module 634 from the multiple use module 650, although the handles can be located elsewhere in the single use module 634. The platform 752 can include one or more orifices (e.g., 717) to allow tubing and/or other components to pass therethrough. The platform 752 can also include one or more integrally formed brackets (e.g., 716) to hold components in place atop the platform 752, such as the fluid injection and/or sampling ports described more fully below. The upper chassis section 750a can also include a flow clamp 190 for regulating the flow of perfusion fluid to the portal vein, as described more fully below. The organ chamber assembly 104 can be configured to mount to the platform 752 via one or more supports 719. Referring specifically to FIG. 13I, the organ chamber assembly 104 can be mounted so that the left and right sides (relative to the main drain) are at approximately a 15° angle with respect to the platform 752. Doing so can help perfusion fluid drain from the organ chamber assembly 104, especially during transient conditions that can be encountered during transport (e.g., takeoff and landing in an airplane).

1. Organ Chamber

The system 600 can include an organ chamber that is configured to hold an ex vivo organ. The design of the organ chamber can vary depending on the type of organ. For example, the design of the organ chamber can vary depending on whether, for example, it is being used to transport a liver, a heart, and/or lungs. While the following description focuses on an organ chamber 104 that is configured to transport a liver, this embodiment is exemplary only, and other configurations are possible. For example, other configurations of the organ chamber 104 can also be used to transport a liver.

(i) Shape/Drain Structure

Referring to FIGS. 14A-14H, an exemplary embodiment of the organ chamber 104 is shown from multiple views. In this embodiment, the organ chamber 104 includes a base 2802, a front piece 2816, a removable lid 2820, and a support surface 2810 (which is described in detail with respect to FIGS. 15A-15D). In some embodiments, the organ chamber 104 can also include a pad 4500 to support the liver. The bottom of the organ chamber 104 can be configured with a quasi-funnel shape where the sides of the funnel are angled at approximately 15° relative to the platform 752, this is illustrated more clearly in FIG. 13I.

The general level, the base member 2802 can include one or more drains (e.g., 2804, 2806), one more orifices (e.g., 2830) for tubing, connectors, and/or instruments to be inserted inside of the organ chamber 104 while the lid (e.g., 2820) is closed, one or more hinge portions (e.g., 2832), and one or more mounting brackets (e.g., 2834). In some embodiments, as shown in FIG. 14I, the mounting brackets 2834 are molded. In some embodiments, the base member 2802 is configured to fit and support the support surface 2810, on which the liver typically rests. The organ chamber 104 and the support surface 2810 can be made from any suitable polymer plastic, for example, polycarbonate.

The base 2802 of chamber 2204 can be shaped and positioned within the system 600 to facilitate the drainage of the perfusion medium from the liver 101. The organ chamber 104 can have two drains: measurement drain 2804, and main drain 2806, which can receive overflow from the measurement drain. The measurement drain 2804 can drain perfusate at a rate of about 0.5 L/min, considerably less than perfusion fluid 250 flow rate through liver 101 of between and 1-3 L/min. The measurement drain 2804 can lead to sensor 140, which can measure $SaO_2$, hematocrit values, and/or temperature, and then leads on to reservoir 160. The main drain 2806 can lead directly to the defoamer/filter 161 without passing through the sensor 140. In some embodiments, the sensor 140 cannot obtain accurate measurements unless perfusion fluid 108 is substantially free of air bubbles. In order to achieve a bubble-free column of perfusate, base 2802 is shaped to collect perfusion fluid 108 draining from liver 101 into a pool that collects above the measurement drain 2804. The perfusate pool typically allows air bubbles to dissipate before the perfusate enters drain 2804. The formation of a pool above drain 2804 can be promoted by optional wall 2808, which can partially block the flow of perfusate from measurement drain 2804 to main drain 2806 until the perfusate pool is large enough to ensure the dissipation of bubbles from the flow. Main drain 2806 can be lower than measurement drain 2804, so once perfusate overflows the depression surrounding drain 2804, it flows around and/or over wall 2808, to drain from main drain 2806.

In an alternate embodiment of the dual drain system, other systems are used to collect perfusion fluid into a pool that feeds the measurement drain. In some embodiments, the flow from the liver is directed to a vessel, such as a small cup 2838, which feeds the measurement drain. The cup 2838 fills with perfusion fluid, and excess blood overflows the cup and is directed to the main drain and thus to the reservoir pool. In this embodiment, the cup 2838 performs a function similar to that of wall 2808 in the embodiment described above by forming a small pool of perfusion fluid from which bubbles can dissipate before the perfusate flows into the measurement drain on its way to the oxygen sensor. In still other embodiments of the measurement drain, a gradual depression can be formed in the bottom of the base 2802 around the measurement drain 2804 that performs the same function as the cup described above.

The top of organ chamber 104 can be covered with a sealable lid that includes front piece 2816, removable lid 2820, inner lid with sterile drape (not shown), and sealing piece 2818. The removable lid 2820 can be hingedely and removably coupled to the base member 2802 via hinge portions 2832. The sealing piece 2818 can seal the front piece 2816 and/or base 2802 to lid 2820 to create a fluid and/or airtight seal. The sealing piece 2818 can be made out of, for example, rubber and/or foam. In some embodiments, the front piece 2816 and lid 2820 is rigid enough to protect the liver 101 from physical contact, indirect or direct.

Figure 14A:
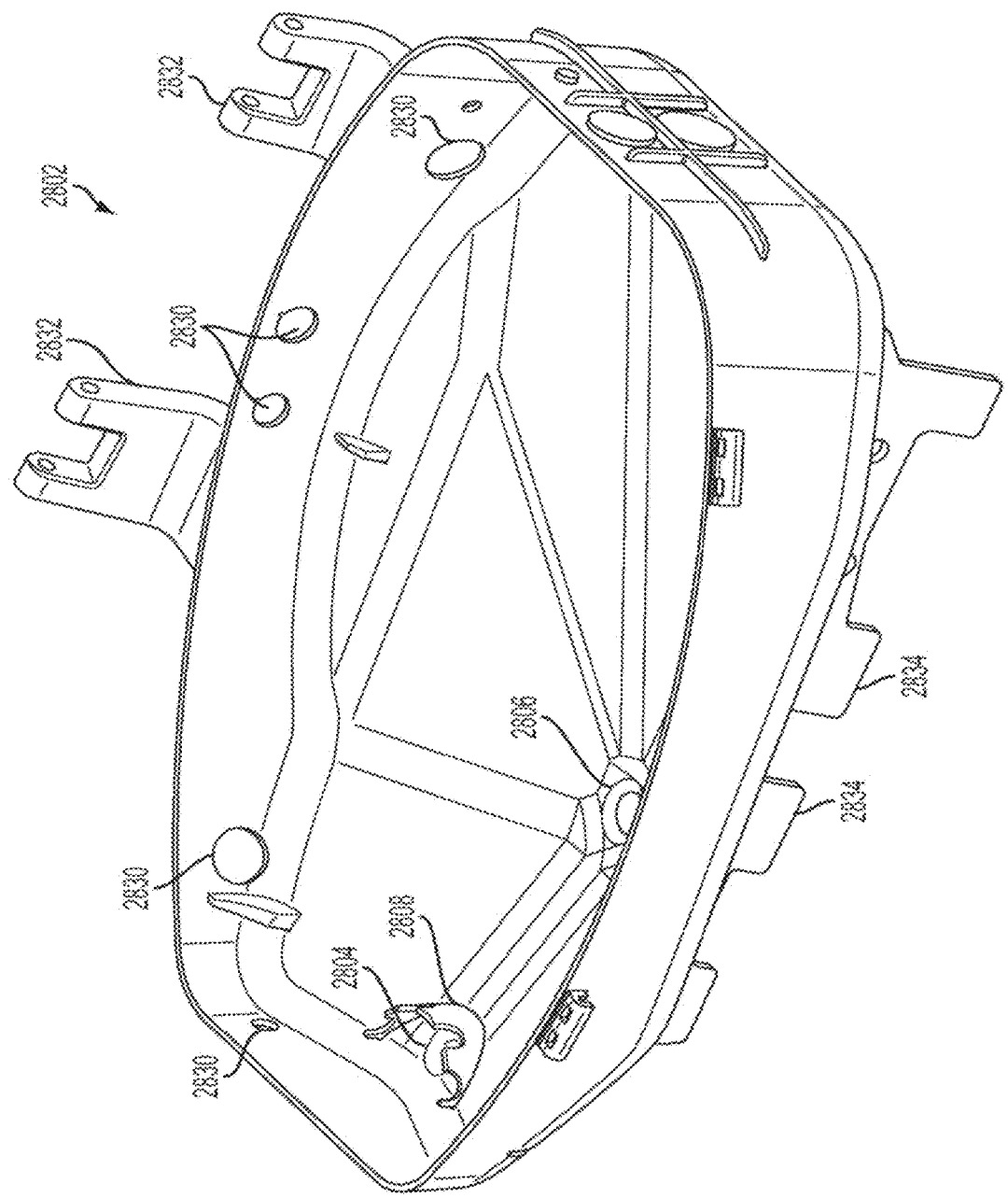
FIGS. 14A-14S show exemplary embodiments of an organ chamber and components thereof that can be used in an embodiment of the organ care system.
Figure 14B:
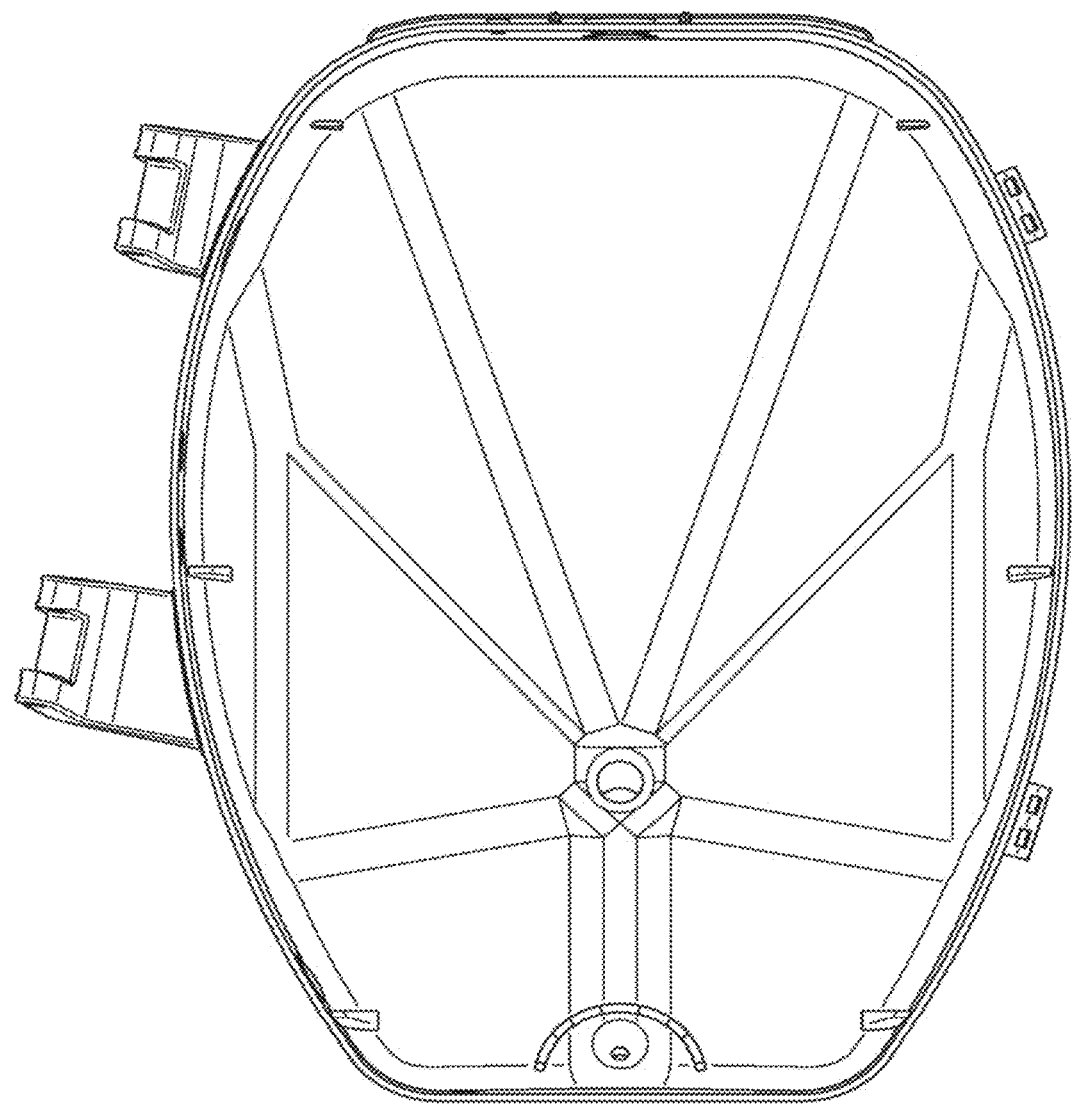
Figure 14C:
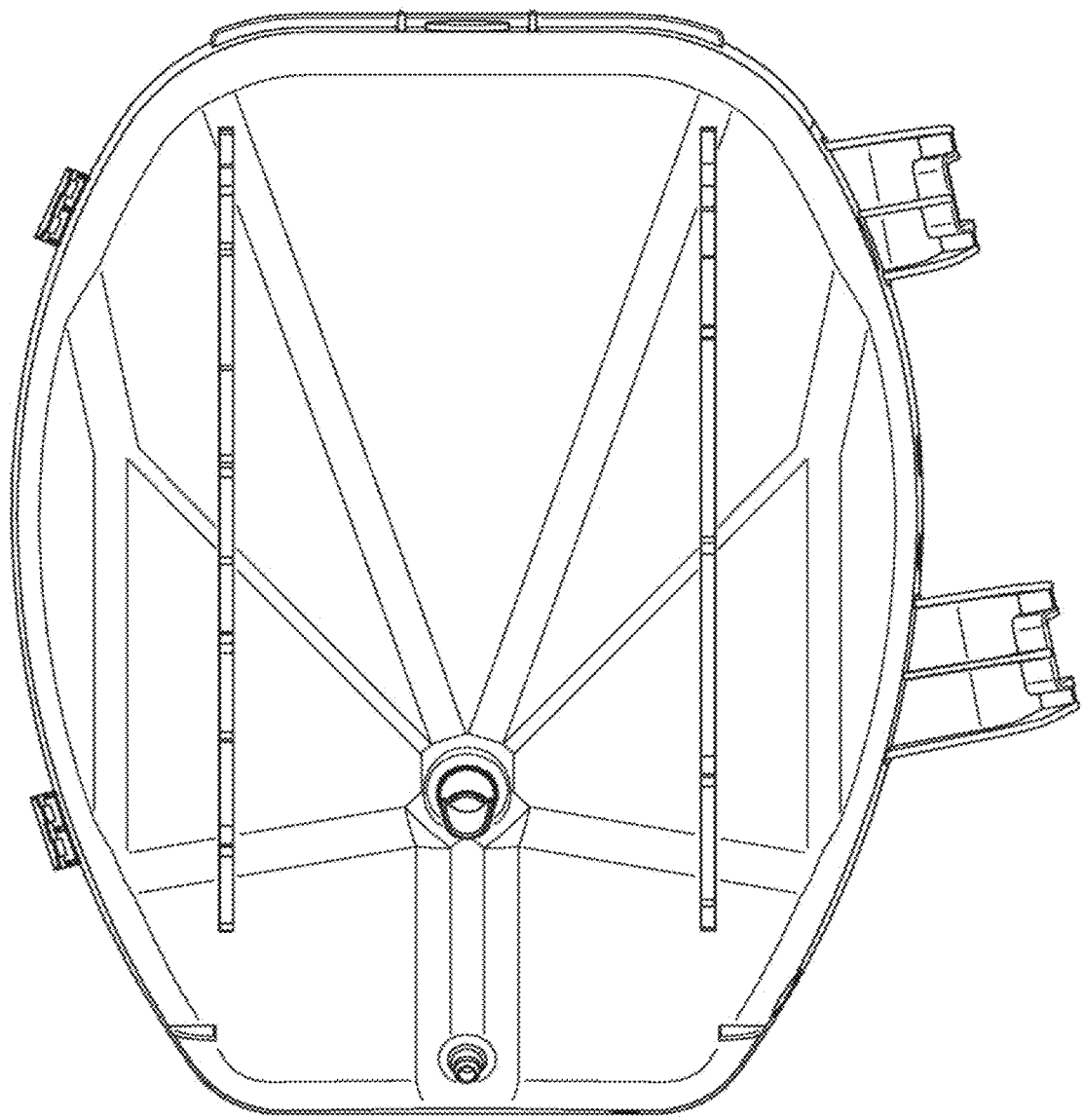
Figure 14D:
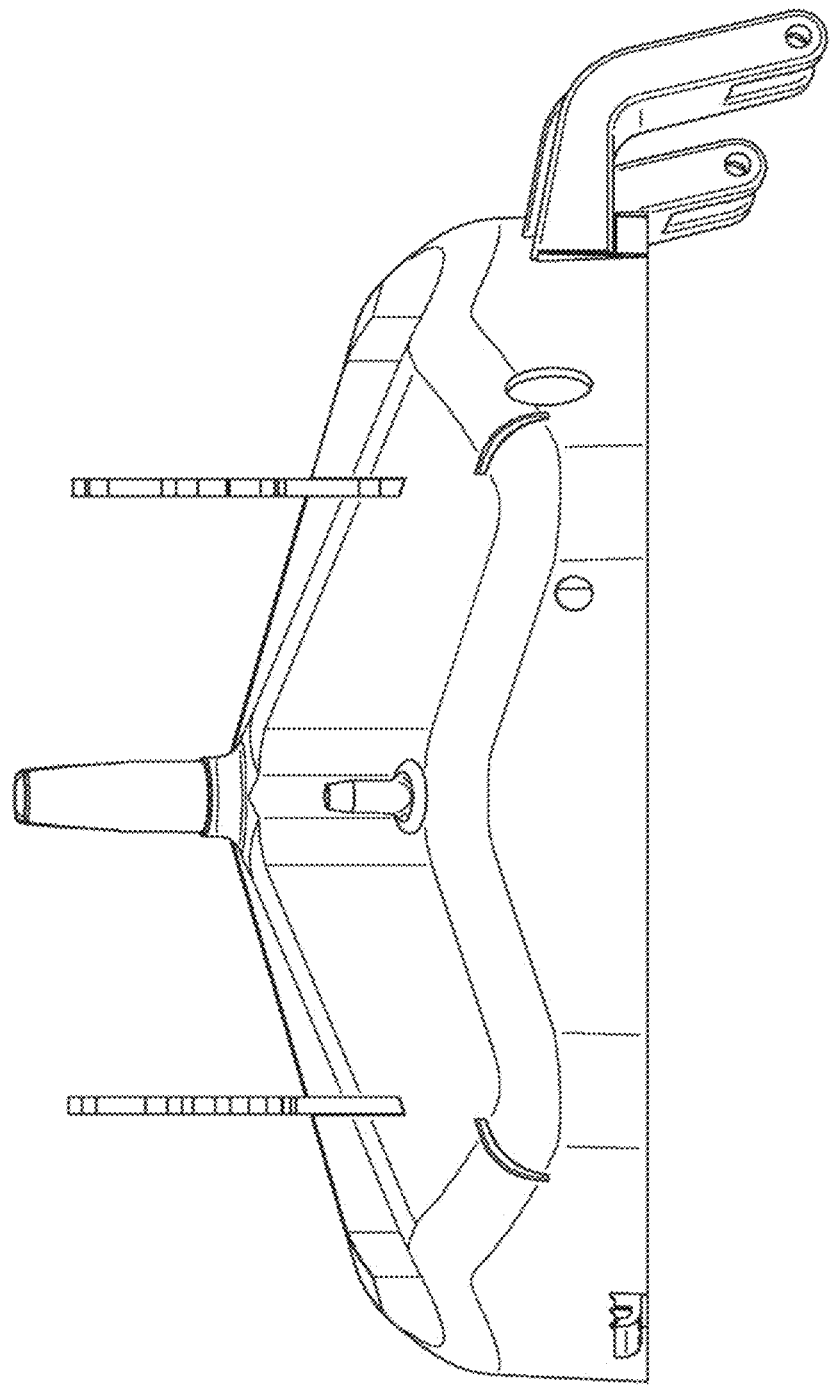
Figure 14E:
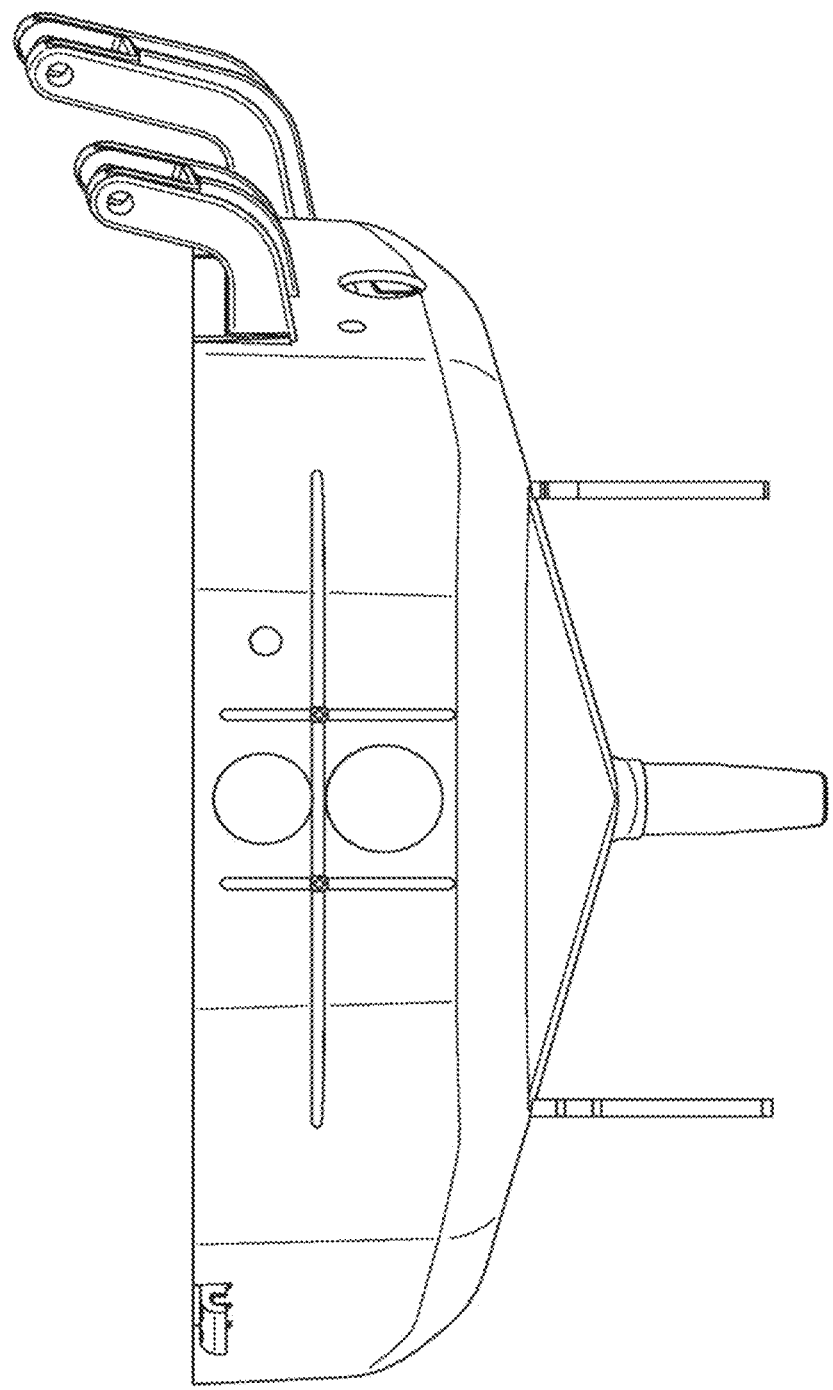
Figure 14F:
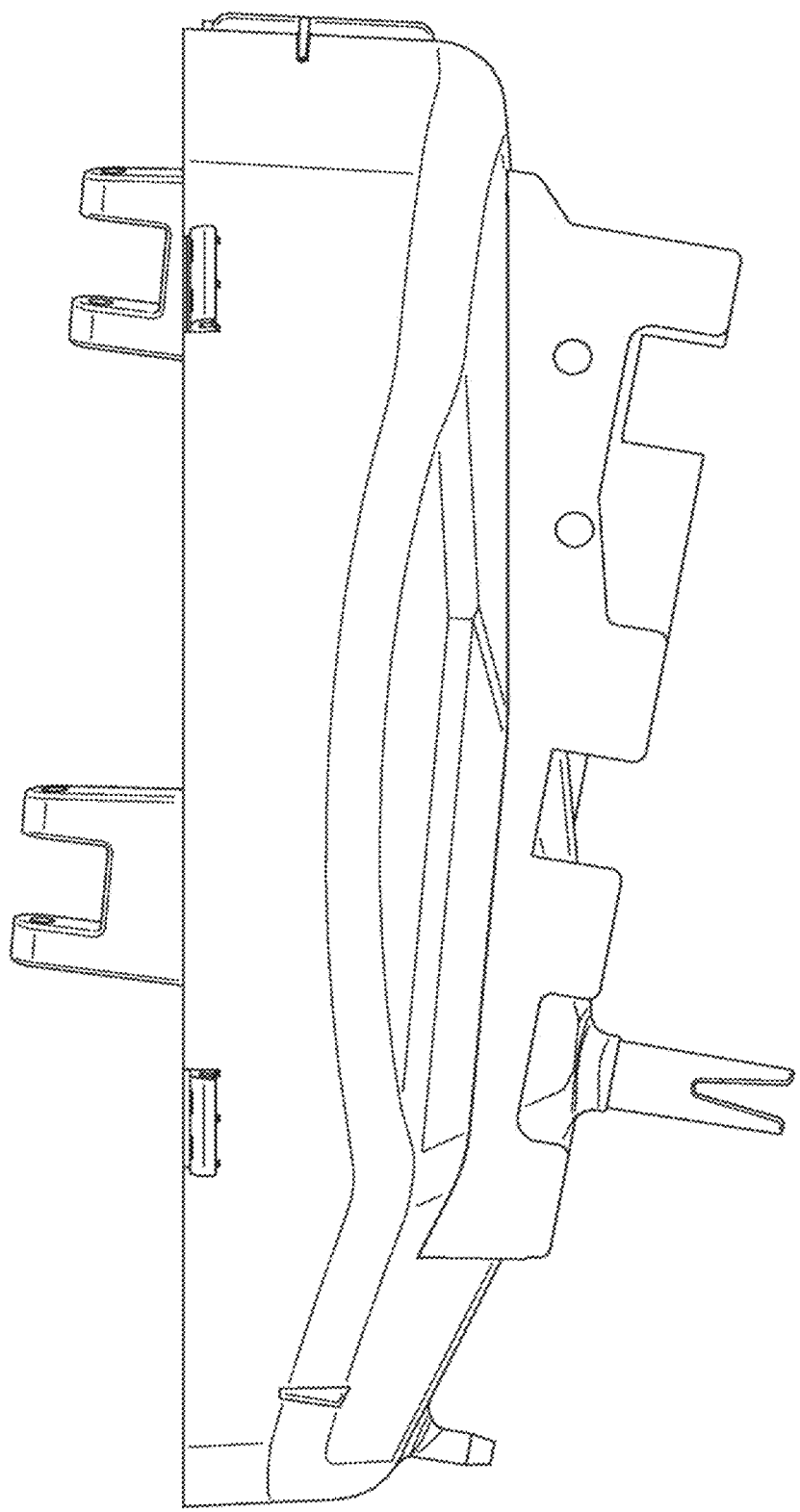
Figure 14G:
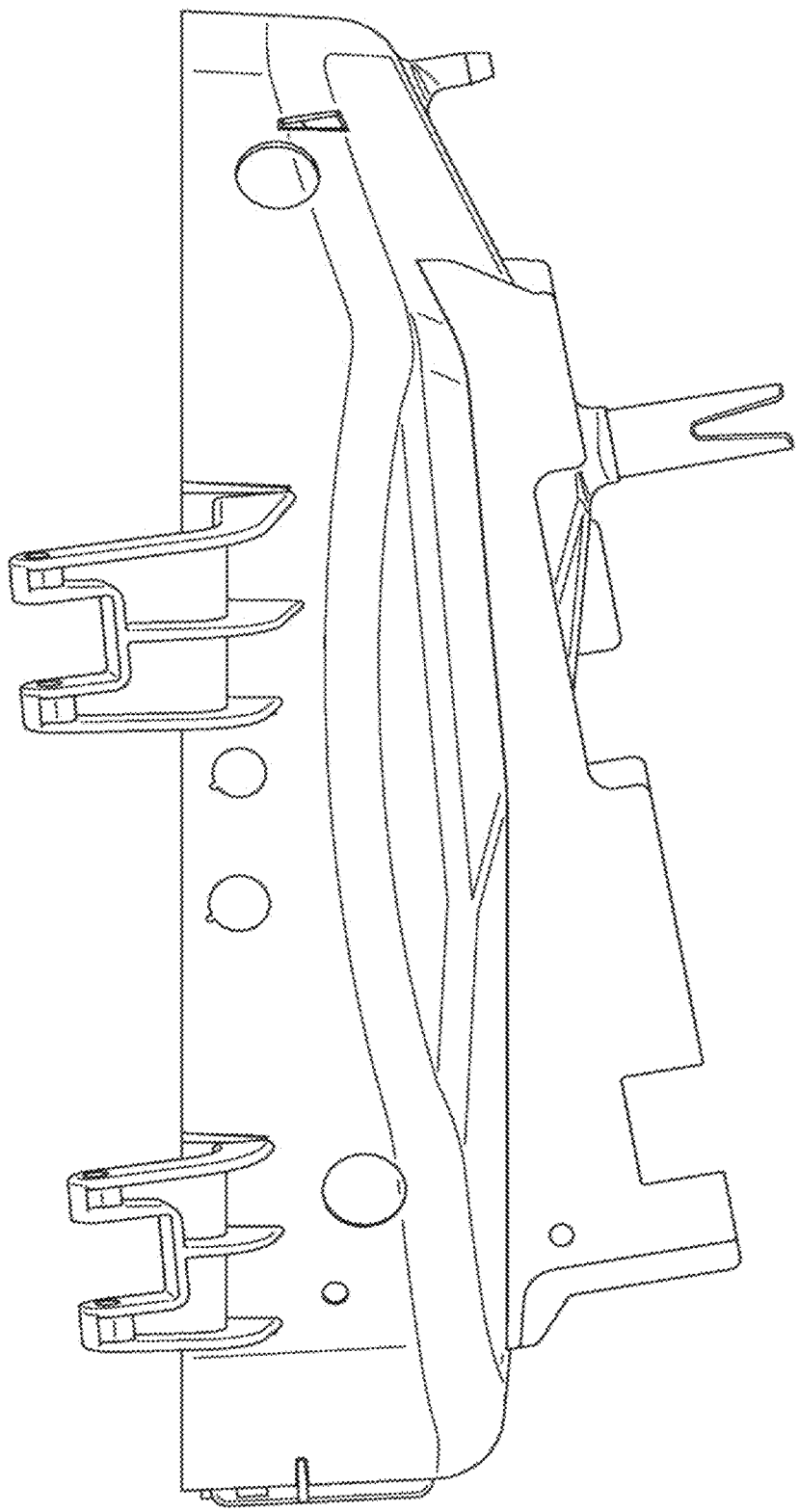
Figure 14H:
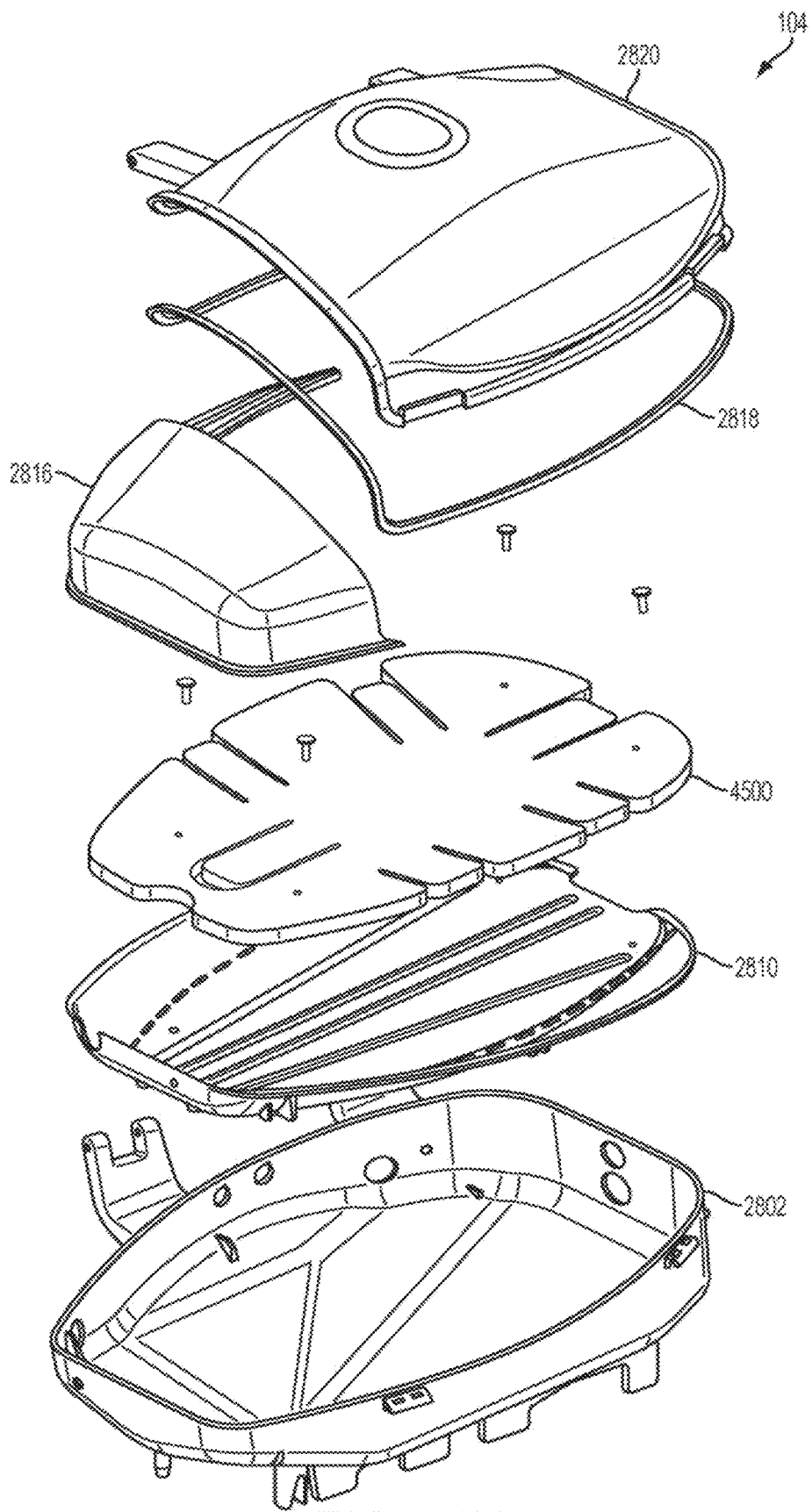
Figure 14J:
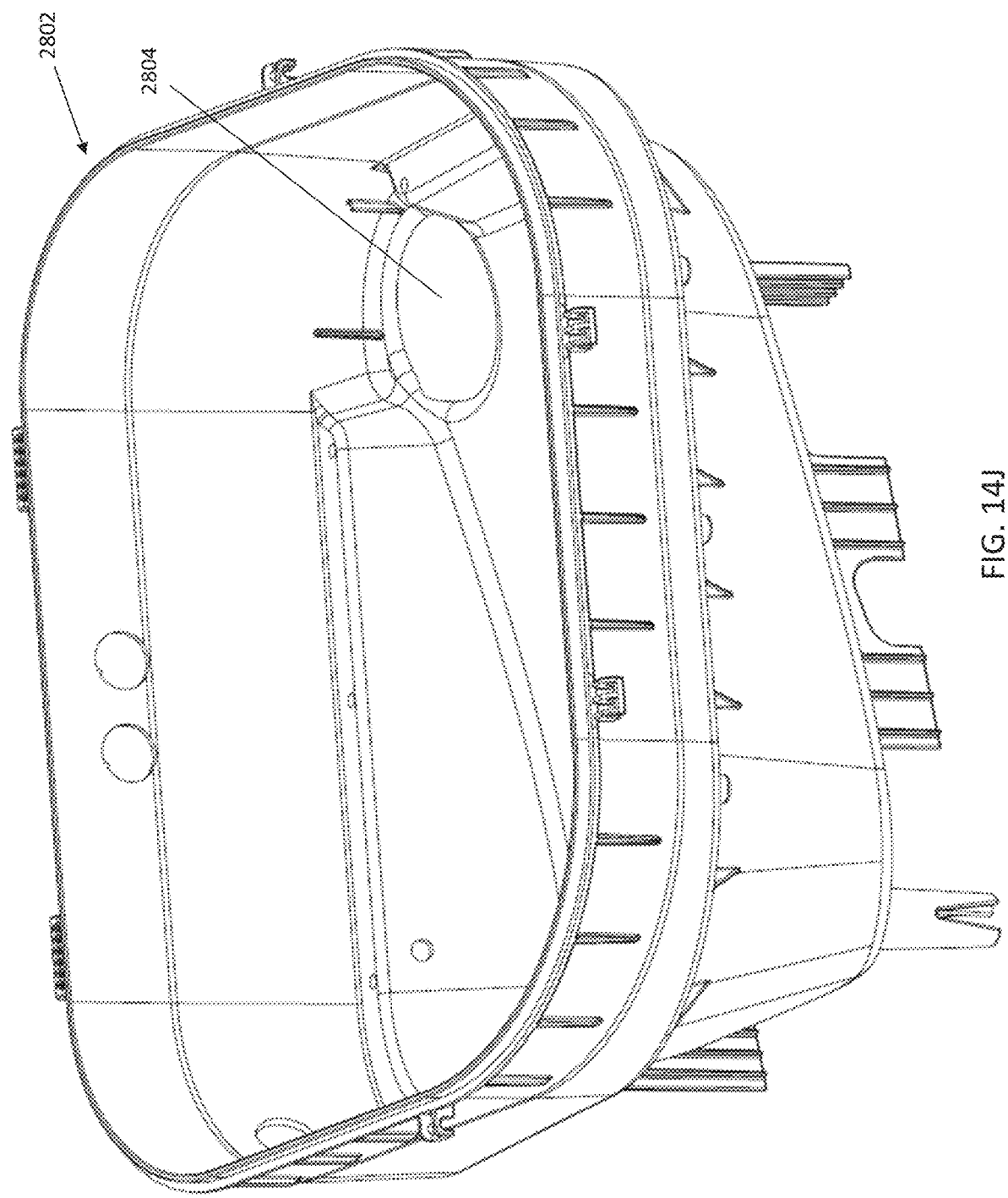
Figure 14L:
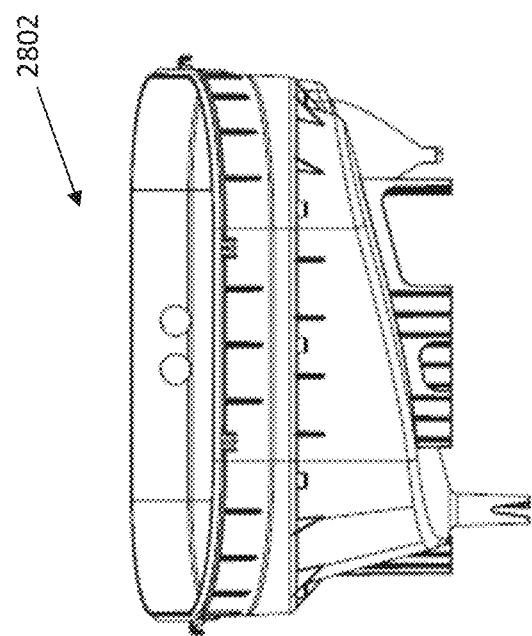
Figure 14K:
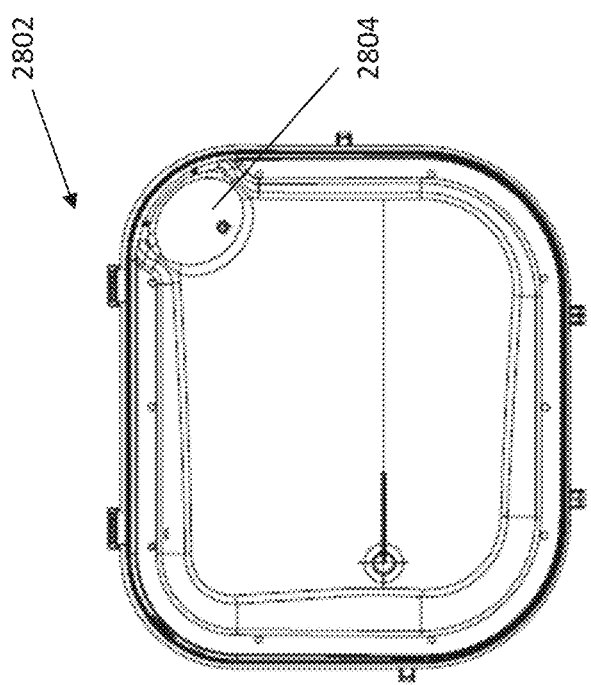
Figure 14O:
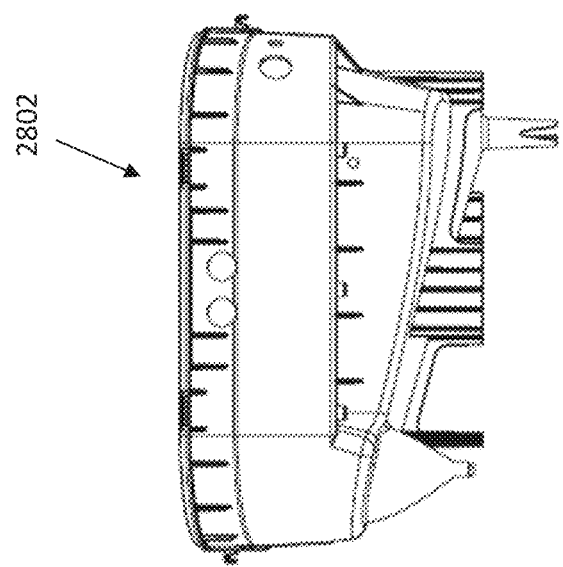
Figure 14N:
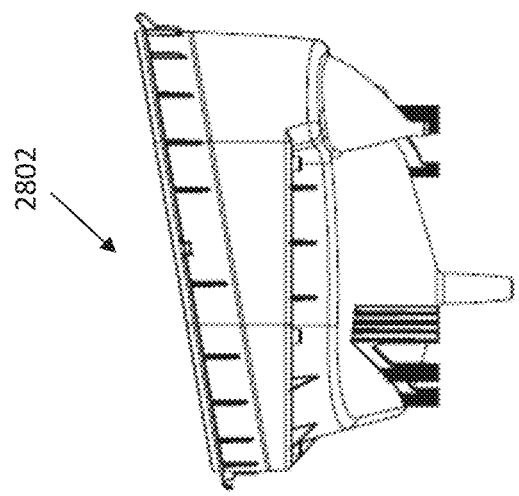
Figure 14M:
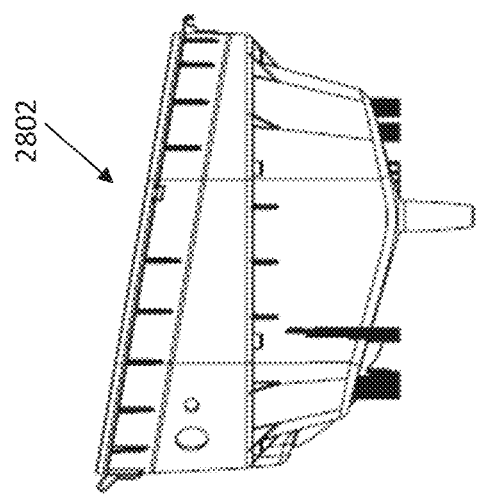
Figure 14R:
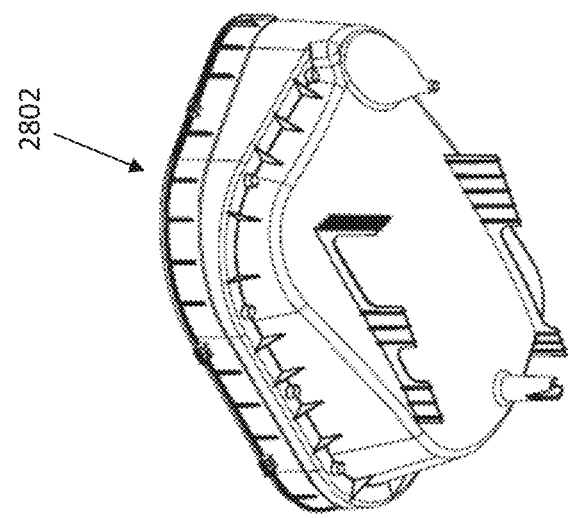
Figure 14Q:
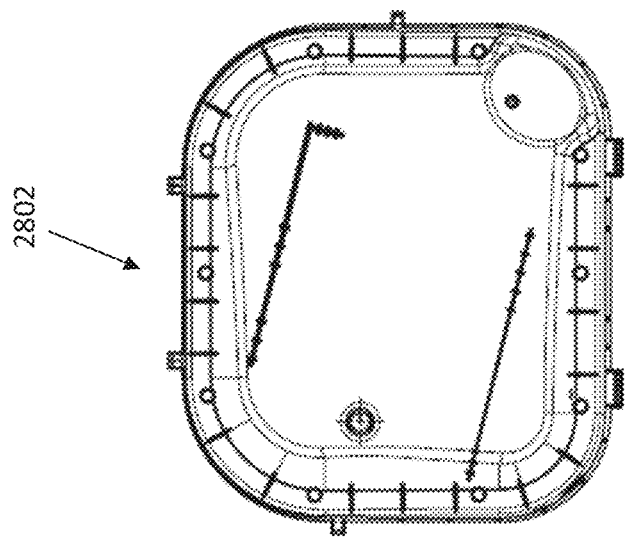
Figure 14P:
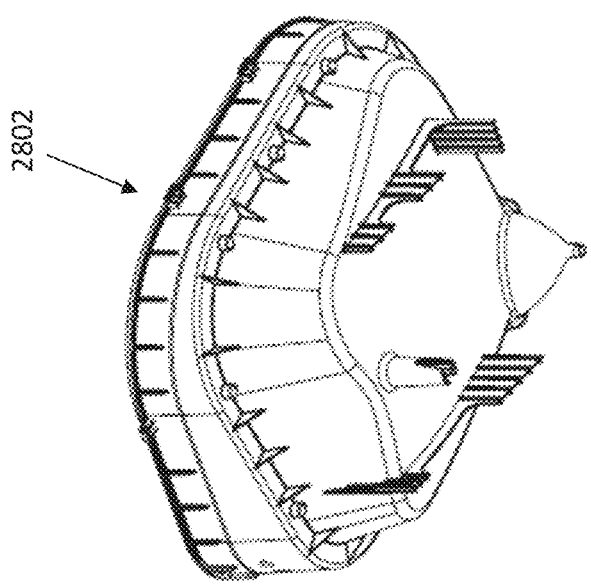
Figure 14S:
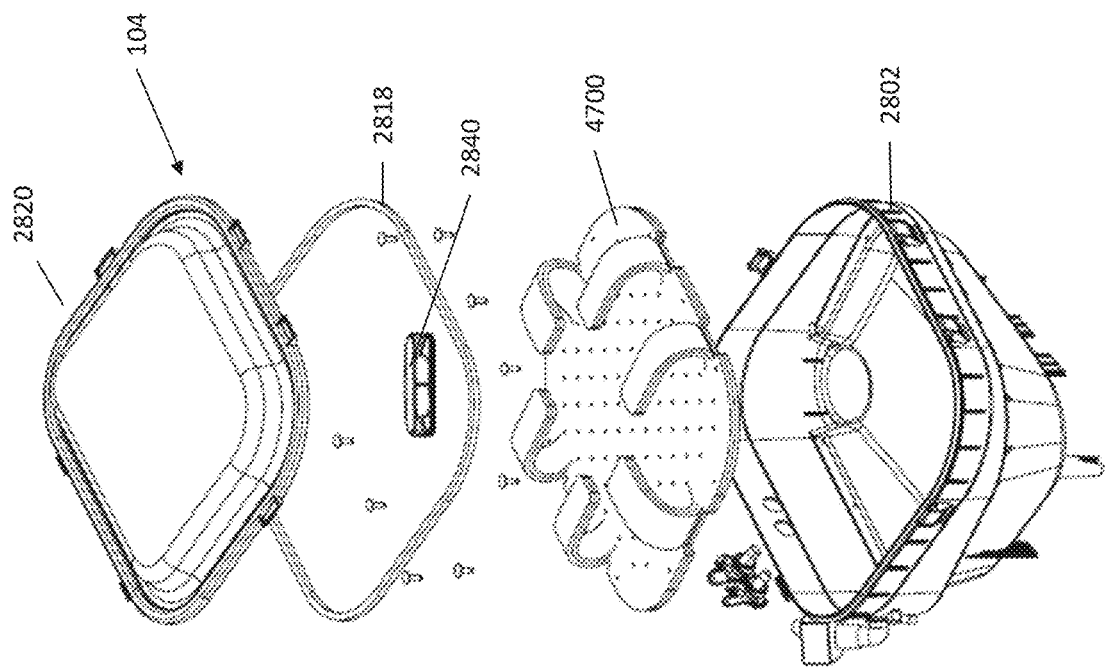
Figure 15A:
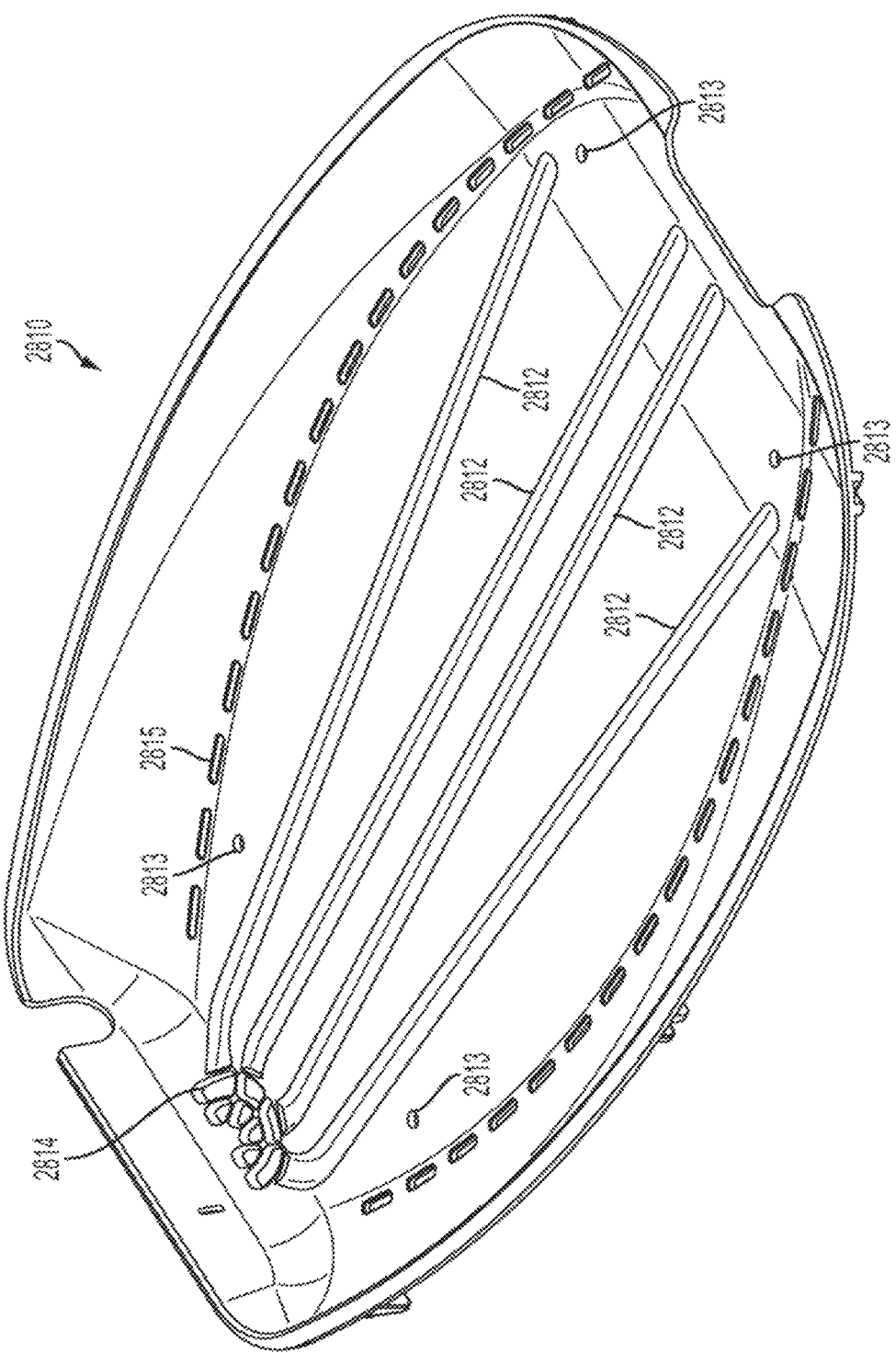
FIGS. 15A-15D show an exemplary embodiment of a support structure that can be used in an embodiment of the organ care system.
Figure 15B:
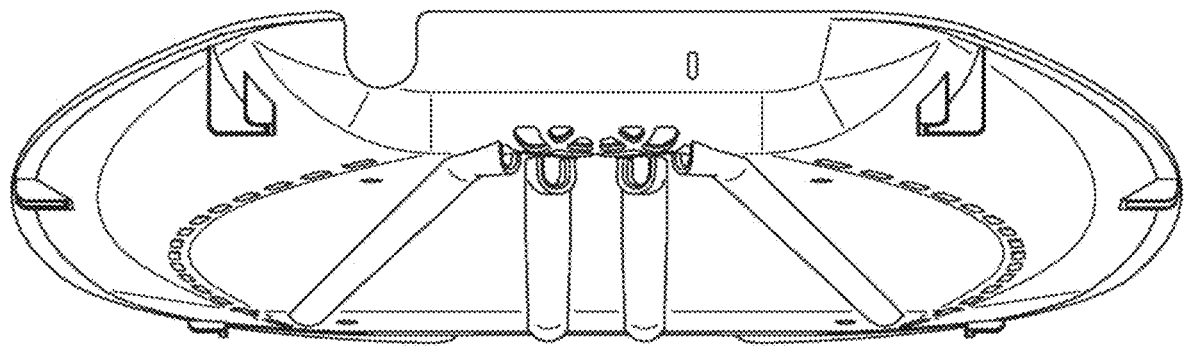
Figure 15C:
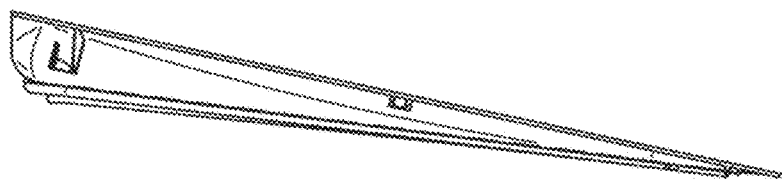
Figure 15D:
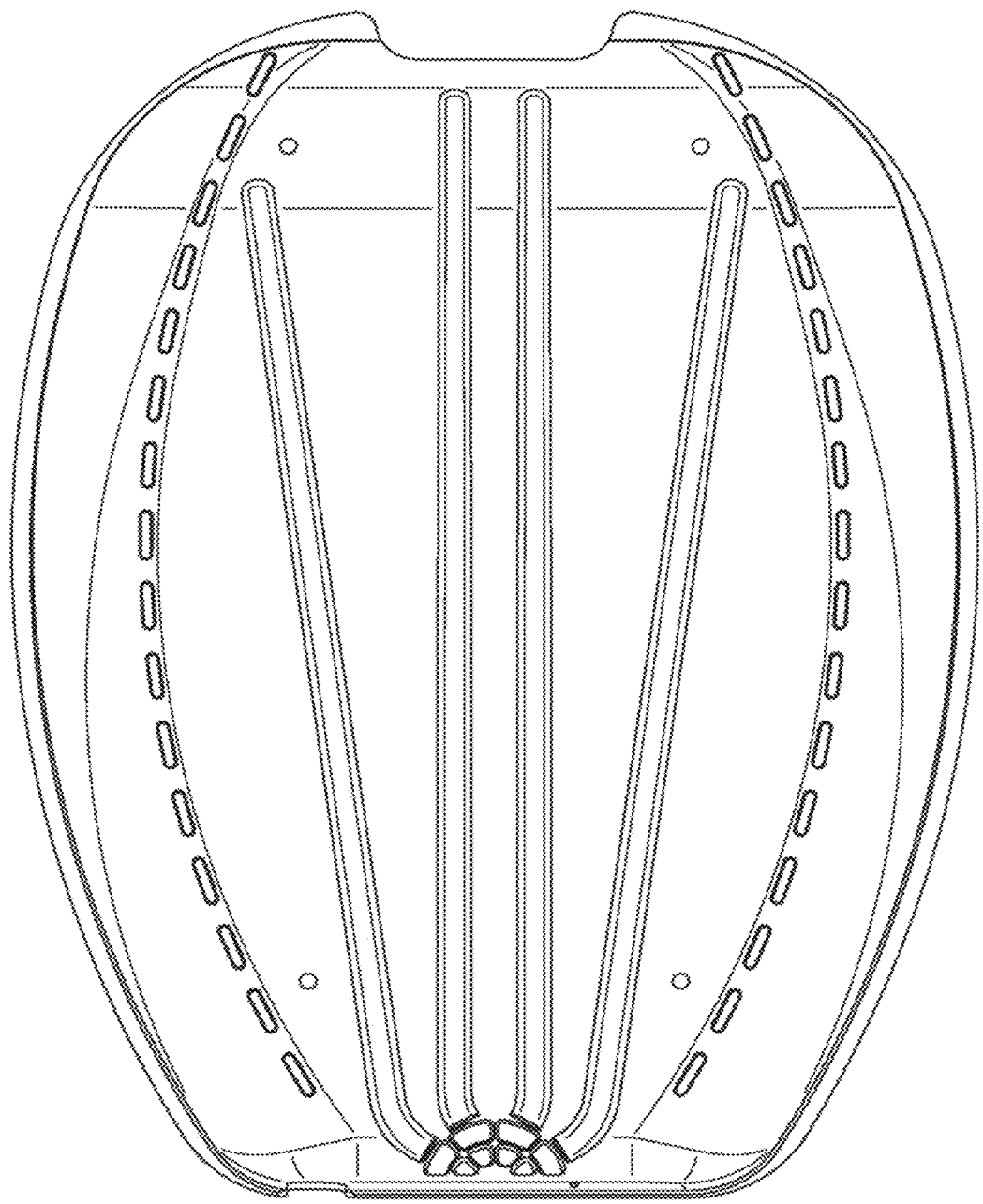

An alternative embodiment of the organ chamber is shown from multiple views in FIGS. 14I-S. In this embodiment, the base 2802 of the organ chamber 104 has a different shape. FIGS. 14I-14K show top views, FIGS. 14L-14O show side views, FIGS. 14P-14R show bottom views, and FIG. 14S shows a break out of the alternative embodiment. The organ chamber 104 includes a base 2802, an organ support surface 2810, and a removable lid 2820.

For example, the top of the organ chamber can be covered with a single sealable lid 2820. The removable lid can be hingedly and removably coupled to the organ chamber base member via hinge portions 2832. The lid is fastened to the base through a series of latches 2836 or other mechanisms. The sealing piece 2818 of the lid can be made of rubber and/or foam, and it can seal the lid to the base to create a fluid or airtight seal. The combination of the lid and base is rigid enough to protect the liver from direct or indirect physical contact. The organ chamber contains orifices (e.g., 2830) for conduit connections for cannulated vessels, including the HA, PV and bile duct. The organ chamber contains a structure 2840 positioned above the measurement drain 2804 that holds the end of the IVC in place during transport of the organ. This structure directs the perfusate exiting from the IVC cannula to the measurement drain.

In an alternate embodiment (not shown), the organ chamber 104 can include a double lid system that includes an inner lid and an outer lid. More particularly, in one embodiment, the organ chamber assembly can include a housing, an outer lid and an intermediate lid. The housing can include a bottom and one or more walls for containing the organ. The intermediate lid can cover an opening to the housing for substantially enclosing the organ within the housing, and can include a frame and a flexible membrane suspended within the frame. The flexible membrane can be transparent, opaque, translucent, or substantially transparent. In some embodiments, the flexible membrane includes sufficient excess membrane material to contact an organ contained within the chamber. This feature can enable a medical operator to touch/examine the organ indirectly through the membrane while still maintaining sterility of the system and the organ. For example, the area of the membrane in the intermediate lid can be 100-300% larger than the area defined by the intermediate lid frame or have an area that is 100-300% larger than a two-dimensional area occupied by the liver. In some embodiments, the flexible membrane can be selected so that an operator can perform an ultrasound of the liver through the membrane while maintaining the sterility and/or environment of the chamber.

In some embodiments, the intermediate lid can be hinged to the housing. The intermediate lid can also include a latch for securing the intermediate lid closed over the opening of the organ chamber. The outer lid may be similarly hinged and latched or completely removable. In some configurations, gaskets are provided for forming a fluid and/or airtight seal between the intermediate lid frame and the one or more organ chamber walls, and/or for forming a fluid and/or airtight seal between the periphery of the outer lid and the frame of the intermediate lid. In this manner, the environment surrounding the liver 101 can be maintained regardless of whether the outer lid is open.

Covering the organ chamber 104 can serve to minimize the exchange of gases between perfusion fluid 108 and ambient air, can help ensure that the oxygen probes measure the desired oxygen values (e.g., values corresponding to perfusate exiting the liver 101), and can help maintain sterility. The closing of organ chamber 2204 can also serve to reduce heat loss from the liver. Heat loss can be considerable because of the large surface area of the liver. Heat loss can be an important issue during transport of the liver when the system 600 may be placed into relatively low temperature environments, such as a vehicle, or the outdoors when moving the system 600 into and out of a vehicle. Furthermore, prior to transplantation, system 600 may be temporarily placed in a hospital holding area or in an operating theater, both of which typically have temperatures in the range of 15-22° C. At such ambient temperatures, it is important to reduce heat loss from organ chamber 2204 in order to allow heater 230 to maintain the desired perfusate and liver temperature. Sealing the liver 101 in the organ chamber 2204 can also help to maintain uniformity of the temperature through liver 101.

Referring also to FIGS. 15A-15D shows an exemplary embodiment of support surface 2810 that is configured to support the liver 101. This embodiment includes drainage channels 2812, drain 2814, and orifices 2815. The drainage channels 2812 are configured to channel perfusate draining from the liver 101 and guide it toward the drain 2814. In some embodiments, when the support surface 2810 is installed in the base 2802, the drain 2814 is located above and/or in the proximity of measurement drain 2804 thereby ensuring that a substantial amount of the perfusate 108 drains from the support surface 2810 into the measurement drain 2804. The orifices 2815 are configured to provide supplemental areas for the perfusion to drain from the support surface 2810. Additionally, the support surface 2810 can be configured to be used with the pad 4500 (described below). The support surface 2810 can also include orifices 2813 that can be used to secure the pad 4500 using, for example, screws or rivets. In some embodiments, when the support surface 2810 is installed in the organ chamber 104, it is installed so that it rests at approximately a 5-degree angle relative to horizontal, although other angles can be used (e.g., 0-60 degrees).

Referring to FIGS. 16F-16J, in an alternate embodiment, the support surface 4700 is a flexible material that supports and cushions the organ, and support surface 2810 is omitted. The material is of a composition such that is provides a compliant, smooth surface on which the sensitive liver tissue can rest. The surface can be perforated in a manner, i.e. the number, arrangement and diameter of the perforations, to allow for drainage from the liver while providing an atraumatic surface for the liver tissue. In this or other embodiments, the support 4700 is a layer of materials, including a top layer 4706 and a bottom layer 4708 of a compliant material 4706 and an inner layer that is a frame 4702 of malleable metal substrate (e.g., aluminum). In some embodiments, the top layer 4706 and bottom layer 4708 can be made out of polyurethane foam and/or a cellular silicone foam.

The assembly is supported by the organ chamber base 2802, suspending the support surface 4700 above the bottom of the organ chamber base 2802 at an appropriate height to provide displacement by the weight of the organ. The frame 4702 of the support surface 4700 can be held in place to the organ chamber base 2802 through the use of fasteners 4704, such as molded pins, rivets, screws, or other hardware, that are inserted through openings 4610 in the frame 4702.

In some embodiments, the malleable metal frame 4702 extends into projections 4712. The projections 4712 may also be enclosed by the top layer 4706 and bottom layer 4708. The projections 4712 can be formed into positions to surround the liver to stabilize the position of the liver in the x, y and z axes. By bending the projections 4712, the user can selectively support the liver in a manner that mimics how the liver is supported in the human body. In some embodiments, portions of the frame 4702 can be tapered and terminated with a circle, as shown in FIG. 16G. The tapering of the portions of the frame 4702 can: i) allow the projections 4712 to be curled more easier and reduce, or even eliminate, the possibility of creasing, and ii) reduce weight of the support surface 4700. The circle can provide a surface that is easily held by the user. The tapered shape of the portions of the frame 4702 can be specifically selected to facilitate its rolling to conform to a natural arc rather than a fold or bend. The projections 4712 can be of any shape desired to surround the liver. In use, the liver is placed on the top layer 4706 of the support surface 4700, allowing the support surface 4700 to depress. Then, the projections 4712 may be formed into positions to surround the liver.

(ii) Stabilization of Liver

In some embodiments, the liver can be stabilized during transport by one or more systems that are designed to support and keep the liver in place without damaging the liver by applying undue pressure thereto. For example, in some embodiments the system 600 can use a soft stabilizing liver pad (e.g., 4500) to support the liver along with a wrap/tarp (e.g., 4600). In some embodiments, the stabilization system can allow some movement of liver up to a predetermined limit (e.g., the system can allow the liver to move up to 2 inches in any direction). In some embodiments the surface on which the liver rests can have a low friction surface, which can also help reduce damage to the liver. The side of the pad in contact with the support surface 2810 can have a high friction surface to help hold the pad in place.

The pad can be designed to form a cradle that selectively and controllably supports the liver 101 without applying undue pressure to the liver 101. That is, were the liver 101 merely placed on the support surface 2810 without anything more, physical damage could result to the portions of the liver on which the liver is resting during transport. For example, the pad can be formed from a material resilient enough to cushion the liver from mechanical vibrations and shocks during transport.

Figure 16C:
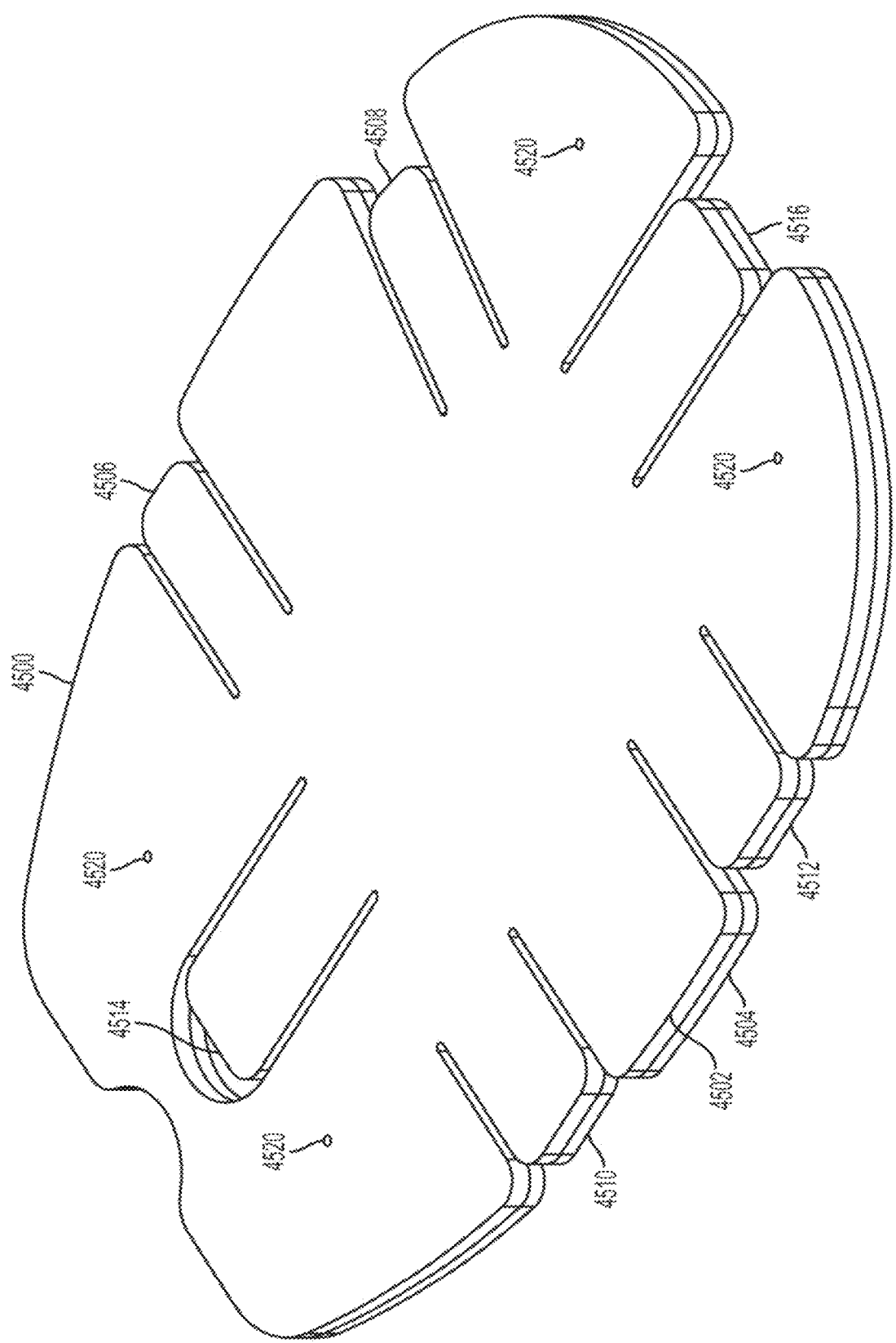
Figure 16D:
Figure 16E:
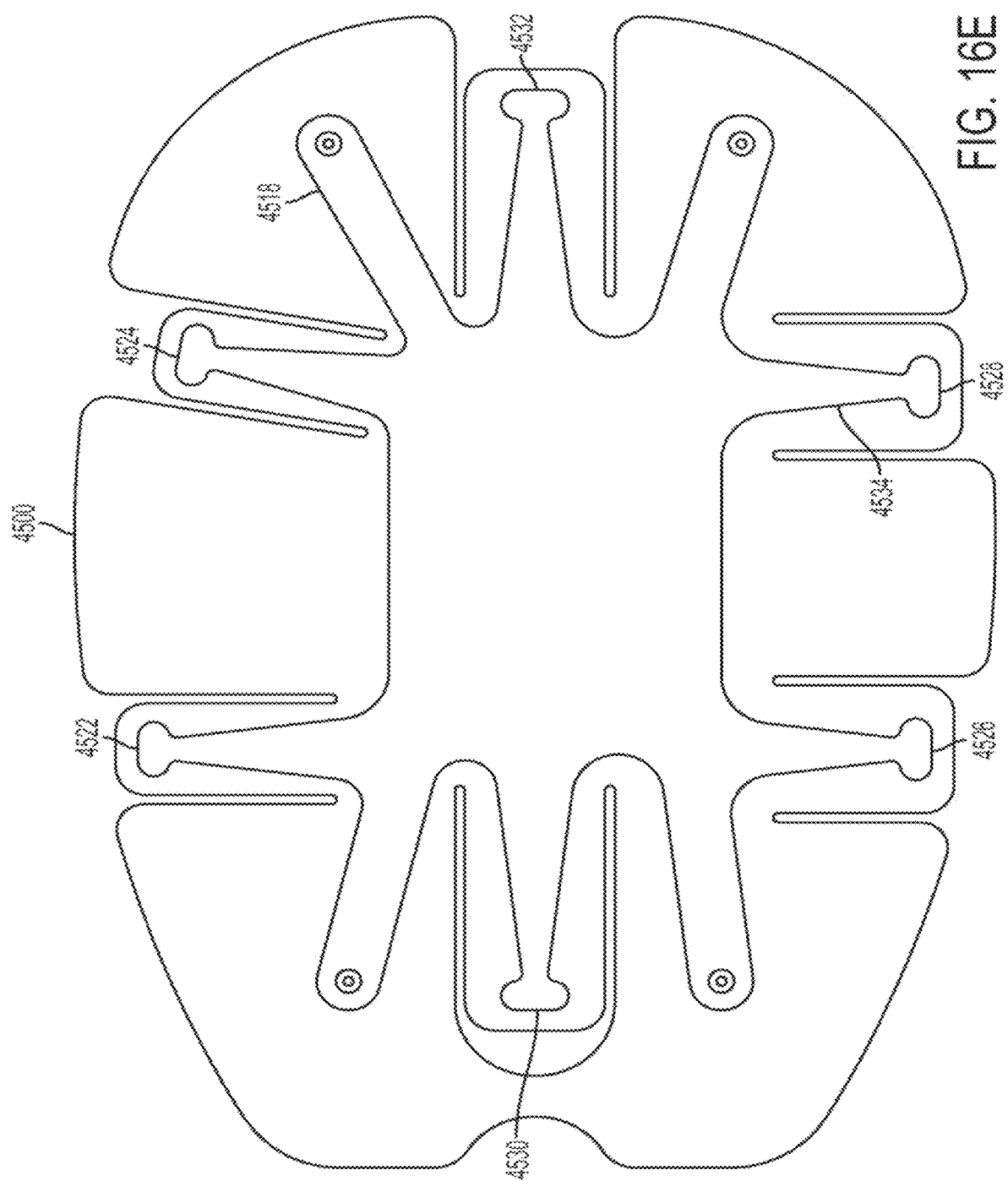
Figure 16G:
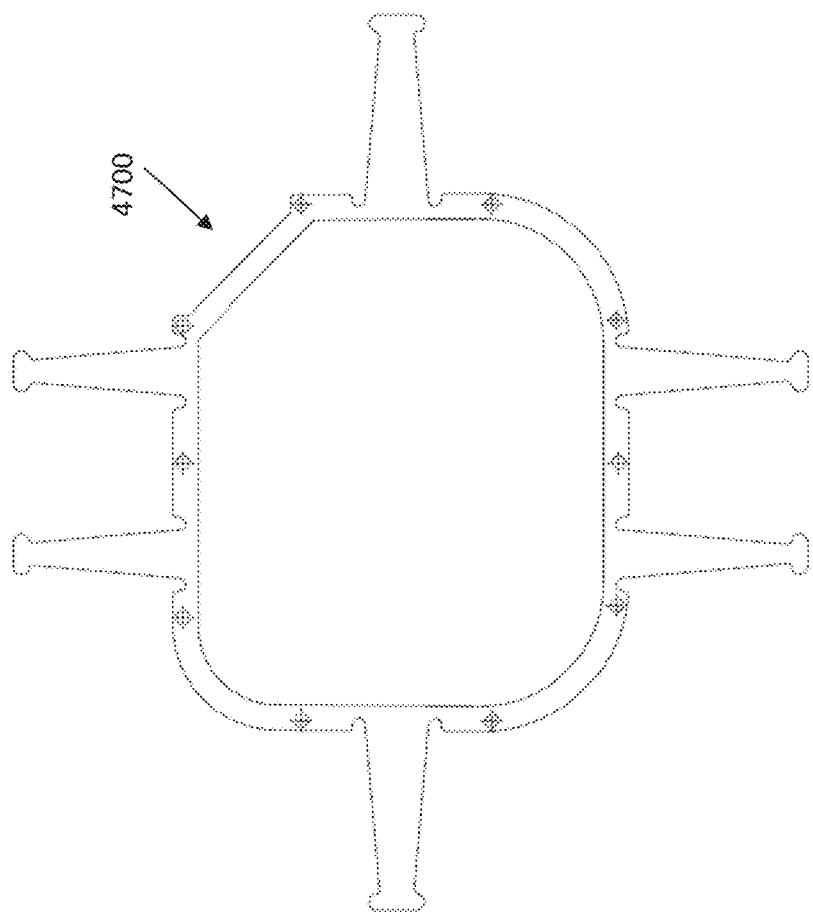
Figure 16F:
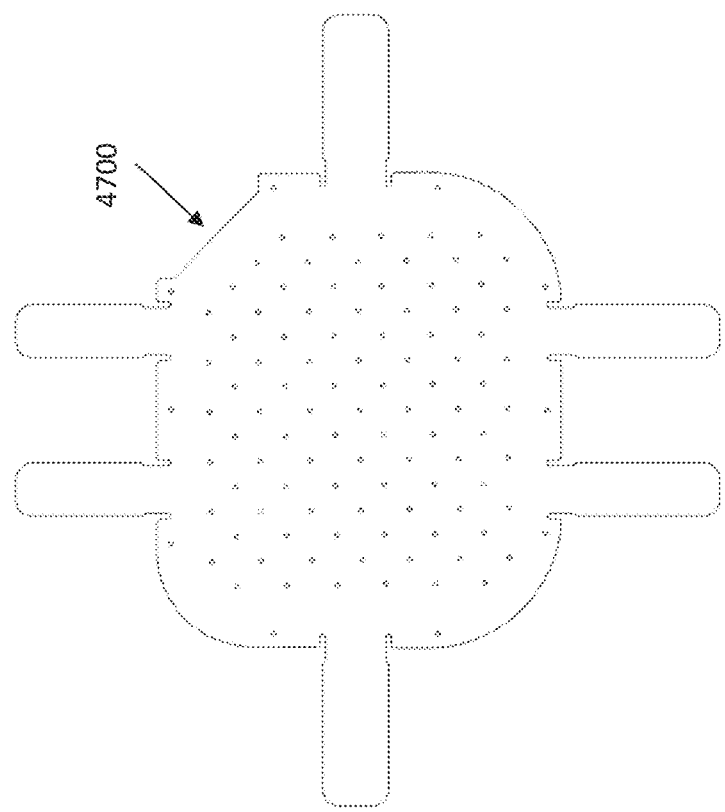
Figure 16H:
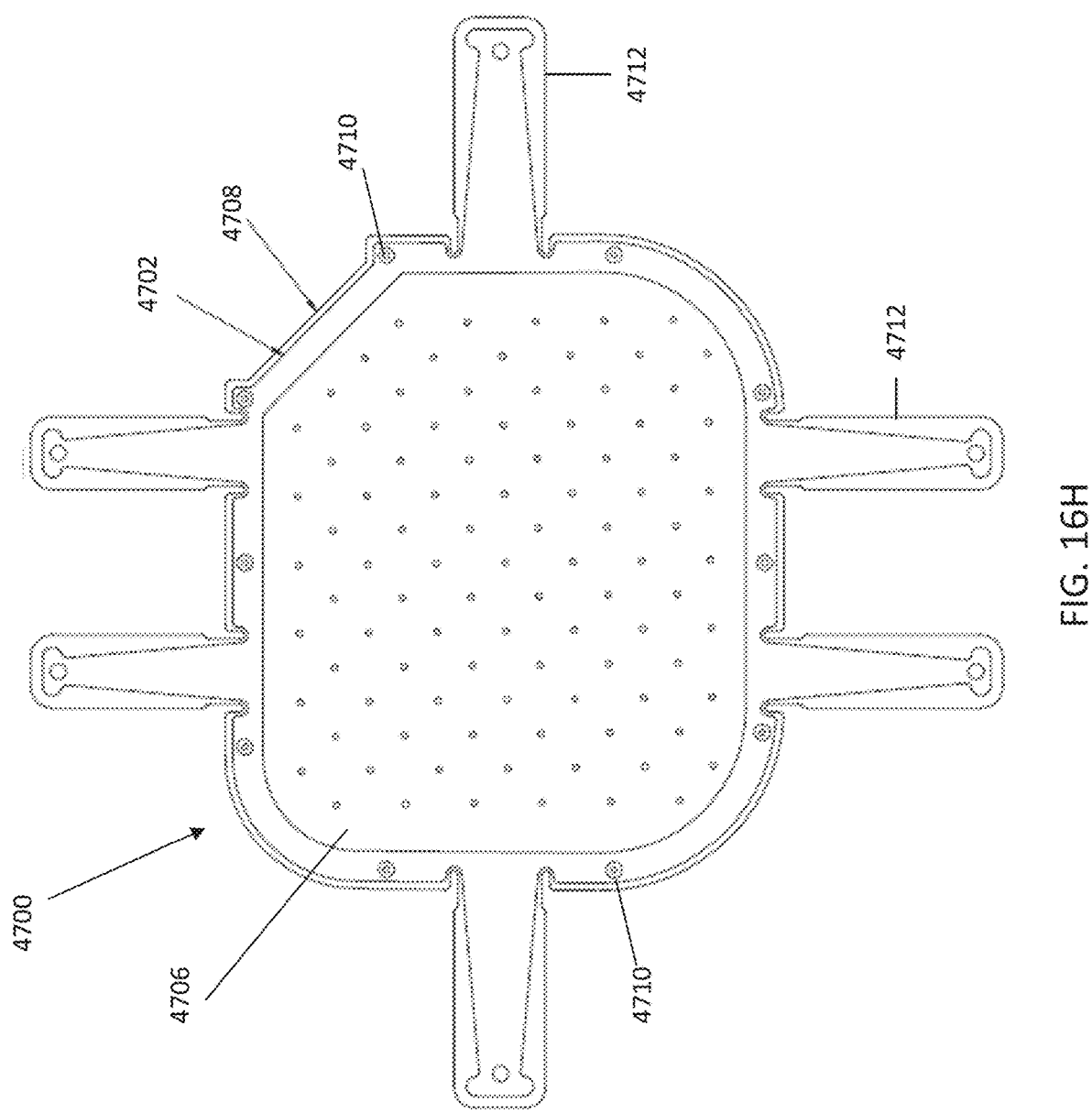
Figure 16I:
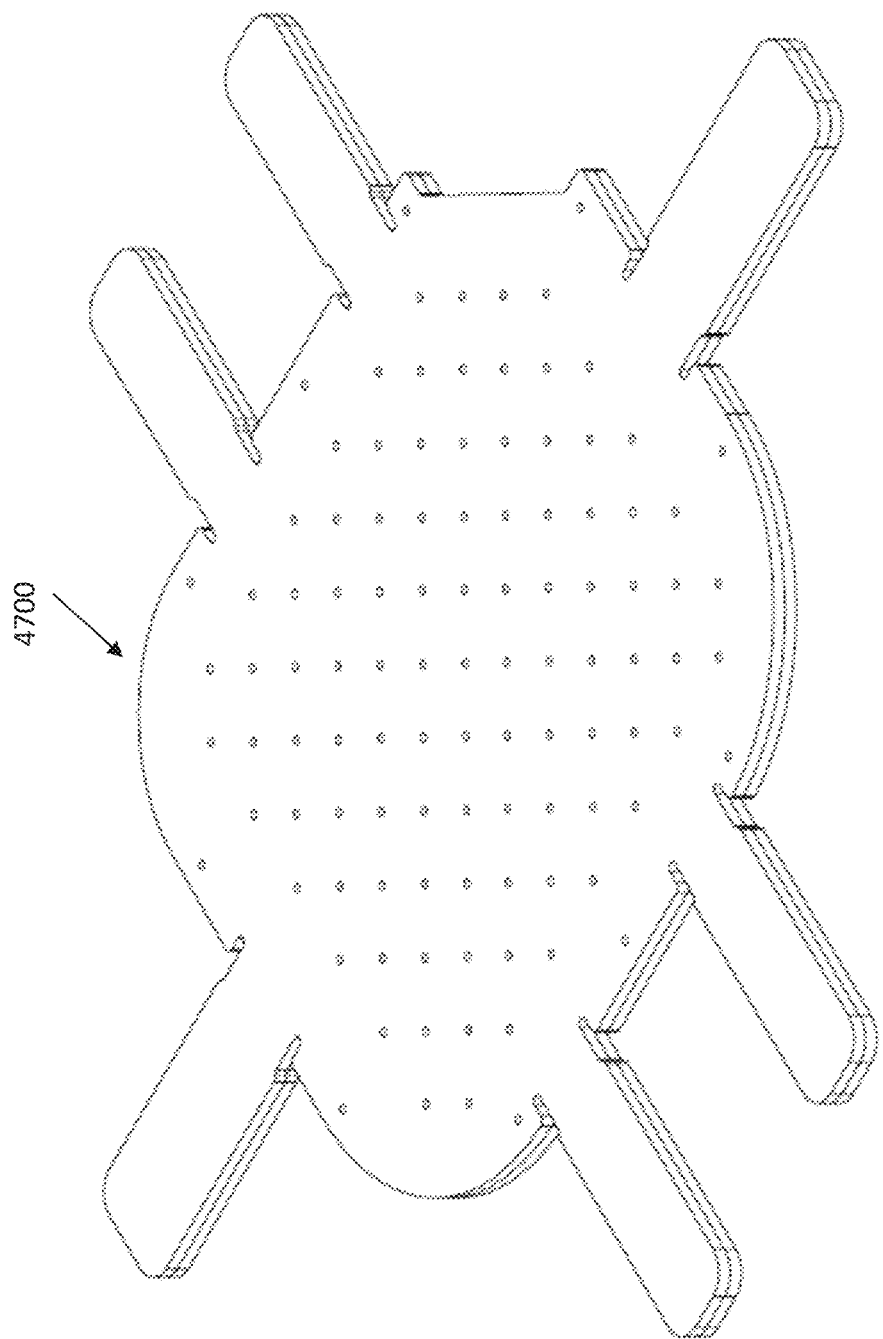

An exemplary embodiment of the stabilizing liver pad and wrap is shown as pad 4500 in FIGS. 16A-16E and wrap 4600 in FIG. 16D. The pad 4500 can include two layers: a top layer 4502 and a bottom layer 4504. In some embodiments, the top layer 4502 can be made out of polyurethane foam and the bottom layer 4504 can be made out of cellular silicone foam. In this embodiment, the top layer 4502 can be 6 mm thick and the bottom layer 4504 can be 3/16" thick, although other thicknesses and materials can be used. The top layer 4502 and the bottom layer 4504 can be bonded to one another using adhesive such as MOMENTIVE Silicone RTV 118 silicone. The shape of the pad 4500 can be optimized for the liver (e.g., as shown in FIG. 16A). For example, the shape of the pad 4500 can include curved corners and one or more fingers (e.g., 4506, 4508, 4510, 4512, 4514, and 4516). The pad 4500 can also include one or more holes 4520 through which the pad 4500 can be secured to the support surface 2810 using, for example, rivets and/or screws. In some embodiments, the pad 4500 can be approximately 16×12 inches in size, although other sizes are possible.

Sandwiched between the top layer 4502 and the bottom layer 4504 can be a deformable metal substrate 4518. The deformable substrate 4518 can be constructed out of a rigid yet pliable material such as metal, although other materials can be used. In some embodiments, the deformable substrate 4518 is aluminum 1100-0 that is 0.04" thick. The substrate 4518 can be configured so that it is manipulated easily by the user, but resists changes to its positioning due to vibration or impact of the liver. The deformable substrate 4518 can include fingers 4522, 4524, 4526, 4528, 4530, 4532 that correspond to the fingers 4506, 4508, 4510, 4512, 4514, 4516, respectively. By bending the various fingers in the pad 4500, the user can selectively support the liver in a manner that mimics how the liver supported in the human body. An exemplary embodiment of the pad 4500 with the fingers in a curled position is shown in FIG. 16D. In some embodiments, each of the fingers in the deformable substrate 4518 can be tapered (e.g., as shown by 4534) and terminated with a circle. The tapering of the fingers in the substrate 4518 can i) allow the fingers to be curled easier and reduce, or even eliminate the possibility of the finger creasing while being bent, and ii) reduce weight of the pad 4500. The circle can provide a surface that is easily held by the user. The tapered shape of the fingers can be specifically selected to facilitate a rolling of the pad finger to conform to a natural arc rather than a fold or bend.

Referring to FIGS. 16F-16J, in an alternate embodiment, the stabilizer may be comprised of three layers. The top layer 4706 and the bottom layer 4708 may be made of cellular silicone foam. Each foam layer can be 3/16" thick, although other thicknesses and materials can be used. The inner layer is a frame 4702 of a deformable metal substrate in the form of a narrow frame. The frame 4702 can be constructed out of a rigid yet pliable material such as metal, although other materials can be used. In some embodiments, the frame 4702 is aluminum 1100-0 that is 0.04" thick. The frame 4702 can be configured so that it is manipulated easily by the user, but resists changes to its positioning due to vibration or impact of the liver.

The top layer 4706 and the bottom layer 4708 can be bonded to one another and to the frame 4702 using adhesive such as MOMENTIVE Silicone RTV 118 silicone. The top and bottom layers 4706, 4708 cover the area inside the frame 4702, thereby creating a compliant support surface 4700 on which the liver is located for transport. The shape of the support surface 4700 can be optimized for the liver. For example, the shape of the support surface 4700 can include curved corners and one or more projections 4712 to constrain the movement of the liver during transport. In some embodiments, a wrap 4600 can be placed over the liver to hold it in place during transport and maintain moisture in the liver. For example, as shown in FIG. 16D, the wrap 4600 can be attached to the pad on one side (e.g., the right side in FIG. 16D) and the remaining portion of the wrap can be draped over the liver. In other embodiments, the wrap can be secured on multiple edges or all edges. The wrap 4600 may also be used with flexible support surface 4700. In some embodiments, the wrap can perform one or more functions such as securing the liver during transplant, helping maintain sterility, and preserving the moisture in the liver by acting as a vapor barrier. The wrap can be made out of a polyurethane sheet and can be opaque or clear to facilitate visual inspection of the liver. The size of the wrap 4600 can vary. For example, it can have a length that is between 0.5 and 24 inches and a width that is between 0.5 and 24 inches.

2. General Description of Perfusion Circuit

As described above, the liver has two blood supply sources: the hepatic artery and the portal vein, which provide approximately 1/3 and 2/3 of the blood supply to the liver, respectively. Typically, when comparing the blood supply provided by the hepatic artery and the portal vein, the hepatic artery provides a blood supply with a higher pressure yet low flow rate and the portal vein provides a blood supply with a lower-pressure yet high flow rate. Also, typically, the hepatic artery provides a pulsatile flow of blood to the liver whereas the portal vein does not.

The system 600 can be configured to supply perfusion solution to the liver in a manner that simulates the human body (e.g., the proper pressures, volumes, and pulsatile flows) using a single pump. For example, in a normal flow mode, the system 600 can circulate the perfusion fluid to the liver in the same manner as blood would circulate in the human body. More particularly, the perfusion fluid enters the liver through the hepatic artery and the portal vein and flows away from the liver via the IVC. In normal flow mode, the system 100 pumps the perfusion fluid to the liver 102 at a near physiological rate of between about 1-3 L/min, although in some embodiments the range can be 1.1-1.75 L/min (although the system can also be configured to provide flow rates outside of this range, e.g., 0-10 L/min). Each of the foregoing numbers is the total flow per minute provided to the hepatic artery and portal vein.

Figure 17:
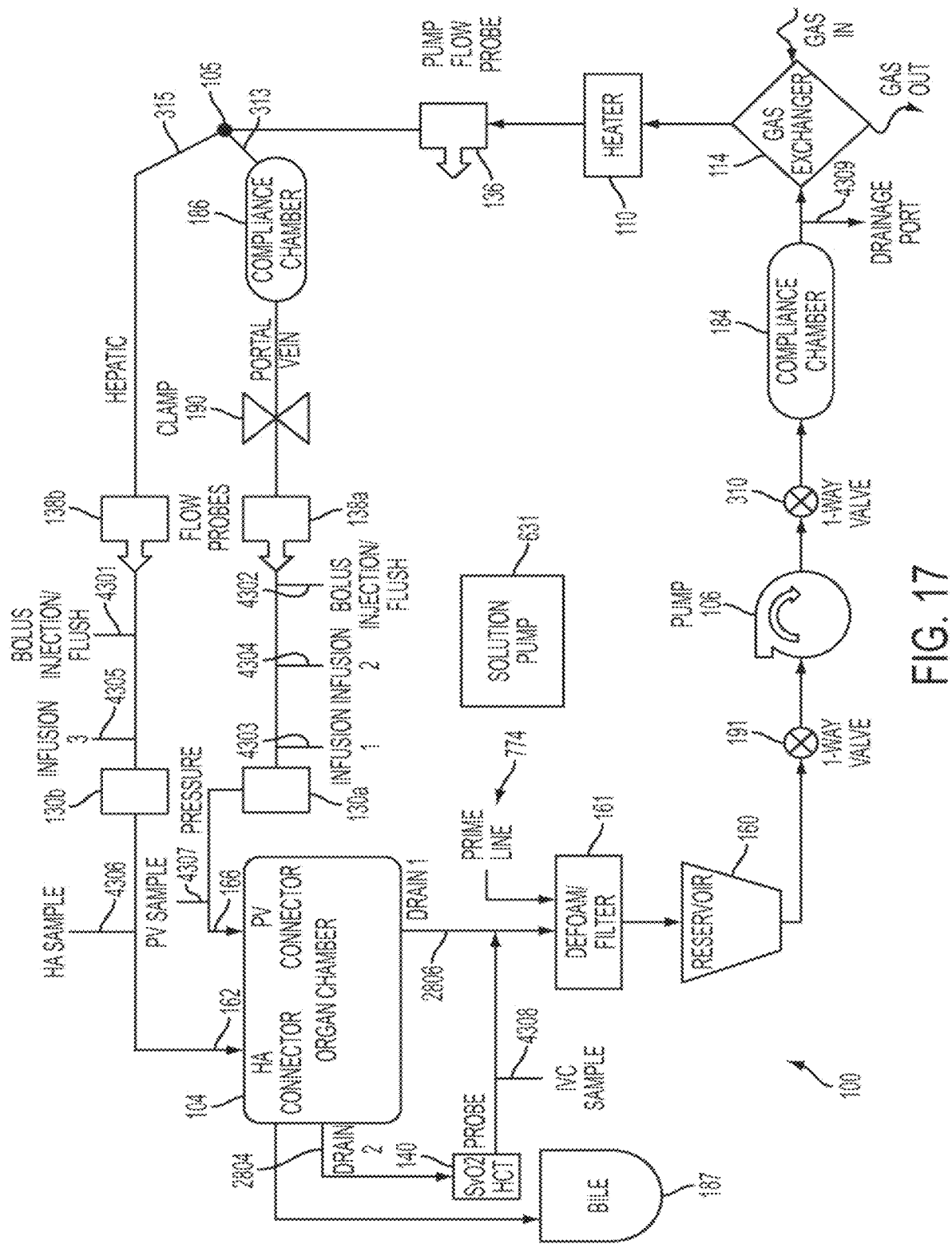
FIG. 17 shows an exemplary system that can be used within an embodiment of the organ care system.

Referring to FIG. 17, an exemplary embodiment of a perfusion set 100 is shown. The perfusion set 100 can include a reservoir 160, a one-way valve 191, a pump 106, a one-way valve 310, compliance chambers 184, 186, a gas exchanger 114, a heater 110, flow meters 136, 138a, 138b, a divider 105, a flow clamp 190 pressure sensors 130a, 130b, organ chamber 104, a sensor 140, defoamer/filter 161, and tubing/interfaces to connect the same. The liver can also be connected to a bag 187 the collects bile produced therefrom. In some embodiments, the perfusion set 100 is contained entirely within the single use module 634, although this is not required. In some embodiments, the inferior vena cava (IVC) is cannulated so that flow from the IVC can be directed to a conduit in which the IVC pressure, flow, and oxygen saturation can be measured. In other embodiments, the IVC is not cannulated and perfusate flows freely from the IVC into the organ chamber 104 (and ultimately into the drain(s) in the organ chamber 104).

In one embodiment, perfusion fluid flows from the reservoir 160 to valve 191 and then to the pump 106. After pump 106, the perfusion can flow to one-way valve 310 to compliance chamber 184. After compliance chamber 184, the perfusion fluid can flow to the gas exchanger 114 and on to the heater 110. After the heater 110 the perfusion fluid can flow to the flow meter 136 which is configured to measure the flow rate at that part of the perfusion circuit. After the flow meter 136 the perfusion fluid flows to the divider 105, which can divide the flow of the perfusion fluid into branches 313 and 315. In some embodiments, the divider 105 can split the flow between the hepatic artery and the portal vein at a ratio of between 1:2 and 1:3. Branch 313 is ultimately provided to the portal vein of the liver whereas branch 315 is ultimately provided to the hepatic artery of the liver. The branch 313 can include flow meter 138a and the compliance chamber 186 which provides perfusion fluid to the flow clamp 190. From the flow clamp 190 the perfusion fluid can flow to the pressure sensor 130a before being provided to the portal vein of the liver. The branch 315 can include a flow meter 138b which provides perfusion fluid to the pressure meter 130b before being provided to the hepatic artery of the liver. After perfusion fluid exits the liver, some of the perfusion fluid is collected by the measurement drain 2804 and the remainder is collected by the main drain 2806. The perfusion fluid collected by the measurement drain 2804 can be provided to the sensor 140. Perfusion fluid exiting the sensor 140 can be provided to the defoamer/filter 161. The perfusion fluid collected by the drain 2806 can be provided directly to the defoamer/filter 161. Perfusion fluid exiting the defoamer/filter 161 can be provided to the reservoir 160. Additionally, bile produced by the liver can be collected in a bag 187.

In some embodiments, the system 100 has at least 1.6 L of perfusion fluid (or other fluid) in it when operating.

3. Reservoir

The single use module 634 can include a perfusate reservoir 160 that is mounted below the organ chamber 104. The reservoir 160 can be configured to store and filter perfusion fluid 108 as it circulates through the perfusion set 100. Reservoir 160 can include one or more one-way valves (not shown) that prevent the flow of perfusion fluid in the wrong direction. In some embodiments, the reservoir 160 has a minimum capacity of 2 L, although smaller capacities can be used. In some embodiments, the reservoir 160 can include a filter (shown separately in FIG. 17 as defoamer/filter 161) that is designed to trap particles in the perfusion fluid 108. In some embodiments, the filter is configured to trap particles in the perfusion fluid 108 that are greater than 20 microns. In some embodiments, the reservoir 160 includes a defoamer (shown separately in FIG. 17 as defoamer/filter 161) that reduces and/or eliminates foam generated from the perfusion fluid 108. In some embodiments, the reservoir 160 can be made of a clear material and can include level markings so that a user may estimate the volume of the perfusion fluid in the reservoir 160. In some embodiments, the reservoir 160 can be configured to allow for a minimum of 4.5 L per minute a fluid ingress from the organ chamber 104, although other flow rates are possible. In some embodiments, the reservoir 160 includes a vent to the atmosphere that includes a sterile barrier (not shown).

The reservoir 160 can be positioned within the system 600 in various locations. For example, the reservoir 160 can be located above the liver, completely below the liver, partially below the liver, next to the liver, etc. Thus, one potential benefit some embodiments described herein is that the reservoir can be positioned below the liver since a gravity-induced pressure head in the perfusion fluid is not required.

4. Valves

In some embodiments, the valves 191 and 310 are one-way valves configured to ensure that the perfusion fluid in the system 100 flows in the correct direction through the system 100. Exemplary embodiments of the valves 191 and 310 are described above with respect to the pump 106.

5. Perfusion Fluid Pump

An exemplary embodiments of the pump 106 is described more fully above with respect to FIGS. 6A-6E. As described above, in some embodiments, the pump is split between the multiple use module 650 and the single use module 634. For example, the single use module 634 can include the pump interface assembly while the multiple use module 650 includes the pump driver portion.

6. Compliance Chamber

While the pump 106 provides a generally pulsatile output, the characteristics of that flow are typically adapted to match the flow typically provided by the human body to the liver. For example, the portal vein typically does not provide a pulsatile flow of blood to a liver when the liver is in vivo. Thus, in some embodiments, in order to provide a non-pulsatile flow of perfusion fluid to the portal vein of the liver, one or more compliance chambers can be used to mitigate the pulsatile flow generated by the pump 106. In some embodiments, the compliance chambers are essentially small in-line fluid accumulators with flexible, resilient walls for simulating the human body's vascular compliance. The compliance chambers can aid the system 600 by more accurately mimicking blood flow in the human body, for example, by filtering/reducing fluid pressure spikes due, for example, to the flow profile from the pump 106. In the embodiment of system 600 described herein, two compliance chambers are used: compliance chamber 184 and 186. Various characteristics of the compliance chambers can be varied to achieve the desired result. For example, the combination i) a pressure versus volume relationship, and ii) the overall volume of the compliance chamber can affect the performance of the compliance chamber. Preferably the characteristics of the respective compliance chambers are chosen to achieve the desired effect.

In some embodiments, the compliance chamber 184 is located between the valve 310 and the gas exchanger 114 and operates to partially smooth the pulsatile output of the pump 106. For example, the compliance chamber 184 can be configured such that the flow of perfusion fluid ultimately provided to the hepatic artery of the liver mimics that of the human body. In some embodiments, the compliance chamber 184 can be omitted if the output of the pump 106 results in a perfusate flow to the hepatic artery that closely mimics that of the human body.

In some embodiments, the compliance chamber 186 is located between the divider 105 and the flow clamp 190. The compliance chamber 186 can operate to substantially reduce, or even eliminate the pulsatile nature of the flow of perfusion fluid ultimately provided to the portal vein. Additionally, while the compliance chamber 186 is positioned before the flow clamp 190 in the branch 313, this is not required. For example, flow clamp 190 can come before the compliance chamber 186. In this embodiment, however, it may be desirable to adjust the parameters of the compliance chamber 186.

7. Gas Exchanger

The system 600 can also include a gas exchanger 114 (also referred to herein as an oxygenator) that is configured to, for example, remove $CO_2$ from the perfusion fluid and add $O_2$. The gas exchanger 114 can receive input gas from an external or onboard source (e.g., gas supply 172 or oxygen concentrator) through a gas regulator and/or a gas flow chamber which can be a pulse-width modulated solenoid valve that controls gas flow, or any other gas control device that allows for precise control of gas flow rate. In some embodiments, the gas exchanger 114 is a standard membrane oxygenator, such as the interventional lung assist membrane ventilator from NOVALUNG or member of the Quadrox series from Maquet of Wayne, NJ In the illustrative embodiment, the gas can be a blend of oxygen, carbon dioxide, and nitrogen. An exemplary blend of gas is: 80% $O_2$, 0.1% $CO_2$, and the balance $N_2$ with a blend process accuracy of 0.030%. In some embodiments, the operation of the gas exchanger, regulator, and/or gas flow chamber can be controlled by the controller 150 using the output of the sensor 140.

In some embodiments, the oxygenator 114 can have an oxygen transfer rate of 27.5 mLpm/LPM minute at a blood flow of 500 mLpm at standard conditions. The oxygenator 114 can also have a carbon dioxide transfer rate of 20 mLpm at a blood flow rate of 500 mLpm at standard conditions. Standard conditions can be, for example: gas=100% $O_2$, blood temp=37.0±0.5° C., hemoglobin=12±1 mg %, $SvO_2$=65±5%, pCO2=45±5 mmHg, and gas to blood ratio of 1:1). The above values are exemplary only and not limiting. Transfer rates higher and/or lower than the rate identified above can be used.

8. Heater/Cooler

The perfusion set 100 can include one or more heaters that are configured to maintain the temperature of the perfusion fluid 108 at a desired level. By warming the perfusion fluid, and the flowing the warmed liquid through the liver, the liver itself can also be warmed. While the heater can be capable of warming the perfusion fluid to a wide range of temperatures (e.g., 0-50° C.), typically, the heater warms the perfusion fluid to a temperature of 30-37° C. In some more specific embodiments, the heater can be configured warm the perfusion fluid to a temperature of 34-37° C., 35-37° C., or any other range that falls within 0-50° C. In some embodiments, the ranges described herein can also extend to 42° C.

Referring to FIGS. 18A-18G, an exemplary embodiment of a heater assembly 110 is shown. FIGS. 18A-18F depict various views of the perfusion fluid heater assembly 110.

The heater assembly 110 can include a housing 234 having an inlet 110a and an outlet 110b. As shown in both the longitudinal cross-sectional and the lateral cross-sectional views, the heater assembly 110 can include a flow channel 240 extending between the inlet 110a and the outlet 110b. The heater assembly 110 can be conceptualized as having upper 236 and lower 238 symmetrical halves. Accordingly, only the upper half is shown in an exploded view in FIG. 18F.

The flow channel 240 can be formed between first 242 and second 244 flow channel plates. The inlet 110a can flow the perfusion fluid into the flow channel 240 and the outlet 110b can flow the perfusion fluid out of the heater 110. The first 242 and second 244 flow channel plates can have substantially bioinert perfusion fluid 108 contacting surfaces for providing direct contact with the perfusion fluid flowing through the channel 240. The fluid contacting surfaces can be formed from a treatment or coating on the plate or may be the plate surface itself. The heater assembly 110 can include first and second electric heaters 246 and 248, respectively. The first heater 246 can be located adjacent to and can couple heat to a first heater plate 250. The first heater plate 250, in turn, can couple the heat to the first flow channel plate 242. Similarly, the second heater 248 can be located adjacent to and can couple heat to a second heater plate 252. The second heater plate 252 can couple the heat to the second flow channel plate 244. According to the illustrative embodiment, the first 250 and second 252 heater plates can be formed from a material, such as aluminum, that conducts and distributes heat from the first 246 and second 248 electric heaters, respectively, relatively uniformly. The uniform heat distribution of the heater plates 250 and 252 can enable the flow channel plates to be formed from a bioinert material, such as titanium, reducing concern regarding its heat distribution characteristic. The heater assembly 110 can also include O-rings 254 and 256 for fluid sealing respective flow channel plates 242 and 244 to the housing 234 to form the flow channel 240. In some embodiments the function of the heater plate and flow channel plate are combined in a single plate.

The heater assembly 110 can further include first assembly brackets 258 and 260. The assembly bracket 258 can mount on the top side 236 of the heater assembly 110 over a periphery of the electric heater 246 to sandwich the heater 246, the heater plate 250 and the flow channel plate 242 between the assembly bracket 258 and the housing 234. The bolts 262a-262j can fit through corresponding through holes in the bracket 258, electric heater 246, heater plate 250 and flow channel plate 242, and thread into corresponding nuts 264a-264j to affix all of those components to the housing 234. The assembly bracket 260 can mount on the bottom side 238 of the heater assembly 110 in a similar fashion to affix the heater 248, the heater plate 252 and the flow channel plate 244 to the housing 234. A resilient pad 268 can interfit within a periphery of the bracket 258. Similarly, a resilient pad 270 can interfit within a periphery of the bracket 260. A bracket 272 can fit over the pad 268. The bolts 278a-278f can interfit through the holes 276a-276f, respectively, in the bracket 272 and thread into the nuts 280a-280f to compress the resilient pad 268 against the heater 246 to provide a more efficient heat transfer to the heater plate 250. The resilient pad 270 can be compressed against the heater 248 in a similar fashion by the bracket 274.

The illustrative heater assembly 110 can include temperature sensors 120 and 122 and dual-sensor 124. The dual sensor 124, which in practice can include a dual thermistor sensor for providing fault tolerance, can measure the temperature of the perfusion fluid 108 exiting the heater assembly 110, and can provide these temperatures to the controller 150. As described in further detail with respect to the heating subsystem 149, the signals from the sensors 120, 122 and 124 can be employed in a feedback loop to control drive signals to the first 246 and/or second 248 heaters to control the temperature of the heaters 256 and 248. Additionally, to ensure that heater plates 250 and 252 and, therefore, the blood contacting surfaces 242 and 244 of the heater plates 250 and 252 do not reach a temperature that might damage the perfusion fluid, the illustrative heater assembly 110 can also include temperature sensors/lead wires 120 and 122 for monitoring the temperature of the heaters 246 and 248, respectively, and providing these temperatures to the controller 150. In practice, the sensors attached to sensors/lead wires 120 and 122 can be RTD (resistance temperature device) based. The signals from the sensors attached to sensors/lead wires 120 and 122 can be employed in a feedback loop to further control the drive signals to the first 246 and/or second 248 heaters to limit the maximum temperature of the heater plates 250 and 252. As a fault protection, there can be sensors for each of the heaters 246 and 248, so that if one should fail, the system can continue to operate with the temperature at the other sensor.

Figure 18A:
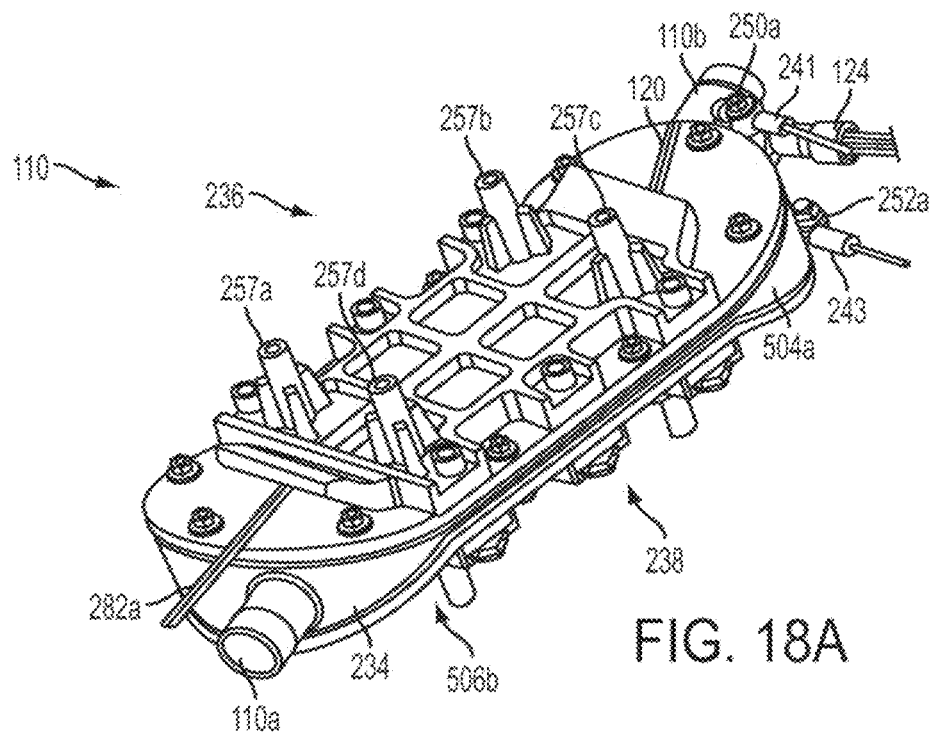
Figure 18B:
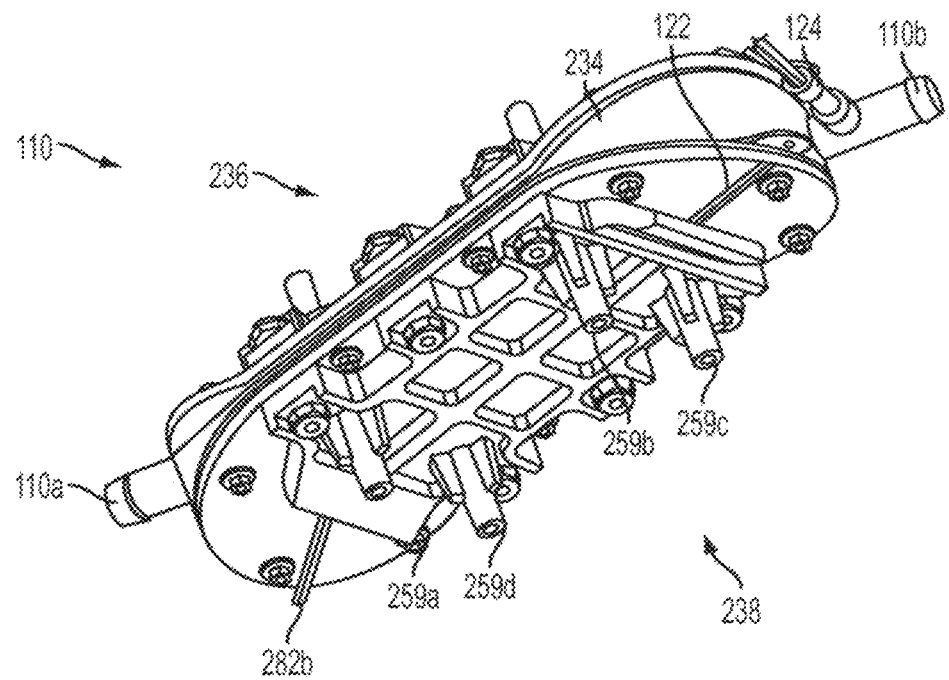
Figure 18C:
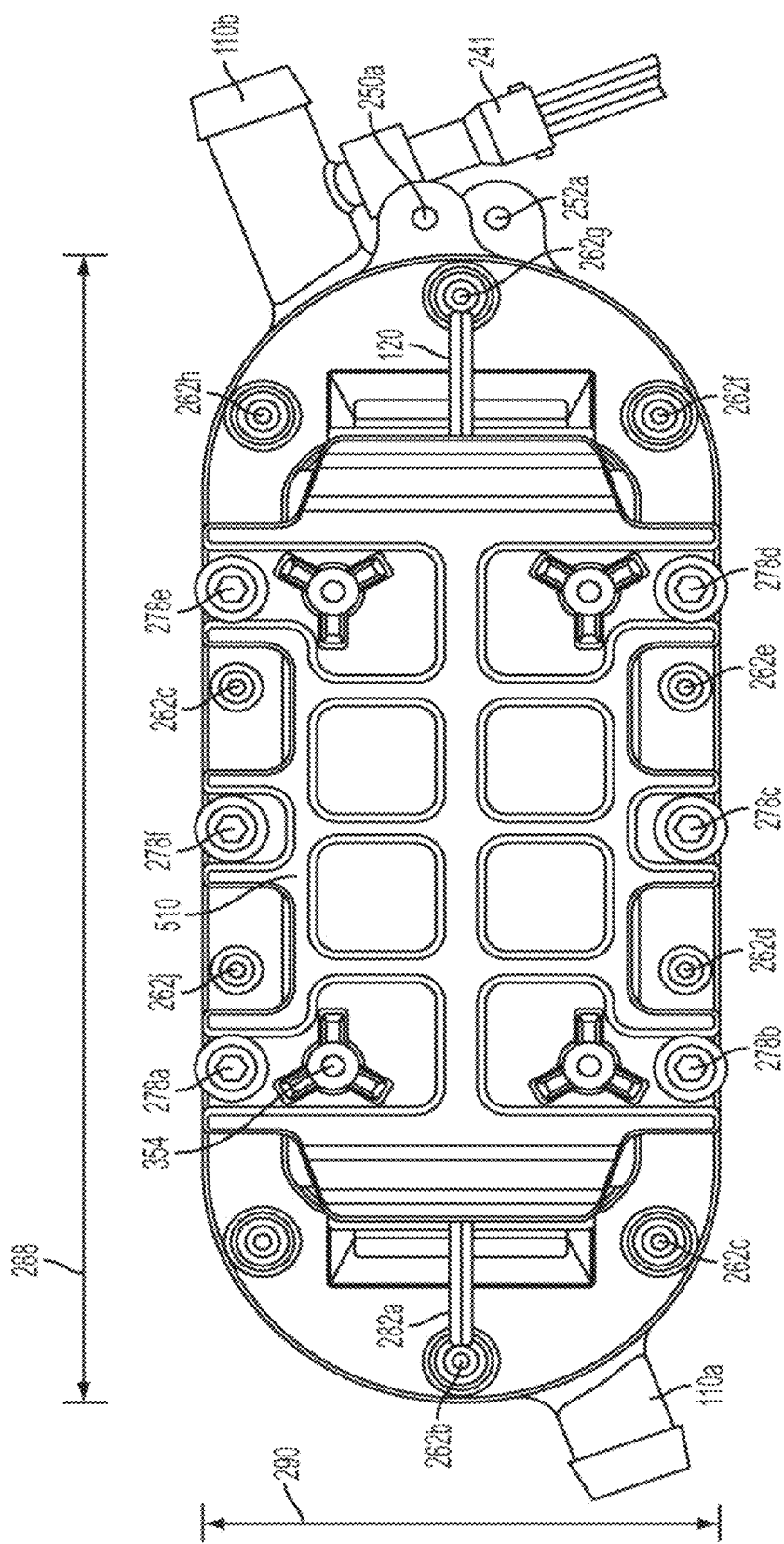
Figure 18D:
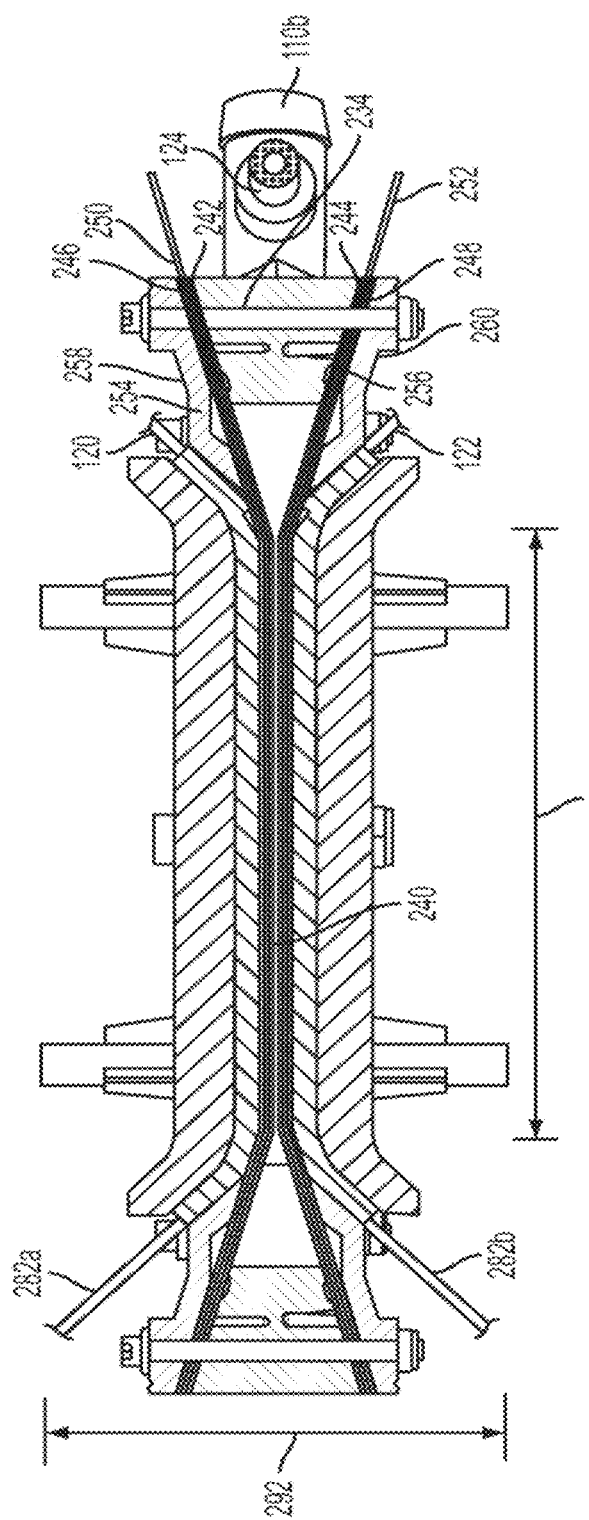
Figure 18F:
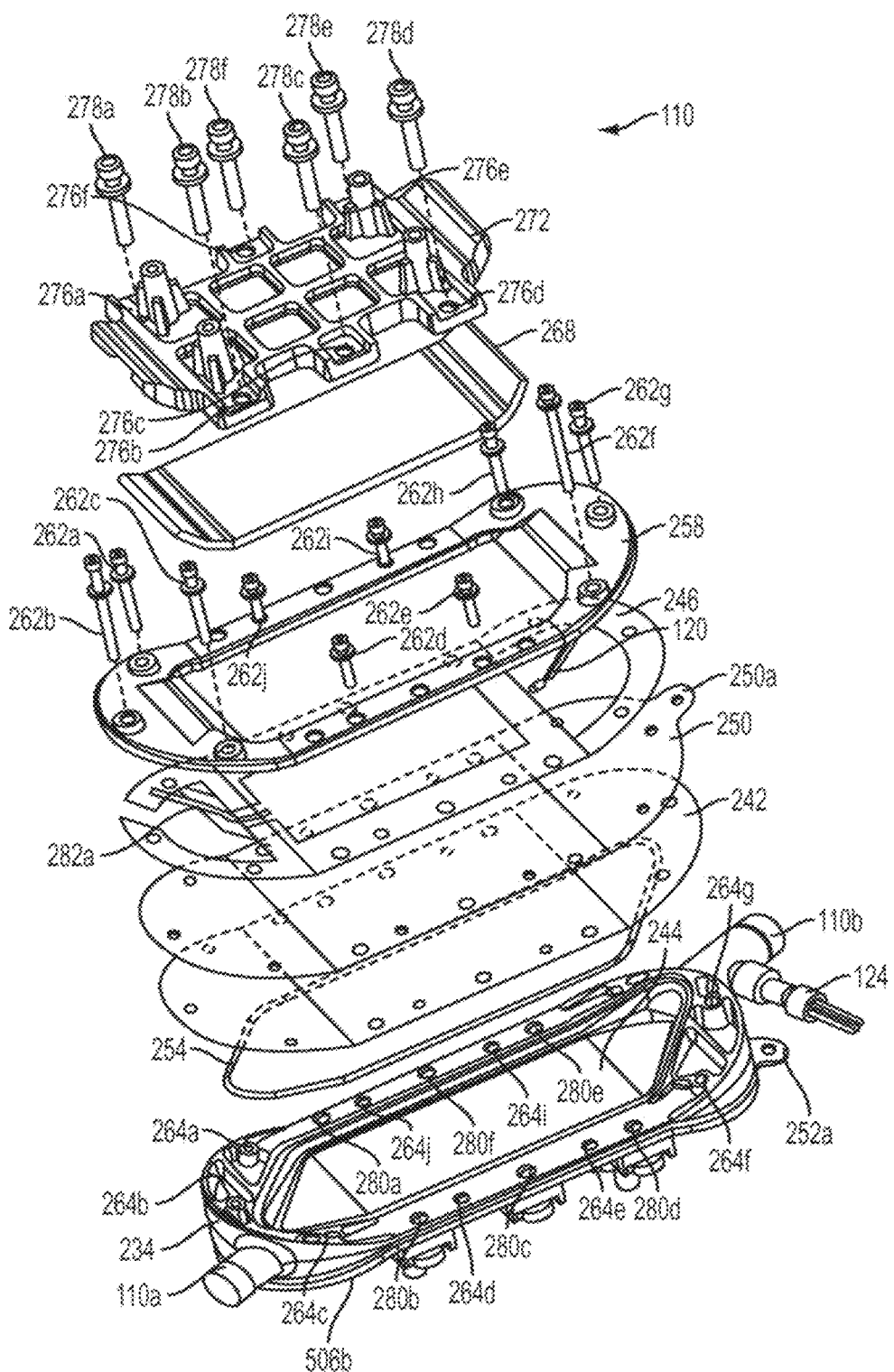
Figure 18G:
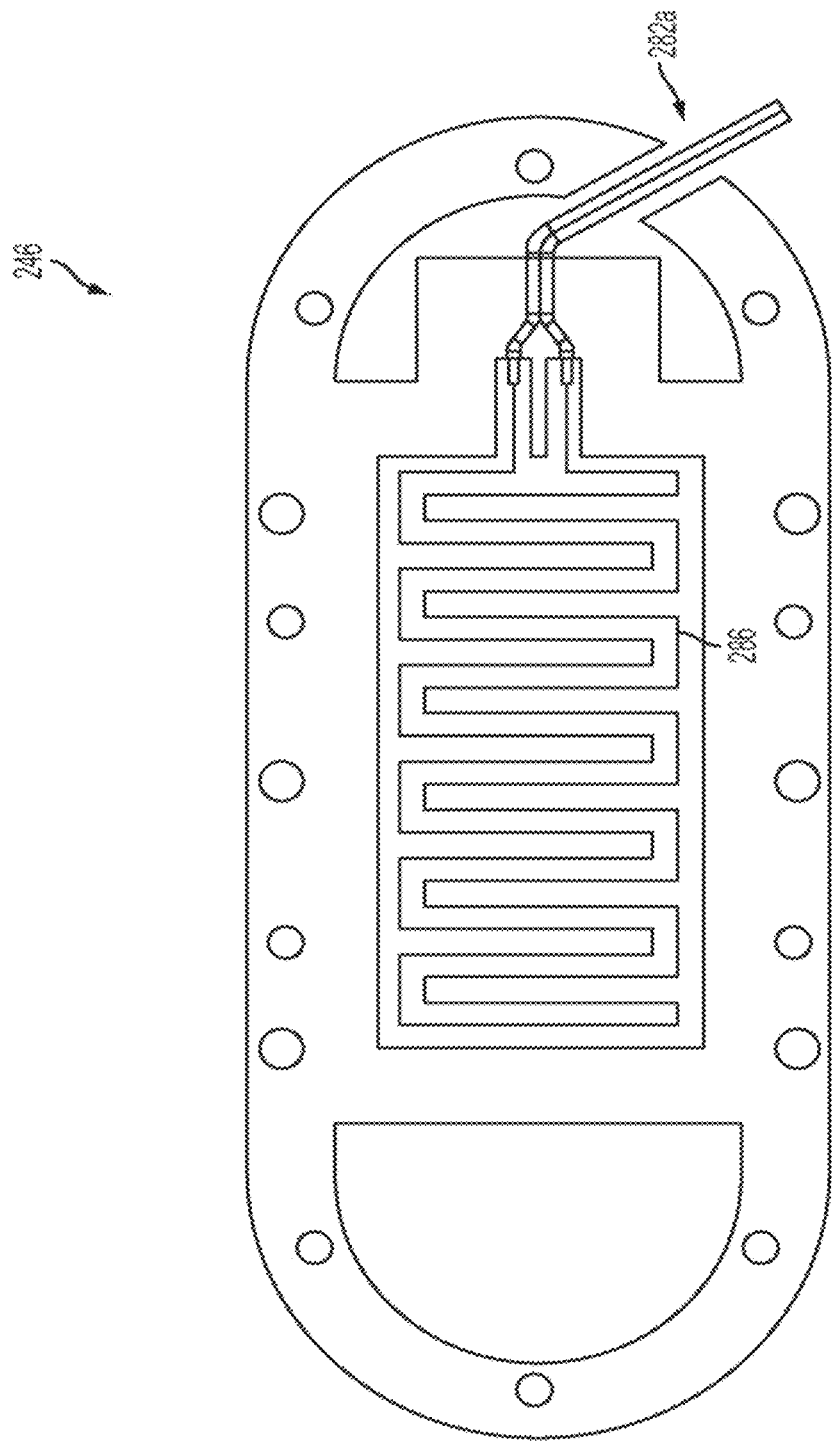

The heater 246 of the heater assembly 110 can receive from the controller 150 drive signals 281a and 281b (collectively 281) onto corresponding drive lead 282a. Similarly, the heater 248 receives from the controller 150 drive signals 283a and 283b (collectively 283) onto drive lead 282b. The drive signals 281 and 283 control the current to, and thus the heat generated by, the respective heaters 246 and 248. More particularly, as shown in FIG. 18G, the drive leads 282a includes a high and a low pair, which connect across a resistive element 286 of the heater 246. The greater the current provided through the resistive element 286, the hotter the resistive element 286 gets. The heater 248 operates in the same fashion with regard to the drive lead 282b. According to the illustrative embodiments, the element 286 has a resistance of about 5 ohms. However, in other illustrative embodiments, the element may have a resistance of between about 3 ohms and about 10 ohms. The heaters 246 and 248 can be controlled independently by the processor 150.

The heater assembly 110 housing components can be formed from a molded plastic, for example, polycarbonate, and can weigh less than about one pound. More particularly, the housing 234 and the brackets 258, 260, 272 and 274 can all be formed from a molded plastic, for example, polycarbonate. According to another feature, the heater assembly can be a single use disposable assembly.

In operation, the illustrative heater assembly 110 can use between about 1 Watt and about 200 Watts of power, and can be sized and shaped to transition perfusion fluid 108 flowing through the channel 240 at a rate of between about 300 ml/min and about 5 L/min from a temperature of less than about 30° C. to a temperature of at least 37° C. in less than about 30 minutes, less than 25 minutes, less than about 20 minutes, less than about 15 minutes, or even less than about 10 minutes, without substantially causing hemolysis of cells, or denaturing proteins or otherwise damaging any blood product portions of the perfusion fluid.

The heater assembly 110 can include housing components, such as the housing 234 and the brackets 258, 260, 272 and 274, that are formed from a polycarbonate and weighs less than about 5 lb. In some embodiments, the heater assembly can weigh less than 4 pounds. In the illustrative embodiment, the heater assembly 110 can have a length 288 of about 6.6 inches, not including the inlet 110a and outlet 110b ports, and a width 290 of about 2.7 inches. The heater assembly 110 can have a height 292 of about 2.6 inches. The flow channel 240 of the heater assembly 110 can have a nominal width 296 of about 1.5 inches, a nominal length 294 of about 3.5 inches, and a nominal height 298 of about 0.070 inches. The height 298 and width 296 can be selected to provide for uniform heating of the perfusion fluid 108 as it passes through the channel 240. The height 298 and width 296 are also selected to provide a cross-sectional area within the channel 240 that is approximately equal to the inside cross-sectional area of fluid conduits that carry the perfusion fluid 108 into and/or away from the heater assembly 110. In one embodiment, the height 298 and width 296 are selected to provide a cross-sectional area within the channel 240 that is approximately equal to the inside cross-sectional area of the inlet fluid conduit 792 and/or substantially equal to the inside cross-sectional area of the outlet fluid conduit 794.

Projections 257a-257d and 259a-259d can be included in the heater assembly 110 and can be used to receive a heat-activated adhesive for binding the heating assembly to the multiple-use unit 650.

In addition to the heater 110, the system 100 can also include an additional heater (not shown) that is placed inside the organ chamber 110 to provide heat (e.g., a resistance heater).

9. Pressure/Flow Probes

In some embodiments, the system 600 can include pressure sensors 130a, 130b and flow sensors 138a, 138b. The probes and/or sensors can be obtained from standard commercial sources. For example, the flow rate sensors 136, 138a, and 138b can be ultrasonic flow sensors, such as those available from Transonic Systems Inc., Ithaca, N.Y. The fluid pressure probes 130a, 130b can be conventional, strain gauge pressure sensors available from MSI or G.E. Thermometrics. Alternatively, a pre-calibrated pressure transducer chip can be embedded into organ chamber connectors and connected to the controller 150. In some embodiments, the sensors can be configured to measure mean, instantaneous, and/or peak values flow/pressure values. In embodiments where a mean value is calculated, the system can be configured to calculate the mean pressure using a running average sampled values. The sensors can also be configured to provide systolic and diastolic measurements. While these are shown as separate devices in FIG. 17, in some embodiments, a single device can measure both pressure and flow. In some embodiments, the sensors can be configured to measure pressures between 0-225 mmHg with an accuracy of ±(7%+10 mmHg) for each transducer. In some embodiments the flow sensor can be configured to measure flow rates between 0-10 L/min with an accuracy of ±12%+0.140 L/min. In some embodiments the pressure and flow sensors can be configured to sample the pressure/flow within the cannula tip, within the vessel, or in the tubing prior to the cannula.

While there is a single sensor 130b and a single sensor 130a, these sensors can include more than one pressure sensor. For example, in some embodiments, the sensor 130a can include two pressure sensors for redundancy. In such an embodiment, when both sensors are working the controller 150 can average the output of both to determine the actual pressure. In embodiments where one of the two pressure sensors in sensor 130a fails, the controller can ignore the malfunctioning sensor.

As described more fully below with respect to FIGS. 23A-23K, the pressure sensors can be contained in a housing 3010 of the connector 3000 (and similarly on the connector 3050).

10. Flow Control

The system 600 can be configured to provide perfusate flow rates varying from 0-10 L/min at the flow sensor 136 (e.g., before the divider 105). In some embodiments, the system can be configured to provide a flow rate of 0.6-4 L/min at the flow sensor 136, or even more specifically, 1.1-1.75 L/min at the flow sensor 136. These ranges are exemplary only and the flow rate at the sensor 136 can be provided within any range that falls within 0-10 L/min. The system 600 can be configured to provide perfusate flow rates varying from 0-10 L/min, and more specifically 0.25-1 L/min to the hepatic artery of the liver (e.g., as measured by the flow sensor 130b). These ranges are exemplary only and the flow rate at hepatic artery can be provided within any range that falls within 0-10 L/min. The system 600 can be configured to provide perfusate flow rates varying from 0-10 L/min, and more specifically 0.75 to 2 L/min to the portal vein of the liver (e.g., as measured by the flow sensor 130a). These ranges are exemplary only and the flow rate at the portal vein can be provided within any range that falls within 0-10 L/min.

In some embodiments, the system 100 can be capable of generating perfusate flow through the perfusion module at rates of 0.3-3.5 L/min with at least 1.8 Liters of perfusion fluid therein. In some embodiments, the pressure provided to the hepatic artery via the branch 315 can be between 25-150 mmHg and more specifically between 50-120 mmHg, and the pressure provided to the portal vein via the branch 313 can be between 1-25 mmHg and more specifically 5-15 mmHg. These ranges are exemplary only and the respective pressures can be provided within any range that falls within 5-150 mmHg.

11. Perfusate Sensors

Figure 19A:
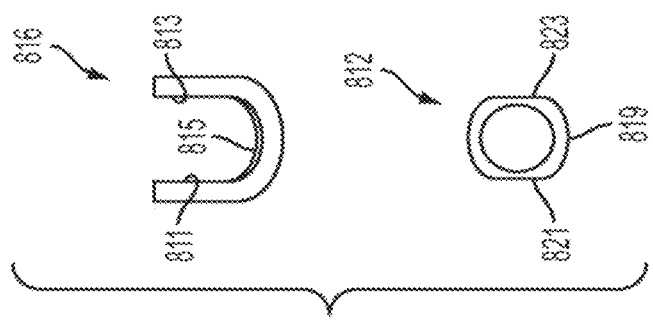
FIG. 19A-19C show an exemplary sensor system that can be used within an embodiment of the organ care system.
Figure 19B:
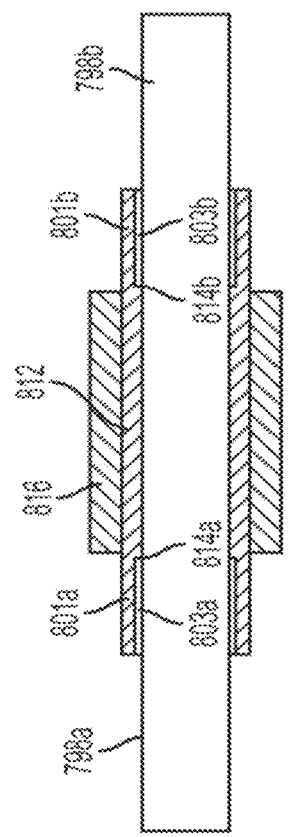
Figure 19C:
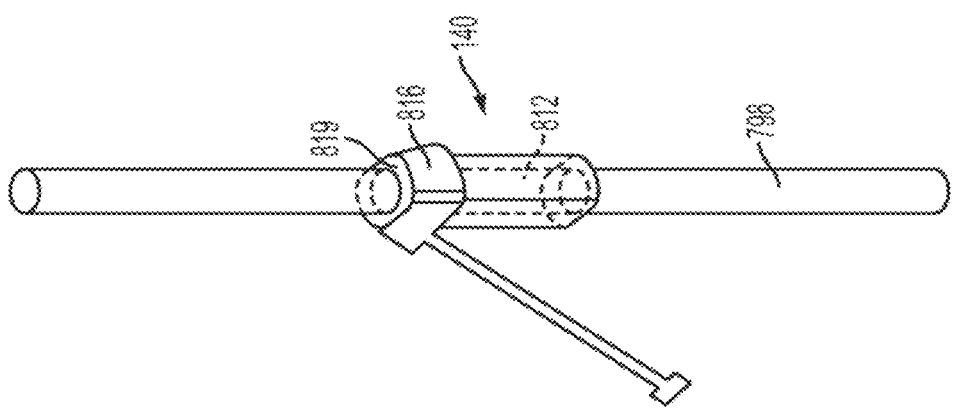

The sensor 140 can sense one or more characteristics of the perfusion fluid flowing from the liver by measuring the amount of light absorbed or reflected by the perfusion fluid 108 when applied at multi-wavelengths. For example, the sensor 140 can be an $O_2$ saturation, hematocrit, and/or temperature sensor. FIGS. 19A-19C depict an exemplary embodiment of the sensor 140. The sensor 140 can include an in-line cuvette shaped section of tube 812 connected to the conduit 798, which can have at least one optically clear window through which an infrared sensor can provide infrared light. Exemplary embodiments of the sensor 140 can be the BLOP4 and/or BLOP4 Plus probes from DATA-MED SRL. The cuvette 812 can be a one-piece molded part having connectors 801a and 801b. The connectors 801a and 801b can be configured to adjoin to connecting receptacles 803a and 803b, respectively, of conduit ends 798a and 798b. This interconnection between cuvette 812 and conduit ends 798a and 798b can be configured so as to provide a substantially constant cross-sectional flow area inside conduit 798 and cuvette 812. The configuration can thereby reduce, and in some embodiments substantially removes, discontinuities at the interfaces 814a and 814b between the cuvette 812 and the conduit 798. Reduction/removal of the discontinuities can enable the blood based perfusion fluid 108 to flow through the cuvette with reduced lysing of red blood cells and reduced turbulence, which can enable a more accurate reading of perfusion fluid oxygen levels. This can also reduce damage to the perfusion fluid 108 by the system 600, which can ultimately reduce damage done to the organ being transplanted.

The cuvette 812 can be formed from a light transmissive material, such as any suitable light transmissive glass or polymer. As shown in FIG. 19A, the sensor 140 can also include an optical transceiver 816 for directing light waves at perfusion fluid 108 passing through the cuvette 812 and for measuring light transmission and/or light reflectance to determine the amount of oxygen in the perfusion fluid 108. In some embodiments a light transmitter can be located on one side of the cuvette 812 and a detector for measuring light transmission through the perfusion fluid 108 can be located on an opposite side of the cuvette 812. FIG. 19C depicts a top cross-sectional view of the cuvette 812 and the transceiver 816. The transceiver 816 can fit around cuvette 812 such that transceiver interior flat surfaces 811 and 813 mate against cuvette flat surfaces 821 and 823, respectively, while the interior convex surface 815 of transceiver 816 mates with the cuvette 812 convex surface 819. In operation, when UV light is transmitted from the transceiver 816, it travels from flat surface 811 through the fluid 108 inside cuvette 812, and is received by flat surface 813. The flat surface 813 can be configured with a detector for measuring the light transmission through the fluid 108.

In some embodiments, the sensor 140 can be configured to measure $SvO_2$ in the range of 0-99%, although in some embodiments this can be limited to 50-99%. To the extent that the sensor 140 also measures hematocrit, the measurement range can be from 0-99%, although in some embodiments this can be limited to 15-50%. In some embodiments, the accuracy of the measurements made by the sensor 140 can be ±5 units and measurements can occur at least once every 10 seconds. In embodiments of the sensor 140 that also measure temperature, the measurement range can be from 0-50° C.

In some embodiments, the system 600 can also include one or more lactate sensors (not shown) that are configured to measure lactate in the perfusion fluid. For example, a lactate sensor can be placed between the measurement drain 2804 and the defoamer/filter 161, in branch 315, and/or in branch 313. In this configuration, the system 600 can be configured to measure lactate values of the perfusion fluid before and/or after processing by the liver. In some embodiments, the lactate sensor can be an in-line lactate analyzer probe. In some embodiments the lactate sensor can also be external to the system 600 and use samples of the perfusion fluid withdrawn from a sampling port.

In some embodiments the system 600 can also include one or more sensors (e.g., the sensor 140 and/or other sensors such as a disposable blood gas analysis probe) to measure pH, $HCO_3$, $pO_2$, $pCO_2$, glucose, sodium, potassium, and/or lactate. Exemplary sensors that can be used to measure the foregoing values include off-the-shelf probes made by Sphere Medical of Cambridge, United Kingdom. As described above, the sensor can be coupled to the measurement drain 2804. Alternatively, a piece of tubing can be used to route perfusion fluid to/from the sensor. Some embodiments of the sensor use calibration fluid before and/or after performing a measurement. In embodiments using such sensors, the system can include a valve that can be used to control the flow of calibration fluid to the sensor. In some embodiments, the valve can be manually actuated and/or automatically actuated by the controller 150. In some embodiments of the sensor, calibration fluid is not used, which can result in a continuous sampling of the perfusion fluid.

In addition to using the foregoing sensors in a feedback loop to control the system 600, some or all of the sensors can also be used to determine the viability of the liver for transplant.

In some embodiments, external blood analyzer sensors can also be used. In these embodiments, blood samples can be drawn from ports in the branches 313, 315 (the ports are described more fully below). The blood samples can be provided for analysis using standard hospital equipment (e.g. radiometer) or via point of care blood gas analysis (e.g., I-STAT1 from Abbott Laboratories or the Epoc from Alere).

12. Sampling/Infusion Ports

The system 600 can include one or more ports that can be used to sample the perfusion fluid and/or infuse fluid into the perfusion fluid. In some embodiments, the ports can be configured to work with standard syringes and/or can be configured with controllable valves. In some embodiments, the ports can be luer ports. Essentially, the system 100 can include infusion/sampling ports at any location therein and the following examples are not limiting.

Referring to FIG. 17, the system 100 can include ports 4301, 4302, 4303, 4304, 4305, 4306, 4307, and 4308. The port 4301 can be used to provide a bolus injection and/or flush (e.g., a post-preservation flush) to the hepatic artery. The port 4302 can be used to provide a bolus injection and/or flush (e.g., post-preservation flush) to the portal vein. The ports 4303, 4304, 4305 can be coupled to the respective channels of the solution pump 631 and can provide infusion to the portal vein (in the case of 4303 and 4304) and to the hepatic artery (in the case of 4305). The ports 4306 and 4307 can be used to obtain a sample of the perfusion fluid flowing into the hepatic artery and portal vein, respectively. The port 4308 can be used to sample the perfusion fluid in the IVC (or hepatic veins, depending on how the liver was harvested). In some embodiments, each of the ports can include a valve that the user operates to obtain a flow from the ports.

The port configuration shown in FIG. 17 is exemplary, and more or fewer ports can be used. Additionally, ports can be located in additional locations such as between the pump 106 and the divider 105, between the organ chamber and bile bag 187, in the bile bag 187, between the main drain 2806 and the defoamer/filter 161.

The single use module 634 can also include a tube 774 for loading priming solution and the exsanguinated blood from the donor or blood products from a blood bank into the reservoir 160. The priming tube 774 can be provided directly to the reservoir 160 and/or it can be located so that an end of it empties directly above the drain 2806 in the organ chamber 104. The single use module 634 can also include non-vented caps for replacing vented caps on selected fluid ports that are used, for example, while running a sterilization gas through the single use module 634.

Some embodiments the system 100 can also include vents and/or air purge ports to eliminate air from the hepatic artery interface, the portal vein interface, or elsewhere in the system 100.

In some embodiments an extra infusion port can be included for the user to provide an imaging contrast medium to the perfusion fluid so that imaging of the liver can be enhanced. For example, an ultrasound contrast medium can be infused to perform a contrast-enhanced ultrasound.

13. Organ Assist

Figure 30:
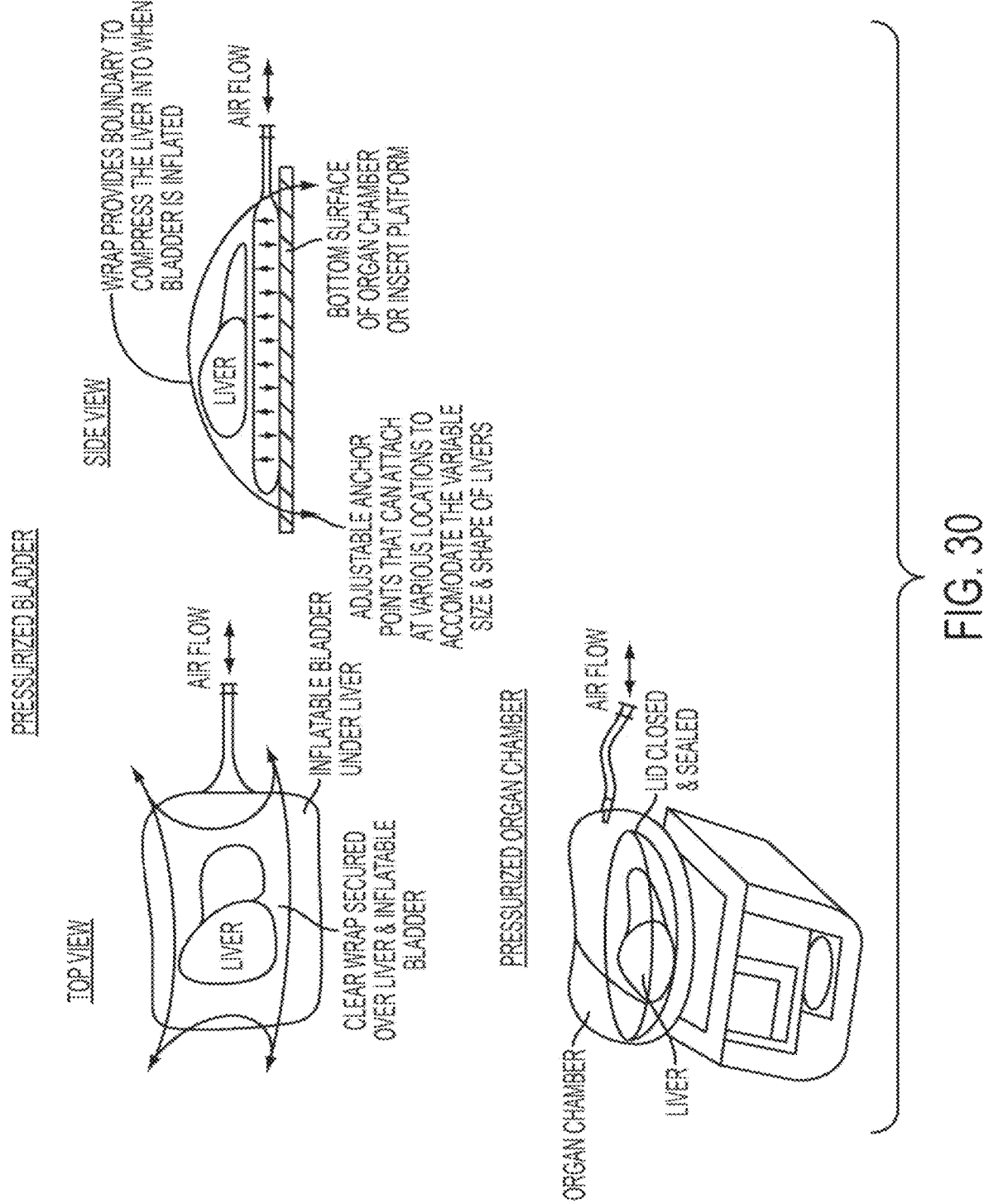
FIG. 30 shows exemplary systems that can be used within an embodiment of the organ care system.

While perfusion fluid can drain naturally from the liver as a result of the pressure applied to the hepatic artery and portal vein, the system 600 can also include additional features that help the perfusion fluid drain from the liver in a manner that mimics the human body. That is, in the human body the diaphragm typically applies pressure to the liver as the person breathes. This pressure can help expel blood from the person's liver. The system 600 can include one or more systems that are designed to mimic the pressure applied by the diaphragm to the liver. Exemplary embodiments include contact and contactless embodiments. In some embodiments, the amount of pressure applied to the liver can be less than the pressure in the portal vein and/or hepatic artery of the liver. Sketches of exemplary embodiments of the organ assist systems are shown in FIG. 30.

One embodiment of a contactless pressure system is a system that varies the air pressure in the organ chamber 104 to simulate pressure applied by the diaphragm to the liver. In this embodiment, the organ chamber 104 can be configured to provide a substantially airtight environment such that the air pressure inside the organ chamber 104 can be maintained at an elevated (or lowered) state when compared to the outside atmosphere. As the air pressure in the organ chamber 104 rises, it can apply pressure to the liver that simulates the pressure applied by the diaphragm thereby increasing the rate at which the liver expels perfusion fluid. In some embodiments, the air pressure can be varied in a manner that mimics a human breathing rate (e.g., 12-15 times per minute), or at other rates (e.g., 0.5 to 50 times per minute). The air pressure in the organ chamber 104 can be varied by various methods including, for example, a dedicated air pump (not shown) and/or the onboard gas supply 172. In some embodiments, the air pressure inside the organ chamber 104 can be controlled by the controller 150. In these embodiments, the controller can also be coupled to an air pressure sensor measuring the pressure inside the organ chamber 104 that is used as part of a feedback control loop.

One embodiment of a contact pressure system is a system that that uses a wrap and/or bladder to apply pressure to the liver. For example, a wrap can be placed over some or all of the liver within the organ chamber 104. The edges of the wrap can then be mechanically tightened to apply pressure to the portion of the liver covered by the wrap. In this example, one or more small motors attached to various points around the periphery of the wrap can be used to tighten the edges of the wrap. In another example of a contact pressure system, a removable bladder can be used (not shown). In this embodiment, an inflatable bladder can be placed between the liver and the top surface (or some other portion) of the organ chamber 104. A pump can then be used to inflate/deflate the bladder. As the bladder inflates, it can press against the top surface (or other portion) of the organ chamber 104 thereby exerting pressure on the liver contained therein. As with the contactless system described above, the pressure applied to the liver can be applied periodically to mimic the natural pressure provided by the diaphragm. In some embodiments, the pressure applied to the liver can be varied in a manner that mimics human breathing rate (e.g., 12-15 times per minute), or at other rates (e.g., 0.5 to 50 times per minute). Regardless of whether the pressure is applied to the liver using a wrap or a bladder, the pressure can be controlled by the controller 150. In some embodiments, one or more sensors that measure the pressure applied to the liver can be included in the organ chamber 104 as part of a feedback control loop. Other methods of providing contact pressure to the liver are also possible.

14. Cannulation

Operationally, in one embodiment, a liver can be harvested from a donor and coupled to the system 600 by a process of cannulation. For example, interface 162 can be cannulated to vascular tissue of the hepatic artery via a conduit located within the organ chamber assembly. Interface 166 can be cannulated to vascular tissue of the portal vein via a conduit located within the organ chamber assembly. The liver emits the perfusate through the inferior vena cava (IVC). In some embodiments, the IVC can be cannulated by interface 170 (not shown) so that the flow can be directed to a conduit in which the IVC pressure, flow and oxygen saturation can be measured. In another embodiment, the IVC can be cannulated by the interface 170 to direct the flow within the organ chamber. In still another embodiment, the IVC is not cannulated and the organ chamber provides a means to direct the perfusate flow for efficient collection to the reservoir.

Each of the interfaces 162, 166 and 170 can be cannulated to the liver by pulling vascular tissue over the end of the interface, then tying or otherwise securing the tissue to the interface. The vascular tissue is preferably a short segment of a blood vessel that remains connected to the liver after the liver is severed and explanted from the donor. In some embodiments, the short vessel segments can be 0.25-5 inches, although other lengths are possible.

Referring to FIGS. 21A-21D, an exemplary embodiment of a hepatic artery cannula 2600 is shown. The cannula 2600 is generally tubular in shape and includes a first portion 2604 that is configured to be inserted into tubing used in the system 100 and includes a first orifice 2612. The first portion 2604 can also include a ring 2602 that can be used to help secure the first portion 2604 inside of the tubing of the system 100 by friction. The cannula 2600 can also include a second portion 2608 that can have a smaller diameter than the first portion 2604 and that forms a second orifice 2614. The second portion 2608 can also include a channel 2610 that is recessed from the surface of the second portion 2608. In some embodiments, when the user ties the hepatic artery to the second portion 2608, the user can place the suture in the channel 2610 to help secure the hepatic artery. Between the first and second portions can be a collar 2606. The outside diameter of the collar can have a slightly larger diameter than the first portion 2604 to prevent the tubing of the system 100 from extending over the second portion 2608 when inserted. Viewing the cross-section shown in FIG. 21D, the inside diameter of the cannula 2600 can vary, with a taper 2616 therebetween. The cannula 2600 can be formed in various sizes, lengths, inside diameters, and outside diameters. In some embodiments of the system 600, it can be advantageous to have a substantially large inside diameter in the first portion 2604 and a much smaller inside diameter in the second portion 2608 to offset pressure and flow changes caused by the cannula 2600.

Referring to FIGS. 21H-21K, in an alternative embodiment the cannula 2600 has a beveled cut end 2618.

The outside diameter of the first portion 2604 can be configured to be press-fit inside of silicone or polyurethane tubing. Thus, while the outside diameter of the first portion 2604 can vary, one exemplary range of possible diameters is 0.280-0.380". The outside diameter of the second portion 2608 can range between 4-50 Fr, but more specifically between 12-20 Fr. Additionally, the cannula 2600 can be made from various biocompatible materials, such as stainless steel, titanium, and/or plastic (the dimensions of the cannula 2600 can be adapted to be manufacturable using different materials).

Figure 21A:
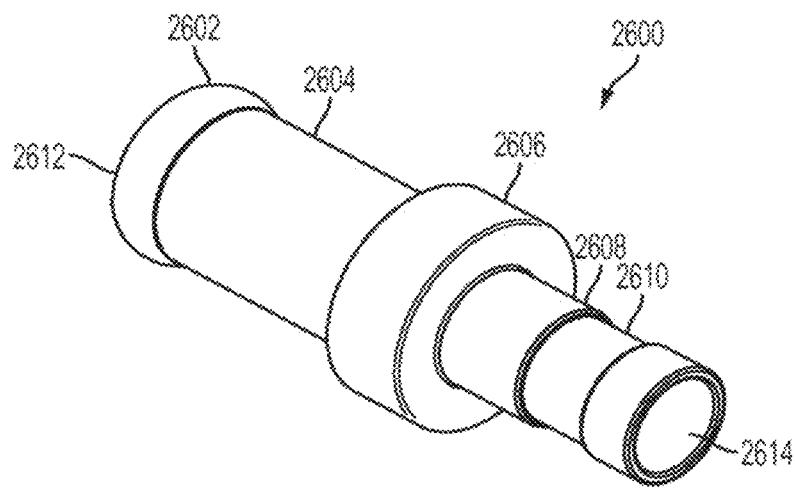
FIGS. 21A-21K show exemplary hepatic artery cannulas that can be used within an embodiment of the organ care system.
Figure 21B:
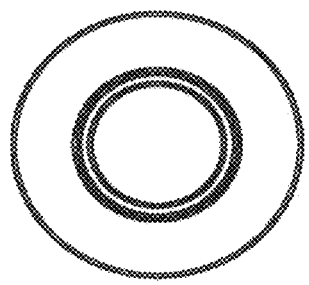
Figure 21C:
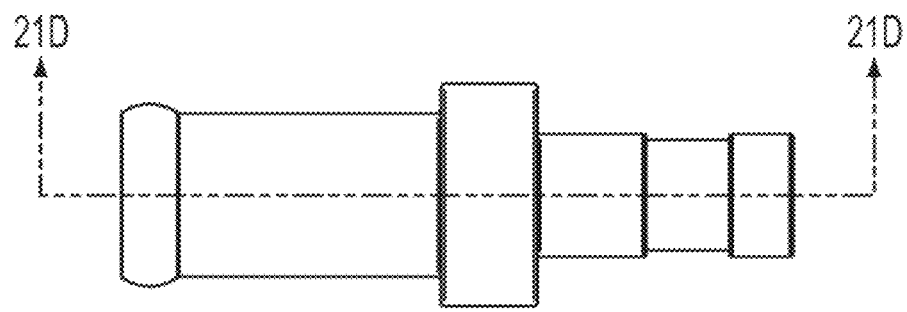
Figure 21D:
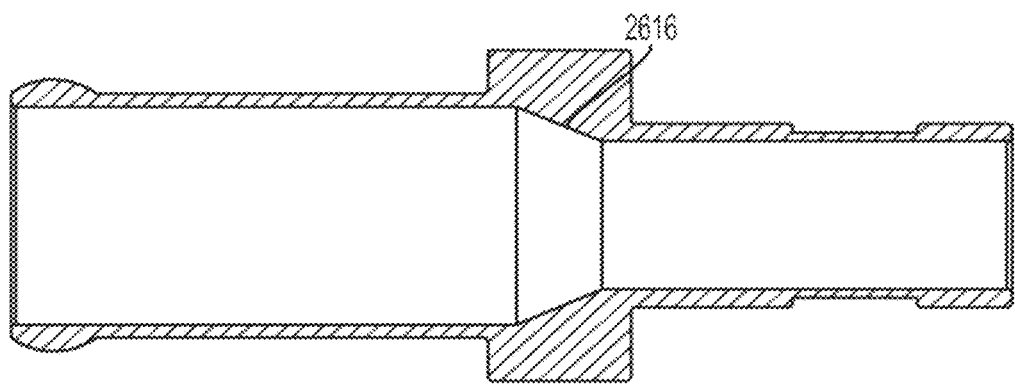
Figure 21E:
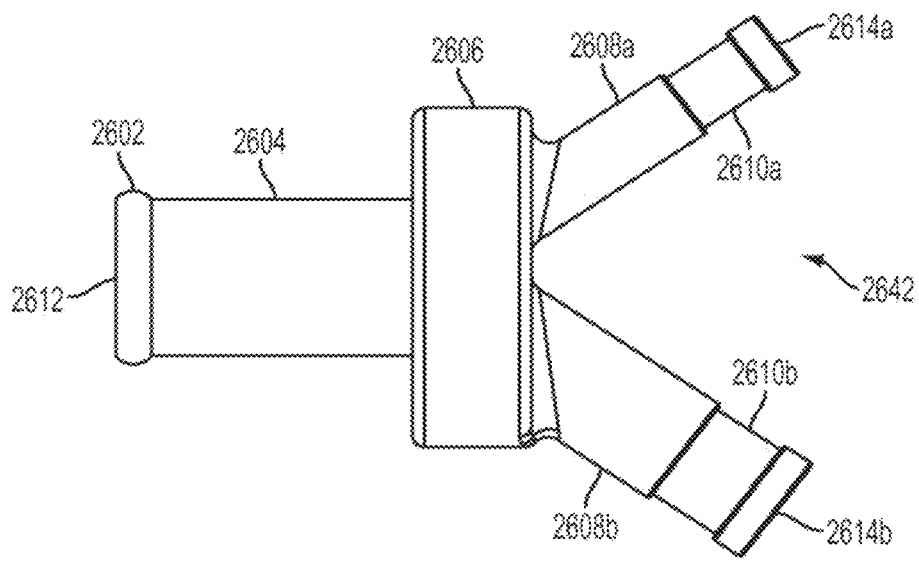
Figure 21F:
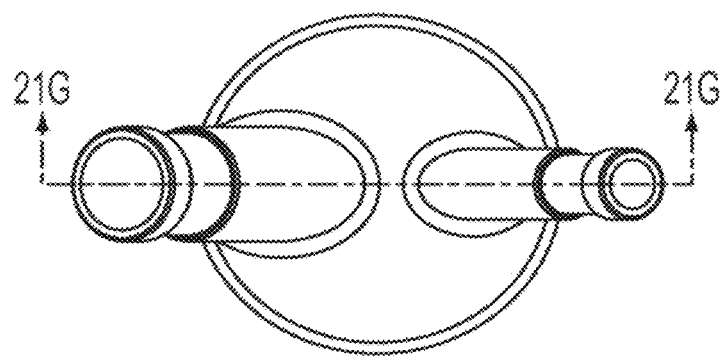
Figure 21G:
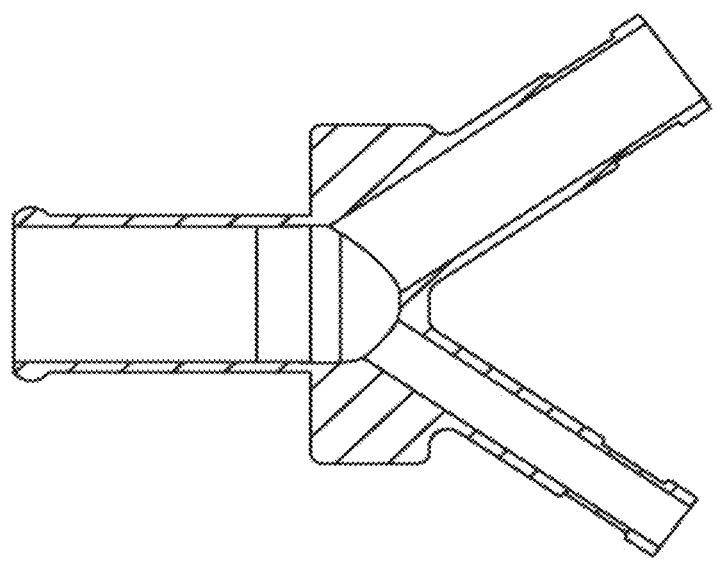
Figure 21I:
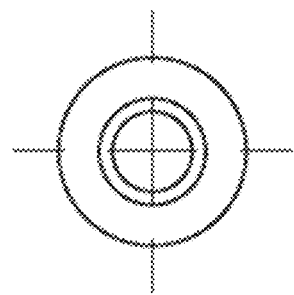
Figure 21K:
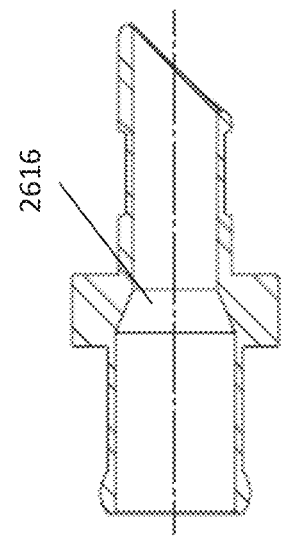
Figure 21H:
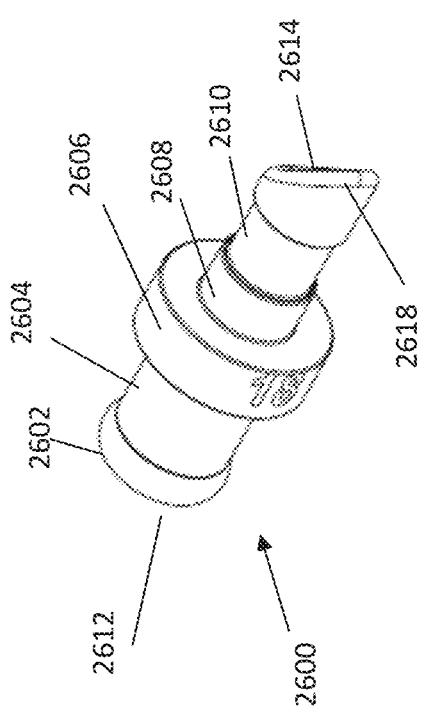
Figure 21J:
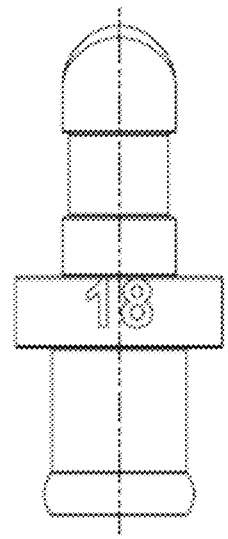

Additionally 10-20% of the population have a genetic variation where the liver includes an accessory hepatic artery. For these instances, the hepatic artery cannula described above can be a double-headed (e.g., Y-shaped) cannula. An exemplary embodiment of a Y-shaped hepatic artery cannula 2642, is shown in FIGS. 21E-21G, where like numbers are used to denote corresponding features in the cannula 2600. The bifurcated design of hepatic artery cannula 2642 can allow the system 100 to treat both vessels as one input for hepatic artery flow without changing the configuration of the system 100 and/or the controller 150.

In an alternative embodiment, when the liver includes an accessory hepatic artery, two hepatic artery cannulas 2600 may be attached to a section of Y-shaped tubing at one end, and the other end may be connected to the organ chamber.

Referring to FIGS. 22A-22D, an exemplary embodiment of a portal vein cannula 2650 is shown. The cannula 2650 is generally tubular in shape and includes a first portion 2654 that is configured to be inserted into tubing used in the system 100 and includes a first orifice 2660. The first portion 2654 can also include a ring 2652 that can be used to help secure the first portion 2654 inside of the tubing of the system 100 by friction. The cannula 2650 can also include a second portion 2656 that can have a larger diameter than the first portion 2654 and that forms a second orifice 2662. The second portion 2656 can also include a channel 2658 that is recessed from the surface of the second portion 2656. In some embodiments, when the user ties the portal vein to the second portion 5626, the user can place the suture in the channel 2658 to help secure the portal vein. Viewing the cross-section shown in FIG. 22D, the inside diameter of the cannula 2600 can vary, with a taper 2664 therebetween. The cannula 2650 can be formed in various sizes, lengths, inside diameters, and outside diameters. In some embodiments of the system 600, it can be advantageous to have a substantially large inside diameter in the first portion 2654 and an even larger inside diameter in the second portion 2656 to offset pressure and flow changes caused by the cannula 2650.

Figure 22A:
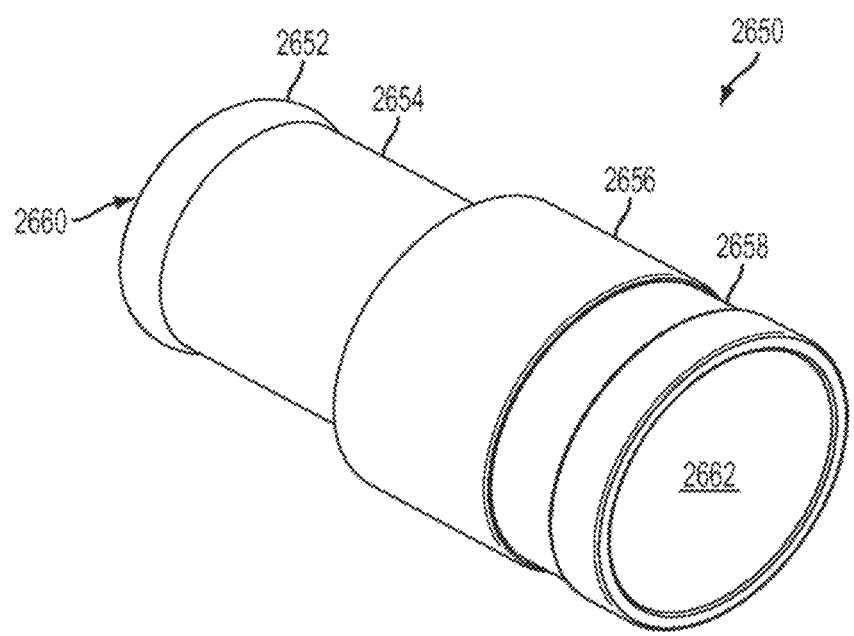
FIGS. 22A-22G show exemplary portal vein cannulas that can be used within an embodiment of the organ care system.
Figure 22B:
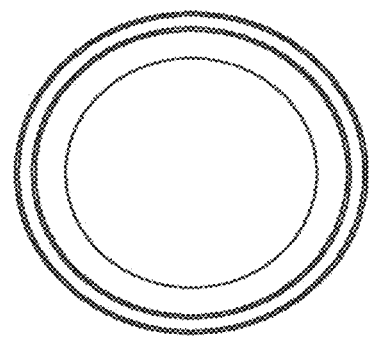
Figure 22C:
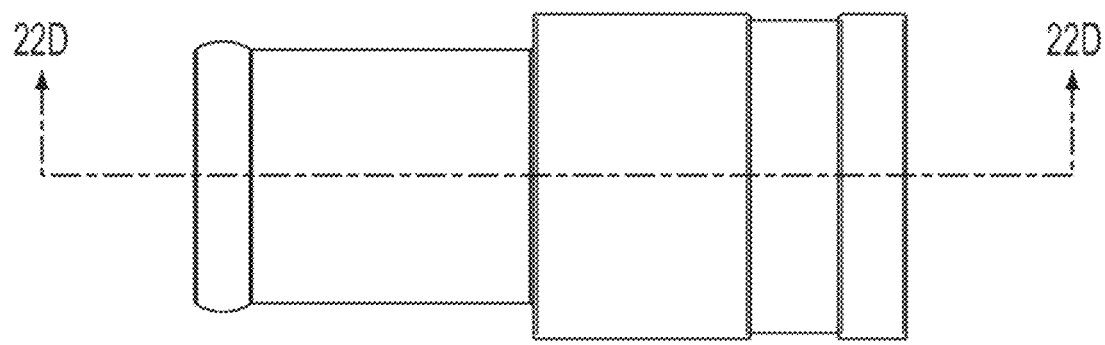
Figure 22D:
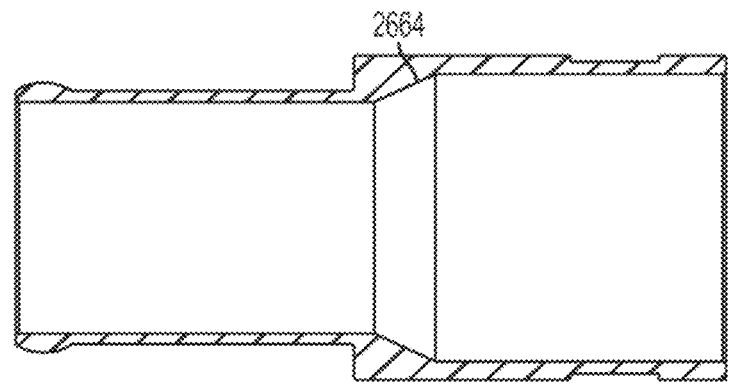
Figure 22E:
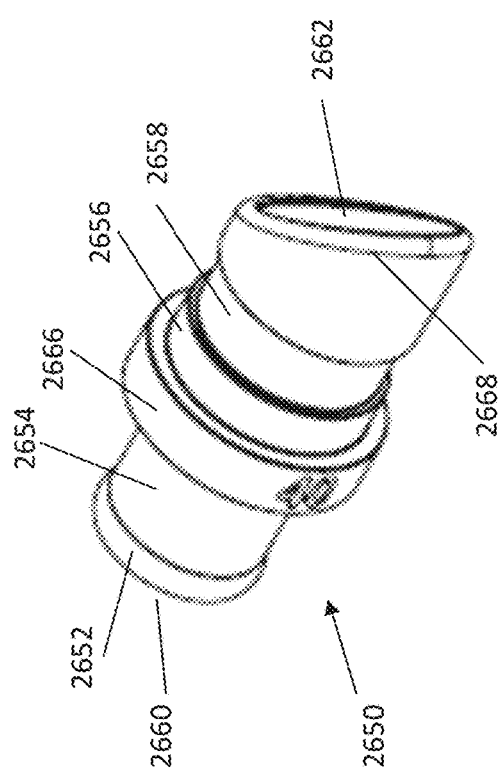
Figure 22G:
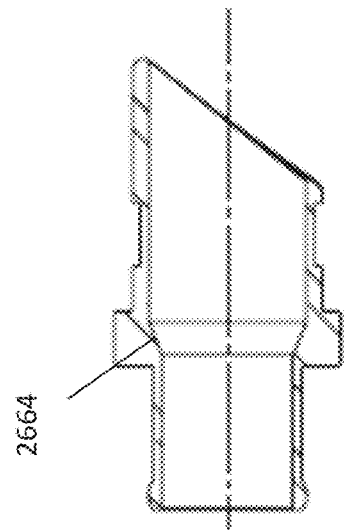
Figure 22F:
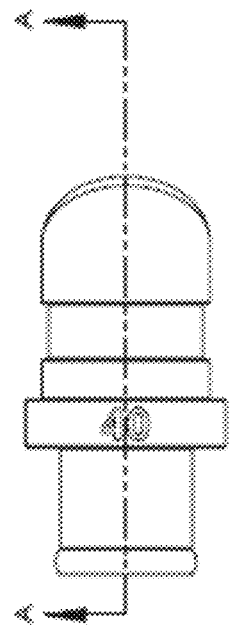

Referring to FIGS. 22E-22G. in an alternative embodiment the cannula 2650 has a collar 2666 between the first and second portions. The outside diameter of the collar can have a slightly larger diameter than the first portion 2654 to prevent the tubing of the system 100 from extending over the second portion 2656 when inserted. The cannula 2650 may also have a beveled cut end 2668.

The outside diameter of the first portion 2654 can be configured to be press-fit inside of silicone or polyurethane tubing. Thus, while the outside diameter of the first portion 2654 can vary, one exemplary range of possible diameters is 0.410-0.510". The outside diameter of the second portion 2656 can range between 25-75 Fr, but more specifically between 40-48 Fr. Additionally, the cannula 2650 can be made from various biocompatible materials, such as stainless steel, titanium, and/or plastic (the dimensions of the cannula 2600 can be adapted to be manufacturable using different materials).

Figure 23A:
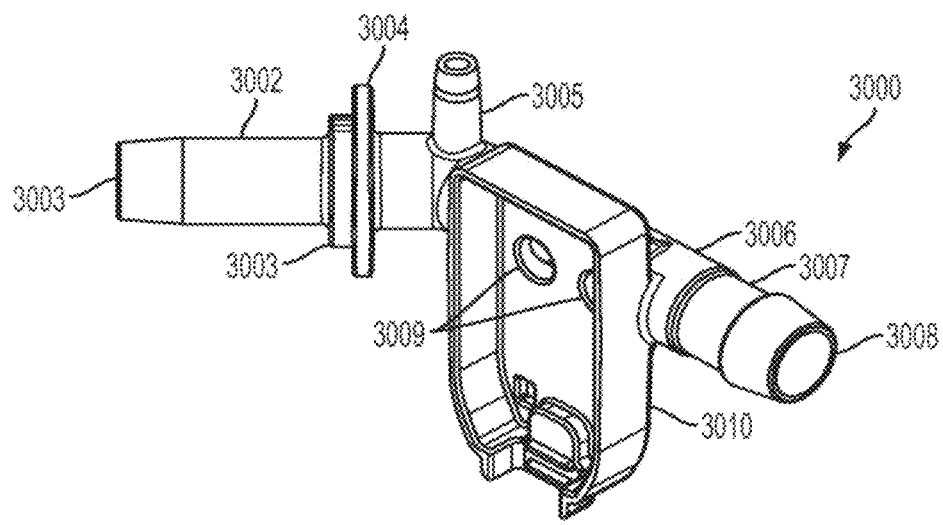
FIGS. 23A-23N show an exemplary connector that can be used within an embodiment of the organ care system.
Figure 23B:
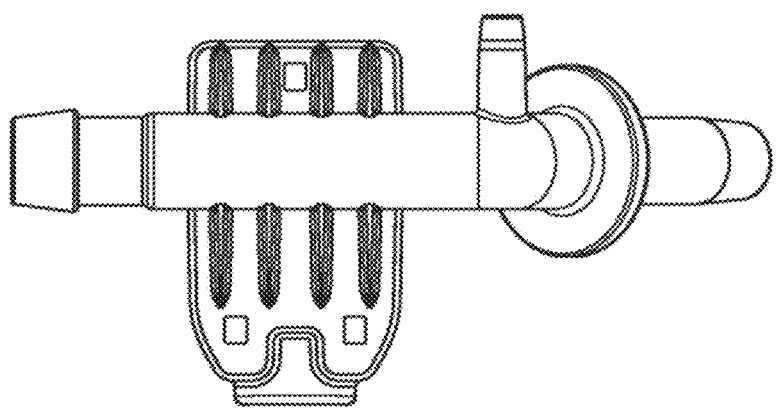
Figure 23C:
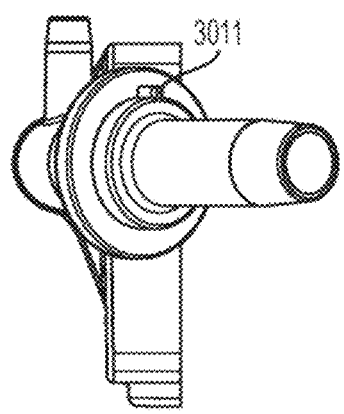
Figure 23D:
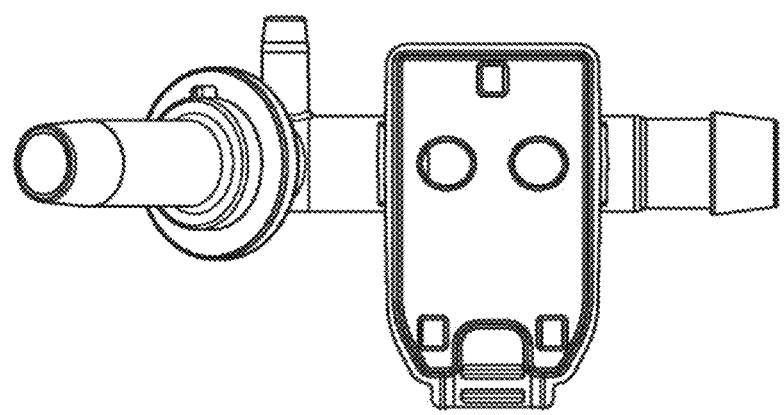
Figure 23E:
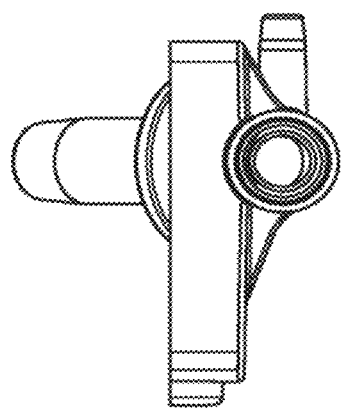
Figure 23F:
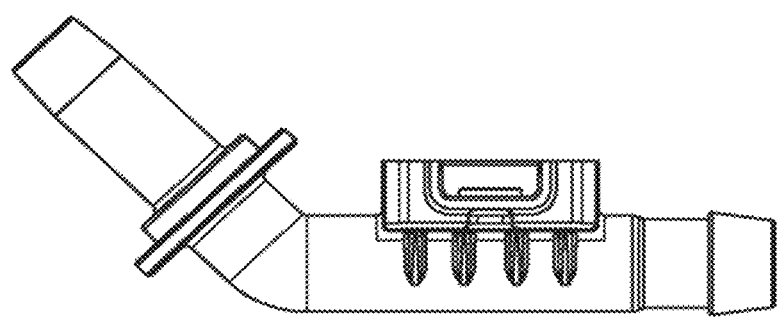
Figure 23G:
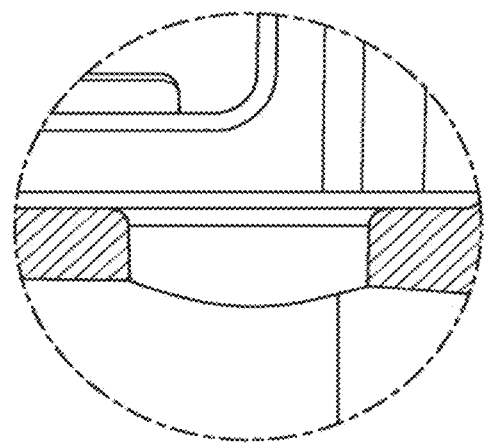
Figure 23H:
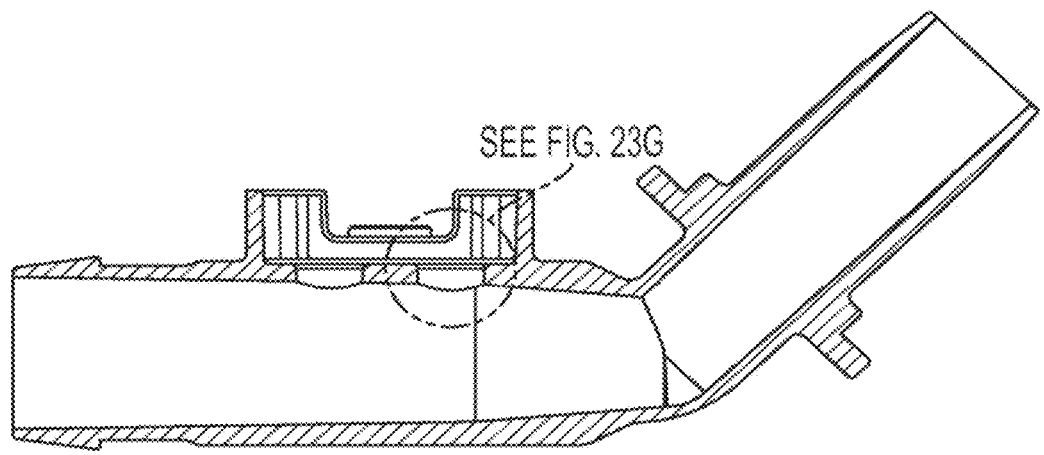
Figure 23I:
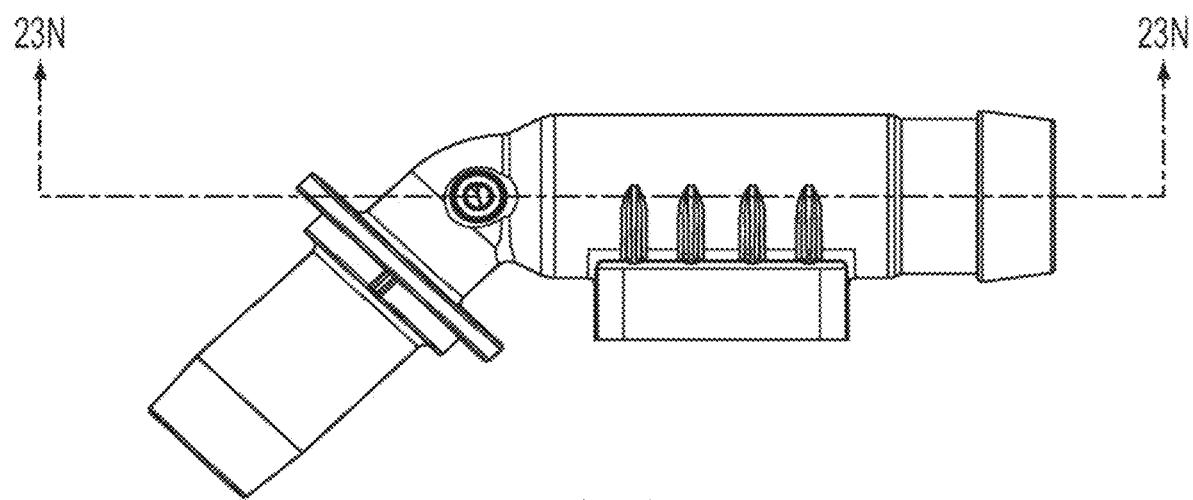
Figure 23J:
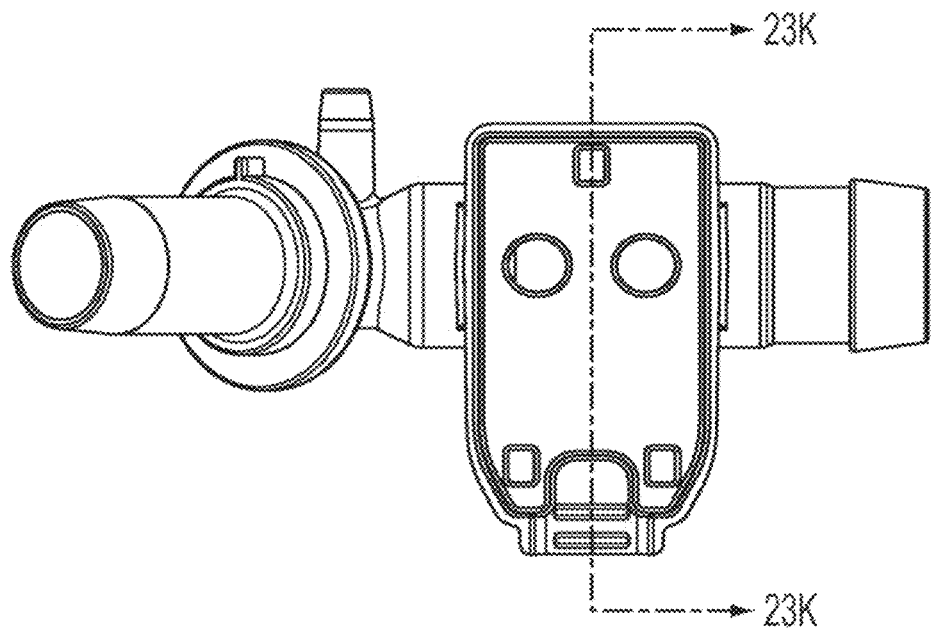
Figure 23K:
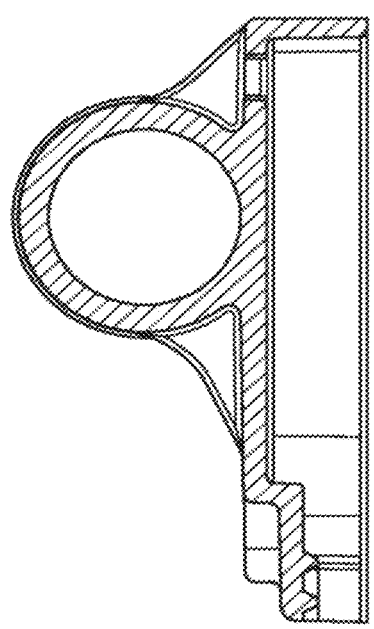
Figure 23L:
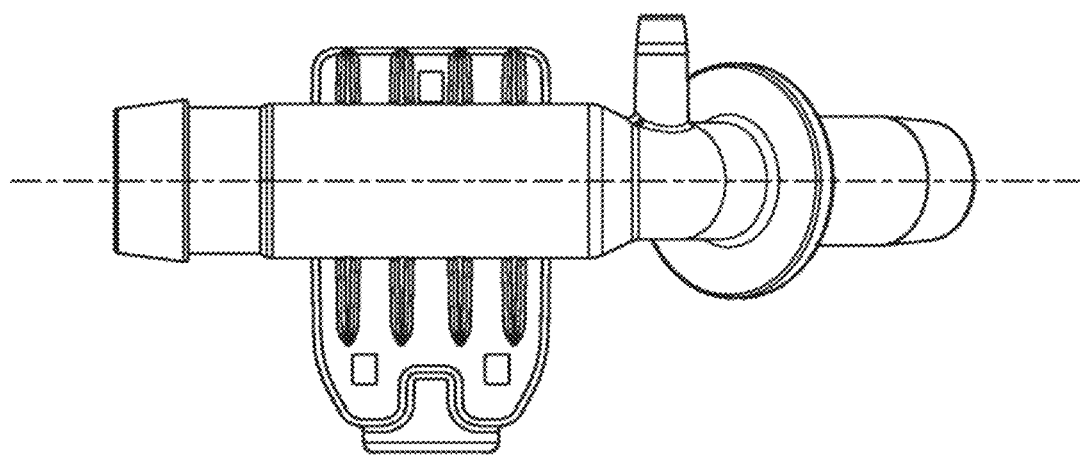
Figure 23M:
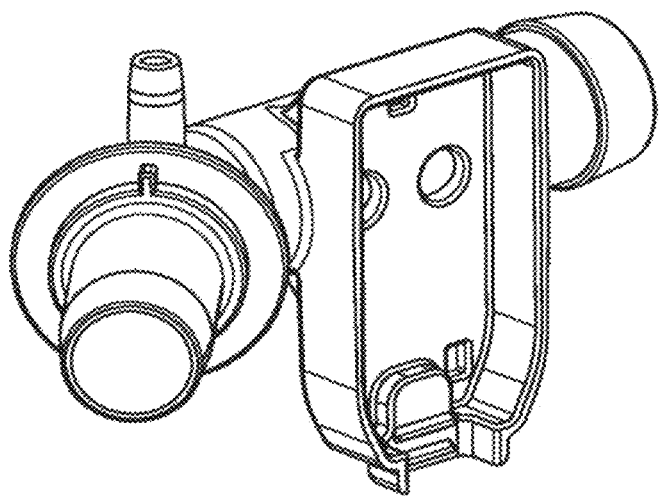
Figure 23N:
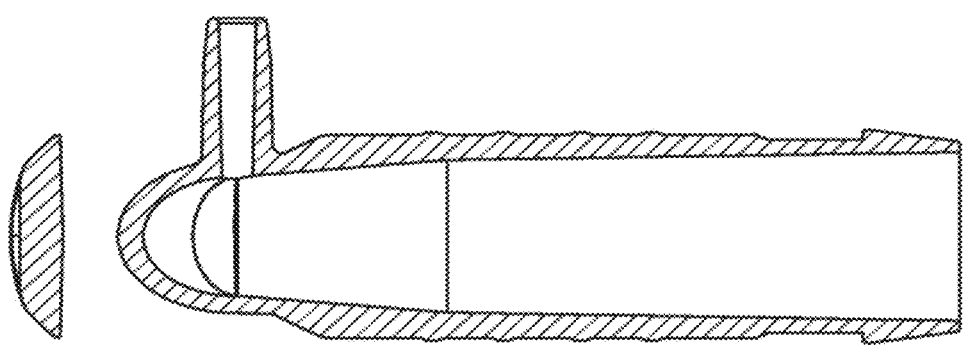

Referring to FIGS. 23A-23N, an exemplary hepatic artery connector 3000 is shown. The connector 3000 can be part of the branch 315 leading to the hepatic artery of the liver. For example, the connector 3000 can be inserted into and secured to the wall of the organ chamber 104. The connector 3000 can include a first portion 3006 that includes a circumferential channel 3007 and defines an opening 3008. In some embodiments, the outside diameter of the first portion 3006 is sized to couple to ¼" tubing, although other diameters are possible. In some embodiments, tubing coupled to the first portion 3006 can coupled using friction and/or a common zip tie (or other similar fastener) can be tied around the channel 3007 to secure the tubing connected thereto. The connector 3000 can also include a second portion 3002 that defines an opening 3003. In some embodiments, the outside diameter of the second portion 3002 can be configured to couple to ¼" tubing using a press/friction connection, although other sizes are possible. In some embodiments, perfusion fluid flows from the opening 3008 toward the opening 3003.

The connector 3000 can include an interface that is configured to mate with an opening in a wall of the organ chamber 104. For example, connector 3000 can include a ridge 3003 that is sized to fit within a corresponding opening in a wall of the organ chamber 104. A backstop 3004 can be larger than the opening to prevent the connector from being inserted too far, and can also provide a surface on which adhesive can be applied to bond the connector 3000 to the organ chamber 104. In some embodiments, the ridge 3003 can include a protrusion 3011 that is configured to rotationally align the connector 3000 within the organ chamber 104. For example, in some embodiments, the protrusion 3011 and corresponding opening in the organ chamber 104 can be configured so that the connector 3000 is rotated about a longitudinal axis of the second portion 3003. In some embodiments, the rotation can be optimized to prevent air bubbles.

The connector 3010 can also including a housing 3010 that is configured to house the pressure sensor 130b. In this embodiment the two pressure sensors make up the pressure sensor 130b. In such an embodiment, the pressure sensors can be mounted in the openings 3009, which can provide direct access to the fluid within the connector 3000. Additionally, some embodiments of the connector 3000 can include an air vent 3005 that can be connected to a valve which can be opened to vent air bubbles trapped within the connector 3000. In operation, a user can attach one end of a tube to the second portion 3002 and the other end of the tube to the hepatic artery cannula 2600 (which can be connected to the hepatic artery). In some embodiments, the user can place a liver into the organ chamber 104, connect a cannula 2600 to an end of a piece of tubing, which can be connected to the hepatic artery using a suture. Next, because the size of the liver can vary, the user can then trim the tubing to the proper length and attach it to the second portion 3003.

Figure 24A:
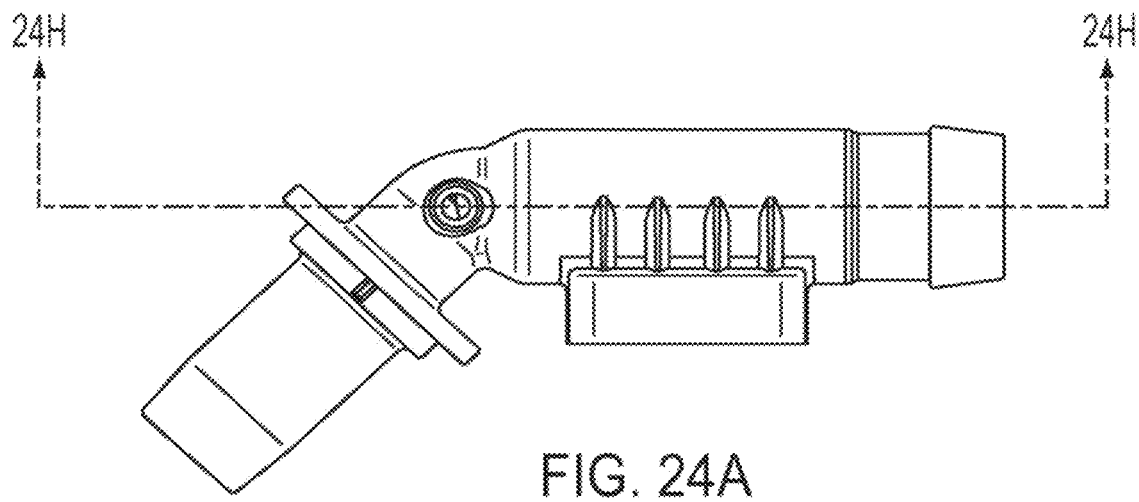
FIGS. 24A-24L show an exemplary connector that can be used within an embodiment of the organ care system.
Figure 24B:
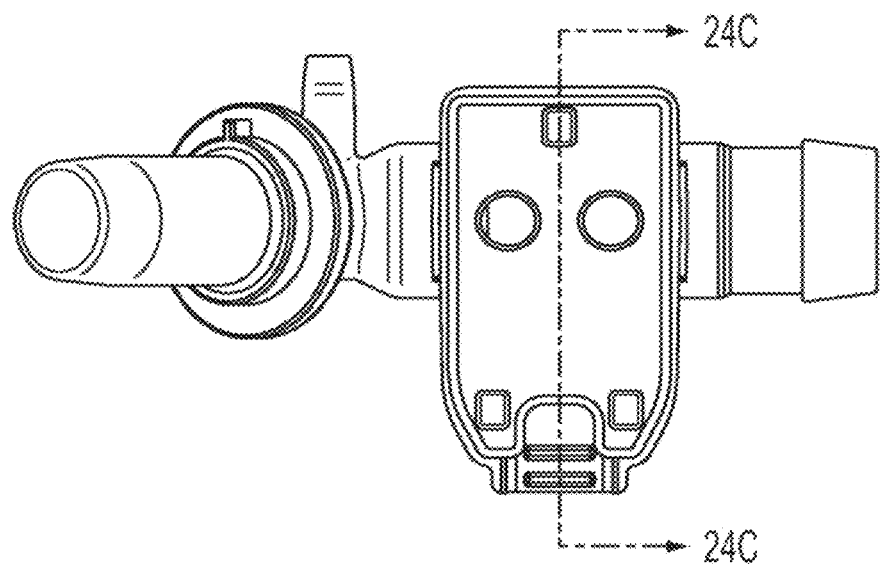
Figure 24C:
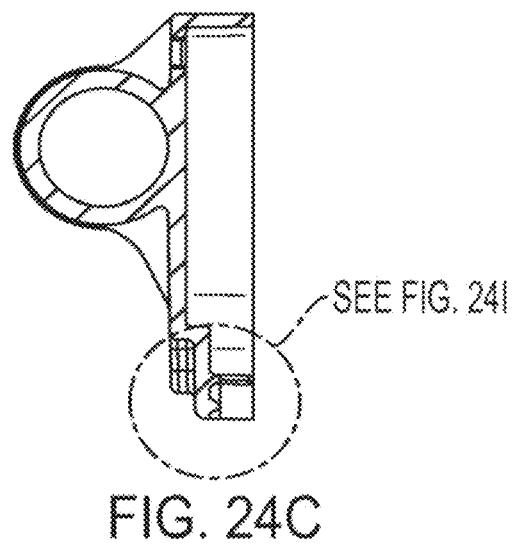
Figure 24D:
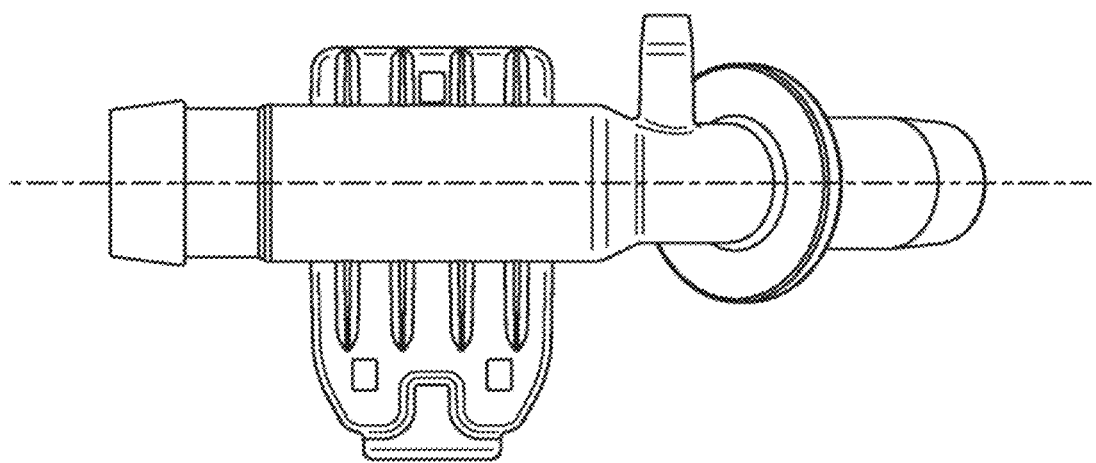
Figure 24E:
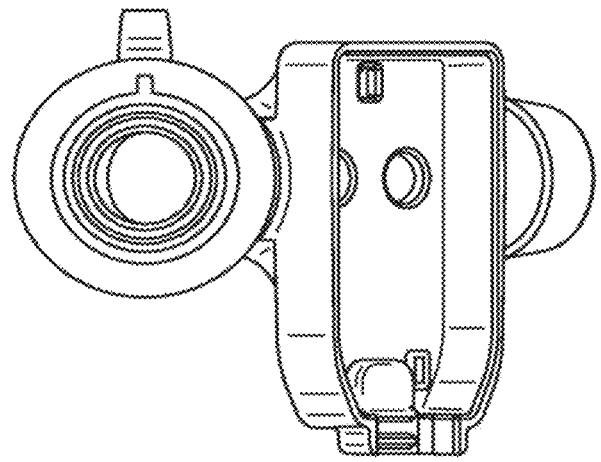
Figure 24F:
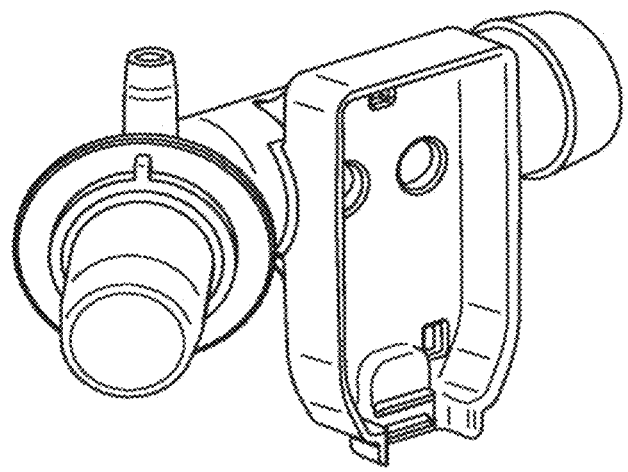
Figure 24G:
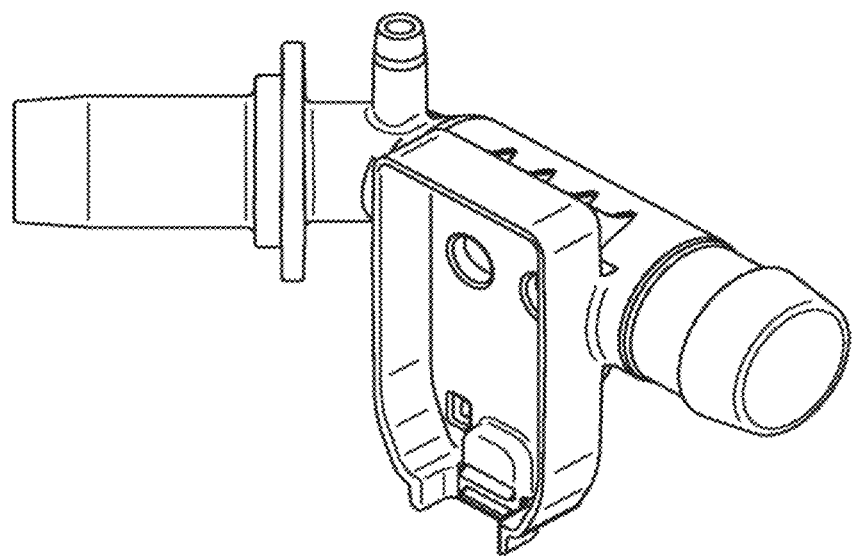
Figure 24H:
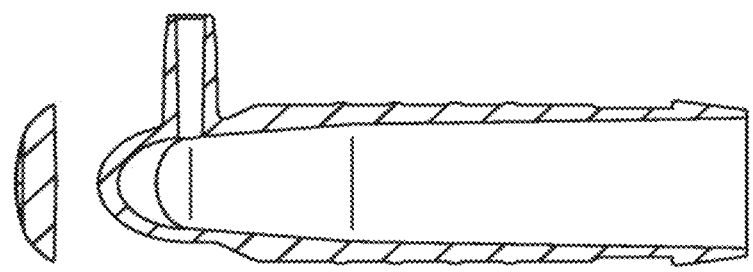
Figure 24I:
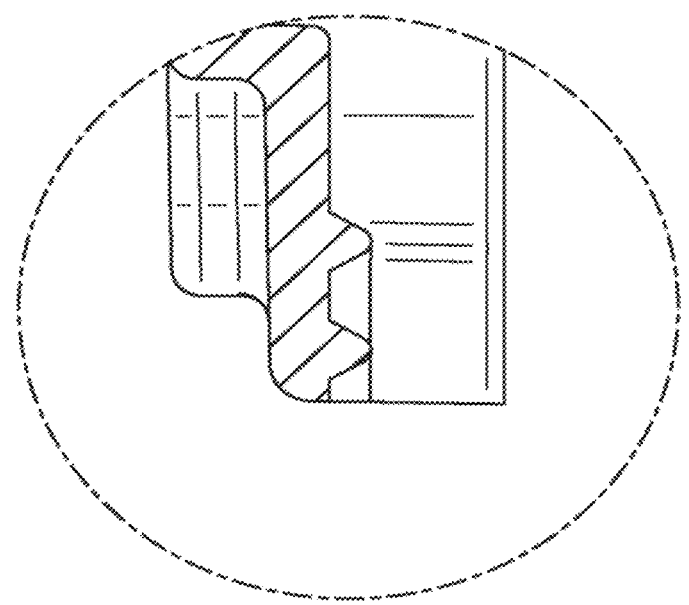
Figure 24J:
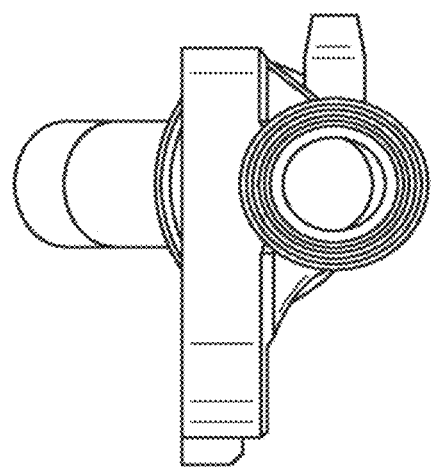
Figure 24K:
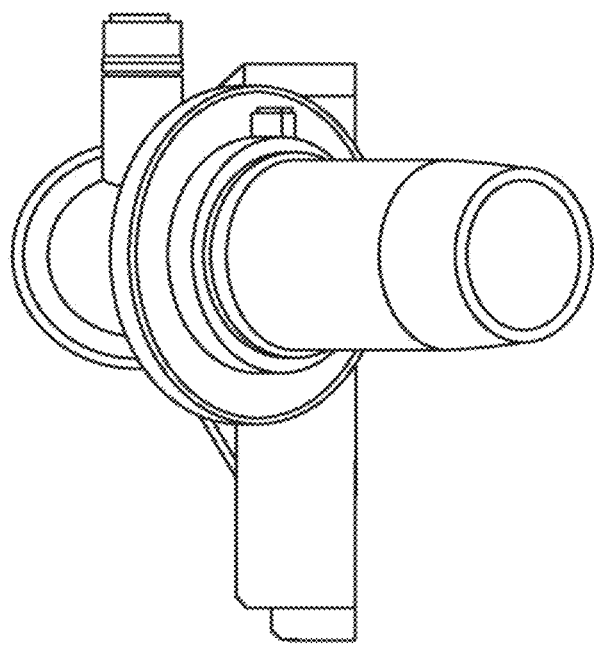
Figure 24L:
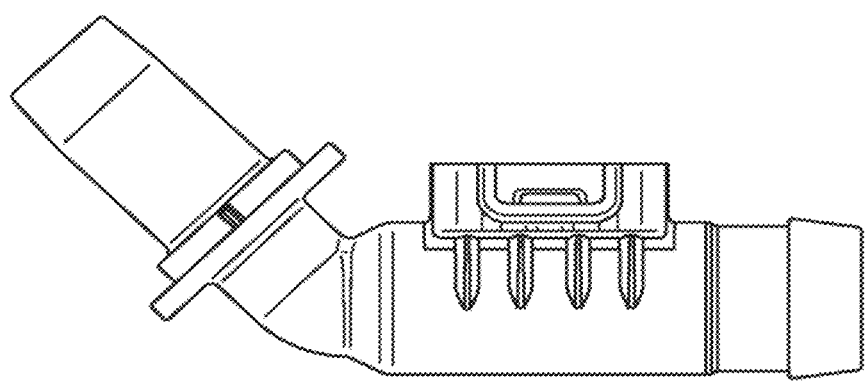

Referring to FIGS. 24A-23L, an exemplary portal vein connector 3050 is shown. In some embodiments the portal vein connector 3050 is configured and functions in the same manner as the connector 3000, except that the first and second portions can be coupled to connect to ⅜" or ½" tubing instead of ¼", although it can be configured to work with other size tubing as well. Also, as should be clear by the name, the portal vein connector can be configured to couple the branch 313 to the portal vein of the liver.

While some dimensions are provided above, these dimensions are exemplary only and each of the foregoing components can sized as necessary to achieve the desired flow characteristics. For example, in some embodiments, it can be beneficial to use the largest diameter cannula to avoid introducing undesirable pressure or flow changes. Additionally, in practice, the diameter of the cannula can be chosen by the surgeon such that the largest cannula is used that will physically fit in the vessel.

It is noted herein that some consider the "Fr" scale to end at "34." Thus, to the extent that a Fr size larger than 34 is identified (or an Fr. number that does not exist in the traditional Fr. scale), the size in mm can be calculated by dividing the identified Fr number by 3.

15. Flow Clamp

Figure 25A:
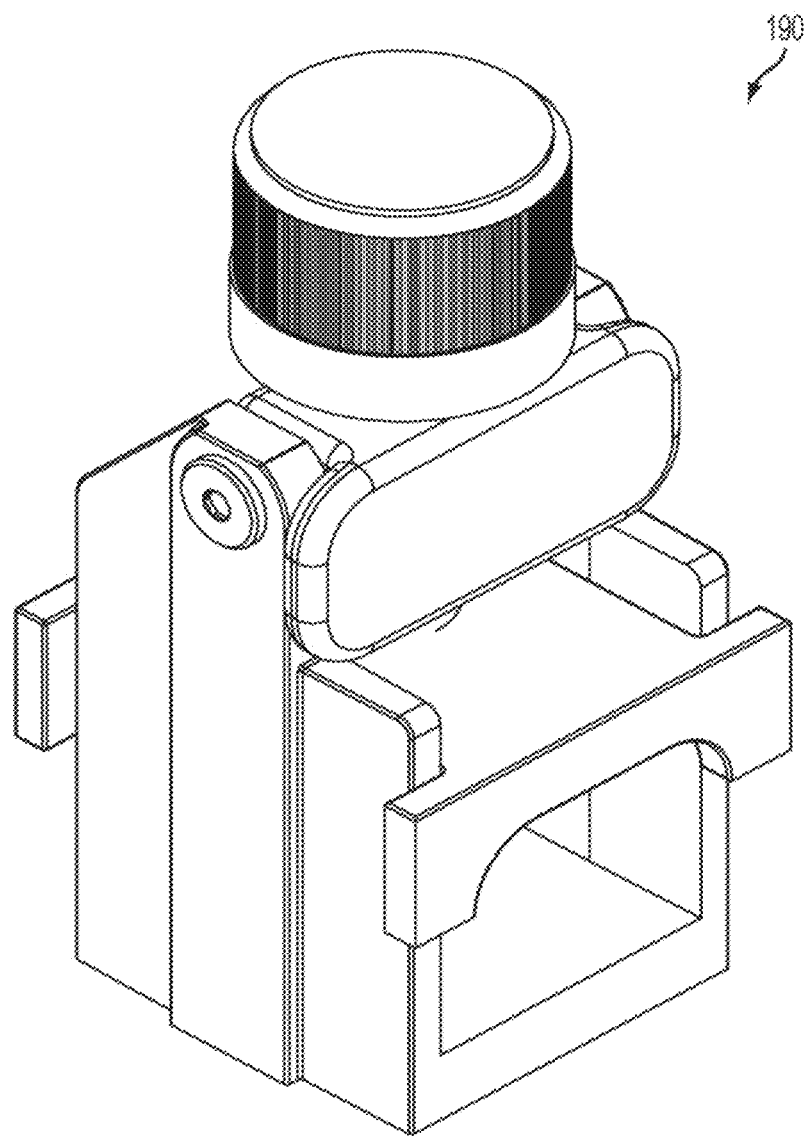
FIGS. 25A-25D show exemplary clamps that can be used within an embodiment of the organ care system.
Figure 25B:
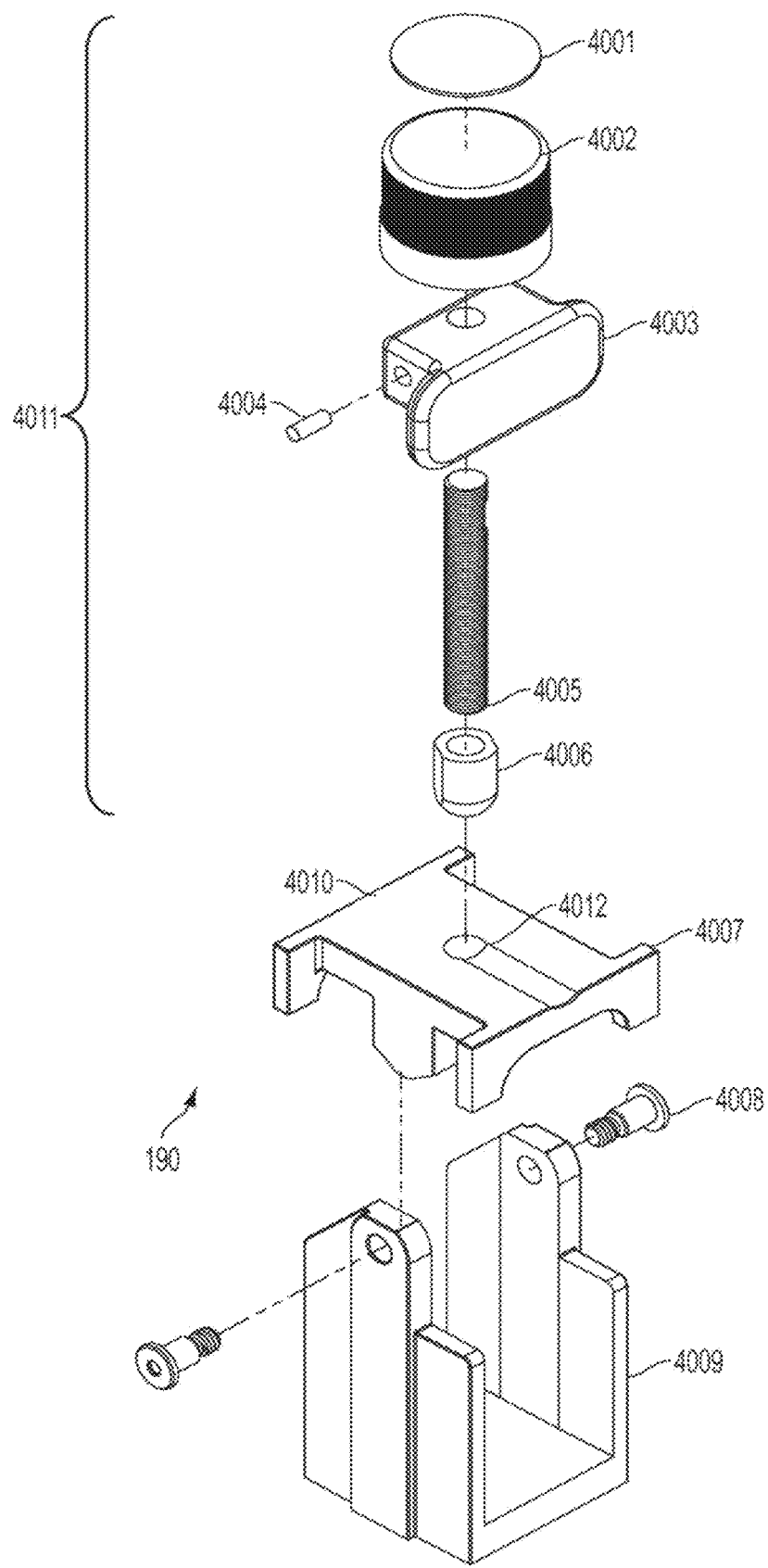
Figure 25D:
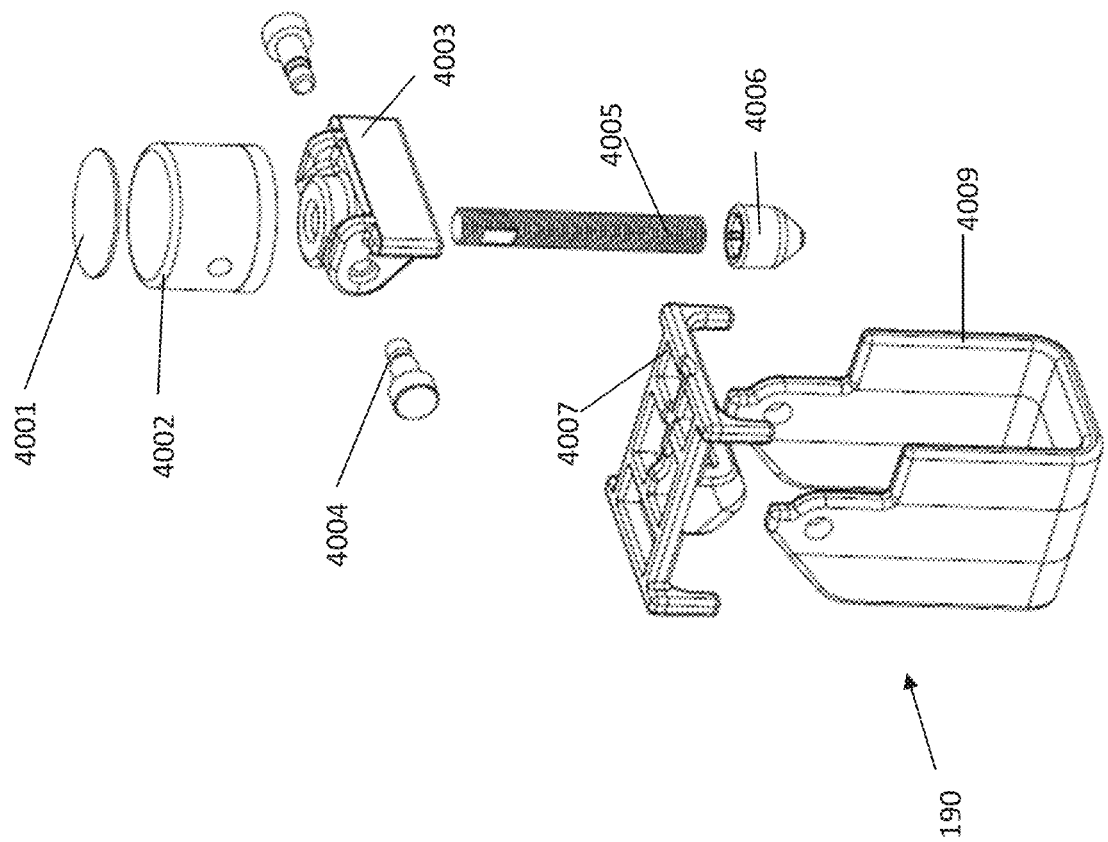
Figure 25C:
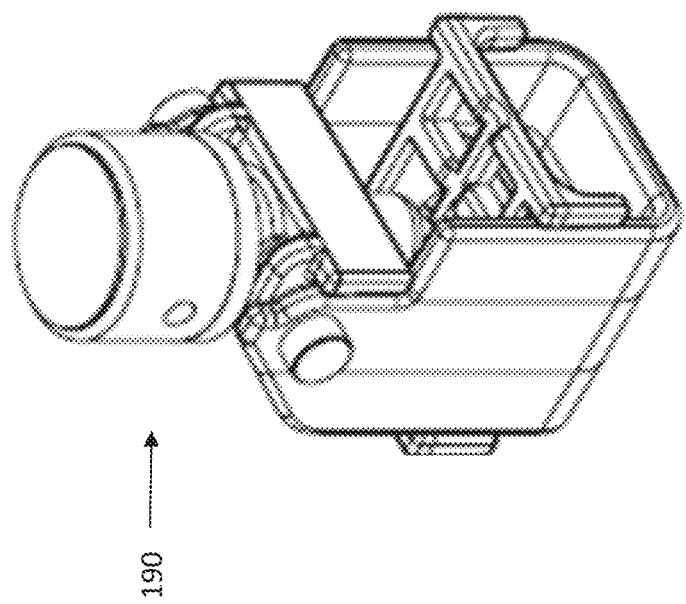

Referring to FIGS. 25A-25B, an exemplary embodiment of the flow clamp 190 is shown. The flow clamp 190 can be used to control the flow and/or pressure of the perfusion fluid to the portal vein of the liver. The flow clamp 190 can include a cover 4001, a knob 4002, a pivot 4003, a pin 4004 a screw 4005, a bearing 4006, a slide 4007, an axle 4008, and a body 4009. The slide 4007 can include a groove 4010 and detent 4012 and can be configured to move up and down within the body 4009. In some embodiments, a tube carrying perfusion fluid is placed within the body 4009 under the slide 4007. FIGS. 25C-25D show the flow clamp 190 with molded components.

The flow clamp 190 can be configured to allow a user to quickly engage and disengage the clamp 190, while still having precise control over the amount of clamping force applied. In this embodiment, the cover 4001, the knob 4002, the pivot 4003, the pin 4004, the screw 4005, and the bearing 4006 make up a switch unit 4011. The pivot 4003 of the switch unit 4011 can rotate about a longitudinal axis formed by the axle 4008 (which can be made up of two separate screws). In this manner, when the switch unit 4011 is engaged (e.g., the screw 4005 is vertical), as shown in FIG. 25A, the bearing 4006 forces the slide 4007 downward in the body 4009 (which can compress the tube carrying the perfusion fluid, if present, and restricts flow therein). How far down the slide is forced is a function of how extended the screw 4005 is relative to the pivot 4003. When the switch unit 4011 is disengaged, it is pivoted sideways so that the screw is no longer vertical and does not restrict the movement of the slide 4007. When the switch unit 4011 is pivoted, the bearing can slide along the grove 4010. In some embodiments, the switch unit 4011 can "lock" into place when the bearing 4006 comes to rest in the detent 4012. The user can adjust the amount of flow restriction is imposed by the flow clamp 190 when engaged by rotating the knob 4002, thereby extending/retracting the screw 4005. In some embodiments, the pitch of the screw can be 4-40 thread, although other pitches can be used adjust the precision of the flow clamp 190.

16. Priming

In some embodiments, the perfusion fluid includes packed red blood cells also known as "bank blood." Alternatively, the perfusion fluid includes blood removed from the donor through a process of exsanguination during harvesting of the liver. Initially, the blood is loaded into the reservoir 160 and the cannulation locations in the organ chamber assembly are connected with a bypass conduit to enable normal mode flow of perfusion fluid through the system without a liver being present, aka "priming tube." Prior to cannulating the harvested liver, the system may be primed by circulating the exsanguinated donor blood through the system to heat, oxygenate, and/or filter it. Nutrients, preservatives, and/or other therapeutics may also be provided during priming via the infusion pump of the nutritional subsystem. During priming, various parameters may also be initialized and calibrated via the operator interface during priming. Once primed and running appropriately, the pump flow can be reduced or cycled off, the bypass conduit is removed from the organ chamber assembly, and the liver can be cannulated into the organ chamber assembly. The pump flow can then be restored or increased, as the case may be. The priming process is described more fully below.

17. IVC Cannulation

In some embodiments, the inferior vena cava (IVC) can be cannulated, though not required. In these embodiments, additional pressure and/or flow sensors can be used to determine the pressure and/or flow of the perfusion fluid flowing from the liver. In some embodiments, the cannulated IVC can be coupled directly to the sensor 140 and/or reservoir. In other embodiments, the IVC can be cannulated for the purpose of directing the drainage of the perfusion fluid (e.g., directed free draining). For example, the uncannulated end of a short tube connected to the IVC can be held in place by a clip so that perfusion fluid drains directly over the measurement drain 2804. In other embodiments, the IVC is not cannulated and perfusion fluid can drain freely therefrom. In still other embodiments, the IVC can be partially tied off.

In embodiments where the IVC is cannulated and connected to tubing, it can be desirable to keep the length of tubing as short as possible to achieve the desired result. That is, because physiologic IVC pressure is low, even a length of narrow tube can result in an elevated IVC pressure. In embodiments of the system 600 that include pressure exertion on the liver to encourage draining (e.g., pressurizing the chamber 104 as discussed above), the liver may be able to tolerate a longer cannula/tubing.

18. Bile Duct Cannulation

In some embodiments of the system 600, the bile duct of the liver can be cannulated using an off the shelf and/or custom cannula. For example, a bile duct cannula of 14 Fr can be used. Additionally, the bile bag 187 can be configured to collect bile produced by the liver. In some embodiments, the bag 187 is clear so the user can visually observe the color of the bile. In some embodiments, the bag 187 can collect up to 0.5 L of bile, although other amounts are possible. In some embodiments, the bag 187 can include graduations that indicate how much bile has been collected. While the system 600 is described as including a soft shell (e.g., the bag 187) to collect bile, a hard shell container can also be used. Some embodiments of the system 600 can include a sensor (e.g., capacitive, ultrasonic, and/or cumulative flow rate) to measure the volume of bile collected. This information can then be displayed to the user and/or sent to the Cloud.

19. Blood Collection/Filter

Some embodiments of the system 600 using whole blood from a donor can include leukocyte filter (not shown). In these embodiments, the leukocyte filter can be used when priming the system to filter blood received from a donor body via a blood collection line connected to a donor's artery and/or vein. In some embodiments, the leukocyte filter can be configured to filter at least 1500 mL of blood in 6 minutes or less (although other rates are possible). In some embodiments, the leukocyte filter can be configured to remove 30% or more of all leukocytes in up to 1500 mL of whole blood.

20. Final Flush Administration Kit

At times during operation, it can be desirable to remove all of the perfusion solution from the liver vasculature (e.g., before the liver is implanted into a recipient) without disconnecting the liver from the system 100. Thus, embodiments of the system 600 can be used with a final flush administration kit. The kit can include a bag (or other container) to collect a volume of liquid (e.g., flush solution and/or perfusate) so that when the flushing solution is administered to the liver (e.g., via ports 4301, 4302), the system 100 is not overwhelmed by the additional volume of fluid. Thus, in some embodiments, the system 100 can include a drain line (not shown) that can be used to drain fluid from the reservoir 160 and/or elsewhere in the system 100 in such a manner that the liver need not be disconnected from the system 100 before adding additional fluid. In some embodiments, the system can also be setup in a bypass operation where the liver is temporarily isolated from the system 100 using one or more valves. For example, in this embodiment, valves can be used before the ports 4301, 4302 to stop fluid flow within the system 100. Additional drainage ports can then be included between the drains 2804, 2806 and the valves. In this embodiment, the flush solution (or any other solution) can be provided via the ports 4301, 4302 and drain out of the additional drainage ports without being circulated in the rest of the system 100. In some embodiments, the drain line can hold at least 3 L of liquid, although this is not required.

D. Interface Between Single/Multi Use Modules

Figure 13J:
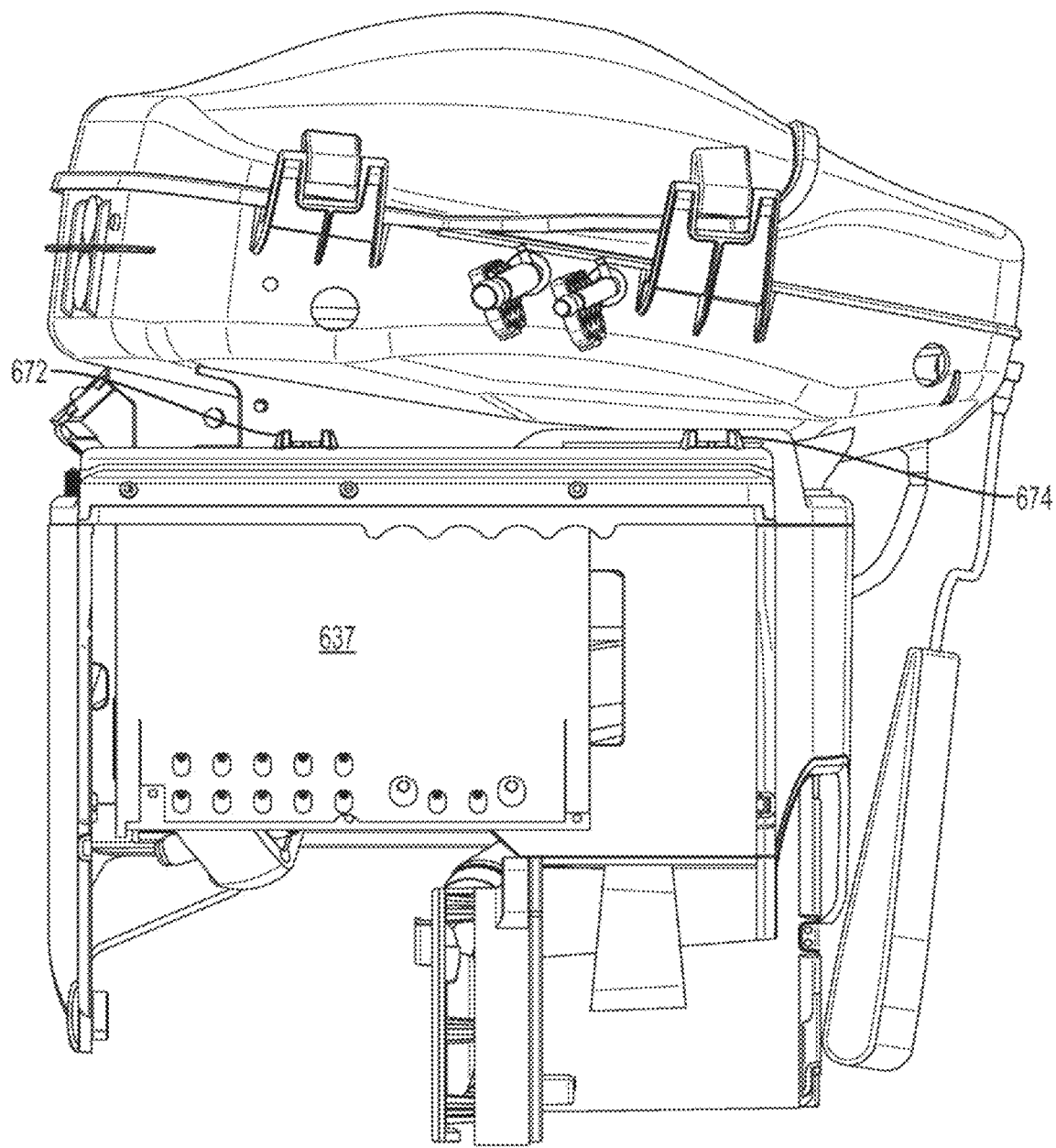
Figure 13K:
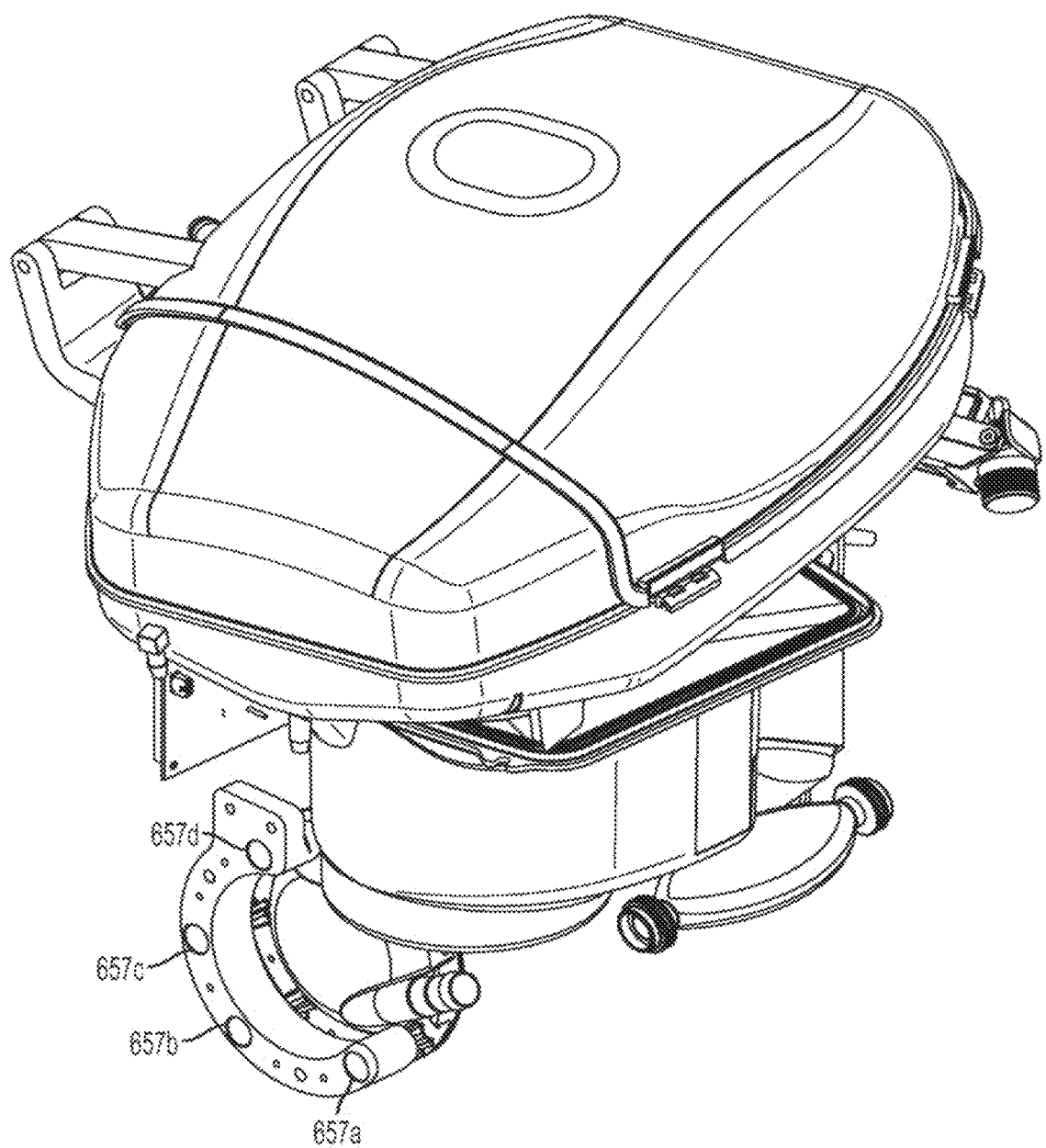
Figure 13L:
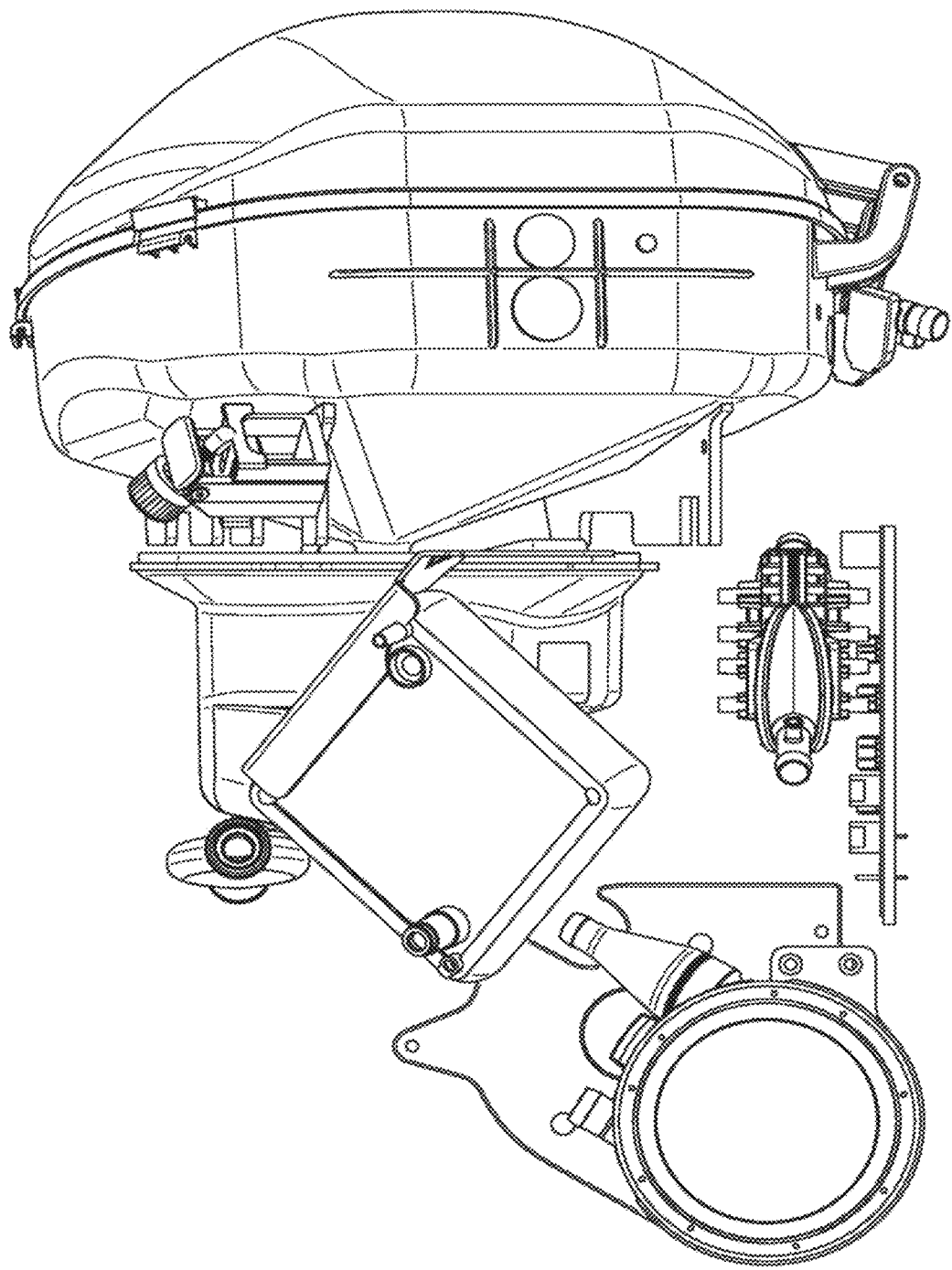
Figure 13M:
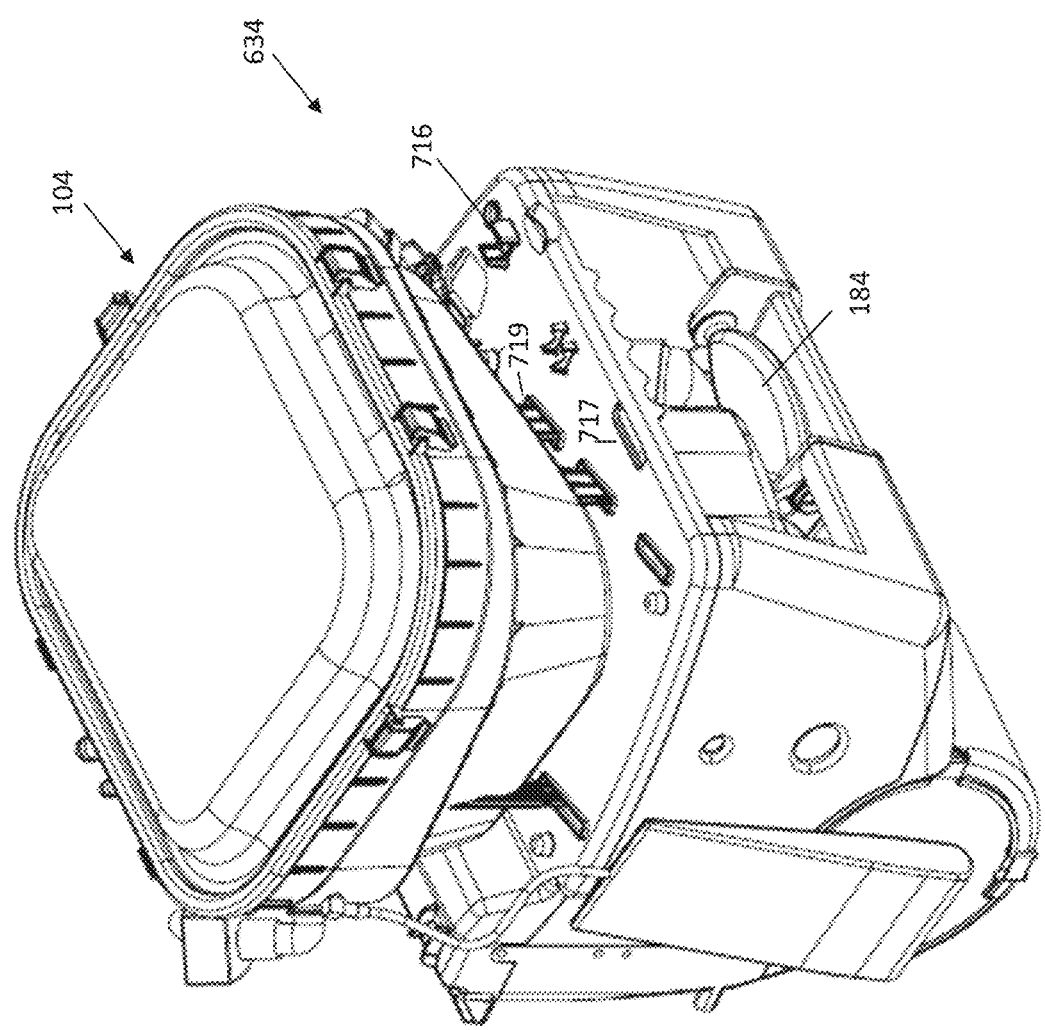
Figure 13P:
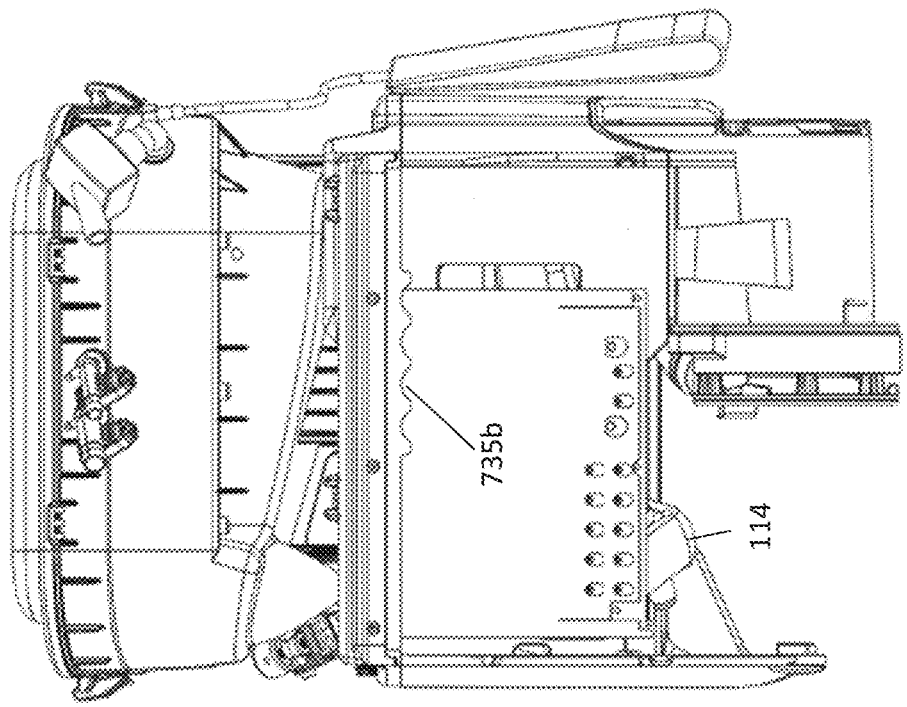
Figure 13O:
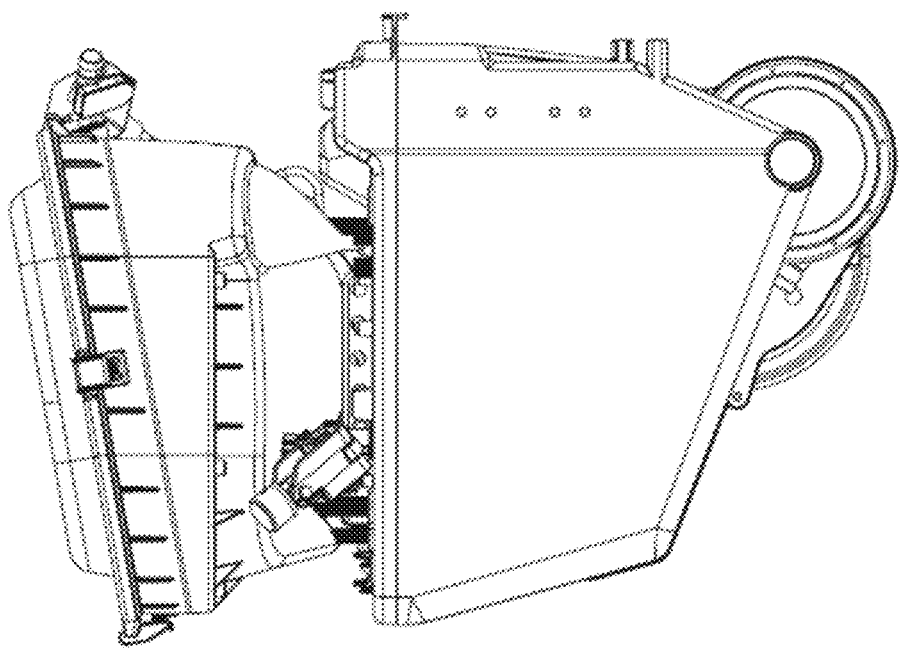
Figure 13R:
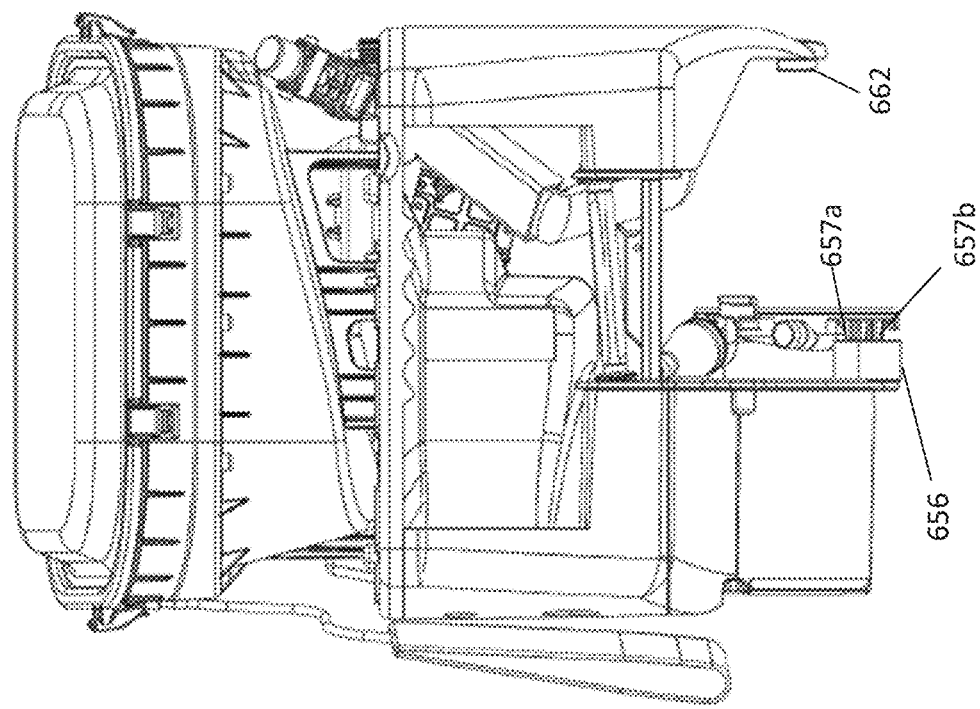
Figure 13Q:
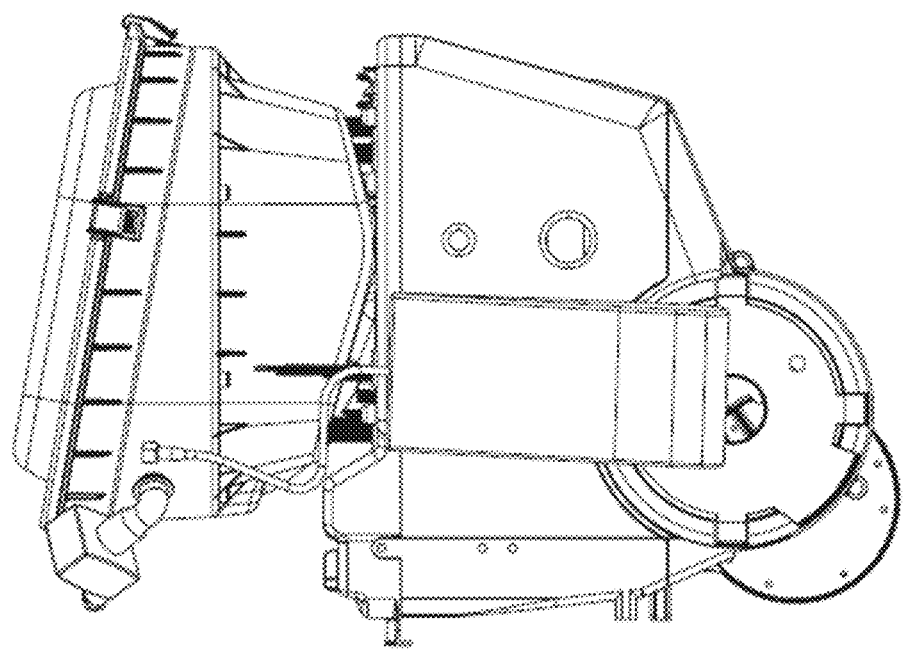
Figure 141:
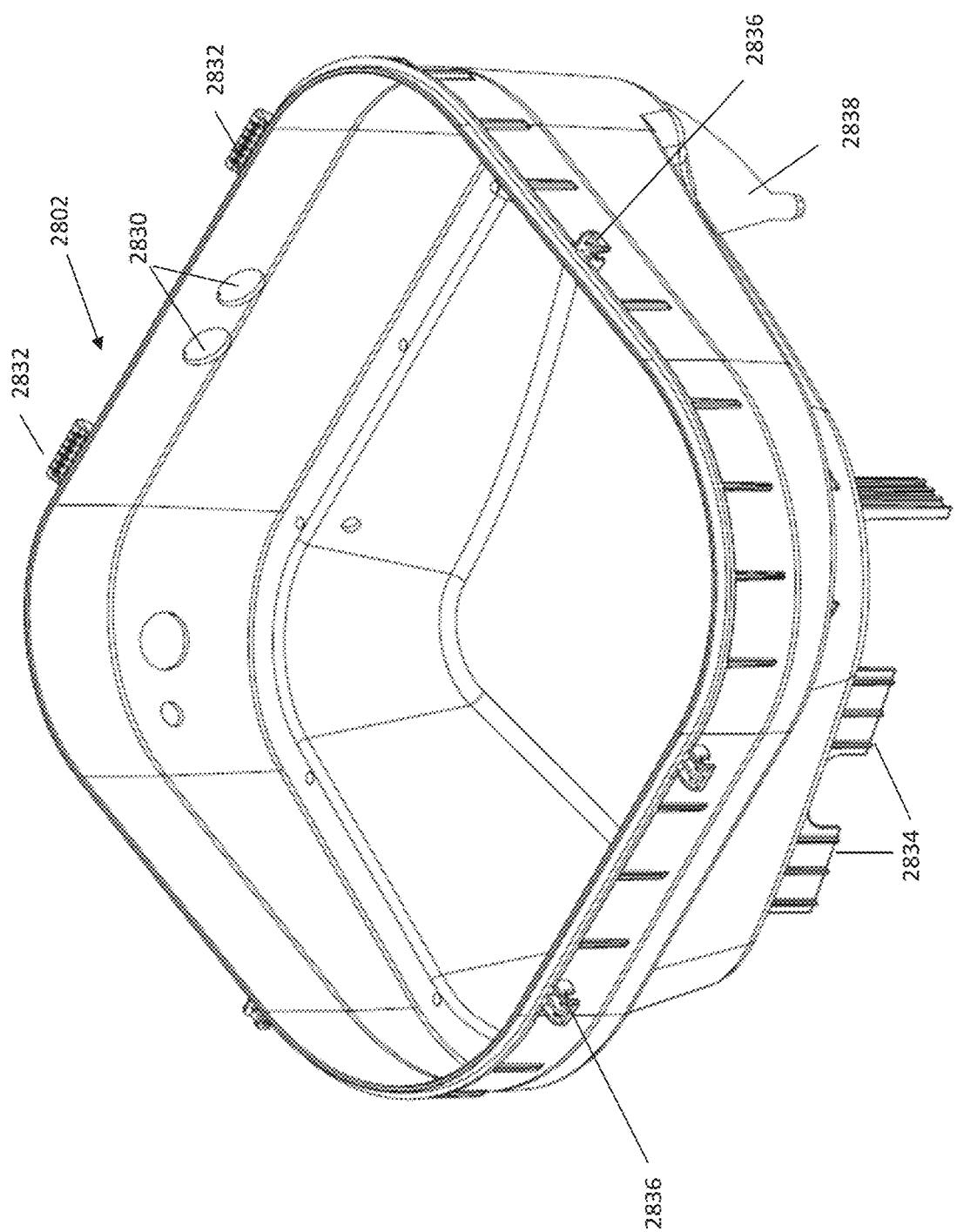

As shown in FIG. 3G and described in further detail below, the multiple use module 650 can include a front-end interface circuit board 636 for interfacing with a front-end circuit board (shown in FIG. 13J at 637) of the disposable module 634. As described more fully below, power and drive signal connections between the multiple use module 650 and the disposable module 634 can be made by way of corresponding electromechanical connectors 640 and 647 on the front end interface circuit board 636 and the front end circuit board 637, respectively. By way of example, the front-end circuit board 637 can receive power for the disposable module 634 from the front-end interface circuit board 636 via the electromechanical connectors 640 and 647. The front end circuit board 637 can also receive drive signals for various components (e.g., the heater assembly 110, the flow clamp 190, and the oxygenator 114) from the controller 150 via the front-end interface circuit board 636 and the electromechanical connectors 640 and 647. The front-end circuit board 637 and the front-end interface circuit board 636 can exchange control and data signals (e.g., between the controller 150 and the single use module 634) by way of optical connectors (shown in FIG. 20B at 648). As described in more detail below, the connector configuration employed between the front-end 637 and front-end interface 636 circuit boards can ensure that critical power and data interconnections between the single and multiple use modules 634 and 650, respectively, continue to operate even during transport over rough terrain, such as may be experienced during organ transport.

Turning now to the installation of the single use module 634 into the multiple use module 650, FIG. 3H shows a detailed view of the above-mentioned bracket assembly 638 located on the multiple use module 650 for receiving and locking into place the single use module 634. FIG. 3F shows a side perspective view of the single use module 634 being installed onto the bracket assembly 638 and into the multiple use module 650, and FIG. 3C shows a side view of the single use module 634 installed within the multiple use module 650. The bracket assembly 638 includes two mounting brackets 642a and 642b, which can mount to an internal side of a back panel of the housing 602 via mounting holes 644a-644d and 646a-646d, respectively. A cross bar 641 extends between and rotatably attaches to the mounting brackets 642a and 642b. Locking arms 643 and 645 are spaced apart along and radially extend from the cross bar 641. Each locking arm 643 and 645 includes a respective downward extending locking projection 643a and 645b. A lever 639 attaches to and extends radially upward from the cross bar 641. Actuating the lever 639 in the direction of the arrow 651 rotates the locking arms 643 and 645 toward the back 606b of the housing 602. Actuating the lever 639 in the direction of the arrow 653 rotates the locking arms 643 and 645 toward the front of the housing 602.

As described above with respect to FIG. 6E, the perfusion pump interface assembly 300 includes four projecting heat staking points 321a-321d. During assembly, the projections 321a-321d are aligned with corresponding apertures (e.g., 657a, 657b in FIG. 13B) and heat staked through the apertures to rigidly mount the outer side 304 of the pump interface assembly 300 onto the C-shaped bracket 656 of the single use module chassis 635.

During installation, in a first step, the single use module 634 is lowered into the multiple use module 650 while tilting the single use module 634 forward (shown in FIG. 3F). This process slides the projection 662 into the slot 660. As shown in FIG. 6E, it also positions the flange 328 of the pump interface assembly 300 within the docking port 342 of the perfusion pump assembly 106, and the tapered projections 323a and 323b of the pump interface assembly 300 on the clockwise side of corresponding ones of the features 344a and 344b of the pump assembly bracket 346. In a second step, the single use module 634 is rotated backwards until locking arm cradles of the single use module chassis 635 engage projections 643 and 645 of spring-loaded locking arm 638, forcing the projections 643 and 645 to rotate upward, until locking projections 643a and 645a clear the height of the locking arm cradles, at which point the springs cause the locking arm 638 to rotate downward, allowing locking projections 643a and 645a to releasably lock with locking arm cradles of the disposable module chassis 635. This motion causes the curved surface of 668 of the single use module projection 662 of FIG. 13B to rotate and engage with a flat side 670 of the basin slot 660 of FIG. 20B. Lever 639 can be used to rotate the locking arm 638 upwards to release the single use module 635.

As shown in FIG. 6E, this motion also causes the pump interface assembly 300 to rotate in a counterclockwise direction relative to the pump assembly 106 to slide the flange 328 into the slot 332 of the docking port 342, and at the same time, to slide the tapered projections 323a and 323b under the respective bracket features 344a and 344b. As the tapered projections 323a and 323b slide under the respective bracket features 344a and 344b, the inner surfaces of the bracket features 344a and 344b engage with the tapered outer surfaces of the tapered projections 323a and 323b to draw the inner side 306 of the pump interface assembly 300 toward the pump driver 334 to form the fluid tight seal between the pump interface assembly 300 and the pump assembly 106. The lever 639 may lock in place to hold the disposable module 634 securely within the multiple use module 650.

Figure 20A:
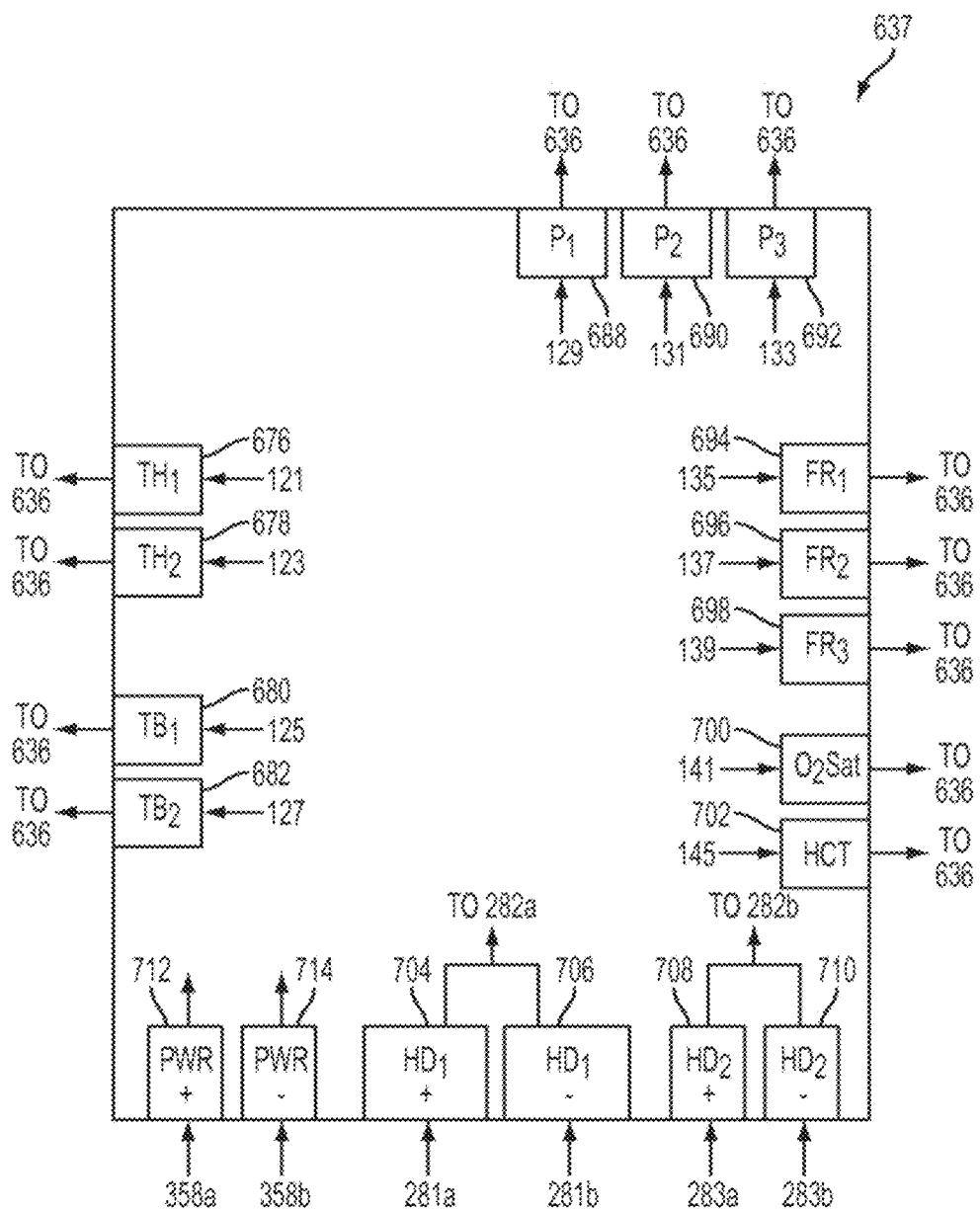
FIGS. 20A-20C show an exemplary system that can be used within an embodiment of the organ care system.

Interlocking the single use module 374 into the multiple use module 650 can form both electrical and optical interconnections between the front end interface circuit board 636 on the multiple use module 650 and the front end circuit board 637 on the single use module 634. The electrical and optical connections enable the multiple use module 650 to power, control and collect information from the single module 634. FIG. 20A is an exemplary conceptual drawing showing various optical couplers and electromechanical connectors on the front end circuit board 637 of the single-use disposable module 634 used to communicate with corresponding optical couplers and electromechanical connectors on the front end interface circuit board 636 of the multiple use module 650. Since this correspondence is one for one, the various optical couplers and electromechanical connectors are described only with reference to the front end circuit board 637, rather than also depicting the front end circuit board 650.

According to the exemplary embodiment, the front end circuit board 637 receives signals from the front end interface circuit board 636 via both optical couplers and electromechanical connectors. For example, the front end circuit board 637 receives power 358 from the front end interface circuit board 636 via the electromechanical connectors 712 and 714. The front end circuit board 637 applies the power to the components of the single use module 634, such as the various sensors and transducers of the single use module 634. Optionally, the front end circuit board 637 converts the power to suitable levels prior to distribution. The front end interface circuit board 636 can also provide the heater drive signals 281a and 281b to the applicable connections 282a on the heater 246 of FIG. 6E via the electromechanical connectors 704 and 706. Similarly, the electromechanical connectors 708 and 710 can couple the heater drive signals 283a and 283b to the applicable connections in 282b of the heater 248.

According to the exemplary embodiment, the front end circuit board 637 can receive signals from temperature, pressure, fluid flow-rate, and oxygenation/hematocrit sensors, amplify the signals, convert the signals to a digital format, and provide them to the front-end interface circuit board 636 by way of electrical and/or optical couplers. For example, the front end circuit board 637 can provide the temperature signal 121 from the sensor 120 on the heater plate 250 to the front end interface circuit board 636 by way of the optical coupler 676. Similarly, the front end circuit board 637 can provide the temperature signal 123 from the sensor 122 on the heater plate 252 to the front end interface circuit board 636 by way of the optical coupler 678. The front end-circuit board 637 can also provide the perfusion fluid temperature signals 125 and 127 from the thermistor sensor 124 to the front end interface circuit board 636 via respective optical couplers 680 and 682. Perfusion fluid pressure signals 129, 131 and 133 can be provided from respective pressure transducers 126, 128 and 130 to the front end interface circuit board 636 via respective optical couplers 688, 690 and 692. The front end circuit board 637 can also provide perfusion fluid flow rate signals 135, 137 and 139 from respective flow rate sensors 134, 136 and 138 to the front end interface circuit board 636 by way of respective optical couplers 694, 696 and 698. Additionally, the front end circuit board 637 can provide the oxygen saturation 141 and hematocrit 145 signals from the sensor 140 to the front end interface circuit board 636 by way of respective optical couplers 700 and 702. In another implementation, the front end circuit receives signals from integrated blood gas analysis probes. In another implementation the front end board passes control signals to a fluid path restrictor to facilitate real time control of the division of perfusate flow between the portal vein and hepatic artery conduits. The controller 150 can employ the signals provided to the front end interface circuit board 636, along with other signals, to transmit data and otherwise control operation of the system 600.

While the front end circuit board 637 is described with the foregoing couplers, more or fewer couplers can be used based on the number of connections necessary.

In some exemplary embodiments, one or more of the foregoing sensors can be wired directly to the main system board 718 for processing and analysis, thus by-passing the front-end interface board 636 and front-end board 637 altogether. Such embodiments can be desirable where the user prefers to re-use one or more of the sensors prior to disposal. In one such example, the flow rate sensors 134, 136 and 138 and the oxygen and hematocrit sensor 140 are electrically coupled directly to the system main board 718 through electrical coupler 611 shown in FIG. 23C, thus by-passing any connection with the circuit boards 636 and 637.

Figure 20B:
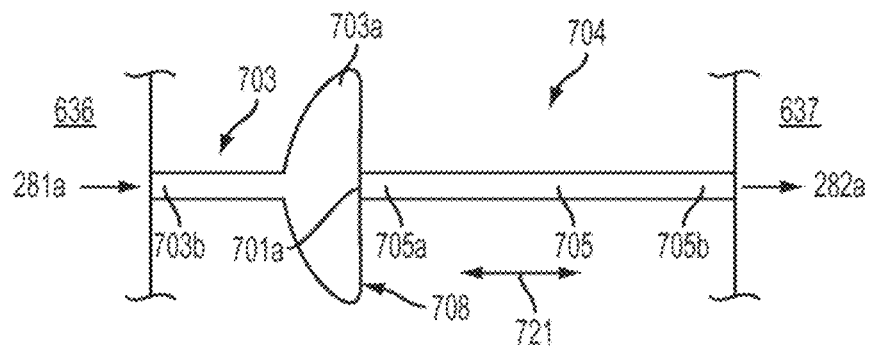
Figure 20C:
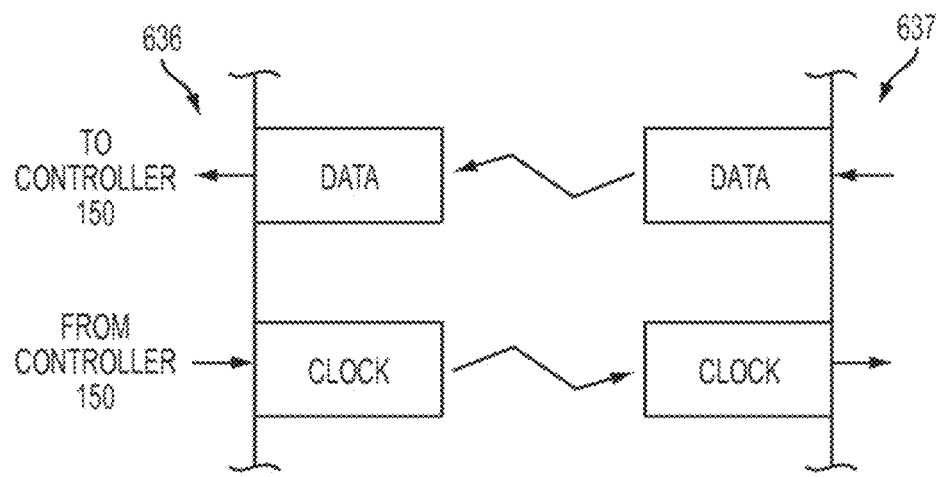

FIG. 20B illustrates the operation of an exemplary electromechanical connector pair of the type employed for the electrical interconnections between the circuit boards 636 and 637. Similarly, FIG. 20C illustrates the operation of an optical coupler pair of the type employed for the optically coupled interconnections between the circuit boards 636 and 637. One advantage of both the electrical connectors and optical couplers employed is that they ensure connection integrity, even when the system 600 is being transported over rough terrain, for example, such as being wheeled along a tarmac at an airport, being transported in an aircraft during bad weather conditions, or being transported in an ambulance over rough roadways. The power for the front end board 637 is isolated in a DC power supply located on the front end interface board 636.

As shown in FIG. 20B, the electromechanical connectors, such as the connector 704, include a portion, such as the portion 703, located on the front end interface circuit board 636 and a portion, such as the portion 705, located on the front end circuit board 637. The portion 703 includes an enlarged head 703a mounted on a substantially straight and rigid stem 703b. The head 703 includes an outwardly facing substantially flat surface 708. The portion 705 includes a substantially straight and rigid pin 705 including an end 705a for contacting the surface 708 and a spring-loaded end 705b. Pin 705 can move axially in and out as shown by the directional arrow 721 while still maintaining electrical contact with the surface 708 of the enlarged head 703a. This feature enables the single use module 634 to maintain electrical contact with the multiple use module 650 even when experiencing mechanical disturbances associated with transport over rough terrain. An advantage of the flat surface 708 is that it allows for easy cleaning of the interior surface of the multiple use module 650. According to the illustrative embodiment, the system 600 employs a connector for the electrical interconnection between the single use disposable 634 and multiple use 650 modules. An exemplary connector is part no. 101342 made by Interconnect Devices. However, any suitable connector may be used.

Optical couplers, such as the optical couplers 684 and 687 of the front end circuit board 637, are used and include corresponding counterparts, such as the optical couplers 683 and 685 of the front end interface circuit board 636. The optical transmitters and optical receiver portions of the optical couplers may be located on either circuit board 636 or 637.

As in the case of the electromechanical connectors employed, allowable tolerance in the optical alignment between the optical transmitters and corresponding optical receivers enables the circuit boards 636 and 637 to remain in optical communication even during transport over rough terrain. According to the illustrative embodiment, the system 100 uses optical couplers made under part nos. 5FH485P and/or 5FH203 PFA by Osram. However, any suitable coupler may be used.

The couplers and connectors can facilitate the transmission of data within the system 600. The front-end interface circuit board 636 and the front-end board 637 transmit data pertaining to the system 600 in a paced fashion. As shown in FIG. 20C, circuit board 636 transmits to the front-end board 637 a clock signal that is synchronized to the clock on the controller 150. The front-end circuit board 637 receives this clock signal and uses it to synchronize its transmission of system data (such as temperatures, pressures, or other desired information) with the clock cycle of the controller 150. This data is digitized by a processor on the front-end circuit board 637 according to the clock signal and a pre-set sequence of data type and source address (i.e. type and location of the sensor providing the data). The front-end interface circuit board 636 receives the data from the front-end board 637 and transmits the data set to the main board 618 for use by the controller 150 in evaluation, display, and system control. Additional optical couplers can be added between the multiple use module and single use module for transmission of control data from the multiple use module to the single use module, such data including heater control signals or clamp/flow restrictor controls.

IV. DESCRIPTION OF EXEMPLARY SYSTEM OPERATION

A. Generally

As described below, the system 600 can be configured to operate in multiple modes such as: perfusion circuit priming mode, organ stabilization mode, maintenance mode, chilling mode, and self-test/diagnostic mode. During each mode the system (vis-à-vis the controller 150) can be configured to operate in different manners. For example, as described more fully below, during the different modes of operation characteristics of, for example, perfusion fluid flow rates, perfusion fluid pressure, perfusion fluid temperature, etc. can vary.

Additionally, some embodiments of the system 600 can include a self-test mode in which diagnostics can be performed. For example, the system 600 can automatically test circuits and sensors in the single use and multiple use modules before the organ is instrumented on the system. The system 600 can also check to ensure that the single use module is installed properly in the multiple use module (e.g., all connections are secure and functioning). In the event of a failure, the system can inform the user and inhibit further operation of the system until the issue is resolved.

B. Temperature Monitoring and Control

In general, the temperature of an organ contained in the system 600 can be controlled by circulating warmed or cooled perfusion fluid therethrough. Thus, the perfusion fluid itself can be used to control the temperature of the organ without using a dedicated heater/cooler within the organ chamber 104.

In some embodiments of the system 600, the controller 150 can be configured to receive signals from one or more temperature sensors such as temperature sensors 120, 122, 124. While these sensors are described as being located at or near the heater 110, this is not required. For example, temperature sensors that measure the temperature of the perfusion fluid can be placed throughout the system 100 such as in the branches 313, 315, in the measurement drain 2804, in the drain 2806, and/or in the reservoir 160. Additional temperature sensors can also be included to measure other temperature aspects of the system 600. For example, the system 600 can include ambient air temperature sensors that measure the temperature of the environment around the system 600, temperature sensors that measure the temperature of the environment within the organ chamber 104, and/or sensors that measure the temperature of a surface and/or internal portion of the organ contained therein.

The controller 150 can use information from the various temperature sensors in the system 600 in order to control the temperature of the environment and/or perfusion fluid therein. For example, in some embodiments the controller 150 can maintain the perfusion fluid exiting the heater at a desired temperature. In some embodiments, the controller 150 can determine a temperature differential between the perfusion fluid flowing into and out of the organ. If the temperature differential is large, the controller 150 can indirectly determine the temperature of the organ and adjust the temperature of the perfusion fluid flowing into the organ to achieve the desired organ temperature. Additionally, in some embodiments the organ chamber 104 can include a heater/cooler that heats/cools the environment within the organ chamber 104, such as a resistive heater or a thermo-electric cooler. Such a heater/cooler can be controlled by the controller 150.

While much of the disclosure herein focuses on heating an organ to a desired temperature, this is not intended to be limiting. In some embodiments, the system 600 can include a cooling unit (not shown) in addition to and/or instead of the heater 110. In such embodiments, the cooling unit can be used to cool the perfusion fluid and ultimately cool the organ itself. This can be useful during, for example, post-preservation chilling procedures used with a heart, lung, kidney, and/or liver. In some embodiments, the cooling unit can be comprised of a gas exchanger with an integrated water cooled feature, although other configurations are possible.

C. Blood Flow Monitoring and Control

Many organs in the human body receive a blood supply with a single set of pressure and flow characteristics (e.g., kidney, lung). To the extent that these organs are maintained ex vivo in an organ care system, a single pump and a single supply line can be used to provide perfusion fluid thereto. The liver, however, is different from other organs in that it has two blood supplies, each with different pressure and flow characteristics. As noted above, the liver receives approximately ⅓ of its blood supply from the hepatic artery and approximately ⅔ of its blood supply from the portal vein. The hepatic artery provides a pulsatile blood flow at a relatively high pressure, but low flow rate. In contrast, the portal vein provides a substantially nonpulsatile blood flow at a relatively low pressure, but high flow rate. Because of these different flow characteristics, providing perfusion fluid to an ex vivo liver can present challenges when a single pump is used. Thus, some embodiments of the organ care system 600 include a system that is configured to provide a dual flow of perfusion fluid in a manner that mimics the human body. Specifically, the branch 315 of the system 100 can provide perfusion fluid to the hepatic artery in a pulsatile, high-pressure, low flow manner. The branch 313 of the system 100 can provide perfusion fluid to the portal vein in a non-pulsatile, low pressure, high flow manner.

As noted above, the pump 106 can provide a flow of perfusion fluid at a predetermined flow rate, which can be split at the divider 105. In some embodiments, the fluid flow can be split between the hepatic artery and the portal vein at a ratio of between 1:2 and 1:3. In some embodiments, the divider is configured such that the branch 313 uses ⅜" tubing and the branch 315 uses ¼" tubing. In some embodiments, a portal vein clamp can be used to help attain this split ratio and/or can be used to restrict the resulting flow in the portal vein leg of the circuit (e.g., branch 313) so as to create higher pressure flow in the hepatic artery leg of the circuit (e.g., branch 315) and lower pressure flow in the parallel portal vein leg of the circuit. In some embodiments, a user can manually adjust the portal vein clamp (e.g., such as the flow clamp 190) to effect a hepatic pressure in the acceptable range and adjust the pump flow rate to provide an acceptable hepatic artery flow rate. The combination of these two adjustments (portal vein clamp and pump flow rate) can result in acceptable hepatic artery flow and pressure and correspondingly acceptable portal vein pressure and flow rate.

In some embodiments, the portal vein clamp can be implemented as mechanism controlled by the system, such as an electromechanical or pneumatically controlled clamp. The system can adjust the pump flow and portal vein clamp in response to pressure and flow values measured on the hepatic artery and portal vein branches to effect pressures and flows in acceptable ranges for these paths. For example, in embodiments that use an automated portal vein clamp, if the controller 150 detects that the flow in the hepatic artery branch 315 is too low, the controller 150 can increase the flow rate provided by the pump 106. Likewise, if the controller detects that the pressure in the hepatic artery branch 315 is too low, the controller 150 can cause the portal vein clamp to close slightly in order to increase the pressure in hepatic artery branch 315.

In some embodiments, the controller 150 can monitor the level of perfusion fluid in the system 600. In the event that the amount of perfusion fluid is below recommended levels, the controller 150 can alert the user to this fact so that they may take recommended action such as adjusting pump flow and/or adding additional perfusion fluid to the system. Additionally, if the level is below a critical level, the controller 150 can automatically reduce the pump flow to a reduced or minimal level while alerting the user.

D. Gas Monitoring and Control

In some embodiments, the system 600 can be configured to automatically control pressure within the system by varying the flow rate of the pump 106 and/or by controlling the infusion of a vasodilator. For example, one of the infusions provided by the solution pump 631 can be, or can contain a vasodilator. When a vasodilator is administered, the perfusion fluid pressure for a given flow rate within the system 100 can drop (due to the dilation of the vasculature in the liver). Thus, for example, reducing the infusion rate of a vasodilator can result in increased perfusate pressure. An optimal balance can be achieved at the least amount of vasodilator that results in adequate liver perfusion.

The system 600 can be configured to control the gas content in the perfusion fluid in such a manner that it mimics the human body. Accordingly, in some embodiments, the system 600 includes a gas exchanger (e.g., gas exchanger 114) that is configured to provide $O_2$ and/or other desirable gases to the perfusion fluid. In principle, a gas exchanger works by facilitating the flow of a high concentration of gas to an area of low concentration of gas. In this way, the $O_2$ in the maintenance gas (e.g., the gas provided to the gas exchanger) can be diffused to the $O_2$ depleted perfusion fluid and the relatively high level of $CO_2$ in the perfusion fluid can be diffused to the maintenance gas before it is exhausted from the gas exchanger. The maintenance gas provided to the gas exchanger can be comprised of the appropriate mixture of $O_2$, $N_2$, and $CO_2$, where the concentration of $O_2$ is higher, and the concentration of $CO_2$ is lower than that in the perfusion solution exiting a metabolically-active liver. In some instances the gas is comprised of only $O_2$ and $N_2$.

Some embodiments of the system 600 include an oxygenation sensor (e.g., sensor 140) that can be used to provide information about the oxygenation of the perfusion fluid. If the oxygenation level is too low, the rate of gas supplied to the gas exchanger can be increased to raise the level of oxygen in the perfusion fluid. Likewise, if the level is too high, the rate of gas supplied to the gas exchanger can be decreased. Control of the gas supply to the gas exchanger can be performed manually by the user (e.g., through the operator interface module 146) and/or automatically. In an automated embodiment, the controller 150 can automatically increase or decrease the gas flow from the onboard gas supply to the gas exchanger to effect the desired change in oxygenation level.

The liver, however, can present an additional challenge providing the proper perfusion fluid gas content. Because of its inherent metabolism, the liver produces $CO_2$ that replaces $O_2$ contained in the perfusate. In some embodiments, measuring the $O_2$ levels alone is not sufficient to determine the amount of $CO_2$ present in the perfusion fluid. Thus, some embodiments the system 600 can be configured to separately monitor the level of $CO_2$ in the perfusion fluid to ensure that it stays within an acceptable range. In these embodiments, the gas exchanger can also be used to reduce or even eliminate $CO_2$ from the perfusion fluid as it passes therethrough.

In order to determine the carbon dioxide level in the perfusate, some embodiments of the system 600 incorporate blood sample ports so that the user can withdraw blood samples to assess the levels of carbon dioxide in the perfusate via a third party blood gas analyzer. Based on this analysis, the user can assign a gas flow rate into the gas exchanger in order to effect an acceptable carbon dioxide level in the perfusate. For example, higher than acceptable levels of carbon dioxide can require a higher gas flow rate to the gas exchanger to reduce the resulting level of carbon dioxide. However, it can be advantageous to keep the gas flow to the gas exchanger as low as possible in order to maximize the life of the onboard gas supply—an important factor in extended transport scenarios.

Some embodiments of the system 600 can incorporate a blood gas analysis system (not shown). In these embodiments, the blood gas analysis system can be configured to sample perfusion fluid flowing within the system 100. For example, the blood gas analysis system can be configured to take samples of perfusion fluid at one or more locations in the system 100 such as in branches 313, 315, in the measurement drain 2804, and/or in the main drain 2806. By measuring the concentration of oxygen and/or carbon dioxide in the perfusate, the controller 150 can automatically increase or decrease, as the case may be, the flow of gas to the gas exchanger to obtain the desired gas levels in the perfusion fluid.

E. Solution Delivery and Control

As noted above, some embodiments of the system 600 can include a solution pump that is configured to provide one or more solutions. In some specific embodiments, the runtime perfusion solution comprises three solutions. The first solution can comprise one or more energy-rich component (e.g., one or more carbohydrates); and/or one or more amino acids; and/or one or more electrolytes; and/or one or more buffering agents (e.g., bicarbonate). In some particular embodiments, the first solution can comprise TPN (Clinimix E), buffering agents (e.g., sodium bicarbonate and phosphates), heparin and insulin. The second solution can comprise one or more vasodilators. In some particular embodiments, the vasodilator used is Flolan®. The third solution can comprise bile acid or salts (e.g., Na Taurocholic acid salt). In some embodiments, the three solutions are kept separate from one another and administered separately (e.g., using the three channels of the solution pump 631). In other embodiments, the three solutions, optionally all aqueous solutions, can be mixed together to form the runtime perfusion solutions. In certain embodiments, a sufficient amount of heparin can be provided (e.g., amount sufficient to maintain activated clotting time (ACT) for about or more than 400 seconds ACT).

V. SOLUTIONS

Exemplary solutions that can be used in the organ care system 600 according to one or more embodiments are now described. Various solutions can be used at different times in the preservation/treatment process.

A. Donor Flush

If the organ being harvested is an abdominal organ, the surgeon performing the harvest can perform a donor flush in vivo or ex vivo to remove donor blood and/or other matter from the organ. The flush used during the donor flush can be an intracellular or extracellular solution such as the University of Wisconsin Solution, a modified University of Wisconsin Solution, or a histidine-tryptophan-ketoglutarate (HTK) solution.

B. Initial Flush Solution

In some embodiments, after the donor flush (regardless of whether the donor flush was done in vivo or ex vivo) and before it is placed in the preservation chamber of the organ care system 600, an initial flush solution can be used to flush the liver in vivo or ex vivo in order to remove the residual blood and any solution used in the donor flush. This flush solution is referred to herein as the initial flush solution, which is optionally a sterile solution. In some embodiments, the main components of the initial flush solution can include a buffered isotonic electrolyte solution, such as Plasmalyte, and an ti-inflammatory, such as SoluMedrol. In some embodiments, the initial flush can be used to remove the fluid used during the donor flush. In some embodiments, the main components of the initial flush solution can include electrolytes and buffering agents. Non-limiting examples of the electrolytes include various salts of sodium, potassium, calcium, magnesium, chloride, hydrogen phosphate, and hydrogen carbonate. A proper combination of the electrolytes in suitable concentrations can help maintain the physiological osmotic pressure of the intracellular and extracellar environment in liver. Non-limiting examples of the buffering agents include bicarbonate ions. The buffering agents in the initial flush solution can serve to maintain the pH value inside the liver organ to be at or close to the physiological state, e.g., about 7.3 to 7.6, 7.4 to 7.6, or 7.4 to 7.5. Preferably, after the liver is subjected to the initial flush and cooled according to one more embodiments described herein, the harvested liver can be placed into the organ care system 600 according to one more embodiments.

C. Priming Solution and Additives

In certain embodiments, prior to the placement of the liver into the organ care system 600, the organ care system 600 can be primed with a priming solution. The priming solution can be sterile and can be used to evaluate the physical integrity of the system and/or to help remove the air in the system. The composition of the priming solution can be similar or identical to that of the runtime perfusion solution, described in more detail below. The priming solution can include certain additives to render the system compatible with liver preservation. For instance, the liver regularly produces coagulation factors promoting blood coagulation. In order to prevent the blood (e.g., donor's blood used as part of the perfusion fluid for preserving the liver on the organ care system 600) from clotting during preservation, anti-clotting agents can be added to the priming solution as additives. Non-limiting examples of anti-clotting agents include heparin. Heparin can be administered throughout the preservation session to maintain ACT (activated clotting time) of ≥400 seconds, although other ACT values can be used. Depending on the liver being maintained, the amount of heparin needed to achieve the desired ACT can vary. In some embodiments, the heparin can be provided continuously or at intervals such as at 0, 3, and 6 hours post-instrumentation on the system 600. In certain embodiments, the organ care system 600 can be primed by a blood product (e.g., donor's blood) or synthetic blood product prior to the placement of the liver into the organ care system 600. In certain embodiments, the system 600 can be primed by the priming solution and/or the blood or synthetic blood product. The system 600 can be primed by the mixture of the priming solution and the blood or synthetic blood product, or by the priming solution and the blood or synthetic blood product sequentially. In some embodiments, the organ care system 600 is primed with the perfusion fluid described herein (e.g., the perfusion fluid used to preserve the organ). Alternatively or additionally, any one of the following combined with either albumen or dextran can also be used: donor blood, red blood cells (RBC), or RBCs plus fresh frozen plasma plus Table 1 sets forth components that can be used in an exemplary priming solution.

TABLE 1

Composition of Exemplary Priming Solution

| Component | Amount | Specification |
|---|---|---|
| pRBCs | 1200-1500 ml | ±about 10% |
| 25% Albumin | 400 ml | ±about 10% |
| PlasmaLyte | 700 ml | ±about 10% |
| Cefazoline or equivalent antibiotic (gram positive and gram negative) | 1 g | ±about 10% |
| Cipro or equivalent antibiotic (gram positive and gram negative) | 100 mg | ±about 10%. |
| Solu-Medrol or equivalent anti-inflammatory | 500 mg | ±about 10%. |
| $HCO_3^-$ | 50 mmol | ±about 10%. |
| Multivitamin | 1 unit | |
| Calcium Gluconate | 4.65 mEq | ±about 10%. |
| Heparin (optional) | 10000 Units | ±about 10%. |

The exemplary priming solution can be added to the organ care system 600 through the priming step 5024, as more fully described with reference to FIG. 29 (described more fully below).

D. Runtime Perfusion Solution

During the preservation of the harvested liver in the organ care system 600 (e.g., during transport), a perfusion fluid or perfusate, can be used to perfuse the liver and maintain the liver function at or near physiological conditions. In certain embodiments, the perfusion fluid comprises a runtime perfusion solution (also referred to as a maintenance solution) and/or a blood product, e.g., donor's blood, other individual's compatible blood, or synthetic blood. The perfusion fluid can be periodically/continuously infused by, for example, the solution pump 631 in order to provide nutrients that can maintain the liver during preservation. In some embodiments, the runtime perfusion solution and/or the blood product are sterile.

The compositions of the runtime perfusion solution and the priming solution are now described in more detail. According to certain embodiments, the runtime perfusion solution with particular solutes and concentration is selected and proportioned to enable the organ to function at physiologic or near physiologic conditions. For example, such conditions include maintaining organ function at or near a physiological temperature and/or preserving the liver in a state that permits normal cellular metabolism, such as protein synthesis, glucose storage, lipid metabolism, and bile production. In some embodiments, the priming solution and runtime solution can be selected to be similar or even identical to one another.

In certain embodiments, the runtime perfusion solution is formed from compositions by combining components with a fluid, from more concentrated solutions by dilution, or from more dilute solutions by concentration. In exemplary embodiments, suitable runtime perfusion solutions include an energy source, and/or one or more stimulants to assist the organ in continuing its normal physiologic function prior to and during transplantation, and/or one or more amino acids selected and proportioned so that the organ continues its cellular metabolism during perfusion. The runtime perfusion solution can include any therapeutic agents described in more detail below. Cellular metabolism includes, for example conducting protein synthesis while functioning during perfusion. Some illustrative solutions are aqueous based, while other illustrative solutions are non-aqueous, for example organic solvent-based, ionic-liquid-based, or fatty-acid-based.

The runtime perfusion solution can include one or more energy-rich components to assist the liver in conducting its normal physiologic function. These components can include energy rich materials that are metabolizable, and/or components of such materials that an organ, e.g., liver, can use to synthesize energy sources during perfusion. Exemplary sources of energy-rich molecules include, for example, one or more carbohydrates. Examples of carbohydrates include monosaccharides, disaccharides, oligosaccharides, polysaccharides, or combinations thereof, or precursors or metabolites thereof. While not meant to be limiting, examples of monosaccharides suitable for the solutions include octoses; heptoses; hexoses, such as fructose, allose, altrose, glucose, mannose, gulose, idose, galactose, and talose; pentoses such as ribose, arabinose, xylose, and lyxose; tetroses such as erythrose and threose; and trioses such as glyceraldehyde. While not meant to be limiting, examples of disaccharides suitable for the solutions include (+)-maltose (4-O-(α-D-glucopyranosyl)-α-D-glucopyranose), (+)-cellobiose (4-O-(β-D-glucopyranosyl)-D-glucopyranose), (+)-lactose (4-O-(β-D-galactopyranosyl)-β-D-glucopyranose), sucrose (2-O-(α-D-glucopyranosyl)-β-D-fructofuranoside). While not meant to be limiting, examples of polysaccharides suitable for the solutions include cellulose, starch, amylose, amylopectin, sulfomucopolysaccharides (such as dermatane sulfate, chondroitin sulfate, sulodexide, mesoglycans, heparan sulfates, idosanes, heparins and heparinoids), dextrin, and glycogen. In some embodiments, monossacharides, disaccharides, and polysaccharides of both aldoses, ketoses, or a combination thereof are used. One or more isomers, including enantiomers, diastereomers, and/or tautomers of monosacharides, disaccharides, and/or polysaccharides, including those described and not described herein, can be employed in the runtime perfusion solution described herein. In some embodiments, one or more monossacharides, disaccharides, and/or polysaccharides can have been chemically modified, for example, by derivatization and/or protection (with protecting groups) of one or more functional groups. In certain embodiments, carbohydrates, such as dextrose or other forms of glucose are preferred.

Other possible energy sources include, co-enzyme A, pyruvate, flavin adenine dinucleotide (FAD), thiamine pyrophosphate chloride (co-carboxylase), β-nicotinamide adenine dinucleotide (NAD), β-nicotinamide adenine dinucleotide phosphate (NADPH), and phosphate derivatives of nucleosides, i.e. nucleotides, including mono-, di-, and tri-phosphates (e.g., UTP, GTP, GDF, and UDP), coenzymes, or other bio-molecules having similar cellular metabolic functions, and/or metabolites or precursors thereof. For example, phosphate derivatives of adenosine, guanosine, thymidine (5-Me-uridine), cytidine, and uridine, as well as other naturally and chemically modified nucleosides are contemplated.

In certain embodiments, one or more carbohydrates can be provided along with a phosphate source, such as a nucleotide. The carbohydrate can help enable the organ to produce ATP or other energy sources during perfusion. The phosphate source can be provided directly through ATP, ADP, AMP or other sources. In other illustrative embodiments, a phosphate is provided through a phosphate salt, such as glycerophosphate, sodium phosphate or other phosphate ions. A phosphate can include any form thereof in any ionic state, including protonated forms and forms with one or more counter ions. The energy source used can depend on the type of organ being perfused (e.g., adenosine can be omitted when perfusing a liver).

One of the liver's important functions is to produce bile liquid. In some embodiments, the runtime perfusion solution comprises one or more compounds supporting the production of bile by the liver. Non-limiting examples of such compounds include cholesterol, primary bile acids, secondary bile acids, glycine, taurine, and bile acids (bile salts) to promote production of bile by the liver ex vivo, all of which can be used by the liver to produce bile. In some specific embodiments, the bile salt is Na Taurocholic acid salt.

Because of the liver's function as the metabolism powerhouse of the body, it is typically in constant need of energy source and oxygen. Thus, in addition to maintaining the proper concentration of the energy source compounds in the perfusion liquid, the organ care system 600 described herein can also configured to provide constant oxygen supply to the preserved liver. In some embodiments, the oxygen is provided by diffusing an oxygen gas flow through the perfusion liquid (e.g., in the gas exchanger 114) or the blood product to dissolve or saturate oxygen in the liquid medium, e.g., by binding oxygen to the hemoglobin in the blood product. In certain embodiments, the perfusion liquid supplied to the liver contains $O_2$ in $PaO_2 \geq 200$ mmHg (arterial perfusate). In certain embodiments, the perfusion liquid supplied to the liver contains less than $PaCO_2 \leq 40$ mmHg of carbon dioxide thereby promoting and maintaining the oxidative metabolic functions of the liver. In certain embodiments, the perfusion liquid contains less than 30 mmHg$\leq$PACO2 of carbon dioxide thereby maintaining the pH value in the liver to maintain its biological functions.

The runtime perfusion solution described herein can include one or more amino acids, preferably a plurality of amino acids, to support protein synthesis by the organ's cells. Suitable amino acids include, for example, any of the naturally-occurring amino acids. The amino acids can be, in various enantiomeric or diastereomeric forms. For example, solutions can employ either D- or L-amino acids, or a combination thereof, i.e., solutions enantioenriched in more of the D- or L-isomer or racemic solutions. Suitable amino acids can also be non-naturally occurring or modified amino acids, such as citrulline, ornithine, homocystein, homoserine, β-amino acids such as β-alanine, amino-caproic acid, or combinations thereof.

Certain exemplary runtime perfusion solutions include some but not all naturally-occurring amino acids. In some embodiments, runtime perfusion solutions include essential amino acids. For example, a runtime perfusion solution can be prepared with one or more or all of the following amino-acids: Glycine, Alanine, Arginine, Aspartic Acid, Glutamic Acid, Histidine, Isoleucine, Leucine, Methionine, Phenylalanine, Proline, Serine, Thereonine, Tryptophan, Tyrosine, Valine, and Lysine acetate.

In certain embodiments, non-essential and/or semi-essential amino acids are not included in the runtime perfusion solution. For example, in some embodiments, asparagine, glutamine, and/or cysteine are not included. In other embodiments, the solution contains one or more non-essential and/or semi-essential amino acids. Accordingly, in some embodiments, asparagine, glutamine, and/or cysteine are included.

The runtime perfusion solution can also contain electrolytes, particularly calcium ions for facilitating enzymatic reactions, and/or maintain osmotic pressure within the liver. Other electrolytes can be used, such as sodium, potassium, chloride, sulfate, magnesium and other inorganic and organic charged species, or combinations thereof. It should be noted that any component provided hereunder can be provided, where valence and stability permit, in an ionic form, in a protonated or unprotonated form, in salt or free base form, or as ionic or covalent substituents in combination with other components that hydrolyze and make the component available in aqueous solutions, as suitable and appropriate.

In certain embodiments, the runtime perfusion solution contains buffering components. For example, suitable buffer systems include 2-morpholinoethanesulfonic acid monohydrate (MES), cacodylic acid, $H_2CO_3/NaHCO_3$ ($pK_{a1}$), citric acid ($pK_{a3}$), bis(2-hydroxyethyl)-imino-tris-(hydroxymethyl)-methane (Bis-Tris), N-carbamoylmethylimidino acetic acid (ADA), 3-bis[tris(hydroxymethyl)methylamino] propane (Bis-Tris Propane) ($pK_{a1}$), piperazine-1,4-bis(2-ethanesulfonic acid) (PIPES), N-(2-Acetamido)-2-aminoethanesulfonic acid (ACES), imidazole, N,N-bis(2-hydroxyethyl)-2-aminoethanesulfonic acid (BES), 3-(N-morpholino)propanesulphonic acid (MOPS), $NaH_2PO_4/Na_2HPO_4$ ($pK_{a2}$), N-tris(hydroxymethyl)methyl-2-aminoethanesulfonic acid (TES), N-(2-hydroxyethyl)-piperazine-N'-2-ethanesulfonic acid (HEPES), N-(2-hydroxyethyl)piperazine-N'-(2-hydroxypropanesulfonic acid) (HEPPSO), triethanolamine, N-[tris(hydroxymethyl)methyl]glycine (Tricine), tris hydroxymethylaminoethane (Tris), glycineamide, N,N-bis(2-hydroxyethyl) glycine (Bicine), glycylglycine ($pK_{a2}$), N-tris(hydroxymethyl)methyl-3-aminopropanesulfonic acid (TAPS), or a combination thereof. In some embodiments, the solutions contain sodium bicarbonate, potassium phosphate, or TRIS buffer.

The runtime perfusion solution can include other components to help maintain the liver and protect it against ischemia, reperfusion injury and other ill effects during perfusion. In certain exemplary embodiments these components can include hormones (e.g., insulin), vitamins (e.g., an adult multi-vitamin, such as multi-vitamin MVI-Adult), and/or steroids (e.g., dexamethasone and SoluMedrol).

In another aspect, a blood product can be provided with the runtime perfusion solution to support the liver during preservation. Exemplary suitable blood products can include whole blood, and/or one or more components thereof such as blood serum, plasma, albumin, and red blood cells. In embodiments where whole blood is used, the blood can be passed through a leukocyte and platelet depleting filter to reduce pyrogens, antibodies and/or other items that can cause inflammation in the organ. Thus, in some embodiments, the perfusion fluid employs whole blood that has been at least partially depleted of leukocytes and/or whole blood that has been at least partially depleted of platelets.

The perfusion fluid comprising the blood product and the runtime perfusion solution can be provided at a physiological temperature and maintained thereabout throughout perfusion and recirculation. As used herein, "physiological temperature" is referred to as temperatures between about 25° C. and about 37° C., for example, between about 30° C. and about 37° C., such as between about 34° C. and about 37° C.

Other components or additives can be added to the runtime perfusion solution, including, for example, adenosine, magnesium, phosphate, calcium, and/or sources thereof. In some embodiments, additional components are provided to assist the liver in conducting its metabolism during perfusion. These components include, for example, forms of adenosine, which can be used for ATP synthesis, for maintaining endothelial function, and/or for attenuating ischemia and/or reperfusion injury. Components can also include other nucleosides, such as guanosine, thymidine (5-Me-uridine), cytidine, and uridine, as well as other naturally and chemically modified nucleosides including nucleotides thereof. According to some embodiments, a magnesium ion source is provided with a phosphate source, and in certain embodiments, with adenosine to further enhance ATP synthesis within the cells of the perfused liver. A plurality of amino acids can also be added to support protein synthesis by the liver cells. Applicable amino acids can include, for example, any of the naturally-occurring amino acids, as well as those mentioned above.

In some embodiments, the runtime perfusion solution further comprises one or more vasodilators (e.g., a vasodilator can be used to increase or decrease vascular tone and thereby the pressure within the vessel). In some particular embodiments, the vasodilator used is Flolan® although other vasodilators can also be used.

Table 2 sets forth components that can be used in a runtime perfusion solution for preserving a liver as described herein. The runtime perfusion solution can include one or more of the components described in Table 2.

TABLE 2

| Component of Exemplary Composition for the Runtime Perfusion Solution | |
|---|---|
| Component | Exemplary Concentration Ranges in Preservative Solution |
| Alanine | about 1 mg/L-about 10 g/L |
| Arginine | about 1 mg/L-about 10 g/L |
| Asparagine | about 1 mg/L-about 10 g/L |
| Aspartic Acid | about 1 mg/L-about 10 g/L |
| Cysteine | about 1 mg/L-about 10 g/L |
| Cystine | about 1 mg/L-about 10 g/L |
| Glutamic Acid | about 1 mg/L-about 10 g/L |
| Glutamine | about 1 mg/L-about 10 g/L |
| Glycine | about 1 mg/L-about 10 g/L |
| Histidine | about 1 mg/L-about 10 g/L |
| Hydroxyproline | about 1 mg/L-about 10 g/L |
| Isoleucine | about 1 mg/L-about 10 g/L |
| Leucine | about 1 mg/L-about 10 g/L |
| Lysine | about 1 mg/L-about 10 g/L |
| Methionine | about 1 mg/L-about 10 g/L |
| Phenylalanine | about 1 mg/L-about 10 g/L |
| Proline | about 1 mg/L-about 10 g/L |
| Serine | about 1 mg/L-about 10 g/L |
| Threonine | about 1 mg/L-about 10 g/L |
| Tryptophan | about 1 mg/L-about 10 g/L |
| Tyrosine | about 1 mg/L-about 10 g/L |
| Valine | about 1 mg/L-about 10 g/L |
| Adenine | about 1 mg/L-about 10 g/L |
| ATP | about 10 ug/L-about 100 g/L |
| Adenylic Acid | about 10 ug/L-about 100 g/L |

TABLE 2-continued

Component of Exemplary Composition
for the Runtime Perfusion Solution

| Component | Exemplary Concentration Ranges in Preservative Solution |
|---|---|
| ADP | about 10 ug/L-about 100 g/L |
| AMP | about 10 ug/L-about 100 g/L |
| Ascorbic Acid | about 1 ug/L-about 10 g/L |
| D-Biotin | about 1 ug/L-about 10 g/L |
| Vitamin D-12 | about 1 ug/L-about 10 g/L |
| Cholesterol | about 1 ug/L-about 10 g/L |
| Dextrose (Glucose) | about 1 g/L-about 150 g/L |
| Multi-vitamin Adult | about 1 mg/L-about 20 mg/L or 1 unit vial |
| Epinephrine | about 1 ug/L-about 1 g/L |
| Folic Acid | about 1 ug/L-about 10 g/L |
| Glutathione | about 1 ug/L-about 10 g/L |
| Guanine | about 1 ug/L-about 10 g/L |
| Inositol | about 1 g/L-about 100 g/L |
| Riboflavin | about 1 ug/L-about 10 g/L |
| Ribose | about 1 ug/L-about 10 g/L |
| Thiamine | about 1 mg/L-about 10 g/L |
| Uracil | about 1 mg/L-about 10 g/L |
| Calcium Chloride | about 1 mg/L-about 100 g/L |
| NaHCO$_3$ | about 1 mg/L-about 100 g/L |
| Magnesium sulfate | about 1 mg/L-about 100 g/L |
| Potassium chloride | about 1 mg/L-about 100 g/L |
| Sodium glycerophosphate | about 1 mg/L-about 100 g/L |
| Sodium Chloride | about 1 mg/L-about 100 g/L |
| Sodium Phosphate | about 1 mg/L-about 100 g/L |
| Insulin | about 1 IU-about 150 IU |
| Serum albumin | about 1 g/L-about 100 g/L |
| Pyruvate | about 1 mg/L-about 100 g/L |
| Coenzyme A | about 1 ug/L-about 10 g/L |
| Serum | about 1 ml/L-about 100 ml/L |
| Heparin | about 500 U/L-about 1500 U/L |
| Solumedrol | about 200 mg/L-about 500 mg/L |
| Dexamethasone | about 1 mg/L-about 1 g/L |
| FAD | about 1 ug/L-about 10 g/L |
| NADP | about 1 ug/L-about 10 g/L |
| guanosine | about 1 mg/L-about 10 g/L |
| GTP | about 10 ug/L-about 100 g/L |
| GDP | about 10 ug/L-about 100 g/L |
| GMP | about 10 ug/L-about 100 g/L |

Table 3 sets forth components that can be used in an exemplary runtime perfusion solution. The amounts provided in Table 3 describe preferred amounts relative to other components in the table and can be scaled to provide compositions of sufficient quantity. In some embodiments, the amounts listed in Table 3 can vary by ± about 10% and still be used in the solutions described herein.

TABLE 3

Components of Exemplary Runtime
Perfusion Solution

| Component | Amount |
|---|---|
| Calcium Chloride dihydrate | About 2100 mg-About 2600 mg |
| Glycine | About 315 mg-About 385 mg |
| L-Alanine | About 150 mg-About 200 mg |
| L-Arginine | About 600 mg-About 800 mg |
| L-Aspartic Acid | About 220 mg-About 270 mg |
| L-Glutamic Acid | About 230 mg-About 290 mg |
| L-Histidine | About 200 mg-About 250 mg |
| L-Isoleucine | About 100 mg about 130 mg |
| L-Leucine | About 300 mg-About 380 mg |
| L-Methionine | About 50 mg-About 65 mg |
| L-Phenylalanine | About 45 mg-About 60 mg |
| L-Proline | About 110 mg-About 140 mg |
| L-Serine | About 80 mg-About 105 mg |
| L-Thereonine | About 60 mg-About 80 mg |
| L-Tryptophan | About 30 mg-About 40 mg |
| L-Tyrosine | About 80 mg-About 110 mg |

TABLE 3-continued

Components of Exemplary Runtime
Perfusion Solution

| Component | Amount |
|---|---|
| L-Valine | About 150 mg-About 190 mg |
| Lysine Acetate | About 200 mg-About 250 mg |
| Magnesium Sulfate Heptahydrate | About 350 mg-About 450 mg |
| Potassium Chloride | About 15 mg-About 25 mg |
| Sodium Chloride | About 1500 mg-About 2000 mg |
| Dextrose | About 25 gm-About 120 gm |
| Epinephrine | About 0.25 mg-About 1.0 mg |
| Insulin | About 75 Units-About 150 Units |
| MVI-Adult | 1 unit vial |
| SoluMedrol | About 200 mg-500 mg |
| Sodium Bicarbonate | About 10-25 mEq |

In the exemplary embodiment of a runtime perfusion solution, the components in Table 3 can be combined in the relative amounts listed therein per about 1 L of aqueous fluid to form the runtime perfusion solution. In some embodiments, the quantity of aqueous fluid in the runtime perfusion solution can vary ±about 10%. The pH of the runtime perfusion solution can be adjusted to be between about 7.0 and about 8.0, for example about 7.3 and about 7.6. The runtime perfusion solution can be sterilized, for example by autoclaving, to provide for improved purity.

Table 4 sets forth another exemplary runtime perfusion solution, comprising a tissue culture media having the components identified in Table 4 and combined with an aqueous fluid, which can be used in the perfusion fluid as described herein. The amounts of components listed in Table 4 are relative to each other and to the quantity of aqueous solution used. In some embodiments, about 500 mL of aqueous fluid is used. In some embodiments, the quantity of aqueous solution can vary ± about 10%. The component amounts and the quantity of aqueous solution can be scaled as appropriate for use. The pH of the runtime perfusion solution, in this embodiment, can be adjusted to be about 7.0 to about 8.0, for example about 7.3 to about 7.6.

TABLE 4

Composition of Another Exemplary Runtime
Perfusion Solution (about 500 mL aqueous solution)

| Tissue Culture Component | Amount | Specification |
|---|---|---|
| Calcium Chloride dihydrate | 2400 mg | ±about 10% |
| Glycine | 350 mg | ±about 10% |
| L-Alanine | 174 mg | ±about 10% |
| L-Arginine | 700 mg | ±about 10% |
| L-Aspartic Acid | 245 mg | ±about 10% |
| L-Glutamic Acid | 258 mg | ±about 10% |
| L-Histidine | 225 mg | ±about 10% |
| L-Isoleucine | 115.5 mg | ±about 10% |
| L-Leucine | 343 mg | ±about 10% |
| L-Methionine | 59 mg | ±about 10% |
| L-Phenylalanine | 52 mg | ±about 10% |
| L-Proline | 126 mg | ±about 10% |
| L-Serine | 93 mg | ±about 10% |
| L-Thereonine | 70 mg | ±about 10% |
| L-Tryptophan | 35 mg | ±about 10% |
| L-Tyrosine | 92 mg | ±about 10% |

TABLE 4-continued

Composition of Another Exemplary Runtime
Perfusion Solution (about 500 mL aqueous solution)

| Tissue Culture Component | Amount | Specification |
|---|---|---|
| L-Valine | 171.5 mg | ±about 10% |
| Lysine Acetate | 225 mg | ±about 10% |
| Magnesium Sulfate Heptahydrate | 400 mg | ±about 10% |
| Potassium Chloride | 20 mg | ±about 10% |
| Sodium Chloride | 1750 mg | ±about 10% |

Since amino acids are the building blocks of proteins, the unique characteristics of each amino acid impart certain important properties on a protein such as the ability to provide structure and to catalyze biochemical reactions. The selection and concentrations of the amino acids provided in the runtime perfusion solutions can provide support of normal physiologic functions such as metabolism of sugars to provide or store energy, regulation of protein metabolism, transport of minerals, synthesis of nucleic acids (DNA and RNA), regulation of blood sugar and support of electrical activity, in addition to providing protein structure. Additionally, the concentrations of specific amino acids found in the runtime perfusion solution can be used to predictably stabilize the pH of the runtime perfusion solution.

In certain embodiments, in order to prevent the blood used as part of the perfusion fluid for preserving the liver on the organ care system 600 from clotting during preservation, anti-clotting agents can be added to the runtime perfusion solution as additives. Non-limiting examples of anti-clotting agents include heparin. In some embodiments, heparin can be included in a sufficient amount to prevent clotting for 500-600 seconds, although other times are possible.

In certain embodiments, the runtime perfusion solution includes a plurality of amino acids. In certain embodiments, the runtime perfusion solution includes electrolytes, such as calcium and magnesium.

In one embodiment, a runtime perfusion solution includes one or more amino acids, and one or more carbohydrates, such as glucose or dextrose. The runtime perfusion solution can also have additives, such as those described herein, administered at the point of use just prior to infusion into the liver perfusion system. For example, additional additives that can be included with the solution or added at the point of use by the user include hormones and steroids, such as dexamethasone and insulin, as well as vitamins, such as an adult multi-vitamin, for example adult multivitamins for infusion, such as MVI-Adult. Additional small molecules and large bio-molecules can also be included with the runtime perfusion solution or added at the point of use by the user, including therapeutics and/or components typically associated with blood or blood plasma, such as albumin.

In some embodiments, therapeutics can be added either before or during perfusion of the liver. The therapeutics can also be added directly to the system independently from the runtime perfusion solution, before or during perfusion of the organ.

With further reference to Table 3 or 4, certain components used in the exemplary runtime perfusion solution are molecules, such as small organic molecules or large bio-molecules, that would be inactivated, for example through decomposition or denaturing, if passed through sterilization. Thus, these components can be prepared separately from the remaining components of the runtime perfusion solution. The separate preparation involves separately purifying each component through known techniques. The remaining components of the runtime perfusion solution are sterilized, for example through an autoclave, then combined with the biological components.

Table 5 lists certain biological components that can be separately purified and added to the solutions (runtime perfusion solution and/or priming solution) described herein after sterilization, according to this two-step process. These additional or supplemental components can be added to runtime perfusion solution, the priming solution or a combination thereof individually, in various combinations, all at once as a composition, or as a combined solution. For example, in certain embodiments, the insulin, and MVI-Adult, listed in Table 5, are added to the runtime perfusion solution. In another example, the SoluMedrol and the sodium bicarbonate, listed in Table 5, are added to the priming solution. The additional components can also be combined in one or more combinations or all together and placed in solution before being added to runtime perfusion solution, and/or the priming solution. In some embodiments, the additional components are added directly to the perfusion fluid. The component amounts listed in Table 5 are relative to each other and/or to the amounts of components listed in one or more of Tables 1-4 as well as the amount of aqueous solution used in preparing the runtime perfusion solution, and/or the priming solution and can be scaled as appropriate for the amount of solution required.

TABLE 5

Exemplary Biological Components
Added to Solutions Prior to Use

| Component | Amount | Type | Specification |
|---|---|---|---|
| Insulin | about 100 Units | Hormone | ±about 10% |
| MVI-Adult | 1 mL unit vial | Vitamin | ±about 10% |
| SoluMedrol | About 250 mg | Steroid | ±about 10% |
| Sodium Bicarbonate | About 20 mEq | Buffer | ±about 10% |

In one embodiment, a composition for use in a runtime perfusion solution is provided comprising one or more carbohydrates, one or more organ stimulants, and a plurality of amino acids. The composition can also include other substances, such as those used in solutions described herein.

In another embodiment, a system for perfusing a liver, is provided comprising a liver and a substantially cell-free composition, comprising one or more carbohydrates, one or more organ stimulants, and a plurality of amino acids. The substantially cell-free composition can include systems that are substantially free from cellular matter; in particular, systems that are not derived from cells. For example, substantially cell-free composition can include compositions and solutions prepared from non-cellular sources.

In another aspect, the runtime perfusion solution and/or the priming solution can be provided in the form of a kit that includes one or more organ maintenance solutions. An exemplary runtime perfusion solution can include components identified above in one or more fluid solutions for use in a liver perfusion fluid. In certain embodiments, the runtime perfusion solution can include multiple solutions which, in various combinations, provide the runtime perfusion solution. Alternatively, the kit can include dry components that can be regenerated in a fluid to form one or more runtime perfusion solution or priming solution. The kit can also comprise components from the runtime perfusion solution or priming solution in one or more concentrated solutions which, on dilution, provide a preservation, nutritional, and/or supplemental solution as described herein. The kit can also include a priming solution.

In certain embodiments, the kit is provided in a single package, wherein the kit includes one or more solutions (or components necessary to formulate the one or more solutions by mixing with an appropriate fluid), and instructions for sterilization, flow and temperature control during perfusion and use and other information necessary or appropriate to apply the kit to organ perfusion. In certain embodiments, a kit is provided with only a single runtime perfusion solution (or set of dry components for use in a solution upon mixing with an appropriate fluid), and along with a set of instructions and other information or materials necessary or useful to operate the runtime perfusion solution or priming solution.

In certain embodiments, the runtime perfusion solution is a singular solution. In other embodiments, the runtime perfusion solution can include a main runtime perfusion solution and one or more nutritional supplement solutions. The nutritional supplement solution can contain any compound or biological component suitable for the runtime perfusion describe above. For instance, the nutritional supplement solution can contain one or more components illustrated in Tables 1-5 above. Additionally, Table 6 sets forth components that are used in an exemplary nutritional supplement solution. In some embodiments, the nutritional solution further includes sodium glycerol phosphate. The amount of components in Table 6 is relative to the amount of aqueous solvent employed in the solution (about 500 mL) and may be scaled as appropriate. In some embodiments, the quantity of aqueous solvent varies ±about 10%. In these embodiments when a main runtime solution and one or more nutritional solutions are used, these solutions can be separately connected to the circulation system of the organ care system 600 and control separately. Thus, when one or more components in a nutritional solution need to be adjusted, the operator may remake this particular nutritional solution with different concentration for these components or adjust only the flow rate and/or pressure for this nutritional solution without affecting the flow rate and/or pressure for the main runtime perfusion solution and other nutritional solutions.

TABLE 6

Components of Exemplary Nutritional Solution (about 500 mL)

| Component | Amount | Specification |
|---|---|---|
| Dextrose | 40 g. | ±about 10%. |

In one embodiment, the runtime perfusion solution and the priming solution have the identical composition which is described in any one of Tables 1-6 or a combination thereof.

In some embodiments, the perfusion liquid comprises 1200-1500 ml of pRBCs, 400 ml of 25% Albumin, 700 ml of PlasmaLyte, antibiotic (gram positive and gram negative) 1 g Cefazoline (or equivalent antibiotic) and 100 mg Cipro (or equivalent antibiotic), 500 mg of Solu-Medrol (or equivalent anti-inflammatory), 50 mmol Hco3, multivitamin, and 10000 unit of Heparin administered at 3 hr and 6 hr PT.

In certain specific embodiments, the perfusion fluid comprises the liver donor's blood, or packed red blood cells (RBCs), or packed RBCs with fresh frozen plasma, and the runtime perfusion solution containing one or more components selected form the group consisting of human albumin or dextran. In certain specific embodiments, the perfusion fluid comprises the liver donor's blood, or packed RBCs or packed RBCs with fresh frozen plasma, and the runtime perfusion solution containing one or more components selected form the group consisting of human albumin, dextran, and one or more electrolyte.

E. Final-Flush Solution

After the suitable recipient of the liver transplant is identified and before the liver is removed from the organ care system 600, the liver organ can be subjected to another flush process by a flush solution. This flush solution has the similar function as the initial flush solution, which is to remove the residual blood therein and stabilize the liver. This flush solution is referred to herein as the final flush solution. In some embodiments, the final flush solution has similar or identical compositions as the initial flush solution described above. The main components of the final flush solution can include electrolytes (e.g., plasmalyte) and buffering agents described herein. In certain embodiments, one or more commercially-available preservation solutions used in hypothermal organ transplant are used as the final flush solution. After the liver is subjected to the final flush and cooled according to one more embodiments described herein, the liver can be removed from the organ care system 600 for implantation into a recipient.

VI. METHODS

Exemplary methods to use the organ care system 600 disclosed herein are now described in more detail. FIG. 29 is a flow diagram 5000 depicting exemplary and non-limiting methodologies for harvesting the donor liver and cannulating it into the organ care system 600 described herein. The process 5000 shown in FIG. 29 is exemplary only and can be modified. For example, the stages described therein can be altered, changed, rearranged, and/or omitted.

A. Harvesting Organ

Figure 29:
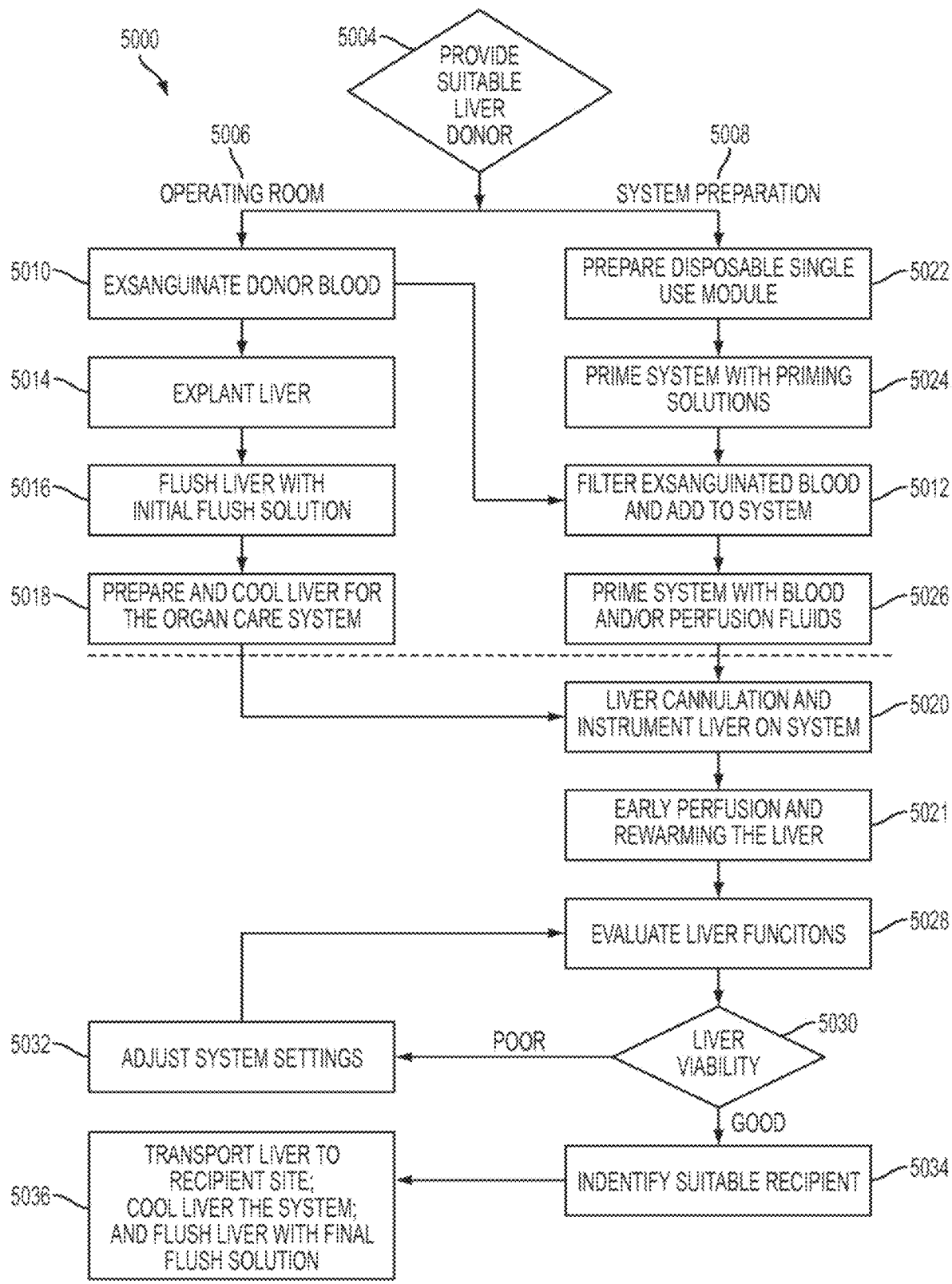
FIG. 29 shows an exemplary process that can be used in embodiments of an organ care system.

As shown in FIG. 29, the process of obtaining and preparing liver for cannulation and transport can begin by providing a suitable liver donor (Stage 5004). The system 600 can be brought to a donor location, whereupon the process of receiving and preparing the donor liver for cannulation and preservation can proceed down pathways 5006 and 5008. The pathway 5006 principally involves preparing the donor liver for preservation, while the pathway 5008 principally involves preparing the system to receive and preserved the liver, and then transport the liver via the organ care system 600 to the recipient site.

As shown in FIG. 29, the first pathway 5006 can include exsanguinating the donor blood (Stage 5010), explanting the liver (Stage 5014), flushing the liver with initial flush solution (Stage 5016), and preparing and cooling the liver for the system (Stage 5018). In particular, in the exsanguination stage 5010, the donor's blood can be partially and/or wholly removed and set aside so it can be used to as the blood product in the perfusion liquid to perfuse the liver during preservation on the system. This stage can be performed by inserting a catheter into either the arterial or venous vasculature of the donor to allow the donor's blood to flow out of the donor and be collected into a blood collection bag. The donor's blood is allowed to flow out until the necessary amount of blood is collected, typically 1.0-2.5 liters, whereupon the catheter is removed. The blood extracted through exsanguination is then optionally filtered and added to a fluid reservoir of the system in preparation for use with the system. Alternatively, the blood can be exsanguinated from the donor and filtered for leukocytes and platelets in a single step that uses an apparatus having a filter integrated with the cannula and blood collection bag. An example of such a filter is a Pall BC2B filter. Alternatively, a blood product can be used instead of the donor's blood in the perfusion liquid (not shown in FIG. 29).

After the donor's blood is exsanguinated, the donor liver can be harvested (Stage 5014). Any standard liver harvesting method known in the art can be used. During liver harvesting, the liver vessels including hepatic artery, portal vein, inferior vena cava (IVC), and bile duct are prepared properly and severed, with sufficient vessel length remained for cannulation (e.g., standard practice, suitable for human or animal transplant). In certain embodiments, the gall bladder is removed during the liver harvesting and care is taken to preserve the common bile duct intact to maintain stable bile fluid flow during the liver preservation. After the liver is removed in hospital settings, it is often flushed (e.g., donor flush) or placed in saline solutions. In stage 5016, the harvested liver can then be flushed by an initial flush solution to remove any residual blood and/or donor flush solution to improve the stability of the liver. An exemplary composition of the initial flush solution is described above in detail.

After the liver is harvested and prior to its placement on the organ care system 600, the liver can be cooled down (Stage 5018) to reduce or halt its metabolic functions to avoid damage to the liver which otherwise can occur during transportation or placement of the liver into the organ care system 600. In certain embodiments, the liver is cooled to about 4° C. to 10° C., 5° C. to 9° C., 5° C. to 8° C., 4° C., 5° C., 6° C., 7° C., 8° C., 9° C., or 10° C., or a temperature within any range bounded by the value described herein. The liver can be cooled by ice or refrigeration. Other temperature ranges below 4° C. and above 10° C. are also possible. Alternatively, the initial flush solution can be cooled first and then used to flush the liver to cool the liver. Thus, in these alternative embodiments, Stages 5016 and 5018 can be performed simultaneously. Once the liver is prepared and cooled to a proper temperature, it can be ready to be placed onto the liver care system 600.

With continued reference to FIG. 29, during the preparation of the liver via path 5006, the system can be prepared through the stages of path 5008 so it is primed and waiting to receive the liver for cannulation and preservation as soon as the liver is prepared and cooled. By quickly transferring the liver from the donor to the system, and subsequently perfusing the liver with the perfusion fluid, a medical operator can minimize the amount of time the liver is deprived of oxygen and other nutrients, and thus reduce ischemia and other ill effects that arise during current organ care techniques. In certain embodiments, the amount of time between infusing the liver with the initial flush solution and beginning flow of the perfusion fluid through the liver via the organ care system 600 is less than about 15 minutes. In other illustrative embodiments, the between-time is less than about ½ hour, less than about 1 hour, less than about 2 hours, or even less than about 3 hours. Similarly, the time between transplanting the liver into the organ care system 600 and bringing the liver to a near physiological temperature (e.g., between about 34° C. and about 37° C.) can occurs within a brief period of time so as to reduce ischemia within the liver tissues. In some illustrative embodiments, the period of time is less than about 5 minutes, while in other applications it can be less than about ½ hour, less than about 1 hour, less than about 2 hours, or even less than about 3 hours. Stated differently, when the cooled liver is first placed into the organ care system 600, the temperature of the liver can gradually be raised to the desired temperature over a predetermined amount of time to reduce any potential damage that could result of a sudden temperature change.

As shown in FIG. 29, the system can be prepared in pathway 5008 through a series of stages, which include preparing the single use module (stage 5022), priming the system with priming solution (stage 5024), filtering the blood from the donor and adding it to the system, e.g., at a reservoir of the system (stage 5012), optionally priming the system with blood and/or perfusion fluids, and connecting the liver into the system (stage 5020). In particular, the step 5022 of preparing the single use module includes assembling the disposable single use module described herein (e.g., single use module 634). After the single use module is assembled, or provided in the appropriate assembly, it is then inserted into and connected to the multiple use module (e.g., multiple use module 650) through the process described herein.

Specifically, in stage 5024, the liver care system 600 can be first primed with a priming solution, the composition of which is described more fully above. In certain embodiments, to aid in priming, the system can provide an organ bypass conduit installed into the organ chamber assembly. For example, in certain specific embodiments, the bypass conduit includes three segments attached to the hepatic artery cannulation interface, the portal vein cannulation interface, and the inferior vena cava (IVC) cannulation interface (if present). Using the bypass conduit attached/cannulated into the liver chamber assembly, an operator can cause the system to circulate the perfusion fluid through all of the paths used during actual operation. This can enable the system to be thoroughly tested and primed prior to cannulating the liver into place.

In stage 5012, blood from the donor can be filtered and added to the system, e.g., in the reservoir 160. The filtering process can help reduce the inflammatory process through the complete or partial removal of leukocytes and platelets. Additionally, the donor blood can be used to optionally prime the system as described above and/or mixed with one or more priming solution or runtime perfusion solution to further prime the system as described above. Additionally, the blood and the run time perfusion solution can be mixed together to form the perfusion fluid used later for infusing and preserving the liver. In stage 5026, the system can be primed with the blood and/or the perfusion fluid by activating the pump and by pumping the blood and/or the perfusion fluid through the system with the bypass conduit (described above) in place. As the perfusion fluid circulates through the system in priming stage 5026, it can optionally be warmed to the desired temperature (e.g., normothermic) as it passes through a heater assembly of the system. Thus, prior to cannulating the harvested liver, the system can be primed by circulating the priming solution, exsanguinated donor blood, and/or the mixture of the two (e.g., the perfusion fluid) through the system to heat, oxygenate and/or filter it. Nutrients, preservatives, and/or other therapeutics can also be provided during priming by addition of the components to the priming solution. During priming, various parameters can also be initialized and calibrated via the operator interface during priming. Once primed and running appropriately, the pump flow can be reduced or cycled off, the bypass conduit can be removed from the organ chamber assembly, and the liver can then be cannulated into the organ chamber assembly.

1. Cannulation

In stage 5020, the liver, while cooled as described above, can be cannulated and placed onto the organ care system

600. During liver preservation, the perfusion fluid can flow into the liver through the hepatic artery and portal vein and flow out of the liver through the inferior vena cava (IVC). Thus, the hepatic artery, inferior vena cava (IVC), and portal vein can be correspondingly cannulated and connected with the relevant flow path of the liver care system 600 to ensure proper perfusion through the liver (as described above). In some embodiments, the IVC is not cannulated and free drains. The bile duct can also be cannulated as well and connected to a reservoir to collect the bile produced by the liver (e.g., bile bag 187).

The system 600 described herein can be designed to be compatible with the human hepatic artery anatomy. In the majority of the patients, the hepatic artery is the only major artery of the liver and thus the organ care system 600 can a single-port cannula to be connected with the hepatic artery. In certain cases (i.e., about 10-20% of the patient population with genetic difference), however, the donor of the liver also has an accessory hepatic artery in addition to the main hepatic artery. Thus, in certain embodiments, the liver care system 600 provides a dual-port cannula configuration (e.g., cannula 2642) so that both the main and accessory hepatic arteries can be cannulated and connected to the same perfusion fluid flow path. In certain specific embodiments, the dual-port cannula has a Y shape. Any other suitable shapes or designs for the dual-port cannula are contemplated.

In certain embodiments, the cannula can be designed to be straight to reduce unnecessary flow pressure drop along the cannula flow path. In other embodiments, the cannula can be designed to be curved or angled as required by the shape, size, or geometry of the organ care system 600's other components. In some specific embodiments, the cannula is designed with a proper shape, e.g., straight, angled, or a combination thereof, so that the overall flow pressure within the cannula is maintained at a desired level that mimics physiologic conditions.

2. Instrumentation

The liver can then be instrumented on the organ care system 600 (Stage 5020) and more specifically, in the organ chamber 104. Care should be taken to avoid excessive movement of the liver during instrumentation to reduce injuries to the liver. As described above in greater detail, the liver chamber can be specially designed to maintain the liver in a stable position that reduces its movement.

B. Preservation/Transport

1. Controlled Early Perfusion and Rewarming

In certain embodiments, once the liver is instrumented on the organ care system 600 with proper cannulation of the vessels, the liver can be subjected to an early perfusion and/or rewarm process to restore the liver to a normothermic temperature (34-37° C.) (Stage 5021). In some embodiments, the organ chamber can contain heating circuit to warm the previously cooled liver to normothermic temperature gradually over a predetermined amount of time. In other embodiments, the initial perfusion fluid (for early perfusion) can be heated to close to or to the normothermic temperature (e.g., 34-37° C.) and perfuse and warm the liver at the same time. As described herein, the liver preserved on the organ care system 600 can be kept at conditions near to physiological state, which includes normothermic temperatures, to maintain the liver's normal biological functions.

After the liver is instrumented onto the system and warmed to normothermic temperature, the pump within the organ care system 600 (e.g., pump 106) can be adjusted to pump perfusion fluid through the liver, e.g., into the hepatic artery and portal vein. The perfusion fluid exiting from the IVC (or hepatic veins, depending on how the liver was harvested) can be collected and subjected to various treatments including re-oxygenation and carbon dioxide removal. Various nutrients can be added to the spent perfusion fluid to increase the nutrient concentrations to required value for recirculation.

In some embodiments, during the liver perfusion on the organ care system 600, the in-flow pressures within the hepatic artery and the portal vein are carefully controlled to ensure the proper delivery of nutrients to the liver to maintain its functions. In some embodiments, the flow pressure within the hepatic artery can be, for example, 50-120 mmHg and the flow pressure in the portal vein can be 5-15 mmHg, although pressures outside these ranges are possible such as 1, 2, 20, 25, 30, 35, 40, 45, 50, 60, 70, 80, 90, 100, 110, 120 mmHg, or a pressure in any range bounded by the values noted here. In some embodiments, the flow rate within the hepatic artery and the portal vein can be maintained at about or more than 0.25-1.0 L/min, and 0.75-2.0 L/min, respectively, or at any range bounded by any of the values noted here. In some embodiments, the flow rate within the hepatic artery and the portal vein can be maintained at about 0.25, 0.30, 0.35, 0.40, 0.45, 0.50, 0.55, 0.60, 0.65, 0.70, 0.75, 0.80, 0.85, 0.90, 0.95, 1.00, 1.10, 1.20, 1.30, 1.40, 1.50, 1.60, 1.70, 1.80, 1.90, 2.1, 2.2, 2.3, 2.4, 2.5 L/min or a rate in any range bounded by the values noted here.

In some embodiments, the fluid flow, e.g., flow rate and/or flow pressure, within the organ care system 600 and hepatic artery and the portal vein can be controlled chemically and/or mechanically. The mechanical or the chemical control of the flow can be achieved automatically or manually.

2. Manual/Automatic Control

The mechanical control of the fluid flow within the organ care system 600 and hepatic artery and the portal vein is first described. In some embodiments, the flow pressure or rate within the flow path of the organ care system 600 can be measured by pressure sensors or rate sensors built in the flow path or in other locations of the systems. Similarly, pressure or rate sensors can be located in the cannulas for the hepatic artery and/or the portal vein, or in the connectors connecting the cannulas to these vessels. The pressure or rate sensors can provide the operator with readings regarding the flow within the flow path and/or within the hepatic artery and/or the portal vein. Any other pressure monitoring methods or techniques known in the art are contemplated. If the pressure or rate reading is deviating from the desired values, the operator can manually adjust the flow pump to increase or decrease the pumping pressure and, thereby, the flow rate for the perfusion fluid. Alternatively, the organ care system 600 can contain a flow control module which has a programmable desired value for flow rate and/or flow pressure and automatically adjusts the pumping pressure of the perfusion fluid and thereby also adjusting the flow rate when the flow pressure and/or rate are deviating from the desired values. Manual and/or automatic control is described more fully above.

3. Chemical Control

In other embodiments, the pressure and/or fluid flow within the organ care system 600 and hepatic artery and the portal vein can be controlled chemically. In some specific embodiments, the pressure can be controlled or increased by using one or more vasodilators (e.g., a vasodilator can be used to increase or decrease vascular tone and thereby the pressure within the vessel). Vasodilation refers to the widening of blood vessels resulting from relaxation of smooth muscle cells within the vessel walls. When blood vessels dilate, the flow of perfusion fluid is increased due to a decrease in vascular resistance. Any vasodilators known in the art can be used to dilate the hepatic artery and/or the portal vein to increase the fluid flow rate therein. In some particular embodiments, the vasodilator used is Flolan®. In particular, when the fluid flow is insufficient as indicated by low flow pressure or rate, and/or by any of the liver-viability evaluation techniques described in greater detail below, the operator can manually add vasodilator into the system's flow module or to the perfusion fluid to increase the fluid flow rate. Alternatively, the organ care system 600 can contain a flow control module which automatically adds one more vasodilators into the flow path or perfusion fluid to increase the flow rate. The amount of the vasodilator provided can be between, for example, 1-100 micrograms/hr, and more specifically between 1-5 micrograms/hr. These ranges are exemplary only and any range falling within 0-100 micrograms an hour can be used.

Some embodiments of the foregoing can be adapted for use with a liver that is being preserved in the system 600. For example, in this embodiment, an algorithm can be used to allow closed loop control of the hepatic artery pressure (HAP). The algorithm used can be a proportional-integral-derivative controller (PID controller). A PID controller can calculate how far away the HAP is from the desired set point and attempt to minimize the error by increasing or decreasing the vasodilator (e.g., Flolan®) flow rate.

Accordingly, in some embodiments, the controller 150 (or other part of the system) can determine the error (e.g., how far the HAP is from the user set-point) and adjust the vasodilator flow rate in an attempt to make the error 0. In embodiments where the algorithm runs once a second the adjustments can be very small. Small, frequent adjustments can help to stabilize the control by ensuring that any noise in the system does not result in dramatic changes in vasodilator flow rate. The algorithm can be trying to get the HAP to the user set point. This means that when the HAP is above the set point the algorithm can increase the vasodilator solution flow rate until the HAP reaches the user set point. If the HAP is below the user set point the algorithm can decrease the vasodilator solution flow rate until the HAP reaches the user set point.

In some embodiments, the PID control algorithm does not decrease the vasodilator flow rate until it has gone under the set point. This can result in undershooting the target pressure. To help offset this, some embodiments can use a virtual set point, which is +3 mmHg (or other value) above the user set point. This can be user definable or hard-programmed. When the HAP is higher than 7 mmHg above the user set point the software can enable the virtual set point and attempt to regulate the HAP to +3 mmHg above the user set point. This can allow for some undershoot of the virtual set point. Once the HAP has stabilized at the virtual set point the software can then regulate the HAP to the user set point. This approach can help "catch" the HAP as it is falling without incurring as dramatic of an undershoot.

Figure 28:
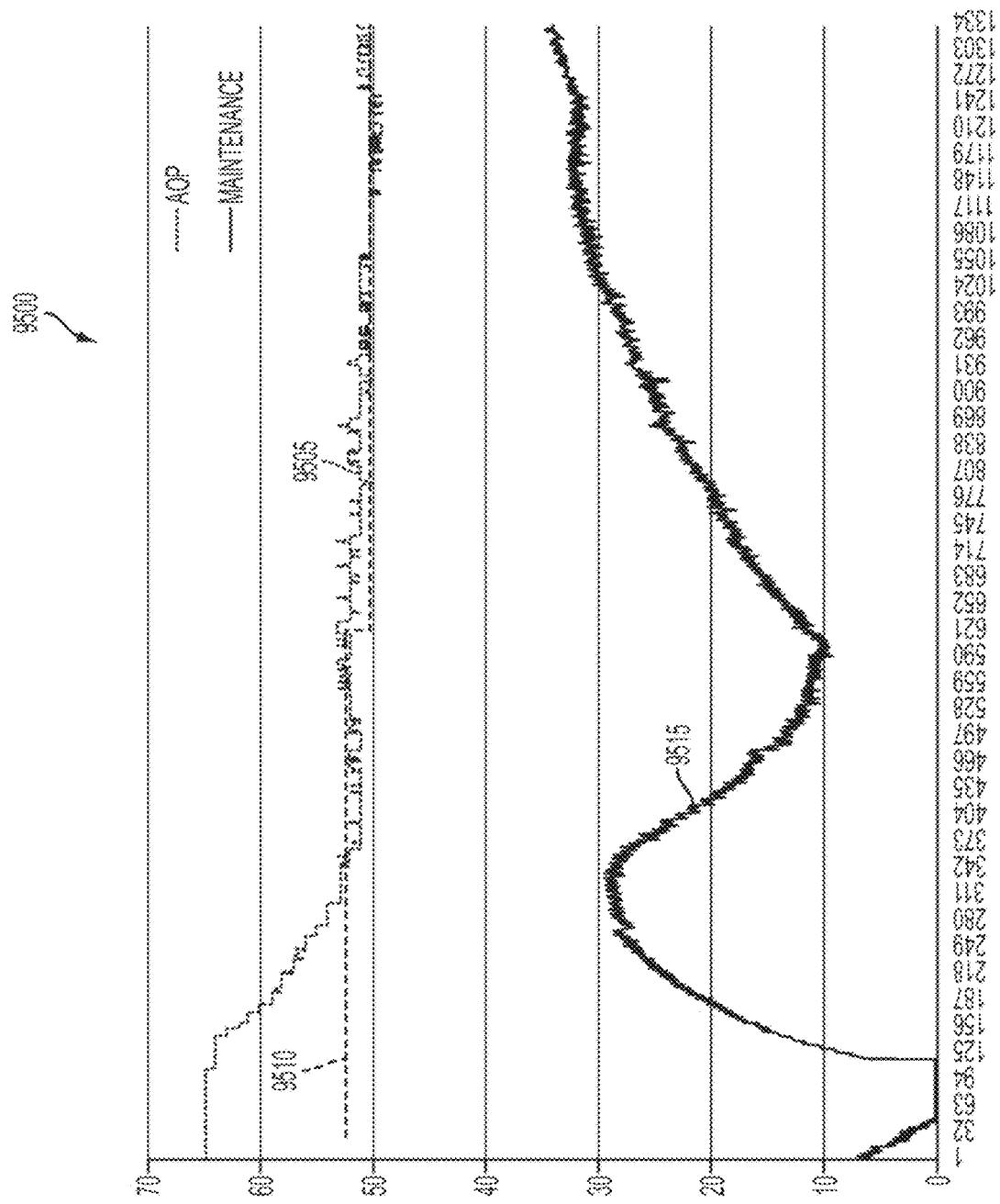
FIG. 28 shows exemplary test results from an embodiment of an organ care system.

Referring to FIG. 28, a graphical representation of the foregoing is shown with respect to ascending aortic pressure in a heart system. In FIG. 28, an exemplary graph 9500 of the foregoing is shown. The image shows the AOP (e.g., 9505) coming down to a virtual set point (9510), undershooting the virtual set point and then coming down softly on the user set point (50 mmHg).

Because some embodiments use a drug to control the HAP it can be beneficial to ensure that the system is not flooding the liver with vasodilator when it is not needed. To accomplish this, the system can analyze how far the HAP is from the set point and when the HAP is above the set point, the system (e.g., the solution pump 631) can add vasodilator at the standard rate. If the HAP is below the set point, the system 600 can decrease the flow rate 4 times faster than if it were adding vasodilator. This can help the system stay just above the HAP set point (e.g., about +0.5 to +1 mmHg) in the "active management" area as well as potentially helping minimize undershoot but decreasing vasodilator rate faster.

While the foregoing description has focused on the liver, the same technique can be adapted for use with the heart by substituting AOP for the HAP.

4. Assessment

During stages 5028 and 5030 the operator can evaluate the liver functions to determine liver viability for transplant (then-current or likely future viability). Illustratively, step 5028 involves evaluating liver functions by using any of the evaluation techniques described in more detail below. For instance, the operator can monitor the fluid flows, pressures, and temperatures of the system while the liver is cannulated. The operator can also monitor one or more liver function biomarkers to assess the liver status. During the evaluation step 5030, based on the data and other information obtained during testing 5028, the operator can determine whether and how to adjust the system properties (e.g., fluid flows, pressures, nutrient concentrations, oxygen concentrations, and temperatures), and whether to provide additional modes of treatment to the liver (e.g., surgeries, medications as described in more detail below). The operator can make any such adjustments in step 5032, can then repeat steps 5028 and 5030 to re-test and re-evaluate the liver and the system. In certain embodiments, the operator can also opt to perform surgical, therapeutic or other procedures on liver (described in more detail below) during the adjustment step 5032 (or at other times). For example, the operator can conduct an evaluation of the liver functions, such as for example, performing an ultrasound or other imaging test on the liver, measuring arterial and venous blood gas levels and other evaluative tests.

Thus, after or while the liver is preserved on the system, the operator can perform surgery on the liver or provide therapeutic or other treatment, such as immunosuppressive treatments, chemotherapy, genetic testing and therapies, or irradiation therapy. Because the system allows the liver to be perfused under near physiological temperature, fluid flow rate, and oxygen saturation levels, the liver can be maintained for a long period of time (e.g., for a period of at least 3 days or more, greater than at least 1 week, at least 3 weeks, or a month or more) to allow for repeated evaluation and treatment.

In some embodiments, the system allows a medical operator to evaluate the liver for compatibility with an intended recipient by identifying suitable recipient (Step 5034). For example, the operator can perform a Human Leukocyte Antigen (HLA) matching test on the liver while the liver is cannulated to the system. Such tests can require 12 hours or longer and are performed to ensure compatibility of the liver with the intended recipient. The preservation of a liver using the system described herein can allow for preservation times in excess of the time needed to complete an HLA match, potentially resulting in improved post-transplant outcomes. In the HLA matching test example, the HLA test can be performed on the liver while a preservation solution is pumping into the liver. Any other matching test known in the art is contemplated.

According to the illustrative embodiment, the testing 5028, evaluation 5030 and adjustment 5032 stages can be conducted with the system operating in normal flow mode. In normal flow mode, the operator can test the function of the liver under normal or near normal physiologic blood flow conditions. Based on the evaluation 5030, the settings of the system can be adjusted in step 5032, if necessary, to modify the flow, heating and/or other characteristics to stabilize the liver in preparation for transport to the recipient site in stage 5036. The system with the preserved liver can be transported to the recipient site at step 5036.

C. Preparation for Transplant

1. Final Flush/Cool Liver

In certain embodiments, before the liver is removed from the system 600 and/or implanted into a recipient, the liver can be flushed by a final flush solution to, for example, remove any residual blood and/or runtime perfusion solution. The composition of the final flush solution is described in detail above.

In certain embodiments, prior to the removal of the liver from the organ care system 600, the liver can be cooled again to a temperature at about 4° C. to 10° C., 5° C. to 9° C., 5° C. to 8° C., 4° C., 5° C., 6° C., 7° C., 8° C., 9° C., or 10° C., or a temperature within any range bounded by the value described herein. The liver can be cooled by contact with ice or refrigeration of the liver preservation chamber. In some embodiments, the system 600 can include a cooling unit that is configured to cool the liver directly and/or cool the fluid circulating in the system 100. The final flush solution can also be chilled first and then used to flush the liver to cool the liver. Thus, in these embodiments, the liver can be finally flushed and cooled simultaneously. Once the liver is prepared and cooled down to a proper temperature, it can be ready to be transplanted into a suitable recipient.

For example, in some embodiments, the liver is cooled and flushed while on the system 600. The user can connect a one liter bag of chilled flush solution to the flush port of the hepatic artery (e.g., port 4301) but leaves the port closed. The user connects two one liter bags of chilled flush solution to the flush port of the portal vein (e.g., port 4302) but leaves the port closed. The user connects a flush collection bag to the perfusion module to the perfusate collection port located just after the perfusion module's pump compliance chamber (e.g., port 4309). The user can then apply a standard surgical clamp to the perfusion module tubing just before the split to the hepatic artery and portal vein simultaneous with the turning off of the circulatory pump 106. The hepatic artery and portal vein flush ports can be opened so that the flush solution will enter the hepatic artery and the portal vein. The perfusate collection bag can be unclamped so that the mixture of perfusate and flush solution fills the bag rather than filling the organ chamber.

In the event that a decision is made to cool the liver at the end of preservation, then the following exemplary procedure can be used:

1. Obtain and set-up a Heater Cooler unit (placed near OCS, electrical line plugged in, power ON, water circuit controls ON, water circuit valve OFF). Do not connect Heater Cooler water lines to Liver Perfusion Module gas exchanger water lines yet.
2. Set Heater Cooler water circuit temperature to near the current liver temperature (e.g., approximately 37° C.) and allow it to reach temperature.
3. Connect Hansen quick connect equipped Heater Cooler water lines to Liver Perfusion Module oxygenator water lines.
4. Turn the heater 100 OFF.
5. Set water circuit temperature of Heater Cooler to a lower temperature than the liver but not more than 10° C. lower and open the valve of the water lines to allow flow to the Liver Perfusion Module gas exchanger 114. As the actual temperature of the perfusion fluid, as reflected on the user interface, approaches the Heater Cooler water temperature set point, adjust the Heater Cooler water temperature set point lower, but not more than 10° C. lower than the perfusate/liver temperature, in increments and keep repeating until the blood/liver have reached the desired temperature.
6. When the liver temperature has reached the desired temperature, remove the liver from the system 600.

While the foregoing has focused on final flush and cooling of a liver, a similar or identical procedure can be used when preserving other organs. For example, in some embodiments, the foregoing final flush/cooling technique can be applied to a heart and/or lung that is being preserved by the system 600.

VII. EVALUATION

In some embodiments of the disclosed subject matter, various techniques or methods to assess the viability of the liver while the liver is preserved on the organ care system 600 are provided (e.g., viability for transplant). Generally, biomarkers known in the art for evaluating liver functions, e.g., liver enzymes, and known imaging techniques can be used to evaluate the biological functions and status of the liver. Additionally, because the liver preserved on the organ care system 600 is readily accessible to the operator, techniques not easily available to the health care profession in vivo, e.g., visual observation of the liver or palpation of the liver, can also be used. Based on the evaluation results, one or more parameters of the organ care system 600, e.g., nutrients or oxygen content in the perfusion fluid or the flow rate and flow pressure of the perfusion fluid, can be adjusted to improve the viability of the liver.

In some embodiments, the perfusion parameters of the organ care system 600 can be used to evaluate the viability of the liver. Specifically, in certain embodiments, the perfusion liquid flow pressures in the cannulated hepatic artery and/or portal vein can be measured as an indicator of the liver viability. In some embodiments, a stable flow pressure in the range of 50-120 mmHg in the hepatic artery line can indicate that the preserved liver is receiving sufficient essential nutrient supply. For example, in some embodiments, a stable flow pressure of about 50, 60, 70, 80, 90, 100, 110, 120 mmHg, or a pressure in any range bounded by the values noted here can indicate that the preserved liver is receiving sufficient essential nutrient supply. A flow pressure outside this range can indicate a leak or blockage in the system, or suggest to the operator to adjust the flow pressure to ensure proper nutrient supply to the liver. In other embodiments, the perfusion liquid flow rate in the cannulated hepatic artery and/or portal vein can be measured as an indicator of the liver viability. In other embodiments, a flow rate in the range of 0.25-1 L/min for the hepatic artery can indicate that the preserved liver is receiving sufficient essential nutrient supply. For example, in some embodiments, a flow rate of about 0.25, 0.30, 0.35, 0.40, 0.45, 0.50, 0.55, 0.60, 0.65, 0.70, 0.75, 0.80, 0.85, 0.90, 0.95, 1.00 L/min or a rate in any range bounded by the values noted here for the hepatic artery can indicate that the preserved liver is receiving sufficient essential nutrient supply. A flow rate outside this range can indicate a leak or blockage in the system, or suggest to the operator to adjust the flow rate to ensure proper nutrient supply to the liver. The flow rate and pressure can be measured using the pressure and/or flow sensors described herein.

In some embodiments, visual observation or examination of the liver can be used to assess the liver viability. For instance, a pink or red color of the liver can indicate that the liver is functioning normally, while a dark or blueish color of the liver can indicate that the liver is functioning abnormally or deteriorating (e.g., is being hypoperfused). In other embodiments, palpation of the liver is used to assess its viability. When the liver feels soft and elastic, the liver is likely functioning normally. On the other hand, if liver feels tense or stiff, the liver is likely functioning abnormally or deteriorating (e.g., is being hypoperfused).

A. Bile Production

In some embodiments, because the bile duct is cannulated and connected to a reservoir of the organ care system 600, the color and amount of bile produced by the liver can be easily examined to evaluate the liver viability. In certain embodiments, black or dark green color bile can indicate normal liver function while a light or clear color of the bile can indicate that the liver is not functioning properly or deteriorating. In still other embodiments, the amount of the bile production can be used to evaluate the liver viability as well (and/or the determination that the liver is producing bile at all can be a good indicator). While any bile production can be a sign of a healthy liver, generally, the more the bile produced, the better the liver function. In certain embodiments, a bile production of from about 250 mL to 1 L, 500 mL to 1 L, 500 mL to 750 mL, 500 mL, 750, or 1 L per day or in any ranges bounded by the values noted herein suggests that the liver preserved on the organ care system 600 is functioning normally and viable.

B. Blood Gas, Liver Enzymes, and Lactate Measurements/Trends

In some embodiments, various biomarkers or compounds in the perfusion liquid can be used to evaluate the liver viability. For instance, metabolic assessment of the liver can be conducted by calculating oxygen delivery, oxygen consumption, and oxygen demand. Specifically, the amount of oxygen and carbon dioxide dissolved in the perfusion liquid can be monitored as indicators of the liver function. The concentrations of these gases in the perfusion liquid (or the blood product) before and after liver perfusion can be measured and compared. In certain specific embodiments, the concentrations of the oxygen and carbon dioxide can be measured by various sensors within the organ care system 600's flow module or subsystem.

In some embodiments, the perfusion fluid before and after liver perfusion (e.g., the perfusion fluid entering the hepatic artery and exiting the IVC) can be sampled using respective oxygen concentration (or other) sensors and the relevant concentrations of the oxygen and carbon dioxide can be measured. A significant increase of the carbon dioxide concentration in the perfusion liquid after liver perfusion, and/or a significant decrease of the oxygen concentration after the liver perfusion, can indicate that the liver is performing its oxidative metabolic functions well. On the other hand, a minor or no increase of the carbon dioxide concentration in the perfusion liquid after liver perfusion, and/or minor or no decrease of the oxygen concentration after the liver perfusion, can indicate that the liver is not performing its oxidative metabolic functions properly. The difference of $PVO_2$ and $PaO_2$ can indicate metabolically active, aerobically active metabolism, oxygen consumption.

In some embodiments, liver function blood test (LEFTs) can be conducted to assess the liver viability. Specifically, in some embodiments, aspartate aminotransferase (AST), alanine aminotransferase (ALT), alkaline phosphates, albumin, bilirubin (direct and indirect) can be measured to evaluate the liver functions. In other embodiments, the fibrinogen blood level can be measured as well as an indication of the liver cells' ability to produce clotting factors.

AST, ALT are liver enzymes and are well-accepted clinical liver biomarkers used for assessing the liver functions and/or suitability for transplant. However, the measurements of AST and ALT are usually complicated and time-consuming, and are typically conducted in hospital or lab settings. Thus, there exists a need for a sensitive and simple indicator for determining the status of the preserved liver. Lactate, also called lactic acid, is a byproduct/end product of anaerobic metabolism in living cells/tissues/organs. Lactate is generated when there is no or low oxygen in the cell to metabolize glucose for basic energy production through the glycolysis pathway. Applicant has discovered that the level of the lactate in the perfusion liquid, e.g., the perfusion liquid exiting from the IVC, can be measured as a surrogate for measuring the AST levels. The lactate concentration can be measured quickly and simply, which provides significant advantages over the time-consuming liver enzyme measurement. Based on the quick feedback provided by lactate measurements, one or more parameters of the organ care system 600, e.g., flow rate, pressure, and nutrient concentrations, can be adjusted to preserve or improve the liver viability quickly. Stated differently, lactate values (e.g., arterial lactate trends) can be correlated to and be indicative of AST levels. For example, a series (over time) of lactate measurements trending lower can correlate and/or be indicative of a trending lower AST. In some embodiments, lactate measurements can be taken in the measurement drain 2804, although this is not required and can occur at any other location in the system 100. Additionally, in some embodiments, the system 600 can be configured to obtain lactate measurements over time from a single location, a differential between a lactate value entering and exiting the liver, and over time at multiple locations.

C. Imaging

In still other embodiments, various other methods known in the art can be used to assess the liver viability. In some specific embodiments, ultrasound analysis of the liver can be conducted to assess liver parenchyma, intra- and extra-hepatic biliary tree. Other non-limiting examples of imaging techniques include Magnetic Resonance Imaging (MRI), Computed Tomography (CT), Positron Emission Tomography (PET), fluoroscopy, Transjugular Intrahepatic Portosystemic Shunt (TIPS), all of which can be used to assess the liver and detect abnormalities. For example, when examining an ultrasound of the liver, the doctor can examine sinusoidal dimensions, potential obstructions in the bile duct, and/or generalized blood flow.

D. Pathology/Biopsy

In still other embodiments, liver biopsy can be used to assess the liver viability. In liver biopsy, a small piece of liver tissue is removed so it can be examined under a microscope for signs of damage or disease. Because the liver is preserved ex vivo on the organ care system 600, it is readily accessible and the biopsy can be easily conducted.

VIII. THE CLOUD

During operation, the system 600 generates information about the system itself and/or the organ being maintained. In some embodiments of the system 600, this information can be stored in an internal memory such as RAM or ROM. In some embodiments the information generated by the system 600 can also be transmitted to a remote storage location such as in the Cloud. The Cloud can be, for example, a series of remote interconnected computers that are configured to provide data and/or services over the Internet. The Cloud can store the information, perform analysis on the information, and/or provide the information to one or more third parties and/or stakeholders.

In some embodiments of the system 600, the system can include a multimodal communication link between itself and one of more other locations, such as servers in the Cloud. This communication link can be controlled by the controller 150 (e.g., via the data management subsystem 151), although this is not required and other components can be used to control communication. The controller 150 can be configured to provide real-time information about the system 600 and/or the organ contained therein to one or more remote locations while the system is at the donor hospital, is in transit, and/or is at the recipient hospital. In some embodiments, communication can be accomplished using communication link such as a wired network connection (e.g., Ethernet), a wireless network connection (e.g., IEEE 802.11), a cellular connection (e.g., LTE), a Bluetooth connection (e.g., IEEE 802.15), infrared connection, and/or a satellite-based network connection. In some embodiments, the controller 150 can maintain a priority list of connections favoring those connections which are more reliable such as a hardwired Internet connection and/or Wi-Fi over less reliable cellular and/or satellite connections. In other embodiments, the priority list can be generated with a preference for lower-cost transmission mediums such as Wi-Fi.

The system 600 can be configured to communicate with the Cloud, and ultimately remote parties via one or more techniques. For example, the system 600 can be configured to communicate with a server in the Cloud and/or directly with one or more remote computers. In some embodiments, the system 600 can be configured to: i) send communications such as emails and/or text messages to predetermined addresses, ii) upload data files to remote storage locations using, for example, FTP, iii) communicate with a dedicated remote server to provide information in a proprietary format, and iv) receive information downloaded from the Cloud and/or other remote computers. In some embodiments, the controller 150 can transmit/receive the information on a regular schedule, which can vary depending on which phase of operation the system is in. For example, the controller 150 can be configured to provide updates every five minutes while the system 600 is located at the donor hospital, every 15 seconds while in transport, and/or every 15 seconds while the system 600 is located at the receiving hospital. The controller 150 can also be configured to transmit/receive information in a secure manner, such as using encryption and/or with a timestamp.

The controller 150 can be configured to provide various types of information to the Cloud and/or remote location such as: an offer for an organ, system readiness information, battery charge level, gas tank level, status of the solution infusion pump, flow rates, pressure rates, oxygenation rates, hematocrit levels, lactate levels, temperature levels, the flow rate at which the pump 106 is set, the temperature at which the heater 110 is set, the position of the flow clamp 190, some or all of the information displayed on the user interface (e.g., circulatory and infusion flow rates, pressures, oxygenation levels, hematocrit levels), geographic location, altitude, a copy of the displayed interface itself, waveforms displayed on the user interface, alarm limits, active alarms, screen captures of the user interface, photographs (e.g. captured using an onboard camera), HAP/HAF/Lacate trends, historical usage information about the system 600 (e.g., the number of hours it has been used), and/or donor information. In heart/lung embodiments additional information such as AOP and/or PEEP can be provided. Essentially, any piece of information that is collected, generated, and/or stored by the system 600 can be transmitted to the Cloud and/or a remote computer.

The controller 150 can be configured to receive various types of information from the Cloud and/or a remote location such as: instructions from a remote user, a "pull" demand for data from a remote location, control inputs, information about the organ recipient, and/or system updates.

In some embodiments, using the information provided by the system 600, a user that is remote from the system 600 can effectively remotely view the same user interface that is displayed on the system 600. Additionally, in some embodiments, a user that is remote to the system 600 can also remotely control the system 600 as if they were there in person. In some embodiments, the remote view can be an enhanced version of what is seen by the attending user. For example, the user interface can be presented in a similar format so that the remote user can visualize what the attending user sees, but the remote view can be enhanced so that it also displays additional information to provide context for the remote viewer. For example donor demographics, geographic location, trends, and/or assessment results can also be displayed. A remote user can also be provided with virtual buttons and/or controls, matching those found on the system 600, which can be used to remotely control operation of the system 600.

In some embodiments, one or more technicians can remotely connect to and access the system 600 to perform diagnostics, update the system, and/or remotely troubleshoot issues. In some embodiments, remote technical assistance can be limited to times when the system 600 is not being used to preserve an organ.

In some embodiments, the information provided by the system 600 can be presented to a remote user through a web portal, mobile application, and/or other interface.

In some embodiments, access to the information provided by the system 600 can be limited to one or more registered users such as, surgical staff at the recipient hospital, a technical support team, and/or administrators. In some embodiments, access to information provided by the system 600 can be tied to an electronic medical file of the recipient. For example, the Cloud-based server can access one or more electronic medical files of the recipient to determine, for example: parties expressly identified as being able to have access to the recipient's health data, parties associated with organizations that are identified as being able to have access to the recipient's health data, and/or individuals working at medical facilities that are within a certain geographic distance of the recipient.

As described herein, sometimes during transport samples of perfusion fluid can be withdrawn for external analysis. In these instances, however, the data obtained through the external analysis is disassociated with the information contained within the system 600. Thus, in some embodiments, the user interface provided by the system 600 can be configured to allow a user to input and store externally generated data about the organ. For example, if the attending user withdraws a sample of the perfusion fluid in order to perform a lactate measurement in an external analyzer, the attending user can then input and store the result in the system 600 along with the data that is generated by the system 600 itself. Along with the result itself, the user can also provide timestamp information and a description of the information. The information inputted by the user can be stored, processed, downloaded, and/or transmitted by the system 600 as if it were generated internally. In this manner, the system 600 can keep a complete record of all information relating to the organ while it was ex vivo regardless of whether the information was generated internally in or externally from the system 600.

Figure 26:
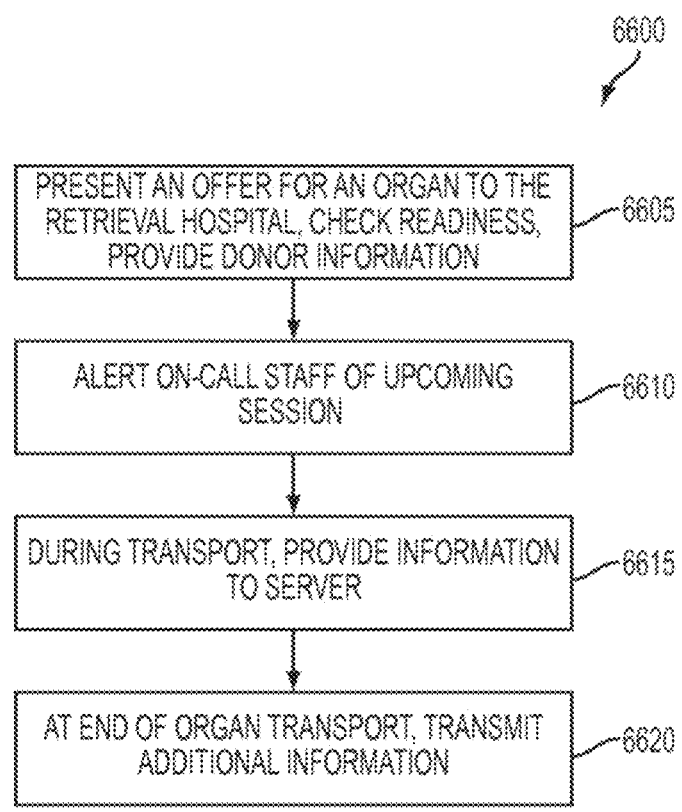
FIGS. 26-27 show exemplary processes that can be used in embodiments of an organ care system.
Figure 27:
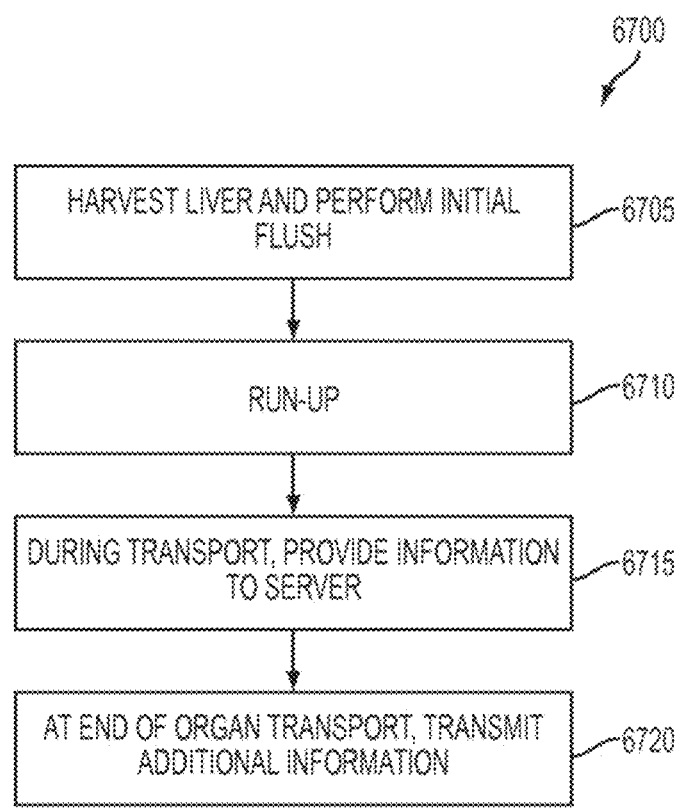

In operation, referring to FIG. 26, a process 6600 describes an exemplary embodiment of how the system 600 can be used with a Cloud-based communication/storage system. The process 6600 is exemplary only and not limiting. For example, the stages described therein can be altered, changed, rearranged, and/or omitted. The process 6600 assumes that the system 600 is in communication with a remote cloud-based server and that the system is being used to transport an organ, although this is not required. This process can be adapted to be used, for example, while an organ is being treated ex vivo for implantation back into the original patient rather than being transplanted into a new recipient.

At stage 6605, an offer for an organ can be presented to the retrieval hospital by the organization that controls organ allocation (e.g., an organ procurement organization). Through a web portal to the system 600, the retrieval hospital's staff can query the readiness (e.g. battery charge level, gas level) of the system 600 and can enter information about the donor. The information can be transferred to the system 600 via the server.

At stage 6610, clinical support that have registered with the server as on-call staff can be alerted to the upcoming transport session via an email, a text message, an automated phone call, and/or any other communication means. The clinical support staff can be, for example, staff employed by the manufacturer of the system 600.

At stage 6615, which typically occurs during transport, the system 600 can transmit system/organ status information to a Cloud-based server via a communication link. The information transmitted to the server can be reviewed in an online portal by third parties such as the transplant surgeon, support staff, and/or any other permitted party (all of which can be at different geographic locations). In some embodiments, the server can perform additional processing on the information received from the system 600 to generate new information, which can then be presented back to the system 600 and/or to third parties. The information displayed to the user on the system 600 can be transmitted (e.g., either the underlying data and/or the image itself) to the server, for example, unsolicited once every 2 minutes. The data can then be stored with a timestamp on the server. For example, in some embodiments, each time information is received by the server from the system 600, this can be placed in a row of an Excel spreadsheet. Additionally, during the stage 6615, remote users that are viewing the information through the portal can "pull" (demand) a screen refresh/snapshot of the data from the OCS rather than waiting for the next 2-minute sample to be "pushed." Additionally, in some embodiments, the remote parties can remotely control the operation of the system 600 via a remote interface.

The remote view can be an enhanced version of what is displayed on the monitor of the system 600. It can be presented in a similar format so that the remote user can visualize what the attending user sees. In some embodiments, however, the remote view can also be enhanced so that it also displays additional information to provide context for the remote viewer, such as donor demographics, trends, and assessment results.

The system 600 can assert alerts through the server to remote third parties such as the transplant surgeon and/or clinical support team. The attending user can trigger contact from one of more remote third parties via a monitor menu action. For example, the attending user can send a request for assistance to technical support who can receive an alert via, for example, text message and/or email and call or otherwise contact the attending user.

The system 600 can automatically assert alerts in certain critical conditions (e.g. HAP>120, or PVP>20 mmHg). The attending user can also snap a photograph using a camera that is integrated into the system 600 (e.g., integrated into the operator interface module 146). The image can automatically be pushed to the server by the system 600.

During stage 6615, the system 600 can automatically provide information to the server and/or other remote computer at regular intervals such as every 15 seconds, every two minutes, every five minutes, or every 10 minutes. In some embodiments, information transmitted between the system 600, the server, and/or the third party can occur in real time so that the remote party can have real time access to and/or control over the system 600 as if they were there in person. In some embodiments, the attending user and/or any other remote parties can initiate an unscheduled information transfer. In some embodiments, if the communication link of the system 600 has been disabled or is inoperable (e.g., during air transport), the controller 150 can be configured to continue generating regular status updates and store them for transmission once the communication link has been re-enabled.

At stage 6620, which typically occurs at the end of the transport session, session files from the system 600 can be pushed to the server. The information provided to the server can include, for example, the trend, error, blood sample, and event files. Preference can be given to WiFi before cellular link for data transmission, to minimize cost.

IX. POSSIBLE BENEFITS

Some embodiments of the system 600 described herein can provide one or more benefits. For example:

Depending on the type of procedure being performed, manually controlling an organ preservation system can be a labor-intensive process that can require specialized training. Additionally, as with any medical procedure, manual control can also be prone to mistakes by those controlling the system. Thus, in some embodiments, the system 600 can automatically control itself in real time. For example, the controller 150 can be configured to automatically control the flow rate of the pump 106, the operation of the gas exchanger 114, the temperature of the heater 110, the operation of the flow clamp 190 (when an automated clamp is used), and/or the transmission of information to the Cloud. The controller 150 can be configured to control operation of the system 600 based upon feedback information from, for example, the sensors contained therein.

Providing automated control of the system 600 can result in improved usability, can reduce the possibility of error, and can reduce the labor intensity of transporting an organ. For example, automating the control process can compensate for user variability that can exist when different people control the system. For example, even if two users receive the same training, one user's judgment may differ from another which can result in inconsistent levels of care across the two users. By automating the control process, a level of consistency between operators can be achieved in a manner that is otherwise difficult to do. Additionally, providing automated control can also provide better care for the organ while ex vivo by updating operational parameters of the system 600 more quickly than is possible with manual control.

The techniques described herein can also improve the utilization of donor organs that are currently not being utilized due to limitations of cold storage methods. In existing cold storage methods, many organs go to waste because the organ cannot be transported to a recipient before it suffers damage as a result of cold storage. This results in many organs that are otherwise suitable for transplantation going to waste each year. Using the techniques described herein, the amount of time that an organ can be maintained in a healthy ex vivo state can be greatly extended thereby increasing the potential donor and recipient pool.

The techniques described herein can also help improve the assessment of whether an organ is suitable for transplant into a recipient. For example, using a liver example, visual observation or examination of the liver can be used to assess the liver viability. For instance, a pink or red color of the liver can indicate that the liver is functioning normally, while a gray or dark color of the liver can indicate that the liver is functioning abnormally or deteriorating. In other embodiments, palpation of the liver can be used to assess its viability. When the liver feels soft and elastic, the liver is likely functioning normally. On the other hand, if liver feels tense or stiff, the liver is likely functioning abnormally or deteriorating.

In still other embodiments, because the bile duct is cannulated and connected to a reservoir of the system 600, the color and amount of bile produced by the liver can be easily examined to evaluate the liver viability. In certain embodiments, black or dark green color bile indicates normal liver function while a light or clear color of the bile indicates that the liver is not functioning properly or deteriorating. In still other embodiments, the amount of the bile production can be used to evaluate the liver viability as well. Generally, the more the bile produced, the better the liver function. In certain embodiments, a bile production of from about 250 mL to 1 L, 500 mL to 1 L, 500 mL to 750 mL, 500 mL, 750, or 1 L per day or in any ranges bounded by the values noted herein suggests that the liver preserved on the organ care system 600 is functioning normally and viable. Many of the foregoing techniques can be difficult, if not impossible when the organ is in vivo.

X. EXAMPLES

Experimental tests and results relating to the some embodiments are described below. As described below, experimental tests included multiple studies and phases. Phase I included studies of 27 liver samples including two groups of organs on the above OCS system for up to 12 hours. Phase II included replicating the clinical steps of liver retrieval, preservation and simulated transplantation processes for multiple sample livers for 4 hours of simulated transplant. Phase III included replicating clinical steps of liver retrieval, preservation and simulated transplantation processes for multiple sample livers for 24 hours of simulated transplant.

A. Phase I

Groups A and B of organs were used for Phase I. Objectives for Phase I include: (1) To optimally perfuse and preserve Livers on the OCS system for up to 12 hours using oncotic adjusted red blood cells ("RBCs") based nutrient enriched perfusate; (2) maintain stable near-physiological heamodynamics (pressure and flow) for both the portal and the hepatic arterial circulation; (3) enable monitoring of organ functionality and stability on the OCS by monitoring bile production rate, liver enzymes trends, stable PH and arterial lactate levels; and (4) histopathology assess the organ post OCS.

The animal model used for the test was the swine model, including 70-95 kg Yorkshires swine. The Yorkshires swine was used as a model due to its similarity to human anatomy and size relative to human adult organ size. The perfusate for the test was red blood cell based. Given that the liver is a highly metabolic active organ, a perfusate with an oxygen carrying capacity and nutrient enriched would be ideal for the organ, mimicking it's in-vivo environment and satisfying the organ's high metabolic demand.

Liver is unique by its dual blood supply. As described previously, the liver gets its blood supply through the portal vein (PV) and the hepatic artery (HA). Portal circulation is a low-pressure circulation (5-10 mm Hg) and the hepatic arterial circulation delivers high-pressure pulsatile blood flow (70-120 mm Hg). Stable perfusion parameters and hemodynamics indicate stable perfusion. Lactate levels were used as a marker of adequate perfusion because lactate is one of the most sensitive physiologic parameters, and is thus a good indicator of the adequacy of perfusion. Lactate is produced under anaerobic conditions denoting inadequate perfusion, and the trend of lactate level is a sensitive marker for perfusion adequacy assessment. Aspartate Aminotransferase ("AST") is a standard marker used clinically to assess livers, and was also used as a marker of viability. The trend of AST level is another marker and indicator of the organ viability. Bile production is a unique function of the liver. Bile production monitoring is another marker for the organ viability and functionality.

Phase I included studies of 27 liver samples. Of those, Group A included 21 samples that were preserved on the OCS for 8 hours using cellular based perfusate. Group B included 6 samples that were preserved on the OCS for 12 hours using cellular based perfusate.

The following protocol was applied for phase I groups A and B testing.

First, animal prep, organ retrieval, cannulation and Pre-OCS flush is described. Each 70-95 kg Yorkshires Swine was sedated in its cage by injecting a combination of Telazol and Xylazine intramuscularly according to the following dose: 6.6 mg/kg Telazol and 2.2 mg/kg Xylazine. The animal was then intubated, an IV line established, then the animal was transferred to the OR table in supine position, then connected to the ventilator and anesthesia machine. The liver was exposed through a right subcostal incision, and the heart through median sternotomy incision. The hepatic artery (HA), portal vein (PV) and the common bile duct were isolated. The right atrium and the superior vena cave were then isolated and cannulated for blood collection. Then 2-3 liters of blood were collected from the animal using a 40 Fr venous cannula through the right atrium. The collected blood was then processed through a cell saver machine (Haemonetics Cell Saver 5+) to collect washed RBCs. Topical cooling was applied to the liver during the blood collection time. Then the liver was harvested.

After harvesting the liver, the hepatic artery (HA), portal vein (PV), the common bile duct, supra hepatic cava and infra hepatic cave were isolated and cannulated using the appropriate size for each. Exemplary sized cannulas include 14 Fr, 16 Fr, 18 Fr for the hepatic artery cannula, 40 Fr and 44 Fr for the portal vein cannula, 12 Fr and 14 Fr for the common bile duct cannula, 40 Fr for the supra-hepatic vena cava, and 40 Fr for the infra-hepatic cava.

The liver was then flushed using 3 L of cold PlasmaLyte® solution, each liter was supplemented with Sodium bicarbonate (NHCO3) at 10 mml/L, Epoprostenol Sodium at 2 mics/L, Methylprednisolone at 160 mg/L. One liter was delivered through the hepatic artery pressurized at ~50-70 mmHg. Two liters were delivered through the portal vein by gravity.

After cannulation, the organ was preserved on the OCS at 34° C. for 12 hours using oncotic adjusted RBCs based perfusate. The OCS-liver system prime perfusate included washed red blood cells, albumen 25%, PlasmaLyte® solution, dexamethasone, sodium bicarbonate (NaHCO3) 8.4%, adult multivitamins for infusion (INFUVITE®), calcium gluconate 10% at (100 mg/ml), gram-positive antibiotic such as cefazolin, and a gram negative antibiotic such as ciprofloxacin. Table 7 below summarizes the liver prime perfusate composition and dose.

TABLE 7

OCS liver prime perfusate composition and dose

| OCS Liver Perfusate Composition | Recommended Dose |
| --- | --- |
| Washed Red Blood Cells (pRBCs) | 1-2 L |
| Albumin 25% | 400 mls |
| PlasmaLyte ® Solution | 700-800 mls |
| Methylprednisolone | 500 mgs |
| Dexamethasone | 20 mgs |
| Sodium Bicarbonate (NaHCO3) 8.4% | 50-70 mmol |
| Adult Multivitamins for infusion INFUVITE ® | 1 unit |
| Calcium Gluconate 10% (100 mg/ml) | 10 mls |
| Antimicrobials: | |
| Gram-positive antibiotic: Cefazolin | 1 gm |
| Gran-negative antibiotic: Ciprofloxacin | 100 mg |

In addition to OCS-Liver circulating perfusate mentioned above, the following were delivered to the perfusate as continuous infusion using an integrated Alaris infusion pump: Total Parenteral Nutrition (TPN): CLINIMIX E (4.25% Amino Acid/10% Dextrose); PLUS Insulin (30IU), Glucose (25 g) and 40,000 units of Heparin; Prostacyclin infusion as needed: (epoprostenol sodium) to optimize the Hepatic Artery Pressure; Bile Salts (Taurocholic acid sodium): as needed for Bile Salt Supplement. Table 8 below illustrates the liver perfusate infusions and rate.

TABLE 8

OCS liver perfusate infusions and rate

| Continuous Infusion Mix | Dose |
| --- | --- |
| Total parenteral nutrition (TPN) Mix: CLINIMIX E TPN (4.25% Amino Acid/ 10% Dextrose); PLUS Insulin 30 IU Glucose 25 gms Heparin 40,000 units | 30-50 ml/hr |

| As Needed Additives | Dose |
| --- | --- |
| Prostacyclin infusion as needed to control Hepatic artery pressure -e.g. Epoprostenol Sodium 0.5 mg | 0-6 mics/hr |
| Bile Salts Taurocholic acid sodium (1 gm/50 ml) | 0-10 ml/hr |
| NaHCO3 8.4% to correct metabolic acidosis | 1.5 meq/1 bas excess |

The Liver was perfused on the OCS by delivering blood based, warm, oxygenated and nutrient enriched perfusate through the hepatic artery and the portal vein. Once the liver was instrumented on the OCS and all cannulae were connected, pump flow was increased gradually and very slowly to achieve the target flow over 10-20 minutes. While the liver was warming up to the temperature set point, the flow control clamp was adjusted to maintain a 1:1 to 1:2 flow ratio between the HA and PV. The vasodilator agent flow rate was adjusted as needed to manage the hepatic artery pressure. An arterial blood sample was collected within the first 15-20 minutes.

The following perfusion parameters were maintained during perfusion on the OCS-liver device: Hepatic Artery Pressure (mean HAP): 75-100 mmHg; Hepatic Artery Flow (HAF): 300-700 ml/min; Portal Vein Pressure (mean PVP): 4-8 mmHg; Portal Vein Flow (PVF): 500-900 ml/min; Perfusate Temperature (Temp): 34 C; Oxygen gas flow 400-700 ml/min.

Lactate levels on the OCS-Liver Perfusion were collected according to the following sampling scheme. One OCS liver arterial sample was collected within 10-20 minutes from a start of perfusion on the OCS-Liver device. Samples continued to be collected from the device at approximately hourly intervals until lactate level was trending down, at which point the lactate samples were taken every 2 hours or after any active HAF or HAP adjustments. Baseline Liver Enzyme was measured from the animal. Liver Enzyme was collected and assessed on the OCS every two hours starting at the second hour.

1. Post OCS Histopathology Sampling.

At the end of the preservation time, OCS perfusion was terminated. The liver was disconnected from the device and all cannulas were removed. Specimens were collected from the Liver and saved in 10% formalin for Histopathology assessment. A section of the Liver was collected for the wet/dry ratio. The section weight was recorded before and after 48 hours in an 80° C. hot oven. The wet/dry ration was then calculated according to the following formula: Water Content (W/D ratio)=1−(Ending Weight/Starting Weight).

A liver was considered acceptable if it met acceptance criteria, including: stable perfusion parameters throughout preservation on the OCS for HAF, HAP, PVF and PVP; stable or trending down arterial lactate; continuous bile production with a rate of >10 ml/hr.; stable or trending down liver enzymes (AST); and normal and stable perfusate PH.

Figure 31:
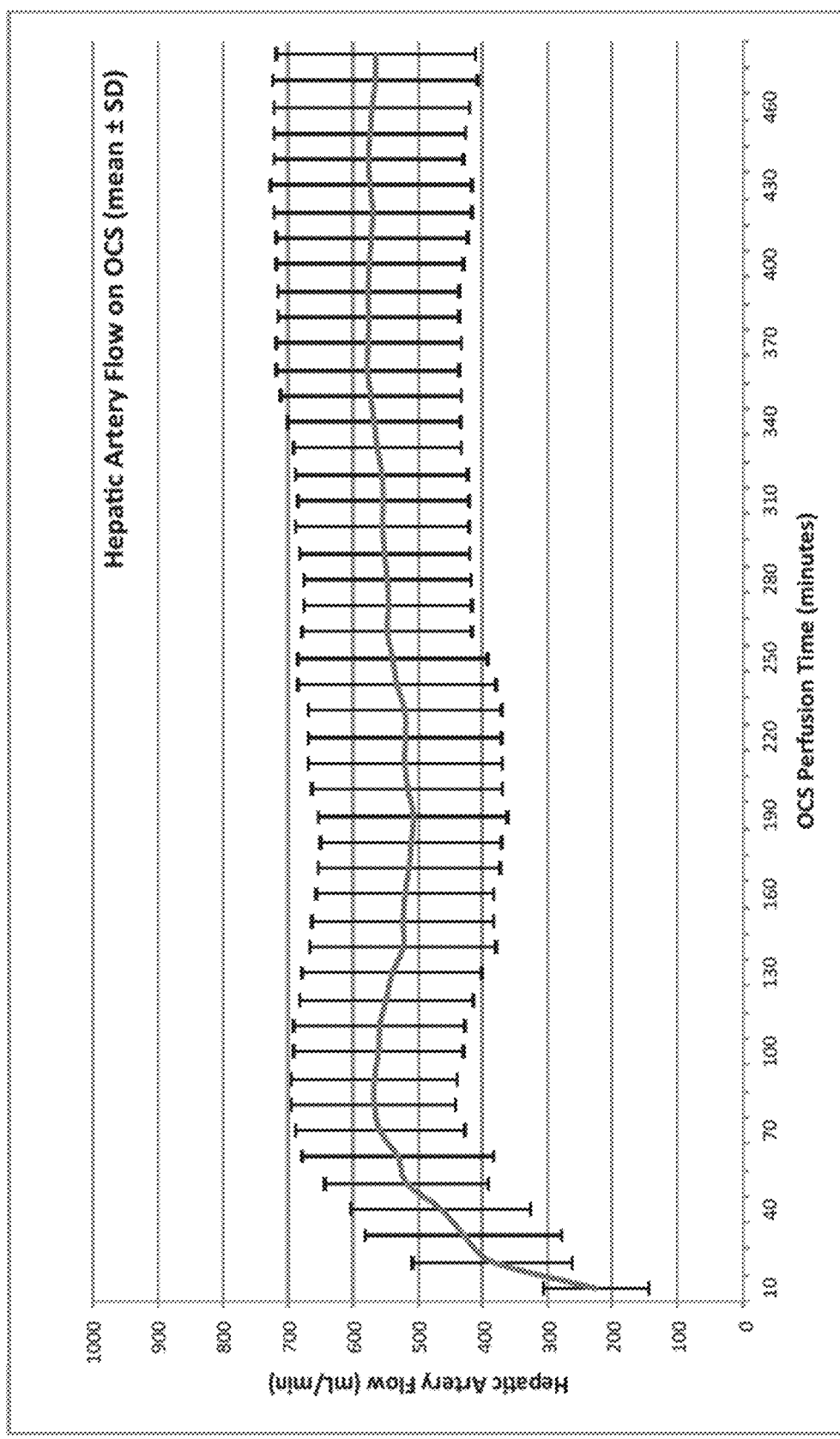
FIG. 31 shows the hepatic artery flow (HAF) trend throughout the course of 8 hours preservation on OCS.
Figure 32:
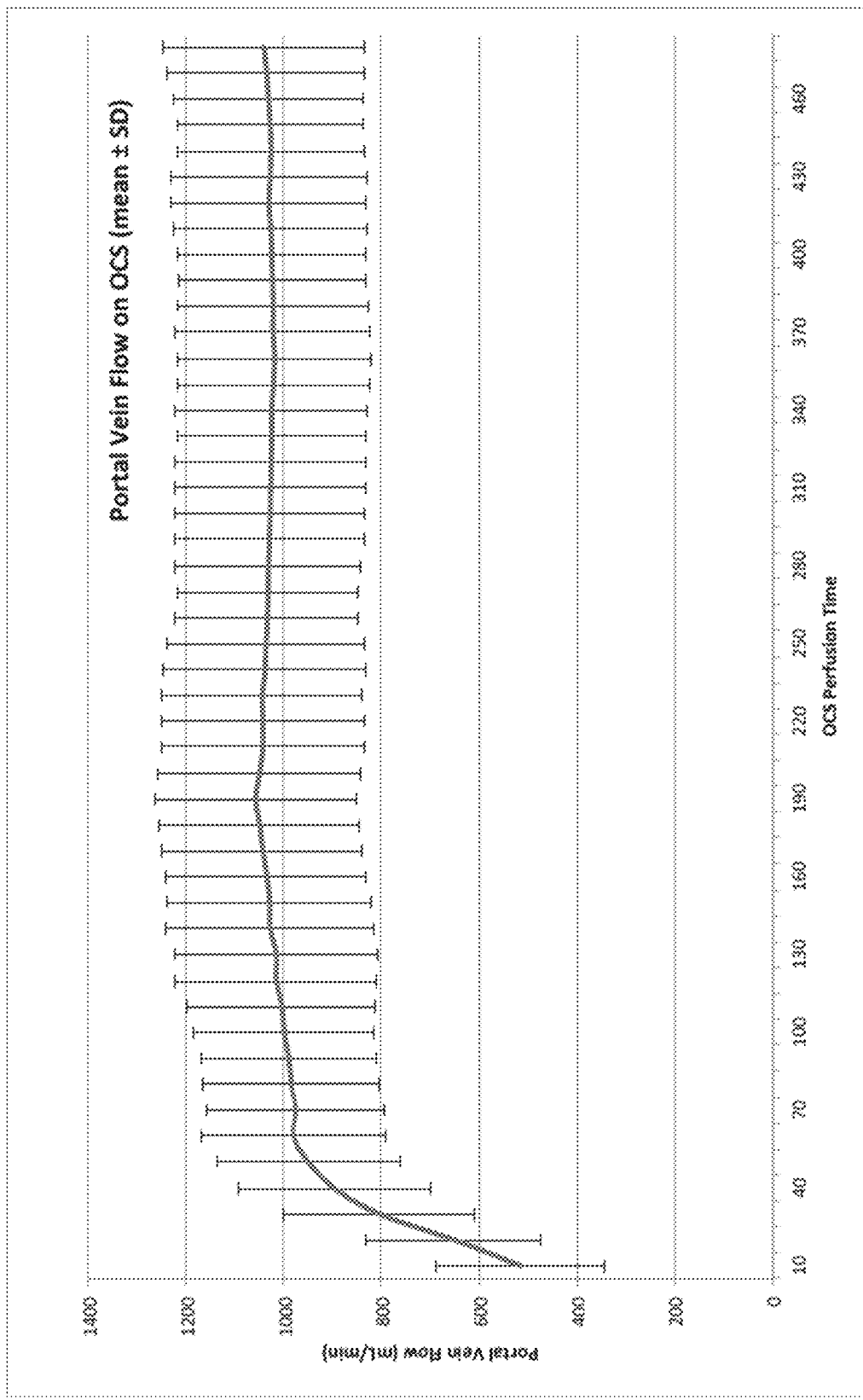
FIG. 32 shows the portal vein flow (PVF) trend throughout the course of 8 hours preservation on OCS.
Figure 33:
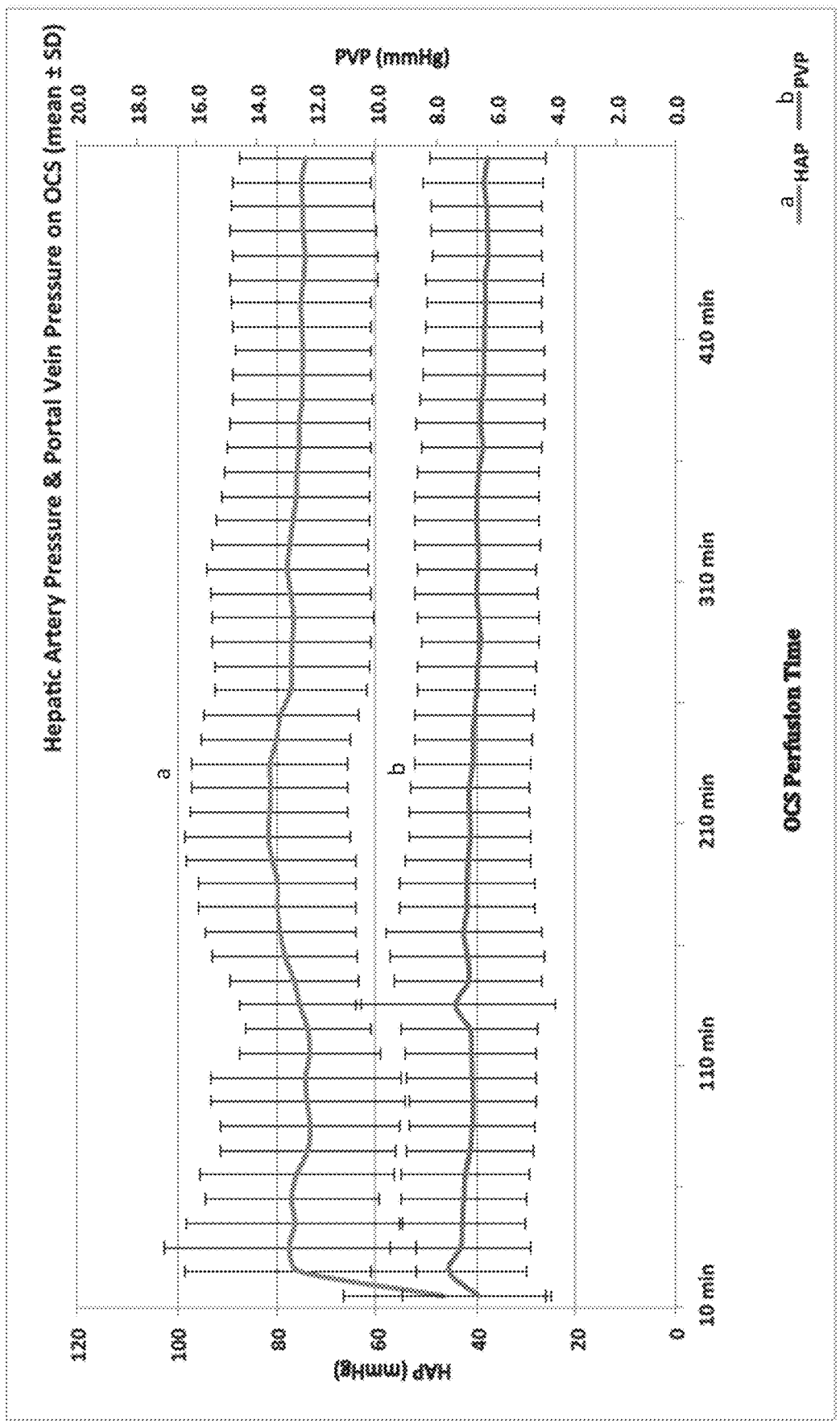
FIG. 33 shows a graphical depiction of hepatic artery pressure versus portal vein pressure throughout the 8 hour OCS-liver perfusion.

The Phase I, Group A, 21 samples successfully met the above identified acceptance criteria. The data for hepatic artery flow over 8 hours of OCS liver perfusion shown in the graph in FIG. 31 demonstrates that OCS perfused swine livers demonstrated stable perfusion, as evidenced by the Hepatic Artery Flow (HAF) trend throughout the course of 8 hours preservation on OCS. The data for portal vein flow over 8 hours of OCS liver perfusion shown in the graph in FIG. 32, which shows PVF trend throughout the course of the 8 hour preservation on OCS, demonstrated stable perfusion, as evidenced by the stable Portal Vein Flow (PVF) trend throughout the course of 8 hours preservation on OCS. FIG. 33 shows a graphical depiction of hepatic artery pressure versus portal vein pressure throughout the 8 hour OCS-liver perfusion. FIG. 33 illustrates that OCS perfused swine livers demonstrated stable perfusion pressure, as evidenced by the stable portal vein pressure and the hepatic artery pressure throughout the course of the 8 hour preservation.

Figure 34:
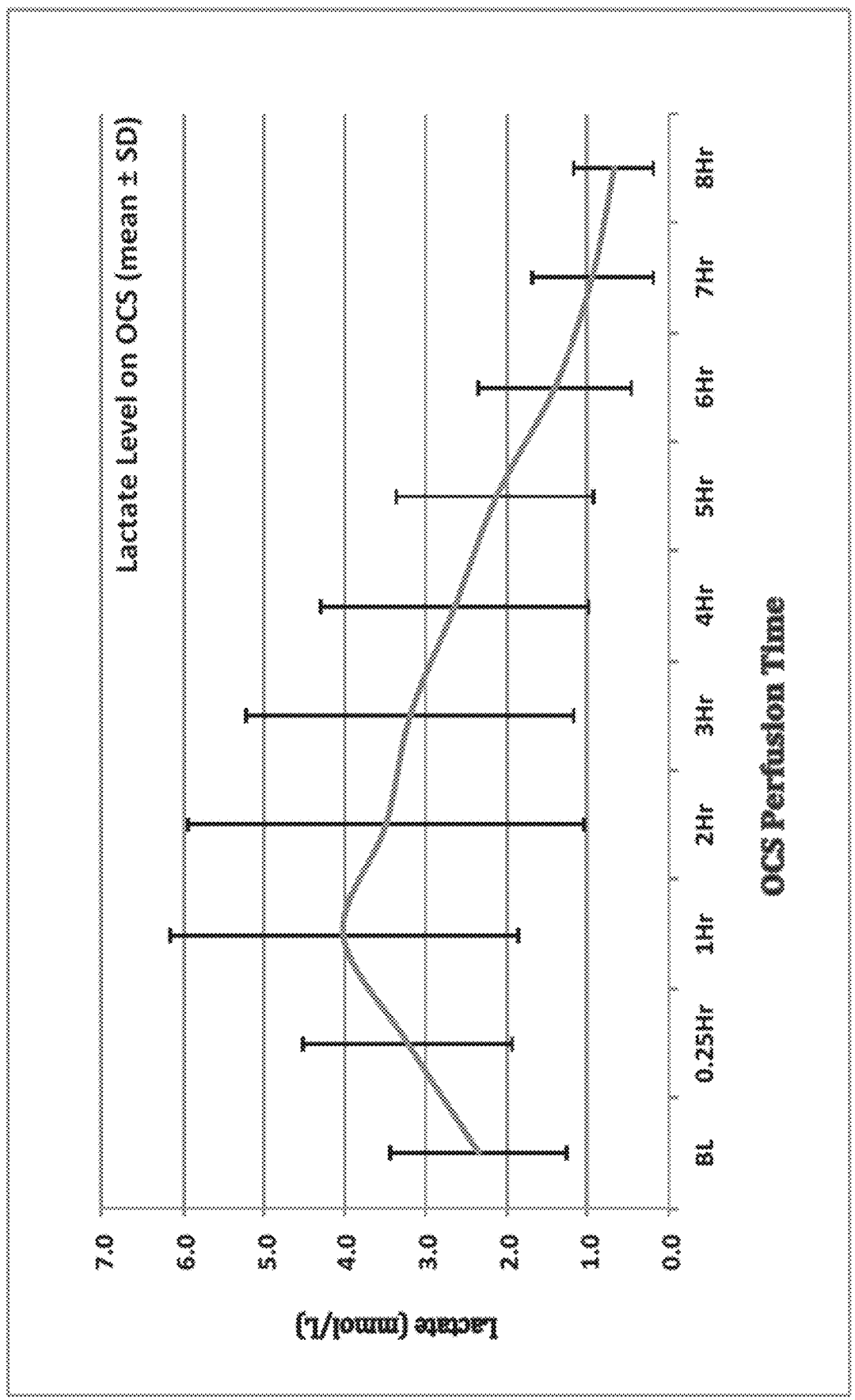
FIG. 34 is a graphical depiction of arterial lactate levels over the 8 hour OCS liver perfusion.
Figure 35:
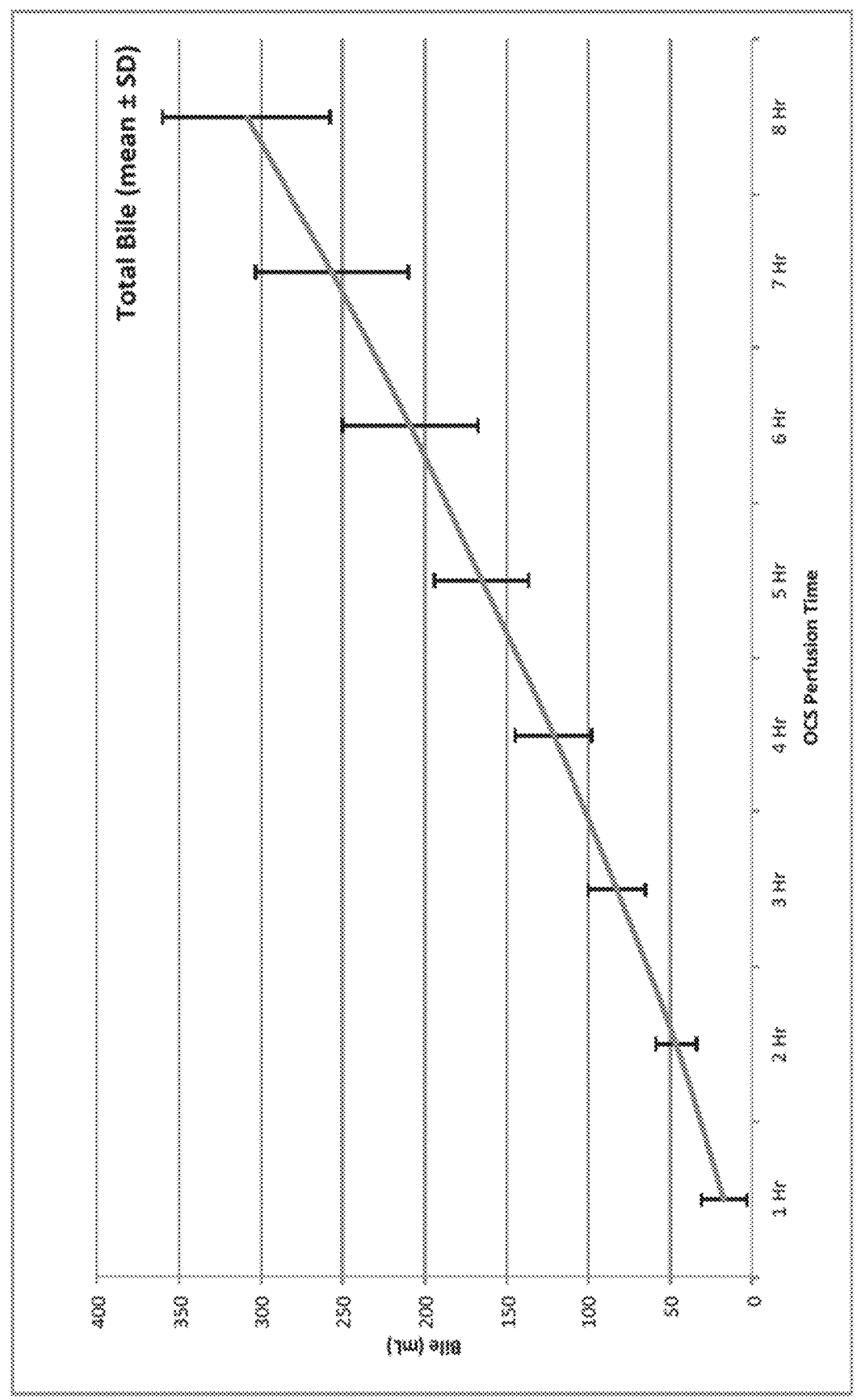
FIG. 35 is a graphical depiction of total bile production over the 8 hour OCS liver perfusion.
Figure 36:
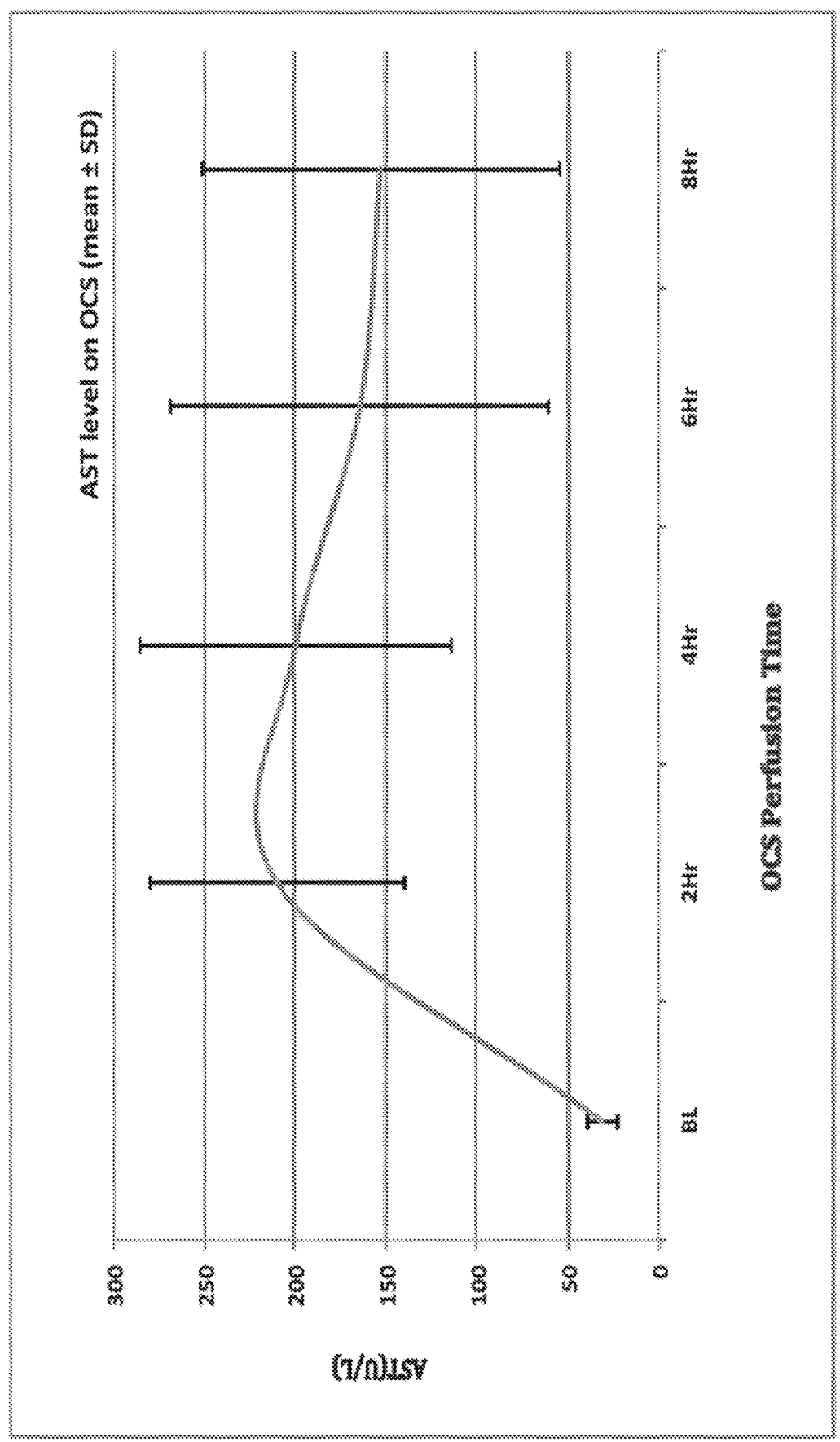
FIG. 36 is a graphical depiction of AST level over the 8 hour OCS liver perfusion.
Figure 37:
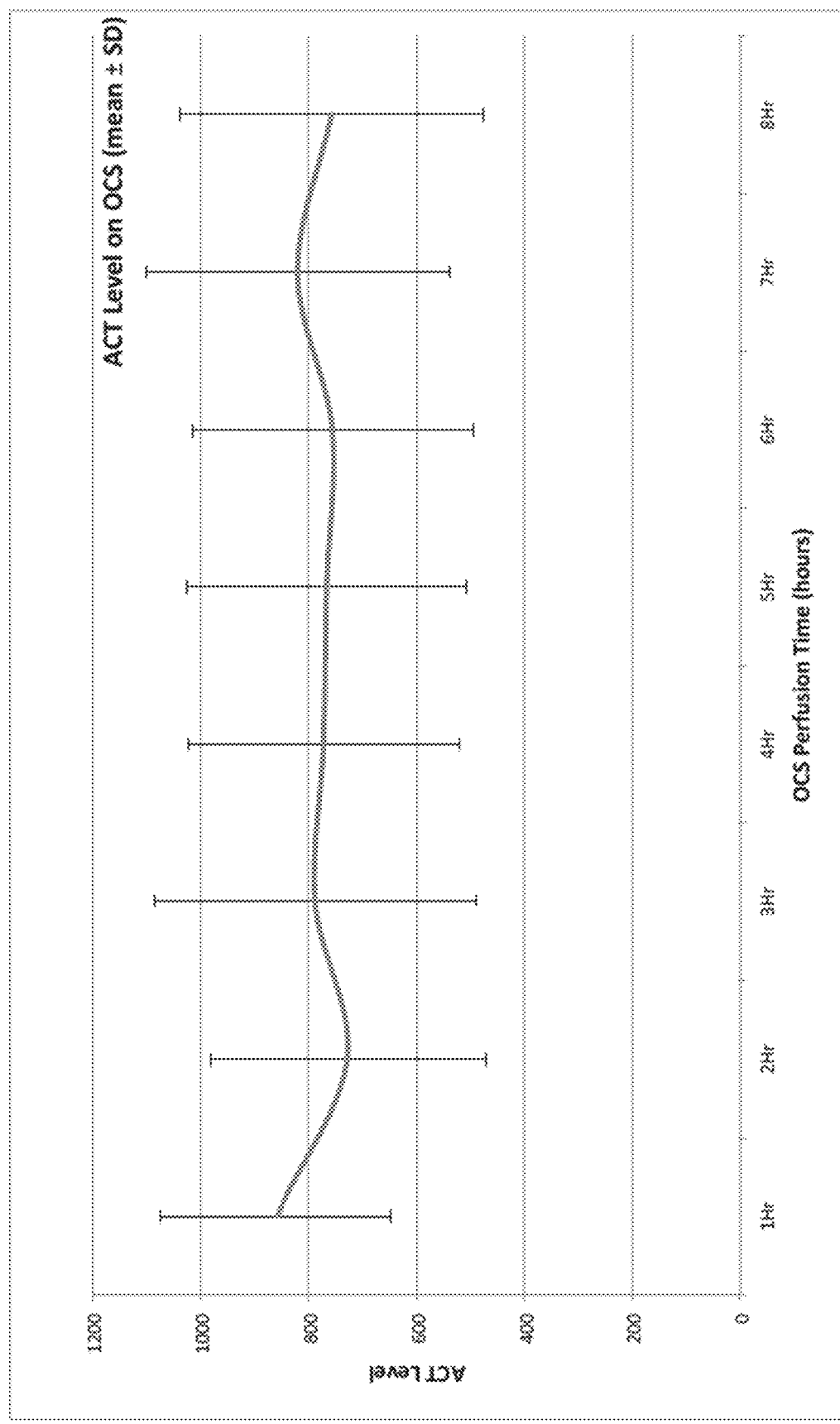
FIG. 37 is a graphical depiction of ACT level over the 8 hour OCS liver perfusion.
Figure 38:
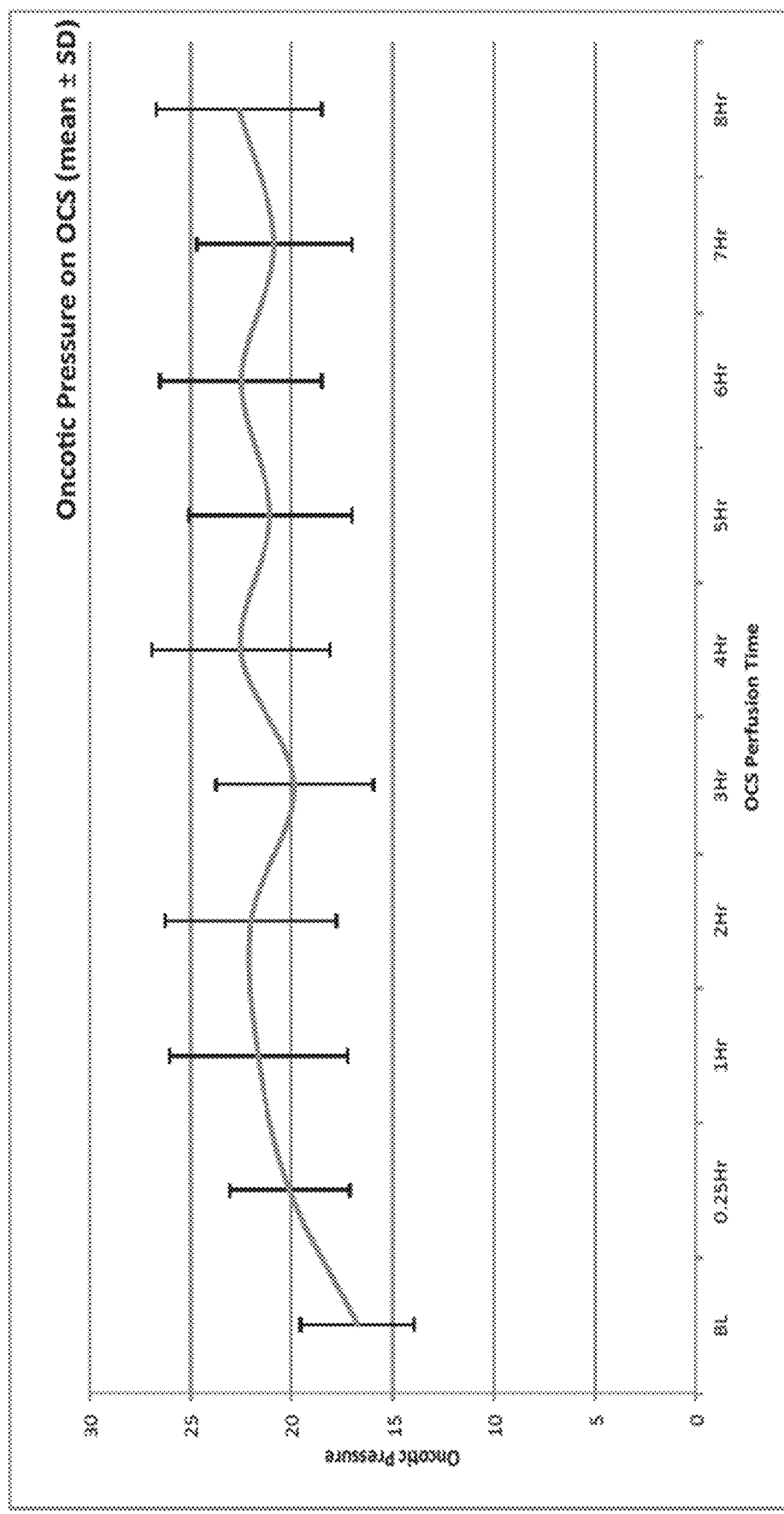
FIG. 38 is a graphical depiction of oncotic pressure throughout the course of 8 hours preservation on OCS.

FIG. 34 is a graphical depiction of arterial lactate levels over the 8 hour OCS liver perfusion. FIG. 34 shows that OCS perfused swine livers demonstrated excellent metabolic function, as evidenced by their ability to clear lactate and trending down lactate throughout the course of 8 hours preservation on OCS. FIG. 35 is a graphical depiction of total bile production over the 8 hour OCS liver perfusion. FIG. 35 shows that OCS perfused livers continued to produce bile at a rate of >10 ml/hr. throughout the course of the 8 hour preservation on OCS indicating preserved organ functionality. FIG. 36 is a graphical depiction of AST level over the 8 hour OCS liver perfusion. Aspartate Aminotransferase (AST) is a standard marker clinically used to assess livers. FIG. 36 graph demonstrates that OCS perfused livers exhibited a trending down AST levels over the course of 8 hours perfusion on the OCS, indicating good liver functionality. FIG. 37 is a graphical depiction of ACT level over the 8 hour OCS liver perfusion. As shown in FIG. 37, activated clotting time (ACT) was maintained above 300 seconds over the course of 8 hours of perfusion on the OCS. FIG. 38 is a graphical depiction of oncotic pressure throughout the course of 8 hours preservation on OCS. As shown in FIG. 38, oncotic pressure remained stable on the OCS.

Figure 39:
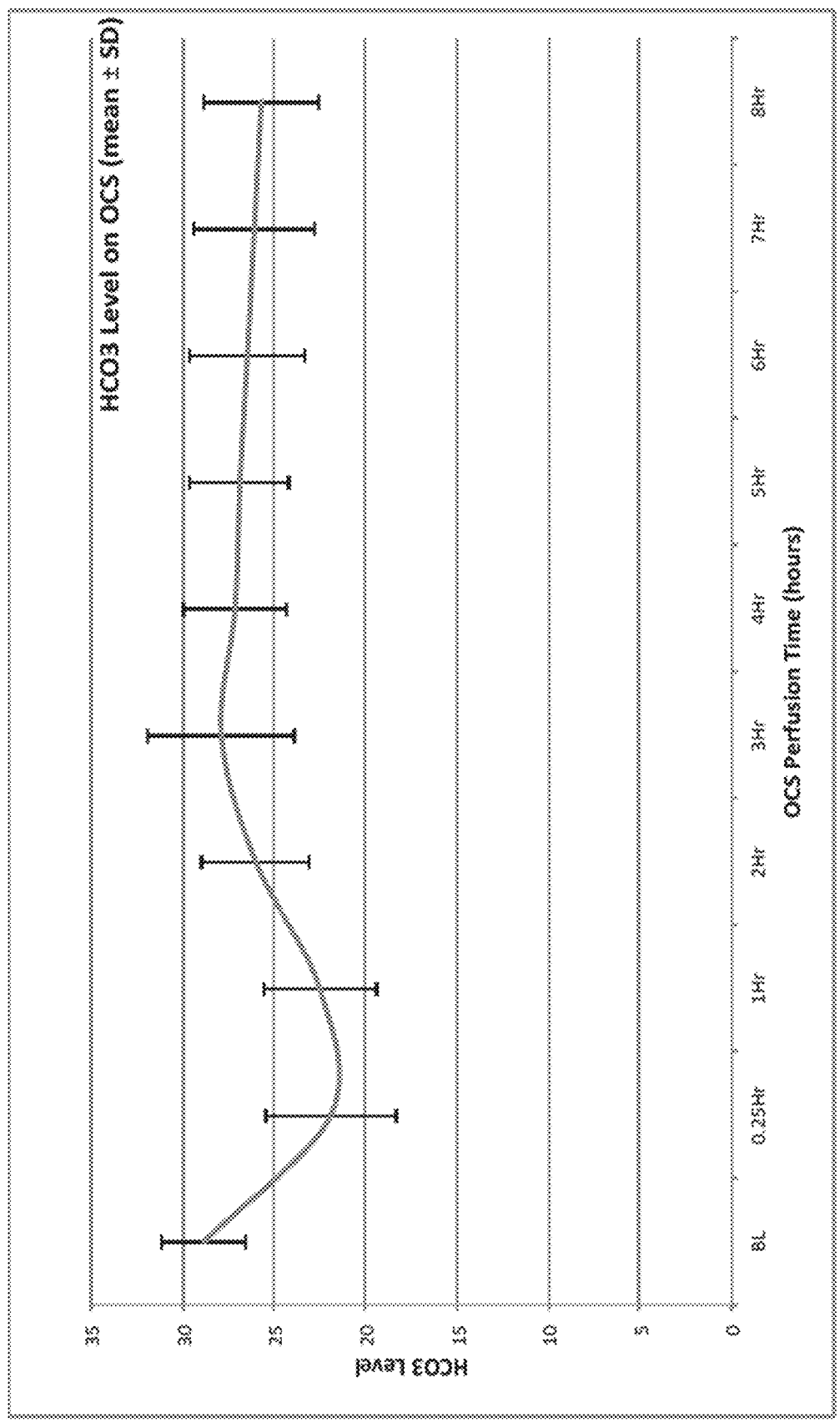
FIG. 39 is a graphical depiction of bicarb levels over the 8 hour OCS liver perfusion.
Figure 40:
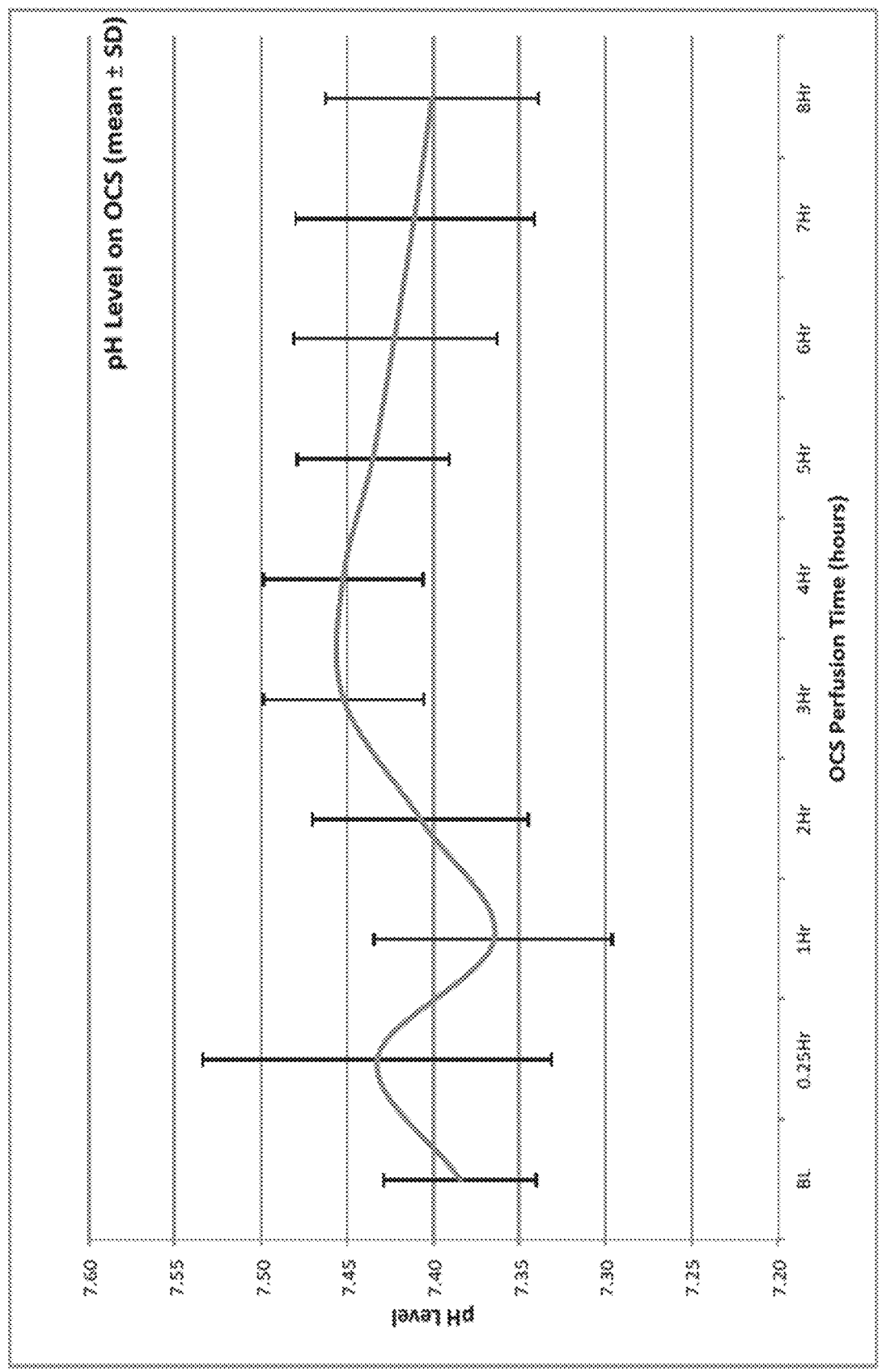
FIG. 40 is a depiction of the detected pH levels throughout the course of 8 hours preservation on OCS.

FIG. 39 is a graphical depiction of bicarb levels over the 8 hour OCS liver perfusion. As shown in FIG. 39, Bicarb (HCO3) levels were maintained within normal physiologic ranges over the course of 8 hours perfusion on the OCS with very minimal doses required of HCO3 for correction, indicating a stable liver metabolic profile. FIG. 40 is a depiction of the detected pH levels throughout the course of 8 hours preservation on OCS. As shown in FIG. 40, stable and normal pH was maintained over the course of 8 hours perfusion on the OCS with no or minimal need to add HCO3 for correction, indicating a good functioning and adequately perfused organ.

Figure 41:
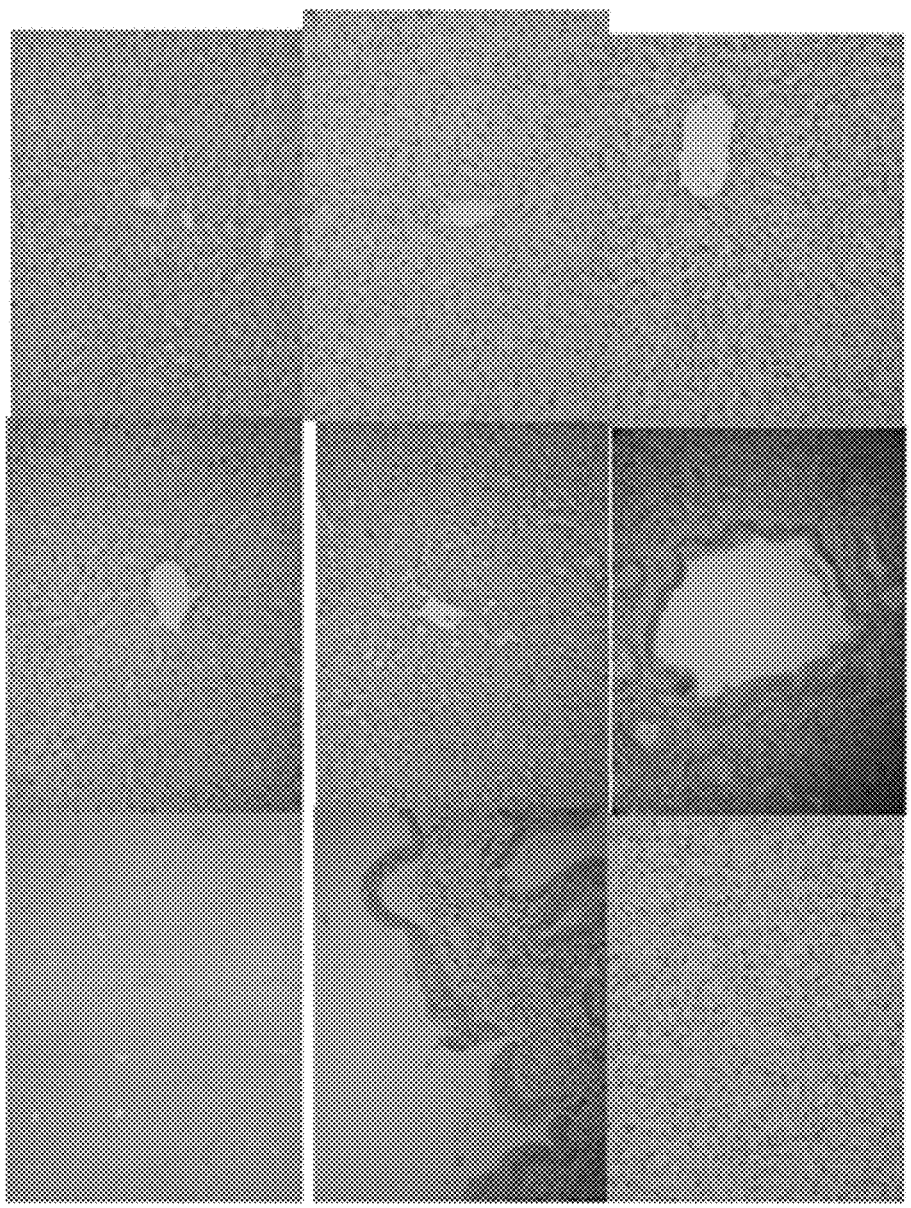
FIG. 41 shows images of tissues taken from samples in Phase I, Group A.

FIG. 41 shows images of tissues taken from samples in Phase I, Group A. Histological examination of parenchymal tissue and bile duct tissue shows normal liver sinusoidal structure with no evidence of necrosis or ischemia and normal bile duct epithelial cells indicating adequate perfusion and lack of ischemic injury.

The results observed for Phase I Group B, organs maintained for 12 hours, exhibited similar acceptable results to those in Group A.

As in Group A above, in Phase I Group B a liver was considered acceptable if it met acceptance criteria, including: stable perfusion parameters throughout preservation on the OCS for HAF, HAP, PVF and PVP; stable or trending down arterial lactate; continuous bile production with a rate of >10 ml/hr.; stable or trending down liver enzymes (AST); and normal and stable perfusate PH.

Figure 42:
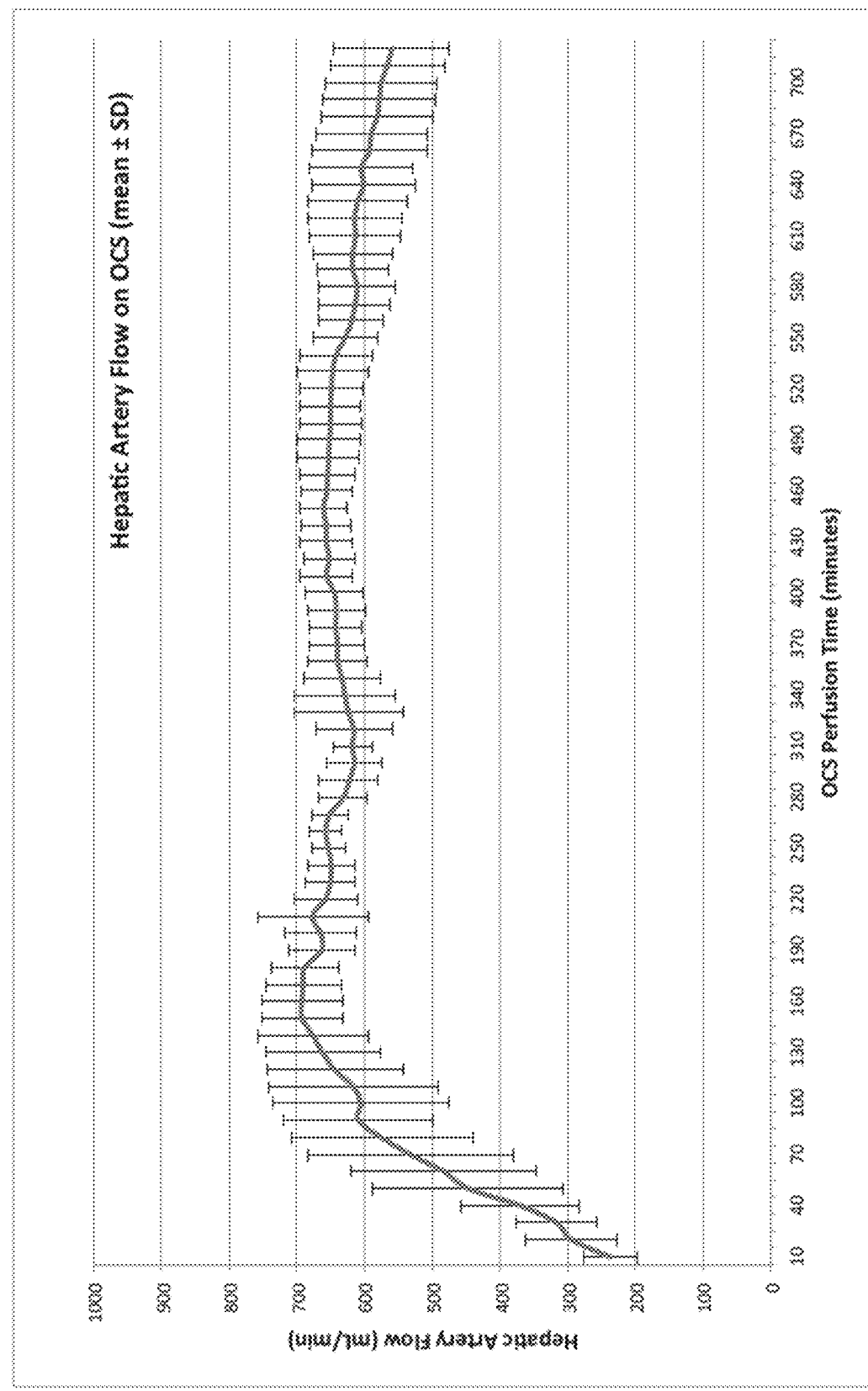
FIG. 42 depicts Hepatic Artery Flow of a 12 hr OCS Liver Perfusion.

FIG. 42 depicts Hepatic Artery Flow of a 12 hr OCS Liver Perfusion. As illustrated, the graph of FIG. 42 shows that OCS perfused swine livers demonstrated stable perfusion, as evidenced by the Hepatic Artery Flow (HAF) trend throughout the course of 8 hours preservation on OCS.

Figure 43:
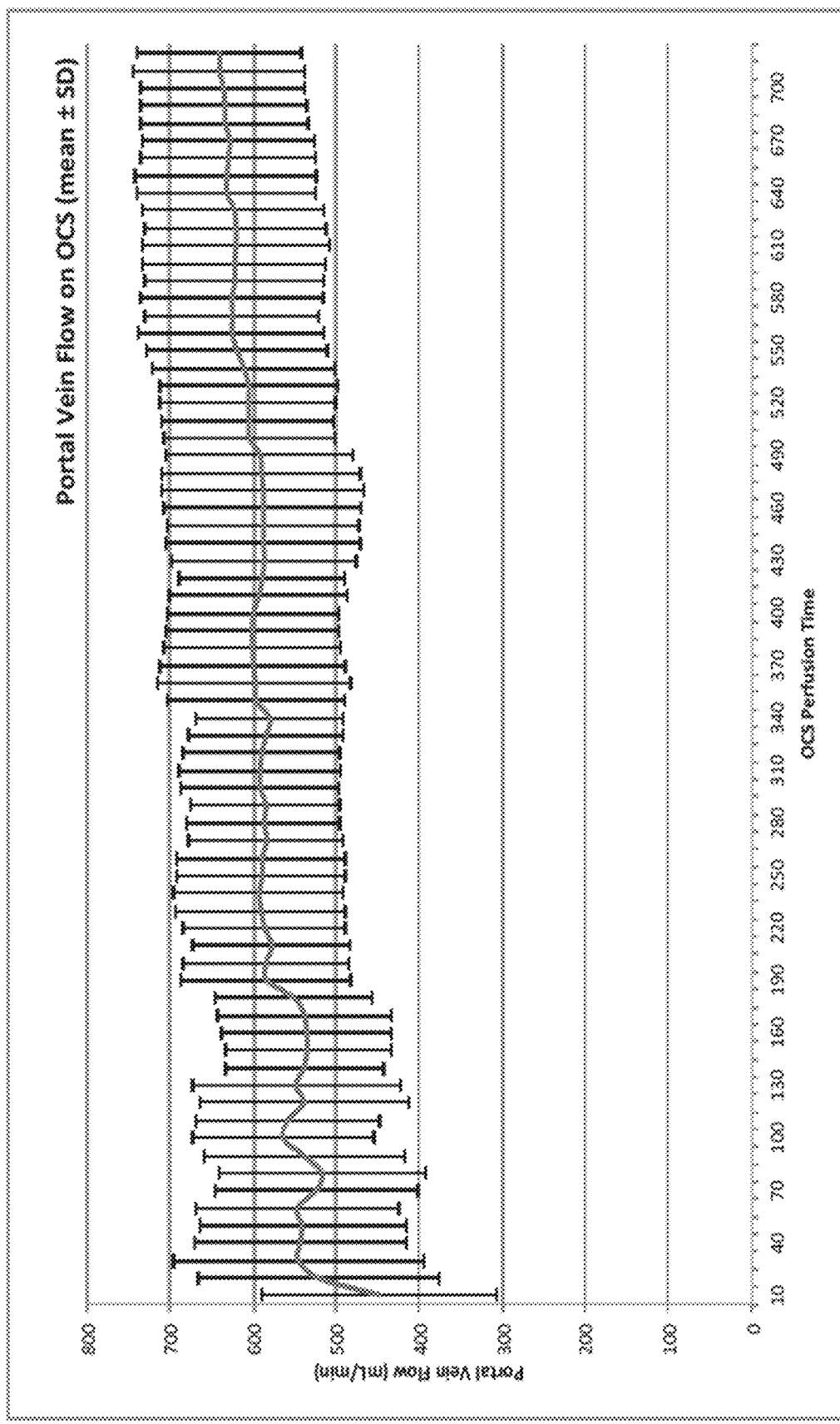
FIG. 43 depicts Portal Vein Flow of a 12 hr OCS Liver Perfusion.

FIG. 43 depicts Portal Vein Flow of a 12 hr OCS Liver Perfusion. As illustrated, the graph of FIG. 43 illustrates OCS perfused swine livers demonstrated stable perfusion, as evidenced by the stable Portal Vein Flow (PVF) trend throughout the course of 12 hours preservation on OCS.

Figure 44:
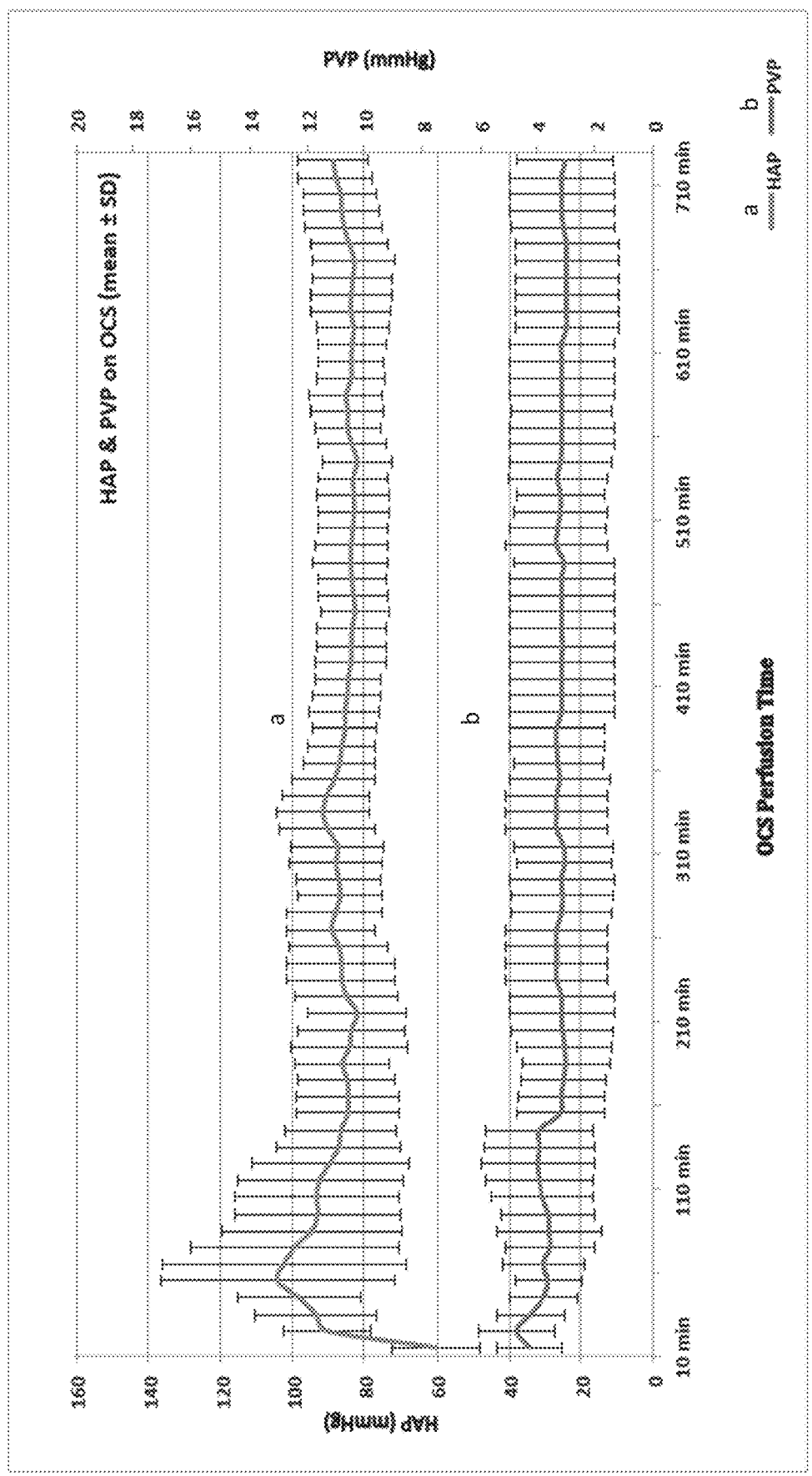
FIG. 44 depicts Hepatic Artery Pressure vs. Portal Vein Pressure in a 12 hr OCS-Liver Perfusion.

FIG. 44 depicts Hepatic Artery Pressure vs. Portal Vein Pressure in a 12 hr OCS-Liver Perfusion. The graph of FIG. 44 demonstrates that OCS perfused swine livers demonstrated stable perfusion pressure, as evidenced by the stable Portal Vein Flow (PVP) and the Hepatic Artery Pressure (HAP) trend throughout the course of 12 hours preservation on OCS.

Figure 45:
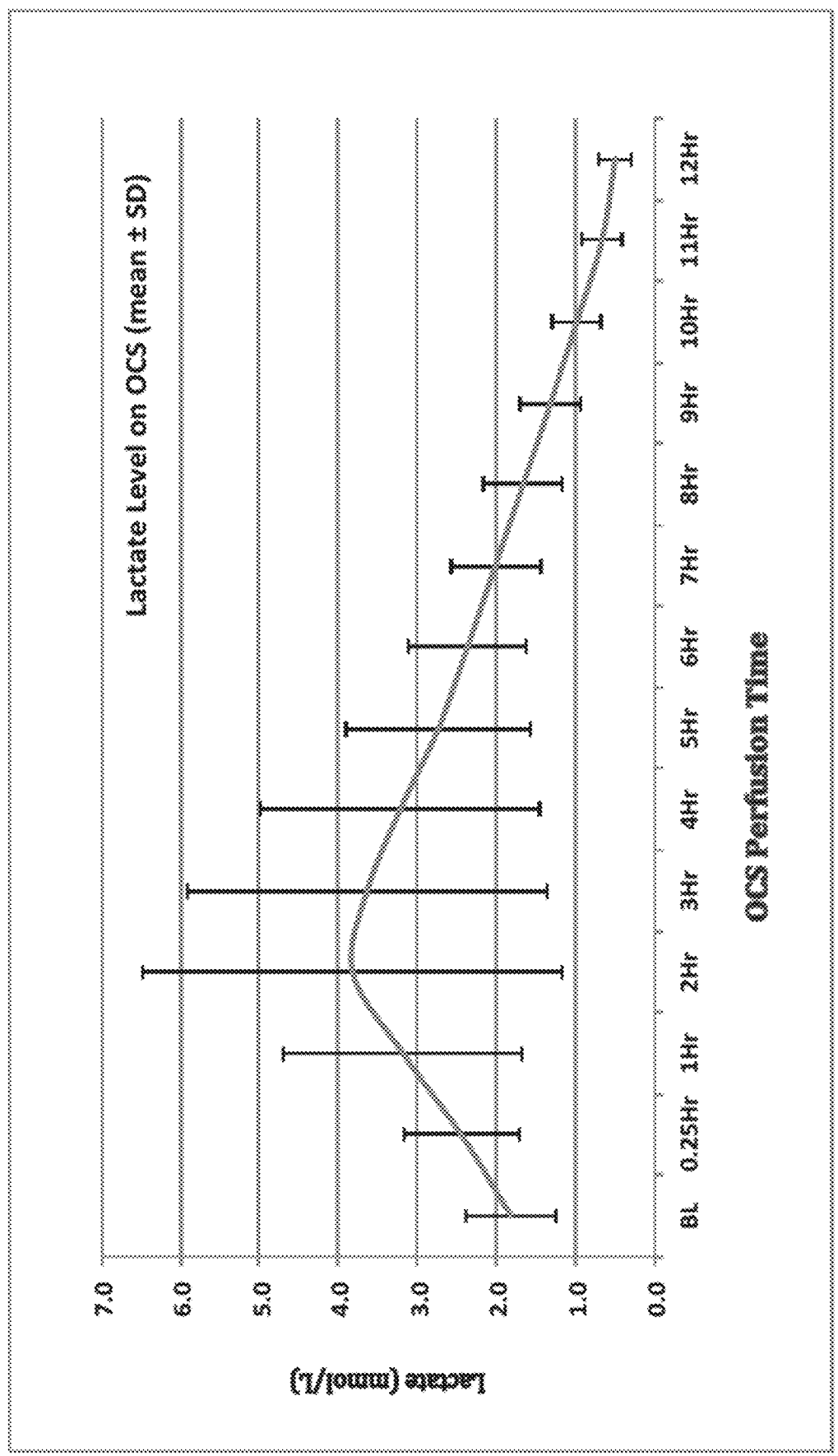
FIG. 45 depicts Arterial Lactate in a 12 hr OCS-Liver Perfusion.

FIG. 45 depicts Arterial Lactate in a 12 hr OCS-Liver Perfusion. The graph of FIG. 45 shows that OCS perfused swine livers demonstrated excellent metabolic function, as evidenced by their ability to clear lactate and trending down lactate levels throughout the course of 12 hours preservation on OCS.

Figure 46:
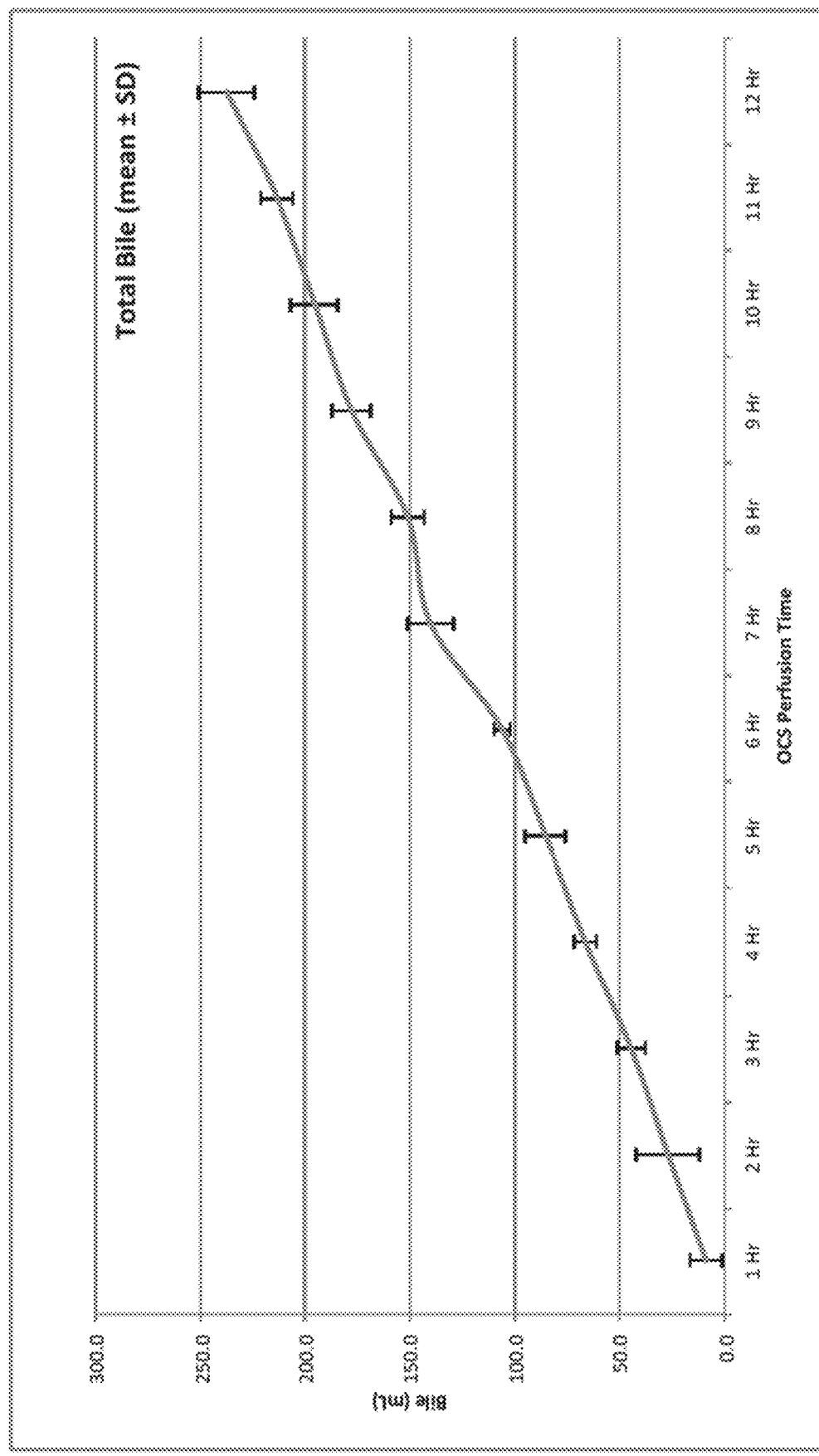
FIG. 46 depicts Bile Production in a 12 hr OCS-Liver Perfusion.

FIG. 46 depicts Bile Production in a 12 hr OCS-Liver Perfusion. The graph of FIG. 46 demonstrates that the OCS perfused Livers continued to produce bile at a rate of >10 ml/hr throughout the course of 12 hours preservation on OCS indicating well preserved organ function.

Figure 47:
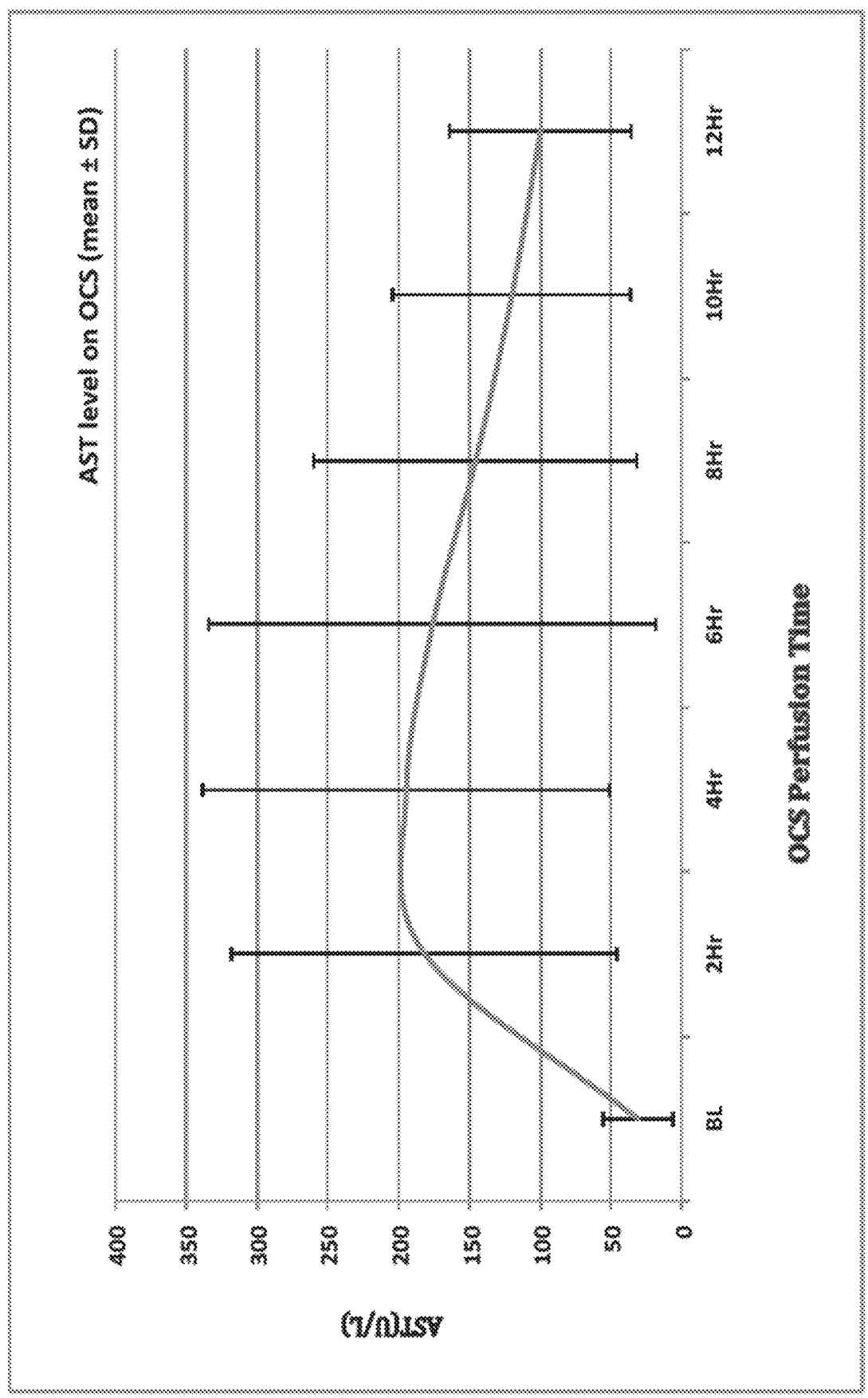
FIG. 47 depicts AST Level of a 12 hr OCS-Liver Perfusion.

FIG. 47 depicts AST Level of a 12 hr OCS-Liver Perfusion. Aspartate Aminotransferase (AST) is a standard marker clinically used to assess livers. The graph of FIG. 47 demonstrates that OCS perfused livers exhibited a trending down AST levels over the course of 12 hours perfusion on the OCS. This indicates good liver functions.

Figure 48:
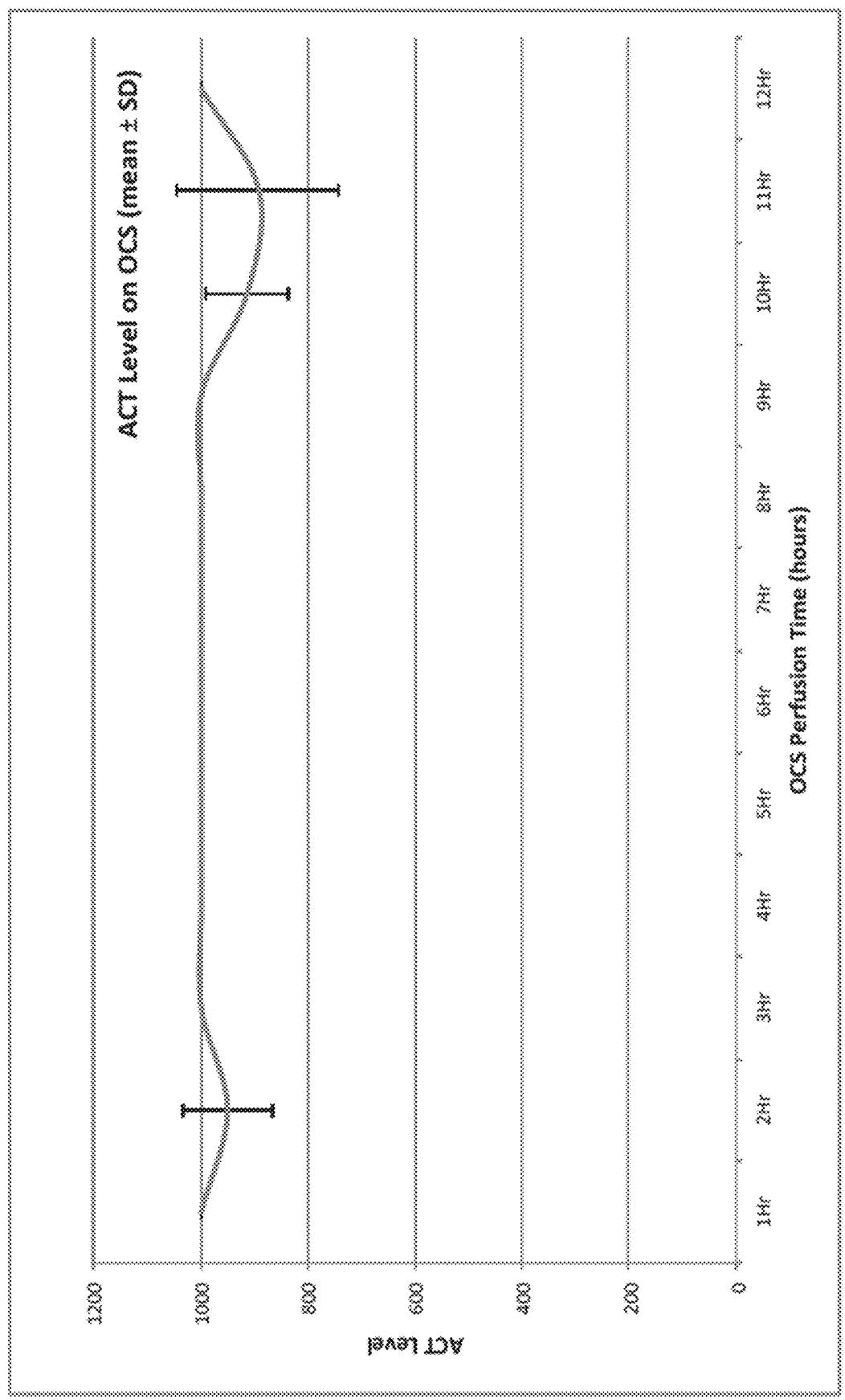
FIG. 48 depicts ACT Levels in a 12 hr OCS-Liver Perfusion.

FIG. 48 depicts ACT Levels in a 12 hr OCS-Liver Perfusion. Activated clotting time (ACT) was maintained above 300 sec over the course of 12 hours perfusion on the OCS, as illustrated in FIG. 48.

B. Phase II

Phase II, or Group C, included studies of 12 liver samples. Of those, 6 samples were preserved on the OCS for 8 hours using cellular based perfusate, and were then subjected to simulated transplant on the OCS for 4 hours of preservation using whole blood as perfusate. The other 6 samples were preserved for 8 hours using cold static preservation in UW solution, and were then subjected to simulated transplant on the OCS for 4 hours of preservation using whole blood as perfusate.

Objectives for Phase II include preserving the liver with OCS using warm perfusion for 8 hours using an RBCs based perfusate, followed by 45 minutes of cold ischemia, then another 4 hours of OCS-Liver warm perfusion using whole blood, (a) to optimally perfuse and preserve Livers on the OCS system for 8 hours using oncotic adjusted RBCs-based nutrient enriched perfusate, (b) maintain stable near-physiological heamodynamics (pressure and flow) for both the portal and the hepatic arterial circulation, (c) enable monitoring of organ functionality and stability on the OCS by monitoring bile production rate, liver enzymes trends, stable PH and arterial lactate levels, (d) subject the organ to 45 minutes of cold ischemia post the first 8 hours on the OCS, (e) followed by 4 hours of simulated transplant on the OCS using whole blood, while monitoring and assessing the organ heamodynamic and perfusion parameters and monitoring organ functionality.

Simulated transplant on the OCS was used to minimize the confounding variables associated with orthotopic transplantation and to isolate the variables to only the ischemia/reperfusion effects.

This group (C) of pre-clinical simulated transplant testing was expanded to include a control arm of cold stored swine livers using standard of care cold liver preservation solution. Except for the cold preservation phase, the protocol for this arm of the group was identical to the OCS simulated transplant arm of the same group (C). The detailed protocol and results are described below.

Like Phase I, 70-95 kg Yorkshires swine were used as a test subject for Phase II. For this phase, two animals were used for each study, with the first animal as the organ donor, and a second animal as a blood donor for the simulated phase of perfusion on the OCS.

In this simulated animal transplant model, the donor organ was exposed to the identical conditions of organ retrieval, preservation, and terminal cooling for transplantation as in orthotopic transplant. The only difference was that in the transplant phase the organ was reperfused with another animal's un-modified whole blood in an ex-vivo OCS perfusion system to control for all the confounding variables of orthotopic transplants that may shadow the true impact of preservation injury on the donor organ. The donor organ's function and markers of injury monitored during simulated transplant phase were identical to the ones that would be monitored during orthotopic transplantation. The acceptance criteria for Phase II samples were the same as those outlined above, and were measured during the 4 hours of simulated transplant.

1. Phase II, Simulated Transplant OCS Arm, 6 Samples (N=6).

This set was achieved by replicating all key clinical steps of liver retrieval, preservation and simulated transplantation processes in the following sequence:

Donor Organ Retrieval (30-45 minutes): During this phase, the donor organ was retrieved, and cold flushed for 30-45 minutes to replicate the clinical condition of donor liver retrieval and instrumentation on the OCS Liver system. The same prep, organ retrieval, cannulation and pre-OCS flush were performed as described in Phase I.

Donor Liver Preservation on OCS (8 hours): During this phase, the donor organ underwent ex-vivo perfusion and assessment using OCS Liver system. During this phase, the liver was monitored and assessed hourly for marker of liver injury (AST level), marker for metabolic function (Lactate level), and bile production rate as a marker for liver function/viability. The same organ preservation was performed for this group as the 8 hour preservation samples described in Phase I.

Post-OCS Preservation Cold Ischemia (45 minutes): During this phase the donor liver was flushed using cold flush solution as specified in the proposed clinical protocol to replicate final cooling of the donor liver required for re-implantation. Donor livers were maintained cold for 45 minutes to replicate the time required for performing the re-implantation procedure in the recipient. Using the Final Flush line included in the OCS Liver perfusion termination set, the liver was flushed and cooled on the OCS using 3 L of Cold PlasmaLyte solution supplemented with Sodium bicarbonate (NHCO3) 10 mml/L, Epoprostenol Sodium 2 mcg/L and Methylprednisolone 160 mg/L flush, supplying 1 liter at ~50-70 mmHg to the hepatic artery, and a 2 liter gravity drain to the portal vein. The liver was then disconnected from the OCS and placed in a cold saline bath for 45 minutes.

Final Reperfusion of the Donor Liver (4 hours): The transplantation was replicated/simulated by the following process to isolate the graft assessment markers of ischemia and reperfusion due to preservation technique from other confounding variables associated with the transplant model (described above). The liver graft was reperfused ex-vivo in a new OCS liver perfusion module using normothermic fresh whole blood from a different swine at 37° C. for 4 hours. For the simulated transplant phase, a new perfusion module was used to perfuse the organ on the OCS. The perfusion pressures/flows were controlled to near physiologic levels and temperature was maintained at 37° C. The liver was monitored hourly for the same markers as in the preservation period. In addition, liver tissue samples were evaluated histologically to assess hepatic tissue architecture and any signs of injury in the same way as described above in Phase I.

2. Phase II, Simulated Transplant Cold Preservation Control Arm (N=6).

This was achieved by replicating all key clinical steps of liver retrieval, preservation and simulated transplantation processes in the following sequence:

Donor Organ Retrieval (30-45 minutes): During this phase, the donor organ was retrieved, for 30-45 minutes to replicate the clinical condition of donor liver retrieval. The same prep, organ retrieval, cannulation and pre-OCS flush were performed as described in Phase I.

Donor liver cold preservation: During this phase, the donor liver was preserved for 8 hours using standard of care cold storage solution Belzer UW® (UW Solution) for liver flush and storage at 2-5° C. to mimic the standard of care for liver cold preservation.

Post-cold Preservation, organ flush and preparation (45 minutes): During this phase the donor liver was flushed with cold flush solution using the final flush line included in the OCS liver perfusion termination set. The liver was flushed using 3 L of cold PlasmaLyte solution supplemented with Sodium bicarbonate (NaHCO3) 10 mml/L, Epoprostenol Sodium 2 mcg/L and Methylprednisolone 160 mg/L flush, supplying 1 liter at ~50-70 mmHg to the hepatic artery, and a 2 liter gravity drain to the portal vein. The liver was then disconnected from the OCS and placed in a cold saline bath for 45 minutes.

Final Reperfusion of the Donor Liver (4 hours): The transplantation was replicated/simulated by the following process to isolate the graft assessment markers of ischemia and reperfusion due to preservation technique from other confounding variables associated with the transplant model (described above). The liver graft was reperfused ex-vivo in a new OCS liver perfusion module using normothermic fresh whole blood from a different swine for 4 hours. The perfusion pressures/flows were controlled to near physiologic levels and temperature was maintained at 37° C. The liver was monitored hourly for the same markers as in the preservation period. In addition, liver tissue samples were evaluated histologically to assess hepatic tissue architecture and any signs of injury in the same way as described above in Phase I.

The results observed for Phase II, indicate that samples that were perfused using the OCS system achieved better post-perfusion results than samples that were subjected to cold storage. The samples that were subject to cold storage, did not meet the acceptance criteria described previously during the 4 hours of simulated transplant, as compared to the OCS arm of the group.

In the cold storage control arm, the metabolic liver functions demonstrated unstable and worsening profile over the course of the 4 hours of the simulated transplant as evidenced by the higher and unstable lactate trend, as compared to the OCS arm of the group, which demonstrated much better metabolic function, as evidenced by trending down arterial lactate. This indicates that the OCS-arm livers had significantly better metabolic function as compared to the cold storage control arm. In the cold storage control arm, the liver enzyme (AST) profile, which is a sensitive marker of liver injury, was unstable and trending up to much higher levels than the OCS arm of the group. This indicates compromised liver functions for liver grafts in the control arm, as compared to the well perseved and good functioning liver grafts in the OCS arm, which was demonstrated by much lower level of Liver enzyme (AST) trend in the OCS arm. In the cold storage control arm, the pH trend required much higher doses of HCO3 to achieve and maintain a stable metabolic profile, than the doses required for the OCS arm of the group. This indicates that the OCS arm was able to maintain a much better metabolic profile than the cold storage control arm. The bile production rate was less in the cold storage control arm than in the OCS arm. This indicates better liver graft functions in the OCS arm as compared to the cold storage control arm. The perfusion parameters were comparable for both arms of the group. Based on the above comparison results, the OCS arm successfully met the protocol pre-specified acceptance criteria while the cold storage control arm did not meet the identical acceptance criteria.

Figure 49:
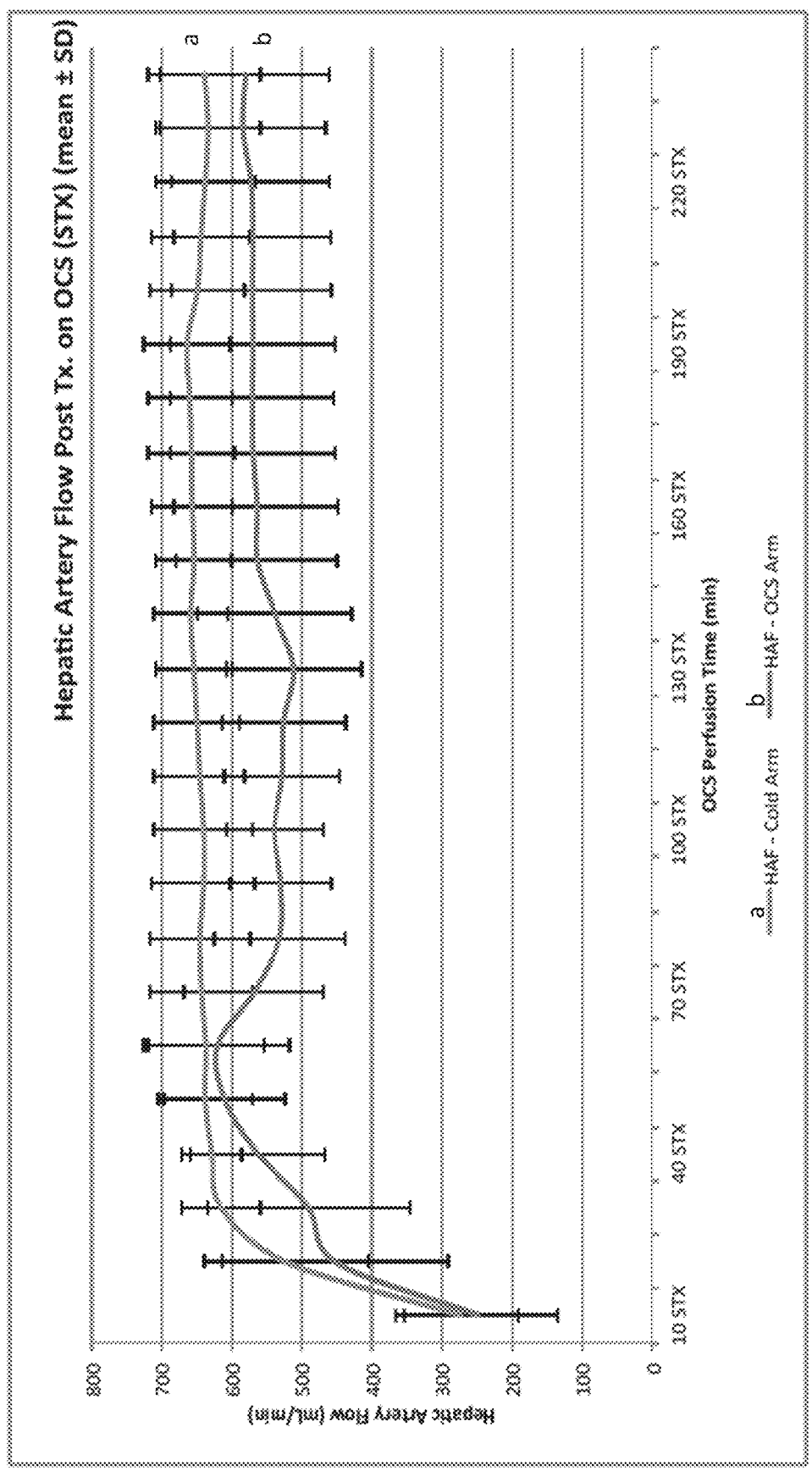
FIG. 49 depicts Hepatic Artery Flow on a simulated transplant OCS-Liver preservation arm vs. a simulated transplant control cold preservation arm.

FIG. 49 depicts Hepatic Artery Flow on a simulated transplant OCS-Liver preservation arm vs. a simulated transplant control cold preservation arm. As illustrated, the graph of FIG. 49 depicts stable Hepatic Artery Flow (HAF) over the course of 4 hours of perfusion on the OCS during the simulated transplant period.

Figure 50:
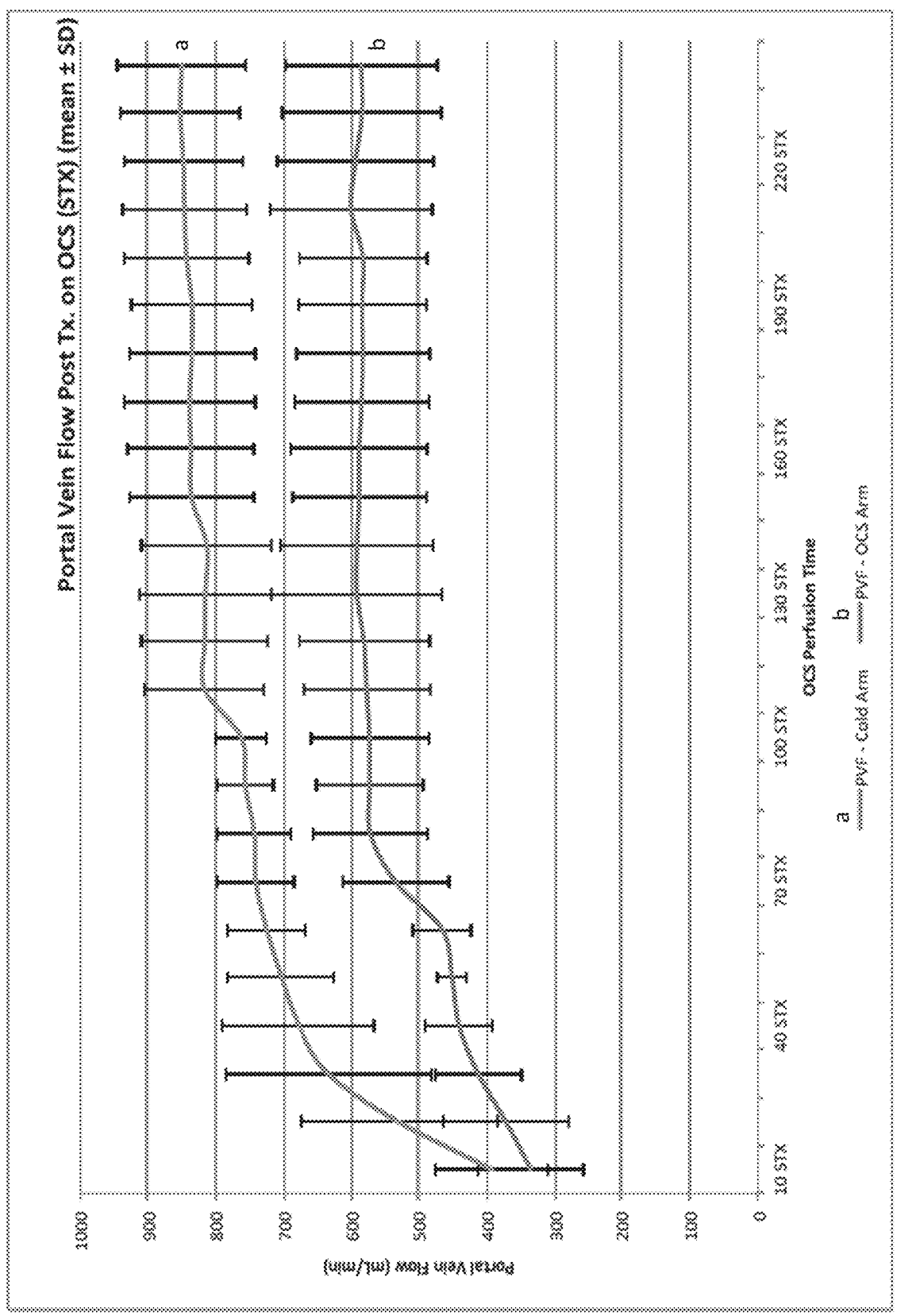
FIG. 50 depicts Portal Vein Flow on a simulated transplant OCS-Liver preservation arm vs. a simulated transplant control cold preservation arm.

FIG. 50 depicts Portal Vein Flow on a simulated transplant OCS-Liver preservation arm vs. a simulated transplant control cold preservation arm. As illustrated in FIG. 50, the graph demonstrates Stable Portal Vein Flow (PVF) over the course of 4 hours perfusion on the OCS during the simulated transplant period.

Figure 51:
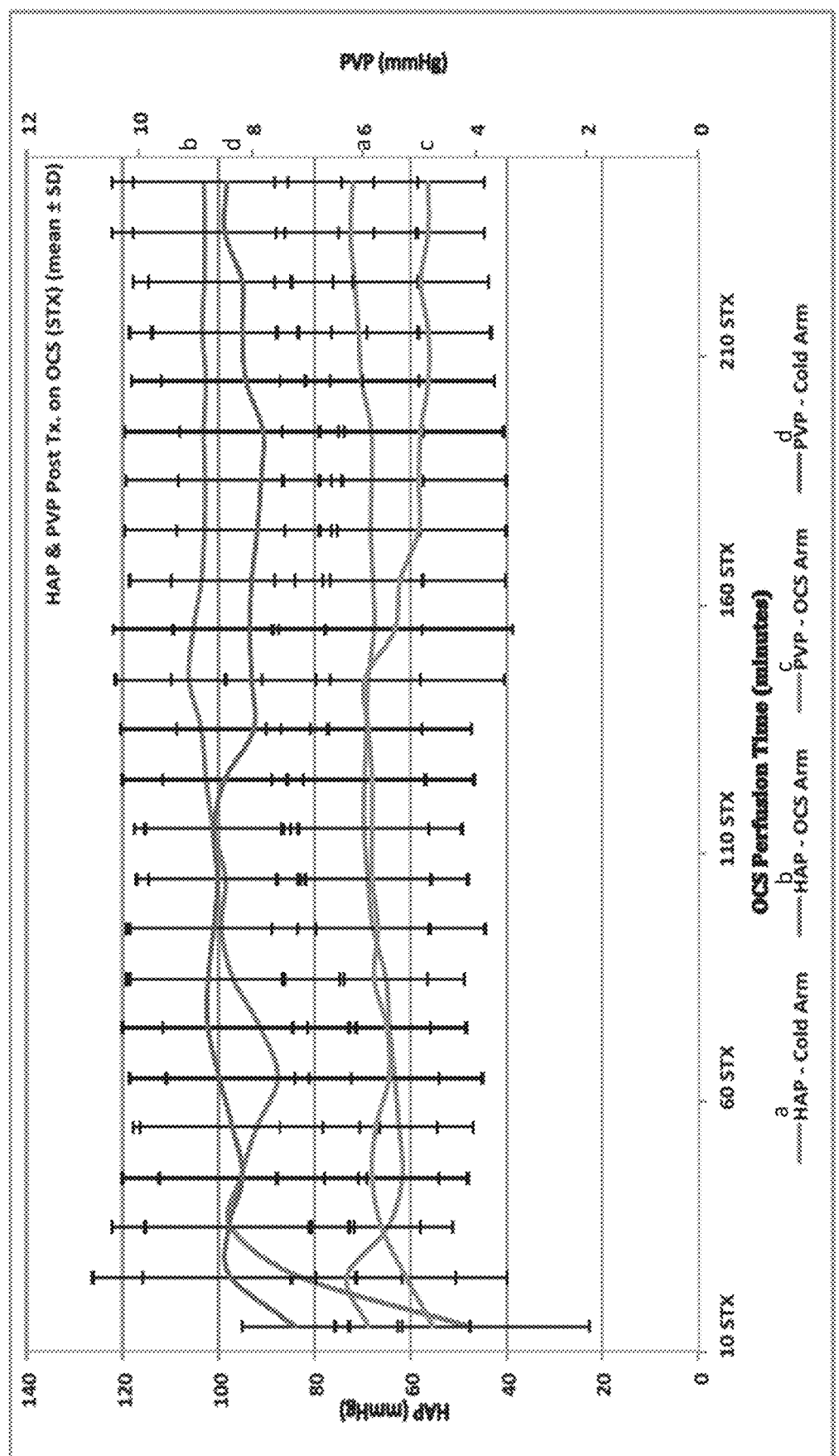
FIG. 51 depicts Hepatic Artery Pressure vs. Portal Vein Pressure in a simulated transplant OCS-Liver preservation arm vs. a simulated transplant control cold preservation arm.

FIG. 51 depicts Hepatic Artery Pressure vs. Portal Vein Pressure in a simulated transplant OCS-Liver preservation arm vs. a simulated transplant control cold preservation arm. The graph of FIG. 51 demonstrates a stable Hepatic Artery Pressure (HAP) and Portal Vein Pressure (PVP) trend over the course of 4 hours perfusion on the OCS.

Figure 52:
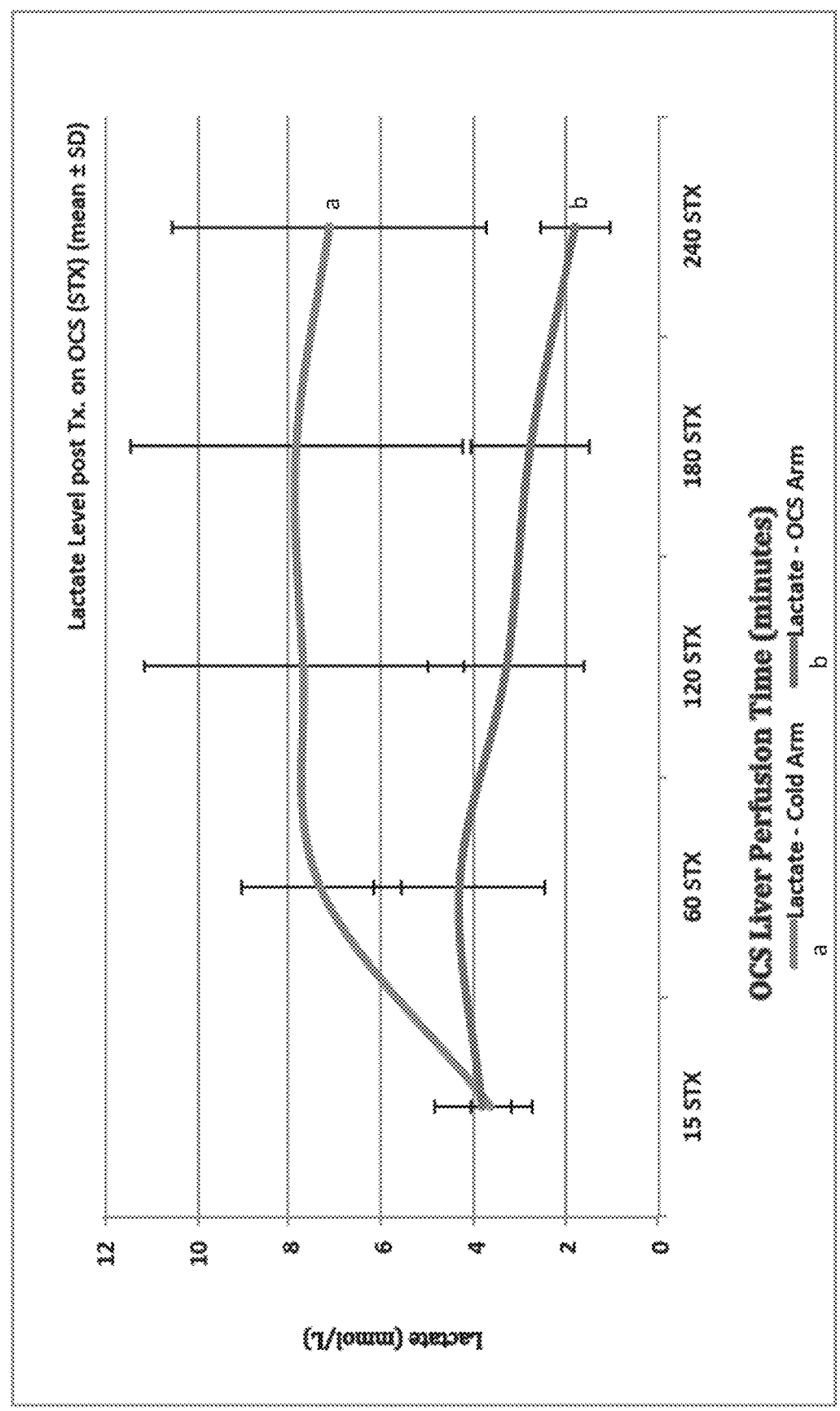
FIG. 52 depicts Arterial Lactate on a simulated transplant OCS-Liver preservation arm vs. a simulated transplant control cold preservation arm.

FIG. 52 depicts Arterial Lactate on a simulated transplant OCS-Liver preservation arm vs. a simulated transplant control cold preservation arm. The graph of FIG. 52 demonstrate that the OCS-arm perfused livers had a much better metabolic function, as evidenced by trending down arterial Lactate. This indicates that the OCS-arm livers had significantly better metabolic function as compared to cold stored arm.

Figure 53:
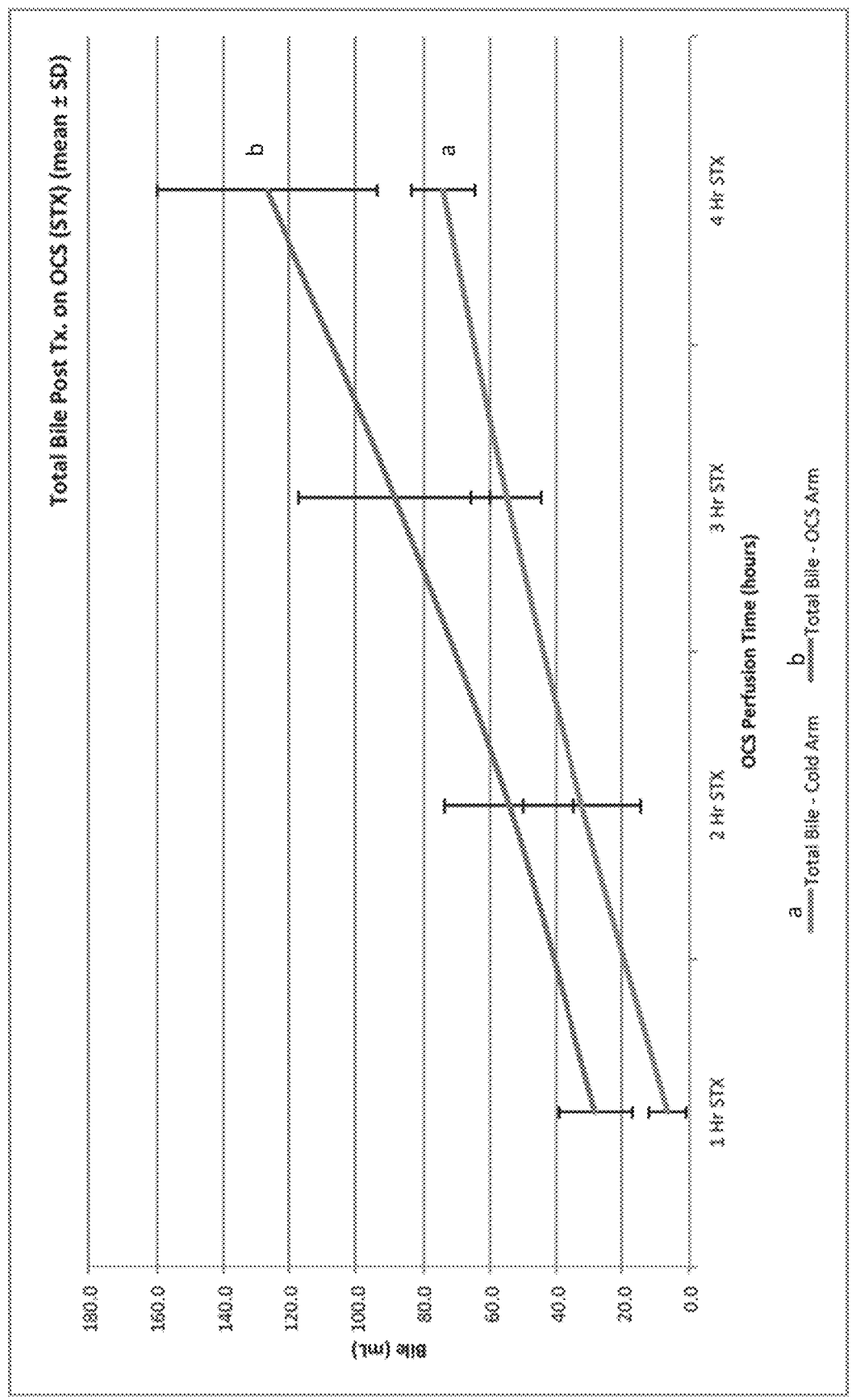
FIG. 53 depicts bile production of a simulated transplant OCS-Liver preservation arm vs. a simulated transplant control cold preservation arm.

FIG. 53 depicts bile production of a simulated transplant OCS-Liver preservation arm vs. a simulated transplant control cold preservation arm. The graph of FIG. 53 demonstrates that the OCS arm perfused livers had a higher bile production rate as compared to cold stored livers. This indicates better liver graft function in the OCS group vs. a cold stored group.

Figure 54:
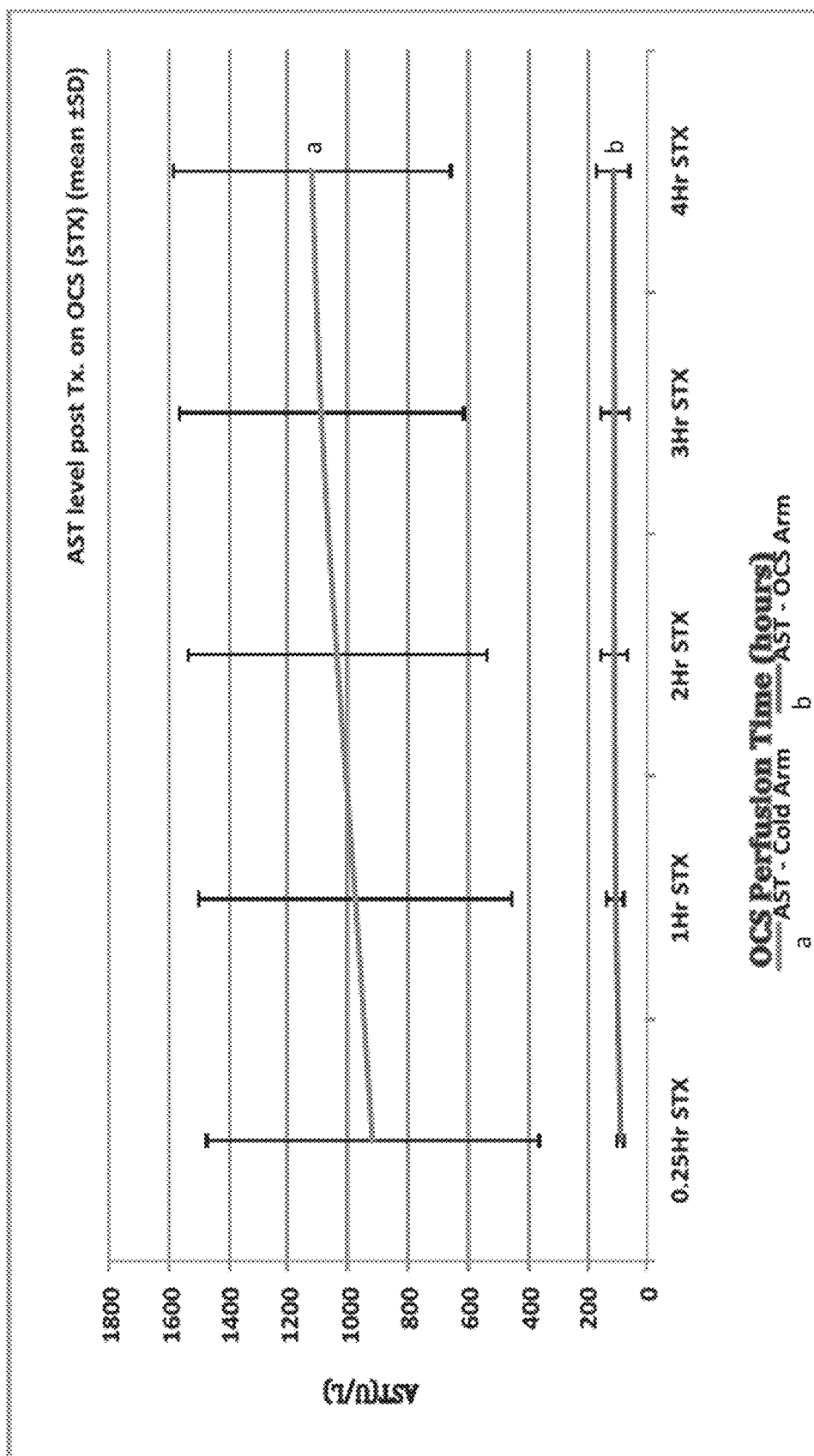
FIG. 54 depicts a AST Level of simulated transplant OCS-Liver preservation arm vs. a simulated transplant control cold preservation arm.

FIG. 54 depicts a AST Level of simulated transplant OCS-Liver preservation arm vs. a simulated transplant control cold preservation arm. The graph of FIG. 54 demonstrates that the OCS perfused livers had a significantly lower AST levels throughout the 4 hour simulated transplant period. This indicates significantly less liver injury to the graft in the OCS group as compared to the cold stored group.

Figure 55:
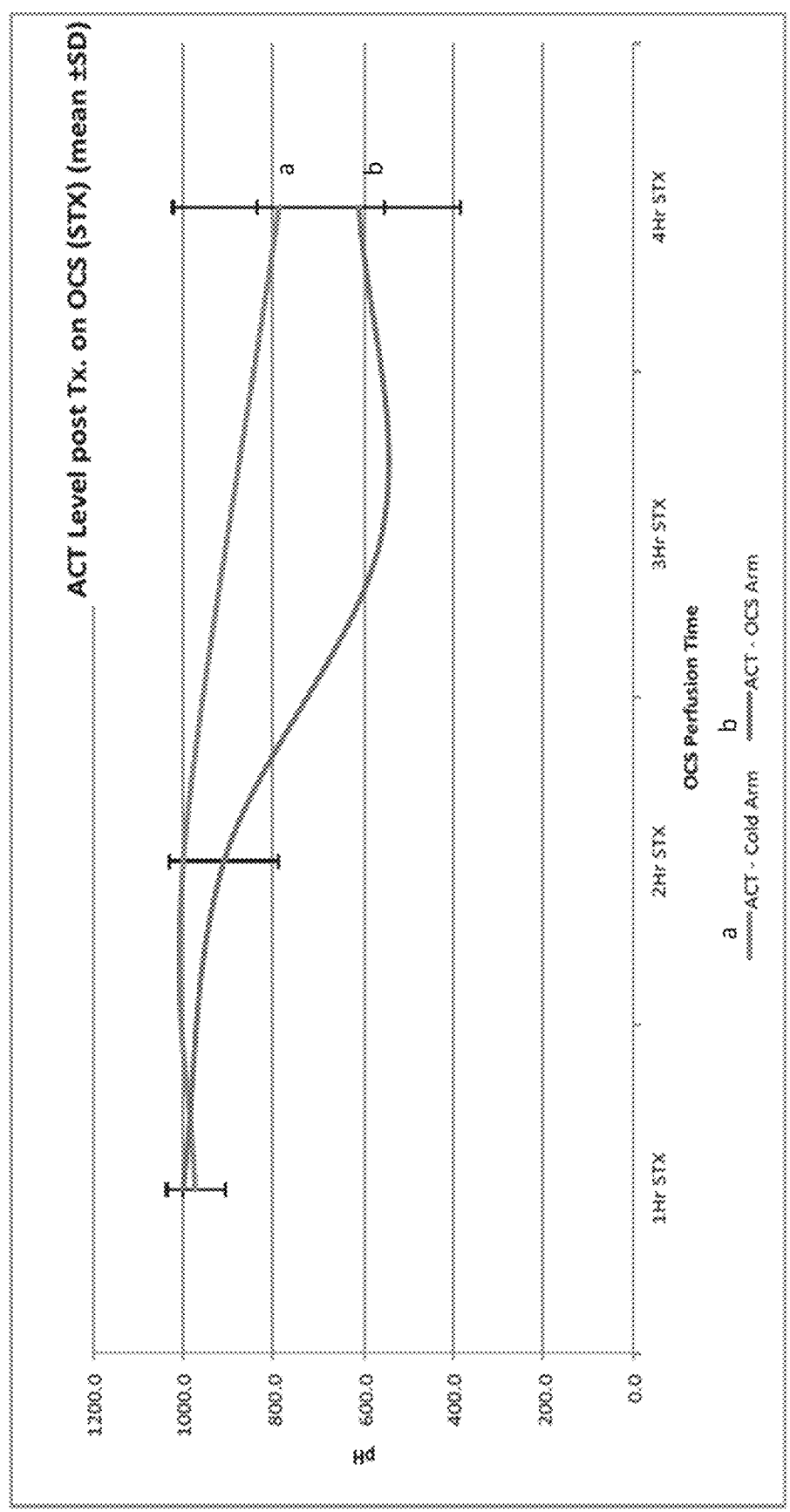
FIG. 55 depicts ACT Levels of a simulated transplant OCS-Liver preservation arm vs. a simulated transplant control cold preservation arm.

FIG. 55 depicts ACT Levels of a simulated transplant OCS-Liver preservation arm vs. a simulated transplant control cold preservation arm. Activated clotting time (ACT) was maintained above 300 sec over the course of 8 hours perfusion on the OCS.

Figure 56:
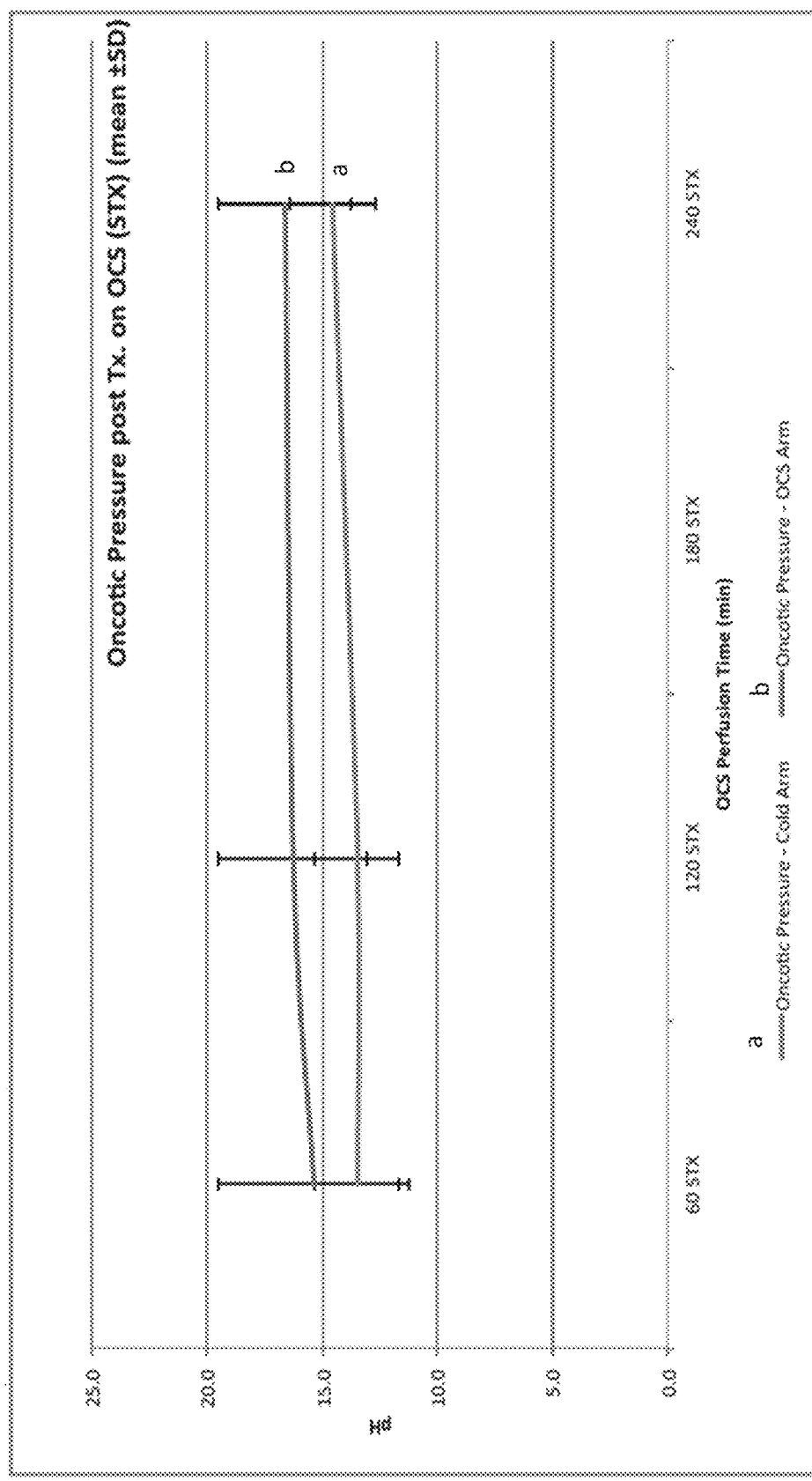
FIG. 56 depicts oncotic pressure of a simulated transplant OCS-Liver preservation arm vs. a simulated transplant control cold preservation arm.

FIG. 56 depicts oncotic pressure of a simulated transplant OCS-Liver preservation arm vs. a simulated transplant control cold preservation arm. As depicted in FIG. 56, there was stable oncotic pressure on the OCS-Liver preservation arm.

Figure 57:
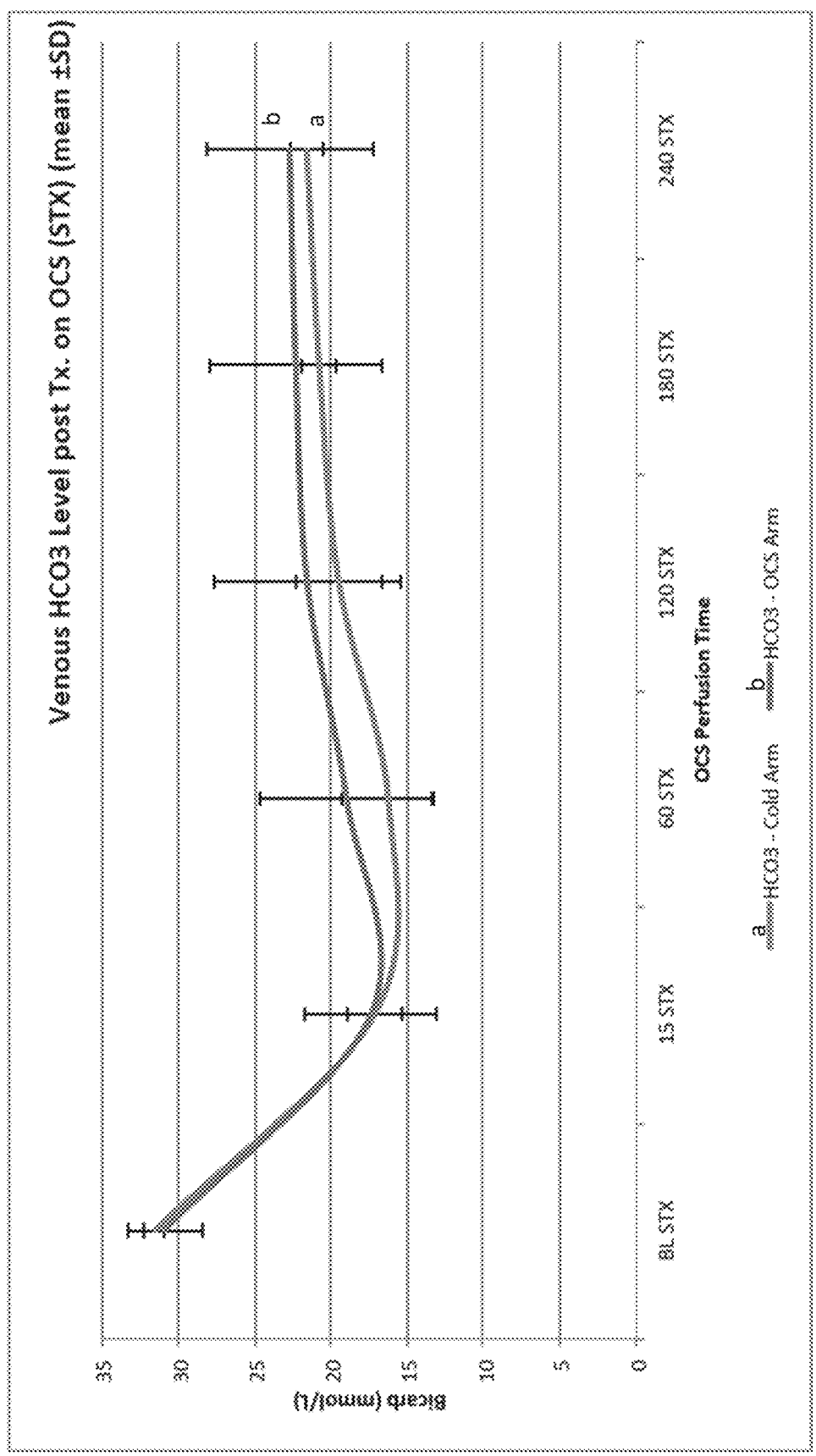
FIG. 57 depicts the Bicarb Level of a simulated transplant OCS-Liver preservation arm vs. a simulated transplant control cold preservation arm.

FIG. 57 depicts the Bicarb Level of a simulated transplant OCS-Liver preservation arm vs. a simulated transplant control cold preservation arm.

Figure 58:
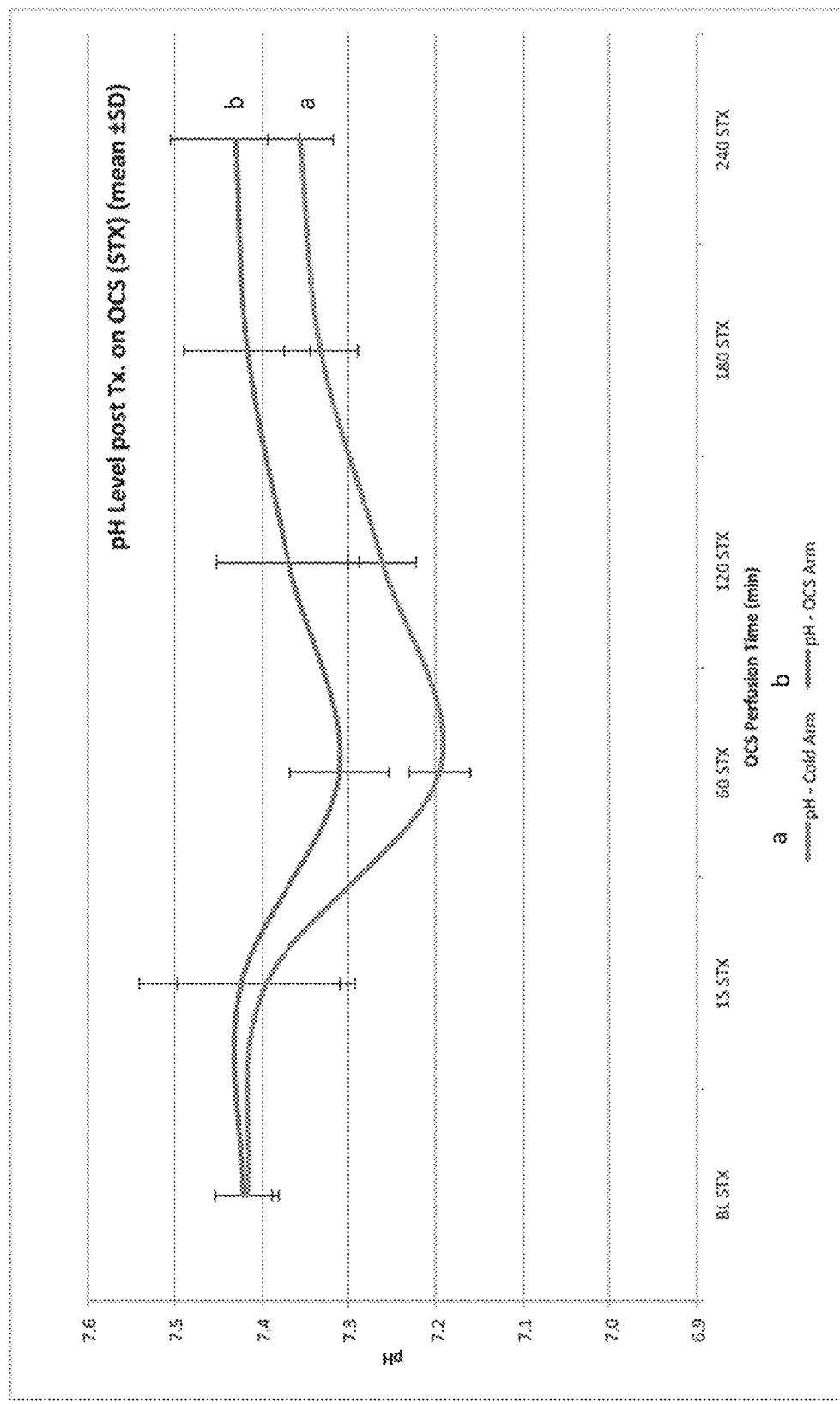
FIG. 58 depicts pH Levels of a simulated transplant OCS-Liver preservation arm vs. a simulated transplant control cold preservation arm.

FIG. 58 depicts pH Levels of a simulated transplant OCS-Liver preservation arm vs. a simulated transplant control cold preservation arm. The graph of FIG. 58 demonstrates that an OCS perfused liver had better pH values over the course of 4 hours of perfusion on the OCS as compared to the cold stored livers. OCS perfused livers needed very minimal HCO3 correction as compared to the cold stored group, this is an indication of better functioning liver grafts in the OCS arm as compared to the control arm.

Figure 59:
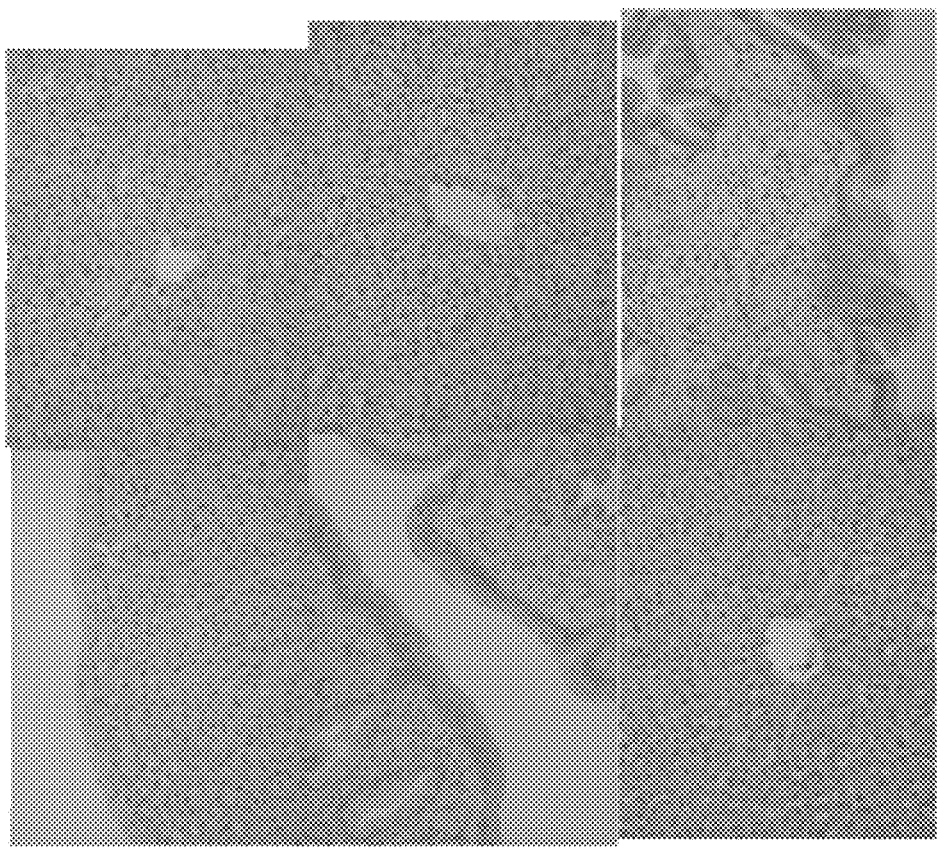
FIG. 59 shows the histological examination of Parenchymal tissue and Bile duct tissue.

As illustrated in FIG. 59, histological examination of Parenchymal tissue and Bile duct tissue shows normal liver sinusoidal structure with no evidence of necrosis or ischemia and normal bile duct epithelial cells indicating adequate perfusion and lack of ischemic injury.

Figure 60:
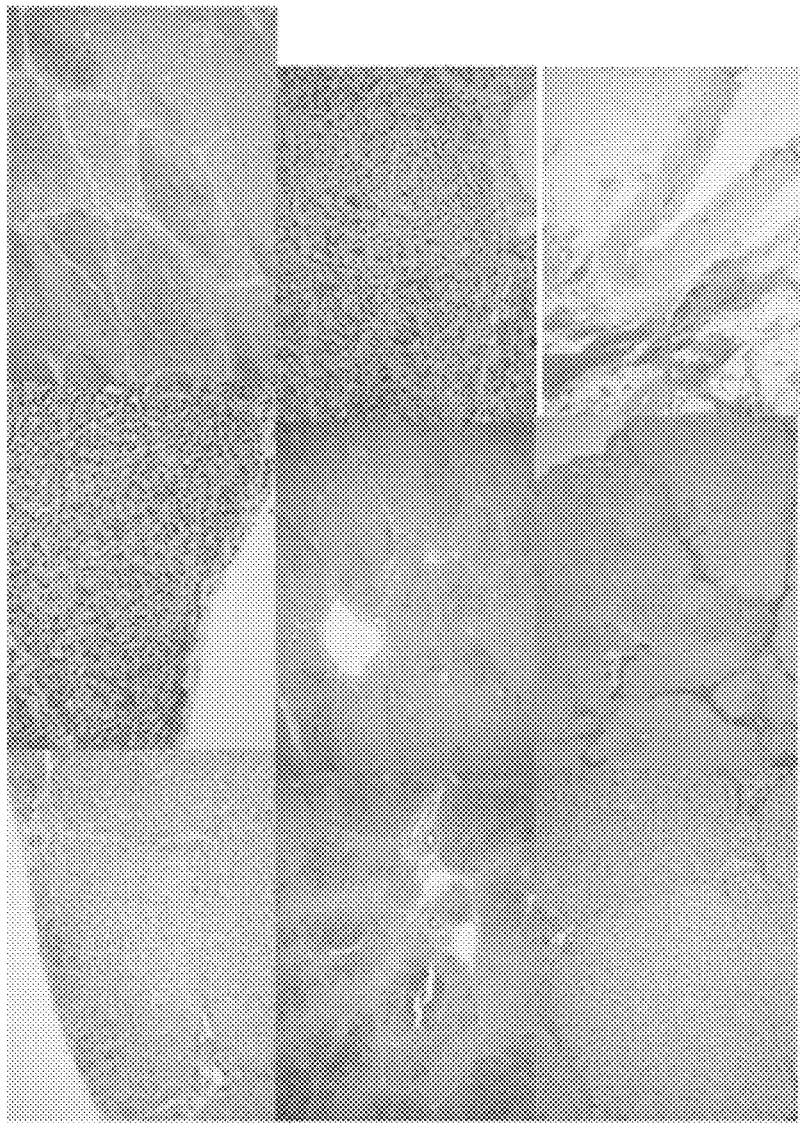
FIG. 60 shows the histological examination of Parenchymal tissue and Bile duct tissue.

As illustrated in FIG. 60, histological examination of Parenchymal tissue and Bile duct tissue shows significant hemorrhage and congestion within the parenchyma, Interlobular hemorrhage, multifocal wide spread interlobular hemorrhage, and Lobular congestion.

C. Phase III

This group of pre-clinical simulated transplant testing was conducted to compare OCS preserved livers (3 samples) for 12 hours versus control arm livers preserved cold (3 samples) using the standard of care cold liver preservation solution Belzer UW® (UW Solution) for 12 hours. Both the OCS arm and the cold storage arm were then assessed for 24 hours in a simulated transplant model on the OCS using leukocyte-reduced blood from a different animal. Except for the cold preservation phase, the protocol for both arms of the group was identical. During the simulated transplant phase, organ function and stability were assessed by monitoring and measuring stable perfusion parameters maintained in pre-specified ranges, bile production, liver biomarkers including AST, ALT, ALP, GGT, and total bilirubin, pH levels, and arterial lactate levels. After the simulated transplant phase, livers were sampled for histopathology assessment. The acceptance criteria for this phase was the same as the acceptance criteria outlined in phase I.

1. OCS Arm:

Donor Organ Retrieval: During this phase, the donor organ was retrieved, and cold flushed to replicate the clinical condition of donor liver retrieval and instrumentation on the OCS Liver system. The same prep, organ retrieval, cannulation and pre-OCS flush were performed as described in Phase I.

Donor Liver Preservation on OCS (12 hours): During this phase, the donor organ underwent ex-vivo perfusion and assessment using OCS Liver system. Similar organ preservation was performed for this group as the 8 hour preservation samples described in phase 1. The prime perfusate was composed of 1500-2000 ml RBCs (Haemonetics Cell Saver), 400 ml Albumin 25%, 700 ml of PlasmaLyte, Antibiotic (gram positive and gram negative) 1 g Cefazolin and 100 mg Levofloxacin, 500 mg of Solu-Medrol, 20 mg, Dexamethasone, 50 mmol Hco3, 1 vial of multivitamin, and 10 ml of Ca gluconate (4.65 mEq)

During preservation, 80% O2 was used starting at a rate of 450 ml/min starting just before organ instrumentation and was adjusted according to the arterial pCO2 and pO2. Temperature was maintained at 34° C.

Continuous infusion was delivered using the integrated OCS-SDS. Flolan was added to the HA inflow at 0-20 mic/hr (0-20 ml/hr), as needed (0.05 mg Flolan in 50 ml of Flolan Diluent "1 mic/ml"). CLINIMIX E TPN with 30 IU of insulin, 25 g of glucose and 40000 U of Heparin added was continuously infused to the PV at a rate of 30 mL/h starting with priming. Na Taurocholic Salt, Gama sterilized Bile salt was infused at a rate of 3 mL/h (concentration 1 g/50 ml sterile water) starting with priming.

Target pressures and flows were: Portal Vein pressure 1-8 mmHg; Portal Vein flow 0.7-1.7 L/min; Hepatic Artery pressure 85-110 mmHg; and Hepatic artery flow 0.3-0.7 L/min.

Using the Final Flush line included in the OCS Liver perfusion termination set, the liver was flushed and cooled on the OCS using 3 L of Cold PlasmaLyte solution, supplying 1 liter at ~50-70 mmHg to the hepatic artery, and a 2 liter gravity drain to the portal vein. The liver was then disconnected from the OCS and placed in a cold saline bath for 45 minutes.

2. Cold Static Preservation Storage Arm:

The same prep, organ retrieval, cannulation and pre-OCS flush were performed as described in Phase I.

After flushing the organ with 3 Liters of UW, it was stored cold in UW solution at temperature ~5 degree for 12 hours. Using the Final Flush line included in the OCS Liver perfusion termination set, the liver was flushed and cooled on the OCS using 3 L of Cold PlasmaLyte solution, supplying 1 liter at ~50--70 mmHg to the hepatic artery, and a 2 liter gravity drain to the portal vein. The liver was then disconnected from the OCS and placed in a cold saline bath for 45 minutes.

Both sets of livers were subjected to the post-transplant phase for 24 hours, where they were instrumented onto an OCS machine and supplied with a post-perfusate solution comprising 1500-3000 ml leukocytes reduced blood, 100 ml Albumin 25%, Antibiotic (gram positive and gram negative) 1 g Cefazolin and 100 mg Levofloxacin, 500 mg of Solu-Medrol, 20 mg, Dexamethasone, 50 mmol HCO3, 1 vial of multivitamin, and 10 ml of Ca gluconate (4.65 mEq). During simulated transplant, 80% O2 was used starting at a rate of 450 ml/min starting just before organ instrumentation and was adjusted according to the arterial pCO2 and pO2. Temperature was maintained at 37° C.

Continuous infusion was delivered using the integrated OCS-SDS. Flolan was added to the HA inflow at 0-20 mic/hr. (0-20 ml/hr.), as needed (0.05 mg Flolan in 50 ml of Flolan Diluent "1 mic/ml"). CLINIMIX E TPN with 30 IU of insulin, 25 g of glucose and 40000 U of Heparin added was continuously infused to the PV at a rate of 30 mL/h starting with priming. Na Taurocholic Salt, Gama sterilized Bile salt was infused at a rate of 3 mL/h (concentration 1 g/50 ml sterile water) starting with priming.

Target pressures and flows were: Portal Vein pressure 1-8 mmHg; Portal Vein flow 0.7-1.7 L/min; Hepatic Artery pressure 85-110 mmHg; and Hepatic artery flow 0.3-0.7 L/min.

Using the Final Flush line included in the OCS Liver perfusion termination set, the liver was flushed and cooled on the OCS using 3 L of Cold PlasmaLyte solution, supplying 1 liter at ~50-70 mmHg to the hepatic artery, and a 2 liter gravity drain to the portal vein. Each Liter will be supplemented by 10 mmol HCO3 and 150 mg of Solu-Medrol. The liver was then disconnected from the OCS and placed in a cold saline bath for 45 minutes. Table 9 below illustrates the liver perfusate infusions and rate.

TABLE 9

OCS liver perfusate infusions and rate

| Continuous Infusion Mix | Dose |
| --- | --- |
| Total parenteral nutrition (TPN) Mix: CLINIMIX E TPN (4.25% Amino Acid/ 10% Dextrose); PLUS Insulin 30 IU Glucose 20 gms Heparin 40,000 units | 30 ml/hr |
| As Needed Additives | Dose |
| Prostacyclin infusion as needed to control Hepatic artery pressure - e.g. Epoprostenol Sodium 0.5 mg | 0-20 mics/hr |

TABLE 9-continued

OCS liver perfusate infusions and rate

| Bile Salts e.g. Taurocholic acid sodium (1 gm/50 ml) | 0-10 ml/hr |
| --- | --- |
| NaHCO3 8.4% to correct metabolic acidosis | 1.5 meq/1 base excess |

Figure 61:
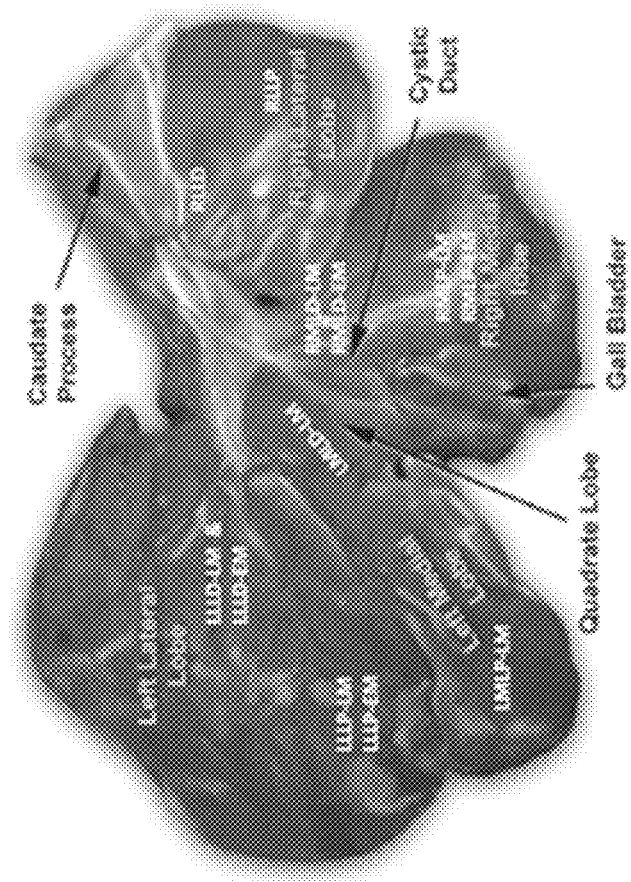
FIG. 61 is a diagram illustrating locations of samples from a liver of a pig.

FIG. 61 is a samples location diagram illustrating locations of samples from a liver of a pig.

The following liver histopathology sampling protocol was followed to assess the sample livers.

Samples collection time: At completion of the experiment (at the end of the 24 hr simulated transplant phase).

Method and Samples Collected:
1. Gross Picture: photographs of capsular and under surface of the OCS and CS livers at the beginning of the gross examination post study.
2. Bile Duct: entire extra-hepatic bile duct and as much adherent surrounding tissue (not surgically dissected from the surrounding tissue) in a neutral-buffered formalin jar.
3. Electron Microscopy (EM): 0.1 cm (1 mm) fragment of the liver tissue from the peripheral and deep aspect of the Left Lateral Lobe and the Right Medial Lobe. Place the tissue specimen in electron microscopy fixative.
4. Hepatic Parenchyma (LM): 1×1 cm sections obtained from the periphery and deep aspects of each lobe (total of 8), and preserved in Formalin. Sections thickness no more than 3-5 mm and fixative volume 15-20 times higher than the specimen volume. Any obvious defect was sampled.

Samples Locations:

Two samples were collected from each lobe according to the FIG. 61 to access the hepatic parenchyma, each sample will be preserved in separate jar filled with 10% formalin and labeled accordingly.
1. Left Lateral Lobe Peripheral-LM (LLLP-LM)
2. Left Lateral Lobe Peripheral-EM (LLLP-EM)
3. Left Lateral Lobe Deep-LM (LLLD-LM)
4. Left Lateral Lobe Deep-EM (LLLD-EM)
5. Left Medial Lobe Peripheral-LM (LMLP-LM)
6. Left Medial Lobe Deep-LM (LMLD-LM)
7. Right Medial Lobe Peripheral-LM (RMLP-LM)
8. Right Medial Lobe Peripheral-EM (RMLP-EM)
9. Right Medial Lobe Deep-LM (RMLD-LM)
10. Right Medial Lobe Deep-EM (RMLD-EM)
11. Right Lateral Lobe Peripheral-LM (RLLP-LM)
12. Right Lateral Lobe Deep-LM (RLLD-LM)
13. Extra-Hepatic Bile Duct (EHBD)

Data Collection and Analysis

Preservation data was summarized in tabular and graphic form, depending on the variable. Then continuous variables were analyzed with means, medians, standard deviations, and minimum and maximum values. After that, AST, ALT, GGT, ALP test results were collected, recorded and attached. Next, arterial lactate was collected, recorded and attached. pH was then measured, recorded and attached. HCO3 levels were then measured, recorded and attached. Lastly, total bile produced volume was collected and recorded.

Results of Phase III.

Figure 62:
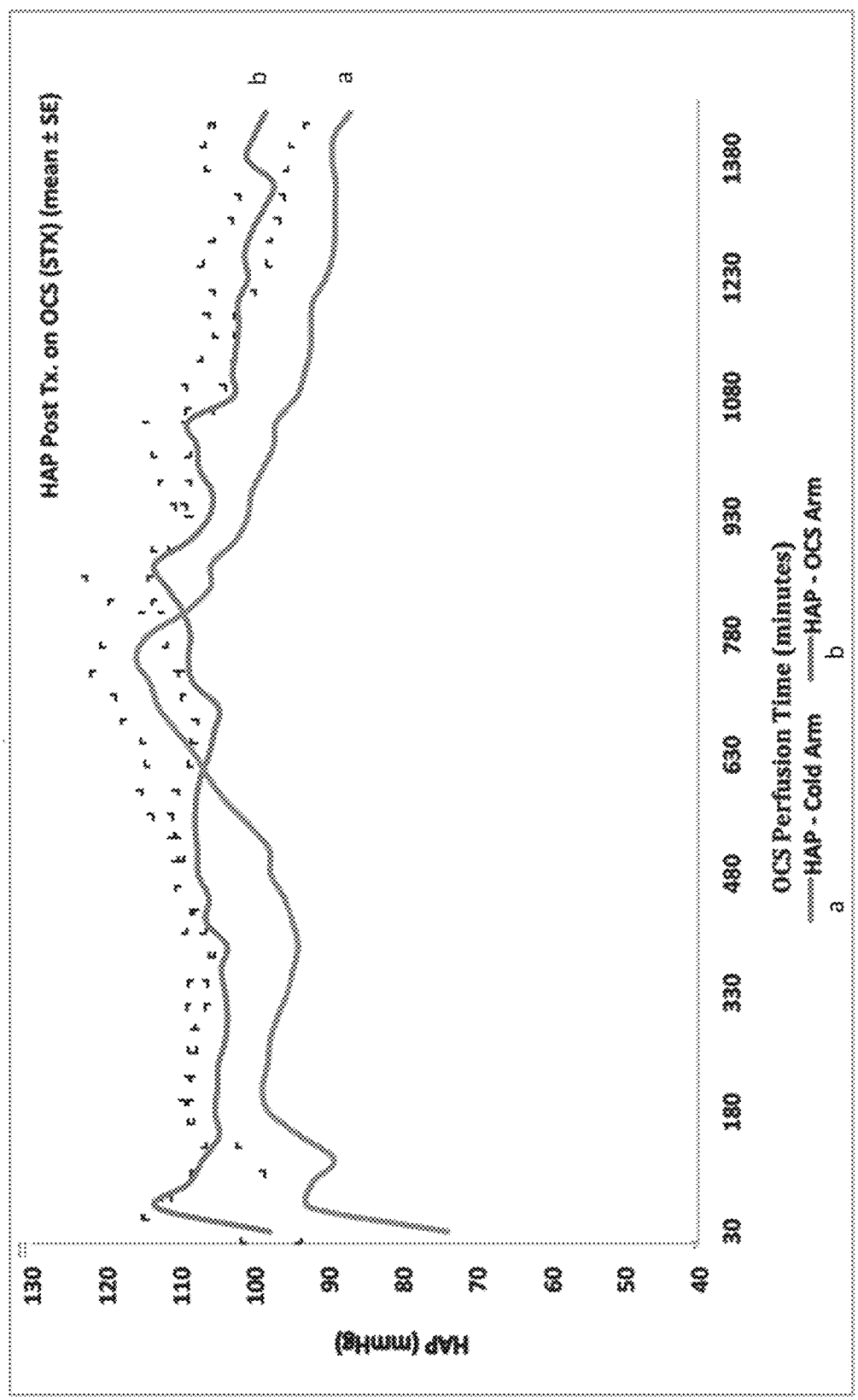
FIG. 62 illustrates the Hepatic Artery Pressure (HAP) trend over the course of 24 hours perfusion on the OCS.

The OCS arm (N=3) of this group successfully met all of the acceptance criteria, which was pre-specified in the protocol, by demonstrating the following throughout the 24 hours of the simulated transplant phase: Stable perfusion parameters throughout preservation on the OCS for HAF, HAP, PVF and PVP, stable or trending down arterial lactate, continuous bile production with a rate of >10 ml/hr., stable or trending down liver enzymes (AST), and normal and stable perfusate PH. For example, FIG. 62 illustrates the Hepatic Artery Pressure (HAP) trend over the course of 24 hours perfusion on the OCS.

Figure 63:
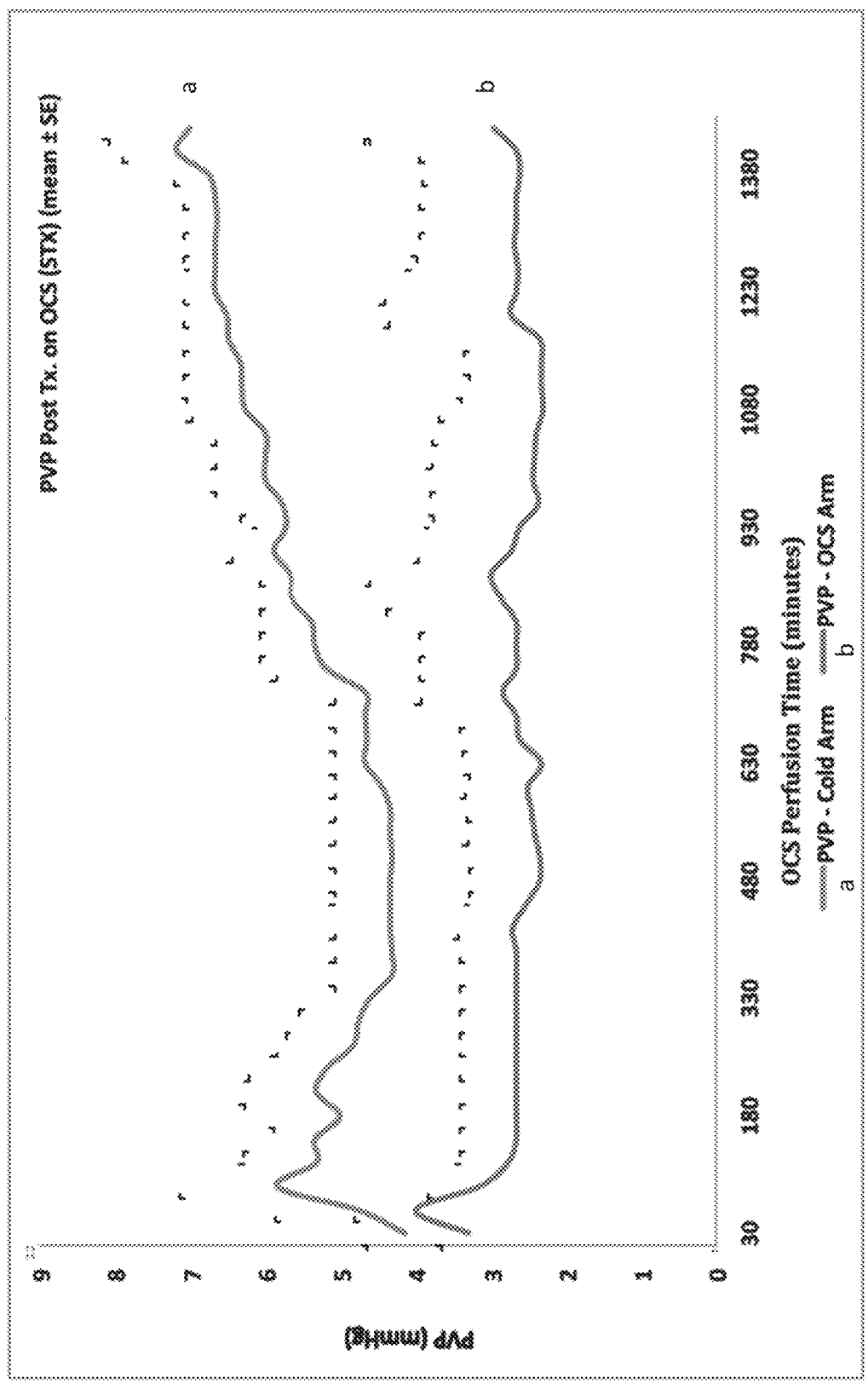
FIG. 63 illustrates the Portal Vein Pressure in an OCS-Liver Preservation arm vs the control Cold preservation arm.

FIG. 63 illustrates the Portal Vein Pressure in an OCS-Liver Preservation arm vs the control Cold preservation arm. FIG. 63 demonstrates the Portal Vein Pressure (PVP) trend over the course of 24 hours perfusion on the OCS; the cold preservation arm demonstrated an increase in the PVP over time compared to stable PVP for the OCS preservation arm.

Figure 64:
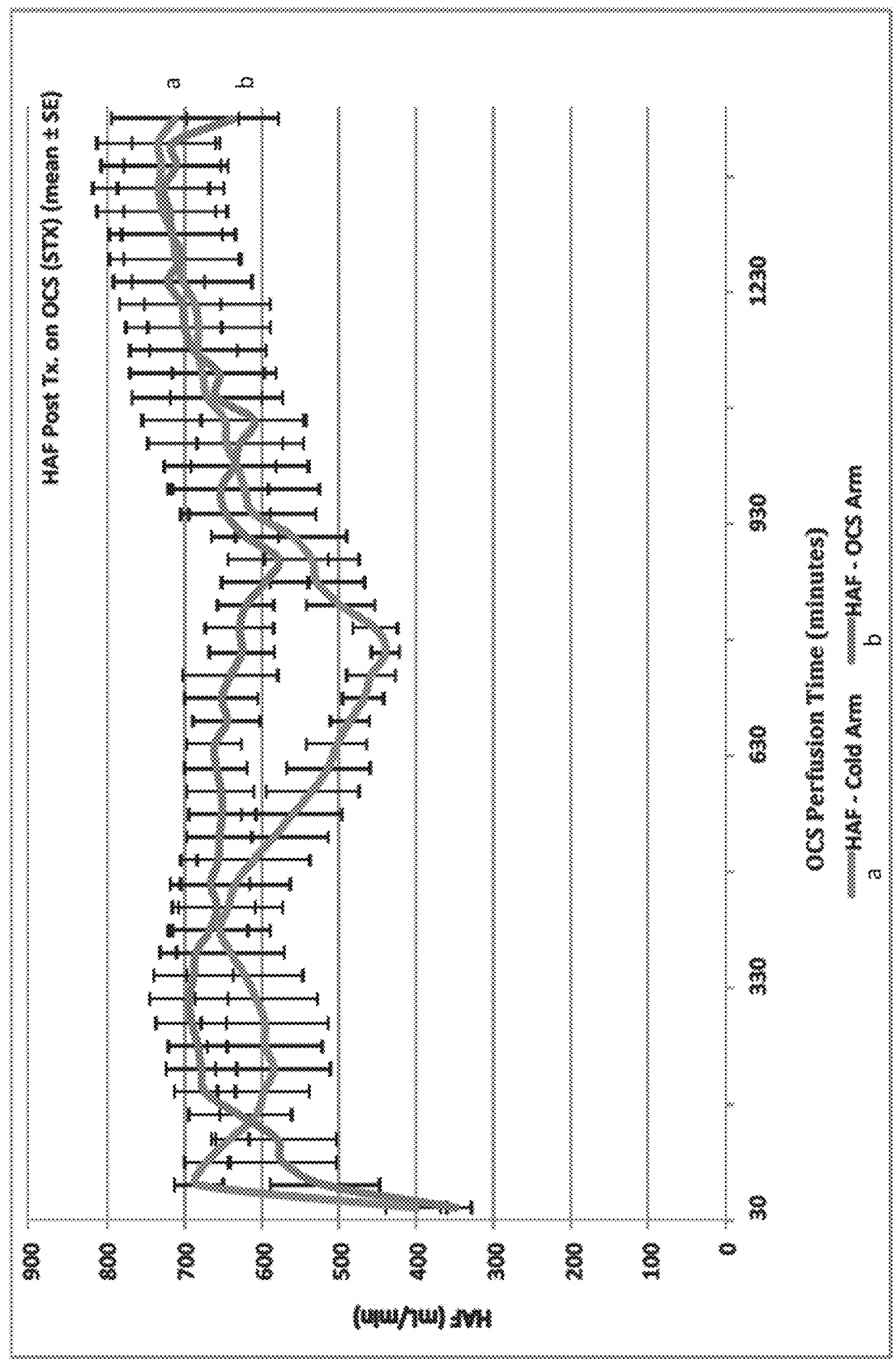
FIG. 64 illustrates a Hepatic Artery Flow in a OCS-Liver Preservation arm vs. control Cold preservation arm.

FIG. 64 illustrates a Hepatic Artery Flow in a OCS-Liver Preservation arm vs. control Cold preservation arm. FIG. 64 demonstrates stable Hepatic Artery Flow (HAF) trend over the course of 24 hours perfusion on the OCS.

Figure 65:
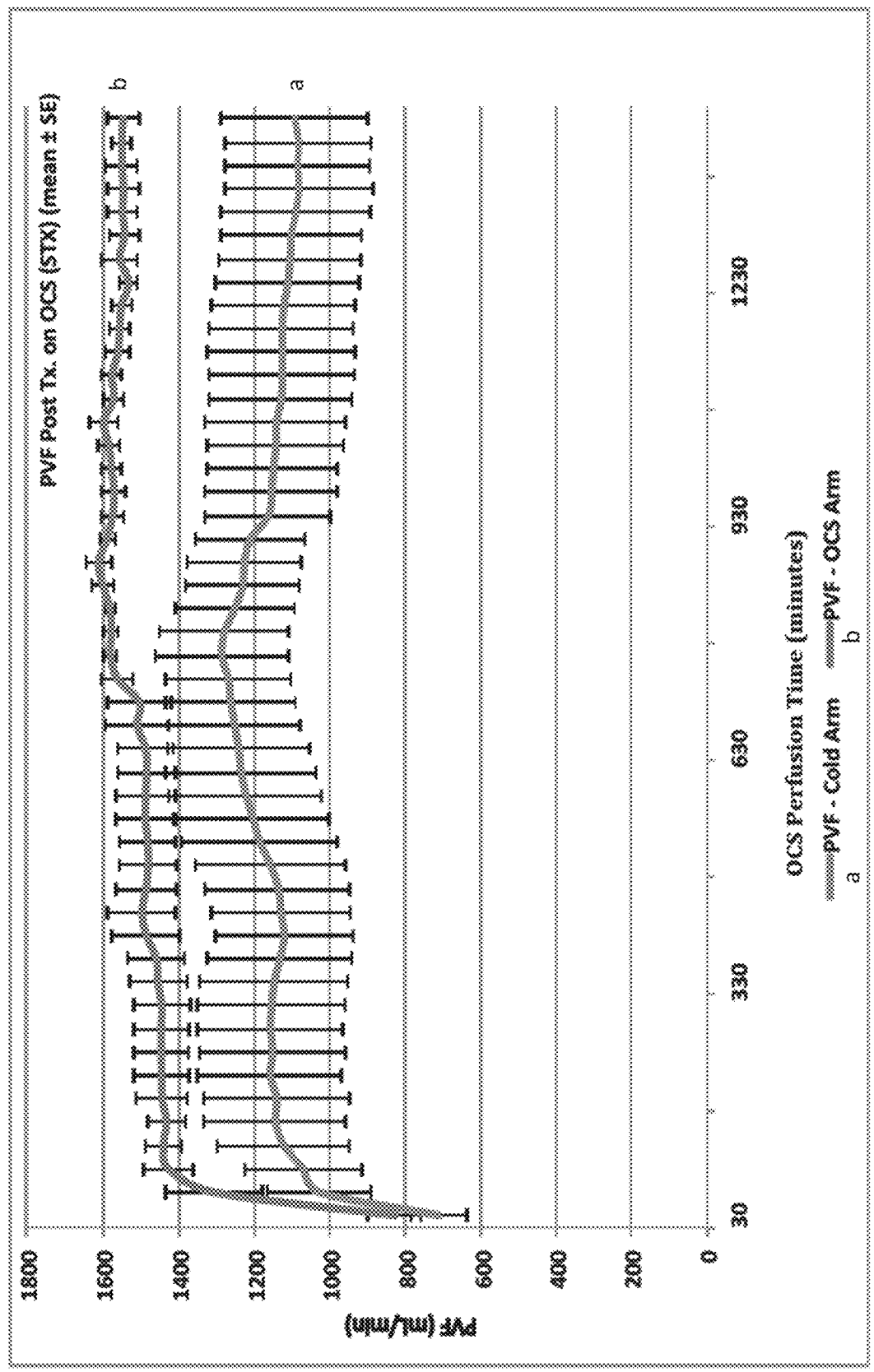
FIG. 65 illustrates a Portal Vein Flow in an OCS-Liver Preservation arm vs. control Cold preservation arm.

FIG. 65 illustrates a Portal Vein Flow in an OCS-Liver Preservation arm vs. control Cold preservation arm. FIG. 65 demonstrates stable Portal Vein Flow (PVF) trend over the course of 24 hours perfusion on the OCS.

Figure 66:
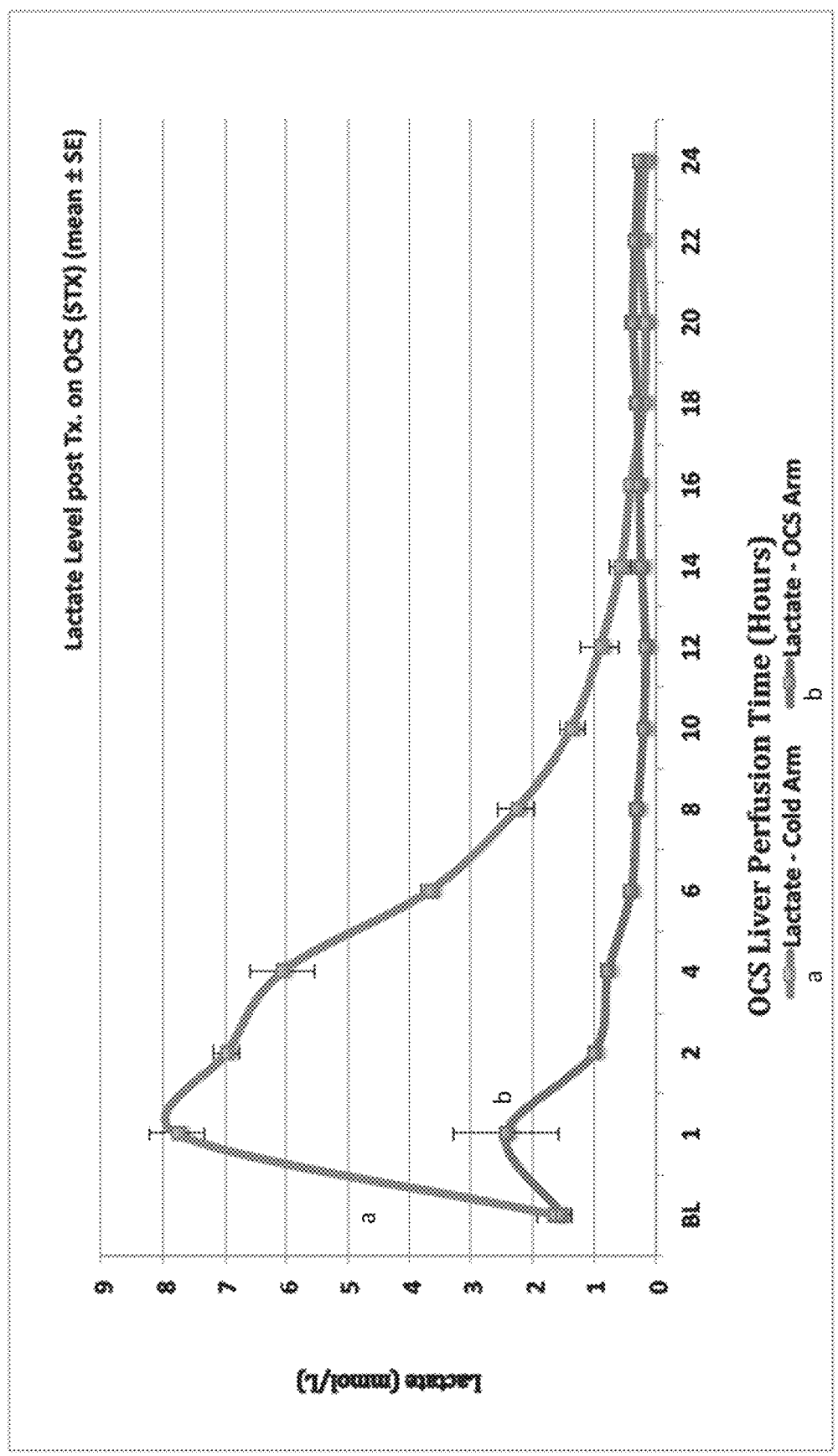
FIG. 66 depicts Arterial Lactate in an OCS-Liver Preservation arm vs. a control Cold preservation arm.

In comparison, the simulated transplant OCS arm (N=3) performed better than the control arm. The perfusion parameters were comparable for both arms of the group however the control arm vascular resistance was higher compared to the OCS arm. The control arm had a much higher peak of the Lactate level at 7.8 mmol/L compared to 2.4 mmol/L for the OCS arm. Both arms continued to produce bile throughout the simulated transplant phase at a rate >10 ml/hr. For example, FIG. 66 depicts Arterial Lactate in an OCS-Liver Preservation arm vs. a control Cold preservation arm. FIG. 66 demonstrates Arterial Lactate in an OCS-Liver Preservation arm vs. control Cold preservation arm. This indicates that the OCS-arm livers had significantly better metabolic function as compared to cold stored arm.

Figure 67:
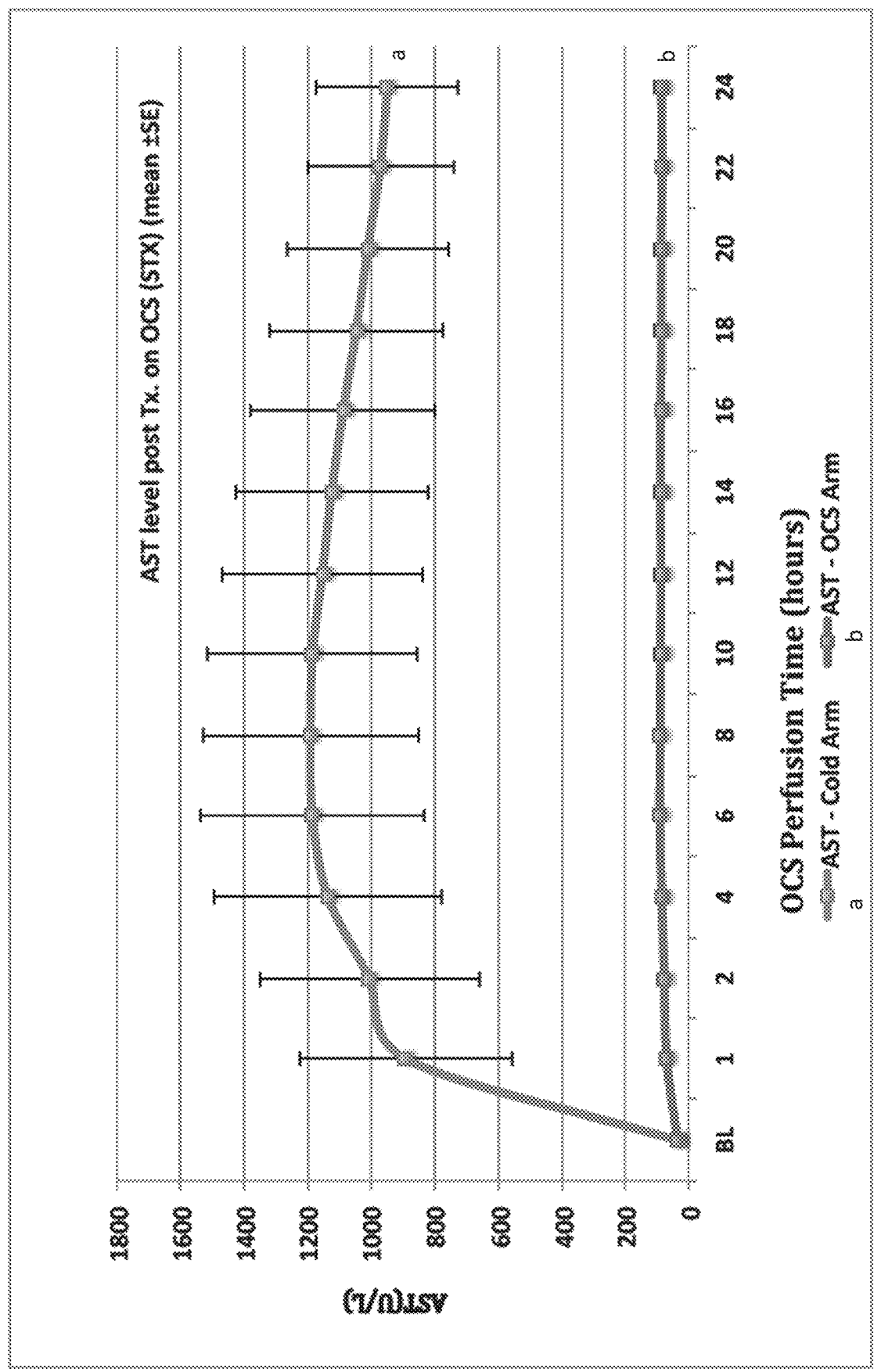
FIG. 67 illustrates an AST Level OCS-Liver Preservation arm vs. control Cold Preservation arm.

Liver enzymes which is a sensitive biomarker of Liver injury (AST, ALT, and the GGT) showed a much higher peaks compared to the OCS arm of the group. Average AST peak was 88.7 in the OCS arm compared to 1188 for the control arm. Average ALT levels peaked at 31.3 for the OCS arm compared to a peak of 82 for the control arm. Average GGT levels peaked at 28.7 for the OCS arm compared to 97 for the control arm. This indicates well preserved Livers and less cell injury for Liver grafts preserved on the OCS arm as compared to the control arm. For example, FIG. 67 illustrates an AST Level OCS-Liver Preservation arm vs. control Cold Preservation arm. FIG. 67 demonstrates that the OCS perfused livers had significantly lower AST levels throughout the 24 hours simulated transplant period. This indicates significantly less liver injury to the graft in the OCS group as compared to the cold stored group.

Figure 68:
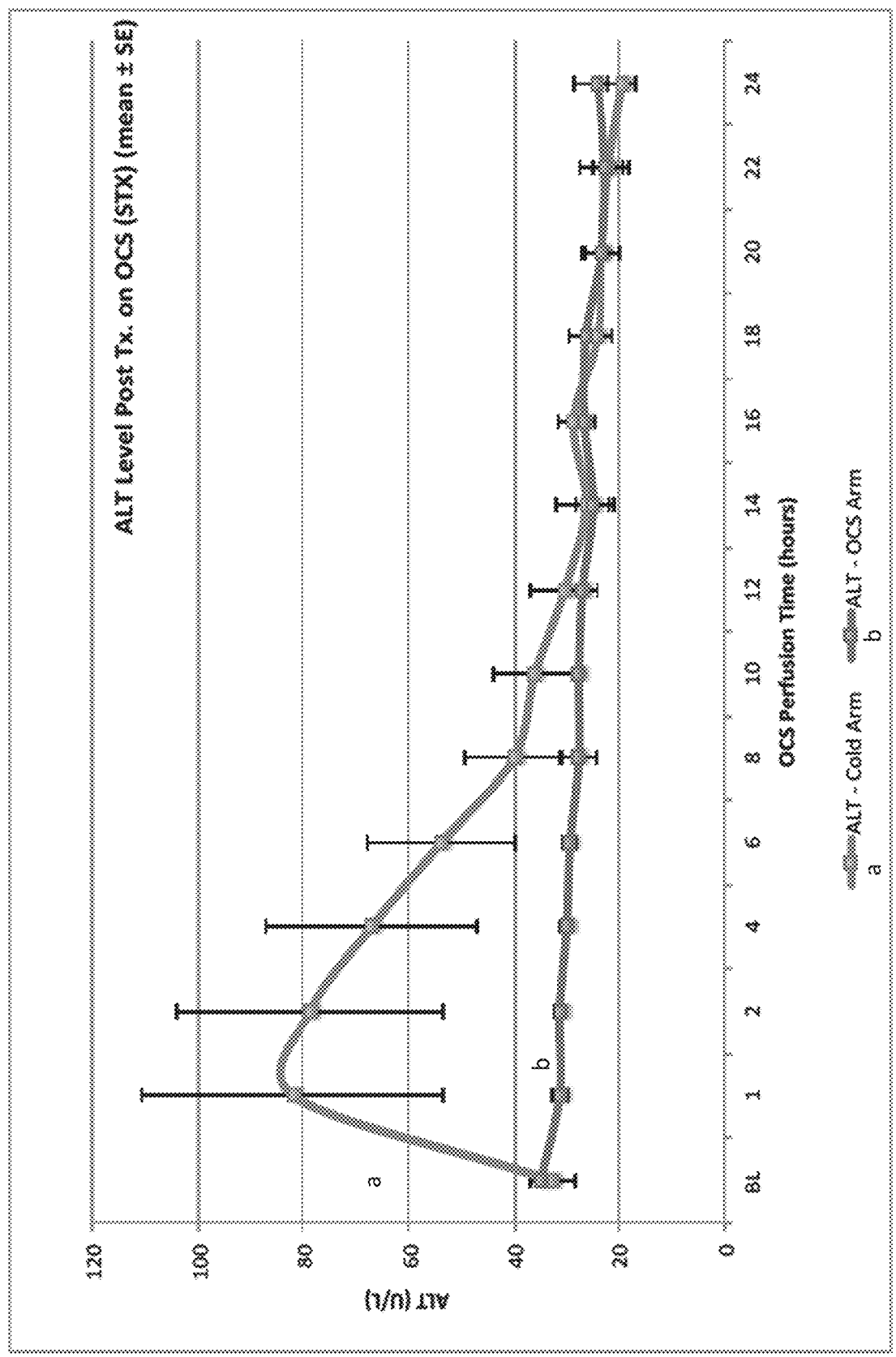
FIG. 68 illustrates an ALT Level OCS-Liver Preservation arm vs. control Cold preservation arm.

FIG. 68 illustrates an ALT Level OCS-Liver Preservation arm vs. control Cold preservation arm. FIG. 68 demonstrates that the OCS perfused livers had lower ALT levels with an average peak at 31.3 compared to average peak of 82 for the control group. This indicates less liver injury to the graft in the OCS arm as compared to the control cold stored arm.

Figure 69:
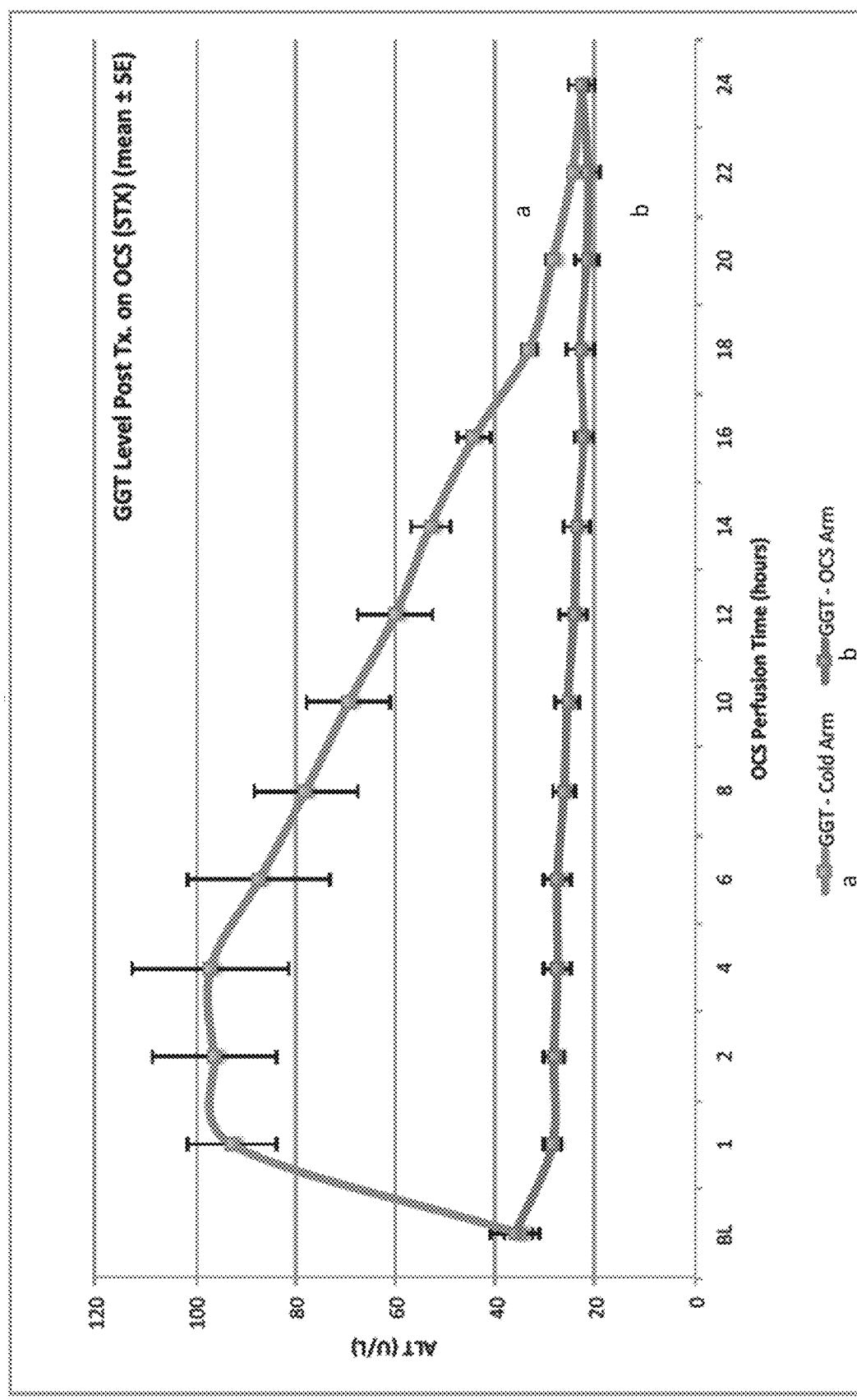
FIG. 69 depicts a GGT Level of an OCS-Liver Preservation arm vs. control Cold preservation arm.

FIG. 69 depicts a GGT Level of an OCS-Liver Preservation arm vs. control Cold preservation arm. FIG. 69 demonstrates that the OCS perfused livers had a much lower GGT levels throughout the 24 hr. period. This indicates better hepatobilliary protection of the graft in the OCS arm as compared to the control cold stored arm.

Figure 70:
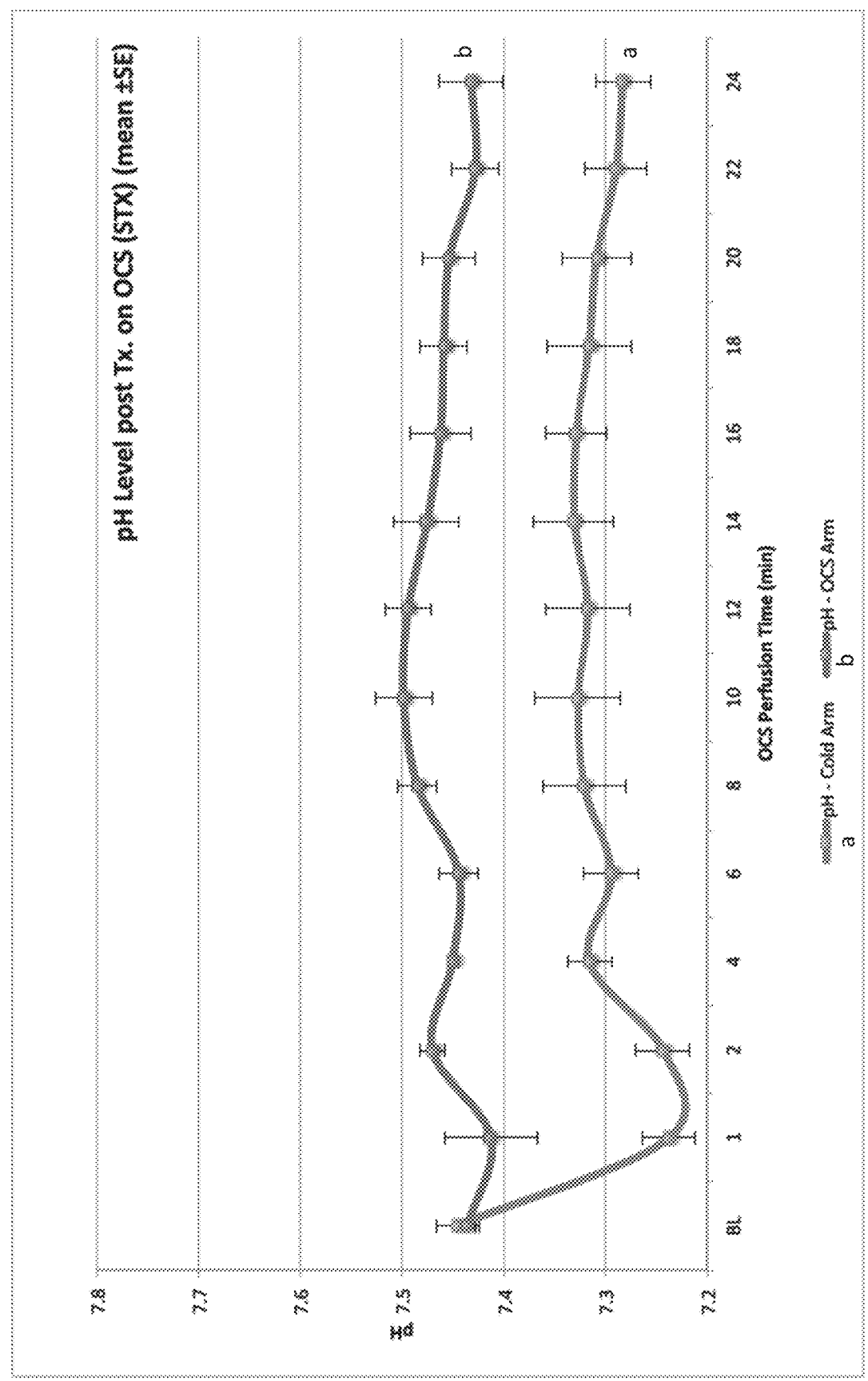
FIG. 70 depicts a PH level of an OCS-Liver Preservation arm vs. a control Cold preservation arm.

The OCS arm demonstrated better metabolic profile compared to the control arm as manifested by the stable and normal pH levels compared to a lower pH for the control arm. This indicates that the OCS arm was able to maintain a much better metabolic profile than the control arm. For example, FIG. 70 depicts a pH level of an OCS-Liver Preservation arm vs. a control Cold preservation arm. As demonstrated by FIG. 70, OCS perfused livers had normal and stable pH values over the course of 24 hours of perfusion as compared to the Control cold preservation arm livers.

Figure 71:
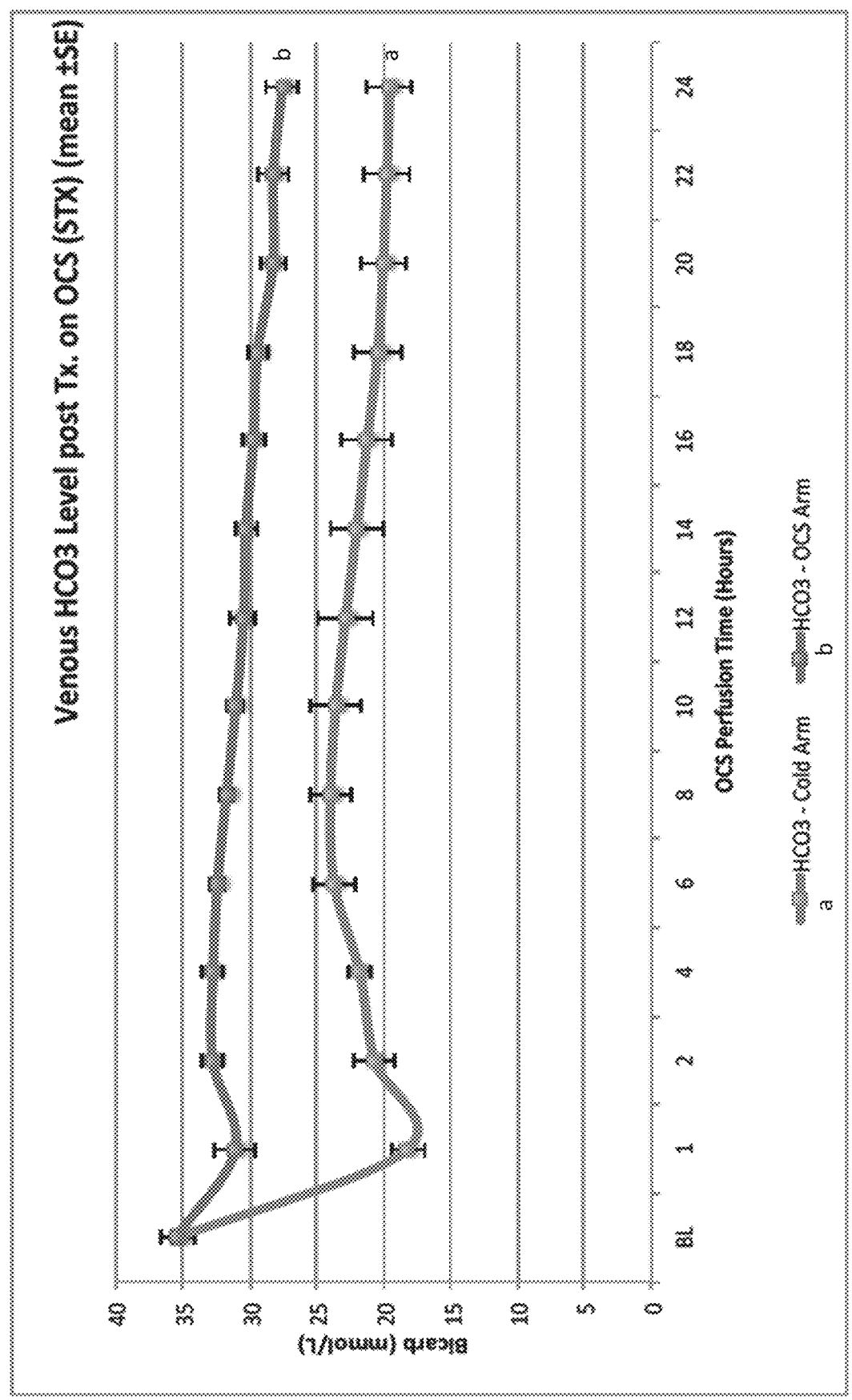
FIG. 71 depicts a HCO3 level in an OCS-Liver Preservation arm vs. a Control Cold preservation arm.

Also the OCS arm demonstrated better metabolic Liver functions as shown by higher HCO3 levels over the course of the 24 hours of the simulated transplant, as compared to the control arm of the group, which demonstrated lower HCO3 throughout the simulated transplant phase. This indicates that the OCS-arm livers had better metabolic function as compared to the control arm. For example, FIG. 71 depicts a HCO3 level in an OCS-Liver Preservation arm vs. a Control Cold preservation arm. As illustrated in FIG. 71, OCS perfused livers had higher HCO3 levels over the course of 24 hours of perfusion as compared to the Control cold preservation arm livers.

Figure 72:
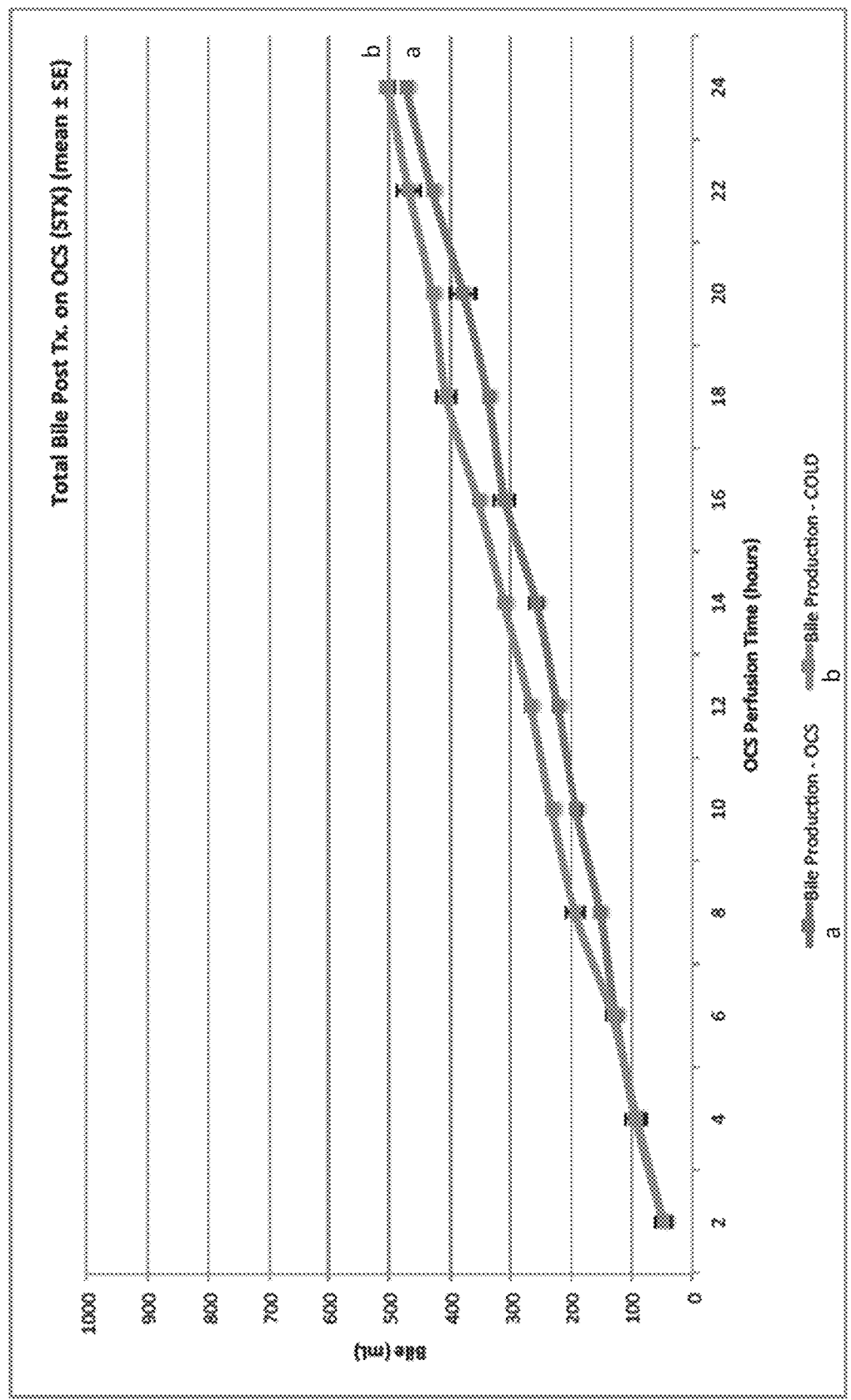
FIG. 72 depicts a bile production OCS-Liver Preservation arm vs. control Cold preservation arm.

FIG. 72 depicts a bile production OCS-Liver Preservation arm vs. control Cold preservation arm. FIG. 72 demonstrates that both arms maintained bile production rate of >10 ml/hr. Based on the above presented data, The OCS has demonstrated stable perfusion and metabolic profile with well-preserved liver graft functions for up to 12 hours of OCS preservation. In addition, when compared to the control arm of cold static preservation, in the simulated transplant model, the OCS perfused swine livers demonstrated a significantly better metabolic function, as evidenced by their ability to metabolize lactate to baseline levels as compared to cold stored livers where lactate continued to rise to significantly higher levels. Additionally, the OCS perfused swine livers had significantly lower AST levels as compared to the much higher level of AST in the simulated transplant control arm, which indicates better Liver graft functions in the OCS arm as compared to the control cold stored arm. The results of this pre-clinical OCS Liver device testing demonstrated that the OCS device is safe and effective in preservation of swine livers, as evidenced by meeting the specified acceptance criteria. The differences observed between the control arm and the OCS arm in Phase III were similar to the differences observed in Phase II, indicating that the OCS arm had better results. Additional uses While preservation of a donor organ which is intended for transplantation has been described above, some embodiments of the organ care system 600 described herein can be used for other purposes. For example, the system 600 can also be used for maintaining an organ during reconstructive or other types of surgery, therapy, and/or treatment (e.g., complicated, high-risk surgeries and/or treatments). That is, some surgeries, therapies, and/or treatments can be damaging to the human body, if the procedure were performed on an in vivo organ. Thus, it can be beneficial to remove the organ from the patient's body, perform surgery on and/or treat the organ ex vivo, and then reimplant the organ back into the patient's body. For example, certain radiation therapies can be damaging to tissue surrounding the organ. Thus, by removing the organ, intensive radiation therapy can be performed on the organ without collateral damage to the patient's body. Other embodiments are possible.

D. Ex-Vivo Treatment of Diseased Livers, Including Cancer, Fatty Livers, Infection, by Delivery of Therapeutics to Organ In some embodiments, the liver preserved on the organ care system 600 can be subjected to ex-vivo therapeutic treatment of liver diseases. Non-limiting examples of liver diseases include cancer, fatty livers, and liver infection. The therapy can be conducted by adding therapeutic agents to the perfusion fluid circulating through the organ care system 600, thereby providing it to the liver itself. Alternatively, the therapeutic agents can be directly added into one or more nutritional solution described herein. In some embodiments, the temperature of the perfusion fluid and/or liver can be maintained at 40° C. or 42° C., which can accelerate the rate of breakdown and dissolution of fatty cells in the liver.

Non-limiting examples of anti-cancer therapeutic agents suitable for ex-vivo therapeutic treatment of liver cancer include microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors. Anti-cancer "Microtubule binding agent" refers to an agent that interacts with tubulin to stabilize or destabilize microtubule formation thereby inhibiting cell division. Examples of microtubule binding agents include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and will be known to those of ordinary skill in the art.

Anti-cancer DNA and/or RNA transcription regulators include, without limitation, actinomycin D, daunorubicin, doxorubicin and derivatives and analogs thereof. DNA intercalators and cross-linking agents include, without limitation, cisplatin, carboplatin, oxaliplatin, mitomycins, such as mitomycin C, bleomycin, chlorambucil, cyclophosphamide and derivatives and analogs thereof. DNA synthesis inhibitors include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Other anti-tumor agents can include adriamycin, apigenin, rapamycin, zebularine, cimetidine, and derivatives and analogs thereof. Any other suitable liver cancer therapeutic agents known in the art are contemplated.

A further advantage of the chemotherapy described above is its specificity: the anticancer agent is specifically delivered to the diseased organ, the liver, without any undesirable toxicity to other healthy organs or tissues.

Non-limiting examples of therapeutic agents suitable for ex vivo therapeutic treatment of fatty liver disease include pioglitazone, rosiglitazone, orlistat, ursodiol, and betaine. Any other suitable fatty liver therapeutic agents known in the art are contemplated.

Non-limiting examples of therapeutic agents suitable for ex-vivo therapeutic treatment of liver infection include terferon alfa-2b, terferon alfa-2a, ribavirin, telaprevir, boceprevir, simeprevir, and sofobuvir. Any other suitable liver infection therapeutic agents known in the art are contemplated.

E. Regenerative Approaches Including Stem Cell or Gene Delivery

In other embodiments, the organ preserved by the organ care system 600 described herein can be subjected to regenerative treatments. Non-limiting examples of the organ regenerative treatments include stem cell therapy or gene delivery therapy. Stem cells are undifferentiated biological cells that can differentiate into specialized cells, e.g., hepatocytes. Adult stem cells can be harvested from blood, adipose, and bone marrow of the donor of the liver with various types of liver diseases, or of another adult with compatible stem cells (stem cells transplantation). The isolated stem cells, e.g., bone marrow cells, can be used to infuse the damaged or diseased liver preserved on the organ care system 600 to repair the liver to a healthier state. For instance, the isolated stem cells can be isolated from the donor and included in the blood product in the perfusion fluid.

In some other embodiments, the liver preserved by the organ care system 600 described herein can be subjected to gene delivery therapy. Gene delivery is the process of introducing foreign DNA into host cells, e.g., liver cells, to effect treatment of diseases. In certain embodiments, the gene delivery therapy is virus-mediated gene delivery utilizing a virus to inject its DNA inside the liver cells. Non-limiting examples of suitable viruses include retrovirus, adenovirus, adeno-associated virus and herpes simplex virus. In some embodiments, a gene that is used to treat certain liver diseases is packaged into a vector (virus or other) and included as part of the perfusion fluid to perfuse the liver or added to the circulation of the organ care system 600 directly.

F. Ex-Vivo Immune Modulation

In other embodiments, the donor's liver preserved by the organ care system 600 described herein can be subjected to immune regulations. Immune responses and their modulation within the liver can affect the outcome liver transplantation. More importantly, a liver disease can be treated by inducing, enhancing, or suppressing an immune response from the liver. For instance, the liver immune system can be activated to attack malicious tissues to treat liver cancer. On the other hand, the liver immune system can be suppressed to treat autoimmune liver disease such as autoimmune hepatitis. Any immunosuppressive agents or immune activating agents known in the art can be used to treat the preserved liver to achieve the desirable effect.

G. Ex-Vivo Surgical Treatment of Livers

In yet other embodiments, the donor's liver preserved by the organ care system 600 described herein can be subjected to surgical treatment such as liver tumor resection or split transplant where the liver is divided between two recipient patients. In yet other embodiments, the donor's liver preserved by the organ care system 600 described herein can be subjected to irradiation therapy to treat certain liver diseases such as liver cancer.

XI. CONCLUSION

Other embodiments are within the scope and spirit of the disclosed subject matter. In some embodiments, a perfusion circuit for perfusing a liver ex-vivo is disclosed, which comprises a pump for providing pulsatile fluid flow of a perfusion fluid through the circuit, a gas exchanger, a divider in fluid communication with the pump configured to divide the perfusion fluid flow into a first branch and a second branch wherein the first branch comprises a hepatic artery interface wherein the first branch is configured to provide a first portion of the perfusion fluid to a hepatic artery of the liver at a high pressure and low flow rate via the hepatic artery interface wherein the first branch is in fluid pressure communication with the pump wherein the second branch comprises a portal vein interface wherein the second branch is configured to provide a second portion of the perfusion fluid to a portal vein of the liver at a low pressure and high flow rate via the portal vein interface the second branch further comprising a clamp located between the divider and the portal vein interface for selectively controlling the flow rate of perfusion fluid to the portal vein the second branch further comprising a compliance chamber configured to reduce the pulsatile flow characteristics of the perfusion fluid from the pump to the portal vein wherein the pump is configured to communicate fluid pressure through the first and second branches to the liver, a drain configured to receive perfusion fluid from an uncannulated inferior vena cava of the liver, and a reservoir positioned below the liver and located between drain and the pump, configured to receive the perfusion fluid from the drain and store a volume of fluid.

In certain embodiments, the second branch of a perfusion circuit comprises a plurality of compliance chambers. In certain embodiments, a compliance chamber in a perfusion circuit is located between the divider and the portal vein interface. In certain embodiments, a portal vein interface of a perfusion circuit has a larger cross sectional area than a hepatic artery interface. In certain embodiments, a perfusion circuit includes at least one flow rate sensor in a second branch, and at least one pressure sensor. In certain embodiments, a pump comprises a pump driver, and the position of the pump driver is adjustable to control the pattern of pulsatile flow to a liver. In some embodiments a clamp comprises an engaged position and a disengaged position, the clamp may be adjusted to select the desired clamping force and corresponding flow rate when the clamp is in the disengaged position, the clamp may be moved to the engaged position to apply the selected clamping force without further adjustment when in the engaged position, such that a user may quickly engage and disengage the clamp while still having precise control over the amount of clamping force applied to the perfusion circuit.

In some embodiments, a system for perfusing an ex vivo liver at near physiologic conditions is disclosed, the system comprising a perfusion circuit comprising a pump for pumping perfusion fluid through the circuit, the pump in fluid communication with a hepatic artery interface and a portal vein interface, wherein the pump provides perfusion fluid to a hepatic artery of the liver at a high pressure and low flow rate via the hepatic artery interface; and wherein the pump provides perfusion fluid to the a portal vein of the liver at a low pressure and high flow rate via the portal vein interface, a gas exchanger, a heating subsystem for maintaining the temperature of the perfusion fluid at a normothermic temperature, a drain configured to receive the perfusion fluid from an inferior vena cava of the liver, a reservoir configured to receive perfusion fluid from the drain and store a volume of fluid. In some embodiments, a heating subsystem is configured to maintain the perfusion fluid at a temperature between 34-37° C. In some embodiments, a the perfusion circuit comprises an inferior vena cava cannula. In some embodiments, a control system for controlling operation of the system is disclosed, comprising an onboard computer system connected to one or more of the components in the system, a data acquisition subsystem comprising at least one sensor for obtaining data relating to the organ, and a data management subsystem for storing and maintaining data relating to operation of the system and with respect to the liver. In some embodiments, a heading subsystem comprises a dual feedback loop for controlling the temperature of the perfusion fluid within the system.

In some embodiments, a system for preserving a liver ex vivo at physiologic conditions is disclosed, comprising a multiple use module comprising a pulsatile pump, a single use module comprising, a perfusion circuit configured to provide perfusion fluid to the liver, a pump interface assembly for translating pulsatile pumping from the pump to the perfusion fluid, a hepatic artery interface configured to deliver perfusion fluid to a hepatic artery of the liver, a portal vein interface configured to deliver perfusion fluid to a portal vein of the liver, a divider to supply perfusion fluid flow from the pump interface assembly to the hepatic artery interface at a high pressure and low flow rate and to the portal vein interface at a low pressure and high flow rate, an organ chamber assembly configured to hold an ex vivo organ, the organ chamber assembly including a housing, a flexible support surface suspended within the organ chamber assembly, and a bile container configured to collect bile produced by the liver.

In some embodiments, flexible support surface is configured to conform to differently sized organs, and further comprising projections to stabilize the liver in the organ chamber assembly. In some embodiments, a flexible support surface comprises a top layer, a bottom layer, and a deformable metal substrate positioned between the top layer and the bottom layer. In some embodiments, a flexible support surface is configured to cradle and controllably support a liver without applying undue pressure to the liver. In some embodiments, a single use module comprises a wrap configured to cover the liver in the organ chamber assembly. In some embodiments, a single use module comprises a sensor to measure the volume of bile collected in the bile container. In some embodiments, a single use module can be sized and shaped for interlocking with a portable chassis of the multiple use module for electrical, mechanical, gas and fluid interoperation with the multiple use module. In some embodiments, multiple and single use modules can communicate with each other via an optical interface, which comes into optical alignment automatically upon the single use disposable module being installed into the portable multiple use module.

The subject matter described herein can be implemented using digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

The invention claimed is:

1. A perfusion circuit comprising:
   a pump configured to pump a perfusion fluid through the perfusion circuit;
   an oxygenator;
   a hepatic artery interface configured to provide the perfusion fluid to a hepatic artery of an ex-vivo liver;
   a portal vein interface configured to provide the perfusion fluid to a portal vein of the ex-vivo liver;
   a clamp adapted to be positioned between the pump and the portal vein interface, the clamp configured to be usable to control a pressure of the perfusion fluid provided to the hepatic artery;
   a solution pump configured to provide a maintenance solution to the perfusion fluid;
   an inferior vena cava interface in fluid communication with an inferior vena cava of the ex-vivo liver; and
   a reservoir configured to receive the perfusion fluid from the inferior vena cava of the ex-vivo liver and store a volume of the perfusion fluid.

2. The perfusion circuit of claim 1, wherein the solution pump is configured to provide a plurality of bile salts.

3. The perfusion circuit of claim 1, wherein the solution pump is configured to detect an occlusion in the perfusion circuit.

4. The perfusion circuit of claim 1, comprising at least one flow rate sensor and at least one pressure sensor.

5. The perfusion circuit of claim 1, wherein the pump is configured to:
   pump the perfusion fluid to the hepatic artery of the ex-vivo liver at a pressure between 25-150 mmHg and a flow rate between 0.25-1 L/min; and
   pump the perfusion fluid to the portal vein of the ex-vivo liver at a flow rate between 0.75-2 L/min.

6. A system for perfusing an ex-vivo liver, the system comprising:
   a pump configured to pump a perfusion fluid through a perfusion circuit, the pump in fluid communication with a hepatic artery interface and a portal vein interface;
   a controller configured to cause the system to:
      provide, via the pump and the hepatic artery interface, the perfusion fluid to a hepatic artery of the ex-vivo liver; and
      provide, via the pump and the portal vein interface, the perfusion fluid to a portal vein of the ex-vivo liver;
   an oxygenator;
   a clamp adapted to be positioned between the pump and the portal vein interface, the clamp configured to be usable to control a pressure of the perfusion fluid provided to the hepatic artery;
   a heater configured to maintain a temperature of the perfusion fluid;
   a solution pump configured to provide a maintenance solution to the perfusion fluid;
   an inferior vena cava interface in fluid communication with an inferior vena cava of the ex-vivo liver; and
   a reservoir configured to receive the perfusion fluid from the inferior vena cava of the ex-vivo liver and store a volume of the perfusion fluid.

7. The system of claim 6, wherein the heater is configured to maintain the temperature of the perfusion fluid at between 34° C. and 37° C.

8. The system of claim 6, wherein the controller is configured to cause the system to:
provide, via the pump and the hepatic artery interface, the perfusion fluid to the hepatic artery of the ex-vivo liver at a pressure between 25-150 mmHg and a flow rate between 0.25-1 L/min; and
provide, via the pump and the portal vein interface, the perfusion fluid to the portal vein of the ex-vivo liver at a flow rate between 0.75-2 L/min.

9. The system of claim 6, wherein the solution pump is configured to provide a vasodilator or a plurality of bile salts.

10. The system of claim 6, wherein the heater comprises a dual feedback loop, and wherein the dual feedback loop is configured to control the temperature of the perfusion fluid.

11. A system for preserving an ex-vivo liver, the system comprising:
a single-use module comprising:
a pump interface assembly configured to translate a pumping from a pump to the perfusion fluid;
a hepatic artery interface configured to provide the perfusion fluid to a hepatic artery of the ex-vivo liver;
a portal vein interface configured to provide the perfusion fluid to a portal vein of the ex-vivo liver; and
an organ chamber configured to hold the ex-vivo liver, wherein the organ chamber comprises:
a housing;
a support surface suspended within the organ chamber; and
a bile container configured to collect bile produced by the ex-vivo liver; and
a multiple-use module comprising:
the pump;
a solution pump configured to provide a maintenance solution to the perfusion circuit; and
a clamp adapted to be positioned between the pump and the portal vein interface, the clamp configured to be usable to control a pressure of the perfusion fluid provided to the hepatic artery.

12. The system of claim 11, wherein the solution pump is configured to provide a vasodilator or a plurality of bile salts.

13. The system of claim 11, wherein the multiple-use module comprises a controller configured to cause the system to:
provide, via the pump and the hepatic artery interface, the perfusion fluid to the hepatic artery of the ex-vivo liver at a pressure between 25-150 mmHg and a flow rate between 0.25-1 L/min; and
provide, via the pump and the portal vein interface, the perfusion fluid to the portal vein of the ex-vivo liver at a flow rate between 0.75-2 L/min.

14. The system of claim 11, wherein the single-use module comprises a sensor, wherein the sensor is configured to measure a volume of the bile produced by the ex-vivo liver.

15. A system for perfusing an ex-vivo liver, the system comprising:
a pump configured to pump a perfusion fluid through a perfusion circuit, the pump in fluid communication with a hepatic artery interface and a portal vein interface;
a clamp adapted to be positioned between the pump and the portal vein interface, the clamp configured to be usable to control a pressure of the perfusion fluid provided to the hepatic artery of an ex-vivo liver;
a controller configured to cause the system to:
provide, via the pump and the hepatic artery interface, the perfusion fluid to a hepatic artery of the ex-vivo liver;
provide, via the pump and the portal vein interface, the perfusion fluid to a portal vein of the ex-vivo liver; and
receive a temperature signal from a temperature sensor; and
a heating subsystem configured to maintain a temperature of the perfusion fluid, wherein the heating subsystem comprises:
a heating assembly comprising a heater in communication with the perfusion fluid;
the temperature sensor configured to measure the temperature of the perfusion fluid; and
a driver configured to convert the temperature signal to a heat drive signal,
wherein the heater is configured to heat the perfusion fluid in response to the heat drive signal.

16. The system of claim 15, wherein the heating assembly comprises a plurality of heaters.

17. The system of claim 15, wherein the temperature sensor is configured to provide at least two signals to the controller, and wherein the at least two signals correspond to the temperature of the perfusion fluid.

18. The system of claim 17, wherein the at least two signals correspond to the temperature of the perfusion fluid in the heating assembly.

19. The system of claim 15, wherein the heating subsystem comprises a second driver.

20. The system of claim 15, wherein the heating subsystem is configured to maintain the temperature of the perfusion fluid between 32° C. and 42° C.

21. The system of claim 15, wherein the heating subsystem comprises a heater temperature sensor configured to measure a temperature of the heater.

22. The system of claim 21, wherein the heater temperature sensor is configured to provide a heater temperature signal to the controller, and wherein the heater temperature signal corresponds to the temperature of the heater.

23. The system of claim 22, wherein the controller is configured to receive the heater temperature signal.

24. The system of claim 23, wherein the driver is configured to convert the heater temperature signal from the controller to a second heat drive signal, and wherein the controller is configured to, in response to the heater temperature signal, reduce or stop the second heat drive signal to cause a change in a supply of power to the heater.

25. The system of claim 24, wherein the controller is configured to override the temperature signal from the temperature sensor when the heater temperature signal corresponds to a temperature above about 42° C.

26. The system of claim 25, wherein the heating subsystem comprises at least two drivers and at least two heaters.

27. A system for perfusing an ex-vivo liver, the system comprising:
a pump configured to pump a perfusion fluid, the pump in fluid communication with a hepatic artery interface and a portal vein interface;

a controller configured to cause the system to:
  provide, via the pump and the hepatic artery interface, the perfusion fluid to a hepatic artery of the ex-vivo liver; and
  provide, via the pump and the portal vein interface, the perfusion fluid to a portal vein of the ex-vivo liver; and
a clamp adapted to be positioned between the pump and the portal vein interface, the clamp configured to be usable to control a pressure of the perfusion fluid provided to the hepatic artery.

28. The system of claim 27, comprising a solution pump configured to provide a maintenance solution to the perfusion fluid.

29. The system of claim 27, comprising an oxygenator.

30. The system of claim 27, comprising:
a pressure sensor configured to measure the pressure of the perfusion fluid provided to the hepatic artery;
a flow rate sensor configured to measure a flow rate of the perfusion fluid provided to the portal vein;
a flow rate sensor configured to measure a flow rate of the perfusion fluid from an inferior vena cava of the ex-vivo liver; and
a pressure sensor configured to measure a pressure of the perfusion fluid from the inferior vena cava.

* * * * *